US007193069B2

(12) United States Patent
Isogai et al.

(10) Patent No.: US 7,193,069 B2
(45) Date of Patent: Mar. 20, 2007

(54) FULL-LENGTH CDNA

(75) Inventors: Takao Isogai, Ibaraki (JP); Tomoyasu Sugiyama, Tokyo (JP); Tetsuji Otsuki, Chiba (JP); Ai Wakamatsu, Chiba (JP); Hiroyuki Sato, Osaka (JP); Shizuko Ishii, Chiba (JP); Jun-ichi Yamamoto, Chiba (JP); Yuuko Isono, Chiba (JP); Yuri Hio, Chiba (JP); Kaoru Otsuka, Saitama (JP); Keiichi Nagai, Tokyo (JP); Ryotaro Irie, Chiba (JP); Ichiro Tamechika, Osaka (JP); Naohiko Seki, Chiba (JP); Tsutomu Yoshikawa, Chiba (JP); Motoyuki Otsuka, Tokyo (JP); Kenji Nagahari, Tokyo (JP); Yasuhiko Masuho, Tokyo (JP)

(73) Assignee: Research Association for Biotechnology, Tokyo (JP)

( * ) Notice: Subject to any disclaimer, the term of this patent is extended or adjusted under 35 U.S.C. 154(b) by 274 days.

(21) Appl. No.: 10/108,260

(22) Filed: Mar. 28, 2002

(65) Prior Publication Data

US 2004/0005560 A1 Jan. 8, 2004

(30) Foreign Application Priority Data

Mar. 22, 2002 (JP) ............................. 2002-137785

(51) Int. Cl.
*C07H 21/04* (2006.01)
(52) U.S. Cl. ...................... 536/23.1; 435/69.1
(58) Field of Classification Search ............... 435/6, 435/69.1, 320.1, 325, 4; 536/23.1, 24.1, 536/24.2; 424/93.2, 200.1
See application file for complete search history.

(56) References Cited

U.S. PATENT DOCUMENTS 6,265,165 B1    7/2001 Xu et al.

FOREIGN PATENT DOCUMENTS

| EP | 1026242 A1 | 9/2000 |
|---|---|---|
| WO | WO 01/53312 A1 | 7/2001 |
| WO | WO 01/57182 A3 | 8/2001 |
| WO | WO 01/57185 A2 | 8/2001 |

OTHER PUBLICATIONS

GenBank Accession No. AC079860 (GI:11990750), "*Homo sapiens* chromosome RPCI-11 clone RP11-671C15, Working Draft", Dec. 23, 2000, [online] [retrieved on Jun. 3, 2004]. <URL:http://www.ncbi.nlm.nih.gov/entrez/viewer.fcgi?db=nucleotide&val=11990750>.*
EMBL Accession No. AF039235; XP-002206836; Jan. 17, 1998.

(Continued)

*Primary Examiner*—Michael Borin
*Assistant Examiner*—Jerry Lin
(74) *Attorney, Agent, or Firm*—Foley & Lardner LLP

(57) ABSTRACT

Novel full-length cDNAs are provided.

2443 cDNA derived from human have been isolated. The full-length nucleotide sequences of the cDNA and amino acid sequences encoded by the nucleotide sequences have been determined. Because the cDNA of the present invention are full-length and contain the translation start site, they provide information useful for analyzing the functions of the polypeptide.

5 Claims, 1 Drawing Sheet

OTHER PUBLICATIONS

SWISSPROT Accession No. Q9BTE6; XP-002206838; Jun. 1, 2001.

Gill et al., "A new dynamic tool to perform assembly of Expressed Sequence Tags (ESTs)," 1997, Comput Appl Biosci; pp. 453-457, vol. 14, No. 4.

O'Brien et al., "Characterization of Five Novel Human Genes in the 11q13-q22 Region," 2000, Biochem Biophys Res Commun, pp. 90-94, vol. 273, No. 1.

Suzuki et al., "Construction and characterization of a full length-enriched and a 5'- end enriched cDNA library," 1997, Gene, pp. 149-156, vol. 200, No. 1-2.

D.L. Bodian, "IBLAST, a fully automated method for cDNA cloning in silico," 1999, Faseb J, p. A1382, vol. 13, No. 7.

S. Sugano et al., Tanpakushitsu Kakusan Koso (Protein, Nucleic Acid and Enzyme), vol. 38, No. 3, pp. 4761-81 (1993) English language abstract attached.

Ota et al., "Complete Sequencing and Characterization of 21,243 Full-Length Human cDNAs," Nature Genetics, vol. 36, No. 1, Jan. 2004, pp. 40-45.

* cited by examiner

FULL-LENGTH CDNA

This application contains a sequence listing submitted in accordance with 37 CFR 1.52(e), on three compact discs containing identical copies of the sequence listing in lieu of a paper copy, said disc copies created on or about Sep. 3, 2002, each file containing the identical sequence listing file (named "H1-A0106-USD1sq.txt") which sequence listing is hereby incorporated into the present specification.

FIELD OF THE INVENTION

The present invention relates to polynucleotides encoding novel polypeptides, polypeptides encoded by the polynucleotides, and new uses of these.

BACKGROUND OF THE INVENTION

Currently, the sequencing projects, the determination and analysis of the genomic DNA of various living organisms have been in progress all over the world. The whole genomic sequences of more than 40 species of prokaryotes, a lower eukaryote, yeast, a multicellular eukaryote, C. elegans, and a higher plants, arabidopsis, etc. are already determined. For human genome, presumably having 3 billion base pairs, the analysis was advanced under global cooperative organization, and a draft sequence was disclosed in 2001. Moreover, all the structures are to be clear and to be disclosed in 2002–2003. The aim of the determination of genomic sequence is to reveal the functions of all genes and their regulation and to understand living organisms as a network of interactions between genes, proteins, cells or individuals through deducing the information in a genome, which is a blueprint of the highly complicated living organisms. To understand living organisms by utilizing the genomic information from various species is not only important as an academic subject, but also socially significant from the viewpoint of industrial application.

However, determination of genomic sequences itself cannot identify the functions of all genes. For example, as for yeast, only the function of approximately half of the 6000 genes, which is predicted based on the genomic sequence, was able to be deduced. On the other hand, the human genome has been estimated to contain about 30,000–40,000 genes. Further, 100,000 or more types of mRNAs are said to exist when variants produced by alternative splicing are taken into consideration. Therefore, it is desirable to establish "a high throughput analysis system of the gene functions" which allows us to identify rapidly and efficiently the functions of vast amounts of the genes obtained by the genomic sequencing.

Many genes in the eukaryotic genome are split by introns into multiple exons. Thus, it is difficult to predict correctly the structure of encoded protein solely based on genomic information. In contrast, cDNA, which is produced from mRNA that lacks introns, encodes a protein as a single continuous amino acid sequence and allows us to identify the primary structure of the protein easily. In human cDNA research, to date, more than three million ESTs (Expression Sequence Tags) are publicly available, and the ESTs presumably cover not less than 80% of all human genes.

The information of ESTs is utilized for analyzing the structure of human genome, or for predicting the exon-regions of genomic sequences or their expression profile. However, many human ESTs have been derived from proximal regions to the 3'-end of cDNA, and information around the 5'-end of mRNA is extremely little. Among human cDNAs, the number of the corresponding mRNAs whose encoding full-length protein sequences are deduced is approximately 13,000.

It is possible to identify the transcription start site of mRNA on the genomic sequence based on the 5'-end sequence of a full-length cDNA, and to analyze factors involved in the stability of mRNA that is contained in the cDNA, or in its regulation of expression at the translation stage. Also, since a full-length cDNA contains atg codon, the translation start site, in the 5'-region, it can be translated into a protein in a correct frame. Therefore, it is possible to produce a large amount of the protein encoded by the CDNA or to analyze biological activity of the expressed protein by utilizing an appropriate expression system. Thus, analysis of a full-length cDNA provides valuable information which complements the information from genome sequencing. Also, full-length cDNA clones that can be expressed are extremely valuable in empirical analysis of gene function and in industrial application.

Therefore, if a novel human full-length cDNA is isolated, it can be used for developing medicines for diseases in which the gene is involved. The protein encoded by the gene can be used as a drug by itself. Thus, it has great significance to obtain a full-length cDNA encoding a novel human protein.

In particular, human secretory proteins or membrane proteins would be useful by itself as a medicine like tissue plasminogen activator (TPA), or as a target of medicines like membrane receptors. In addition, genes for signal transduction-related proteins (protein kinases, etc.), glycoprotein-related proteins, transcription-related proteins, etc. are genes whose relationships to human diseases have been elucidated. Moreover, genes for disease-related proteins form a gene group rich in genes whose relationships to human diseases have been elucidated.

Therefore, it has great significance to isolate novel full-length cDNA clones of human, only few of which has been isolated. Especially, isolation of a novel cDNA clone encoding a secretory protein or membrane protein is desired since the protein itself would be useful as a medicine, and also the clones potentially include a gene involved in diseases. In addition, genes encoding proteins that are involved in signal transduction, glycoprotein, transcription, or diseases are expected to be useful as target molecules for therapy, or as medicines themselves. These genes form a gene group predicted to be strongly involved in diseases. Thus, identification of the full-length cDNA clones encoding those proteins has great significance.

SUMMARY OF THE INVENTION

An objective of the present invention is to provide polynucleotides encoding novel polypeptides, polypeptides encoded by the polynucleotides, and novel usages of these.

The inventors have developed a method for efficiently cloning, from a cDNA library having very high fullness-ratio, a human full-length cDNA that is predicted to be a full-length cDNA clone, where the CDNA library is synthesized by an improved method (WO 01/04286) of the oligo-capping method (K. Maruyama and S. Sugano, Gene, 138: 171–174 (1994); Y. Suzuki et al., Gene, 200: 149–156 (1997)). Then, the nucleotide sequences of cDNA clones whose fullness ratio is high, obtained by this method, were determined mainly from their 5'-ends, and, if required, from 3'-ends.

Further, representative clones, which were estimated to be novel and full-length, among the clones obtained, were analyzed for their full-length nucleotide sequences. The determined full-length nucleotide sequences were analyzed by BLAST homology search of the databases shown below. Because the homology search of the present invention is carried out based on the information of full-length cDNAs including the entire coding regions, homology to every part of a polypeptide can be analyzed. Thus, in the present invention, the reliability of homology search has been greatly improved.

[1] SwissProt

[2] GenBank

[3] UniGene

[4] nr (a protein database, which has been constructed b combining data of coding sequences (CDS) in nucleotide sequences deposited in GenBank, and data of SwissProt, PDB, PIR, and PRF; overlapping sequences have been removed).

Further, the gene expression profiles of cDNA clones whose full-length nucleotide sequence had been determined were studied by analyzing the large-scale cDNA database constructed based on the 5'-end nucleotide sequences of cDNAs obtained. In addition to the analysis for the expression profile by computer, the profiles of gene expression in living cells were also determined by PCR. The present inventors revealed the usefulness of the genes of the present invention based on these analysis results.

In the present invention, gene functions were revealed by the analysis of expression profiles in silico based on the information of full-length nucleotide sequences. The expression profiles used in the expression frequency analysis were studied based on the database containing sufficient amount of fragment sequence data. The expression frequency analysis was carried out by referring, for these expression profiles, to the full-length nucleotide sequences of many cDNA clones obtained in the present invention. Thus, a highly reliable analysis can be achieved by referring to the full-length nucleotide sequences of a wide variety of genes for the sufficiently large population for analysis (expression profiles). Namely, the results of expression frequency analysis using the full-length sequences of the present invention more precisely reflect the gene expression frequency in tissues and cells from which a certain cDNA library was derived. In other words, the information of full-length cDNA nucleotide sequence of the present invention made it possible to achieve- the highly reliable expression frequency analysis.

The full-length cDNA clones of this invention were obtained by the method comprising the steps of [1] preparing libraries containing cDNAs with the high fullness ratio by oligo-capping, and [2] assembling 5'-end sequences and selecting one with the highest probability of completeness in length in the cluster formed (there are many clones longer in the 5'-end direction) However, the uses of -primers designed based on the 5'- and 3'-end sequences of polynucleotides provided by the present invention enable readily obtaining full-length cDNAs without such a special technique. The primer, which is designed to be used for obtaining cDNAs capable of being expressed, is not limited to the 5'- and 3'-end sequences of polynucleotide.

Specifically, the present invention relates to a polynucleotide selected from the group consisting of the following (a) to (g):

(a) a polynucleotide comprising a protein-coding region of the nucleotide sequence of any one of SEQ ID NOs shown in Table 1;

(b) a polynucleotide encoding a polypeptide comprising the amino acid sequence of any one of SEQ ID NOs shown in Table 1;

(c) a polynucleotide comprising a nucleotide sequence encoding a polypeptide comprising the amino acid sequence of any one of SEQ ID NOs shown in Table 1, wherein, in said amino acid sequence, one or more amino acids have been substituted, deleted, inserted, and/or added, and wherein said nucleotide sequence encodes a polypeptide functionally equivalent to a polypeptide comprising the selected amino acid sequence;

(d) a polynucleotide hybridizing under stringent conditions to a polynucleotide comprising the nucleotide sequence of any one of SEQ ID NOs shown in Table 1, wherein said nucleotide sequence encodes a polypeptide functionally equivalent to a polypeptide encoded by the selected nucleotide sequence;

(e) a polynucleotide comprising a nucleotide sequence encoding a partial amino acid sequence of a polypeptide encoded by the polynucleotide according to any one of (a) to (d);

(f) a polynucleotide comprising a nucleotide sequence having at least 70% identity to the nucleotide sequence of (a); and (g) a polynucleotide comprising a nucleotide sequence having at least 90% identity to the nucleotide sequence of (a).

The present invention also relates to a polypeptide encoded by the above-mentioned polynucleotide or a partial peptide thereof, an antibody binding to the polypeptide or the peptide, and a method for immunologically assaying the polypeptide or the peptide, which comprises the steps of contacting the polypeptide or the peptide with the antibody, and observing the binding between the two.

Furthermore, the present invention features a vector comprising the above-mentioned polynucleotide, a transformant carrying the polynucleotide or the vector, a transformant carrying the polynucleotide or the vector in an expressible manner, and a method for producing the polypeptide or the peptide, which comprises the steps of culturing the transformant and recovering an expression product.

Another feature of the present invention is an oligonucleotide comprising at least 15 nucleotides, said oligonucleotide comprising a nucleotide sequence complementary to the nucleotide sequence of any one of SEQ ID NOs: 1 to 2443 or to a complementary strand thereof. This oligonucleotide can be used as a primer for synthesizing the above-mentioned polynucleotide or used as a probe for detecting the polynucleotide. The present invention includes an antisense polynucleotide against the polynucleotide or a part thereof, and a method for detecting the polynucleotide, which comprises the following steps of:

a) incubating a target polynucleotide with the oligonucleotide under hybridizable conditions, and b) detecting hybridization of the target polynucleotide with the oligonucleotide.

Still another feature of the present invention is a database of polynucleotides and/or polypeptides, said database comprising information on at least one of the nucleotide sequences of SEQ ID NOs: 1 to 2443 and/or on at least one of the amino acid sequences of SEQ ID NOs: 2444 to 4886.

Herein, "polynucleotide" is defined as a molecule, such as DNA and RNA, in which multiple nucleotides are polymerized. There are no limitations on the number of the polymerized nucleotides. In case that the polymer contains relatively low number of nucleotides, it is also described as an "oligonucleotide", which is included in the "polynucleotide" of the present invention. The polynucleotide or the oligonucleotide of the present invention can be a natural or chemically synthesized product. Alternatively, it can be synthesized using a template polynucleotide by an enzymatic reaction such as PCR. Furthermore, the polynucleotide of the present invention may be modified chemically. Moreover, not only a single-strand polynucleotide but also a double-strand polynucleotide is included in the present invention. In this specification, especially in claims, when the polynucleotide is described merely as "polynucleotide", it means not only a single-strand polynucleotide but also a double-strand polynucleotide. When it means double-strand polynucleotide, the nucleotide sequence of only one chain is indicated. However, based on the nucleotide sequence of a sense chain, the nucleotide sequence of the complementary strand thereof is essentially determined.

As used herein, an "isolated polynucleotide" is a polynucleotide the structure of which is not identical to that of any naturally occurring polynucleotide or to that of any fragment of a naturally occurring genomic polynucleotide spanning more than three separate genes. The term therefore includes, for example, (a) a DNA which has the sequence of part of a naturally occurring genomic DNA molecule in the genome of the organism in which it naturally occurs; (b) a polynucleotide incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion polypeptide. Specifically excluded from this definition are polynucleotides of DNA molecules present in mixtures of different (i) DNA molecules, (ii) transfected cells, or (iii) cell clones; e.g., as these occur in a DNA library such as a cDNA or genomic DNA library.

The term "substantially pure" as used herein in reference to a given protein or polypeptide means that the protein or polypeptide is substantially free from other biological macromolecules. For example, the substantially pure protein or polypeptide is at least 75%, 80%, 85%, 95%, or 99% pure by dry weight. Purity can be measured by any appropriate standard method known in the art, for example, by column chromatography, polyacrylamide gel electrophoresis, or HPLC analysis.

All the cDNAs provided by the present invention are full-length cDNAs. The "full-length cDNA" herein means that the cDNA contains the ATG codon, which is the start point of translation therein. The untranslated regions upstream and downstream of the protein-coding region, both of which are naturally contained in natural mRNAs, are not indispensable. It is preferable that the full-length cDNAs of the present invention contain the stop codon.

DETAILED DESCRIPTION OF THE INVENTION

Figure 1:
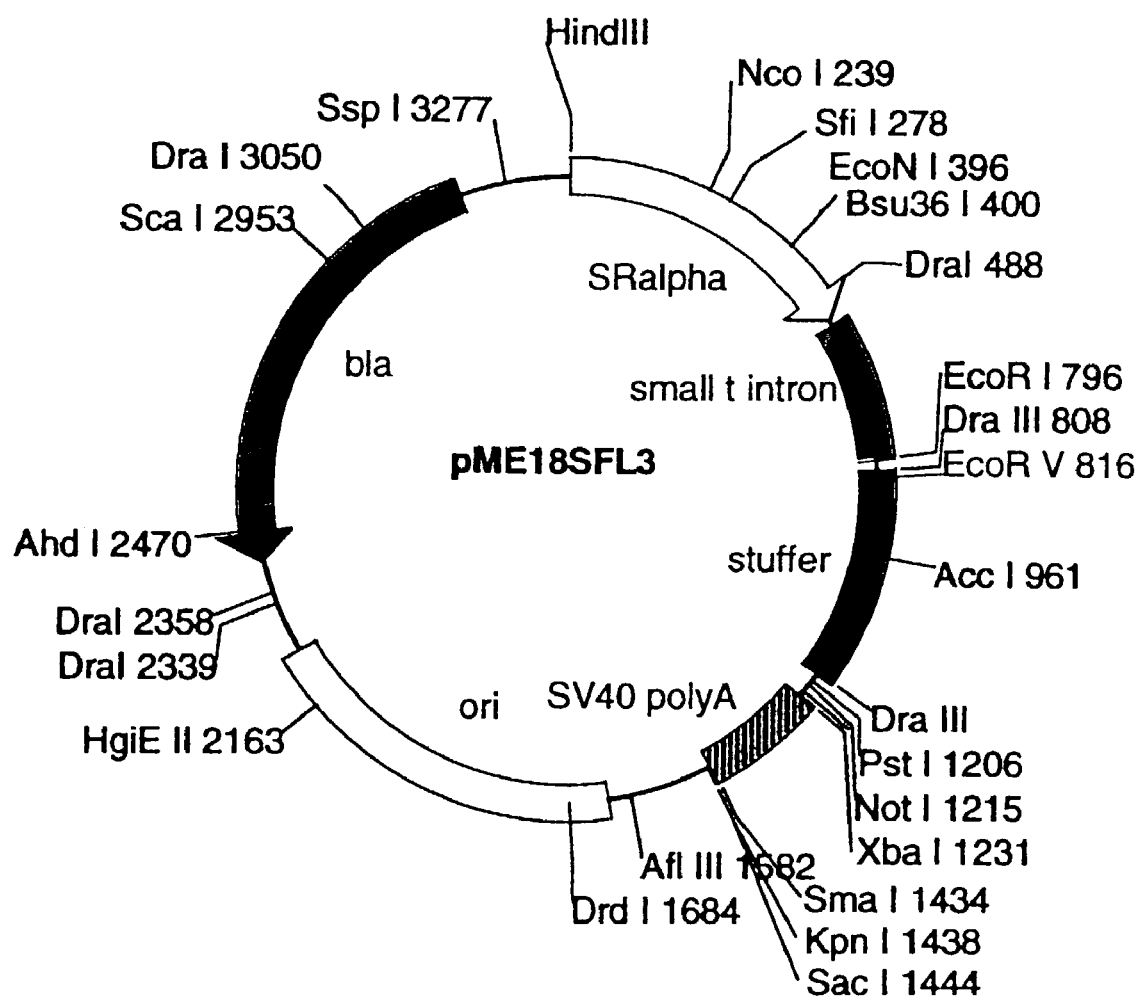
FIG. 1 shows the restriction map of the vector pME18SFL3.

All the clones (2443 clones) of the present invention are novel and encode the full-length polypeptides. Further, all the clones are cDNAs with the high fullness ratio, which were obtained by oligo-capping method, and also clones which are not identical to any of known human mRNAs (namely, novel clones) selected by searching, for the 5'-end sequences, mRNA sequences with the annotation of "complete cds" in the GenBank and UniGene databases by using the BLAST homology search [S. F. Altschul, W. Gish, W. Miller, E. W. Myers & D. J. Lipman, J. Mol. Biol., 215: 403–410 (1990); W. Gish & D. J. States, Nature Genet., 3: 266–272 (1993)]; they are also clones that were assumed to have higher fullness ratio among the members in the cluster formed by assembling. Most of the clones assessed to have high fullness ratio in the cluster had the nucleotide sequences longer in the 5'-end direction.

All the full-length cDNAs of the present invention can be synthesized by a method such as PCR (Current protocols in Molecular Biology edit. Ausubel et al. (1987) Publish. John Wiley & Sons Section 6.1–6.4) using primer sets designed based on the 5'-end and 3'-end sequences or using primer sets of primers designed based on the 5'-end sequences and a primer of oligo dT sequence corresponding to poly A sequence. Table 1 contains the clone names of full-length cDNA of 2443 clones of the present invention, SEQ ID NOs of the full-length nucleotide sequences, CDS portions deduced from the full-length nucleotide sequences, and SEQ ID NOs of the translated amino acids. The positions of CDS are shown according to the rule of "DDBJ/EMBL/GenBank Feature Table Definition". The start position number corresponds to the first letter of "ATG" that is the nucleotide triplet encoding methionine; the termination position number corresponds to the third letter of the stop codon. These are indicated being flanked with the mark "..". However, with respect to the clones having no stop codon, the termination position is indicated by the mark ">" according to the above rule.

TABLE 1

| Clone name | SEQ ID NO. of nucleotide sequence | Position of CDS | SEQ ID NO. of amino acid sequence |
| --- | --- | --- | --- |
| 3NB6910001910 | 1 | 30 ... 1661 | 2444 |
| 3NB6920014080 | 2 | 80 ... 922 | 2445 |
| 3NB6920014590 | 3 | 1 ... 693 | 2446 |
| ADIPS10000640 | 4 | 127 ... 1098 | 2447 |
| ADIPS20004250 | 5 | 170 ... 2212 | 2448 |
| ADRGL10001470 | 6 | 368 ... 829 | 2449 |
| ADRGL20000640 | 7 | 599 ... 1345 | 2450 |
| ADRGL20011190 | 8 | 61 ... >2254 | 2451 |
| ADRGL20012870 | 9 | 827 ... 1300 | 2452 |
| ADRGL20013010 | 10 | 1127 ... 1444 | 2453 |
| ADRGL20013520 | 11 | 226 ... 837 | 2454 |
| ADRGL20018300 | 12 | 320 ... 2233 | 2455 |
| ADRGL20018540 | 13 | 55 ... 363 | 2456 |
| ADRGL20028570 | 14 | 218 ... 976 | 2457 |
| ADRGL20035850 | 15 | 55 ... 522 | 2458 |
| ADRGL20044590 | 16 | 692 ... 1042 | 2459 |
| ADRGL20048330 | 17 | 189 ... 2204 | 2460 |
| ADRGL20061930 | 18 | 293 ... >1899 | 2461 |
| ADRGL20067670 | 19 | 108 ... 512 | 2462 |
| ADRGL20068170 | 20 | 217 ... 615 | 2463 |
| ADRGL20068460 | 21 | 576 ... 1280 | 2464 |
| ADRGL20073570 | 22 | 556 ... 891 | 2465 |
| ADRGL20076360 | 23 | 159 ... 515 | 2466 |
| ADRGL20078100 | 24 | 418 ... 1563 | 2467 |
| ADRGL20083310 | 25 | 871 ... 1368 | 2468 |
| ASTRO10001650 | 26 | 369 ... 2168 | 2469 |
| ASTRO20001410 | 27 | 319 ... 744 | 2470 |
| ASTRO20005330 | 28 | 196 ... 642 | 2471 |
| ASTRO20008010 | 29 | 735 ... 1169 | 2472 |
| ASTRO20012490 | 30 | 286 ... 783 | 2473 |
| ASTRO20027430 | 31 | 129 ... 848 | 2474 |
| ASTRO20032120 | 32 | 860 ... 1189 | 2475 |

TABLE 1-continued

| Clone name | SEQ ID NO. of nucleotide sequence | Position of CDS | SEQ ID NO. of amino acid sequence |
|---|---|---|---|
| ASTRO20033160 | 33 | 139 ... 1014 | 2476 |
| ASTRO20055750 | 34 | 16 ... 2007 | 2477 |
| ASTRO20058630 | 35 | 28 ... 957 | 2478 |
| ASTRO20064750 | 36 | 1381 ... >2654 | 2479 |
| ASTRO20072210 | 37 | 274 ... >1868 | 2480 |
| ASTRO20084250 | 38 | 35 ... 1381 | 2481 |
| ASTRO20100720 | 39 | 394 ... 714 | 2482 |
| ASTRO20105820 | 40 | 205 ... 1368 | 2483 |
| ASTRO20106150 | 41 | 138 ... 1811 | 2484 |
| ASTRO20108190 | 42 | 791 ... 2539 | 2485 |
| ASTRO20111490 | 43 | 517 ... 921 | 2486 |
| ASTRO20114370 | 44 | 145 ... 1782 | 2487 |
| ASTRO20114610 | 45 | 53 ... 433 | 2488 |
| ASTRO20125520 | 46 | 1674 ... 2456 | 2489 |
| ASTRO20130500 | 47 | 15 ... 2417 | 2490 |
| ASTRO20136710 | 48 | 319 ... 657 | 2491 |
| ASTRO20138020 | 49 | 285 ... 995 | 2492 |
| ASTRO20141350 | 50 | 394 ... 1767 | 2493 |
| ASTRO20143630 | 51 | 103 ... 1305 | 2494 |
| ASTRO20145760 | 52 | 347 ... 2008 | 2495 |
| ASTRO20152140 | 53 | 760 ... 1233 | 2496 |
| ASTRO20155290 | 54 | 208 ... 2298 | 2497 |
| ASTRO20166810 | 55 | 7 ... 381 | 2498 |
| ASTRO20168470 | 56 | 334 ... 1329 | 2499 |
| ASTRO20173480 | 57 | 119 ... 724 | 2500 |
| ASTRO20181690 | 58 | 84 ... 1967 | 2501 |
| ASTRO20190390 | 59 | 2282 ... 2662 | 2502 |
| BEAST20004540 | 60 | 1022 ... 1513 | 2503 |
| BGGI110000240 | 61 | 123 ... 1649 | 2504 |
| BGGI110001930 | 62 | 81 ... 1307 | 2505 |
| BGGI120006160 | 63 | 6 ... 680 | 2506 |
| BLADE20003400 | 64 | 71 ... 1876 | 2507 |
| BLADE20003890 | 65 | 555 ... 2405 | 2508 |
| BLADE20004630 | 66 | 58 ... 405 | 2509 |
| BNGH420088500 | 67 | 2 ... 1270 | 2510 |
| BRACE20003070 | 68 | 310 ... 1563 | 2511 |
| BRACE20006400 | 69 | 32 ... 364 | 2512 |
| BRACE20011070 | 70 | 21 ... 1553 | 2513 |
| BRACE20019540 | 71 | 538 ... 993 | 2514 |
| BRACE20027620 | 72 | 24 ... 1289 | 2515 |
| BRACE20037660 | 73 | 143 ... 469 | 2516 |
| BRACE20038000 | 74 | 646 ... 2187 | 2517 |
| BRACE20038470 | 75 | 963 ... 1307 | 2518 |
| BRACE20038480 | 76 | 1838 ... 2626 | 2519 |
| BRACE20038850 | 77 | 1099 ... 1413 | 2520 |
| BRACE20039040 | 78 | 1273 ... 1671 | 2521 |
| BRACE20039440 | 79 | 216 ... 797 | 2522 |
| BRACE20039540 | 80 | 1153 ... 1905 | 2523 |
| BRACE20050900 | 81 | 115 ... 1788 | 2524 |
| BRACE20051380 | 82 | 1433 ... 1783 | 2525 |
| BRACE20051690 | 83 | 380 ... 742 | 2526 |
| BRACE20052160 | 84 | 20 ... 1024 | 2527 |
| BRACE20053280 | 85 | 736 ... 1524 | 2528 |
| BRACE20053480 | 86 | 24 ... 875 | 2529 |
| BRACE20053630 | 87 | 81 ... 950 | 2530 |
| BRACE20054500 | 88 | 364 ... 669 | 2531 |
| BRACE20055180 | 89 | 156 ... 656 | 2532 |
| BRACE20056810 | 90 | 338 ... 940 | 2533 |
| BRACE20057190 | 91 | 1016 ... 1660 | 2534 |
| BRACE20057420 | 92 | 539 ... 856 | 2535 |
| BRACE20057620 | 93 | 1226 ... 1588 | 2536 |
| BRACE20057730 | 94 | 819 ... 1592 | 2537 |
| BRACE20058580 | 95 | 146 ... 1330 | 2538 |
| BRACE20058810 | 96 | 40 ... 345 | 2539 |
| BRACE20059370 | 97 | 192 ... 1574 | 2540 |
| BRACE20060550 | 98 | 197 ... 1687 | 2541 |
| BRACE20060720 | 99 | 220 ... 618 | 2542 |
| BRACE20060840 | 100 | 37 ... 927 | 2543 |
| BRACE20060890 | 101 | 170 ... 964 | 2544 |
| BRACE20061050 | 102 | 1130 ... 1573 | 2545 |
| BRACE20061740 | 103 | 434 ... 865 | 2546 |
| BRACE20062400 | 104 | 1310 ... 1732 | 2547 |
| BRACE20062640 | 105 | 278 ... 2089 | 2548 |
| BRACE20062740 | 106 | 753 ... 1151 | 2549 |
| BRACE20063630 | 107 | 414 ... 800 | 2550 |
| BRACE20063780 | 108 | 11 ... 892 | 2551 |
| BRACE20063800 | 109 | 70 ... 435 | 2552 |
| BRACE20063930 | 110 | 1795 ... 2433 | 2553 |
| BRACE20064880 | 111 | 365 ... 1420 | 2554 |
| BRACE20067430 | 112 | 875 ... 1189 | 2555 |
| BRACE20068590 | 113 | 260 ... 1759 | 2556 |
| BRACE20069090 | 114 | 1484 ... 1960 | 2557 |
| BRACE20081720 | 115 | 1182 ... 1565 | 2558 |
| BRACE20082950 | 116 | 1713 ... 2018 | 2559 |
| BRACE20090440 | 117 | 58 ... 444 | 2560 |
| BRACE20096200 | 118 | 168 ... 1130 | 2561 |
| BRACE20096540 | 119 | 43 ... 729 | 2562 |
| BRACE20097320 | 120 | 51 ... 509 | 2563 |
| BRACE20099570 | 121 | 3 ... 425 | 2564 |
| BRACE20101700 | 122 | 579 ... 968 | 2565 |
| BRACE20101710 | 123 | 187 ... 681 | 2566 |
| BRACE20106690 | 124 | 335 ... 691 | 2567 |
| BRACE20106840 | 125 | 19 ... 402 | 2568 |
| BRACE20107530 | 126 | 437 ... 1063 | 2569 |
| BRACE20108130 | 127 | 927 ... 1229 | 2570 |
| BRACE20108880 | 128 | 417 ... 782 | 2571 |
| BRACE20109370 | 129 | 1197 ... 1778 | 2572 |
| BRACE20109830 | 130 | 747 ... 1382 | 2573 |
| BRACE20111830 | 131 | 366 ... 737 | 2574 |
| BRACE20114780 | 132 | 515 ... 886 | 2575 |
| BRACE20115450 | 133 | 399 ... 764 | 2576 |
| BRACE20115920 | 134 | 41 ... 937 | 2577 |
| BRACE20116110 | 135 | 830 ... 1150 | 2578 |
| BRACE20116460 | 136 | 84 ... 509 | 2579 |
| BRACE20118380 | 137 | 657 ... 1421 | 2580 |
| BRACE20121850 | 138 | 474 ... 857 | 2581 |
| BRACE20136240 | 139 | 111 ... 518 | 2582 |
| BRACE20141080 | 140 | 148 ... 534 | 2583 |
| BRACE20142320 | 141 | 164 ... 499 | 2584 |
| BRACE20142570 | 142 | 591 ... 926 | 2585 |
| BRACE20147800 | 143 | 133 ... 513 | 2586 |
| BRACE20148210 | 144 | 1101 ... 1541 | 2587 |
| BRACE20148240 | 145 | 713 ... 2128 | 2588 |
| BRACE20150310 | 146 | 94 ... 408 | 2589 |
| BRACE20151320 | 147 | 137 ... 1189 | 2590 |
| BRACE20152870 | 148 | 207 ... 653 | 2591 |
| BRACE20153680 | 149 | 87 ... 956 | 2592 |
| BRACE20154120 | 150 | 351 ... 989 | 2593 |
| BRACE20163150 | 151 | 699 ... 1085 | 2594 |
| BRACE20163350 | 152 | 443 ... 1597 | 2595 |
| BRACE20165830 | 153 | 401 ... 709 | 2596 |
| BRACE20171240 | 154 | 62 ... 439 | 2597 |
| BRACE20172980 | 155 | 20 ... 445 | 2598 |
| BRACE20175870 | 156 | 67 ... 396 | 2599 |
| BRACE20177200 | 157 | 1178 ... 1675 | 2600 |
| BRACE20179340 | 158 | 47 ... 1171 | 2601 |
| BRACE20185680 | 159 | 880 ... 1341 | 2602 |
| BRACE20188470 | 160 | 1247 ... 2926 | 2603 |
| BRACE20190040 | 161 | 6 ... 464 | 2604 |
| BRACE20190440 | 162 | 382 ... 1287 | 2605 |
| BRACE20192440 | 163 | 1199 ... 2062 | 2606 |
| BRACE20195100 | 164 | 251 ... 736 | 2607 |
| BRACE20201570 | 165 | 661 ... 1056 | 2608 |
| BRACE20210140 | 166 | 248 ... 550 | 2609 |
| BRACE20220300 | 167 | 1057 ... 1392 | 2610 |
| BRACE20223280 | 168 | 6 ... 1976 | 2611 |
| BRACE20223330 | 169 | 97 ... 2373 | 2612 |
| BRACE20224480 | 170 | 1568 ... 1924 | 2613 |
| BRACE20224500 | 171 | 1674 ... 2081 | 2614 |
| BRACE20228480 | 172 | 1268 ... 2176 | 2615 |
| BRACE20229280 | 173 | 239 ... 700 | 2616 |
| BRACE20230700 | 174 | 354 ... 752 | 2617 |
| BRACE20232840 | 175 | 79 ... 2019 | 2618 |
| BRACE20235400 | 176 | 213 ... 593 | 2619 |
| BRACE20237270 | 177 | 3 ... 494 | 2620 |
| BRACE20238000 | 178 | 135 ... 437 | 2621 |
| BRACE20240740 | 179 | 83 ... 1546 | 2622 |
| BRACE20248260 | 180 | 682 ... 1533 | 2623 |
| BRACE20253160 | 181 | 26 ... 559 | 2624 |
| BRACE20253330 | 182 | 220 ... 1041 | 2625 |

TABLE 1-continued

| Clone name | SEQ ID NO. of nucleotide sequence | Position of CDS | SEQ ID NO. of amino acid sequence |
|---|---|---|---|
| BRACE20257100 | 183 | 1638 ... 2021 | 2626 |
| BRACE20262930 | 184 | 256 ... 681 | 2627 |
| BRACE20262940 | 185 | 259 ... 591 | 2628 |
| BRACE20266750 | 186 | 58 ... 1143 | 2629 |
| BRACE20267250 | 187 | 139 ... 612 | 2630 |
| BRACE20269200 | 188 | 4 ... 408 | 2631 |
| BRACE20269710 | 189 | 338 ... 1063 | 2632 |
| BRACE20273890 | 190 | 1365 ... 1766 | 2633 |
| BRACE20274080 | 191 | 350 ... 655 | 2634 |
| BRACE20276430 | 192 | 232 ... >2028 | 2635 |
| BRACE20283920 | 193 | 717 ... 1025 | 2636 |
| BRACE20284100 | 194 | 1026 ... 1865 | 2637 |
| BRACE20286360 | 195 | 170 ... 727 | 2638 |
| BRACE20287410 | 196 | 603 ... 956 | 2639 |
| BRALZ20013500 | 197 | 215 ... 640 | 2640 |
| BRALZ20014450 | 198 | 6 ... 374 | 2641 |
| BRALZ20017430 | 199 | 232 ... 747 | 2642 |
| BRALZ20018340 | 200 | 879 ... 1481 | 2643 |
| BRALZ20019660 | 201 | 180 ... 773 | 2644 |
| BRALZ20054710 | 202 | 135 ... 1223 | 2645 |
| BRALZ20058880 | 203 | 102 ... 1607 | 2646 |
| BRALZ20059500 | 204 | 722 ... 1081 | 2647 |
| BRALZ20064740 | 205 | 24 ... 350 | 2648 |
| BRALZ20065600 | 206 | 25 ... 624 | 2649 |
| BRALZ20069760 | 207 | 14 ... 319 | 2650 |
| BRALZ20073760 | 208 | 576 ... 1124 | 2651 |
| BRALZ20075450 | 209 | 775 ... 1200 | 2652 |
| BRALZ20075760 | 210 | 148 ... 726 | 2653 |
| BRALZ20077900 | 211 | 1900 ... 2529 | 2654 |
| BRALZ20077930 | 212 | 50 ... 2077 | 2655 |
| BRALZ20080310 | 213 | 1304 ... 2005 | 2656 |
| BRALZ20088690 | 214 | 104 ... 661 | 2657 |
| BRAMY10001300 | 215 | 2352 ... 2795 | 2658 |
| BRAMY10001570 | 216 | 696 ... 1604 | 2659 |
| BRAMY20000520 | 217 | 329 ... 1204 | 2660 |
| BRAMY20000860 | 218 | 246 ... 548 | 2661 |
| BRAMY20002770 | 219 | 76 ... 447 | 2662 |
| BRAMY20004110 | 220 | 145 ... 540 | 2663 |
| BRAMY20011140 | 221 | 2661 ... 3011 | 2664 |
| BRAMY20025840 | 222 | 1058 ... 2002 | 2665 |
| BRAMY20039260 | 223 | 101 ... 424 | 2666 |
| BRAMY20045240 | 224 | 662 ... 1792 | 2667 |
| BRAMY20054880 | 225 | 508 ... 981 | 2668 |
| BRAMY20060920 | 226 | 110 ... 439 | 2669 |
| BRAMY20063970 | 227 | 246 ... 551 | 2670 |
| BRAMY20071850 | 228 | 178 ... 705 | 2671 |
| BRAMY20102080 | 229 | 513 ... 1136 | 2672 |
| BRAMY20103570 | 230 | 114 ... 1001 | 2673 |
| BRAMY20104640 | 231 | 334 ... 1410 | 2674 |
| BRAMY20110640 | 232 | 1400 ... 1735 | 2675 |
| BRAMY20111960 | 233 | 534 ... 854 | 2676 |
| BRAMY20112800 | 234 | 31 ... 606 | 2677 |
| BRAMY20116790 | 235 | 2348 ... 2794 | 2678 |
| BRAMY20120910 | 236 | 182 ... 976 | 2679 |
| BRAMY20121190 | 237 | 81 ... 398 | 2680 |
| BRAMY20121620 | 238 | 51 ... 1688 | 2681 |
| BRAMY20124260 | 239 | 95 ... 1759 | 2682 |
| BRAMY20134140 | 240 | 1 ... 510 | 2683 |
| BRAMY20135900 | 241 | 4 ... 1053 | 2684 |
| BRAMY20136210 | 242 | 1810 ... 2145 | 2685 |
| BRAMY20137560 | 243 | 2220 ... 2795 | 2686 |
| BRAMY20144620 | 244 | 892 ... 1326 | 2687 |
| BRAMY20147540 | 245 | 147 ... 611 | 2688 |
| BRAMY20148130 | 246 | 204 ... 2138 | 2689 |
| BRAMY20152110 | 247 | 1257 ... 1580 | 2690 |
| BRAMY20153110 | 248 | 11 ... 763 | 2691 |
| BRAMY20157820 | 249 | 94 ... 1740 | 2692 |
| BRAMY20160700 | 250 | 1686 ... 2015 | 2693 |
| BRAMY20162510 | 251 | 186 ... 1757 | 2694 |
| BRAMY20163250 | 252 | 96 ... 719 | 2695 |
| BRAMY20163270 | 253 | 531 ... 1010 | 2696 |
| BRAMY20167060 | 254 | 347 ... 865 | 2697 |
| BRAMY20167710 | 255 | 900 ... 1532 | 2698 |
| BRAMY20168920 | 256 | 91 ... 1275 | 2699 |
| BRAMY20170140 | 257 | 115 ... 681 | 2700 |
| BRAMY20174550 | 258 | 74 ... 2179 | 2701 |
| BRAMY20178640 | 259 | 226 ... 2025 | 2702 |
| BRAMY20181220 | 260 | 678 ... 980 | 2703 |
| BRAMY20182730 | 261 | 208 ... 738 | 2704 |
| BRAMY20183080 | 262 | 213 ... 653 | 2705 |
| BRAMY20184670 | 263 | 871 ... 1548 | 2706 |
| BRAMY20195090 | 264 | 2087 ... 2476 | 2707 |
| BRAMY20196000 | 265 | 50 ... 439 | 2708 |
| BRAMY20204450 | 266 | 34 ... 462 | 2709 |
| BRAMY20205740 | 267 | 177 ... 554 | 2710 |
| BRAMY20210400 | 268 | 131 ... 703 | 2711 |
| BRAMY20211390 | 269 | 1407 ... 2303 | 2712 |
| BRAMY20211420 | 270 | 131 ... 2407 | 2713 |
| BRAMY20213100 | 271 | 245 ... 2026 | 2714 |
| BRAMY20215230 | 272 | 207 ... 515 | 2715 |
| BRAMY20217460 | 273 | 612 ... 1217 | 2716 |
| BRAMY20218250 | 274 | 161 ... 2167 | 2717 |
| BRAMY20218670 | 275 | 338 ... 652 | 2718 |
| BRAMY20229800 | 276 | 1270 ... 1662 | 2719 |
| BRAMY20229840 | 277 | 1022 ... 1678 | 2720 |
| BRAMY20230600 | 278 | 614 ... 1840 | 2721 |
| BRAMY20231720 | 279 | 429 ... 773 | 2722 |
| BRAMY20240040 | 280 | 693 ... 2660 | 2723 |
| BRAMY20242470 | 281 | 1527 ... 2243 | 2724 |
| BRAMY20245300 | 282 | 59 ... 2482 | 2725 |
| BRAMY20247110 | 283 | 321 ... 1382 | 2726 |
| BRAMY20247280 | 284 | 611 ... 925 | 2727 |
| BRAMY20248490 | 285 | 1723 ... 2079 | 2728 |
| BRAMY20250240 | 286 | 1179 ... 1619 | 2729 |
| BRAMY20250320 | 287 | 18 ... 323 | 2730 |
| BRAMY20252180 | 288 | 1150 ... 1506 | 2731 |
| BRAMY20252720 | 289 | 595 ... 1113 | 2732 |
| BRAMY20260910 | 290 | 67 ... 2646 | 2733 |
| BRAMY20261680 | 291 | 298 ... 1041 | 2734 |
| BRAMY20266850 | 292 | 26 ... 685 | 2735 |
| BRAMY20267130 | 293 | 235 ... 708 | 2736 |
| BRAMY20268990 | 294 | 137 ... 460 | 2737 |
| BRAMY20270730 | 295 | 124 ... 2118 | 2738 |
| BRAMY20271400 | 296 | 177 ... >3011 | 2739 |
| BRAMY20273960 | 297 | 48 ... 1826 | 2740 |
| BRAMY20277140 | 298 | 1135 ... 1485 | 2741 |
| BRAMY20277170 | 299 | 545 ... 2221 | 2742 |
| BRAMY20280720 | 300 | 103 ... 489 | 2743 |
| BRAMY20284910 | 301 | 1059 ... 1415 | 2744 |
| BRAMY20285160 | 302 | 1483 ... 1977 | 2745 |
| BRAMY20285930 | 303 | 811 ... 1143 | 2746 |
| BRAMY20286820 | 304 | 1463 ... 1777 | 2747 |
| BRAWH10000930 | 305 | 843 ... 1454 | 2748 |
| BRAWH20002320 | 306 | 162 ... 716 | 2749 |
| BRAWH20004600 | 307 | 66 ... 1361 | 2750 |
| BRAWH20011710 | 308 | 229 ... 1872 | 2751 |
| BRAWH20012390 | 309 | 71 ... 562 | 2752 |
| BRAWH20012410 | 310 | 291 ... 593 | 2753 |
| BRAWH20014920 | 311 | 353 ... 1378 | 2754 |
| BRAWH20015350 | 312 | 1285 ... 1641 | 2755 |
| BRAWH20015890 | 313 | 806 ... 1837 | 2756 |
| BRAWH20016620 | 314 | 1721 ... 2254 | 2757 |
| BRAWH20016660 | 315 | 51 ... 1205 | 2758 |
| BRAWH20016860 | 316 | 548 ... 877 | 2759 |
| BRAWH20017010 | 317 | 155 ... 628 | 2760 |
| BRAWH20018730 | 318 | 56 ... 1570 | 2761 |
| BRAWH20028110 | 319 | 123 ... 1718 | 2762 |
| BRAWH20029630 | 320 | 929 ... 1276 | 2763 |
| BRAWH20030250 | 321 | 264 ... 1421 | 2764 |
| BRAWH20064050 | 322 | 272 ... 1591 | 2765 |
| BRAWH20075700 | 323 | 349 ... 1407 | 2766 |
| BRAWH20096780 | 324 | 272 ... 1840 | 2767 |
| BRAWH20100690 | 325 | 1430 ... 1849 | 2768 |
| BRAWH20101360 | 326 | 163 ... 852 | 2769 |
| BRAWH20103180 | 327 | 1081 ... 1659 | 2770 |
| BRAWH20103290 | 328 | 71 ... 2626 | 2771 |
| BRAWH20105840 | 329 | 139 ... 1083 | 2772 |
| BRAWH20106180 | 330 | 628 ... 933 | 2773 |
| BRAWH20107540 | 331 | 1 ... 540 | 2774 |
| BRAWH20110660 | 332 | 156 ... 578 | 2775 |

TABLE 1-continued

| Clone name | SEQ ID NO. of nucleotide sequence | Position of CDS | SEQ ID NO. of amino acid sequence |
|---|---|---|---|
| BRAWH20110790 | 333 | 1994 ... 2338 | 2776 |
| BRAWH20110960 | 334 | 74 ... 1210 | 2777 |
| BRAWH20111550 | 335 | 569 ... 949 | 2778 |
| BRAWH20112940 | 336 | 850 ... 1968 | 2779 |
| BRAWH20113430 | 337 | 135 ... 869 | 2780 |
| BRAWH20114000 | 338 | 72 ... 1619 | 2781 |
| BRAWH20117950 | 339 | 465 ... 1568 | 2782 |
| BRAWH20118230 | 340 | 146 ... 565 | 2783 |
| BRAWH20121640 | 341 | 98 ... 1516 | 2784 |
| BRAWH20122580 | 342 | 104 ... 721 | 2785 |
| BRAWH20122770 | 343 | 1283 ... 1612 | 2786 |
| BRAWH20125380 | 344 | 382 ... 918 | 2787 |
| BRAWH20126190 | 345 | 154 ... 459 | 2788 |
| BRAWH20126980 | 346 | 222 ... 686 | 2789 |
| BRAWH20128270 | 347 | 295 ... 1020 | 2790 |
| BRAWH20132190 | 348 | 157 ... 561 | 2791 |
| BRAWH20137480 | 349 | 273 ... 1313 | 2792 |
| BRAWH20138660 | 350 | 261 ... 1376 | 2793 |
| BRAWH20139410 | 351 | 13 ... 354 | 2794 |
| BRAWH20142340 | 352 | 99 ... 413 | 2795 |
| BRAWH20147290 | 353 | 460 ... 810 | 2796 |
| BRAWH20149340 | 354 | 442 ... 1620 | 2797 |
| BRAWH20155950 | 355 | 8 ... 2074 | 2798 |
| BRAWH20158530 | 356 | 138 ... 1136 | 2799 |
| BRAWH20160280 | 357 | 2093 ... 2587 | 2800 |
| BRAWH20162690 | 358 | 33 ... 1085 | 2801 |
| BRAWH20164460 | 359 | 345 ... >2067 | 2802 |
| BRAWH20166790 | 360 | 224 ... 571 | 2803 |
| BRAWH20171030 | 361 | 152 ... 1996 | 2804 |
| BRAWH20173050 | 362 | 1272 ... 1604 | 2805 |
| BRAWH20182060 | 363 | 118 ... 1740 | 2806 |
| BRAWH20185060 | 364 | 248 ... 607 | 2807 |
| BRCAN10001490 | 365 | 60 ... 452 | 2808 |
| BRCAN20003460 | 366 | 239 ... 1030 | 2809 |
| BRCAN20006200 | 367 | 908 ... 1234 | 2810 |
| BRCAN20006390 | 368 | 252 ... 743 | 2811 |
| BRCAN20054490 | 369 | 345 ... 1067 | 2812 |
| BRCAN20060190 | 370 | 206 ... 595 | 2813 |
| BRCAN20064010 | 371 | 134 ... 685 | 2814 |
| BRCAN20071190 | 372 | 192 ... 1586 | 2815 |
| BRCAN20091560 | 373 | 190 ... 2004 | 2816 |
| BRCAN20103740 | 374 | 207 ... 530 | 2817 |
| BRCAN20124080 | 375 | 187 ... 2079 | 2818 |
| BRCAN20126130 | 376 | 580 ... 897 | 2819 |
| BRCAN20143700 | 377 | 14 ... 817 | 2820 |
| BRCAN20147880 | 378 | 121 ... 519 | 2821 |
| BRCAN20216690 | 379 | 66 ... 383 | 2822 |
| BRCAN20224720 | 380 | 549 ... 1544 | 2823 |
| BRCAN20237240 | 381 | 23 ... 796 | 2824 |
| BRCAN20263400 | 382 | 316 ... 729 | 2825 |
| BRCAN20273100 | 383 | 76 ... 468 | 2826 |
| BRCAN20273340 | 384 | 50 ... 352 | 2827 |
| BRCAN20273550 | 385 | 652 ... 1848 | 2828 |
| BRCAN20273640 | 386 | 131 ... 1201 | 2829 |
| BRCAN20275130 | 387 | 374 ... 847 | 2830 |
| BRCAN20279700 | 388 | 2372 ... 2839 | 2831 |
| BRCAN20280210 | 389 | 644 ... 1393 | 2832 |
| BRCAN20280360 | 390 | 265 ... 1548 | 2833 |
| BRCAN20280400 | 391 | 1280 ... 1618 | 2834 |
| BRCAN20283190 | 392 | 416 ... 1321 | 2835 |
| BRCAN20283380 | 393 | 93 ... 533 | 2836 |
| BRCAN20284600 | 394 | 97 ... 549 | 2837 |
| BRCAN20285450 | 395 | 118 ... 567 | 2838 |
| BRCOC10000870 | 396 | 186 ... 602 | 2839 |
| BRCOC20001860 | 397 | 1061 ... 2179 | 2840 |
| BRCOC20004040 | 398 | 383 ... 1171 | 2841 |
| BRCOC20004870 | 399 | 199 ... 765 | 2842 |
| BRCOC20006370 | 400 | 21 ... 455 | 2843 |
| BRCOC20008160 | 401 | 166 ... >2490 | 2844 |
| BRCOC20008500 | 402 | 151 ... >2854 | 2845 |
| BRCOC20020850 | 403 | 1371 ... 1820 | 2846 |
| BRCOC20021550 | 404 | 1121 ... 2110 | 2847 |
| BRCOC20023230 | 405 | 682 ... 1500 | 2848 |
| BRCOC20026640 | 406 | 148 ... 516 | 2849 |
| BRCOC20027510 | 407 | 369 ... 1088 | 2850 |
| BRCOC20031000 | 408 | 207 ... 581 | 2851 |
| BRCOC20031250 | 409 | 799 ... 1122 | 2852 |
| BRCOC20031870 | 410 | 375 ... 1031 | 2853 |
| BRCOC20035130 | 411 | 171 ... 527 | 2854 |
| BRCOC20037320 | 412 | 547 ... 3384 | 2855 |
| BRCOC20037400 | 413 | 152 ... 493 | 2856 |
| BRCOC20041750 | 414 | 230 ... 535 | 2857 |
| BRCOC20055420 | 415 | 99 ... 1556 | 2858 |
| BRCOC20059510 | 416 | 199 ... 582 | 2859 |
| BRCOC20074760 | 417 | 10 ... >1918 | 2860 |
| BRCOC20077690 | 418 | 867 ... 1202 | 2861 |
| BRCOC20078640 | 419 | 849 ... 1208 | 2862 |
| BRCOC20090520 | 420 | 1157 ... 1663 | 2863 |
| BRCOC20091960 | 421 | 1371 ... 1895 | 2864 |
| BRCOC20093800 | 422 | 204 ... 590 | 2865 |
| BRCOC20099370 | 423 | 1 ... 1890 | 2866 |
| BRCOC20101230 | 424 | 94 ... 810 | 2867 |
| BRCOC20105100 | 425 | 2393 ... 2716 | 2868 |
| BRCOC20107300 | 426 | 709 ... 1086 | 2869 |
| BRCOC20110100 | 427 | 369 ... 713 | 2870 |
| BRCOC20114180 | 428 | 167 ... 487 | 2871 |
| BRCOC20117690 | 429 | 152 ... 781 | 2872 |
| BRCOC20119960 | 430 | 147 ... 500 | 2873 |
| BRCOC20121720 | 431 | 26 ... 2983 | 2874 |
| BRCOC20122290 | 432 | 92 ... 448 | 2875 |
| BRCOC20128130 | 433 | 150 ... 1364 | 2876 |
| BRCOC20134480 | 434 | 587 ... 1060 | 2877 |
| BRCOC20135730 | 435 | 1603 ... 2064 | 2878 |
| BRCOC20136750 | 436 | 2876 ... 3229 | 2879 |
| BRCOC20144000 | 437 | 64 ... 459 | 2880 |
| BRCOC20147480 | 438 | 228 ... 578 | 2881 |
| BRCOC20148330 | 439 | 169 ... 1290 | 2882 |
| BRCOC20155970 | 440 | 111 ... 632 | 2883 |
| BRCOC20158240 | 441 | 1357 ... 2178 | 2884 |
| BRCOC20176520 | 442 | 185 ... 1153 | 2885 |
| BRCOC20178270 | 443 | 244 ... 1257 | 2886 |
| BRCOC20178560 | 444 | 65 ... 1000 | 2887 |
| BRHIP10001290 | 445 | 838 ... 1731 | 2888 |
| BRHIP10001740 | 446 | 148 ... 594 | 2889 |
| BRHIP20000870 | 447 | 1235 ... 1540 | 2890 |
| BRHIP20001630 | 448 | 287 ... 1486 | 2891 |
| BRHIP20003120 | 449 | 170 ... 1951 | 2892 |
| BRHIP20005340 | 450 | 597 ... 1853 | 2893 |
| BRHIP20005530 | 451 | 30 ... 1052 | 2894 |
| BRHIP20096170 | 452 | 119 ... 817 | 2895 |
| BRHIP20096850 | 453 | 311 ... 1582 | 2896 |
| BRHIP20103090 | 454 | 1345 ... 1737 | 2897 |
| BRHIP20104440 | 455 | 166 ... 576 | 2898 |
| BRHIP20105710 | 456 | 1056 ... 1466 | 2899 |
| BRHIP20106100 | 457 | 314 ... 1060 | 2900 |
| BRHIP20107440 | 458 | 827 ... 1528 | 2901 |
| BRHIP20110800 | 459 | 577 ... 1083 | 2902 |
| BRHIP20111200 | 460 | 261 ... 578 | 2903 |
| BRHIP20115080 | 461 | 762 ... 1751 | 2904 |
| BRHIP20115760 | 462 | 877 ... 1182 | 2905 |
| BRHIP20118380 | 463 | 2 ... 316 | 2906 |
| BRHIP20118910 | 464 | 82 ... 426 | 2907 |
| BRHIP20119330 | 465 | 420 ... 2564 | 2908 |
| BRHIP20121410 | 466 | 68 ... 505 | 2909 |
| BRHIP20123140 | 467 | 73 ... 432 | 2910 |
| BRHIP20129720 | 468 | 934 ... 1809 | 2911 |
| BRHIP20132860 | 469 | 1 ... 897 | 2912 |
| BRHIP20135100 | 470 | 423 ... 743 | 2913 |
| BRHIP20137230 | 471 | 71 ... 1180 | 2914 |
| BRHIP20139720 | 472 | 33 ... 3254 | 2915 |
| BRHIP20140630 | 473 | 3521 ... 3922 | 2916 |
| BRHIP20142850 | 474 | 259 ... 612 | 2917 |
| BRHIP20143730 | 475 | 229 ... 1638 | 2918 |
| BRHIP20143860 | 476 | 1159 ... 1638 | 2919 |
| BRHIP20149540 | 477 | 155 ... 544 | 2920 |
| BRHIP20153560 | 478 | 1134 ... 1445 | 2921 |
| BRHIP20153600 | 479 | 40 ... 675 | 2922 |
| BRHIP20167880 | 480 | 183 ... 656 | 2923 |
| BRHIP20169680 | 481 | 27 ... 347 | 2924 |
| BRHIP20169900 | 482 | 68 ... 502 | 2925 |

TABLE 1-continued

| Clone name | SEQ ID NO. of nucleotide sequence | Position of CDS | SEQ ID NO. of amino acid sequence |
|---|---|---|---|
| BRHIP20170100 | 483 | 166 ... 936 | 2926 |
| BRHIP20173150 | 484 | 494 ... 820 | 2927 |
| BRHIP20174040 | 485 | 71 ... 2923 | 2928 |
| BRHIP20175420 | 486 | 3 ... 872 | 2929 |
| BRHIP20176420 | 487 | 914 ... 1756 | 2930 |
| BRHIP20179200 | 488 | 2532 ... 2870 | 2931 |
| BRHIP20180140 | 489 | 1028 ... 1345 | 2932 |
| BRHIP20183690 | 490 | 148 ... 1620 | 2933 |
| BRHIP20186120 | 491 | 322 ... 723 | 2934 |
| BRHIP20186500 | 492 | 3089 ... 3727 | 2935 |
| BRHIP20189980 | 493 | 247 ... 1002 | 2936 |
| BRHIP20190070 | 494 | 65 ... 433 | 2937 |
| BRHIP20191490 | 495 | 1929 ... 2270 | 2938 |
| BRHIP20191770 | 496 | 191 ... 502 | 2939 |
| BRHIP20191860 | 497 | 282 ... 2084 | 2940 |
| BRHIP20194940 | 498 | 119 ... 1312 | 2941 |
| BRHIP20195890 | 499 | 1002 ... 1376 | 2942 |
| BRHIP20196410 | 500 | 2371 ... 2706 | 2943 |
| BRHIP20198190 | 501 | 2979 ... 3407 | 2944 |
| BRHIP20205090 | 502 | 270 ... 593 | 2945 |
| BRHIP20207430 | 503 | 370 ... 687 | 2946 |
| BRHIP20207990 | 504 | 90 ... 1628 | 2947 |
| BRHIP20208270 | 505 | 967 ... 1353 | 2948 |
| BRHIP20208420 | 506 | 103 ... 462 | 2949 |
| BRHIP20208590 | 507 | 212 ... 607 | 2950 |
| BRHIP20214950 | 508 | 1637 ... 2020 | 2951 |
| BRHIP20217620 | 509 | 2731 ... 3087 | 2952 |
| BRHIP20218580 | 510 | 1930 ... 2589 | 2953 |
| BRHIP20222280 | 511 | 269 ... 1768 | 2954 |
| BRHIP20227080 | 512 | 1613 ... 2011 | 2955 |
| BRHIP20230710 | 513 | 198 ... 554 | 2956 |
| BRHIP20232290 | 514 | 110 ... 502 | 2957 |
| BRHIP20233090 | 515 | 1782 ... 2105 | 2958 |
| BRHIP20234380 | 516 | 15 ... 1079 | 2959 |
| BRHIP20236950 | 517 | 29 ... >2580 | 2960 |
| BRHIP20238600 | 518 | 154 ... 729 | 2961 |
| BRHIP20238690 | 519 | 51 ... 383 | 2962 |
| BRHIP20238880 | 520 | 13 ... 2625 | 2963 |
| BRHIP20240460 | 521 | 2151 ... 2540 | 2964 |
| BRHIP20243470 | 522 | 2929 ... 3579 | 2965 |
| BRHIP20249110 | 523 | 134 ... 2887 | 2966 |
| BRHIP20252450 | 524 | 123 ... >3738 | 2967 |
| BRHIP20253660 | 525 | 255 ... 1031 | 2968 |
| BRHIP20254480 | 526 | 362 ... 994 | 2969 |
| BRHIP20277620 | 527 | 124 ... 1074 | 2970 |
| BRHIP20283030 | 528 | 219 ... 4088 | 2971 |
| BRHIP20284800 | 529 | 217 ... 606 | 2972 |
| BRHIP20285830 | 530 | 611 ... 1321 | 2973 |
| BRHIP20285930 | 531 | 105 ... 779 | 2974 |
| BRHIP30001110 | 532 | 1740 ... 2294 | 2975 |
| BRHIP30004570 | 533 | 189 ... 1034 | 2976 |
| BRHIP30004880 | 534 | 191 ... 2902 | 2977 |
| BRSSN10000920 | 535 | 1850 ... 2215 | 2978 |
| BRSSN20003120 | 536 | 359 ... >2933 | 2979 |
| BRSSN20006340 | 537 | 937 ... 1401 | 2980 |
| BRSSN20013420 | 538 | 111 ... 2741 | 2981 |
| BRSSN20014260 | 539 | 167 ... 1069 | 2982 |
| BRSSN20015030 | 540 | 105 ... 458 | 2983 |
| BRSSN20015790 | 541 | 542 ... 1639 | 2984 |
| BRSSN20018690 | 542 | 110 ... 463 | 2985 |
| BRSSN20021600 | 543 | 13 ... 1497 | 2986 |
| BRSSN20028570 | 544 | 424 ... 726 | 2987 |
| BRSSN20038200 | 545 | 86 ... 1555 | 2988 |
| BRSSN20038410 | 546 | 187 ... 852 | 2989 |
| BRSSN20039370 | 547 | 900 ... 1628 | 2990 |
| BRSSN20043040 | 548 | 1959 ... 2342 | 2991 |
| BRSSN20046570 | 549 | 18 ... 368 | 2992 |
| BRSSN20046790 | 550 | 253 ... 1014 | 2993 |
| BRSSN20046860 | 551 | 406 ... 1461 | 2994 |
| BRSSN20066110 | 552 | 725 ... 1165 | 2995 |
| BRSSN20097020 | 553 | 1352 ... 2092 | 2996 |
| BRSSN20101100 | 554 | 1851 ... 2330 | 2997 |
| BRSSN20105870 | 555 | 8 ... 3064 | 2998 |
| BRSSN20105960 | 556 | 183 ... 497 | 2999 |
| BRSSN20108300 | 557 | 92 ... 415 | 3000 |
| BRSSN20117990 | 558 | 733 ... 1428 | 3001 |
| BRSSN20120810 | 559 | 770 ... 1687 | 3002 |
| BRSSN20121030 | 560 | 18 ... 890 | 3003 |
| BRSSN20137020 | 561 | 1097 ... 1429 | 3004 |
| BRSSN20142940 | 562 | 1411 ... 1803 | 3005 |
| BRSSN20146100 | 563 | 181 ... 2376 | 3006 |
| BRSSN20151990 | 564 | 15 ... 401 | 3007 |
| BRSSN20152380 | 565 | 17 ... 418 | 3008 |
| BRSSN20159070 | 566 | 393 ... 728 | 3009 |
| BRSSN20159820 | 567 | 867 ... 1661 | 3010 |
| BRSSN20169050 | 568 | 118 ... 636 | 3011 |
| BRSSN20176820 | 569 | 13 ... 1917 | 3012 |
| BRSSN20177570 | 570 | 303 ... 2651 | 3013 |
| BRSSN20187310 | 571 | 163 ... 1332 | 3014 |
| BRSTN10000830 | 572 | 216 ... 959 | 3015 |
| BRSTN20000580 | 573 | 617 ... 1672 | 3016 |
| BRSTN20002200 | 574 | 159 ... 515 | 3017 |
| BRSTN20005360 | 575 | 43 ... 1173 | 3018 |
| BRTHA20000570 | 576 | 641 ... 988 | 3019 |
| BRTHA20004740 | 577 | 192 ... 1082 | 3020 |
| BRTHA20046290 | 578 | 1657 ... 2298 | 3021 |
| BRTHA20046390 | 579 | 191 ... 571 | 3022 |
| BRTHA20046420 | 580 | 446 ... 835 | 3023 |
| CD34C30001250 | 581 | 59 ... >3188 | 3024 |
| CD34C30003140 | 582 | 458 ... 2803 | 3025 |
| CD34C30004240 | 583 | 430 ... 1290 | 3026 |
| CD34C30004940 | 584 | 970 ... 1299 | 3027 |
| COLON10001350 | 585 | 18 ... 1544 | 3028 |
| COLON20043180 | 586 | 451 ... 867 | 3029 |
| COLON20093370 | 587 | 1261 ... 1779 | 3030 |
| CTONG10000100 | 588 | 90 ... 1118 | 3031 |
| CTONG10000220 | 589 | 191 ... 847 | 3032 |
| CTONG10000620 | 590 | 94 ... 2943 | 3033 |
| CTONG10000930 | 591 | 18 ... 2621 | 3034 |
| CTONG10000940 | 592 | 182 ... 868 | 3035 |
| CTONG10001650 | 593 | 1916 ... 2512 | 3036 |
| CTONG10002770 | 594 | 182 ... >3049 | 3037 |
| CTONG20002180 | 595 | 90 ... 554 | 3038 |
| CTONG20004690 | 596 | 301 ... 885 | 3039 |
| CTONG20009770 | 597 | 321 ... 3287 | 3040 |
| CTONG20014280 | 598 | 176 ... 1723 | 3041 |
| CTONG20027090 | 599 | 280 ... 2370 | 3042 |
| CTONG20028410 | 600 | 600 ... 2936 | 3043 |
| CTONG20038890 | 601 | 961 ... 1371 | 3044 |
| CTONG20049410 | 602 | 157 ... 669 | 3045 |
| CTONG20050280 | 603 | 157 ... 1944 | 3046 |
| CTONG20052650 | 604 | 1210 ... 1647 | 3047 |
| CTONG20052900 | 605 | 130 ... 1548 | 3048 |
| CTONG20075860 | 606 | 63 ... 1391 | 3049 |
| CTONG20076130 | 607 | 11 ... 994 | 3050 |
| CTONG20077790 | 608 | 270 ... 635 | 3051 |
| CTONG20082690 | 609 | 75 ... 896 | 3052 |
| CTONG20085950 | 610 | 905 ... 2125 | 3053 |
| CTONG20091080 | 611 | 166 ... 717 | 3054 |
| CTONG20091320 | 612 | 1223 ... 1627 | 3055 |
| CTONG20092570 | 613 | 690 ... 1601 | 3056 |
| CTONG20092580 | 614 | 1555 ... 1920 | 3057 |
| CTONG20092680 | 615 | 365 ... 823 | 3058 |
| CTONG20092700 | 616 | 224 ... 928 | 3059 |
| CTONG20093950 | 617 | 205 ... 2388 | 3060 |
| CTONG20095270 | 618 | 1147 ... 1611 | 3061 |
| CTONG20095290 | 619 | 312 ... 749 | 3062 |
| CTONG20095340 | 620 | 109 ... 2631 | 3063 |
| CTONG20096430 | 621 | 311 ... 1384 | 3064 |
| CTONG20096750 | 622 | 738 ... 1184 | 3065 |
| CTONG20097660 | 623 | 133 ... 876 | 3066 |
| CTONG20098440 | 624 | 206 ... 1132 | 3067 |
| CTONG20099380 | 625 | 1417 ... 1806 | 3068 |
| CTONG20099550 | 626 | 74 ... 1939 | 3069 |
| CTONG20099630 | 627 | 99 ... 2060 | 3070 |
| CTONG20100240 | 628 | 620 ... 2155 | 3071 |
| CTONG20101480 | 629 | 13 ... 411 | 3072 |
| CTONG20103480 | 630 | 30 ... 356 | 3073 |
| CTONG20105080 | 631 | 28 ... 1260 | 3074 |
| CTONG20105660 | 632 | 75 ... 674 | 3075 |

TABLE 1-continued

| Clone name | SEQ ID NO. of nucleotide sequence | Position of CDS | SEQ ID NO. of amino acid sequence |
|---|---|---|---|
| CTONG20106230 | 633 | 2015 . . . >3067 | 3076 |
| CTONG20106520 | 634 | 1693 . . . 3147 | 3077 |
| CTONG20108210 | 635 | 234 . . . 1319 | 3078 |
| CTONG20114290 | 636 | 388 . . . 3225 | 3079 |
| CTONG20114740 | 637 | 1191 . . . 1832 | 3080 |
| CTONG20118150 | 638 | 144 . . . 2831 | 3081 |
| CTONG20118250 | 639 | 52 . . . 840 | 3082 |
| CTONG20119200 | 640 | 2128 . . . 2637 | 3083 |
| CTONG20120770 | 641 | 2946 . . . 3341 | 3084 |
| CTONG20121010 | 642 | 143 . . . 1732 | 3085 |
| CTONG20121580 | 643 | 97 . . . >2930 | 3086 |
| CTONG20124010 | 644 | 206 . . . 1369 | 3087 |
| CTONG20124220 | 645 | 177 . . . 2477 | 3088 |
| CTONG20124470 | 646 | 701 . . . 1237 | 3089 |
| CTONG20124730 | 647 | 894 . . . 1280 | 3090 |
| CTONG20125540 | 648 | 616 . . . 1071 | 3091 |
| CTONG20125640 | 649 | 756 . . . 1688 | 3092 |
| CTONG20126070 | 650 | 42 . . . 2843 | 3093 |
| CTONG20127450 | 651 | 2271 . . . 2642 | 3094 |
| CTONG20128430 | 652 | 330 . . . 2180 | 3095 |
| CTONG20128470 | 653 | 916 . . . 1479 | 3096 |
| CTONG20129960 | 654 | 118 . . . 3249 | 3097 |
| CTONG20131490 | 655 | 1191 . . . 1553 | 3098 |
| CTONG20131560 | 656 | 242 . . . >2879 | 3099 |
| CTONG20132220 | 657 | 1155 . . . 1598 | 3100 |
| CTONG20133390 | 658 | 679 . . . 2304 | 3101 |
| CTONG20133480 | 659 | 86 . . . 391 | 3102 |
| CTONG20133520 | 660 | 128 . . . 2140 | 3103 |
| CTONG20136300 | 661 | 1078 . . . 1521 | 3104 |
| CTONG20138030 | 662 | 3061 . . . 3396 | 3105 |
| CTONG20139070 | 663 | 2508 . . . 2819 | 3106 |
| CTONG20139340 | 664 | 1182 . . . 1535 | 3107 |
| CTONG20139860 | 665 | 28 . . . 2169 | 3108 |
| CTONG20140320 | 666 | 2454 . . . 2786 | 3109 |
| CTONG20140580 | 667 | 74 . . . 1180 | 3110 |
| CTONG20141650 | 668 | 190 . . . 570 | 3111 |
| CTONG20143690 | 669 | 169 . . . 2583 | 3112 |
| CTONG20146300 | 670 | 1195 . . . 1674 | 3113 |
| CTONG20146970 | 671 | 1201 . . . 1536 | 3114 |
| CTONG20147050 | 672 | 1304 . . . 1648 | 3115 |
| CTONG20149460 | 673 | 149 . . . 1942 | 3116 |
| CTONG20149950 | 674 | 42 . . . 371 | 3117 |
| CTONG20150910 | 675 | 792 . . . 1130 | 3118 |
| CTONG20153300 | 676 | 755 . . . 2338 | 3119 |
| CTONG20153580 | 677 | 488 . . . 1858 | 3120 |
| CTONG20155180 | 678 | 486 . . . >3005 | 3121 |
| CTONG20155400 | 679 | 1940 . . . 2458 | 3122 |
| CTONG20156780 | 680 | 33 . . . 3104 | 3123 |
| CTONG20158040 | 681 | 152 . . . 1297 | 3124 |
| CTONG20158150 | 682 | 66 . . . 2057 | 3125 |
| CTONG20158660 | 683 | 171 . . . 2258 | 3126 |
| CTONG20159530 | 684 | 231 . . . 1094 | 3127 |
| CTONG20160560 | 685 | 79 . . . >2796 | 3128 |
| CTONG20161850 | 686 | 27 . . . 734 | 3129 |
| CTONG20162170 | 687 | 156 . . . 734 | 3130 |
| CTONG20163550 | 688 | 772 . . . 1134 | 3131 |
| CTONG20164990 | 689 | 1343 . . . 1753 | 3132 |
| CTONG20165050 | 690 | 1575 . . . 2018 | 3133 |
| CTONG20186320 | 691 | 78 . . . 1595 | 3134 |
| CTONG20200310 | 692 | 2 . . . 2254 | 3135 |
| CTONG20265130 | 693 | 419 . . . 892 | 3136 |
| CTONG20267700 | 694 | 2046 . . . 2432 | 3137 |
| CTONG20273610 | 695 | 513 . . . 923 | 3138 |
| D3OST10001090 | 696 | 50 . . . 1462 | 3139 |
| D3OST10002670 | 697 | 77 . . . 853 | 3140 |
| D3OST10002700 | 698 | 84 . . . 461 | 3141 |
| D3OST20006180 | 699 | 148 . . . 2259 | 3142 |
| D3OST20006540 | 700 | 140 . . . 442 | 3143 |
| D3OST20007340 | 701 | 369 . . . 1220 | 3144 |
| D3OST20013280 | 702 | 756 . . . 1118 | 3145 |
| D3OST20024170 | 703 | 1373 . . . 1714 | 3146 |
| D3OST20024360 | 704 | 1984 . . . 2361 | 3147 |
| D3OST20024520 | 705 | 3 . . . 422 | 3148 |
| D3OST20036070 | 706 | 122 . . . 1039 | 3149 |
| D3OST20037970 | 707 | 256 . . . 735 | 3150 |
| D3OST20038560 | 708 | 1976 . . . 2350 | 3151 |
| D3OST30002580 | 709 | 1509 . . . 2957 | 3152 |
| D3OST30002910 | 710 | 1811 . . . 2248 | 3153 |
| D6OST20003580 | 711 | 1760 . . . 2167 | 3154 |
| D6OST20004450 | 712 | 1513 . . . 2547 | 3155 |
| D6OST20005070 | 713 | 2835 . . . 3398 | 3156 |
| D9OST20000310 | 714 | 239 . . . 637 | 3157 |
| D9OST20002780 | 715 | 644 . . . 1360 | 3158 |
| D9OST20015470 | 716 | 187 . . . 1386 | 3159 |
| D9OST20023970 | 717 | 872 . . . 1327 | 3160 |
| D9OST20026730 | 718 | 145 . . . 3159 | 3161 |
| D9OST20031370 | 719 | 616 . . . 1251 | 3162 |
| D9OST20033970 | 720 | 24 . . . 1811 | 3163 |
| D9OST20035800 | 721 | 524 . . . 1057 | 3164 |
| D9OST20035940 | 722 | 217 . . . 867 | 3165 |
| D9OST20040180 | 723 | 189 . . . 1127 | 3166 |
| DFNES10000030 | 724 | 897 . . . 1322 | 3167 |
| DFNES10001850 | 725 | 471 . . . 899 | 3168 |
| DFNES20001530 | 726 | 26 . . . 382 | 3169 |
| DFNES20010910 | 727 | 159 . . . 1136 | 3170 |
| DFNES20014040 | 728 | 148 . . . 1272 | 3171 |
| DFNES20025880 | 729 | 1080 . . . 1415 | 3172 |
| DFNES20031920 | 730 | 631 . . . 1104 | 3173 |
| DFNES20037420 | 731 | 186 . . . 2090 | 3174 |
| DFNES20055270 | 732 | 159 . . . 818 | 3175 |
| DFNES20071130 | 733 | 248 . . . 1156 | 3176 |
| DFNES20082800 | 734 | 258 . . . 698 | 3177 |
| FCBBF10000240 | 735 | 507 . . . 2942 | 3178 |
| FCBBF10000380 | 736 | 1024 . . . 1344 | 3179 |
| FCBBF10000630 | 737 | 533 . . . 1654 | 3180 |
| FCBBF10000770 | 738 | 56 . . . 1810 | 3181 |
| FCBBF10001150 | 739 | 351 . . . 2555 | 3182 |
| FCBBF10001210 | 740 | 38 . . . 1066 | 3183 |
| FCBBF10001550 | 741 | 60 . . . 653 | 3184 |
| FCBBF10001710 | 742 | 322 . . . 2133 | 3185 |
| FCBBF10001820 | 743 | 10 . . . 1032 | 3186 |
| FCBBF10002430 | 744 | 349 . . . 1158 | 3187 |
| FCBBF10002700 | 745 | 189 . . . 551 | 3188 |
| FCBBF10002800 | 746 | 485 . . . 2818 | 3189 |
| FCBBF10003220 | 747 | 479 . . . 832 | 3190 |
| FCBBF10003670 | 748 | 139 . . . 1266 | 3191 |
| FCBBF10003740 | 749 | 407 . . . 2365 | 3192 |
| FCBBF10003760 | 750 | 1044 . . . 1358 | 3193 |
| FCBBF10003770 | 751 | 242 . . . >3001 | 3194 |
| FCBBF10004120 | 752 | 142 . . . 816 | 3195 |
| FCBBF10004370 | 753 | 432 . . . 1511 | 3196 |
| FCBBF10005060 | 754 | 1340 . . . 2323 | 3197 |
| FCBBF10005460 | 755 | 179 . . . 2092 | 3198 |
| FCBBF10005500 | 756 | 1518 . . . 2123 | 3199 |
| FCBBF10005740 | 757 | 954 . . . 1667 | 3200 |
| FCBBF10006780 | 758 | 356 . . . 679 | 3201 |
| FCBBF20014270 | 759 | 49 . . . 315 | 3202 |
| FCBBF20023700 | 760 | 251 . . . 589 | 3203 |
| FCBBF20032970 | 761 | 845 . . . 1186 | 3204 |
| FCBBF20035280 | 762 | 13 . . . 393 | 3205 |
| FCBBF20042170 | 763 | 186 . . . 1337 | 3206 |
| FCBBF20042560 | 764 | 115 . . . 576 | 3207 |
| FCBBF20049300 | 765 | 32 . . . 631 | 3208 |
| FCBBF20051220 | 766 | 523 . . . 948 | 3209 |
| FCBBF20054280 | 767 | 119 . . . 535 | 3210 |
| FCBBF20056370 | 768 | 57 . . . 704 | 3211 |
| FCBBF20059090 | 769 | 928 . . . 1245 | 3212 |
| FCBBF20064520 | 770 | 368 . . . 1243 | 3213 |
| FCBBF20067810 | 771 | 68 . . . 1231 | 3214 |
| FCBBF20068820 | 772 | 74 . . . 712 | 3215 |
| FCBBF20071860 | 773 | 384 . . . 911 | 3216 |
| FCBBF20072650 | 774 | 1471 . . . 1944 | 3217 |
| FCBBF20075560 | 775 | 730 . . . 1086 | 3218 |
| FCBBF20076330 | 776 | 684 . . . 998 | 3219 |
| FCBBF30001840 | 777 | 1503 . . . 1832 | 3220 |
| FCBBF30007680 | 778 | 9 . . . 2117 | 3221 |
| FCBBF30008470 | 779 | 1157 . . . 1504 | 3222 |
| FCBBF30010810 | 780 | 149 . . . 1483 | 3223 |
| FCBBF30012350 | 781 | 419 . . . 1507 | 3224 |
| FCBBF30012810 | 782 | 372 . . . >2409 | 3225 |

TABLE 1-continued

| Clone name | SEQ ID NO. of nucleotide sequence | Position of CDS | SEQ ID NO. of amino acid sequence |
|---|---|---|---|
| FCBBF30013770 | 783 | 375 . . . 2795 | 3226 |
| FCBBF30015940 | 784 | 24 . . . >2507 | 3227 |
| FCBBF30016320 | 785 | 990 . . . 1877 | 3228 |
| FCBBF30016570 | 786 | 574 . . . 999 | 3229 |
| FCBBF30018550 | 787 | 231 . . . >3402 | 3230 |
| FCBBF30019120 | 788 | 54 . . . 398 | 3231 |
| FCBBF30024750 | 789 | 126 . . . 560 | 3232 |
| FCBBF30025560 | 790 | 171 . . . 1301 | 3233 |
| FCBBF30028180 | 791 | 258 . . . 830 | 3234 |
| FCBBF30033050 | 792 | 7 . . . 1089 | 3235 |
| FCBBF30039020 | 793 | 955 . . . 2727 | 3236 |
| FCBBF30049550 | 794 | 222 . . . >4213 | 3237 |
| FCBBF30052180 | 795 | 2829 . . . 4214 | 3238 |
| FCBBF30054440 | 796 | 33 . . . 2822 | 3239 |
| FCBBF30057290 | 797 | 143 . . . 2068 | 3240 |
| FCBBF30062880 | 798 | 1135 . . . >3256 | 3241 |
| FCBBF30070770 | 799 | 1049 . . . 2113 | 3242 |
| FCBBF30071520 | 800 | 280 . . . 735 | 3243 |
| FCBBF30078290 | 801 | 280 . . . 1875 | 3244 |
| FCBBF30083620 | 802 | 125 . . . 1159 | 3245 |
| FCBBF30083820 | 803 | 298 . . . 774 | 3246 |
| FCBBF30086440 | 804 | 192 . . . 863 | 3247 |
| FCBBF30090690 | 805 | 545 . . . 1657 | 3248 |
| FCBBF30095260 | 806 | 204 . . . 686 | 3249 |
| FCBBF30123470 | 807 | 1084 . . . 1614 | 3250 |
| FCBBF30129630 | 808 | 257 . . . 973 | 3251 |
| FCBBF30170590 | 809 | 1313 . . . 1672 | 3252 |
| FCBBF30172550 | 810 | 1350 . . . 1703 | 3253 |
| FCBBF30175310 | 811 | 120 . . . 1280 | 3254 |
| FCBBF30178730 | 812 | 348 . . . 833 | 3255 |
| FCBBF30189490 | 813 | 1935 . . . 2468 | 3256 |
| FCBBF30190850 | 814 | 43 . . . 1560 | 3257 |
| FCBBF30195640 | 815 | 577 . . . >2751 | 3258 |
| FCBBF30199610 | 816 | 972 . . . 1391 | 3259 |
| FCBBF30215060 | 817 | 42 . . . 446 | 3260 |
| FCBBF30225660 | 818 | 231 . . . 2750 | 3261 |
| FCBBF30233680 | 819 | 28 . . . >4395 | 3262 |
| FCBBF30238870 | 820 | 587 . . . 2761 | 3263 |
| FCBBF30240020 | 821 | 248 . . . 1747 | 3264 |
| FCBBF30240960 | 822 | 465 . . . 1520 | 3265 |
| FCBBF30242250 | 823 | 271 . . . >2723 | 3266 |
| FCBBF30243640 | 824 | 339 . . . 665 | 3267 |
| FCBBF30246230 | 825 | 1893 . . . 2357 | 3268 |
| FCBBF30246630 | 826 | 19 . . . 2070 | 3269 |
| FCBBF30247930 | 827 | 558 . . . 1187 | 3270 |
| FCBBF30250730 | 828 | 116 . . . >2647 | 3271 |
| FCBBF30251420 | 829 | 2590 . . . 2904 | 3272 |
| FCBBF30252520 | 830 | 27 . . . 380 | 3273 |
| FCBBF30252800 | 831 | 139 . . . 1110 | 3274 |
| FCBBF30252850 | 832 | 45 . . . 1022 | 3275 |
| FCBBF30262360 | 833 | 51 . . . 446 | 3276 |
| FCBBF30262510 | 834 | 36 . . . 2327 | 3277 |
| FCBBF30266780 | 835 | 2080 . . . 2382 | 3278 |
| FCBBF30266920 | 836 | 5 . . . 316 | 3279 |
| FCBBF30278630 | 837 | 492 . . . 821 | 3280 |
| FCBBF30279030 | 838 | 1653 . . . 2447 | 3281 |
| FCBBF30281880 | 839 | 83 . . . 2221 | 3282 |
| FCBBF30284720 | 840 | 230 . . . 751 | 3283 |
| FCBBF30285280 | 841 | 185 . . . 3043 | 3284 |
| FCBBF40001420 | 842 | 364 . . . 681 | 3285 |
| FCBBF40001730 | 843 | 105 . . . 932 | 3286 |
| FCBBF40005480 | 844 | 119 . . . 589 | 3287 |
| FEBRA10001880 | 845 | 494 . . . 2236 | 3288 |
| FEBRA10001900 | 846 | 6 . . . 389 | 3289 |
| FEBRA20002100 | 847 | 375 . . . 1064 | 3290 |
| FEBRA20003210 | 848 | 10 . . . 414 | 3291 |
| FEBRA20004620 | 849 | 297 . . . 1568 | 3292 |
| FEBRA20007620 | 850 | 61 . . . 2400 | 3293 |
| FEBRA20009090 | 851 | 667 . . . 1032 | 3294 |
| FEBRA20010120 | 852 | 608 . . . 1216 | 3295 |
| FEBRA20017050 | 853 | 1775 . . . 2197 | 3296 |
| FEBRA20018280 | 854 | 16 . . . 678 | 3297 |
| FEBRA20018690 | 855 | 664 . . . 981 | 3298 |
| FEBRA20024100 | 856 | 68 . . . 2659 | 3299 |
| FEBRA20025270 | 857 | 116 . . . >2317 | 3300 |
| FEBRA20025520 | 858 | 669 . . . 1133 | 3301 |
| FEBRA20026110 | 859 | 233 . . . 2692 | 3302 |
| FEBRA20026280 | 860 | 54 . . . 623 | 3303 |
| FEBRA20027810 | 861 | 155 . . . 2740 | 3304 |
| FEBRA20029860 | 862 | 29 . . . 757 | 3305 |
| FEBRA20034360 | 863 | 1288 . . . 2013 | 3306 |
| FEBRA20034680 | 864 | 240 . . . 1955 | 3307 |
| FEBRA20037260 | 865 | 2376 . . . 2702 | 3308 |
| FEBRA20037500 | 866 | 10 . . . 1308 | 3309 |
| FEBRA20040530 | 867 | 76 . . . 1407 | 3310 |
| FEBRA20042190 | 868 | 1590 . . . 1925 | 3311 |
| FEBRA20052910 | 869 | 1136 . . . 1486 | 3312 |
| FEBRA20060610 | 870 | 599 . . . 1201 | 3313 |
| FEBRA20072120 | 871 | 106 . . . 2877 | 3314 |
| FEBRA20079310 | 872 | 2384 . . . 2806 | 3315 |
| FEBRA20080810 | 873 | 679 . . . 1401 | 3316 |
| FEBRA20082010 | 874 | 106 . . . 1779 | 3317 |
| FEBRA20082100 | 875 | 1042 . . . 1524 | 3318 |
| FEBRA20086620 | 876 | 215 . . . 1591 | 3319 |
| FEBRA20088360 | 877 | 2964 . . . 3521 | 3320 |
| FEBRA20090290 | 878 | 383 . . . 823 | 3321 |
| FEBRA20092890 | 879 | 198 . . . 2297 | 3322 |
| FEBRA20093520 | 880 | 651 . . . 1070 | 3323 |
| FEBRA20095140 | 881 | 264 . . . >2245 | 3324 |
| FEBRA20095880 | 882 | 1872 . . . 2186 | 3325 |
| FEBRA20097310 | 883 | 74 . . . 2101 | 3326 |
| FEBRA20098460 | 884 | 291 . . . 686 | 3327 |
| FEBRA20111460 | 885 | 859 . . . 1221 | 3328 |
| FEBRA20113560 | 886 | 22 . . . 558 | 3329 |
| FEBRA20125070 | 887 | 10 . . . 1002 | 3330 |
| FEBRA20130190 | 888 | 131 . . . 1192 | 3331 |
| FEBRA20132740 | 889 | 770 . . . 1111 | 3332 |
| FEBRA20140100 | 890 | 1664 . . . 2377 | 3333 |
| FEBRA20144170 | 891 | 342 . . . 1976 | 3334 |
| FEBRA20145780 | 892 | 1262 . . . 1564 | 3335 |
| FEBRA20161120 | 893 | 173 . . . 484 | 3336 |
| FEBRA20166540 | 894 | 101 . . . 511 | 3337 |
| FEBRA20167390 | 895 | 429 . . . 869 | 3338 |
| FEBRA20171380 | 896 | 338 . . . 2002 | 3339 |
| FEBRA20174410 | 897 | 125 . . . 2029 | 3340 |
| FEBRA20176800 | 898 | 1320 . . . 1877 | 3341 |
| FEBRA20184330 | 899 | 36 . . . 533 | 3342 |
| FEBRA20192420 | 900 | 2120 . . . 3799 | 3343 |
| FEBRA20195820 | 901 | 175 . . . 678 | 3344 |
| FEBRA20196370 | 902 | 353 . . . 2032 | 3345 |
| FEBRA20196630 | 903 | 482 . . . 2359 | 3346 |
| FEBRA20197110 | 904 | 632 . . . 1222 | 3347 |
| FEBRA20204000 | 905 | 1958 . . . 2482 | 3348 |
| FEBRA20204060 | 906 | 366 . . . 728 | 3349 |
| FEBRA20211710 | 907 | 282 . . . 929 | 3350 |
| FEBRA20214970 | 908 | 620 . . . 1264 | 3351 |
| FEBRA20215500 | 909 | 726 . . . 1256 | 3352 |
| FEBRA20216360 | 910 | 1398 . . . 1904 | 3353 |
| FEBRA20222040 | 911 | 954 . . . 1391 | 3354 |
| FEBRA20223220 | 912 | 1254 . . . 1898 | 3355 |
| FEBRA20225040 | 913 | 13 . . . 1692 | 3356 |
| FEBRA20226010 | 914 | 1439 . . . 1933 | 3357 |
| FEBRA20229560 | 915 | 37 . . . 381 | 3358 |
| FEBRA20229630 | 916 | 184 . . . 987 | 3359 |
| FEBRA20232850 | 917 | 774 . . . 1193 | 3360 |
| FEBRA20233770 | 918 | 64 . . . 636 | 3361 |
| FEBRA20235500 | 919 | 1206 . . . >2520 | 3362 |
| FEBRA20237640 | 920 | 331 . . . 933 | 3363 |
| FEHRT20003250 | 921 | 173 . . . 1243 | 3364 |
| FELNG20002410 | 922 | 1257 . . . 1577 | 3365 |
| HCASM10000500 | 923 | 300 . . . 1754 | 3366 |
| HCHON10001760 | 924 | 238 . . . 1182 | 3367 |
| HCHON20000380 | 925 | 210 . . . 644 | 3368 |
| HCHON20001560 | 926 | 565 . . . 1611 | 3369 |
| HCHON20002260 | 927 | 694 . . . 1389 | 3370 |
| HCHON20003220 | 928 | 23 . . . >2278 | 3371 |
| HCHON20003440 | 929 | 1982 . . . >2519 | 3372 |
| HCHON20007380 | 930 | 163 . . . 1248 | 3373 |
| HCHON20007510 | 931 | 189 . . . 2636 | 3374 |
| HCHON20008150 | 932 | 204 . . . >2358 | 3375 |

TABLE 1-continued

| Clone name | SEQ ID NO. of nucleotide sequence | Position of CDS | SEQ ID NO. of amino acid sequence |
|---|---|---|---|
| HCHON20008180 | 933 | 671 . . . 1087 | 3376 |
| HCHON20008320 | 934 | 1240 . . . >2284 | 3377 |
| HCHON20008980 | 935 | 578 . . . 904 | 3378 |
| HCHON20009350 | 936 | 63 . . . 422 | 3379 |
| HCHON20009560 | 937 | 1644 . . . 2489 | 3380 |
| HCHON20010990 | 938 | 531 . . . 1085 | 3381 |
| HCHON20011160 | 939 | 839 . . . 1156 | 3382 |
| HCHON20014970 | 940 | 302 . . . 2143 | 3383 |
| HCHON20015230 | 941 | 950 . . . 1453 | 3384 |
| HCHON20015350 | 942 | 647 . . . >2887 | 3385 |
| HCHON20015980 | 943 | 100 . . . 1413 | 3386 |
| HCHON20016040 | 944 | 3 . . . 323 | 3387 |
| HCHON20016650 | 945 | 44 . . . 3418 | 3388 |
| HCHON20022470 | 946 | 1526 . . . 1978 | 3389 |
| HCHON20035130 | 947 | 1192 . . . 1614 | 3390 |
| HCHON20036420 | 948 | 356 . . . 811 | 3391 |
| HCHON20036760 | 949 | 228 . . . 647 | 3392 |
| HCHON20040020 | 950 | 257 . . . 1288 | 3393 |
| HCHON20043590 | 951 | 263 . . . 712 | 3394 |
| HCHON20059870 | 952 | 198 . . . 2297 | 3395 |
| HCHON20064590 | 953 | 66 . . . 2063 | 3396 |
| HCHON20067220 | 954 | 313 . . . 642 | 3397 |
| HCHON20067700 | 955 | 160 . . . 591 | 3398 |
| HCHON20068410 | 956 | 116 . . . >2811 | 3399 |
| HCHON20068710 | 957 | 335 . . . 688 | 3400 |
| HCHON20074820 | 958 | 19 . . . 735 | 3401 |
| HCHON20076500 | 959 | 1778 . . . 2473 | 3402 |
| HCHON20086720 | 960 | 133 . . . 864 | 3403 |
| HCHON20097490 | 961 | 1434 . . . 2819 | 3404 |
| HCHON20100740 | 962 | 138 . . . 1277 | 3405 |
| HEART20003060 | 963 | 109 . . . 1407 | 3406 |
| HEART20005410 | 964 | 302 . . . 784 | 3407 |
| HEART20017730 | 965 | 19 . . . 2064 | 3408 |
| HEART20021840 | 966 | 22 . . . 507 | 3409 |
| HEART20025980 | 967 | 293 . . . 1180 | 3410 |
| HEART20034320 | 968 | 31 . . . 2013 | 3411 |
| HEART20037810 | 969 | 803 . . . 1108 | 3412 |
| HEART20049400 | 970 | 178 . . . 549 | 3413 |
| HEART20049410 | 971 | 44 . . . 613 | 3414 |
| HEART20049800 | 972 | 15 . . . 509 | 3415 |
| HEART20061950 | 973 | 153 . . . 1961 | 3416 |
| HEART20063340 | 974 | 220 . . . 1281 | 3417 |
| HEART20067870 | 975 | 256 . . . 855 | 3418 |
| HEART20067890 | 976 | 3 . . . 338 | 3419 |
| HEART20072310 | 977 | 47 . . . 1057 | 3420 |
| HEART20074430 | 978 | 205 . . . 540 | 3421 |
| HEART20077670 | 979 | 90 . . . 1223 | 3422 |
| HEART20083640 | 980 | 192 . . . 1376 | 3423 |
| HEART20089940 | 981 | 150 . . . 1523 | 3424 |
| HEART20090000 | 982 | 197 . . . 2116 | 3425 |
| HEART20095990 | 983 | 523 . . . 1077 | 3426 |
| HHDPC10000650 | 984 | 920 . . . 1531 | 3427 |
| HHDPC10000830 | 985 | 110 . . . 520 | 3428 |
| HHDPC20001040 | 986 | 2080 . . . 2442 | 3429 |
| HHDPC20006920 | 987 | 1758 . . . 2066 | 3430 |
| HHDPC20014320 | 988 | 5 . . . 526 | 3431 |
| HHDPC20030490 | 989 | 71 . . . 529 | 3432 |
| HHDPC20031130 | 990 | 369 . . . 2249 | 3433 |
| HHDPC20034390 | 991 | 94 . . . 705 | 3434 |
| HHDPC20034720 | 992 | 167 . . . 868 | 3435 |
| HHDPC20057420 | 993 | 44 . . . 484 | 3436 |
| HHDPC20057940 | 994 | 1 . . . 393 | 3437 |
| HHDPC20064600 | 995 | 231 . . . 1493 | 3438 |
| HHDPC20068620 | 996 | 515 . . . 1816 | 3439 |
| HHDPC20084140 | 997 | 163 . . . 2109 | 3440 |
| HHDPC20091140 | 998 | 160 . . . 504 | 3441 |
| HHDPC20091780 | 999 | 49 . . . 1623 | 3442 |
| HHDPC20092080 | 1000 | 133 . . . 702 | 3443 |
| HHDPC20095280 | 1001 | 332 . . . 745 | 3444 |
| HLUNG10000550 | 1002 | 729 . . . 1058 | 3445 |
| HLUNG20016330 | 1003 | 86 . . . >1958 | 3446 |
| HLUNG20016770 | 1004 | 919 . . . 1242 | 3447 |
| HLUNG20017120 | 1005 | 644 . . . 1144 | 3448 |
| HLUNG20023340 | 1006 | 228 . . . 1181 | 3449 |
| HLUNG20033780 | 1007 | 156 . . . 2285 | 3450 |
| HLUNG20084390 | 1008 | 542 . . . 997 | 3451 |
| IMR3220002430 | 1009 | 34 . . . 1176 | 3452 |
| KIDNE20002520 | 1010 | 22 . . . 1593 | 3453 |
| KIDNE20003940 | 1011 | 187 . . . 1986 | 3454 |
| KIDNE20006780 | 1012 | 164 . . . 829 | 3455 |
| KIDNE20007210 | 1013 | 27 . . . 350 | 3456 |
| KIDNE20007770 | 1014 | 27 . . . 1415 | 3457 |
| KIDNE20008010 | 1015 | 127 . . . >1986 | 3458 |
| KIDNE20009470 | 1016 | 9 . . . >2664 | 3459 |
| KIDNE20011170 | 1017 | 347 . . . 817 | 3460 |
| KIDNE20011400 | 1018 | 1798 . . . 2334 | 3461 |
| KIDNE20013730 | 1019 | 373 . . . 777 | 3462 |
| KIDNE20017130 | 1020 | 226 . . . 1740 | 3463 |
| KIDNE20018730 | 1021 | 35 . . . 631 | 3464 |
| KIDNE20018970 | 1022 | 232 . . . 546 | 3465 |
| KIDNE20020150 | 1023 | 215 . . . 1645 | 3466 |
| KIDNE20021680 | 1024 | 140 . . . 1096 | 3467 |
| KIDNE20021910 | 1025 | 15 . . . 2018 | 3468 |
| KIDNE20021980 | 1026 | 1578 . . . 1910 | 3469 |
| KIDNE20022620 | 1027 | 112 . . . 2277 | 3470 |
| KIDNE20024830 | 1028 | 1912 . . . >2715 | 3471 |
| KIDNE20027250 | 1029 | 359 . . . 955 | 3472 |
| KIDNE20027950 | 1030 | 97 . . . 543 | 3473 |
| KIDNE20028390 | 1031 | 31 . . . 519 | 3474 |
| KIDNE20028720 | 1032 | 70 . . . 1122 | 3475 |
| KIDNE20028830 | 1033 | 107 . . . 1258 | 3476 |
| KIDNE20029800 | 1034 | 1056 . . . 1358 | 3477 |
| KIDNE20067330 | 1035 | 930 . . . 1865 | 3478 |
| KIDNE20079440 | 1036 | 192 . . . 539 | 3479 |
| KIDNE20096280 | 1037 | 266 . . . 1354 | 3480 |
| KIDNE20096470 | 1038 | 31 . . . 639 | 3481 |
| KIDNE20100070 | 1039 | 471 . . . 2204 | 3482 |
| KIDNE20100840 | 1040 | 167 . . . 778 | 3483 |
| KIDNE20101370 | 1041 | 9 . . . 503 | 3484 |
| KIDNE20101510 | 1042 | 62 . . . 1795 | 3485 |
| KIDNE20102650 | 1043 | 322 . . . 1614 | 3486 |
| KIDNE20102710 | 1044 | 791 . . . 1501 | 3487 |
| KIDNE20104300 | 1045 | 188 . . . >1957 | 3488 |
| KIDNE20106740 | 1046 | 55 . . . 411 | 3489 |
| KIDNE20107390 | 1047 | 85 . . . 399 | 3490 |
| KIDNE20107500 | 1048 | 180 . . . 641 | 3491 |
| KIDNE20107620 | 1049 | 222 . . . 2213 | 3492 |
| KIDNE20109730 | 1050 | 57 . . . 1121 | 3493 |
| KIDNE20109890 | 1051 | 254 . . . >2578 | 3494 |
| KIDNE20112000 | 1052 | 430 . . . 750 | 3495 |
| KIDNE20115080 | 1053 | 76 . . . 1092 | 3496 |
| KIDNE20118580 | 1054 | 962 . . . 1387 | 3497 |
| KIDNE20120090 | 1055 | 1334 . . . 1813 | 3498 |
| KIDNE20121880 | 1056 | 192 . . . 866 | 3499 |
| KIDNE20122910 | 1057 | 1623 . . . 2006 | 3500 |
| KIDNE20124400 | 1058 | 532 . . . 2499 | 3501 |
| KIDNE20125630 | 1059 | 67 . . . 504 | 3502 |
| KIDNE20126010 | 1060 | 991 . . . 1407 | 3503 |
| KIDNE20126130 | 1061 | 285 . . . 701 | 3504 |
| KIDNE20127100 | 1062 | 265 . . . 1944 | 3505 |
| KIDNE20127450 | 1063 | 570 . . . 1088 | 3506 |
| KIDNE20127750 | 1064 | 175 . . . 1488 | 3507 |
| KIDNE20130450 | 1065 | 177 . . . 512 | 3508 |
| KIDNE20131580 | 1066 | 194 . . . 1912 | 3509 |
| KIDNE20132180 | 1067 | 894 . . . 1256 | 3510 |
| KIDNE20137340 | 1068 | 889 . . . 1710 | 3511 |
| KIDNE20138010 | 1069 | 1564 . . . 2046 | 3512 |
| KIDNE20141190 | 1070 | 71 . . . 856 | 3513 |
| KIDNE20144890 | 1071 | 385 . . . 738 | 3514 |
| KIDNE20148900 | 1072 | 487 . . . 981 | 3515 |
| KIDNE20163880 | 1073 | 327 . . . 1364 | 3516 |
| KIDNE20180710 | 1074 | 379 . . . 855 | 3517 |
| KIDNE20181660 | 1075 | 1109 . . . 1564 | 3518 |
| KIDNE20182690 | 1076 | 553 . . . 2019 | 3519 |
| KIDNE20186780 | 1077 | 837 . . . 1541 | 3520 |
| KIDNE20190740 | 1078 | 321 . . . 653 | 3521 |
| LIVER10001260 | 1079 | 1413 . . . 1748 | 3522 |
| LIVER10004790 | 1080 | 112 . . . 1113 | 3523 |
| LIVER20002160 | 1081 | 79 . . . 1944 | 3524 |
| LIVER20011130 | 1082 | 898 . . . 1569 | 3525 |

TABLE 1-continued

| Clone name | SEQ ID NO. of nucleotide sequence | Position of CDS | SEQ ID NO. of amino acid sequence |
|---|---|---|---|
| LIVER20011910 | 1083 | 27 ... 425 | 3526 |
| LIVER20028420 | 1084 | 1305 ... 1724 | 3527 |
| LIVER20035110 | 1085 | 551 ... 940 | 3528 |
| LIVER20035680 | 1086 | 873 ... 1283 | 3529 |
| LIVER20038540 | 1087 | 6 ... 308 | 3530 |
| LIVER20045650 | 1088 | 2359 ... 2886 | 3531 |
| LIVER20055200 | 1089 | 82 ... 618 | 3532 |
| LIVER20055440 | 1090 | 1611 ... 2240 | 3533 |
| LIVER20059810 | 1091 | 1597 ... 1899 | 3534 |
| LIVER20062510 | 1092 | 631 ... 999 | 3535 |
| LIVER20064100 | 1093 | 279 ... 785 | 3536 |
| LIVER20064690 | 1094 | 172 ... 1161 | 3537 |
| LIVER20075680 | 1095 | 2568 ... 2939 | 3538 |
| LIVER20080530 | 1096 | 44 ... 1426 | 3539 |
| LIVER20084730 | 1097 | 240 ... 788 | 3540 |
| LIVER20085800 | 1098 | 99 ... 416 | 3541 |
| LIVER20087060 | 1099 | 140 ... 2056 | 3542 |
| LIVER20087510 | 1100 | 478 ... 1200 | 3543 |
| LIVER20091180 | 1101 | 18 ... 374 | 3544 |
| MAMGL10000830 | 1102 | 40 ... 1551 | 3545 |
| MESAN10001260 | 1103 | 80 ... 2137 | 3546 |
| MESAN20004570 | 1104 | 354 ... >2589 | 3547 |
| MESAN20014500 | 1105 | 78 ... 1976 | 3548 |
| MESAN20025190 | 1106 | 1679 ... 2323 | 3549 |
| MESAN20027090 | 1107 | 144 ... 653 | 3550 |
| MESAN20029400 | 1108 | 210 ... >2998 | 3551 |
| MESAN20031900 | 1109 | 138 ... 2348 | 3552 |
| MESAN20035290 | 1110 | 99 ... 797 | 3553 |
| MESAN20036460 | 1111 | 1203 ... 1844 | 3554 |
| MESAN20038510 | 1112 | 639 ... 1016 | 3555 |
| MESAN20089360 | 1113 | 386 ... 802 | 3556 |
| MESAN20101140 | 1114 | 250 ... 504 | 3557 |
| MESAN20103120 | 1115 | 143 ... 1201 | 3558 |
| MESAN20106640 | 1116 | 71 ... 712 | 3559 |
| MESAN20115970 | 1117 | 234 ... 644 | 3560 |
| MESAN20121130 | 1118 | 7 ... 942 | 3561 |
| MESAN20125860 | 1119 | 1396 ... 1875 | 3562 |
| MESAN20127350 | 1120 | 297 ... 1724 | 3563 |
| MESAN20130220 | 1121 | 106 ... 1626 | 3564 |
| MESAN20132110 | 1122 | 1363 ... 2433 | 3565 |
| MESAN20136110 | 1123 | 188 ... 1582 | 3566 |
| MESAN20138450 | 1124 | 249 ... 647 | 3567 |
| MESAN20139360 | 1125 | 195 ... 611 | 3568 |
| MESAN20141920 | 1126 | 250 ... 2724 | 3569 |
| MESAN20152770 | 1127 | 64 ... 585 | 3570 |
| MESAN20153910 | 1128 | 141 ... 443 | 3571 |
| MESAN20154010 | 1129 | 24 ... 620 | 3572 |
| MESAN20157080 | 1130 | 1336 ... 1677 | 3573 |
| MESAN20161590 | 1131 | 767 ... 1081 | 3574 |
| MESAN20164090 | 1132 | 273 ... 2471 | 3575 |
| MESAN20171520 | 1133 | 103 ... 774 | 3576 |
| MESAN20174170 | 1134 | 1375 ... 1743 | 3577 |
| MESAN20182090 | 1135 | 5 ... >2440 | 3578 |
| MESAN20186700 | 1136 | 1333 ... >3058 | 3579 |
| NESOP10001080 | 1137 | 149 ... 1489 | 3580 |
| NOVAR10000150 | 1138 | 1470 ... 1895 | 3581 |
| NOVAR10000910 | 1139 | 247 ... 1482 | 3582 |
| NOVAR10001020 | 1140 | 136 ... 519 | 3583 |
| NOVAR20000380 | 1141 | 422 ... 844 | 3584 |
| NOVAR20003520 | 1142 | 898 ... 1377 | 3585 |
| NT2NE20003740 | 1143 | 28 ... 555 | 3586 |
| NT2NE20010050 | 1144 | 1240 ... 1725 | 3587 |
| NT2NE20010210 | 1145 | 231 ... 626 | 3588 |
| NT2NE20010400 | 1146 | 923 ... 1546 | 3589 |
| NT2NE20010490 | 1147 | 105 ... 1499 | 3590 |
| NT2NE20015240 | 1148 | 251 ... 646 | 3591 |
| NT2NE20021620 | 1149 | 785 ... 2266 | 3592 |
| NT2NE20043780 | 1150 | 815 ... 1285 | 3593 |
| NT2NE20053580 | 1151 | 9 ... 413 | 3594 |
| NT2NE20068130 | 1152 | 237 ... 1601 | 3595 |
| NT2NE20072200 | 1153 | 94 ... 855 | 3596 |
| NT2NE20074250 | 1154 | 9 ... 377 | 3597 |
| NT2NE20080170 | 1155 | 129 ... 2219 | 3598 |
| NT2NE20089610 | 1156 | 1976 ... 2329 | 3599 |
| NT2NE20089970 | 1157 | 150 ... 488 | 3600 |
| NT2NE20108540 | 1158 | 504 ... 806 | 3601 |
| NT2NE20110360 | 1159 | 44 ... 415 | 3602 |
| NT2NE20118960 | 1160 | 197 ... 2044 | 3603 |
| NT2NE20122430 | 1161 | 1474 ... 2016 | 3604 |
| NT2NE20124480 | 1162 | 135 ... 482 | 3605 |
| NT2NE20125050 | 1163 | 59 ... 1462 | 3606 |
| NT2NE20130190 | 1164 | 728 ... 1438 | 3607 |
| NT2NE20131890 | 1165 | 2276 ... 2611 | 3608 |
| NT2NE20132170 | 1166 | 585 ... 1694 | 3609 |
| NT2NE20142210 | 1167 | 177 ... 2585 | 3610 |
| NT2NE20146810 | 1168 | 387 ... 707 | 3611 |
| NT2NE20152750 | 1169 | 190 ... 726 | 3612 |
| NT2NE20155110 | 1170 | 486 ... 893 | 3613 |
| NT2NE20156260 | 1171 | 286 ... 633 | 3614 |
| NT2NE20157470 | 1172 | 222 ... 1199 | 3615 |
| NT2NE20158600 | 1173 | 348 ... 749 | 3616 |
| NT2NE20159740 | 1174 | 68 ... 664 | 3617 |
| NT2NE20172590 | 1175 | 799 ... 1131 | 3618 |
| NT2NE20174800 | 1176 | 525 ... 860 | 3619 |
| NT2NE20174920 | 1177 | 53 ... 538 | 3620 |
| NT2NE20177520 | 1178 | 636 ... 2108 | 3621 |
| NT2NE20181650 | 1179 | 496 ... 1605 | 3622 |
| NT2NE20183760 | 1180 | 1087 ... 1548 | 3623 |
| NT2NE20184900 | 1181 | 2947 ... >3371 | 3624 |
| NT2NE20187390 | 1182 | 170 ... 580 | 3625 |
| NT2RI20001330 | 1183 | 84 ... 1901 | 3626 |
| NT2RI20003480 | 1184 | 166 ... 1905 | 3627 |
| NT2RI20005750 | 1185 | 66 ... 1088 | 3628 |
| NT2RI20009870 | 1186 | 127 ... 1053 | 3629 |
| NT2RI20022600 | 1187 | 1040 ... 1621 | 3630 |
| NT2RI20023160 | 1188 | 165 ... 947 | 3631 |
| NT2RI20023590 | 1189 | 666 ... 1058 | 3632 |
| NT2RI20023910 | 1190 | 546 ... 2945 | 3633 |
| NT2RI20025400 | 1191 | 315 ... 902 | 3634 |
| NT2RI20025640 | 1192 | 989 ... 1660 | 3635 |
| NT2RI20028470 | 1193 | 140 ... 1297 | 3636 |
| NT2RI20036670 | 1194 | 334 ... 852 | 3637 |
| NT2RI20040930 | 1195 | 362 ... 1075 | 3638 |
| NT2RI20040990 | 1196 | 124 ... 2169 | 3639 |
| NT2RI20041880 | 1197 | 79 ... 1368 | 3640 |
| NT2RI20046080 | 1198 | 36 ... 824 | 3641 |
| NT2RI20048840 | 1199 | 330 ... 1349 | 3642 |
| NT2RI20050960 | 1200 | 223 ... 1701 | 3643 |
| NT2RI20054050 | 1201 | 172 ... 2154 | 3644 |
| NT2RI20055790 | 1202 | 489 ... 1178 | 3645 |
| NT2RI20056700 | 1203 | 115 ... 1491 | 3646 |
| NT2RI20069730 | 1204 | 607 ... 1209 | 3647 |
| NT2RI20076290 | 1205 | 145 ... 1197 | 3648 |
| NT2RI20086220 | 1206 | 67 ... 1068 | 3649 |
| NT2RI20091730 | 1207 | 113 ... >2585 | 3650 |
| NT2RI20091940 | 1208 | 699 ... 1181 | 3651 |
| NT2RI20198260 | 1209 | 70 ... 372 | 3652 |
| NT2RI20203900 | 1210 | 176 ... 481 | 3653 |
| NT2RI20217030 | 1211 | 33 ... 1181 | 3654 |
| NT2RI20216250 | 1212 | 812 ... 1312 | 3655 |
| NT2RI20240080 | 1213 | 176 ... 1090 | 3656 |
| NT2RI20244600 | 1214 | 195 ... 1010 | 3657 |
| NT2RI20244960 | 1215 | 161 ... 595 | 3658 |
| NT2RI20250750 | 1216 | 263 ... 1186 | 3659 |
| NT2RI20252550 | 1217 | 927 ... 1622 | 3660 |
| NT2RI20273230 | 1218 | 40 ... 1215 | 3661 |
| NT2RP60000770 | 1219 | 1147 ... 2223 | 3662 |
| NT2RP60000850 | 1220 | 44 ... >2927 | 3663 |
| NT2RP70010740 | 1221 | 23 ... 466 | 3664 |
| NT2RP70027380 | 1222 | 86 ... 3466 | 3665 |
| NT2RP70032610 | 1223 | 1348 ... 2514 | 3666 |
| NT2RP70036880 | 1224 | 145 ... 1491 | 3667 |
| NT2RP70037240 | 1225 | 221 ... 2002 | 3668 |
| NT2RP70043480 | 1226 | 134 ... 1912 | 3669 |
| NT2RP70044280 | 1227 | 91 ... 1506 | 3670 |
| NT2RP70045590 | 1228 | 29 ... 877 | 3671 |
| NT2RP70056750 | 1229 | 177 ... 3578 | 3672 |
| NT2RP70062230 | 1230 | 310 ... 2748 | 3673 |
| NT2RP70063950 | 1231 | 499 ... 3750 | 3674 |
| NT2RP70072690 | 1232 | 1108 ... 1545 | 3675 |

TABLE 1-continued

| Clone name | SEQ ID NO. of nucleotide sequence | Position of CDS | SEQ ID NO. of amino acid sequence |
|---|---|---|---|
| NT2RP70075240 | 1233 | 308 . . . 814 | 3676 |
| NT2RP70077660 | 1234 | 2025 . . . 2441 | 3677 |
| NT2RP70078420 | 1235 | 622 . . . 2025 | 3678 |
| NT2RP70080850 | 1236 | 59 . . . 4003 | 3679 |
| NT2RP70081610 | 1237 | 41 . . . 730 | 3680 |
| NT2RP70085440 | 1238 | 1856 . . . 2317 | 3681 |
| NT2RP70102350 | 1239 | 225 . . . 1043 | 3682 |
| NT2RP70105210 | 1240 | 132 . . . 1880 | 3683 |
| NT2RP70110860 | 1241 | 803 . . . 1129 | 3684 |
| NT2RP70111320 | 1242 | 271 . . . 627 | 3685 |
| NT2RP70122910 | 1243 | 789 . . . 1112 | 3686 |
| NT2RP70125160 | 1244 | 10 . . . 624 | 3687 |
| NT2RP70130020 | 1245 | 372 . . . 692 | 3688 |
| NT2RP70133740 | 1246 | 109 . . . 972 | 3689 |
| NT2RP70134990 | 1247 | 24 . . . 392 | 3690 |
| NT2RP70137290 | 1248 | 10 . . . 381 | 3691 |
| NT2RP70137640 | 1249 | 315 . . . >2113 | 3692 |
| NT2RP70143480 | 1250 | 482 . . . 1177 | 3693 |
| NT2RP70147210 | 1251 | 258 . . . 566 | 3694 |
| NT2RP70150800 | 1252 | 32 . . . 445 | 3695 |
| NT2RP70157890 | 1253 | 170 . . . 1006 | 3696 |
| NT2RP70159960 | 1254 | 308 . . . 967 | 3697 |
| NT2RP70169110 | 1255 | 123 . . . 485 | 3698 |
| NT2RP70175670 | 1256 | 89 . . . 421 | 3699 |
| NT2RP70179710 | 1257 | 94 . . . 2604 | 3700 |
| NT2RP70181970 | 1258 | 59 . . . 364 | 3701 |
| NT2RP70188020 | 1259 | 380 . . . 796 | 3702 |
| NT2RP70188710 | 1260 | 491 . . . 1024 | 3703 |
| NT2RP70190640 | 1261 | 72 . . . 1880 | 3704 |
| NT2RP70192730 | 1262 | 180 . . . 1253 | 3705 |
| NT2RP70194450 | 1263 | 1074 . . . 1901 | 3706 |
| NT2RP70195430 | 1264 | 201 . . . 1256 | 3707 |
| NT2RP70198350 | 1265 | 131 . . . 832 | 3708 |
| NT2RP70203790 | 1266 | 2156 . . . >2479 | 3709 |
| NTONG20009770 | 1267 | 124 . . . 1947 | 3710 |
| NTONG20013620 | 1268 | 1798 . . . 2325 | 3711 |
| NTONG20015870 | 1269 | 65 . . . 1627 | 3712 |
| NTONG20028070 | 1270 | 9 . . . 545 | 3713 |
| NTONG20029480 | 1271 | 318 . . . 1898 | 3714 |
| NTONG20029700 | 1272 | 242 . . . 1693 | 3715 |
| NTONG20046140 | 1273 | 308 . . . 1108 | 3716 |
| NTONG20048060 | 1274 | 1488 . . . 1961 | 3717 |
| NTONG20049910 | 1275 | 47 . . . 679 | 3718 |
| NTONG20050620 | 1276 | 141 . . . 521 | 3719 |
| NTONG20050860 | 1277 | 59 . . . 877 | 3720 |
| NTONG20051530 | 1278 | 78 . . . 1697 | 3721 |
| NTONG20052650 | 1279 | 84 . . . >2351 | 3722 |
| NTONG20056570 | 1280 | 226 . . . 1326 | 3723 |
| NTONG20061870 | 1281 | 100 . . . 996 | 3724 |
| NTONG20063010 | 1282 | 219 . . . 1856 | 3725 |
| NTONG20064400 | 1283 | 11 . . . 1330 | 3726 |
| NTONG20064840 | 1284 | 1500 . . . 2447 | 3727 |
| NTONG20065010 | 1285 | 156 . . . 494 | 3728 |
| NTONG20066460 | 1286 | 121 . . . 1458 | 3729 |
| NTONG20067090 | 1287 | 1046 . . . 1513 | 3730 |
| NTONG20067830 | 1288 | 17 . . . 1006 | 3731 |
| NTONG20070200 | 1289 | 318 . . . 1418 | 3732 |
| NTONG20070340 | 1290 | 284 . . . 1228 | 3733 |
| NTONG20075220 | 1291 | 242 . . . >2591 | 3734 |
| NTONG20076930 | 1292 | 26 . . . 1534 | 3735 |
| NTONG20077560 | 1293 | 241 . . . 567 | 3736 |
| NTONG20083650 | 1294 | 242 . . . 1711 | 3737 |
| NTONG20088620 | 1295 | 60 . . . >2536 | 3738 |
| NTONG20090600 | 1296 | 517 . . . 1134 | 3739 |
| NTONG20090680 | 1297 | 673 . . . 1389 | 3740 |
| NTONG20092290 | 1298 | 307 . . . 1539 | 3741 |
| NTONG20092330 | 1299 | 229 . . . 2235 | 3742 |
| OCBBF10000540 | 1300 | 858 . . . 1916 | 3743 |
| OCBBF10001750 | 1301 | 245 . . . 1144 | 3744 |
| OCBBF10001850 | 1302 | 419 . . . 2233 | 3745 |
| OCBBF20005230 | 1303 | 56 . . . 640 | 3746 |
| OCBBF20006770 | 1304 | 29 . . . 2275 | 3747 |
| OCBBF20013890 | 1305 | 1978 . . . 2289 | 3748 |
| OCBBF20019380 | 1306 | 69 . . . 1364 | 3749 |
| OCBBF20019830 | 1307 | 325 . . . 1536 | 3750 |
| OCBBF20020150 | 1308 | 2507 . . . 2917 | 3751 |
| OCBBF20020830 | 1309 | 92 . . . 2869 | 3752 |
| OCBBF20022900 | 1310 | 88 . . . 1779 | 3753 |
| OCBBF20023570 | 1311 | 47 . . . 1276 | 3754 |
| OCBBF20026630 | 1312 | 18 . . . 455 | 3755 |
| OCBBF20028050 | 1313 | 128 . . . 1108 | 3756 |
| OCBBF20028650 | 1314 | 706 . . . 2286 | 3757 |
| OCBBF20029800 | 1315 | 334 . . . 699 | 3758 |
| OCBBF20030280 | 1316 | 263 . . . 898 | 3759 |
| OCBBF20030910 | 1317 | 383 . . . 1258 | 3760 |
| OCBBF20032460 | 1318 | 347 . . . 805 | 3761 |
| OCBBF20035930 | 1319 | 65 . . . 895 | 3762 |
| OCBBF20037440 | 1320 | 413 . . . 1024 | 3763 |
| OCBBF20039250 | 1321 | 24 . . . 821 | 3764 |
| OCBBF20041680 | 1322 | 967 . . . 1278 | 3765 |
| OCBBF20045330 | 1323 | 1407 . . . 1886 | 3766 |
| OCBBF20046120 | 1324 | 82 . . . 1641 | 3767 |
| OCBBF20046470 | 1325 | 400 . . . 1137 | 3768 |
| OCBBF20046690 | 1326 | 156 . . . 1730 | 3769 |
| OCBBF20047570 | 1327 | 182 . . . 577 | 3770 |
| OCBBF20048660 | 1328 | 292 . . . 663 | 3771 |
| OCBBF20049300 | 1329 | 721 . . . 2553 | 3772 |
| OCBBF20049840 | 1330 | 246 . . . >2607 | 3773 |
| OCBBF20050770 | 1331 | 724 . . . >2679 | 3774 |
| OCBBF20051610 | 1332 | 41 . . . 493 | 3775 |
| OCBBF20053430 | 1333 | 586 . . . 2478 | 3776 |
| OCBBF20053490 | 1334 | 736 . . . 1068 | 3777 |
| OCBBF20053730 | 1335 | 87 . . . 2090 | 3778 |
| OCBBF20054200 | 1336 | 315 . . . 869 | 3779 |
| OCBBF20054760 | 1337 | 195 . . . 1016 | 3780 |
| OCBBF20059560 | 1338 | 224 . . . >3045 | 3781 |
| OCBBF20060300 | 1339 | 1389 . . . 2171 | 3782 |
| OCBBF20061720 | 1340 | 711 . . . 1139 | 3783 |
| OCBBF20062140 | 1341 | 444 . . . 749 | 3784 |
| OCBBF20062410 | 1342 | 1920 . . . 2240 | 3785 |
| OCBBF20063320 | 1343 | 145 . . . 519 | 3786 |
| OCBBF20066390 | 1344 | 2159 . . . 2713 | 3787 |
| OCBBF20068490 | 1345 | 15 . . . 2702 | 3788 |
| OCBBF20071210 | 1346 | 2029 . . . 3486 | 3789 |
| OCBBF20071840 | 1347 | 45 . . . 1670 | 3790 |
| OCBBF20071960 | 1348 | 1294 . . . 1698 | 3791 |
| OCBBF20072240 | 1349 | 335 . . . 1432 | 3792 |
| OCBBF20072320 | 1350 | 1749 . . . 2087 | 3793 |
| OCBBF20073540 | 1351 | 56 . . . 1132 | 3794 |
| OCBBF20074140 | 1352 | 81 . . . >3793 | 3795 |
| OCBBF20076220 | 1353 | 1552 . . . 2013 | 3796 |
| OCBBF20078920 | 1354 | 849 . . . 1340 | 3797 |
| OCBBF20079310 | 1355 | 240 . . . 1349 | 3798 |
| OCBBF20079460 | 1356 | 12 . . . 2099 | 3799 |
| OCBBF20080050 | 1357 | 159 . . . 2150 | 3800 |
| OCBBF20080410 | 1358 | 122 . . . 1672 | 3801 |
| OCBBF20081380 | 1359 | 742 . . . 1140 | 3802 |
| OCBBF20082830 | 1360 | 139 . . . 1209 | 3803 |
| OCBBF20084660 | 1361 | 74 . . . 1621 | 3804 |
| OCBBF20085200 | 1362 | 659 . . . 1207 | 3805 |
| OCBBF20086400 | 1363 | 63 . . . 797 | 3806 |
| OCBBF20086910 | 1364 | 541 . . . 2304 | 3807 |
| OCBBF20087010 | 1365 | 325 . . . 633 | 3808 |
| OCBBF20088140 | 1366 | 1575 . . . 1916 | 3809 |
| OCBBF20088220 | 1367 | 2505 . . . 2915 | 3810 |
| OCBBF20091150 | 1368 | 256 . . . 648 | 3811 |
| OCBBF20094240 | 1369 | 82 . . . 1122 | 3812 |
| OCBBF20097720 | 1370 | 471 . . . 815 | 3813 |
| OCBBF20100400 | 1371 | 407 . . . 3043 | 3814 |
| OCBBF20103130 | 1372 | 114 . . . 1439 | 3815 |
| OCBBF20104040 | 1373 | 310 . . . 612 | 3816 |
| OCBBF20105570 | 1374 | 2404 . . . 2874 | 3817 |
| OCBBF20107090 | 1375 | 127 . . . 1935 | 3818 |
| OCBBF20107920 | 1376 | 1692 . . . 2018 | 3819 |
| OCBBF20108190 | 1377 | 278 . . . 1591 | 3820 |
| OCBBF20108430 | 1378 | 832 . . . 1851 | 3821 |
| OCBBF20108580 | 1379 | 1152 . . . 2354 | 3822 |
| OCBBF20108630 | 1380 | 249 . . . 1133 | 3823 |
| OCBBF20109310 | 1381 | 34 . . . 2355 | 3824 |
| OCBBF20111770 | 1382 | 291 . . . 629 | 3825 |

TABLE 1-continued

| Clone name | SEQ ID NO. of nucleotide sequence | Position of CDS | SEQ ID NO. of amino acid sequence |
|---|---|---|---|
| OCBBF20116850 | 1383 | 117 ... 2354 | 3826 |
| OCBBF20118970 | 1384 | 361 ... 855 | 3827 |
| OCBBF20120390 | 1385 | 129 ... 2282 | 3828 |
| OCBBF20121390 | 1386 | 524 ... 2254 | 3829 |
| OCBBF20122620 | 1387 | 990 ... 1544 | 3830 |
| OCBBF20124360 | 1388 | 1223 ... 1951 | 3831 |
| OCBBF20125530 | 1389 | 379 ... 2310 | 3832 |
| OCBBF20126780 | 1390 | 1270 ... 1599 | 3833 |
| OCBBF20127040 | 1391 | 177 ... 2327 | 3834 |
| OCBBF20127140 | 1392 | 1018 ... 1530 | 3835 |
| OCBBF20127550 | 1393 | 103 ... >2362 | 3836 |
| OCBBF20128120 | 1394 | 118 ... 1311 | 3837 |
| OCBBF20129360 | 1395 | 378 ... >3283 | 3838 |
| OCBBF20130110 | 1396 | 132 ... 452 | 3839 |
| OCBBF20130910 | 1397 | 2527 ... 2892 | 3840 |
| OCBBF20132850 | 1398 | 1172 ... 3331 | 3841 |
| OCBBF20139260 | 1399 | 772 ... 2592 | 3842 |
| OCBBF20140640 | 1400 | 241 ... 894 | 3843 |
| OCBBF20140890 | 1401 | 39 ... >4369 | 3844 |
| OCBBF20145760 | 1402 | 894 ... 1757 | 3845 |
| OCBBF20148280 | 1403 | 87 ... 1787 | 3846 |
| OCBBF20148730 | 1404 | 50 ... 1855 | 3847 |
| OCBBF20149280 | 1405 | 1385 ... 2035 | 3848 |
| OCBBF20151150 | 1406 | 135 ... 2216 | 3849 |
| OCBBF20153340 | 1407 | 135 ... >2621 | 3850 |
| OCBBF20153350 | 1408 | 1616 ... 1942 | 3851 |
| OCBBF20155060 | 1409 | 102 ... 3245 | 3852 |
| OCBBF20164050 | 1410 | 50 ... 370 | 3853 |
| OCBBF20164670 | 1411 | 40 ... 1077 | 3854 |
| OCBBF20170690 | 1412 | 159 ... 503 | 3855 |
| OCBBF20173060 | 1413 | 63 ... 383 | 3856 |
| OCBBF20173250 | 1414 | 315 ... 692 | 3857 |
| OCBBF20173980 | 1415 | 262 ... 1857 | 3858 |
| OCBBF20178150 | 1416 | 1245 ... 2231 | 3859 |
| OCBBF20178880 | 1417 | 2740 ... 3207 | 3860 |
| OCBBF20178990 | 1418 | 1328 ... 1819 | 3861 |
| OCBBF20180120 | 1419 | 218 ... 1780 | 3862 |
| OCBBF20180840 | 1420 | 1169 ... 1540 | 3863 |
| OCBBF20186870 | 1421 | 1278 ... 1736 | 3864 |
| OCBBF20188730 | 1422 | 320 ... 766 | 3865 |
| OCBBF20189560 | 1423 | 1512 ... 2165 | 3866 |
| PANCR10000910 | 1424 | 1219 ... >1943 | 3867 |
| PEBLM10000240 | 1425 | 306 ... 674 | 3868 |
| PEBLM10000710 | 1426 | 1719 ... 1940 | 3869 |
| PEBLM20013120 | 1427 | 26 ... 952 | 3870 |
| PEBLM20024320 | 1428 | 612 ... 1406 | 3871 |
| PEBLM20024550 | 1429 | 1179 ... 1499 | 3872 |
| PEBLM20040150 | 1430 | 1731 ... 2165 | 3873 |
| PEBLM20042900 | 1431 | 226 ... >2439 | 3874 |
| PEBLM20044520 | 1432 | 922 ... 1974 | 3875 |
| PEBLM20052820 | 1433 | 411 ... 782 | 3876 |
| PEBLM20060310 | 1434 | 1731 ... >2083 | 3877 |
| PEBLM20060360 | 1435 | 58 ... 330 | 3878 |
| PEBLM20060490 | 1436 | 431 ... 892 | 3879 |
| PEBLM20071880 | 1437 | 497 ... 814 | 3880 |
| PEBLM20072960 | 1438 | 128 ... 1093 | 3881 |
| PEBLM20074370 | 1439 | 60 ... 458 | 3882 |
| PEBLM20075980 | 1440 | 53 ... 1153 | 3883 |
| PEBLM20078320 | 1441 | 5 ... 1672 | 3884 |
| PEBLM20085760 | 1442 | 122 ... 763 | 3885 |
| PERIC10000250 | 1443 | 689 ... 1516 | 3886 |
| PERIC20002140 | 1444 | 151 ... 1239 | 3887 |
| PERIC20003860 | 1445 | 33 ... 359 | 3888 |
| PERIC20003870 | 1446 | 40 ... 2817 | 3889 |
| PERIC20004220 | 1447 | 130 ... 1935 | 3890 |
| PERIC20004780 | 1448 | 132 ... 956 | 3891 |
| PLACE50000660 | 1449 | 329 ... 2527 | 3892 |
| PLACE60003480 | 1450 | 35 ... 877 | 3893 |
| PLACE60004630 | 1451 | 216 ... 533 | 3894 |
| PLACE60060420 | 1452 | 34 ... 246 | 3895 |
| PLACE60079250 | 1453 | 336 ... >3307 | 3896 |
| PLACE60086400 | 1454 | 279 ... 764 | 3897 |
| PLACE60119750 | 1455 | 28 ... 570 | 3898 |
| PLACE60121080 | 1456 | 769 ... 1182 | 3899 |
| PLACE60136500 | 1457 | 1900 ... 2241 | 3900 |
| PLACE60136720 | 1458 | 78 ... 2519 | 3901 |
| PLACE60138830 | 1459 | 750 ... 1202 | 3902 |
| PLACE60153220 | 1460 | 247 ... 561 | 3903 |
| PLACE60155130 | 1461 | 833 ... 1171 | 3904 |
| PLACE60161600 | 1462 | 77 ... 1099 | 3905 |
| PLACE60169420 | 1463 | 165 ... 1097 | 3906 |
| PLACE60177140 | 1464 | 1321 ... 2190 | 3907 |
| PLACE60181070 | 1465 | 1355 ... 1708 | 3908 |
| PLACE60187690 | 1466 | 1606 ... 1941 | 3909 |
| PLACE60188340 | 1467 | 430 ... 1224 | 3910 |
| PROST10003220 | 1468 | 187 ... 933 | 3911 |
| PROST10004800 | 1469 | 87 ... 419 | 3912 |
| PROST20005050 | 1470 | 673 ... 1164 | 3913 |
| PROST20005670 | 1471 | 1132 ... >2293 | 3914 |
| PROST20021010 | 1472 | 612 ... 926 | 3915 |
| PROST20024890 | 1473 | 14 ... 514 | 3916 |
| PROST20029270 | 1474 | 1016 ... 1363 | 3917 |
| PROST20047270 | 1475 | 1300 ... 2250 | 3918 |
| PROST20047390 | 1476 | 163 ... 2283 | 3919 |
| PROST20050670 | 1477 | 1622 ... 2074 | 3920 |
| PROST20052280 | 1478 | 326 ... 634 | 3921 |
| PROST20057930 | 1479 | 237 ... >2116 | 3922 |
| PROST20059040 | 1480 | 1047 ... 1355 | 3923 |
| PROST20066880 | 1481 | 1937 ... 2521 | 3924 |
| PROST20079500 | 1482 | 863 ... 1957 | 3925 |
| PROST20083600 | 1483 | 209 ... 1087 | 3926 |
| PROST20087700 | 1484 | 481 ... 1287 | 3927 |
| PROST20097950 | 1485 | 91 ... 405 | 3928 |
| PROST20100460 | 1486 | 63 ... 1796 | 3929 |
| PROST20104000 | 1487 | 1059 ... 2012 | 3930 |
| PROST20107820 | 1488 | 304 ... 1524 | 3931 |
| PROST20111050 | 1489 | 772 ... 1281 | 3932 |
| PROST20112970 | 1490 | 66 ... 671 | 3933 |
| PROST20114390 | 1491 | 1291 ... 1749 | 3934 |
| PROST20116600 | 1492 | 4 ... 339 | 3935 |
| PROST20120050 | 1493 | 176 ... 589 | 3936 |
| PROST20120160 | 1494 | 283 ... 597 | 3937 |
| PROST20121900 | 1495 | 68 ... 385 | 3938 |
| PROST20123530 | 1496 | 1619 ... 2044 | 3939 |
| PROST20127400 | 1497 | 1156 ... 1524 | 3940 |
| PROST20127800 | 1498 | 942 ... 2120 | 3941 |
| PROST20130530 | 1499 | 416 ... 1588 | 3942 |
| PROST20132600 | 1500 | 1447 ... 2040 | 3943 |
| PROST20133270 | 1501 | 2 ... 529 | 3944 |
| PROST20144220 | 1502 | 1011 ... 1367 | 3945 |
| PROST20146010 | 1503 | 298 ... 1953 | 3946 |
| PROST20149160 | 1504 | 1677 ... 1991 | 3947 |
| PROST20149250 | 1505 | 635 ... 1201 | 3948 |
| PROST20151240 | 1506 | 300 ... 938 | 3949 |
| PROST20152460 | 1507 | 1542 ... 2084 | 3950 |
| PROST20153320 | 1508 | 184 ... 540 | 3951 |
| PROST20159240 | 1509 | 286 ... 612 | 3952 |
| PROST20161950 | 1510 | 90 ... 716 | 3953 |
| PROST20164440 | 1511 | 2570 ... 3004 | 3954 |
| PROST20166680 | 1512 | 53 ... 874 | 3955 |
| PROST20168290 | 1513 | 1757 ... 2143 | 3956 |
| PROST20169800 | 1514 | 168 ... 1763 | 3957 |
| PROST20170980 | 1515 | 28 ... 1245 | 3958 |
| PROST20171280 | 1516 | 306 ... 1493 | 3959 |
| PROST20175290 | 1517 | 1538 ... 2323 | 3960 |
| PROST20176170 | 1518 | 998 ... 2053 | 3961 |
| PROST20178360 | 1519 | 72 ... 566 | 3962 |
| PROST20185830 | 1520 | 1200 ... 2015 | 3963 |
| PROST20189770 | 1521 | 219 ... 2018 | 3964 |
| PROST20191640 | 1522 | 318 ... 1229 | 3965 |
| PUAEN10000850 | 1523 | 121 ... 2040 | 3966 |
| PUAEN20003740 | 1524 | 104 ... 409 | 3967 |
| PUAEN20011880 | 1525 | 28 ... 2028 | 3968 |
| PUAEN20015260 | 1526 | 141 ... 881 | 3969 |
| PUAEN20015860 | 1527 | 71 ... 1846 | 3970 |
| PUAEN20018820 | 1528 | 41 ... 1870 | 3971 |
| PUAEN20025680 | 1529 | 667 ... 1584 | 3972 |
| PUAEN20027580 | 1530 | 36 ... 512 | 3973 |
| PUAEN20030180 | 1531 | 127 ... 978 | 3974 |
| PUAEN20040670 | 1532 | 326 ... 2644 | 3975 |

TABLE 1-continued

| Clone name | SEQ ID NO. of nucleotide sequence | Position of CDS | SEQ ID NO. of amino acid sequence |
|---|---|---|---|
| PUAEN20044000 | 1533 | 541 . . . 957 | 3976 |
| PUAEN20045110 | 1534 | 335 . . . 886 | 3977 |
| PUAEN20045250 | 1535 | 335 . . . 1054 | 3978 |
| PUAEN20051100 | 1536 | 228 . . . 1319 | 3979 |
| PUAEN20052470 | 1537 | 1699 . . . 2046 | 3980 |
| PUAEN20055020 | 1538 | 295 . . . 2553 | 3981 |
| PUAEN20078980 | 1539 | 6 . . . 989 | 3982 |
| PUAEN20081230 | 1540 | 62 . . . 469 | 3983 |
| PUAEN20083140 | 1541 | 104 . . . 1687 | 3984 |
| PUAEN20085150 | 1542 | 167 . . . 502 | 3985 |
| PUAEN20108240 | 1543 | 2 . . . 1993 | 3986 |
| RECTM10001410 | 1544 | 426 . . . 1631 | 3987 |
| RECTM20003490 | 1545 | 876 . . . 1193 | 3988 |
| RECTM20005100 | 1546 | 149 . . . 1273 | 3989 |
| SALGL10001710 | 1547 | 271 . . . 1722 | 3990 |
| SKMUS20001980 | 1548 | 75 . . . 1034 | 3991 |
| SKMUS20003610 | 1549 | 86 . . . 910 | 3992 |
| SKMUS20007010 | 1550 | 24 . . . 977 | 3993 |
| SKMUS20007800 | 1551 | 708 . . . >1835 | 3994 |
| SKMUS20011640 | 1552 | 16 . . . 408 | 3995 |
| SKMUS20012010 | 1553 | 300 . . . 1019 | 3996 |
| SKMUS20016220 | 1554 | 80 . . . 1267 | 3997 |
| SKMUS20018230 | 1555 | 98 . . . 442 | 3998 |
| SKMUS20018500 | 1556 | 273 . . . 1172 | 3999 |
| SKMUS20020840 | 1557 | 79 . . . 1014 | 4000 |
| SKMUS20021530 | 1558 | 432 . . . 2135 | 4001 |
| SKMUS20024750 | 1559 | 201 . . . 1208 | 4002 |
| SKMUS20028210 | 1560 | 358 . . . 753 | 4003 |
| SKMUS20028400 | 1561 | 18 . . . 644 | 4004 |
| SKMUS20029200 | 1562 | 174 . . . 1130 | 4005 |
| SKMUS20031680 | 1563 | 171 . . . 485 | 4006 |
| SKMUS20046670 | 1564 | 234 . . . 617 | 4007 |
| SKMUS20048970 | 1565 | 104 . . . 1132 | 4008 |
| SKMUS20049030 | 1566 | 191 . . . 1096 | 4009 |
| SKMUS20077400 | 1567 | 170 . . . 772 | 4010 |
| SKMUS20084740 | 1568 | 83 . . . >1516 | 4011 |
| SKNMC20006220 | 1569 | 1176 . . . 1856 | 4012 |
| SKNSH20008190 | 1570 | 490 . . . 2289 | 4013 |
| SKNSH20020540 | 1571 | 2184 . . . 2924 | 4014 |
| SKNSH20028660 | 1572 | 192 . . . 581 | 4015 |
| SKNSH20031740 | 1573 | 120 . . . 563 | 4016 |
| SKNSH20034660 | 1574 | 562 . . . 996 | 4017 |
| SKNSH20051940 | 1575 | 1006 . . . 1488 | 4018 |
| SKNSH20062340 | 1576 | 85 . . . 453 | 4019 |
| SKNSH20063040 | 1577 | 91 . . . 768 | 4020 |
| SKNSH20080430 | 1578 | 81 . . . 524 | 4021 |
| SKNSH20087770 | 1579 | 107 . . . >1808 | 4022 |
| SKNSH20089400 | 1580 | 34 . . . 1092 | 4023 |
| SKNSH20091970 | 1581 | 181 . . . 489 | 4024 |
| SMINT20001760 | 1582 | 267 . . . 1706 | 4025 |
| SMINT20005410 | 1583 | 138 . . . 557 | 4026 |
| SMINT20008240 | 1584 | 1123 . . . 1500 | 4027 |
| SMINT20009840 | 1585 | 31 . . . 750 | 4028 |
| SMINT20011140 | 1586 | 1254 . . . 1664 | 4029 |
| SMINT20011580 | 1587 | 131 . . . 811 | 4030 |
| SMINT20011990 | 1588 | 132 . . . 512 | 4031 |
| SMINT20013480 | 1589 | 87 . . . 686 | 4032 |
| SMINT20014580 | 1590 | 57 . . . 410 | 4033 |
| SMINT20015590 | 1591 | 1375 . . . 1818 | 4034 |
| SMINT20022020 | 1592 | 133 . . . 726 | 4035 |
| SMINT20023280 | 1593 | 890 . . . 1345 | 4036 |
| SMINT20024570 | 1594 | 1852 . . . 2370 | 4037 |
| SMINT20026890 | 1595 | 541 . . . 2790 | 4038 |
| SMINT20028820 | 1596 | 1240 . . . 1749 | 4039 |
| SMINT20029760 | 1597 | 236 . . . 1282 | 4040 |
| SMINT20033170 | 1598 | 539 . . . 931 | 4041 |
| SMINT20033400 | 1599 | 20 . . . 778 | 4042 |
| SMINT20035690 | 1600 | 11 . . . 1411 | 4043 |
| SMINT20040860 | 1601 | 39 . . . 1169 | 4044 |
| SMINT20042990 | 1602 | 397 . . . 750 | 4045 |
| SMINT20047810 | 1603 | 109 . . . 588 | 4046 |
| SMINT20049090 | 1604 | 99 . . . 641 | 4047 |
| SMINT20050750 | 1605 | 101 . . . 907 | 4048 |
| SMINT20051610 | 1606 | 56 . . . 1513 | 4049 |
| SMINT20053300 | 1607 | 1251 . . . 1598 | 4050 |
| SMINT20053870 | 1608 | 85 . . . 894 | 4051 |
| SMINT20056210 | 1609 | 356 . . . 754 | 4052 |
| SMINT20058000 | 1610 | 200 . . . 565 | 4053 |
| SMINT20060780 | 1611 | 18 . . . 554 | 4054 |
| SMINT20065960 | 1612 | 859 . . . 1314 | 4055 |
| SMINT20068010 | 1613 | 136 . . . 1026 | 4056 |
| SMINT20071400 | 1614 | 212 . . . 1183 | 4057 |
| SMINT20073650 | 1615 | 59 . . . 1549 | 4058 |
| SMINT20076470 | 1616 | 1678 . . . 1983 | 4059 |
| SMINT20080540 | 1617 | 1280 . . . 1606 | 4060 |
| SMINT20089170 | 1618 | 54 . . . 530 | 4061 |
| SMINT20092330 | 1619 | 169 . . . 858 | 4062 |
| SMINT20092720 | 1620 | 1640 . . . 2293 | 4063 |
| SMINT20095050 | 1621 | 733 . . . 1107 | 4064 |
| SMINT20098320 | 1622 | 112 . . . 465 | 4065 |
| SMINT20100680 | 1623 | 237 . . . 614 | 4066 |
| SMINT20101440 | 1624 | 187 . . . 2109 | 4067 |
| SMINT20102780 | 1625 | 26 . . . 1642 | 4068 |
| SMINT20103690 | 1626 | 208 . . . 960 | 4069 |
| SMINT20105000 | 1627 | 194 . . . 514 | 4070 |
| SMINT20105330 | 1628 | 1580 . . . 2020 | 4071 |
| SMINT20106290 | 1629 | 501 . . . 1802 | 4072 |
| SMINT20106720 | 1630 | 80 . . . 1498 | 4073 |
| SMINT20108530 | 1631 | 185 . . . 523 | 4074 |
| SMINT20109970 | 1632 | 1444 . . . >1974 | 4075 |
| SMINT20110330 | 1633 | 1398 . . . 2222 | 4076 |
| SMINT20110660 | 1634 | 1108 . . . 1500 | 4077 |
| SMINT20112730 | 1635 | 80 . . . 1564 | 4078 |
| SMINT20115880 | 1636 | 679 . . . 1746 | 4079 |
| SMINT20121220 | 1637 | 263 . . . >1798 | 4080 |
| SMINT20121950 | 1638 | 6 . . . 443 | 4081 |
| SMINT20122850 | 1639 | 454 . . . 777 | 4082 |
| SMINT20122910 | 1640 | 1516 . . . 2094 | 4083 |
| SMINT20127350 | 1641 | 622 . . . 1449 | 4084 |
| SMINT20127930 | 1642 | 67 . . . 1554 | 4085 |
| SMINT20130320 | 1643 | 178 . . . 2601 | 4086 |
| SMINT20131810 | 1644 | 583 . . . 1257 | 4087 |
| SMINT20132280 | 1645 | 293 . . . 655 | 4088 |
| SMINT20136130 | 1646 | 1291 . . . 1752 | 4089 |
| SMINT20138900 | 1647 | 87 . . . 1439 | 4090 |
| SMINT20144430 | 1648 | 54 . . . 647 | 4091 |
| SMINT20144800 | 1649 | 171 . . . 1394 | 4092 |
| SMINT20144890 | 1650 | 209 . . . 520 | 4093 |
| SMINT20152940 | 1651 | 386 . . . 985 | 4094 |
| SMINT20153260 | 1652 | 135 . . . 1838 | 4095 |
| SMINT20153530 | 1653 | 1186 . . . 1524 | 4096 |
| SMINT20154540 | 1654 | 107 . . . 1339 | 4097 |
| SMINT20155180 | 1655 | 20 . . . 763 | 4098 |
| SMINT20157450 | 1656 | 669 . . . 1118 | 4099 |
| SMINT20158100 | 1657 | 30 . . . 587 | 4100 |
| SMINT20161220 | 1658 | 397 . . . 1977 | 4101 |
| SMINT20162860 | 1659 | 36 . . . 494 | 4102 |
| SMINT20163960 | 1660 | 665 . . . 1036 | 4103 |
| SMINT20164400 | 1661 | 125 . . . 706 | 4104 |
| SMINT20164770 | 1662 | 529 . . . 870 | 4105 |
| SMINT20168570 | 1663 | 1593 . . . 2069 | 4106 |
| SMINT20173190 | 1664 | 251 . . . 829 | 4107 |
| SMINT20173240 | 1665 | 253 . . . 582 | 4108 |
| SMINT20174360 | 1666 | 978 . . . 1733 | 4109 |
| SMINT20177360 | 1667 | 172 . . . 771 | 4110 |
| SMINT20178550 | 1668 | 51 . . . 692 | 4111 |
| SMINT20179740 | 1669 | 78 . . . 1865 | 4112 |
| SMINT20183530 | 1670 | 1130 . . . 2530 | 4113 |
| SMINT20190170 | 1671 | 80 . . . 1567 | 4114 |
| SMINT20191420 | 1672 | 49 . . . 1365 | 4115 |
| SMINT20191530 | 1673 | 40 . . . 2040 | 4116 |
| SMINT20192000 | 1674 | 49 . . . 435 | 4117 |
| SPLEN10000830 | 1675 | 1586 . . . 2053 | 4118 |
| SPLEN20000640 | 1676 | 27 . . . 755 | 4119 |
| SPLEN20002220 | 1677 | 87 . . . 434 | 4120 |
| SPLEN20003070 | 1678 | 684 . . . 1046 | 4121 |
| SPLEN20006070 | 1679 | 78 . . . 2837 | 4122 |
| SPLEN20008390 | 1680 | 375 . . . 2378 | 4123 |
| SPLEN20008740 | 1681 | 66 . . . 1547 | 4124 |
| SPLEN20008820 | 1682 | 31 . . . 1872 | 4125 |

TABLE 1-continued

| Clone name | SEQ ID NO. of nucleotide sequence | Position of CDS | SEQ ID NO. of amino acid sequence |
|---|---|---|---|
| SPLEN20011410 | 1683 | 199 ... 2394 | 4126 |
| SPLEN20013540 | 1684 | 978 ... 1310 | 4127 |
| SPLEN20016260 | 1685 | 906 ... 1748 | 4128 |
| SPLEN20019450 | 1686 | 180 ... 680 | 4129 |
| SPLEN20020070 | 1687 | 65 ... 451 | 4130 |
| SPLEN20021660 | 1688 | 130 ... 771 | 4131 |
| SPLEN20022230 | 1689 | 133 ... 1026 | 4132 |
| SPLEN20023140 | 1690 | 1153 ... 1605 | 4133 |
| SPLEN20026950 | 1691 | 855 ... 3383 | 4134 |
| SPLEN20027440 | 1692 | 29 ... 2488 | 4135 |
| SPLEN20029310 | 1693 | 70 ... 585 | 4136 |
| SPLEN20031600 | 1694 | 1658 ... 2083 | 4137 |
| SPLEN20032040 | 1695 | 357 ... 746 | 4138 |
| SPLEN20032190 | 1696 | 441 ... 785 | 4139 |
| SPLEN20033960 | 1697 | 16 ... 1026 | 4140 |
| SPLEN20039240 | 1698 | 1177 ... 1929 | 4141 |
| SPLEN20040600 | 1699 | 60 ... 368 | 4142 |
| SPLEN20054290 | 1700 | 187 ... 2421 | 4143 |
| SPLEN20076530 | 1701 | 254 ... 586 | 4144 |
| SPLEN20077500 | 1702 | 79 ... 1941 | 4145 |
| SPLEN20079260 | 1703 | 535 ... 1506 | 4146 |
| SPLEN20079510 | 1704 | 1880 ... >2197 | 4147 |
| SPLEN20084600 | 1705 | 13 ... 1878 | 4148 |
| SPLEN20095410 | 1706 | 816 ... 1541 | 4149 |
| SPLEN20095550 | 1707 | 193 ... >2558 | 4150 |
| SPLEN20095810 | 1708 | 248 ... 670 | 4151 |
| SPLEN20097330 | 1709 | 1448 ... 1849 | 4152 |
| SPLEN20099700 | 1710 | 91 ... >3025 | 4153 |
| SPLEN20101190 | 1711 | 1864 ... 2250 | 4154 |
| SPLEN20103950 | 1712 | 25 ... 507 | 4155 |
| SPLEN20106250 | 1713 | 295 ... 711 | 4156 |
| SPLEN20117660 | 1714 | 662 ... 1099 | 4157 |
| SPLEN20118300 | 1715 | 332 ... 1486 | 4158 |
| SPLEN20119810 | 1716 | 526 ... 1644 | 4159 |
| SPLEN20121750 | 1717 | 464 ... 1021 | 4160 |
| SPLEN20126190 | 1718 | 274 ... 2688 | 4161 |
| SPLEN20128000 | 1719 | 96 ... 1664 | 4162 |
| SPLEN20129610 | 1720 | 207 ... 557 | 4163 |
| SPLEN20140800 | 1721 | 387 ... 2144 | 4164 |
| SPLEN20141360 | 1722 | 491 ... 799 | 4165 |
| SPLEN20141990 | 1723 | 443 ... 745 | 4166 |
| SPLEN20142100 | 1724 | 301 ... 996 | 4167 |
| SPLEN20143180 | 1725 | 50 ... 448 | 4168 |
| SPLEN20144520 | 1726 | 2002 ... 2463 | 4169 |
| SPLEN20145720 | 1727 | 1205 ... >1939 | 4170 |
| SPLEN20146450 | 1728 | 362 ... 862 | 4171 |
| SPLEN20146690 | 1729 | 1966 ... 2550 | 4172 |
| SPLEN20147110 | 1730 | 313 ... 2067 | 4173 |
| SPLEN20147390 | 1731 | 169 ... 1479 | 4174 |
| SPLEN20149110 | 1732 | 2 ... 769 | 4175 |
| SPLEN20149190 | 1733 | 26 ... 364 | 4176 |
| SPLEN20149240 | 1734 | 787 ... 2490 | 4177 |
| SPLEN20150940 | 1735 | 79 ... 2385 | 4178 |
| SPLEN20151210 | 1736 | 66 ... 1715 | 4179 |
| SPLEN20152610 | 1737 | 986 ... 1453 | 4180 |
| SPLEN20152760 | 1738 | 284 ... 628 | 4181 |
| SPLEN20157300 | 1739 | 426 ... 728 | 4182 |
| SPLEN20157880 | 1740 | 35 ... 769 | 4183 |
| SPLEN20158900 | 1741 | 1643 ... 2032 | 4184 |
| SPLEN20158990 | 1742 | 843 ... 1172 | 4185 |
| SPLEN20160450 | 1743 | 552 ... 1115 | 4186 |
| SPLEN20160690 | 1744 | 734 ... 1099 | 4187 |
| SPLEN20160980 | 1745 | 124 ... 456 | 4188 |
| SPLEN20162680 | 1746 | 646 ... 2007 | 4189 |
| SPLEN20163560 | 1747 | 86 ... 2173 | 4190 |
| SPLEN20165310 | 1748 | 80 ... 1492 | 4191 |
| SPLEN20166270 | 1749 | 1134 ... 1814 | 4192 |
| SPLEN20167200 | 1750 | 223 ... 570 | 4193 |
| SPLEN20169220 | 1751 | 160 ... 576 | 4194 |
| SPLEN20169720 | 1752 | 72 ... 2492 | 4195 |
| SPLEN20170310 | 1753 | 125 ... 1039 | 4196 |
| SPLEN20171210 | 1754 | 7 ... 837 | 4197 |
| SPLEN20171470 | 1755 | 41 ... 2272 | 4198 |
| SPLEN20171890 | 1756 | 1312 ... 1716 | 4199 |
| SPLEN20172120 | 1757 | 138 ... 500 | 4200 |
| SPLEN20173510 | 1758 | 235 ... 1785 | 4201 |
| SPLEN20174260 | 1759 | 99 ... 428 | 4202 |
| SPLEN20176200 | 1760 | 36 ... 431 | 4203 |
| SPLEN20179180 | 1761 | 173 ... 1201 | 4204 |
| SPLEN20179810 | 1762 | 1374 ... 3224 | 4205 |
| SPLEN20181810 | 1763 | 641 ... 1183 | 4206 |
| SPLEN20186430 | 1764 | 80 ... 979 | 4207 |
| SPLEN20193110 | 1765 | 1744 ... 2118 | 4208 |
| SPLEN20194050 | 1766 | 1351 ... 2331 | 4209 |
| SPLEN20198110 | 1767 | 1260 ... 1562 | 4210 |
| SPLEN20204170 | 1768 | 202 ... 594 | 4211 |
| SPLEN20211220 | 1769 | 601 ... 1500 | 4212 |
| SPLEN20211570 | 1770 | 174 ... 521 | 4213 |
| SPLEN20211940 | 1771 | 241 ... 1155 | 4214 |
| SPLEN20212730 | 1772 | 979 ... 1830 | 4215 |
| SPLEN20212950 | 1773 | 283 ... 2055 | 4216 |
| SPLEN20213830 | 1774 | 137 ... 460 | 4217 |
| SPLEN20214400 | 1775 | 28 ... 387 | 4218 |
| SPLEN20214580 | 1776 | 300 ... 602 | 4219 |
| SPLEN20222270 | 1777 | 241 ... 927 | 4220 |
| SPLEN20225220 | 1778 | 672 ... 1199 | 4221 |
| SPLEN20242320 | 1779 | 136 ... 522 | 4222 |
| SPLEN20242730 | 1780 | 2343 ... 2732 | 4223 |
| SPLEN20243830 | 1781 | 197 ... 556 | 4224 |
| SPLEN20245300 | 1782 | 945 ... 1529 | 4225 |
| SPLEN20249560 | 1783 | 889 ... 1584 | 4226 |
| SPLEN20250170 | 1784 | 457 ... 3012 | 4227 |
| SPLEN20250390 | 1785 | 1327 ... 1788 | 4228 |
| SPLEN20252190 | 1786 | 1413 ... 2609 | 4229 |
| SPLEN20261440 | 1787 | 511 ... 894 | 4230 |
| SPLEN20264110 | 1788 | 1195 ... 1662 | 4231 |
| SPLEN20267650 | 1789 | 39 ... 1331 | 4232 |
| SPLEN20273950 | 1790 | 608 ... 1222 | 4233 |
| SPLEN20279950 | 1791 | 1874 ... 2518 | 4234 |
| SPLEN20280660 | 1792 | 1286 ... 1612 | 4235 |
| SPLEN20283650 | 1793 | 13 ... 621 | 4236 |
| SPLEN20284240 | 1794 | 282 ... 1175 | 4237 |
| SPLEN20292950 | 1795 | 9 ... 2456 | 4238 |
| SPLEN20293800 | 1796 | 73 ... 858 | 4239 |
| SPLEN20303970 | 1797 | 778 ... 1104 | 4240 |
| SPLEN20304950 | 1798 | 7 ... 1011 | 4241 |
| SPLEN20305620 | 1799 | 1356 ... 1853 | 4242 |
| SPLEN20329240 | 1800 | 5 ... 361 | 4243 |
| STOMA20001830 | 1801 | 81 ... 1574 | 4244 |
| STOMA20005390 | 1802 | 59 ... 1567 | 4245 |
| STOMA20005670 | 1803 | 81 ... 1478 | 4246 |
| STOMA20006400 | 1804 | 80 ... 1687 | 4247 |
| STOMA20006780 | 1805 | 41 ... 1975 | 4248 |
| STOMA20006860 | 1806 | 1272 ... 1988 | 4249 |
| STOMA20008880 | 1807 | 112 ... 1485 | 4250 |
| STOMA20010250 | 1808 | 66 ... 419 | 4251 |
| STOMA20013890 | 1809 | 2151 ... 2486 | 4252 |
| STOMA20026880 | 1810 | 548 ... 874 | 4253 |
| STOMA20032890 | 1811 | 1710 ... 2600 | 4254 |
| STOMA20034770 | 1812 | 81 ... 1583 | 4255 |
| STOMA20036460 | 1813 | 311 ... 772 | 4256 |
| STOMA20046680 | 1814 | 768 ... 1154 | 4257 |
| STOMA20048520 | 1815 | 160 ... 663 | 4258 |
| STOMA20048840 | 1816 | 936 ... 1487 | 4259 |
| STOMA20051200 | 1817 | 140 ... 619 | 4260 |
| STOMA20056640 | 1818 | 49 ... 555 | 4261 |
| STOMA20056670 | 1819 | 81 ... 1556 | 4262 |
| STOMA20057820 | 1820 | 60 ... 1226 | 4263 |
| STOMA20062130 | 1821 | 35 ... 427 | 4264 |
| STOMA20062290 | 1822 | 289 ... 693 | 4265 |
| STOMA20063250 | 1823 | 109 ... 438 | 4266 |
| STOMA20063980 | 1824 | 97 ... 480 | 4267 |
| STOMA20064470 | 1825 | 78 ... 1118 | 4268 |
| STOMA20067800 | 1826 | 35 ... 397 | 4269 |
| STOMA20069040 | 1827 | 364 ... 792 | 4270 |
| STOMA20072690 | 1828 | 351 ... 701 | 4271 |
| STOMA20076800 | 1829 | 311 ... 784 | 4272 |
| STOMA20077450 | 1830 | 780 ... 2300 | 4273 |
| STOMA20080500 | 1831 | 59 ... 1735 | 4274 |
| STOMA20083610 | 1832 | 80 ... 1564 | 4275 |

TABLE 1-continued

| Clone name | SEQ ID NO. of nucleotide sequence | Position of CDS | SEQ ID NO. of amino acid sequence |
|---|---|---|---|
| STOMA20086140 | 1833 | 201 . . . 746 | 4276 |
| STOMA20088380 | 1834 | 48 . . . 1535 | 4277 |
| STOMA20092530 | 1835 | 80 . . . 1501 | 4278 |
| STOMA20092560 | 1836 | 68 . . . 439 | 4279 |
| STOMA20092890 | 1837 | 105 . . . 1223 | 4280 |
| SYNOV20001520 | 1838 | 25 . . . 735 | 4281 |
| SYNOV20001730 | 1839 | 56 . . . 1480 | 4282 |
| SYNOV20002510 | 1840 | 79 . . . 1629 | 4283 |
| SYNOV20002790 | 1841 | 59 . . . 1480 | 4284 |
| SYNOV20002970 | 1842 | 56 . . . 1471 | 4285 |
| SYNOV20003970 | 1843 | 357 . . . 881 | 4286 |
| SYNOV20004260 | 1844 | 80 . . . 1489 | 4287 |
| SYNOV20007000 | 1845 | 55 . . . 1485 | 4288 |
| SYNOV20008240 | 1846 | 61 . . . 1494 | 4289 |
| SYNOV20009230 | 1847 | 40 . . . 1515 | 4290 |
| SYNOV20010880 | 1848 | 61 . . . 1479 | 4291 |
| SYNOV20011110 | 1849 | 56 . . . 1468 | 4292 |
| SYNOV20013000 | 1850 | 30 . . . 1433 | 4293 |
| SYNOV20013560 | 1851 | 79 . . . 1494 | 4294 |
| SYNOV20013900 | 1852 | 81 . . . 1499 | 4295 |
| SYNOV20017080 | 1853 | 466 . . . 1905 | 4296 |
| SYNOV30001840 | 1854 | 146 . . . 2443 | 4297 |
| TBAES20000590 | 1855 | 1697 . . . >2237 | 4298 |
| TBAES20002550 | 1856 | 16 . . . 1896 | 4299 |
| TBAES20003150 | 1857 | 42 . . . 1064 | 4300 |
| TBAES20003770 | 1858 | 117 . . . 3437 | 4301 |
| TCOLN20001390 | 1859 | 237 . . . 1106 | 4302 |
| TESOP20000900 | 1860 | 110 . . . 448 | 4303 |
| TESOP20003120 | 1861 | 42 . . . 929 | 4304 |
| TESOP20004000 | 1862 | 295 . . . 1125 | 4305 |
| TESOP20005270 | 1863 | 568 . . . 921 | 4306 |
| TESOP20005690 | 1864 | 230 . . . 574 | 4307 |
| TESTI10000940 | 1865 | 127 . . . 1752 | 4308 |
| TESTI20001000 | 1866 | 129 . . . 944 | 4309 |
| TESTI20001170 | 1867 | 107 . . . 1291 | 4310 |
| TESTI20001720 | 1868 | 204 . . . 722 | 4311 |
| TESTI20002720 | 1869 | 92 . . . >2187 | 4312 |
| TESTI20002780 | 1870 | 821 . . . 1471 | 4313 |
| TESTI20004890 | 1871 | 140 . . . 1231 | 4314 |
| TESTI20011200 | 1872 | 1615 . . . 1968 | 4315 |
| TESTI20017950 | 1873 | 62 . . . 2023 | 4316 |
| TESTI20018230 | 1874 | 506 . . . 1024 | 4317 |
| TESTI20023510 | 1875 | 100 . . . 1935 | 4318 |
| TESTI20029930 | 1876 | 597 . . . 1847 | 4319 |
| TESTI20030310 | 1877 | 1362 . . . 1757 | 4320 |
| TESTI20030890 | 1878 | 1736 . . . 2167 | 4321 |
| TESTI20031270 | 1879 | 820 . . . 1332 | 4322 |
| TESTI20031810 | 1880 | 235 . . . 1926 | 4323 |
| TESTI20035960 | 1881 | 80 . . . 1327 | 4324 |
| TESTI20036380 | 1882 | 125 . . . 2110 | 4325 |
| TESTI20037560 | 1883 | 16 . . . 1986 | 4326 |
| TESTI20038270 | 1884 | 42 . . . 347 | 4327 |
| TESTI20039400 | 1885 | 63 . . . 1430 | 4328 |
| TESTI20041690 | 1886 | 194 . . . 2320 | 4329 |
| TESTI20044230 | 1887 | 76 . . . 1308 | 4330 |
| TESTI20044310 | 1888 | 307 . . . 1899 | 4331 |
| TESTI20046750 | 1889 | 56 . . . 871 | 4332 |
| TESTI20057750 | 1890 | 154 . . . 495 | 4333 |
| TESTI20060400 | 1891 | 102 . . . 1754 | 4334 |
| TESTI20061110 | 1892 | 102 . . . 1574 | 4335 |
| TESTI20063830 | 1893 | 186 . . . 1793 | 4336 |
| TESTI20066670 | 1894 | 345 . . . 1823 | 4337 |
| TESTI20066770 | 1895 | 867 . . . 1937 | 4338 |
| TESTI20067200 | 1896 | 25 . . . 1149 | 4339 |
| TESTI20076850 | 1897 | 864 . . . 1307 | 4340 |
| TESTI20082330 | 1898 | 12 . . . 2249 | 4341 |
| TESTI20083200 | 1899 | 80 . . . 967 | 4342 |
| TESTI20083940 | 1900 | 60 . . . 1973 | 4343 |
| TESTI20086210 | 1901 | 65 . . . 1465 | 4344 |
| TESTI20087620 | 1902 | 116 . . . 2191 | 4345 |
| TESTI20088220 | 1903 | 318 . . . 2435 | 4346 |
| TESTI20094020 | 1904 | 341 . . . 1885 | 4347 |
| TESTI20094120 | 1905 | 402 . . . 1184 | 4348 |
| TESTI20094230 | 1906 | 1397 . . . 2158 | 4349 |
| TESTI20094470 | 1907 | 428 . . . 1540 | 4350 |
| TESTI20098350 | 1908 | 137 . . . 1849 | 4351 |
| TESTI20098530 | 1909 | 220 . . . 564 | 4352 |
| TESTI20102800 | 1910 | 278 . . . 640 | 4353 |
| TESTI20105720 | 1911 | 1542 . . . 1901 | 4354 |
| TESTI20108720 | 1912 | 101 . . . 1123 | 4355 |
| TESTI20110280 | 1913 | 212 . . . 1396 | 4356 |
| TESTI20112940 | 1914 | 579 . . . 899 | 4357 |
| TESTI20114070 | 1915 | 1575 . . . 1937 | 4358 |
| TESTI20116650 | 1916 | 43 . . . 387 | 4359 |
| TESTI20116830 | 1917 | 825 . . . 1208 | 4360 |
| TESTI20121550 | 1918 | 191 . . . 1900 | 4361 |
| TESTI20122310 | 1919 | 149 . . . 826 | 4362 |
| TESTI20123080 | 1920 | 432 . . . 767 | 4363 |
| TESTI20123560 | 1921 | 249 . . . >816 | 4364 |
| TESTI20127760 | 1922 | 149 . . . 1141 | 4365 |
| TESTI20128350 | 1923 | 178 . . . 591 | 4366 |
| TESTI20129150 | 1924 | 241 . . . 969 | 4367 |
| TESTI20129220 | 1925 | 366 . . . 773 | 4368 |
| TESTI20130010 | 1926 | 866 . . . 1420 | 4369 |
| TESTI20130120 | 1927 | 119 . . . 748 | 4370 |
| TESTI20135660 | 1928 | 961 . . . 1374 | 4371 |
| TESTI20136100 | 1929 | 71 . . . 406 | 4372 |
| TESTI20136710 | 1930 | 14 . . . >1826 | 4373 |
| TESTI20136990 | 1931 | 1903 . . . 2292 | 4374 |
| TESTI20137370 | 1932 | 37 . . . 339 | 4375 |
| TESTI20137670 | 1933 | 181 . . . 561 | 4376 |
| TESTI20143240 | 1934 | 486 . . . 908 | 4377 |
| TESTI20143390 | 1935 | 52 . . . 1068 | 4378 |
| TESTI20143620 | 1936 | 970 . . . 1332 | 4379 |
| TESTI20148000 | 1937 | 250 . . . 2004 | 4380 |
| TESTI20152460 | 1938 | 222 . . . 1499 | 4381 |
| TESTI20155900 | 1939 | 1095 . . . 1499 | 4382 |
| TESTI20156100 | 1940 | 31 . . . 1200 | 4383 |
| TESTI20157100 | 1941 | 481 . . . 1149 | 4384 |
| TESTI20157520 | 1942 | 55 . . . >1880 | 4385 |
| TESTI20159140 | 1943 | 424 . . . >1611 | 4386 |
| TESTI20161970 | 1944 | 138 . . . 1658 | 4387 |
| TESTI20164100 | 1945 | 60 . . . 470 | 4388 |
| TESTI20168480 | 1946 | 91 . . . 1341 | 4389 |
| TESTI20168630 | 1947 | 1219 . . . 1608 | 4390 |
| TESTI20168960 | 1948 | 37 . . . 570 | 4391 |
| TESTI20169960 | 1949 | 801 . . . 1139 | 4392 |
| TESTI20170350 | 1950 | 1106 . . . 1429 | 4393 |
| TESTI20171020 | 1951 | 11 . . . >2194 | 4394 |
| TESTI20178160 | 1952 | 1084 . . . 1452 | 4395 |
| TESTI20179320 | 1953 | 191 . . . 664 | 4396 |
| TESTI20183370 | 1954 | 190 . . . 870 | 4397 |
| TESTI20184620 | 1955 | 123 . . . 2417 | 4398 |
| TESTI20185650 | 1956 | 75 . . . 1904 | 4399 |
| TESTI20185810 | 1957 | 243 . . . 587 | 4400 |
| TESTI20189410 | 1958 | 16 . . . >1759 | 4401 |
| TESTI20192280 | 1959 | 10 . . . 906 | 4402 |
| TESTI20192800 | 1960 | 193 . . . >2366 | 4403 |
| TESTI20193360 | 1961 | 66 . . . 854 | 4404 |
| TESTI20194300 | 1962 | 70 . . . 576 | 4405 |
| TESTI20194810 | 1963 | 78 . . . 473 | 4406 |
| TESTI20197940 | 1964 | 771 . . . >1987 | 4407 |
| TESTI20199170 | 1965 | 244 . . . 558 | 4408 |
| TESTI20199750 | 1966 | 92 . . . 1957 | 4409 |
| TESTI20200260 | 1967 | 307 . . . 846 | 4410 |
| TESTI20200710 | 1968 | 190 . . . 1749 | 4411 |
| TESTI20202650 | 1969 | 55 . . . 1299 | 4412 |
| TESTI20203440 | 1970 | 1109 . . . 1600 | 4413 |
| TESTI20204450 | 1971 | 417 . . . 1916 | 4414 |
| TESTI20208400 | 1972 | 1027 . . . 1782 | 4415 |
| TESTI20208710 | 1973 | 70 . . . 2046 | 4416 |
| TESTI20209460 | 1974 | 1035 . . . 1400 | 4417 |
| TESTI20209810 | 1975 | 872 . . . 1405 | 4418 |
| TESTI20209990 | 1976 | 106 . . . 549 | 4419 |
| TESTI20211160 | 1977 | 627 . . . 1424 | 4420 |
| TESTI20211220 | 1978 | 1561 . . . 1944 | 4421 |
| TESTI20211240 | 1979 | 150 . . . >1469 | 4422 |
| TESTI20213150 | 1980 | 380 . . . 1303 | 4423 |
| TESTI20213580 | 1981 | 338 . . . 697 | 4424 |
| TESTI20214250 | 1982 | 46 . . . 933 | 4425 |

TABLE 1-continued

| Clone name | SEQ ID NO. of nucleotide sequence | Position of CDS | SEQ ID NO. of amino acid sequence |
|---|---|---|---|
| TESTI20215990 | 1983 | 428 . . . 2635 | 4426 |
| TESTI20216370 | 1984 | 572 . . . 1195 | 4427 |
| TESTI20220100 | 1985 | 539 . . . 1264 | 4428 |
| TESTI20220650 | 1986 | 164 . . . 481 | 4429 |
| TESTI20224620 | 1987 | 221 . . . 532 | 4430 |
| TESTI20226230 | 1988 | 335 . . . >1500 | 4431 |
| TESTI20226490 | 1989 | 1044 . . . 1367 | 4432 |
| TESTI20229600 | 1990 | 342 . . . 2669 | 4433 |
| TESTI20230250 | 1991 | 1310 . . . 1693 | 4434 |
| TESTI20230850 | 1992 | 246 . . . 2567 | 4435 |
| TESTI20231920 | 1993 | 949 . . . 1392 | 4436 |
| TESTI20231940 | 1994 | 382 . . . 975 | 4437 |
| TESTI20232140 | 1995 | 26 . . . 1237 | 4438 |
| TESTI20234140 | 1996 | 182 . . . 1738 | 4439 |
| TESTI20234270 | 1997 | 334 . . . 642 | 4440 |
| TESTI20234360 | 1998 | 23 . . . 460 | 4441 |
| TESTI20237520 | 1999 | 172 . . . 1734 | 4442 |
| TESTI20238000 | 2000 | 978 . . . 1322 | 4443 |
| TESTI20238610 | 2001 | 150 . . . 1373 | 4444 |
| TESTI20239470 | 2002 | 132 . . . 2294 | 4445 |
| TESTI20239510 | 2003 | 701 . . . 1333 | 4446 |
| TESTI20240090 | 2004 | 10 . . . 1179 | 4447 |
| TESTI20241530 | 2005 | 594 . . . 1985 | 4448 |
| TESTI20241920 | 2006 | 1309 . . . 1632 | 4449 |
| TESTI20242830 | 2007 | 42 . . . 2306 | 4450 |
| TESTI20242990 | 2008 | 968 . . . 1330 | 4451 |
| TESTI20244190 | 2009 | 80 . . . 1630 | 4452 |
| TESTI20244760 | 2010 | 1258 . . . 1647 | 4453 |
| TESTI20249990 | 2011 | 698 . . . 1960 | 4454 |
| TESTI20254220 | 2012 | 81 . . . 1376 | 4455 |
| TESTI20254540 | 2013 | 997 . . . 1830 | 4456 |
| TESTI20254860 | 2014 | 205 . . . >2004 | 4457 |
| TESTI20255820 | 2015 | 120 . . . 1565 | 4458 |
| TESTI20258460 | 2016 | 37 . . . 1212 | 4459 |
| TESTI20262330 | 2017 | 928 . . . 1521 | 4460 |
| TESTI20262910 | 2018 | 335 . . . 1336 | 4461 |
| TESTI20265250 | 2019 | 1751 . . . 2095 | 4462 |
| TESTI20265370 | 2020 | 46 . . . 378 | 4463 |
| TESTI20265970 | 2021 | 258 . . . 1961 | 4464 |
| TESTI20266740 | 2022 | 88 . . . 1203 | 4465 |
| TESTI20269570 | 2023 | 643 . . . 1047 | 4466 |
| TESTI20271850 | 2024 | 202 . . . 504 | 4467 |
| TESTI20272060 | 2025 | 1379 . . . 3253 | 4468 |
| TESTI20272390 | 2026 | 123 . . . 767 | 4469 |
| TESTI20272960 | 2027 | 982 . . . 1932 | 4470 |
| TESTI20275030 | 2028 | 98 . . . 583 | 4471 |
| TESTI20275620 | 2029 | 1508 . . . 1840 | 4472 |
| TESTI20277360 | 2030 | 298 . . . 1704 | 4473 |
| TESTI20278200 | 2031 | 48 . . . 698 | 4474 |
| TESTI20278400 | 2032 | 70 . . . >1856 | 4475 |
| TESTI20280980 | 2033 | 619 . . . 1071 | 4476 |
| TESTI20282540 | 2034 | 310 . . . 1356 | 4477 |
| TESTI20284880 | 2035 | 683 . . . 1114 | 4478 |
| TESTI20285830 | 2036 | 494 . . . 853 | 4479 |
| TESTI20288110 | 2037 | 234 . . . 899 | 4480 |
| TESTI20288910 | 2038 | 51 . . . 965 | 4481 |
| TESTI20289850 | 2039 | 198 . . . 698 | 4482 |
| TESTI20291310 | 2040 | 106 . . . 2034 | 4483 |
| TESTI20291620 | 2041 | 1611 . . . 2021 | 4484 |
| TESTI20291960 | 2042 | 809 . . . 1921 | 4485 |
| TESTI20294700 | 2043 | 898 . . . 1236 | 4486 |
| TESTI20297850 | 2044 | 1 . . . 837 | 4487 |
| TESTI20301360 | 2045 | 114 . . . 506 | 4488 |
| TESTI20303220 | 2046 | 288 . . . 2711 | 4489 |
| TESTI20303360 | 2047 | 767 . . . 2050 | 4490 |
| TESTI20303420 | 2048 | 34 . . . 768 | 4491 |
| TESTI20305540 | 2049 | 97 . . . 2949 | 4492 |
| TESTI20305560 | 2050 | 49 . . . 582 | 4493 |
| TESTI20307540 | 2051 | 88 . . . 513 | 4494 |
| TESTI20307700 | 2052 | 32 . . . 412 | 4495 |
| TESTI20308600 | 2053 | 72 . . . 1307 | 4496 |
| TESTI20309170 | 2054 | 722 . . . 2233 | 4497 |
| TESTI20310070 | 2055 | 205 . . . 2097 | 4498 |
| TESTI20311290 | 2056 | 940 . . . 1398 | 4499 |
| TESTI20314180 | 2057 | 1073 . . . 1744 | 4500 |
| TESTI20316870 | 2058 | 25 . . . 813 | 4501 |
| TESTI20317600 | 2059 | 107 . . . 1420 | 4502 |
| TESTI20318090 | 2060 | 1012 . . . 1644 | 4503 |
| TESTI20319190 | 2061 | 384 . . . 1481 | 4504 |
| TESTI20320440 | 2062 | 200 . . . 1861 | 4505 |
| TESTI20320670 | 2063 | 259 . . . 1257 | 4506 |
| TESTI20326810 | 2064 | 832 . . . 1377 | 4507 |
| TESTI20327680 | 2065 | 135 . . . 1730 | 4508 |
| TESTI20327740 | 2066 | 132 . . . 518 | 4509 |
| TESTI20328280 | 2067 | 87 . . . 2135 | 4510 |
| TESTI20330310 | 2068 | 315 . . . 1307 | 4511 |
| TESTI20332420 | 2069 | 682 . . . 1461 | 4512 |
| TESTI20333000 | 2070 | 366 . . . 1586 | 4513 |
| TESTI20333950 | 2071 | 76 . . . 1500 | 4514 |
| TESTI20334410 | 2072 | 167 . . . 1630 | 4515 |
| TESTI20335050 | 2073 | 340 . . . 1389 | 4516 |
| TESTI20335200 | 2074 | 612 . . . 968 | 4517 |
| TESTI20336410 | 2075 | 17 . . . 325 | 4518 |
| TESTI20337100 | 2076 | 40 . . . 384 | 4519 |
| TESTI20342430 | 2077 | 322 . . . 642 | 4520 |
| TESTI20343070 | 2078 | 530 . . . 2563 | 4521 |
| TESTI20343570 | 2079 | 900 . . . 1568 | 4522 |
| TESTI20345060 | 2080 | 15 . . . 1382 | 4523 |
| TESTI20347180 | 2081 | 3 . . . 710 | 4524 |
| TESTI20347300 | 2082 | 623 . . . 931 | 4525 |
| TESTI20347740 | 2083 | 100 . . . 1599 | 4526 |
| TESTI20347770 | 2084 | 37 . . . 351 | 4527 |
| TESTI20351830 | 2085 | 919 . . . 1773 | 4528 |
| TESTI20352620 | 2086 | 182 . . . 907 | 4529 |
| TESTI20355020 | 2087 | 8 . . . 1651 | 4530 |
| TESTI20357750 | 2088 | 547 . . . 951 | 4531 |
| TESTI20357930 | 2089 | 1148 . . . 1498 | 4532 |
| TESTI20357960 | 2090 | 363 . . . 725 | 4533 |
| TESTI20358980 | 2091 | 85 . . . 1332 | 4534 |
| TESTI20361140 | 2092 | 801 . . . 1514 | 4535 |
| TESTI20366910 | 2093 | 5 . . . 1396 | 4536 |
| TESTI20367360 | 2094 | 324 . . . 629 | 4537 |
| TESTI20368330 | 2095 | 201 . . . 1856 | 4538 |
| TESTI20369130 | 2096 | 243 . . . 611 | 4539 |
| TESTI20369220 | 2097 | 118 . . . 441 | 4540 |
| TESTI20369650 | 2098 | 633 . . . 2204 | 4541 |
| TESTI20369690 | 2099 | 306 . . . 1208 | 4542 |
| TESTI20370020 | 2100 | 346 . . . 1830 | 4543 |
| TESTI20370550 | 2101 | 160 . . . 462 | 4544 |
| TESTI20370810 | 2102 | 223 . . . 2334 | 4545 |
| TESTI20371030 | 2103 | 209 . . . 1180 | 4546 |
| TESTI20371060 | 2104 | 140 . . . 1177 | 4547 |
| TESTI20373820 | 2105 | 237 . . . 1109 | 4548 |
| TESTI20375340 | 2106 | 387 . . . 1559 | 4549 |
| TESTI20377230 | 2107 | 574 . . . 1314 | 4550 |
| TESTI20378190 | 2108 | 380 . . . 1795 | 4551 |
| TESTI20378450 | 2109 | 489 . . . >2419 | 4552 |
| TESTI20380650 | 2110 | 961 . . . 1272 | 4553 |
| TESTI20381040 | 2111 | 339 . . . 1394 | 4554 |
| TESTI20382750 | 2112 | 1159 . . . 1797 | 4555 |
| TESTI20383880 | 2113 | 419 . . . 988 | 4556 |
| TESTI20385960 | 2114 | 684 . . . 1637 | 4557 |
| TESTI20386230 | 2115 | 748 . . . 1059 | 4558 |
| TESTI20386440 | 2116 | 185 . . . 514 | 4559 |
| TESTI20388580 | 2117 | 405 . . . 788 | 4560 |
| TESTI20390260 | 2118 | 142 . . . 522 | 4561 |
| TESTI20390410 | 2119 | 1604 . . . 1969 | 4562 |
| TESTI20391130 | 2120 | 185 . . . 2224 | 4563 |
| TESTI20391210 | 2121 | 1259 . . . 1801 | 4564 |
| TESTI20391770 | 2122 | 237 . . . 1634 | 4565 |
| TESTI20392090 | 2123 | 405 . . . 881 | 4566 |
| TESTI20392250 | 2124 | 1057 . . . 1941 | 4567 |
| TESTI20392270 | 2125 | 316 . . . 1185 | 4568 |
| TESTI20392760 | 2126 | 306 . . . 2279 | 4569 |
| TESTI20393530 | 2127 | 194 . . . 1198 | 4570 |
| TESTI20396130 | 2128 | 338 . . . 682 | 4571 |
| TESTI20397760 | 2129 | 371 . . . 1129 | 4572 |
| TESTI20400940 | 2130 | 231 . . . 2705 | 4573 |
| TESTI20401020 | 2131 | 583 . . . 1281 | 4574 |
| TESTI20401280 | 2132 | 53 . . . 379 | 4575 |

TABLE 1-continued

| Clone name | SEQ ID NO. of nucleotide sequence | Position of CDS | SEQ ID NO. of amino acid sequence |
|---|---|---|---|
| TESTI20401430 | 2133 | 340 . . . 651 | 4576 |
| TESTI20404240 | 2134 | 1110 . . . 1550 | 4577 |
| TESTI20406420 | 2135 | 186 . . . 1340 | 4578 |
| TESTI20408150 | 2136 | 195 . . . 752 | 4579 |
| TESTI20408970 | 2137 | 247 . . . 1170 | 4580 |
| TESTI20409440 | 2138 | 17 . . . 337 | 4581 |
| TESTI20409890 | 2139 | 120 . . . 1082 | 4582 |
| TESTI20413300 | 2140 | 66 . . . 503 | 4583 |
| TESTI20415170 | 2141 | 45 . . . 419 | 4584 |
| TESTI20415640 | 2142 | 1 . . . 324 | 4585 |
| TESTI20416640 | 2143 | 1092 . . . 1574 | 4586 |
| TESTI20417300 | 2144 | 107 . . . 1807 | 4587 |
| TESTI20419560 | 2145 | 5 . . . 331 | 4588 |
| TESTI20420620 | 2146 | 334 . . . 2139 | 4589 |
| TESTI20421490 | 2147 | 2188 . . . 2628 | 4590 |
| TESTI20422640 | 2148 | 974 . . . 2149 | 4591 |
| TESTI20423020 | 2149 | 252 . . . >1770 | 4592 |
| TESTI20424000 | 2150 | 339 . . . 842 | 4593 |
| TESTI20424730 | 2151 | 928 . . . 1263 | 4594 |
| TESTI20425070 | 2152 | 1145 . . . 1726 | 4595 |
| TESTI20427830 | 2153 | 42 . . . 380 | 4596 |
| TESTI20428060 | 2154 | 230 . . . 598 | 4597 |
| TESTI20429280 | 2155 | 925 . . . 1551 | 4598 |
| TESTI20429580 | 2156 | 970 . . . 1458 | 4599 |
| TESTI20432750 | 2157 | 56 . . . 1399 | 4600 |
| TESTI20432820 | 2158 | 18 . . . 1232 | 4601 |
| TESTI20433130 | 2159 | 247 . . . 549 | 4602 |
| TESTI20436560 | 2160 | 103 . . . 1578 | 4603 |
| TESTI20438570 | 2161 | 1252 . . . 1719 | 4604 |
| TESTI20438660 | 2162 | 2227 . . . 2622 | 4605 |
| TESTI20441940 | 2163 | 613 . . . 1596 | 4606 |
| TESTI20442760 | 2164 | 82 . . . >2054 | 4607 |
| TESTI20443090 | 2165 | 201 . . . 1019 | 4608 |
| TESTI20444130 | 2166 | 79 . . . 417 | 4609 |
| TESTI20444180 | 2167 | 26 . . . 547 | 4610 |
| TESTI20447540 | 2168 | 184 . . . 516 | 4611 |
| TESTI20449200 | 2169 | 672 . . . 1766 | 4612 |
| TESTI20451710 | 2170 | 429 . . . 731 | 4613 |
| TESTI20451990 | 2171 | 210 . . . 2264 | 4614 |
| TESTI20455090 | 2172 | 489 . . . 1268 | 4615 |
| TESTI20455620 | 2173 | 110 . . . 1351 | 4616 |
| TESTI20456110 | 2174 | 4 . . . 1191 | 4617 |
| TESTI20458190 | 2175 | 235 . . . 579 | 4618 |
| TESTI20463520 | 2176 | 998 . . . 1402 | 4619 |
| TESTI20463580 | 2177 | 577 . . . 2037 | 4620 |
| TESTI20465350 | 2178 | 317 . . . 1258 | 4621 |
| TESTI20465520 | 2179 | 535 . . . 1026 | 4622 |
| TESTI20465690 | 2180 | 214 . . . 1074 | 4623 |
| TESTI20467210 | 2181 | 435 . . . 1613 | 4624 |
| TESTI20467320 | 2182 | 951 . . . 1922 | 4625 |
| TESTI20467970 | 2183 | 332 . . . 1690 | 4626 |
| TESTI20468630 | 2184 | 380 . . . 688 | 4627 |
| TESTI20471410 | 2185 | 97 . . . 1464 | 4628 |
| TESTI20471470 | 2186 | 31 . . . 369 | 4629 |
| TESTI20471530 | 2187 | 2264 . . . 2641 | 4630 |
| TESTI20472120 | 2188 | 517 . . . 876 | 4631 |
| TESTI20473420 | 2189 | 140 . . . 607 | 4632 |
| TESTI20473830 | 2190 | 951 . . . 1532 | 4633 |
| TESTI20477920 | 2191 | 1387 . . . 1860 | 4634 |
| TESTI20478010 | 2192 | 169 . . . 558 | 4635 |
| TESTI20478180 | 2193 | 428 . . . 754 | 4636 |
| TESTI20478850 | 2194 | 949 . . . 1323 | 4637 |
| TESTI20479300 | 2195 | 663 . . . 1205 | 4638 |
| THYMU10005360 | 2196 | 48 . . . 899 | 4639 |
| THYMU10005540 | 2197 | 84 . . . 1508 | 4640 |
| THYMU20000570 | 2198 | 216 . . . 728 | 4641 |
| THYMU20011950 | 2199 | 45 . . . 626 | 4642 |
| THYMU20015210 | 2200 | 1003 . . . 1314 | 4643 |
| THYMU20018190 | 2201 | 336 . . . 758 | 4644 |
| THYMU20023380 | 2202 | 1426 . . . 1728 | 4645 |
| THYMU20027560 | 2203 | 63 . . . 602 | 4646 |
| THYMU20029100 | 2204 | 215 . . . 928 | 4647 |
| THYMU20032870 | 2205 | 1042 . . . 1404 | 4648 |
| THYMU20039810 | 2206 | 54 . . . 2204 | 4649 |
| THYMU20045120 | 2207 | 66 . . . 425 | 4650 |
| THYMU20058070 | 2208 | 984 . . . 1388 | 4651 |
| THYMU20061700 | 2209 | 40 . . . 435 | 4652 |
| THYMU20066100 | 2210 | 188 . . . 814 | 4653 |
| THYMU20070360 | 2211 | 1333 . . . 1635 | 4654 |
| THYMU20075320 | 2212 | 1186 . . . 1767 | 4655 |
| THYMU20081490 | 2213 | 127 . . . >2055 | 4656 |
| THYMU20095960 | 2214 | 304 . . . 945 | 4657 |
| THYMU20100410 | 2215 | 219 . . . 1415 | 4658 |
| THYMU20101610 | 2216 | 1087 . . . 1446 | 4659 |
| THYMU20101920 | 2217 | 765 . . . 1310 | 4660 |
| THYMU20105190 | 2218 | 850 . . . 1713 | 4661 |
| THYMU20106710 | 2219 | 89 . . . 493 | 4662 |
| THYMU20108310 | 2220 | 97 . . . 642 | 4663 |
| THYMU20111180 | 2221 | 33 . . . 1367 | 4664 |
| THYMU20111420 | 2222 | 914 . . . 1303 | 4665 |
| THYMU20111830 | 2223 | 38 . . . 796 | 4666 |
| THYMU20114470 | 2224 | 122 . . . 502 | 4667 |
| THYMU20115850 | 2225 | 1500 . . . 1805 | 4668 |
| THYMU20118060 | 2226 | 355 . . . 687 | 4669 |
| THYMU20118520 | 2227 | 220 . . . 567 | 4670 |
| THYMU20119390 | 2228 | 118 . . . 525 | 4671 |
| THYMU20122730 | 2229 | 343 . . . 1140 | 4672 |
| THYMU20126900 | 2230 | 163 . . . 1446 | 4673 |
| THYMU20128070 | 2231 | 2 . . . 349 | 4674 |
| THYMU20128260 | 2232 | 76 . . . 411 | 4675 |
| THYMU20130890 | 2233 | 221 . . . 757 | 4676 |
| THYMU20141670 | 2234 | 196 . . . 1152 | 4677 |
| THYMU20142040 | 2235 | 24 . . . 653 | 4678 |
| THYMU20142970 | 2236 | 495 . . . 1499 | 4679 |
| THYMU20143270 | 2237 | 524 . . . 1549 | 4680 |
| THYMU20147770 | 2238 | 80 . . . 1501 | 4681 |
| THYMU20153160 | 2239 | 1303 . . . 1920 | 4682 |
| THYMU20158250 | 2240 | 117 . . . 488 | 4683 |
| THYMU20159430 | 2241 | 79 . . . 1581 | 4684 |
| THYMU20161640 | 2242 | 110 . . . 679 | 4685 |
| THYMU20162190 | 2243 | 299 . . . 646 | 4686 |
| THYMU20169680 | 2244 | 718 . . . 1395 | 4687 |
| THYMU20172150 | 2245 | 375 . . . 956 | 4688 |
| THYMU20173980 | 2246 | 355 . . . 813 | 4689 |
| THYMU20180280 | 2247 | 1352 . . . 1699 | 4690 |
| THYMU20186390 | 2248 | 461 . . . 1495 | 4691 |
| THYMU20186730 | 2249 | 194 . . . 535 | 4692 |
| THYMU20187720 | 2250 | 284 . . . 661 | 4693 |
| THYMU20193640 | 2251 | 659 . . . 1165 | 4694 |
| THYMU20194360 | 2252 | 257 . . . 955 | 4695 |
| THYMU20194420 | 2253 | 1080 . . . 1403 | 4696 |
| THYMU20195990 | 2254 | 344 . . . 673 | 4697 |
| THYMU20201980 | 2255 | 1094 . . . 2023 | 4698 |
| THYMU20202890 | 2256 | 935 . . . 2188 | 4699 |
| THYMU20204160 | 2257 | 654 . . . 1199 | 4700 |
| THYMU20204990 | 2258 | 65 . . . 385 | 4701 |
| THYMU20208300 | 2259 | 144 . . . 542 | 4702 |
| THYMU20209590 | 2260 | 193 . . . 2061 | 4703 |
| THYMU20215090 | 2261 | 862 . . . 1380 | 4704 |
| THYMU20215970 | 2262 | 1004 . . . 1552 | 4705 |
| THYMU20216840 | 2263 | 605 . . . 2074 | 4706 |
| THYMU20222890 | 2264 | 1896 . . . 2198 | 4707 |
| THYMU20226600 | 2265 | 246 . . . 1232 | 4708 |
| THYMU20228540 | 2266 | 109 . . . 426 | 4709 |
| THYMU20229220 | 2267 | 259 . . . 894 | 4710 |
| THYMU20232090 | 2268 | 111 . . . 539 | 4711 |
| THYMU20235760 | 2269 | 357 . . . 674 | 4712 |
| THYMU20239000 | 2270 | 44 . . . 1672 | 4713 |
| THYMU20239430 | 2271 | 656 . . . 982 | 4714 |
| THYMU20240710 | 2272 | 680 . . . 2077 | 4715 |
| THYMU20241210 | 2273 | 77 . . . 511 | 4716 |
| THYMU20241850 | 2274 | 63 . . . 890 | 4717 |
| THYMU20246840 | 2275 | 110 . . . 415 | 4718 |
| THYMU20247480 | 2276 | 4 . . . 1176 | 4719 |
| THYMU20250420 | 2277 | 222 . . . 707 | 4720 |
| THYMU20251890 | 2278 | 1433 . . . 1777 | 4721 |
| THYMU20253250 | 2279 | 713 . . . 1540 | 4722 |
| THYMU20255570 | 2280 | 882 . . . 1550 | 4723 |
| THYMU20255720 | 2281 | 88 . . . 645 | 4724 |
| THYMU20259090 | 2282 | 1763 . . . 2092 | 4725 |

TABLE 1-continued

| Clone name | SEQ ID NO. of nucleotide sequence | Position of CDS | SEQ ID NO. of amino acid sequence |
|---|---|---|---|
| THYMU20265300 | 2283 | 60 . . . 1949 | 4726 |
| THYMU20271250 | 2284 | 681 . . . 1628 | 4727 |
| THYMU20272490 | 2285 | 174 . . . 560 | 4728 |
| THYMU20277390 | 2286 | 930 . . . 1541 | 4729 |
| THYMU20279750 | 2287 | 716 . . . 1114 | 4730 |
| THYMU20283790 | 2288 | 253 . . . 804 | 4731 |
| THYMU20284120 | 2289 | 178 . . . 525 | 4732 |
| THYMU20286290 | 2290 | 287 . . . 1981 | 4733 |
| THYMU20286320 | 2291 | 1214 . . . 1594 | 4734 |
| TKIDN10000010 | 2292 | 386 . . . 838 | 4735 |
| TKIDN20004640 | 2293 | 549 . . . 1172 | 4736 |
| TKIDN20005210 | 2294 | 294 . . . 1133 | 4737 |
| TKIDN20030590 | 2295 | 143 . . . 1558 | 4738 |
| TKIDN20030620 | 2296 | 25 . . . 531 | 4739 |
| TKIDN20047480 | 2297 | 1038 . . . 1460 | 4740 |
| TOVAR20004760 | 2298 | 675 . . . 1454 | 4741 |
| TOVAR20005750 | 2299 | 348 . . . 713 | 4742 |
| TRACH20002870 | 2300 | 77 . . . 613 | 4743 |
| TRACH20003590 | 2301 | 244 . . . 1773 | 4744 |
| TRACH20005020 | 2302 | 75 . . . 1463 | 4745 |
| TRACH20005400 | 2303 | 57 . . . 728 | 4746 |
| TRACH20007020 | 2304 | 271 . . . 1830 | 4747 |
| TRACH20016210 | 2305 | 122 . . . 1132 | 4748 |
| TRACH20019960 | 2306 | 112 . . . 1410 | 4749 |
| TRACH20027840 | 2307 | 61 . . . 384 | 4750 |
| TRACH20028030 | 2308 | 161 . . . 1441 | 4751 |
| TRACH20029540 | 2309 | 1410 . . . 1859 | 4752 |
| TRACH20032720 | 2310 | 830 . . . 1354 | 4753 |
| TRACH20033230 | 2311 | 560 . . . 2110 | 4754 |
| TRACH20034840 | 2312 | 1985 . . . >3328 | 4755 |
| TRACH20037360 | 2313 | 1 . . . 309 | 4756 |
| TRACH20041830 | 2314 | 424 . . . 1035 | 4757 |
| TRACH20042920 | 2315 | 77 . . . 1540 | 4758 |
| TRACH20048450 | 2316 | 511 . . . 1845 | 4759 |
| TRACH20050040 | 2317 | 70 . . . 594 | 4760 |
| TRACH20056980 | 2318 | 405 . . . 1055 | 4761 |
| TRACH20057690 | 2319 | 1448 . . . 1993 | 4762 |
| TRACH20060150 | 2320 | 3 . . . 329 | 4763 |
| TRACH20067620 | 2321 | 166 . . . 603 | 4764 |
| TRACH20068660 | 2322 | 63 . . . 890 | 4765 |
| TRACH20068700 | 2323 | 144 . . . 1811 | 4766 |
| TRACH20069180 | 2324 | 63 . . . 1625 | 4767 |
| TRACH20076740 | 2325 | 779 . . . 1669 | 4768 |
| TRACH20076760 | 2326 | 1737 . . . 2183 | 4769 |
| TRACH20077540 | 2327 | 1859 . . . 2455 | 4770 |
| TRACH20079690 | 2328 | 144 . . . 2144 | 4771 |
| TRACH20082780 | 2329 | 1675 . . . 2103 | 4772 |
| TRACH20084720 | 2330 | 38 . . . 1819 | 4773 |
| TRACH20085400 | 2331 | 223 . . . 2346 | 4774 |
| TRACH20085830 | 2332 | 41 . . . 1567 | 4775 |
| TRACH20091230 | 2333 | 1660 . . . 2067 | 4776 |
| TRACH20092680 | 2334 | 56 . . . 457 | 4777 |
| TRACH20096610 | 2335 | 417 . . . 935 | 4778 |
| TRACH20099340 | 2336 | 156 . . . 494 | 4779 |
| TRACH20105870 | 2337 | 1418 . . . 2176 | 4780 |
| TRACH20107710 | 2338 | 13 . . . 474 | 4781 |
| TRACH20109650 | 2339 | 1421 . . . 1849 | 4782 |
| TRACH20111130 | 2340 | 1548 . . . 1937 | 4783 |
| TRACH20115740 | 2341 | 507 . . . 893 | 4784 |
| TRACH20118940 | 2342 | 1781 . . . 2083 | 4785 |
| TRACH20121380 | 2343 | 795 . . . 1808 | 4786 |
| TRACH20128110 | 2344 | 1233 . . . 1796 | 4787 |
| TRACH20128230 | 2345 | 80 . . . 1657 | 4788 |
| TRACH20134950 | 2346 | 675 . . . 1001 | 4789 |
| TRACH20135520 | 2347 | 425 . . . 2335 | 4790 |
| TRACH20136710 | 2348 | 42 . . . 545 | 4791 |
| TRACH20139820 | 2349 | 1630 . . . 1998 | 4792 |
| TRACH20140820 | 2350 | 196 . . . 738 | 4793 |
| TRACH20141240 | 2351 | 270 . . . 875 | 4794 |
| TRACH20145440 | 2352 | 243 . . . 1511 | 4795 |
| TRACH20147250 | 2353 | 834 . . . 1196 | 4796 |
| TRACH20149970 | 2354 | 124 . . . 1776 | 4797 |
| TRACH20153810 | 2355 | 216 . . . 635 | 4798 |
| TRACH20154860 | 2356 | 3 . . . 1439 | 4799 |
| TRACH20162860 | 2357 | 98 . . . 364 | 4800 |
| TRACH20163170 | 2358 | 267 . . . 1028 | 4801 |
| TRACH20164980 | 2359 | 657 . . . 2165 | 4802 |
| TRACH20167220 | 2360 | 986 . . . 2422 | 4803 |
| TRACH20168350 | 2361 | 200 . . . 589 | 4804 |
| TRACH20169800 | 2362 | 1922 . . . 2359 | 4805 |
| TRACH20180840 | 2363 | 1288 . . . 1593 | 4806 |
| TRACH20183170 | 2364 | 1029 . . . 2252 | 4807 |
| TRACH20184490 | 2365 | 214 . . . 1596 | 4808 |
| TRACH20187180 | 2366 | 1322 . . . 1639 | 4809 |
| TRACH20190240 | 2367 | 1624 . . . 2313 | 4810 |
| TSTOM10001860 | 2368 | 96 . . . 1859 | 4811 |
| TSTOM20001390 | 2369 | 241 . . . 1671 | 4812 |
| TSTOM20003150 | 2370 | 103 . . . 1245 | 4813 |
| TSTOM20005690 | 2371 | 370 . . . 1626 | 4814 |
| TUTER20002830 | 2372 | 172 . . . 930 | 4815 |
| UMVEN10001560 | 2373 | 130 . . . 669 | 4816 |
| UMVEN10001860 | 2374 | 198 . . . >2048 | 4817 |
| UMVEN20000690 | 2375 | 6 . . . 1118 | 4818 |
| UMVEN20003540 | 2376 | 4 . . . 519 | 4819 |
| UTERU20000740 | 2377 | 2062 . . . 2400 | 4820 |
| UTERU20004240 | 2378 | 38 . . . 385 | 4821 |
| UTERU20006290 | 2379 | 101 . . . 406 | 4822 |
| UTERU20006960 | 2380 | 106 . . . 555 | 4823 |
| UTERU20020010 | 2381 | 54 . . . 431 | 4824 |
| UTERU20022940 | 2382 | 735 . . . 1232 | 4825 |
| UTERU20030570 | 2383 | 184 . . . 1737 | 4826 |
| UTERU20040610 | 2384 | 92 . . . 409 | 4827 |
| UTERU20046640 | 2385 | 15 . . . 2699 | 4828 |
| UTERU20046980 | 2386 | 216 . . . 926 | 4829 |
| UTERU20050690 | 2387 | 619 . . . 924 | 4830 |
| UTERU20054460 | 2388 | 557 . . . >2294 | 4831 |
| UTERU20055330 | 2389 | 45 . . . 632 | 4832 |
| UTERU20055480 | 2390 | 92 . . . 1765 | 4833 |
| UTERU20055930 | 2391 | 90 . . . 869 | 4834 |
| UTERU20056010 | 2392 | 65 . . . 484 | 4835 |
| UTERU20059050 | 2393 | 809 . . . 1459 | 4836 |
| UTERU20061030 | 2394 | 994 . . . 1389 | 4837 |
| UTERU20064000 | 2395 | 153 . . . 479 | 4838 |
| UTERU20064860 | 2396 | 26 . . . 1780 | 4839 |
| UTERU20065930 | 2397 | 37 . . . 2097 | 4840 |
| UTERU20067050 | 2398 | 641 . . . 952 | 4841 |
| UTERU20068990 | 2399 | 945 . . . 1319 | 4842 |
| UTERU20070040 | 2400 | 36 . . . 383 | 4843 |
| UTERU20070810 | 2401 | 761 . . . 1219 | 4844 |
| UTERU20076390 | 2402 | 71 . . . 499 | 4845 |
| UTERU20081300 | 2403 | 2063 . . . 2464 | 4846 |
| UTERU20084260 | 2404 | 494 . . . 1321 | 4847 |
| UTERU20094350 | 2405 | 293 . . . 802 | 4848 |
| UTERU20095380 | 2406 | 872 . . . 1213 | 4849 |
| UTERU20095400 | 2407 | 737 . . . 1456 | 4850 |
| UTERU20097760 | 2408 | 1232 . . . 1759 | 4851 |
| UTERU20099720 | 2409 | 201 . . . 746 | 4852 |
| UTERU20101240 | 2410 | 210 . . . 602 | 4853 |
| UTERU20114100 | 2411 | 538 . . . 963 | 4854 |
| UTERU20115740 | 2412 | 469 . . . 933 | 4855 |
| UTERU20116570 | 2413 | 327 . . . 1694 | 4856 |
| UTERU20118110 | 2414 | 87 . . . 485 | 4857 |
| UTERU20118970 | 2415 | 229 . . . 549 | 4858 |
| UTERU20119060 | 2416 | 1192 . . . 2436 | 4859 |
| UTERU20119680 | 2417 | 676 . . . 1185 | 4860 |
| UTERU20120310 | 2418 | 68 . . . 1066 | 4861 |
| UTERU20124070 | 2419 | 368 . . . 733 | 4862 |
| UTERU20126880 | 2420 | 524 . . . 1045 | 4863 |
| UTERU20134910 | 2421 | 1070 . . . 1489 | 4864 |
| UTERU20135860 | 2422 | 676 . . . 1965 | 4865 |
| UTERU20143980 | 2423 | 68 . . . 370 | 4866 |
| UTERU20144640 | 2424 | 231 . . . 1148 | 4867 |
| UTERU20145480 | 2425 | 172 . . . 2193 | 4868 |
| UTERU20146310 | 2426 | 114 . . . 1580 | 4869 |
| UTERU20146680 | 2427 | 524 . . . 1045 | 4870 |
| UTERU20150870 | 2428 | 47 . . . 499 | 4871 |
| UTERU20151980 | 2429 | 220 . . . 981 | 4872 |
| UTERU20158300 | 2430 | 342 . . . 686 | 4873 |
| UTERU20158800 | 2431 | 161 . . . 1318 | 4874 |
| UTERU20161570 | 2432 | 295 . . . 1209 | 4875 |

TABLE 1-continued

| Clone name | SEQ ID NO. of nucleotide sequence | Position of CDS | SEQ ID NO. of amino acid sequence |
|---|---|---|---|
| UTERU20164260 | 2433 | 54 . . . 890 | 4876 |
| UTERU20168220 | 2434 | 835 . . . 1530 | 4877 |
| UTERU20176130 | 2435 | 27 . . . 1184 | 4878 |
| UTERU20176320 | 2436 | 108 . . . 1364 | 4879 |
| UTERU20178100 | 2437 | 2178 . . . 2528 | 4880 |
| UTERU20179880 | 2438 | 172 . . . 2379 | 4881 |
| UTERU20183640 | 2439 | 2289 . . . 2828 | 4882 |
| UTERU20185230 | 2440 | 125 . . . 1927 | 4883 |
| UTERU20186740 | 2441 | 851 . . . 1156 | 4884 |
| UTERU20188110 | 2442 | 125 . . . 1135 | 4885 |
| UTERU20188810 | 2443 | 84 . . . 389 | 4886 |

Namely, primers used to synthesize polynucleotides can be designed based on the nucleotide sequences of polynucleotides of the present invention shown in SEQ ID NOs in the above Table 1. When one intends to synthesize full-length cDNAs, an oligo dT primer can be used as the 3'-end primer. The length of the primers is usually 15–100 bp, and favorably between 15–35 bp. In case of LA PCR, which is described below, the primer length of 25–35 bp may provide a good result.

A method to design a primer that enables a specific amplification based on the aimed nucleotide sequence is known to those skilled in the art (Current Protocols in Molecular Biology, Ausubel et al. edit, (1987) John Wiley & Sons, Section 6.1–6.4). In designing a primer based on the 5'-end sequence, the primer is designed so as that, in principle, the amplification products will include the translation start site. Accordingly, for example, when the 5'-end primer is designed based on the nucleotide sequence of 5' untranslated region (5' UTR), any part of the 5'-end, which ensures the specificity to the cDNA of interest, can be selected as the primer.

When synthesizing a full-length cDNA, the target nucleotide sequence to be amplified can extend to several thousand bp in some cDNA. However, it is possible to amplify such a long nucleotides by using such as LA PCR (Long and Accurate PCR). It is advantageous to use LA PCR when synthesizing long DNA. In LA PCR, in which a special DNA polymerase having 3'->5' exonuclease activity is used, misincorporated nucleotides can be removed. Accordingly, accurate synthesis of the complementary strand can be achieved even with a long nucleotide sequence. By using LA PCR, it is reported that amplification of a nucleotide with 20 kb longer can be achieved under desirable conditions (Takeshi Hayashi (1996) Jikken-Igaku Bessatsu, "Advanced Technologies in PCR" Youdo-sha).

A template DNA for synthesizing the full-length cDNA of the present invention can be obtained by using cDNA libraries that are prepared by various methods. The full-length cDNA clones of the present invention are clones with high probability of completeness in length, which were obtained by the method comprising the steps of [1] preparing libraries containing cDNAs with the very high fullness ratio by oligo-capping, and [2] assembling the 5'-end sequences and selecting one with the highest probability of completeness in length in the cluster formed (there are many clones longer in the 5'-end direction).

However, the uses of primers designed based on the full-length nucleotide sequences provided by the present invention enable easily obtaining full-length cDNAs without such a special technique.

The problem with the cDNA libraries prepared by the known methods or commercially available is that mRNA contained in the libraries has very low fullness ratio. Thus, it is difficult to screen full-length cDNA clone directly from the library using ordinary cloning methods. The present invention has revealed a nucleotide sequence of novel full-length cDNA. If a full-length nucleotide sequence is provided, it is possible to synthesize a target full-length cDNA by using enzymatic reactions such as PCR. In particular, a full-length-enriched cDNA library, synthesized by methods such as oligo-capping, is desirable to synthesize a full-length cDNA with more reliability.

The 5'-end sequence of the full-length cDNA clones of the invention can be used to isolate the regulatory element of transcription including the promoter on the genome. A rough draft of the human genome (analysis of human genomic sequence with lower accuracy), which covers 90% of the genome, has been reported (Nature, Vol. 409, 814–823, 2001), and by the year 2003, analysis of the entire human genomic sequence is going to be finished. However, it is hard to analyze with software the transcription start sites on the human genome, in which long introns exist. By contrast, it is easy to specify the transcription start site on the genomic sequence using the nucleotide sequence which includes the 5'-end of the full-length cDNA clone of the present invention, and thus it is easy to obtain the genomic region involved in transcription regulation, which includes the promoter that is contained in the upstream of the transcription start site.

The polypeptide encoded by the full-length cDNA of the invention can be prepared as a recombinant polypeptide or as a natural polypeptide. For example, the recombinant polypeptide can be prepared by inserting the polynucleotide encoding the polypeptide of the invention into a vector, introducing the vector into an appropriate host cell and purifying the polypeptide expressed within the transformed host cell, as described below. In contrast, the natural polypeptide can be prepared, for example, by utilizing an affinity column to which an antibody against the polypeptide of the invention (Current Protocols in Molecular Biology (1987) Ausubel et al. edit, John Wiley & Sons, Section 16.1–16.19) is attached. The antibody used for affinity purification may be either a polyclonal antibody, or a monoclonal antibody. Alternatively, in vitro translation (See, for example, "On the fidelity of mRNA translation in the nuclease-treated rabbit reticulocyte lysate system." Dasso M. C., and Jackson R. J. (1989) Nucleic Acids Res. 17: 3129–3144) may be used for preparing the polypeptide of the invention.

Polypeptides functionally equivalent to the polypeptides of the present invention can be prepared based on the activities, which were clarified in the above-mentioned manner, of the polypeptides of the present invention. Using the biological activity possessed by the polypeptide of the invention as an index, it is possible to verify whether or not a particular polypeptide is functionally equivalent to the polypeptide of the invention by examining whether or not the polypeptide has said activity.

Polypeptides functionally equivalent to the polypeptides of the present invention can be prepared by those skilled in the art, for example, by using a method for introducing mutations into an amino acid sequence of a polypeptide (for example, site-directed mutagenesis (Current Protocols in Molecular Biology, edit, Ausubel et al., (1987) John Wiley & Sons, Section 8.1–8.5) Besides, such polypeptides can be generated by spontaneous mutations. The present invention also includes a polypeptide comprising the amino acid sequence shown in Table 1 in which one or more amino acids are substituted, deleted, inserted, and/or added, as long as the polypeptides have the equivalent functions to those of the polypeptides identified in the present Examples described later.

There are no limitations on the number and sites of amino acid mutations, as long as the polypeptides maintain the functions thereof. The number of mutations typically corresponds to 30% or less, or 20% or less, or 10% or less, preferably 5% or less, or 3% or less of the total amino acids, more preferably 2% or less or 1% or less of the total amino acids. Alternatively, herein, substitution of one or more amino acids includes substitution of several amino acids. As used herein, the term "several amino acids" means, for example, 5 amino acids, preferably 4 or 3 amino acids, more preferably 2 amino acids, and further preferably 1 amino acid.

From the viewpoint of maintaining the polypeptide function, it is preferable that a substituted amino acid has a similar property to that of the original amino acid. For example, Ala, Val, Leu, Ile, Pro, Met, Phe and Trp are assumed to have similar properties to one another because they are all classified into a group of non-polar amino acids. Similarly, substitution can be performed among non-charged amino acid such as Gly, Ser, Thr, Cys, Tyr, Asn, and Gln, acidic amino acids such as Asp and Glu, and basic amino acids such as Lys, Arg, and His.

In addition, polypeptides functionally equivalent to the polypeptides of the present invention can be isolated by using techniques of hybridization or gene amplification known to those skilled in the art. Specifically, using the hybridization technique (Current Protocols in Molecular Biology, edit, Ausubel et al., (1987) John Wiley & Sons, Section 6.3–6.4)), those skilled in the art can usually isolate a polynucleotide highly homologous to the polynucleotide encoding the polypeptide identified in the present Example based on the identified nucleotide sequence (Table 1) or a portion thereof and obtain the functionally equivalent polypeptide from the isolated polynucleotide. The present invention include polypeptides encoded by the polynucleotides hybridizing with the polynucleotides encoding the polypeptides identified in the present Example, as long as the polypeptides are functionally equivalent to the polypeptides identified in the present Example. Organisms from which the functionally equivalent polypeptides are isolated are illustrated by vertebrates such as human, mouse, rat, rabbit, pig and bovine, but are not limited to these animals.

Washing conditions of hybridization for the isolation of polynucleotides encoding the functionally equivalent polypeptides are usually "1×SSC, 0.1% SDS, 37° C."; more stringent conditions are "0.5×SSC, 0.1% SDS, 42° C."; and still more stringent conditions are "0.1×SSC, 0.1% SDS, 65° C.". Alternatively, the following conditions can be given as hybridization conditions of the present invention. Namely, conditions in which the hybridization is done at "6×SSC, 40% Formamide, 25° C.", and the washing at "1×SSC, 55° C." can be given. More preferable conditions are those in which the hybridization is done at "6×SSC, 40% Formamide, 37° C.", and the washing at "0.2×SSC, 55° C.". Even more preferable are those in which the hybridization is done at "6×SSC, 50% Formamide, 37° C.", and the washing at "0.1×SSC, 62° C.". The more stringent the conditions of hybridization are, the more frequently the polynucleotides highly homologous to the probe sequence are isolated. Therefore, it is preferable to conduct hybridization under stringent conditions. Examples of stringent conditions in the present invention are, washing conditions of "0.5×SSC, 0.1% SDS, 42° C.", or alternatively, hybridization conditions of "6×SSC, 40% Formamide, 37° C.", and the washing at "0.2×SSC, 55° C.".

One skilled in the art can suitably select various conditions, such as dilution ratios of SSC, formamide concentrations, and temperatures to accomplish a similar stringency.

However, the above-mentioned combinations of SSC, SDS and temperature conditions are indicated just as examples. Those skilled in the art can select the hybridization conditions with similar stringency to those mentioned above by properly combining the above-mentioned or other factors (for example, probe concentration, probe length and duration of hybridization reaction) that determines the stringency of hybridization.

The amino acid sequences of polypeptides isolated by using the hybridization techniques usually have high identity to those of the polypeptides of the present invention, which are shown in Table 1. The present invention encompasses a polynucleotide comprising a nucleotide sequence that has a high identity to the nucleotide sequence of claim 1 (a). Furthermore, the present invention encompasses a peptide, or polypeptide comprising an amino acid sequence that has a high identity to the amino acid sequence encoded by the polynucleotide of claim 1 (b). The term "high identity" indicates sequence identity-of at least 40% or more; preferably 60% or more; and more preferably 70% or more. Alternatively, more preferable is identity of 90% or more, or 93% or more, or 95% or more, furthermore, 97% or more, or 99% or more. The identity can be determined by using the BLAST search algorithm.

As used herein, "percent identity" of amino acid sequences or nucleic acids is determined using the algorithm BLAST of Karlin and Altschul (Proc. Natl. Acad. Sci. USA 90:5873–5877, 1993). Such an algorithm is incorporated into the BLASTN and BLASTX programs of Altschul et al. (J. Mol. Biol.215:403–410, 1990). BLAST nucleotide searches are performed with the BLASTN program, for example, score=100, wordlength=12. BLAST protein searches are performed with the BLASTX program, for example, score=50, wordlength=3. When utilizing BLAST and Gapped BLAST programs, the default parameters of the respective programs are used.

With the gene amplification technique (PCR) (Current Protocols in Molecular Biology, edit, Ausubel et al., (1987) John Wiley & Sons, Section 6.1–6.4)) using primers designed based on the nucleotide sequence (Table 1) or a portion thereof identified in the present Example, it is possible to isolate a polynucleotide fragment highly homologous to the polynucleotide sequence or a portion thereof and to obtain functionally equivalent polypeptide to a particular polypeptide identified in the present Example based on the isolated polynucleotide fragment.

The present invention also provides a polynucleotide containing at least 15 nucleotides complementary to a polynucleotide comprising a nucleotide sequence of SEQ ID NOs shown in Table 1 or the complementary strand thereof. Herein, the term "complementary strand" is defined as one strand of a double strand DNA composed of A:T and G:C base pair to the other strand. Also, "complementary" is defined as not only those completely matching within a continuous region of at least 15 nucleotides, but also having a identity of at least 70%, favorably 80% or higher, more favorably 90% or higher, and most favorably 95% or higher within that region. The identity may be determined using the algorithm described herein.

Such a polynucleotide includes probes and primers used for the detection and amplification of a polynucleotide encoding the inventive polypeptide. When used as a primer, the polynucleotide usually comprises 15 to 100 bp, and preferably of 15 to 35 bp. When used as a probe, the polynucleotide comprises the whole or a part of the sequence of a polynucleotide of the invention, and comprises at least 15 bp. When used as primers, such polynucleotides are complementary at the 3'-end, and restriction enzyme recognition sequences or tags can be added to the 5'-end.

Furthermore, polynucleotides of the present invention include an antisense polynucleotide for suppressing the expression of a polypeptide of the invention, which comprises an amino acid sequence of SEQ ID NOs shown in Table 1. To exert an antisense effect, an antisense polynucleotide has at least 15 bp or more, for example 50 bp or more, preferably 100 bp or more, and more preferably 500 bp or more, and usually has 3000 bp or less, and preferably 2000 bp or less. Antisense polynucleotides can be used in the gene therapy of diseases caused by abnormalities of the polypeptides of the invention (abnormal function or abnormal expression). An antisense polynucleotide can be prepared, for example, by the phosphorothioate method ("Physicochemical properties of phosphorothioate oligodeoxynucleotides." Stein (1988) Nucleic Acids Res. 16: 3209–3221) based on the sequence information of polynucleotide encoding a polypeptide of the invention (for example, the nucleotide sequences of SEQ ID NO: 1 to 2443).

The polynucleotides or antisense polynucleotides of the present invention can be used in, for example, gene therapy. As target diseases, for example, cancers or various inflammatory diseases may be preferable. These molecules can be used for gene therapy, for example, by administrating them to patients by the in vivo or ex vivo method using virus vectors such as retrovirus vectors, adenovirus vectors, and adeno-related virus vectors, or non-virus vectors such as liposomes.

The present invention also includes a partial peptide of the polypeptides of the invention. The partial peptide comprises a polypeptide generated as a result that a signal peptide has been removed from a secretory protein. If the polypeptide of the present invention has an activity as a receptor or a ligand, the partial peptide may function as a competitive inhibitor of the polypeptide and may bind to the receptor (or ligand). In addition, the present invention includes an antigen peptide for raising antibodies. For the peptides to be specific for the polypeptide of the invention, the peptides comprise at least 7 amino acids, preferably 8 amino acids or more, more preferably 9 amino acids or more, and even more preferably 10 amino acids or more. The peptide can be used for preparing antibodies against the polypeptide of the invention, or competitive inhibitors of them, and also screening for a receptor that binds to the polypeptide of the invention. The partial peptides of the invention can be produced, for example, by genetic engineering methods, known methods for synthesizing peptides, or digesting the polypeptide of the invention with an appropriate peptidase.

The present invention also relates to a vector into which a polynucleotide of the invention is inserted. The vector of the invention is not limited as long as it contains the inserted polynucleotide stably. For example, if E. coli is used as a host, vectors such as pBluescript vector (Stratagene) are preferable as a cloning vector. To produce the polypeptide of the invention, expression vectors are especially useful. Any expression vector can be used as long as it is capable of expressing the polypeptide in vitro, in E. coli, in cultured cells, or in vivo. For example, pBEST vector (Promega) is preferable for in vitro expression, pET vector (Invitrogen) for E. coli, pME18S-FL3 vector (GenBank Accession No. AB009864) for cultured cells, and pME18S vector (Mol. Cell. Biol. (1988) 8: 466–472) for in vivo expression. To insert the polynucleotide of the invention, ligation utilizing restriction sites can be performed according to the standard method (Current Protocols in Molecular Biology (1987) Ausubel et al. edit, John Wiley & Sons, Section 11.4–11.11).

Recently, the technique of GATEWAY™ system (Invitrogen), which is an expression vector construction system for polypeptide expression, has been developed (Experimental Medicine, Vol. 18, No. 19 (December), p2716–2717, 2000). This system includes two types of site-specific recombinases (BP CLONASE™ and LR CLONASE™) derived from lambda phage and uses BP CLONASE™— specific recombination sites for an Entry Vector and LR CLONASE™—specific recombination sites for a Destination Vector, which may comprise a tag useful for polypeptide purification. With this system, an expression vector can be obtained by using homologous recombination.

First, a polynucleotide fragment of interest is inserted into the entry vector using the first recombination. Then, the secondary recombination is allowed to take place between the entry vector, where the polynucleotide fragment of interest has been inserted, and the destination vector. Thus, the expression vector can be prepared rapidly and highly efficiently. With the above-mentioned typical method using restriction enzyme and ligase reactions, the step of expression vector construction and expression of polypeptide of interest takes about 7 to 10 days. However, with the GATEWAY™ system, the polypeptide of interest can be expressed and prepared in only 3 to 4 days. Thus, the system ensures a high-throughput functional analysis for expressed polypeptides.

The present invention also relates to a transformant carrying the vector of the invention. Any cell can be used as a host into which the vector of the invention is inserted, and various kinds of host cells can be used depending on the purposes. For strong expression of the polypeptide in eukaryotic cells, COS cells or CHO cells can be used, for example.

Introduction of the vector into host cells can be performed, for example, by calcium phosphate precipitation method, electroporation method (Current Protocols in Molecular Biology (1987) Ausubel et al. edit, John Wiley & Sons, Section 9.1–9.9), lipofectamine method (GIBCO-BRL), or microinjection method, etc.

Further, a polynucleotide containing at least 15 nucleotides comprising a nucleotide sequence of any one of the polynucleotides comprising the nucleotide sequences of SEQ ID NOs shown in Table 1 or the complementary strand thereof can be used not only as a primer for synthesizing full-length cDNAs but also for testing and diagnosing the abnormalities of the polypeptide encoded by the full-length CDNA of the present invention. For examples, by utilizing polymerase chain reaction (genomic DNA-PCR, or RT-PCR) using the polynucleotide of the invention as a primer, polynucleotide encoding the polypeptide of the invention can be amplified. It is also possible to obtain the regulatory region of expression in the 5'-upstream by using PCR or hybridization since the transcription start site within the genomic sequence can be easily specified based on the 5'-end sequence of the full-length cDNA. The obtained genomic region can be used for detection and/or diagnosis of the abnormality of the sequence by RFLP analysis, SSCP, or sequencing. Especially, in the case where expression of the mRNA of the present invention varies according to a specific disease, analysis of the amount of expression of the mRNA using the polynucleotide of the present invention as a probe or a primer enables detection and diagnosis of the disease.

The present invention also relates to antibodies that bind to the polypeptide of the invention. There are no limitations in the form of the antibodies of the invention. They include polyclonal antibodies, monoclonal antibodies, or their portions that can bind to an antigen. They also include antibodies of all, classes. Furthermore, special antibodies such as humanized antibodies and chimeric antibodies are also included.

The polyclonal antibody of the invention can be obtained according to the standard method by synthesizing an oligopeptide corresponding to the amino acid sequence and immunizing rabbits with the peptide (Current Protocols in Molecular Biology (1987) Ausubel et al. edit, John Wiley & Sons, Section 11.12–11.13). The monoclonal antibody of the invention can be obtained according to the standard method by purifying the polypeptide expressed in $E.$ $coli$, immunizing mice with the polypeptide, and producing a hybridoma cell by fusing the spleen cells and myeloma cells (Current Protocols in Molecular Biology (1987) Ausubel et al. edit, John Wiley & Sons, Section 11.4–11.11).

The antibody binding to the polypeptide of the present invention can be used for purification of the polypeptide of the invention, and also for detection and/or diagnosis of the abnormalities of the expression and structure of the polypeptide. Specifically, polypeptides can be extracted, for example, from tissues, blood, or cells, and the polypeptide of the invention is detected by Western blotting, immunoprecipitation, or ELISA, etc. for the above purpose.

Furthermore, the antibody binding to the polypeptide of the present invention can be utilized for treating the diseases that associates with the polypeptide of the invention. If the antibodies are used for treating patients, human antibodies, humanized antibodies, or chimeric antibodies are preferable in terms of their low antigenicity. The human antibodies can be prepared by immunizing a mouse whose immune system is replaced with that of human (e.g., see "Functional transplant of megabase human immunoglobulin loci recapitulates human antibody response in mice" Mendez, M. J. et al. (1997) Nat. Genet. 15: 146–156). The humanized antibodies can be prepared by recombination of the hypervariable region of a monoclonal antibody (Methods in Enzymology (1991) 203: 99–121).

A cDNA of the present invention encodes, for example, an amino acid sequence of a protein that is predicted to have the following function. The use of the amino acid sequences of the polypeptides encoded by the cDNAs of the present invention enables predicting that the polypeptides have the following functions. It can be predict, from the results of homology search of SwissProt, GenBank, UniGene, or nr, that these polypeptides have such functions. Specifically, for instance, as shown in Examples, searching for a known gene or polypeptide that is homologous to the partial sequence of the full-length cDNA of the invention (2443 clone) and referring the function of the gene and of the polypeptide encoded by the gene make it possible to predict the function of the polypeptide encoded by the cDNA of the invention. In this way, each of 1216 clones out of the 2443 full-length cDNA clones of the invention was predicted to encode a polypeptide that was classified into the following categories.

Secretory and/or membrane protein (632 clones)
Glycoprotein-related protein (128 clones)
Signal transduction-related protein (84 clones)
Transcription-related protein (144 clones)
Disease-related protein (387 clones)
Enzyme and/or metabolism-related protein (206 clones)
Cell division- and/or cell proliferation-related protein (33 clones)
Cytoskeleton-related protein (75 clones)
Nuclear protein and/or RNA synthesis-related protein (65 clones)
Protein synthesis- and/or transport-related protein (62 clones)
Cellular defense-related protein (15 clones)
Development and/or differentiation-related protein (13 clones)
DNA- and/or RNA-binding protein (174 clones)
ATP- and/or GTP-binding protein (68 clones)

The functions of the polypeptides encoded by the cDNAs of the present invention can be predicted by assessing the presence of signal sequence, transmembrane region, nuclear translocation signal, glycosylation signal, phosphorylation site, and zinc finger motif, SH3 domain, etc. in the amino acid sequences. The programs, PSORT (Nakai K., and Kanehisa M. (1992) Genomics 14: 897–911), SOSUI (Hirokawa T. et al. (1998) Bioinformatics 14: 378–379) (Mitsui Knowledge Industry), and MEMSAT (Jones D. T., Taylor W. R., and Thornton J. M. (1994) Biochemistry 33: 3038–3049) can be used to predict the existence of the signal sequence or transmembrane region. Alternatively, a partial amino acid sequence of the polypeptide is fused with another polypeptide such as GFP, the fusion polypeptide is transfected into cultured cells, and the localization is analyzed to predict the function of the original polypeptide.

Based on the determined nucleotide sequences of the full-length cDNAs obtained in the present invention, it is possible to predict more detailed functions of the polypeptides encoded by the cDNA clones, for example, by searching the databases such as GenBank, Swiss-Prot, UniGene, and nr for homologies of the cDNA5; or by searching the amino acid sequences deduced from the full-length cDNA5 for signal sequences by using software programs such as PSORT, for transmembrane regions by using software programs such as SOSUI or for motifs by using software programs such as Pfam and PROSITE. As a matter of course, the functions are often predictable by using partial sequence information (preferably 300 nucleotides or more) instead of the full-length nucleotide sequences. However, the result of the prediction by using partial nucleotide sequence does not always agree with the result obtained by using full-length nucleotide sequence, and thus, it is needless to say that the prediction of function is preferably performed based on the full-length nucleotide sequences.

GenBank, Swiss-Prot, UniGene and nr databases were searched for homologies of the full-length nucleotide sequences of the 2443 clones (see Example 6). The amino acid sequences deduced from the full-length nucleotide sequences were searched for functional domains by PSORT, SOSUI and Pfam. Prediction of functions of polypeptides encoded by the, clones and the categorization thereof were performed based on these results obtained. The categorization was carried out by the following method.

[1] Firstly, the cDNA clones were classified into the above-mentioned 14 functional categories based on the results of annotation-based categorization (using the keywords in the case of Swiss-Prot hit data; using Definition or Reference information in the case of GenBank, UniGene, or nr hit data), and the signal sequence search of the deduced ORFs by PSORT and the transmembrane region search by SOSUI.

[2] Secondly, clones which had been unassignable to the categories by the method of [1] were searched for functional domains and/or motifs by Pfam. Based on the results, the clones were additionally classified into the above-mentioned 14 types of categories when they had a functional domain and/or motif assignable to any one of the categories.

The following 632 clones presumably belong to secretory and/or membrane proteins.

ADIPS10000640, ADRGL10001470, ADRGL20013520, ADRGL20018540, ADRGL20035850, ASTRO20001410, ASTRO20005330, ASTRO20033160, ASTRO20055750, ASTRO20058630, ASTRO20190390, BEAST20004540, BGGI110000240, BNGH420088500, BRACE20006400, BRACE20038000, BRACE20038470, BRACE20039040, BRACE20039540, BRACE20051380, BRACE20053630, BRACE20059370, BRACE20060550, BRACE20061050, BRACE20063630, BRACE20067430, BRACE20069090, BRACE20081720, BRACE20101700, BRACE20101710, BRACE20116110, BRACE20147800, BRACE20153680, BRACE20163350, BRACE20179340, BRACE20188470, BRACE20195100, BRACE20201570, BRACE20210140, BRACE20224480, BRACE20224500, BRACE20228480, BRACE20232840, BRACE20238000, BRACE20273890, BRACE20274080, BRALZ20013500, BRALZ20054710, BRALZ20064740, BRALZ20069760, BRALZ20073760, BRALZ20077930, BRAMY20000860, BRAMY20002780, BRAMY20025840, BRAMY20039260, BRAMY20060920, BRAMY20063970, BRAMY20111960, BRAMY20112800, BRAMY20124260, BRAMY20134140, BRAMY20135900, BRAMY20136210, BRAMY20144620, BRAMY20152110, BRAMY20174550, BRAMY20181220, BRAMY20195090, BRAMY20211390, BRAMY20211420, BRAMY20215230, BRAMY20218250, BRAMY20218670, BRAMY20229800, BRAMY20231720, BRAMY20247280, BRAMY20252180, BRAMY20273960, BRAMY20277170, BRAMY20284910, BRAMY20285160, BRAWH20015350, BRAWH20015890, BRAWH20016860, BRAWH20018730, BRAWH20030250, BRAWH20064050, BRAWH20110790, BRAWH20112940, BRAWH20117950, BRAWH20118230, BRAWH20121640, BRAWH20122580, BRAWH20132190, BRCAN20064010, BRCAN20071190, BRCAN20091560, BRCAN20103740, BRCAN20224720, BRCAN20273550, BRCAN20280360, BRCAN20285450, BRCOC10000870, BRCOC20004040, BRCOC20006370, BRCOC20041750, BRCOC20077690, BRCOC20078640, BRCOC20090520, BRCOC20101230, BRCOC20107300, BRCOC20114180, BRCOC20121720, BRCOC20134480, BRCOC20136750, BRHIP10001290, BRHIP20000870, BRHIP20003120, BRHIP20103090, BRHIP20111200, BRHIP20118380, BRHIP20118910, BRHIP20121410, BRHIP20135100, BRHIP20174040, BRHIP20179200, BRHIP20183690, BRHIP20191490, BRHIP20191770, BRHIP20198190, BRHIP20207430, BRHIP20208270, BRHIP20208590, BRHIP20217620, BRHIP20233090, BRHIP20234380, BRHIP20238880, BRHIP20283030, BRHIP30004570, BRSSN20003120, BRSSN20043040, BRSSN20066110, BRSSN20120810, BRSSN20137020, BRSSN20142940, BRSSN20146100, BRSSN20151990, BRSSN20169050, BRSTN20002200, BRTHA20004740, BRTHA20046290, BRTHA20046420, COLON10001350, COLON20093370, CTONG10000100, CTONG10000940, CTONG10001650, CTONG20004690, CTONG20009770, CTONG20092570, CTONG20092580, CTONG20095340, CTONG20099380, CTONG20103480, CTONG20105080, CTONG20114740, CTONG20119200, CTONG20120770, CTONG20124730, CTONG20131490, CTONG20132220, CTONG20133480, CTONG20139340, CTONG20149950, CTONG20155400, CTONG20158660, CTONG20159530, CTONG20161850, CTONG20267700, D30ST10001090, D30ST20036070, D30ST20038560, D30ST30002580, D60ST20005070, D90ST20002780, D90ST20015470, D90ST20023970, D90ST20026730, D90ST20035940, D90ST20040180, DFNES20025880, FCBBF10000240, FCBBF10000380, FCBBF10001150, FCBBF10001210, FCBBF10001550, FCBBF10002430, FCBBF10002700, FCBBF10003220, FCBBF10003760, FCBBF10005460, FCBBF10005740, FCBBF20032970, FCBBF20042560, FCBBF20049300, FCBBF20051220, FCBBF30008470, FCBBF30024750, FCBBF30078290, FCBBF30083620, FCBBF30086440, FCBBF30090690, FCBBF30095260, FCBBF30123470, FCBBF30172550, FCBBF30175310, FCBBF30190850, FCBBF30215060, FCBBF30238870, FCBBF30251420, FCBBF30279030, FEBRA20002100, FEBRA20004620, FEBRA20009090, FEBRA20029860, FEBRA20037260, FEBRA20080810, FEBRA20086620, FEBRA20092890, FEBRA20093520, FEBRA20095880, FEBRA20111460, FEBRA20125070, FEBRA20130190, FEBRA20140100, FEBRA20145780, FEBRA20211710, FEBRA20223220, FEBRA20229630, FEBRA20235500, HCHON20000380, HCHON20008180, HCHON20015980, HCHON20016040, HCHON20016650, HCHON20040020, HCHON20064590, HCHON20067700, HCHON20068710, HCHON20086720, HCHON20100740, HEART20003060, HEART20005410, HEART20034320, HEART20049410, HEART20049800, HEART20072310, HHDPC20001040, HHDPC20014320, HHDPC20034720, HHDPC20068620, HHDPC20084140, HHDPC20091780, HHDPC20092080, HLUNG10000550, KIDNE20003940, KIDNE20007770, KIDNE20011400, KIDNE20021910, KIDNE20022620, KIDNE20100070, KIDNE20101510, KIDNE20109730, KIDNE20121880, KIDNE20125630, KIDNE20126010, KIDNE20126130, KIDNE20127450, KIDNE20130450, KIDNE20131580, KIDNE20137340, KIDNE20181660, LIVER20035110, LIVER20045650, LIVER20055200, LIVER20062510, LIVER20064690, LIVER20075680, LIVER20087060, LIVER20091180, MESAN10001260, MESAN20014500, MESAN20027090, MESAN20038510, MESAN20089360, MESAN20103120, MESAN20115970, MESAN20125860, MESAN20139360, MESAN2Q152770, MESAN20153910, MESAN20174170, NOVAR20000380, NT2NE20010050, NT2NE20021620, NT2NE20068130, NT2NE20118960, NT2NE20124480, NT2NE20131890, NT2NE20132170, NT2NE20155110, NT2NE20156260, NT2NE20157470, NT2NE20159740, NT2NE20177520, NT2NE20183760, NT2RI20003480, NT2RI20023910, NT2RI20025400, NT2RI20028470, NT2RI20040930, NT2RI20054050, NT2RI20056700, NT2RI20076290, NT2RI20086220, NT2RI20091940, NT2RI20244600, NT2RP70072690, NT2RP70081610, NT2RP70122910, NT2RP70125160, NT2RP70133740, NT2RP70134990, NT2RP70137290, NT2RP70179710, NT2RP70188020, NT2RP70192730, NT2RP70198350, NTONG20028070, NTONG20029700, NTONG20048060, NTONG20049910, NTONG20051530, NTONG20061870, NTONG20063010, NTONG20067830, NTONG20076930, NTONG20092330, OCBBF10001750, OCBBF20013890, OCBBF20019830, OCBBF20023570, OCBBF20026630, OCBBF20046690, OCBBF20050770, OCBBF20059560, OCBBF20063320, OCBBF20071210, OCBBF20072320, OCBBF20080050, OCBBF20086400, OCBBF20086910, OCBBF20087010, OCBBF20088140, OCBBF20091150, OCBBF20107090, OCBBF20108630, OCBBF20116850,

OCBBF20120390, OCBBF20122620, OCBBF20130910, OCBBF20132850, OCBBF20145760, OCBBF20155060, OCBBF20178880, OCBBF20180120, OCBBF20180840, OCBBF20188730, PANCR10000910, PEBLM10000710, PEBLM20024320, PEBLM20040150, PEBLM20074370, PEBLM20075980, PERIC20004220, PLACE60086400, PLACE60121080, PLACE60161600, PLACE60177140, PROST20005050, PROST20050670, PROST20107820, PROST20116600, PROST20120160, PROST20127800, PROST20146010, PROST20164440, PROST20169800, PROST20170980, PROST20175290, PUAEN20003740, PUAEN20030180, SALGL10001710, SKMUS20003610, SKMUS20007800, SKMUS20011640, SKMUS20020840, SKMUS20028210, SKMUS20028400, SKMUS20077400, SKNSH20028660, SKNSH20031740, SKNSH20051940, SKNSH20063040, SMINT20009840, SMINT20011990, SMINT20022020, SMINT20029760, SMINT20040860, SMINT20050750, SMINT20053870, SMINT20073650, SMINT20095050, SMINT20100680, SMINT20105330, SMINT20106720, SMINT20121950, SMINT20127930, SMINT20144430, SMINT20144890, SMINT20153260, SMINT20154540, SMINT20157450, SMINT20173240, SMINT20178550, SMINT20191420, SMINT20192000, SPLEN20003070, SPLEN20021660, SPLEN20029310, SPLEN20079510, SPLEN20095810, SPLEN20097330, SPLEN20118300, SPLEN20141360, SPLEN20141990, SPLEN20142100, SPLEN20144520, SPLEN20152760, SPLEN20157880, SPLEN20165310, SPLEN20167200, SPLEN20169220, SPLEN20169720, SPLEN20171890, SPLEN20172120, SPLEN20179810, SPLEN20186430, SPLEN20211570, SPLEN20211940, SPLEN20213830, SPLEN20273950, SPLEN20292950, SPLEN20293800, SPLEN20304950, SPLEN20329240, STOMA20005390, STOMA20005670, STOMA20006400, STOMA20006780, STOMA20008880, STOMA20051200, STOMA20056640, STOMA20056670, STOMA20062130, STOMA20077450, STOMA20080500, STOMA20088380, STOMA20092530, SYNOV20001520, SYNOV20001730, SYNOV20002510, SYNOV20002790, SYNOV20002970, SYNOV20004260, SYNOV20007000, SYNOV20008240, SYNOV20009230, SYNOV20010880, SYNOV20011110, SYNOV20013000, SYNOV20013560, SYNOV20013900, SYNOV30001840, TBAES20003150, TESOP20004000, TESOP20005690, TESTI20001720, TESTI20036380, TESTI20037560, TESTI20094120, TESTI20110280, TESTI20123080, TESTI20123560, TESTI20128350, TESTI20136100, TESTI20136710, TESTI20143390, TESTI20148000, TESTI20164100, TESTI20193360, TESTI20209810, TESTI20209990, TESTI20211220, TESTI20214250, TESTI20216370, TESTI20230250, TESTI20231940, TESTI20242990, TESTI20244190, TESTI20254220, TESTI20254860, TESTI20265970, TESTI20271850, TESTI20272960, TESTI20284880, TESTI20291310, TESTI20291960, TESTI20303220, TESTI20303360, TESTI20303420, TESTI20307700, TESTI20309170, TESTI20314180, TESTI20316870, TESTI20333000, TESTI20335200, TESTI20347180, TESTI20347300, TESTI20352620, TESTI20357960, TESTI20370810, TESTI20373820, TESTI20383880, TESTI20390260, TESTI20390410, TESTI20391770, TESTI20393530, TESTI20396130, TESTI20397760, TESTI20401020, TESTI20401280, TESTI20415170, TESTI20421490, TESTI20422640, TESTI20441940, TESTI20442760, TESTI20444130, TESTI20444180, TESTI20449200, TESTI20463520, TESTI20463580, TESTI20465350, THYMU10005360, THYMU10005540, THYMU20027560, THYMU20032870, THYMU20039810, THYMU20066100, THYMU20081490, THYMU20100410, THYMU20106710, THYMU20111830, THYMU20141670, THYMU20147770, THYMU20159430, THYMU20161640, THYMU20162190, THYMU20173980, THYMU20194420, THYMU20208300, THYMU20216840, THYMU20222890, THYMU20229220, THYMU20241850, THYMU20277390, TKIDN20005210, TRACH20002870, TRACH20003590, TRACH20016210, TRACH20019960, TRACH20029540, TRACH20033230, TRACH20034840, TRACH20042920, TRACH20050040, TRACH20067620, TRACH20068660, TRACH20069180, TRACH20076740, TRACH20085400, TRACH20085830, TRACH20109650, TRACH20111130, TRACH20121380, TRACH20128110, TRACH20128230, TRACH20134950, TRACH20136710, TRACH20139820, TRACH20140820, TRACH20145440, TRACH20168350, TRACH20180840, TRACH20190240, UMVEN20000690, UTERU20030570, UTERU20040610, UTERU20046980, UTERU20055480, UTERU20064860, UTERU20076390, UTERU20094350, UTERU20135860, UTERU20144640, UTERU20158300, UTERU20158800, UTERU20161570, UTERU20178100, UTERU20183640, UTERU20186740

The following 128 clones presumably belong to glycoprotein-related proteins.

ADIPS10000640, BRACE20059370, BRACE20163350, BRAMY20277170, BRAMY20285160, BRAWH20064050, BRAWH20112940, BRAWH20117950, BRAWH20118230, BRCAN20103740, BRCOC20004040, BRCOC20006370, BRHIP10001290, BRHIP20103090, BRHIP20283030, BRHIP30004570, BRSSN20003120, BRSSN20146100, BRTHA20046290, COLON10001350, CTONG20159530, D90ST20023970, D90ST20040180, FCBBF10001150, FCBBF20049300, FCBBF30024750, FCBBF30083620, FCBBF30190850, FCBBF30238870, FEBRA20086620, FEBRA20092890, HCHON20015980, HCHON20016040, HCHON20064590, HCHON20086720, HCHON20100740, HEART20003060, HHDPC20014320, HHDPC20068620, HHDPC20092080, KIDNE20003940, KIDNE20007770, KIDNE20101510, LIVER20064690, MESAN20125860, NT2NE20118960, NT2NE20157470, NT2NE20177520, NT2RI20003480, NT2RI20056700, NT2RP70192730, NTONG20051530, NTONG20076930, OCBBF20107090, OCBBF20108630, OCBBF20120390, OCBBF20145760, OCBBF20155060, PLACE60177140, SMINT20050750, SMINT20073650, SMINT20105330, SMINT20106720, SMINT20112730, SMINT20127930, SMINT20153260, SMINT20179740, SMINT20190170, SPLEN20021660, SPLEN20142100, SPLEN20157880, SPLEN20165310, SPLEN20179810, SPLEN20186430, STOMA20001830, STOMA20005390, STOMA20005670, STOMA20006400, STOMA20008880, STOMA20034770, STOMA20056640, STOMA20056670, STOMA20083610, STOMA20088380, STOMA20092530, SYNOV20001520, SYNOV20001730, SYNOV20002510, SYNOV20002790, SYNOV20002970, SYNOV20004260, SYNOV20007000, SYNOV20008240, SYNOV20009230, SYNOV20010880, SYNOV20011110, SYNOV20013000, SYNOV20013560, SYNOV20013900, TESOP20004000, TESTI20136100, TESTI20216370, TESTI20244190, TESTI20254860, TESTI20303220, TESTI20335200, TESTI20352620, TESTI20358980, TESTI20442760, TESTI20449200, TESTI20455090, THYMU10005360, THYMU10005540, THYMU20147770, THYMU20159430, THYMU20241850, TRACH20016210,

TRACH20050040, TRACH20067620, TRACH20069180, TRACH20076740, TRACH20128230, UTERU20046980, UTERU20064860, UTERU20144640, UTERU20158800, UTERU20161570, UTERU20183640

The following 84 clones presumably belong to signal transduction-related proteins.

ASTRO20108190, BRACE20115920, BRACE20154120, BRACE20177200, BRACE20237270, BRAMY20104640, BRAMY20242470, BRAMY20271400, BRAWH20016620, BRAWH20103290, BRAWH20149340, BRCOC20021550, BRCOC20091960, BRHIP20189980, BRHIP20218580, BRHIP20238600, BRSSN20038200, CD34C30004240, CTONG20118150, CTONG20127450, CTONG20200310, FCBBF30012350, FCBBF40001730, FEBRA10001880, FEBRA20004620, FEBRA20132740, FEBRA20144170, FEHRT20003250, HCHON20007510, HLUNG20033780, IMR3220002430, KIDNE20008010, KIDNE20102710, KIDNE20107620, NT2NE20080170, NT2NE20181650, NT2RP70027380, NT2RP70036880, NT2RP70063950, NT2RP70078420, NT2RP70159960, NTONG20046140, NTONG20056570, OCBBF20028050, OCBBF20053430, OCBBF20054760, OCBBF20124360, OCBBF20127140, OCBBF20149280, OCBBF20173980, PEBLM20013120, PEBLM20085760, PROST20161950, PUAEN20015260, PUAEN20015860, PUAEN20083140, SMINT20028820, SMINT20049090, SMINT20110660, SPLEN20011410, SPLEN20121750, SPLEN20170310, SPLEN20181810, SPLEN20222270, SPLEN20250170, SPLEN20283650, TESTI20035960, TESTI20288910, TESTI20305540, TESTI20326810, TESTI20369650, TESTI20392250, TESTI20416640, TESTI20432750, TESTI20467320, THYMU20169680, THYMU20172150, THYMU20201980, THYMU20202890, TKIDN20004640, TKIDN20047480, TRACH20057690, UMVEN10001860, UTERU20146310

The following 144 clones presumably belong to transcription-related proteins.

3NB6920014590, ADIPS20004250, ASTRO20008010, ASTRO20168470, BLADE20003400, BLADE20003890, BRACE20060890, BRACE20068590, BRACE20257100, BRAMY20210400, BRAMY20260910, BRAMY20270730, BRAWH20028110, BRAWH20075700, BRAWH20096780, BRCAN20280210, BRCOC20144000, BRCOC20178270, BRHIP20005340, BRHIP20096170, BRHIP20119330, BRHIP20191860, BRHIP20195890, BRHIP20222280, BRSSN20039370, BRSSN20046790, BRSSN20176820, CTONG20050280, CTONG20075860, CTONG20085950, CTONG20091080, CTONG20092700, CTONG20121010, CTONG20124220, CTONG20133390, CTONG20133520, D90ST20033970, FCBBF10001710, FCBBFl0004370, FCBBF20059090, FCBBF20068820, FCBBF30007680, FCBBF30010810, FCBBF30018550, FCBBF30025560, FCBBF30057290, FCBBF30083820, FCBBF30129630, FCBBF30240960, FCBBF30246230, FEBRA20018690, FEBRA20026110, FEBRA20034680, FEBRA20040530, FEBRA20082010, FEBRA20171380, FEBRA20195820, FEBRA20233770, HCHON20008320, HCHON20009560, HCHON20035130, HHDPC10000830, HHDPC20030490, HHDPC20031130, KIDNE20027250, KIDNE20027950, KIDNE20182690, LIVER20055440, NT2NE20010490, NT2NE20089970, NT2NE20142210, NT2NE20184900, NT2RP60000770, NT2RP70043480, NT2RP70063950, NT2RP70102350, NT2RP70157890, NTONG20070200, OCBBF10001850, OCBBF20020830, OCBBF20037440, OCBBF20046120, OCBBF20049300, OCBBF20054200, OCBBF20066390, OCBBF20071840, OCBBF20080410, OCBBF20108190, OCBBF20125530, OCBBF20148280, PEBLM20060360, PEBLM20078320, PERIC20003870, PROST10003220, PROST20047390, PROST20066880, PROST20185830, PROST20189770, PROST20191640, SKNSH20008190, SMINT20001760, SMINT20028820, SMINT20130320, SMINT20144800, SPLEN20026950, SPLEN20054290, SPLEN20079260, SPLEN20095410, SPLEN20117660, SPLEN20140800, SPLEN20147390, SPLEN20160450, SPLEN20162680, SPLEN20243830, SPLEN20250170, SPLEN20252190, SPLEN20267650, STOMA20032890, STOMA20063250, TESTI20039400, TESTI20041690, TESTI20067200, TESTI20088220, TESTI20130010, TESTI20156100, TESTI20230850, TESTI20318090, TESTI20320670, TESTI20378190, TESTI20385960, TESTI20409890, TESTI20420620, TESTI20432820, TESTI20456110, THYMU20247480, TRACH20079690, TRACH20154860, TRACH20163170, TRACH20164980, TRACH20184490, UTERU20099720, UTERU20116570, UTERU20145480, UTERU20176130

The following 387 clones presumably belong to disease-related proteins.

ADIPSZ0004250, ADRGL10001470, ADRGL20011190, ADRGL20018300, ADRGL20035850, ADRGL20078100, ASTRO10001650, ASTRO20008010, ASTRO20027430, ASTRO20106150, ASTRO20108190, ASTRO20168470, BLADE20003400, BLADE20003890, BRACE20038480, BRACE20039540, BRACE20059370, BRACE20108130, BRACE20108880, BRACE20115920, BRACE20116460, BRACE20232840, BRACE20248260, BRACE20253330, BRACE20284100, BRALZ20013500, BRALZ20017430, BRALZ20018340, BRAMY20000520, BRAMY20025840, BRAMY20120910, BRAMY20134140, BRAMY20135900, BRAMY20162510, BRAMY20174550, BRAMY20210400, BRAMY20211390, BRAMY20242470, BRAMY20245300, BRAMY20266850, BRAMY20285160, BRAWH20016620, BRAWH20028110, BRAWH20064050, BRAWH20096780, BRAWH20110960, BRAWH20113430, BRAWH20114000, BRAWH20118230, BRAWH20121640, BRAWH20128270, BRAWH20137480, BRCAN20103740, BRCAN20224720, BRCAN20279700, BRCAN20280210, BRCAN20283190, BRCOC20001860, BRCOC20006370, BRCOC20027510, BRCOC20055420, BRCOC20099370, BRCOC20178270, BRCOC20178560, BRHIP20003120, BRHIP20005340, BRHIP20174040, BRHIP20176420, BRHIP20191490, BRHIP20191860, BRHIP20194940, BRHIP20195890, BRHIP20222280, BRHIP20249110, BRHIP20285930, BRHIP30004880, BRSSN20013420, BRSSN20038200, BRSSN20039370, BRSSN20046790, BRSSN20066110, BRSSN20101100, BRSSN20120810, BRSSN20187310, BRTHA20046290, CD34C30004240, COLON10001350, CTONG20004690, CTONG20052650, CTONG20099550, CTONG20124220, CTONG20125640, CTONG20128430, CTONG20131560, CTONG20133390, CTONG20153300, CTONG20153580, CTONG20158040, CTONG20159530, D60ST20003580, D90ST20023970, DFNES20001530, DFNES20037420, FCBBF10001210, FCBBF10001710, FCBBF10003770, FCBBF20059090, FCBBF20064520, FCBBF20068820, FCBBF30010810, FCBBF30024750, FCBBF30025560, FCBBF30039020, FCBBF30049550, FCBBF30057290, FCBBF30083620, FCBBF30129630, FCBBF30190850, FCBBF30238870, FCBBF30240960, FCBBF30243640, FCBBF30279030, FCBBF30281880, FCBBF40001730, FEBRA10001880, FEBRA20004620,

FEBRA20010120, FEBRA20018690, FEBRA20082010, FEBRA20097310, FEBRA20130190, FEBRA20132740, FEBRA20144170, FEBRA20195820, FEBRA20223220, FEBRA20233770, FEBRA20235500, FEHRT20003250, HCHON10001760, HCHON20007380, HCHON20008320, HCHON20009560, HCHON20015230, HCHON20015980, HCHON20016040, HCHON20035130, HCHON20036420, HCHON20064590, HCHON20067700, HCHON20086720, HCHON20100740, HEART20003060, HEART20017730, HEART20025980, HEART20049410, HHDPC20014320, HHDPC20030490, HHDPC20084140, HHDPC20091140, HHDPC20091780, HHDPC20092080, HLUNG20033780, IMR3220002430, KIDNE20007770, KIDNE20020150, KIDNE20021680, KIDNE20022620, KIDNE20024830, KIDNE20027950, KIDNE20101370, KIDNE20101510, KIDNE20182690, LIVER20002160, LIVER20055200, LIVER20055440, LIVER20059810, LIVER20064690, MESAN20101140, MESAN20125860, MESAN20130220, MESAN20154010, MESAN20174170, NOVAR10000910, NT2NE20010490, NT2NE20118960, NT2NE20157470, NT2RI20040990, NT2RI20041880, NT2RI20048840, NT2RI20050960, NT2RI20240080, NT2RP60000770, NT2RP70027380, NT2RP70032610, NT2RP70037240, NT2RP70192730, NT2RP70198350, NTONG20013620, NTONG20015870, NTONG20028070, NTONG20067830, NTONG20070200, NTONG20090600, NTONG20092330, OCBBF20006770, OCBBF20037440, OCBBF20046120, OCBBF20049300, OCBBF20053490, OCBBF20053730, OCBBF20054760, OCBBF20071840, OCBBF20072240, OCBBF20078920, OCBBF20108430, OCBBF20108580, OCBBF20127140, OCBBF20129360, OCBBF20145760, OCBBF20153350, OCBBF20173980, OCBBF20178880, PEBLM10000710, PEBLM20013120, PERIC10000250, PLACE60060420, PLACE60177140, PROST20100460, PROST20159240, PROST20169800, PROST20176170, PUAEN20018820, PUAEN20030180, PUAEN20055020, PUAEN20083140, SKMUS20018230, SKMUS20018500, SKMUS20021530, SKMUS20024750, SKMUS20029200, SKMUS20048970, SKMUS20049030, SKNSH20008190, SKNSH20089400, SMINT20001760, SMINT20026890, SMINT20028820, SMINT20050750, SMINT20073650, SMINT20105330, SMINT20112730, SMINT20121220, SMINT20127350, SMINT20127930, SMINT20136310, SMINT20138900, SMINT20153260, SMINT20155180, SMINT20179740, SMINT20190170, SMINT20191420, SPLEN20006070, SPLEN20011410, SPLEN20026950, SPLEN20027440, SPLEN20039240, SPLEN20079260, SPLEN20095410, SPLEN20146450, SPLEN20147390, SPLEN20151210, SPLEN20160450, SPLEN20170310, SPLEN20179180, SPLEN20186430, SPLEN20212730, SPLEN20243830, SPLEN20245300, SPLEN20250390, SPLEN20252190, SPLEN20267650, SPLEN20305620, STOMA20001830, STOMA20005390, STOMA20008880, STOMA20010250, STOMA20034770, STOMA20046680, STOMA20056670, STOMA20064470, STOMA20077450, STOMA20080500, STOMA20083610, STOMA20088380, SYNOV20001520, SYNOV20001730, SYNOV20002790, SYNOV20002970, SYNOV20007000, SYNOV20008240, SYNOV20009230, SYNOV20010880, SYNOV20011110, TBAES20003770, TESOP20004000, TESOP20005270, TESTI20031270, TESTI20036380, TESTI20044310, TESTI20067200, TESTI20116830, TESTI20121550, TESTI20156100, TESTI20168480, TESTI20208400, TESTI20215990, TESTI20231940, TESTI20234360, TESTI20237520, TESTI20238610, TESTI20239510, TESTI20249990, TESTI20266740, TESTI20316870, TESTI20318090, TESTI20335050, TESTI20335200, TESTI20343570, TESTI20352620, TESTI20368330, TESTI20369650, TESTI20385960, TESTI20392250, TESTI20400940, TESTI20404240, TESTI20420620, TESTI20436560, TESTI20438570, TESTI20441940, TESTI20442760, TESTI20443090, TESTI20449200, TESTI20455090, TESTI20455620, TESTI20456110, TESTI20463580, TESTI20465350, TESTI20465690, TESTI20467210, THYMU20122730, THYMU20126900, THYMU20130890, THYMU20159430, THYMU20169680, THYMU20172150, THYMU20180280, THYMU20193640, THYMU20209590, THYMU20232090, THYMU20247480, TKIDN10000010, TKIDN20004640, TKIDN20047480, TRACH20016210, TRACH20019960, TRACH20050040, TRACH20057690, TRACH20067620, TRACH20077540, TRACH20079690, TRACH20096610, TRACH20105870, TRACH20121380, TRACH20154860, TRACH20162860, TRACH20163170, TRACH20164980, TRACH20190240, TSTOM20005690, TUTER20002830, UTERU20030570, UTERU20116570, UTERU20144640, UTERU20151980, UTERU20158800, UTERU20183640, UTERU20185230

The following 206 clones presumably belong to the category of enzymes and/or metabolism-related proteins.

3NB6910001910, ADRGL10001470, ADRGL20035850, ADRGL20078100, ASTRO20105820, ASTRO20106150, ASTRO20130500, ASTRO20145760, BRACE20027620, BRACE20038000, BRACE20062640, BRACE20096200, BRACE20107530, BRACE20108130, BRACE20108880, BRACE20116460, BRACE20148240, BRACE20185680, BRACE20253160, BRALZ20017430, BRALZ20018340, BRAMY20104640, BRAMY20134140, BRAMY20153110, BRAMY20213100, BRAMY20252720, BRAWH20016620, BRAWH20105840, BRAWH20112940, BRAWH20114000, BRAWH20117950, BRAWH20125380, BRAWH20132190, BRAWH20171030, BRCAN20054490, BRCAN20224720, BRCAN20280360, BRCAN20283190, BRCAN20283380, BRCOC20001860, BRCOC20031250, BRCOC20055420, BRCOC20091960, BRCOC20144000, BRHIP10001290, BRHIP20005530, BRHIP20096850, BRHIP20103090, BRHIP20174040, BRHIP20249110, BRSSN20013420, BRSSN20015790, BRSSN20120810, BRSSN20146100, CTONG20095340, CTONG20106520, CTONG20118250, CTONG20127450, CTONG20140580, CTONG20153300, CTONG20158040, D30ST20006180, D60ST20003580, DFNES20031920, DFNES20071130, FCBBF10001820, FCBBF10003670, FCBBF30012350, FCBBF30012810, FCBBF30175310, FCBBF30243640, FEBRA10001880, FEBRA20007620, FEBRA20130190, FEBRA20144170, FEBRA20167390, FEBRA20196630, FEHRT20003250, HCHON10001760, HCHON20003220, HCHON20015350, HEART20034320, HEART20090000, HHDPC20014320, KIDNE20002520, KIDNE20008010, KIDNE20021680, KIDNE20022620, KIDNE20028390, KIDNE20028720, KIDNE20107620, LIVER20059810, MESAN20154010, NT2NE20118960, NT2NE20157470, NT2RI20005750, NT2RI20244600, NT2RI20273230, NT2RP70032610, NT2RP70045590, NT2RP70192730, NT2RP70195430, NTONG20009770, NTONG20013620, NTONG20046140, OCBBF20028650, OCBBF20030910, OCBBF20046690, OCBBF20050770, OCBBF20053430, OCBBF20053490, OCBBF20053730, OCBBF20054760, OCBBF20078920, OCBBF20124360, OCBBF20129360, OCBBF20178880, PEBLM20044520, PEBLM20052820, PEBLM20060490, PERIC10000250, PLACE50000660, PROST20083600,

PROST20169800, PUAEN20015260, PUAEN20030180, SKMUS20018230, SMINT20028820, SMINT20049090, SMINT20102780, SMINT20105330, SMINT20106290, SMINT20110660, SMINT20152940, SMINT20191420, SMINT20191530, SPLEN20021660, SPLEN20026950, SPLEN20121750, SPLEN20145720, SPLEN20149240, SPLEN20150940, SPLEN20151210, SPLEN20173510, SPLEN20212730, SPLEN20250390, SPLEN20305620, STOMA20006860, STOMA20077450, TBAES20002550, TBAES20003150, TESOP20004000, TESOP20005270, TESTI20001000, TESTI20002720, TESTI20002780, TESTI20060400, TESTI20066670, TESTI20082330, TESTI20083200, TESTI20108720, TESTI20116830, TESTI20143390, TESTI20148000, TESTI20216370, TESTI20232140, TESTI20234360, TESTI20237520, TESTI20239510, TESTI20266740, TESTI20314180, TESTI20334410, TESTI20343570, TESTI20352620, TESTI20355020, TESTI20366910, TESTI20368330, TESTI20369650, TESTI20375340, TESTI20397760, TESTI20416640, TESTI20432750, TESTI20463580, TESTI20465350, TESTI20471410, TESTI20473830, THYMU20023380, THYMU20111830, THYMU20126900, THYMU20169680, THYMU20202890, TKIDN20004640, TKIDN20047480, TRACH20003590, TRACH20016–210, TRACH20019960, TRACH20041830, TRACH20057690, TRACH20067620, TRACH20084720, TRACH20085830, TRACH20162860, UTERU20064860, UTERU20144640, UTERU20146310, UTERU20151980

The following 33 clones presumably belong to the category of cell division- and/or cell proliferation-related proteins.

BRALZ20077900, BRAMY20135900, BRAWH20002320, BRAWH20128270, BRCAN20071190, BRCAN20273640, BRHIP20096170, CTONG10000940, CTONG20124220, FCBBF30247930, FEBRA20113560, HCASM10000500, HCHON20097490, MESAN20025190, NT2RI20050960, OCBBF20039250, OCBBF20054760, OCBBF20072240, SMINT20051610, SPLEN20147110, SPLEN20284240, TESOP20005690, TESTI20234360, TESTI20305540, TESTI20332420, TESTI20335050, TESTI20368330, TESTI20392760, TESTI20400940, THYMU20161640, TKIDN20047480,.UTERU20097760, UTERU20185230

The following 75 clones presumably belong to the category of cytoskeleton-related proteins.

ADRGL20011190, ADRGL20018300, ASTRO10001650, ASTRO20055750, BRACE20003070, BRACE20059370, BRACE20163350, BRAMY20121620, BRAMY20157820, BRAMY20242470, BRAWH20028110, BRAWH20137480, BRCAN20003460, BRCOC20008160, BRCOC20059510, BRHIP20115080, BRHIP20137230, BRHIP20167880, BRHIP20283030, BRHIP20285830, BRSSN20187310, CTONG10002770, CTONG20052900, CTONG20121580, FCBBF10001150, FCBBF30013770, FCBBF30015940, FCBBF30049550, FEBRA20024100, FEBRA20237640, HCHON20015980, HCHON20068410, HEART20017730, HEART20025980, HEART20061950, HEART20077670, HLUNG20016330, KIDNE20118580, MESAN20004570, NT2RI20040990, NT2RI20041880, NT2RP70037240, NT2RP70062230, NTONG20015870, NTONG20056570, NTONG20067830, NTONG20090600, OCBBF20107090, OCBBF20155060, PLACE60079250, PUAEN20040670, SKMUS20001980, SKMUS20016220, SKMUS20048970, SKMUS20049030, SMINT20024570, SMINT20026890, SMINT20121220, SMINT20138900, SPLEN20006070, SPLEN20027440, SPLEN20142100, TESTI20063830, TESTI20094230, TESTI20278400, TESTI20371030, TESTI20417300, TESTI20436560, TESTI20455090, THYMU20105190, THYMU20172150, THYMU20209590, TRACH20096610, UMVEN10001560, UTERU20116570

The following 65 clones presumably belong to the category of nuclear proteins and/or RNA synthesis-related proteins.

BRACE20057190, BRACE20064880, BRACE20248260, BRACE20253160, BRAMY20000520, BRAMY20120910, BRAWH20113430, BRAWH20171030, BRCAN10001490, BRCAN20283190, BRCOC20037320, BRCOC20178560, BRHIP20106100, BRHIP20176420, BRHIP20243470, BRSSN20101100, CTONG20114290, CTONG20125540, CTONG20131560, CTONG20140580, DFNES20001530, FCBBF20064520, FEBRA20007620, FEBRA20010120, FEBRA20097310, FEBRA20144170, FEBRA20174410, FEBRA20215500, IMR3220002430, MESAN20101140, NT2RI20273230, OCBBF20028650, OCBBF20030910, OCBBF20078920, PROST20104000, PUAEN20018820, SKMUS20007010, SMINT20127350, SMINT20177360, SMINT20191530, SPLEN20008740, SPLEN20146450, STOMA20046680, TESTI20082330, TESTI20094470, TESTI20121550, TESTI20208400, TESTI20234360, TESTI20237520, TESTI20249990, TESTI20334410, TESTI20355020, TESTI20368330, TESTI20392760, TESTI20408970, TESTI20436560, TESTI20438570, TESTI20443090, THYMU20193640, THYMU20202890, THYMU20241210, TRACH20096610, TUTER20002830, UTERU20151980, UTERU20176320

The following 62 clones presumably belong to the category of protein synthesis- and/or protein transport-related proteins.

3NB6910001910, ASTRO20106150, ASTRO20130500, ASTRQ20141350, BRACE20038480, BRACE20052160, BRACE20057620, BRACE20106840, BRACE20172980, BRACE20192440, BRAWH20110960, BRCOC20037320, BRHIP20005530, BRSSN20120810, BRSTN20005360, CTONG20009770, CTONG20114290, CTONG20125640, CTONG20153300, D60ST20003580, DFNES20037420, FCBBF30012810, FEBRA20080810, HCHON20064590, HHDPC20014320, HHDPC20084140, HLUNG20017120, LIVER20064690, NT2NE20132170, NT2NE20157470, NT2RP70133740, NTONG20009770, NTONG20075220, NTONG20076930, OCBBF20030910, OCBBF20035930, OCBBF20153340, PLACE60060420, SMINT20152940, SPLEN20008740, SPLEN20103950, SPLEN20118300, SPLEN20212730, SPLEN20250390, STOMA20077450, TBAES20002550, TESOP20004000, TESTI20239510, TESTI20278400, TESTI20314180, TESTI20463580, THYMU20111830, THYMU20122730, THYMU20130890, THYMU20232090, TKIDN10000010, TRACH20084720, TRACH20105870, TRACH20139820, TRACH20149970, UTERU20120310, UTERU20188110

The following 15 clones presumably belong to the category of cellular defense-related proteins.

BRCOC20144000, CTONG20092680, KIDNE20020150, LIVER20002160, NT2RI20050960, NT2RP70045590, OCBBF20128120, PLACE60003480, SKNSH20089400, SMINT20106290, SPLEN20039240, TESTI20001000, TESTI20455620, TRACH20028030, UTERU20176320

The following 13 clones presumably belong to the category of development and/or differentiation-related proteins.

3NB6920014590, BRAMY20211390, CTONG20091080, CTONG20121010, FCBBF30024750, KIDNE20027250, NT2NE20142210, OCBBF20054200, PROST10003220, SKMUS20007010, SPLEN20179810, STOMA20063250, TESTI20291960

The following 174 clones presumably belong to the category of DNA- and/or RNA-binding proteins.

3NB6920014590, ADIPS20004250, ASTRO20008010, ASTRO20168470, BLADE20003400, BLADE20003890, BRACE20057620, BRACE20060890, BRACE20064880, BRACE20068590, BRACE20248260, BRACE20253160, BRAMY20000520, BRAMY20213100, BRAMY20260910, BRAMY20270730, BRAWH20028110, BRAWH20075700, BRAWH20096780, BRAWH20113430, BRCAN10001490, BRCAN20280210, BRCAN20283190, BRCOC20144000, BRCOC20178270, BRCOC20178560, BRHIP20005340, BRHIP20106100, BRHIP20119330, BRHIP20153600, BRHIP20176420, BRHIP20191860, BRHIP20195890, BRHIP20222280, BRSSN20039370, BRSSN20046790, BRSSN20176820, CTONG20050280, CTONG20075860, CTONG20085950, CTONG20091080, CTONG20092700, CTONG20121010, CTONG20124220, CTONG20125540, CTONG20133390, CTONG20133520, CTONG20140580, CTONG20156780, D90ST20033970, FCBBF10001710, FCBBF10004370, FCBBF20059090, FCBBF20064520, FCBBF20068820, FCBBF30007680, FCBBF30010810, FCBBF30018550, FCBBF30025560, FCBBF30057290, FCBBF30083820, FCBBF30129630, FCBBF30240960, FCBBF30246230, FEBRA20010120, FEBRA20018690, FEBRA20026110, FEBRA20034680, FEBRA20040530, FEBRA20082010, FEBRA20097310, FEBRA20171380, FEBRA20195820, FEBRA20196630, FEBRA20233770, HCHON20008320, HCHON20009560, HCHON20035130, HHDPC10000830, HHDPC20031130, KIDNE20017130, KIDNE20027250, KIDNE20027950, KIDNE20107390, KIDNE20182690, LIVER20055440, MESAN20101140, NT2NE20010490, NT2NE20089970, NT2NE20142210, NT2NE20184900, NT2RP60000770, NT2RP70044280, NT2RP70102350, NT2RP70158890, NTONG20070200, OCBBF10001850, OCBBF20020830, OCBBF20037440, OCBBF20046120, OCBBF20049300, OCBBF20066390, OCBBF20071840, OCBBF20078920, OCBBF20080410, OCBBF20108190, OCBBF20125530, OCBBF20148280, PEBLM20060360, PEBLM20060490, PEBLM20078320, PERIC10000250, PROST10003220, PROST20047390, PROST20066880, PROST20185830, PROST20189770, PROST20191640, PUAEN20018820, SKNSH20008190, SKNSH20089400, SMINT20001760, SMINT20127350, SMINT20144800, SMINT20177360, SMINT20191530, SPLEN20054290, SPLEN20079260, SPLEN20095410, SPLEN20140800, SPLEN20147390, SPLEN20160450, SPLEN20252190, SPLEN20267650, STOMA20010250, STOMA20032890, STOMA20046680, STOMA20063250, TESTI20039400, TESTI20067200, TESTI20088220, TESTI20094470, TESTI20121550, TESTI20130010, TESTI20156100, TESTI20204450, TESTI20230850, TESTI20237520, TESTI20266740, TESTI20318090, TESTI20320670, TESTI20334410, TESTI20355020, TESTI20378190, TESTI20385960, TESTI20432820, TESTI20443090, TESTI20456110, THYMU20193840, THYMU20241210, THYMU20247480, TRACH20079690, TRACH20105870, TRACH20139820, TRACH20154860, TRACH20163170, TRACH20164980, TRACH20184490, TUTER20002830, UTERU20099720, UTERU20116570, UTERU20145480, UTERU20176130, UTERU20185230

The following 68 clones presumably belong to the category of ATP- and/or GTP-binding proteins.

3NB6910001910, BRACE20108130, BRACE20148240, BRAMY20134140, BRAMY20157820, BRAMY20174550, BRAWH20164460, BRCAN20003460, BRCAN20054490, BRCAN20283190, BRCOC20059510, BRCOC20144000, BRHIP20103090, BRHIP20115080, BRHIP20167880, BRSTN20005360, CD34C30004240, CTONG20095340, CTONG20121580, CTONG20200310, DFNES20037420, FCBBF20067810, FCBBF30012350, FCBBF30015940, FEBRA20007620, FEBRA20024100, FEBRA20144170, KIDNE20020150, KIDNE20028720, LIVER20002160, LIVER20087060, NT2RI20005750, NT2RI20041880, NT2RI20048840, NT2RI20273230, OCBBF20028650, OCBBF20046690, OCBBF20054760, OCBBF20108430, OCBBF20108630, SMINT20121220, SMINT20183530, SMINT20191530, SPLEN20026950, SPLEN20039240, SPLEN20099700, SPLEN20145720, SPLEN20179180, STOMA20006860, TESTI20035960, TESTI20355020, TESTI20397760, TESTI20400940, TESTI20417300, TESTI20443090, TESTI20455620, THYMU20105190, THYMU20202890, THYMU20209590, TKIDN20004640, TKIDN20047480, TRACH20005400, TRACH20019960, TRACH20057690, TRACH20084720, UTERU20168220, UTERU20176320, UTERU20185230

Among the clones other than the ones shown above, BRAMY20248490, FCBBF10002800, NTONG20092290, OCBBF20127040, SMINT20163960, THYMU20279750, TRACH20167220, are clones which were predicted to highly possibly belong to the category of secretory protein and/or membrane protein based on the result of domain search by Pfam.

FCBBF10002800, NTONG20092290, OCBBF20127040, SMINT20163960, TESTI20478850, THYMU20279750

The 6 clones shown above are clones which were predicted to highly possibly belong to the category of glycoprotein-related protein based on the result of domain search by Pfam. BRACE20060720, BRACE20223330, BRALZ20058880, BRAMY20148130, BRAWH20101360, BRCAN20124080, BRHIP20253660, CTONG10000620, CTONG20014280, CTONG20124010, KIDNE20109890, MESAN20171520, OCBBF20109310, OCBBF20140640, PROST20079500, PUAEN20078980, SPLEN20077500, SPLEN20143180, TESTI20017950, TESTI20184620, TESTI20208710, TESTI20211160, TESTI20226230, TESTI20234140, TESTI20258460, TESTI20275030

The 26 clones shown above are clones which were predicted to highly possibly belong to the category of signal transduction-related protein based on the result of domain search by Pfam.

ADRGL20048330, ASTRO20064750, ASTRO20084250, BRACE20151320, BRALZ20058880, BRHIP20207990, CTONG20093950, FCBBF30195640, FEBRA10001900, FEBRA20090290, FEBRA20214970, FEBRA20222040, KIDNE20109890, LIVER20087510, MESAN20029400, MESAN20031900, MESAN20035290, MESAN20136110, NT2NE20130190, PEBLM20060310, PERIC20004780, PROST20171280, PUAEN20078980, SMINT20115880, SPLEN20095550, TESTI20023510, TESTI20083940, TESTI20152460, TESTI20185650, TESTI20189410, TESTI20200710, TESTI20308600, TESTI20343070, TESTI20369690, TESTI20381040, UTERU20050690

The 36 clones shown above are clones which were predicted to highly possibly belong to the category of transcription-related protein based on the result of domain search by Pfam.

BGGI120006160, BRACE20053480, BRACE20190040, BRACE20223330, BRAWH20101360, BRAWH20185060, BRCOC20023230, BRHIP20252450, BRSSN20105870, BRSSN20117990, BRTHA20000570, CTONG20098440, CTONG20129960, CTONG20146300, CTONG20155180, FEBRA20025270, HEART20083640, KIDNE20009470, LIVER20035680, MESAN20029400, MESAN20031900, MESAN20186700, NOVAR10000150, NTONG20029480, OCBBF20079310, OCBBF20082830, PEBLM20042900, PLACE60136500, PLACE60136720, PROST20114390, SKNSH20020540, SMINT20013480, SMINT20174360, SPLEN20077500, SPLEN20119810, SPLEN20126190, SPLEN20174260, SPLEN20211220, TESTI20046750, TESTI20057750, TESTI20061110, TESTI20197940, TESTI20211160, TESTI20226230, TESTI20255820, TESTI20317600, TESTI20377230, THYMU20111180, THYMU20115850, THYMU20143270, THYMU20240710, UTERU20055330, UTERU20055930, UTERU20064000, UTERU20119060

The 55 clones shown above are clones which were predicted to highly possibly belong to the category of enzyme and/or metabolism-related protein based on the result of domain search by Pfam.

TESTI20127760, TESTI20392270

The 2 clone shown above is a clone which was predicted to highly possibly belong to the category of cell division and/or cell proliferation-related protein based on the result of domain search by Pfam.

FCBBF30262510, MESAN20031900, NT2NE20125050, SMINT20068010, SPLEN20163560, STOMA20092890, TESTI20382750

The 7 clones shown above are clones which were predicted to highly possibly belong to the category of cytoskeleton-related protein based on the result of domain search by Pfam. THYMU20118520

The clone shown above is clone which was predicted to highly possibly belong to the category of Nuclear protein and/or RNA synthesis-related protein based on the result of domain search by Pfam. BRACE20053480, BRACE20240740, KIDNE20009470, OCBBF20140890, SMINT20035690, UTERU20064000

The 6 clones shown above are clones which were predicted to highly possibly belong to the category of Protein synthesis- and/or transport-related protein based on the result of domain search by Pfam.

ADRGL20048330, ASTRO20064750, ASTRO20084250, BRACE20151320, BRACE20190040, BRACE20223330, BRALZ20058880, BRAMY20103570, BRCOC20023230, BRHIP20207990, BRTHA20000570, CTONG20093950, CTONG20129960, CTONG20146300, CTONG20155180, CTONG20160560, FCBBF10004120, FCBBF30195640, FEBRA10001900, FEBRA20090290, FEBRA20214970, FEBRA20222040, HCHON20008150, HEART20083640, KIDNE20109890, LIVER20035680, LIVER20087510, MESAN20029400, MESAN20031900, MESAN20035290, MESAN20136110, MESAN20186700, NT2NE20130190, NT2RI20025640, NTONG20029480, PEBLM20060310, PERIC20004780, PROST20114390, PROST20171280, PUAEN20078980, SMINT20115880, SPLEN20095550, SPLEN20119810, TESTI20023510, TESTI20057750, TESTI20083940, TESTI20152460, TESTI20185650, TESTI20189410, TESTI20200710, TESTI20308600, TESTI20343070, TESTI20369690, TESTI20381040, THYMU20115850, UTERU20050690, UTERU20055330

The 57 clones shown above are clones which were predicted to highly possibly belong to the category of DNA- and/or RNA-binding protein based on the result of domain search by Pfam. PLACE60136720

The clone shown above is a clone which was predicted to highly possibly belong to the category of ATP- and/or GTP-binding proteins based on the result of domain search by Pfam.

The 213 clones shown below are clones which were unassignable to any of the above-mentioned categories, but have been predicted to have some functions based on homology search using their full-length nucleotide sequences and motif search in their estimated ORFs. Clone Name, Definition in the result of homology search or Motif Name in the motif search, demarcated by a double slash mark (//), are shown below.

ADRGL20028570//*Rattus norvegicus* MG87 mRNA, complete cds.

ADRGL20061930//transposon-derived Buster1 transposase-like protein

ASTRO20012490//Eukaryotic initiation factor 1A

ASTRO20072210//PERIAXIN.

ASTRO20114370//*Mus musculus* SMAR1 mRNA, complete cds.

ASTRO20125520//dnaj protein [Schizosaccharomyces pombe]

ASTRO20143630//KH domain// Bacterial regulatory proteins, crp family

ASTRO20155290//TPR Domain// TPR Domain// TPR Domain

ASTRO20181690//oocyte-specific protein P100

BGGI110001930//UBX domain

BRACE20011070//*Mus musculus* F-box protein FBX15 mRNA, partial cds.

BRACE20039440//*Drosophila melanogaster* CHARYBDE (charybde) mRNA, complete cds.

BRACE20050900//TPR Domain// TPR Domain// TPR Domain// TPR Domain

BRACE20053280//*Mus musculus* Pdz-containing protein (Pdzx) mRNA, complete cds.

BRACE20057730//toxin sensitivity protein KTI12 homolog

BRACE20058580//*Homo sapiens* HCMOGT-1 mRNA for sperm antigen, complete cds.

BRACE20063780//NOL1/NOP2/sun family

BRACE20269200//Heat-labile enterotoxin alpha chain

BRACE20276430//*Homo sapiens* retinoblastoma-associated protein RAP140 mRNA, complete cds.

BRACE20286360//Alpha adaptin carboxyl-terminal domain

BRAMY10001300//*Homo sapiens* MAGE-E1b mRNA, complete cds.

BRAMY20045240//Flagellar L-ring protein

BRAMY20054880//*Rattus norvegicus* KPL2 (Kpl2) mRNA, complete cds.

BRAMY20167060//Collagen triple helix repeat (20 copies)

BRAMY20184670//*Homo sapiens* mRNA for ALEXI, complete cds.

BRAMY20217460//*Homo sapiens* cardiac voltage gated potassium channel modulatory subunit mRNA, complete cds, alternatively spliced.

BRAMY20240040//*Homo sapiens* suppressor of white apricot homolog 2 (SWAP2) mRNA, complete cds.

BRAMY20247110//*Mus musculus* semaphorin cytoplasmic domain-associated protein 3A (Semcap3) mRNA, complete cds.

BRAWH20004600//*Mus musculus* mRNA for NAKAP95, complete cds.

BRAWH20011710//cytoplasmic linker 2

BRAWH20012390//Trichomonas vaginalis mRNA for centrin (cel gene).

BRAWH20017010//*Homo sapiens* testes development-related NYD-SP22 mRNA, complete cds.

BRAWH20029630//*Homo sapiens* bet3 (BET3) mRNA, complete cds.

BRAWH20138660//*Homo sapiens* stonin 2 mRNA, complete cds.

BRCOC20008500//Human ras inhibitor mRNA, 3' end.

BRCOC20026640//Gag P30 core shell protein

BRCOC20035130//14-3-3 PROTEIN EPSILON (MITOCHONDRIAL IMPORT STIMULATION FACTOR L SUBUNIT) (PROTEIN KINASE C INHIBITOR PROTEIN-1) (KCIP-1) (14-3-3E).

BRCOC20074760//CDC4-LIKE PROTEIN (FRAGMENT).

BRCOC20110100//Integrase core domain

BRCOC20176520//*Rattus norvegicus* mRNA for type II brain 4.1, complete cds.

BRHIP20001630//Protein of unknown function DUF16

BRHIP20132860//*Homo sapiens* rhophilin-like protein mRNA, complete cds.

BRHIP20143730//MYND finger

BRHIP20175420//*Mus musculus* partial mRNA for stretch responsive protein 278 (sr278 gene).

BRHIP20236950//Outer Capsid protein VP4 (Hemagglutinin)

BRSSN20014260//RIBONUCLEASE INHIBITOR.

BRSSN20018690//*Homo sapiens* NY-REN-25 antigen mRNA, partial cds.

BRSSN20021600//RING CANAL PROTEIN (KELCH PROTEIN).

BRSSN20177570//Phosducin

BRSTN10000830//Kelch motif// Kelch motif// Kelch motif// Kelch motif

CTONG10000220//*Mus musculus* cerebellar postnatal development protein-1 (Cpd1) mRNA, partial cds.

CTONG10000930//Armadillo/beta-catenin-like repeats

CTONG20027090//Glypican// Leucine Rich Repeat// Leucine Rich Repeat

CTONG20076130//ZINC FINGER PROTEIN 185 (LIM-DOMAIN PROTEIN ZNF185) (P1-A).

CTONG20096750//Disintegrin

CTONG20100240//*Mus musculus* radial spokehead-L protein (Rshl1) mRNA, complete cds.

CTONG20139860//*Homo sapiens* nasopharyngeal carcinoma susceptibility protein LZ16 mRNA, complete cds.

CTONG20143690//MYND finger

CTONG20149460//RING CANAL PROTEIN (KELCH PROTEIN).

CTONG20165050//Keratin, high sulfur B2 protein

CTONG20186320//RING CANAL PROTEIN (KELCH PROTEIN).

D30ST20013280//ARP2/3 COMPLEX 16 KDA SUBUNIT (P16-ARC).

D30ST20024360//*Homo sapiens* neuroendocrine differentiation factor mRNA, complete cds.

D90ST20031370//*Homo sapiens* mRNA for partial putative TCPTP-interacting protein (ptpip5 gene).

DFNES20014040//TRICHOHYALIN.

FCBBF10000630//*Homo sapiens* huntingtin interacting protein HYPB mRNA, partial cds.

FCBBF10000770//*Homo sapiens* REC8 mRNA, partial cds.

FCBBF10005060//CELLULAR RETINALDEHYDE-BINDING PROTEIN (CRALBP).

FCBBF10005500//Keratin, high sulfur B2 protein

FCBBF20014270//ACYL-COA-BINDING PROTEIN (ACBP) (DIAZEPAM BINDING INHIBITOR) (DBI) (ENDOZEPINE) (EP).

FCBBF20042170//Homo sapiens NIBAN mRNA, complete cds.

FCBBF30016320//SecA protein, amino terminal region

FCBBF30033050//Sm protein

FCBBF30054440//PLAT/LH2 domain

FCBBF30225660//Ank repeat// Ank repeat// Ank repeat// K+ channel tetramerisation domain// BTB/POZ domain FCBBF30233680//G10 protein FCBBF30246630//*H.sapiens* mRNA for ZYG homologue.

FCBBF30250730//TRICHOHYALIN.

FCBBF30252520//*Homo sapiens* bicaudal-D (BICD) mRNA, alternatively spliced, partial cds.

FCBBF30252800//NDRG1 PROTEIN (DIFFERENTIATION-RELATED GENE 1 PROTEIN) (DRG1) (REDUCING AGENTS AND TUNICAMYCIN-RESPONSIVE PROTEIN) (RTP) (NICKEL-SPECIFIC INDUCTION PROTEIN CAP43).

FCBBF30252850//*Mus musculus* peripherial benzodiazepine receptor associated protein (Pap7) mRNA, complete cds.

FCBBF30285280//Keratin, high sulfur B2 protein// Bacterial regulatory proteins, gntR family FEBRA20088360//ALPHA-ADAPTIN C (CLATHRIN ASSEMBLY PROTEIN COMPLEX 2 ALPHA-C LARGE CHAIN) (100 KDA COATED VESICLE PROTEIN C) (PLASMA MEMBRANE ADAPTOR HA2/AP2 ADAPTIN ALPHA C SUBUNIT).

FEBRA20184330//*Rattus norvegicus* glutamate receptor interacting protein 2 (GRIP2) mRNA, complete cds.

FEBRA20192420//Cyclin-dependent kinase inhibitor// IQ calmodulin-binding motif// IQ calmodulin-binding motif// IQ calmodulin-binding motif// IQ calmodulin-binding motif FEBRA20196370//Cyclin-dependent kinase inhibitor// IQ calmodulin-binding motif// IQ calmodulin-binding motif// IQ calmodulin-binding motif// IQ calmodulin-binding motif FEBRA20225040//high-glucose-regulated protein 8

HCHON20001560//TRANSCRIPTION FACTOR-LIKE PROTEIN MORF4.

HCHON20003440//*Homo sapiens* cyclin-D binding Myb-like protein mRNA, complete cds.

HCHON20010990//TPR Domain

HCHON20059870//Hypothetical protein.

HHDPC20034390//Cereal trypsin/alpha-amylase inhibito

HHDPC20057420//*Mus musculus* proline-rich protein (Bprp) mRNA, complete cds.

HHDPC20064600//SUPPRESSOR PROTEIN SRP40.

HLUNG20023340//*Mus musculus* SLM-1 (Slm1) mRNA, complete cds.

KIDNE20007210//*Xenopus laevis* mRNA for RPA interacting protein alpha (ripalpha gene).

KIDNE20028830//K-box region

KIDNE20115080//*Homo sapiens* mRNA for hNBL4, complete cds.

KIDNE20124400//*Homo sapiens* mRNA for ALEX1, complete cds.

KIDNE20127100//*Drosophila melanogaster* Diablo (dbo) mRNA, complete cds.

KIDNE20127750//*Homo sapiens* partial mRNA for transport-secretion protein 2.1 (TTS-2.1 gene).

KIDNE20190740//*Rattus norvegicus* SNIP-b mRNA, complete cds.

LIVER10004790//EF hand

LIVER20011130//*Homo sapiens* F-box protein FBL9 mRNA, partial cds.

LIVER20064100//*Ciona intestinalis* mRNA for myoplasmin-C1, complete cds.

LIVER20080530//*Drosophila melanogaster* forked mRNA for large Forked protein, complete cds.

MAMGL10000830//*Drosophila melanogaster* L82B (L82) mRNA, complete cds.

MESAN20036460//Corticotropin-releasing factor family

MESAN20127350//myelin expression factor-3

MESAN20141920//Human ovarian cancer downregulated myosin heavy chain homolog (Doc1) mRNA, complete cds.

NT2NE20010400//*Homo sapiens* GL013 mRNA, complete cds.

NT2NE20122430//GLYOXYLATE-INDUCED PROTEIN.

NT2NE20158600//erythroid ankyrin—*Synechocystis* sp. (strain PCC 6803).

NT2RI20001330//*Homo sapiens* KE03 protein mRNA, partial cds.

NT2RI20009870//lunatic fringe precursor [Mus musculus]

NT2RI20046080//recA bacterial DNA recombination proteins

NT2RI20091730//Molluscan rhodopsin C-terminal tail

NT2RP60000850//Bos taurus RPGR-interacting protein-1 (RPGRIP1) mRNA, complete cds.

NT2RP70080850//SPRY domain// Adenovirus-EB1 55K protein / large t-an

NT2RP70105210//Myc amino-terminal region

NT2RP70188710//Yeast PIR proteins

NT2RP70194450//Bacterial regulatory proteins, crp family

NTONG20052650//Gallus gallus Xin mRNA, complete cds.

NTONG20064400//REPETIN.

NTONG20064840//*Mus musculus* slp1 mRNA for synaptotagmin-like protein 1, complete cds.

NTONG20066460//*Mus musculus* Gd mRNA for gasdermin, complete cds.

NTONG20067090//*Mus musculus* mRNA for Sh3yl1, complete cds.

NTONG20070340//collagen alpha 1(IX) chain

NTONG20083650//TPR Domain// TPR Domain// TPR Domain// PPR repeat// TPR Domain// PPR repeat// TPR Domain NTONG20088620//*Homo sapiens* genethonin 3 mRNA, partial cds.

OCBBF10000540//*Mus musculus* ris (rjs) mRNA, complete cds.

OCBBF20019380//seizure related gene 6

OCBBF20022900//*Homo sapiens* SCHIP-1 mRNA, complete cds.

OCBBF20030280//*Rattus norvegicus* hfb2 mRNA, complete cds.

OCBBF20046470//ARFAPTIN 1.

OCBBF20049840//*Homo sapiens* mRNA for neurabin II protein.

OCBBF20068490//*Mus musculus* RW1 protein mRNA, complete cds.

OCBBF20071960//Coturnix coturnix japonica qMEF2D gene.

OCBBF20073540//*Homo sapiens* p30 DBC mRNA, complete cds.

OCBBF20121390//RING CANAL PROTEIN (KELCH PROTEIN).

OCBBF20127550//Outer Capsid protein VP4 (Hemagglutinin)

OCBBF20148730//RING CANAL PROTEIN (KELCH PROTEIN).

OCBBF20178150//Plasmodium falciparum ADA2-like protein gene, partial cds.

PEBLM10000240//Domain found in Dishevelled, Egl-10, and Ple

PROST20047270//CRAL/TRIO domain.

PROST20112970//Sterile alpha motif (SAM)/Pointed domain// SAM domain (Sterile alpha motif)

PUAEN10000850//Uncharacterized protein family UPF0025// Sec1 family

PUAEN20011880//*Mus musculus* mRNA for MIWI (piwi), complete cds.

PUAEN20051100//*Mus musculus* otogelin mRNA, complete cds.

PUAEN20108240//*Drosophila melanogaster* ankyrin 2 (Ank2) mRNA, complete cds.

SKMUS20084740//Syndecan domain

SMINT20053300//*Homo sapiens* hepatocellular carcinoma-associated antigen 59 mRNA, complete cds.

SMINT20071400//NOL1/NOP2/sun family

SMINT20101440//Human cisplatin resistance associated alpha protein (hCRA alpha) mRNA, complete cds.

SMINT20110330//pKID domain

SMINT20122910//*Mus musculus* StAR-related protein 1-4E mRNA, partial cds.

SMINT20131810//ENV polyprotein (coat polyprotein)

SMINT20168570//*Homo sapiens* mRNA for stabilin-1 (stab1 gene).

SPLEN20008390//Human placenta (Diff48) mRNA, complete cds.

SPLEN20084600//RING CANAL PROTEIN (KELCH PROTEIN).

SPLEN20128000//*Xenopus laevis* XMAB21 (Xmab-21) mRNA, complete cds.

SPLEN20149110//Dishevelled specific domain

SPLEN20171470//Keratin, high sulfur B2 protein

SPLEN20194050//*Homo sapiens* HOTTL protein mRNA, complete cds.

SPLEN20214580//*Mus musculus* mdgl-1 mRNA, complete cds.

STOMA20057820//Uncharacterized protein family UPF0024

STOMA20063980//Collagen triple helix repeat (20 copies)

STOMA20069040//Keratin, high sulfur B2 protein

SYNOV20017080//UBX domain

TBAES20000590//Cytochrome P450// Cytochrome P450

TESTI20001170//HORMA domain

TESTI20031810//Bacterial luciferase// Domain of unknown function DUF28

TESTI20044230//*Mus musculus* testis-specific Y-encoded-like protein (Tspyl1) mRNA, complete cds.

TESTI20098350//VAT-Nn domain

TESTI20157520//K+ channel tetramerisation domain// K+ channel tetramerisation domain
TESTI20170350//Cystine-knot domain
TESTI20192800//*Homo sapiens* nasopharyngeal carcinoma susceptibility protein LZ16 mRNA, complete cds.
TESTI20199750//TRICHOHYALIN.
TESTI20202650//Repeat in HS1/Cortactin
TESTI20229600//*Drosophila melanogaster* SP2353 mRNA, complete cds.
TESTI20231920//Gag P30 core shell protein
TESTI20242830//E2 (early) protein, C terminal// Syndecan domain
TESTI20254540//*Homo sapiens* hepatocellular carcinoma-associated antigen 59 mRNA, complete cds.
TESTI20320440//THIOREDOXIN.
TESTI20327680//EF hand// EF hand
TESTI20328280//KE2 family protein// Troponin
TESTI20351830//K-box region
TESTI20370020//Bleomycin resistance protein
TESTI20391210//IQ calmodulin-binding motif
TESTI20408150//Keratin, high sulfur B2 protein
TESTI20451990//SAP domain
TESTI20467970//Neurohypophysial hormones, N-terminal Domain// Neurohypophysial hormones, N-terminal Domain// Neurohypophysial hormones, N-terminal Domain// Neurohypophysial hormones, N-terminal Domain// Neurohypophysial hormones, N-terminal Domain// Neurohypophysial hormones, N-terminal Domain// Neurohypophysial hormones, N-terminal Domain// Neurohypophysial hormones, N-terminal Domain// Neurohypophysial hormones, N-terminal Domain
THYMU20108310//Mouse NCBP-29 mRNA for PW29, complete cds.
THYMU20142040//WISKOTT-ALDRICH SYNDROME PROTEIN HOMOLOG (WASP).
THYMU20194360//Kelch motif
THYMU20239000//collagen alpha 1(XI) chain
TOVAR20004760//Leucine Rich Repeat// Leucine Rich Repeat// Leucine Rich Repeat
TRACH20005020//Ank repeat// MutT-like domain
TRACH20007020//TRICHOHYALIN.
TRACH20048450//PROTEIN K4 (PROTEIN K3).
TRACH20068700//*Homo sapiens* adaptor protein CIKS mRNA, complete cds.
TRACH20076760//Keratin, high sulfur B2 protein
TRACH20135520//TBC domain// Rhodanese-like domain
TRACH20141240//*Mus musculus* G21 protein mRNA, complete cds.
TRACH20183170//*Rattus norvegicus* Sprague-Dawley SM-20 mRNA, complete cds.
UTERU20000740//Human fusion protein mRNA, complete cds.
UTE
RU20004240//CGI-96 protein
UTERU20006960//endoplasmic reticulum resident protein 58
UTERU20022940//Human (p23) mRNA, complete cds.
UTERU20046640//*Mus musculus* ld1Bp (LDLB) mRNA, complete cds.
UTERU20065930//GTP-RHO BINDING PROTEIN 1 (RHOPHILIN).
UTERU20115740//Human PMS2 related (hPMSR3) gene, complete cds.
UTERU20179880//TPR Domain// TPR Domain// TPR Domain// TPR Domain Further, the reason is that a polypeptide does not always belong solely to a single category of the above-described functional categories, and therefore, a polypeptide may belong to any of the predicted functional categories. Besides, additional functions can be found for the clones classified into these functional categories by further analyses.

Since the polypeptide encoded by clones of the invention contains full-length amino acid sequence, it is possible to analyze its biological activity, and its effect on cellular conditions such as cell proliferation and differentiation by expressing the polypeptide as a recombinant polypeptide using an appropriate expression system, injecting the recombinant into the cell, or raising a specific antibody against the polypeptide.

The biological activities of respective polypeptides can be analyzed by the methods as shown below. Secretory protein, transmembrane protein:
"Ion Channels" (Ed., R. H. Ashley, 1995) of "The Practical Approach Series" (IRL PRESS),
"Growth Factors" (Eds., I. McKay, I. Leigh, 1993),
"Extracellular Matrix" (Eds., M. A. Haralson, J. R. Hassell, 1995);

Glycoprotein-related Protein:
"Glycobiology" (Eds., M. Fukuda, A. Kobata, 1993) of "The Practical Approach Series" (IRL PRESS),
"Glycoprotein Analysis in Biomedicine" (Ed., Elizabeth F.Hounsell, 1993) of "Method in Molecular Biology" (Humana Press) series;

Signal Transduction-related Protein:
"Signal Transduction" (Ed., G. Milligan, 1992) of "The Practical Approach Series" (IRL PRESS),
"Protein Phosphorylation" (Ed., D. G. Hardie, 1993), or
"Signal Transduction Protocols" (Eds., David A. Kendall, Stephen J. Hill, 1995) of "Method in Molecular Biology" (Humana Press) series;

Transcription-related Protein:
"Gene Transcription" (Eds., B. D. Hames, S. J. Higgins, 1993) of "The Practical Approach Series" (IRL PRESS),
"Transcription Factors" (Ed., D. S. Latchman, 1993);

Enzyme and/or Metabolism-related Protein:
"Enzyme Assays" (Eds., ROBERT EISENTHAL and MICHAEL J. DANSON, 1992) of "The Practical Approach Series" (IRL PRESS);

Cell Division and/or Cell Proliferation-related Protein:
"Cell Growth, Differentiation and Senescence" (Ed., GEORGE STUDZINSKI, 2000) of "The Practical Approach Series" (IRL PRESS);

Cytoskeleton-related Protein:
"Cytoskeleton: Signalling and Cell Regulation" (Eds., KERMIT L. CARRAWAY and CAROLIE A. CAROTHERS CARRAWAY, 2000) of "The Practical Approach Series" (IRL PRESS),
"Cytoskeleton Methods and Protocols" (Ed., Gavin, Ray H., 2000) of "Method in Molecular Biology" (Humana Press) series;

Nuclear Protein and/or RNA Synthesis-related Protein:
"Nuclear Receptors" (Ed., DIDIER PICARD, 1999) of "The Practical Approach Series" (IRL PRESS),
"RNA Processing" (Eds., STEPHEN J. HIGGINS and B. DAVID HAMES, 1994);

Protein Synthesis and/or Transport-related Protein:
"Membrane Transport" (Ed., STEPHEN A. BALDWIN, 2000) of "The Practical Approach Series" (IRL PRESS),
"Protein Synthesis Methods and Protocols" (Eds., Martin, Robin, 1998) of "Method in Molecular Biology" (Humana Press) series;

Cellular Defense-related Protein:
"DNA Repair Protocols" (Henderson, Daryl S., 1999) of "Method in Molecular Biology" (Humana Press) series,
"Chaperonin Protocols" (Eds., Schneider, Christine, 2000);

Development and/or Differentiation-related Protein:
"Developmental Biology Protocols" (Eds., ROBERT EISENTHAL and MICHAEL J. DANSON, 1992) of "Method in Molecular Biology" (Humana Press) series;

DNA- and/or RNA-Binding Protein:
"DNA-Protein Interactions Principles and Protocols" (Eds., Kneale, G. Geoff, 1994) of "Method in Molecular Biology" (Humana Press) series,
"RNA-Protein Interaction Protocols" (Eds., Haynes, Susan R., 1999);

ATP- and/or GTP-Binding Protein:
"Signal Transduction Protocols" (Eds., David A. Kendall, Stephen J. Hill, 1995) of "Method in Molecular Biology" (Humana Press) series.

In the categorization, the clone predicted to belong to the category of secretory and/or membrane protein means a clone having hit data with some annotation, such as growth factor, cytokine, hormone, signal, transmembrane, membrane, extracellular matrix, receptor, G-protein coupled receptor, ionic channel, voltage-gated channel, calcium channel, cell adhesion, collagen, connective tissue, etc., suggesting that it was a secretory or membrane protein, or a clone in which the presence of nucleotide sequence encoding a signal sequence or transmembrane region was suggested by the results of PSORT and SOSUI analyses for deduced ORF.

The clone predicted to belong to the category of glycoprotein-related protein means a clone having hit data with some annotation, such as glycoprotein, suggesting that the clone encodes a glycoprotein-related protein.

The clone predicted to belong to the category of signal transduction-related protein means a clone having hit data with some annotation, such as serine/threonine-protein kinase, tyrosine-protein kinase, SH3 domain, SH2 domain, etc., suggesting that the clone encodes a signal transduction-related protein.

The clone predicted to belong to the category of transcription-related protein means a clone having hit data with some annotation, such as transcription regulation, zinc finger, homeobox, etc., suggesting that the clone encodes a transcription-related protein.

The clone predicted to belong to the category of disease-related protein means a clone having hit data with some annotation, such as disease mutation, syndrome, etc., suggesting that the clone encodes a disease-related protein, or a clone whose full-length nucleotide sequence has hit data for Swiss-Prot, GenBank, UniGene, or nr, where the hit data corresponds to genes or polypeptides which have been deposited in the Online Mendelian Inheritance in Man (OMIM), which is the human gene and disease database described later.

The clone predicted to belong to the category of enzyme and/or metabolism-related protein means a clone having hit data with some annotation, such as metabolism, oxidoreductase, E. C. No. (Enzyme commission number), etc., suggesting that the clone encodes an enzyme and/or metabolism-related protein.

The clone predicted to belong to the category of cell division and/or cell proliferation-related protein means a clone having hit data with some annotation, such as cell division, cell cycle, mitosis, chromosomal protein, cell growth, apoptosis, etc., suggesting that the clone encodes a cell division and/or cell proliferation-related protein.

The clone predicted to belong to the category of cytoskeleton-related protein means a clone having hit data with some annotation, such as structural protein, cytoskeleton, actin-binding, microtubles, etc., suggesting that the clone encodes a cytoskeleton-related protein.

The clone predicted to belong to the category of nuclear protein and/or RNA synthesis-related protein means a clone having hit data with some annotation, such as nuclear protein, RNA splicing, RNA processing, RNA helicase, polyadenylation, etc., suggesting that the clone encodes a nuclear protein and/or RNA synthesis-related protein.

The clone predicted to belong to the category of protein synthesis and/or transport-related protein means a clone having hit data with some annotation, such as translation regulation, protein biosynthesis, amino-acid biosynthesis, ribosomal protein, protein transport, signal recognition particle, etc., suggesting that the clone encodes a protein synthesis and/or transport-related protein.

The clone predicted to belong to the category of cellular defense-related protein means a clone having hit data with some annotation, such as heat shock, DNA repair, DNA damage, etc., suggesting that the clone encodes a cellular defense-related protein.

The clone predicted to belong to the category of development and/or differentiation-related proteins means a clone having hit data with some annotation, such as developmental protein, etc., suggesting that the clone encodes a development and/or differentiation-related protein.

The clone predicted to belong to the category of DNA- and/or RNA-binding protein means a clone having hit data with some annotation, such as DNA-binding, RNA-binding, etc.

The clone predicted to belong to the category of ATP- and/or GTP-binding protein means a clone having hit data with some annotation, such as ATP-binding, GTP-binding, etc.

As to a protein involved in a disease, it is possible to perform a functional analysis as described above, but also possible to analyze correlation between the expression or the activity of the protein and a certain disease by using a specific antibody that is obtained by using expressed protein. Alternatively, it is possible to utilize the database OMIM, which is a database of human genes and diseases, to analyze the protein. Further, new information is constantly being deposited in the OMIM database. Therefore, it is possible for one skilled in the art to find a new relationship between a particular disease and a gene of the present invention in the most up-to-date database. The proteins involved in diseases are useful for developing a diagnostic marker or medicines for regulation of their expression and activity, or as a target of gene therapy.

Also, as for a secretory protein, membrane protein, signal transduction-related protein, glycoprotein-related protein, or transcription-related protein, etc., search of the OMIM with the following keywords resulted in the finding that the proteins are involved in many diseases (the result of the OMIM search for secrete and membrane proteins is shown below). Also, association between proteins related to signal transduction or transcription and diseases is reported in "Transcription Factor Research-1999" (Fujii, Tamura, Morohashi, Kageyama, and Satake edit, (1999) Jikken-Igaku Zoukan, Vol. 17, No. 3), and "Gene Medicine" (1999) Vol. 3, No. 2). When cancer is used as an example, as described in "Biology of Cancer" (S. Matsubara, 1992) of Life Science series (Shokabo), many proteins are involved in cancers, which include enzyme and/or metabolism-related proteins, cytoskeleton-related proteins, cell division and/or cell proliferation-related proteins as well as secretory proteins, membrane proteins, signal transduction-related proteins, glycoprotein-related proteins, transcription-related proteins. As clearly seen by the above example, it is evident that not only disease-related proteins, but also secretory proteins, membrane proteins, signal transduction-related proteins, glycoprotein-related proteins, transcription-related proteins, etc. are often involved in diseases, and thus they can be useful targets in the field of medical industry.

The result of the OMIM search for secretory and membrane proteins is shown below, in which the keywords,
(1) secretion protein,
(2) membrane protein,
(3) channel, and
(4) extracellular matrix were used.

Shown in the search result are only the accession numbers in the OMIM. Using the number, data showing the relationship between a disease and a gene or protein can be seen. The OMIM data has been renewed everyday.

1) Secretion Protein

354 Entries Found, Searching for "Secretion Protein"
*604667, *104760, *176860, *151675, *139320, *107400, *604029, *118910, #200100, *176880, *603850, *147572, *604028, *179513, *125950, *139250, *246700, *600946, *600560, *602926, 185860, *605083, *603215, *602421, *157147, *179512, *600174, *109270, *604710, *138120, *179510, *600998, *179509, *170280, *179511, *600626, *603831, *601489, *154545, *179490, *603826, *122559, *603216, *102720, *147290, *164160, *603062, *112262, *602672, *605435, *605322, *131230, *601652, *603166, *601746, *601591, *179508, #160900, *104311, *600759, *147545, *167805, #104300, *167770, #219700, *168470, *601684, *602049, *601146, *605227, *602434, *602534, *114840, *603489, *604323, *107470, *600753, *600768, *118825, *600564, *604252, *173120, *134370, *192340, *308230, *600322, *605359, *600046, *300090, 106160, *600041, #262500, *605563, *150390, *158106, *182590, #103580, *104610, #173900, *134797, *143890, #145980, *306900, *308700, *176300, *227500, *137350, #154700, *138079, *600760, *107730, *142410, *147670, *124092, *590050, *152760, *600509, *605646, *201910, *227600, *152790, *300200, *300300, 300800, *138160, *107741, *120150, *601199, *120180, *120160, *176730, *133170, *122560, *107300; *137241, *120140, *101000, *193400, *217000, *272800, *600937, #201710, *600377, #174800, *106100, #274600, *173350, #177170, *147620, *214500, *131244, *202110, *120120, *601007, *191160, *147470, *603372, *600733, *252800, *190160, *138040, *158070, *162151, #125700, #130070, *113811, *603355, *171060, *136435, *184700, *603732, *190180, *164008, *186590, *120220, *604312, *152200, *138130, *605085, *605353, *600840, #166210, *188545, *207750, *173360, *601933, *194050, *153450, *138850, *253200, *307030, *157145, *600514, *600262, *264080, *147380, *600281, #204000, #227810, *232200, *188826, *232800, *161561, #166200, *188400, *153620, *182099, *218040, *265800, *172400, #177200, *176805, #211600, *214700, #176410, *152780, *600633, *601771, *301500, *605402, *601922, *307800, *147892, *147720, *312060, #520000, *147660, *106150, *602358, *107270, *601769, *147440, *604558, *131530, *600270, *601610, *603692, *603401, *600423, *601604, *603345, #125853, *602843, *142640, *603044, *605740, *134830, *602779, *130660, *139191, *137035, *600761, *601340, *600823, *107740, *130160, *600877, *605110, *600945, *130080, *600957, #130050, *605580, *118444, *601124, *124020, 122470, *120700, *603201, *137216, *601185, *138945, *218030, *600839, #240600, #262400, #162300, *162330, *188450, #265850, *263200, *162641, *300159, *601038, #191390, *201810, *601398, *602384, *131240, *602423, *139392, *142703, *602663, *232700, *602682, #602722, *602730, *600734, *188540, *182452, *601538, *603061, *146880, *603140, *603160, *142704, #252650, *182280, *125255, *603252, #131750, *182139, *182100, #259420, #261100, *603493, *601745, *182098, *603795, *123812, *600264, *147940, *180246, *180245, *118888, #604284, *168450, *118455, *604398, *604433, *601919, *118445, *600031, *604961, *605032, *605033, *171050, #171300, *131243, *109160, *605254, 274900, #171400, *600042, *151670, *184600, *605470, *605546, *176760, *602008, *102200, *605720, *600732, *605901

2) Membrane Protein

1489 Entries Found, Searching for "Membrane Protein"
*130500, *605704, *305360, *153330, *173610, *109270, *170995, *170993, *104776, *602333, *309060, *605703, *120920, *605943, *602690, *159430, *600897, *133090, *601178, *602413, *602003, *604405, *605940, *603237, *109280, *600378, *602173, *107776, *602334, *602335, *125305, *601134, *309845, *605731, *154045, *603241, *603718, *600594, *603214, *185881, *603657, *600182, *603177, *605331, *601476, *605456, *601114, *605190, *600723, *603904, *136950, *300222, *602879, *185880, *605348, *300096, *602257, *177070, *310200, *603062, *603344, *600039, *602977, *300100, *128240, *600959, *600322, *227400, *186945, *600946, *602534, *602048, *182900, *601097, *600267, *602625, *136430, *602421, *601047, *107450, *143450, *603141, *184756, *164730, *159440, *154050, *600579, *312080, *604202, *603700, *600447, *256540, *604691, *158343, *600403, *602414, *137290, *176640, *176981, *600179, *600754, *604456, *604693, *605875, *604605, *188860, *300172, *602910, *604323, *219800, *601848, *603179, *600279, *602251, #222700, *603831, *605072, *605377, *601028, *604155, *108733, *104225, *601896, *601510, *173335, *107770, *601767, *600046, *603850, *600040, *603784, *603234, 188560, *605863, *121015, *605862, *605861, *186946, *604252, *603215, *142461, *604597, *603143, *605264, *603735, *176860, *605536, *176801, *180721, *603355, *104760, *131560, *310300, *602631, *304700, #309400, *603142, *143890, *605431, *600753, *115501, *176790, *600266, *601691, *168468, *601239, *602216, #104300, *605613, *601595, *605550, *125950, *605475, *602217, *602261, *603534, *602262, *604631, *190315, *601313, *604306, *104311, *604672, *605000, *602461, *605548, *602296, *604376, *121014, *121011, *600691, *604262, *139310, *304040, *605445, *179514, *179512, *151460, #160900, *120130, *128239, *601158, *601403, *176943, *601014, 300800, *300294, *601757, *185470, *273800, *605034, *602887, #185000, *604871, *603593, *603583, *605454, *104775, *605872, *141180, *602713, *603531, *139150, *601531, *601832, *605452, *134651, *604156, *120620, *605883, *604142, *166945, *605324, *600816, *604699, *300112, *605182, *600164, *182180,

*605071, *300023, *605057, *308240, *300249, *176947,
*176894, *605081, *605035, *602044, *182860, *107271,
*305100, *153390, *113730, *602689, *180069, *603518,
*300017, *191275, *177061, *601693, *601789, *604241,
*600934, *138160, *604424, *603868, *600174, *600718,
*600523, *604141, *601009, *605251, *600481, *600874,
*155550, *605227, *601017, *162230, 601138, *604157,
*601212, *600763, *604110, *604158, *601107, *601326,
600621, *600587, 601137, *600917, *600855, *605058,
*194355, *605194, *603291, *102720, *136425, *170715,
*603216, *605547, *135630, *602926, *600168, *605002,
*602474, *600157, *603025, *603893, *231200, *120090,
*601966, *131230, *604722, *604721, *604515, *246700,
*602101, *605628, *303630, *605787, *602857, *602285,
*605708, *602488, *605025, *603817, *300051, *603293,
*176878, *603646, 605707, 185860, *112205, *300187,
*602654, *120070, *603648, *604850, *602655, *602514,
*300118, *182309, *179590, *602701, *600759, *204200,
*604170, *175100, #103580, *147670, *306400, *143100,
*182870, *257220, *180380, #116920, *301000, *193300,
*157147, *131550, *139200, *139130, *190195, *605406,
*155760, *155960, *605734, *155970, *605385, *111700,
*155975, *150370, 605709, *151430, *605438, *151510,
*116952, *157655, *158105, *605777, *176877, *153619,
*120131, *185430, *109190, *120190, *109170, *605093,
*605250, *153432, *107777, *186590, *160993, *605699,
*605698, *605813, *605697, *605616, *605300, *162060,
*605219, *163970, *135620, *165040, *605478, *604964,
*103195, *604932, *604923, *605906, *605496, *605914,
*166490, 138277, *604915, *114070, *605213, *605933,
*180297, *101000, *191163, *191164, *605101, *603167,
*600772, *603164, *600708, *604001, *191328, *313440,
*602672, *604009, *604299, *192974, *604256, *603048,
*600515, *604221, *602632, *604196, *601179, 603290,
*604661, *601023, *601110, *304800, *203200, *300212,
*602933, *603352, *208900, *604418, *604838, *600551,
212140, *604837, *602049, *600552, *600553, *300213,
*602574, *600583, *600932, *603452, *604775, *516020,
*604617, *604464, *603498, *300145, *601523, *602694,
*600632, *604762, *604492, *400015, *604504, *601717,
*601728, *300242, *602426, *604194, *603821, *604730,
*600695, *603823, *603869, *300241, *600707, *603822,
*602370, *602202, *604193, *601181, *604089, *602507,
*604195, *602306, *300284, *601805, *601895, *601275,
*604660, *600752, *603820, *604192, *602207, *308230,
*600894, *312600, *603199, *604029, *602500, *102680,
*235200, #256300, *601633, #219700, 262890, *156225,
*173470, *193400, *173910, *600354, *113705, *600065,
*107741, *107400, *600024, *131195, *113811, #118220,
*601638, *300011, *276903, *604144, *311770, *601758,
173900, *604592, *120120, *179605, *603130, *603372,
*110750, *222900, *602509, *256100, *602469, *602281,
*229300, *224100, *110900, *190180, *261600, *602997,
*603616, *603189, 601791, *601567, *312700, *171060,
*308700, *604027, *162643, *516000, *176261, *604028,
*314850, #145980, *601383, *600930, *305900, *601253,
*136350, *605537, *138140, *604033, *605070, *139250,
*300500, *603967, *300041, *603866, #130600, *120150,
*601050, *604942, *605204, *605248, *272750, *600163,
*604235, *600682, *107266, *306900, *191092, #262500,
*600106, *152790, *186720, *227650, *153700, *308380,
*103390, *605646, *164920, *604478, *252650, *173850,
*173350, *602505, *246530, *194380, *602575, *603030,
*209920, *212138, *214100, *605767, *600582, *189980,
176200, *604653, *604678, *256550, *300037, *253700,
253300, *226700, *604766, *244400, *190000, *188040,
*604824, *214500, #237500, *232300, *605014, *604477,

*190930, *605124, *604475, *604594, #227810, *306700,
301050, *600135, *600143, *605145, #269920, *300104,
*277900, *300135, *300231, *192500, *182138, *191190,
*176805, *600185, *186591, *604889, *603051, *165360,
*147545, *601040, #156575, *107269, *603009, *602934,
*123825, *601081, *602924, *163890, *600381, *602909,
*150330, *109690, *123900, *603434, *603491, *110700,
*602581, *125647, #154700, *114760, *141900, *603690,
*120220, *601199, #145500, *601309, *602382, *120325,
*600877, *604205, *604090, *601497, *602377, *605464,
*138720, *603728, *120950, *604026, *600580, *601610,
*137167, *603960, *603931, *601880, *603126, *138190,
*130130, *601997, *601975, *600395, *516040, *600418,
*600650, *605245, *605172, *600509, *164761, *310400,
*600308, *605109, *600544, *600359, *600103, *605267,
*312610, *176100, *308100, *158070, *605123, *173325,
312750, *600839, *158120, #604369, *604465, *173510,
161200, *151525, *605369, *604237, *516050, #600886,
*604517, *165180, *605381, *605399, *307800, *604365,
*155740, *147795, 601709, *604673, *147730, *602122,
*147557, *193245, *600978, *604990, *603261, *603274,
*601007, *131100, *602941, *107941, *146710, *276901,
*131244, *602872, *603411, *186357, *176290, *601066,
*185050, *232200, *143030, *601843, #236700, *604122,
*142800, *134638, *604985, *182380, *603930, *142410,
*137060, *604586, *601193, *120650, *252500, *253800,
*120930, *604858, *605874, 601274, *602158, *605873,
*193210, *203100, *601295, *604095, #201710, *126150,
*108740, #205400, *601373, *300167, *109545, *602894,
*603361, #300257, *266200, *603401, *131390, *180470,
*605908, *604798, #221770, *223360, *180901, *605641,
*605745, *604018, *300200, *604603, *230800, *602676,
604004, *605692, *602640, *601599, *134637, *245900,
*118425, 601614, *605725, *120110, *300189, *300035,
*603102, *250800, *602282, *602458, *123610, *603754,
*300278, *601463, *300224, *601581, *182160, *601653,
*139191, *601733, *600748, *142460, *601194, *152390,
*153620, *601615, *601814, *601617, *601613, *300191,
308300, *600798, 601858, *601872, *601597, #601588,
*600821, *147840, *152427, *138850, *600823, *601492,
*300256, *600840, *300267, *601411, *139080, *139090,
600851, *300334, *179080, *602095, *601284, *601282,
177200, *601681, *601252, *176000, *602184, *602188,
266510, #154020, *186711, *257200, *601711, *600667,
*602241, *186745, *255125, *300126, *600644, *123890,
255120, #175200, *600004, *302060, *123580, *186760,
*122561, *602316, *600017, *120940, 140300, *151690,
*120700, *602354, *600019, *600857, *182175, *600536,
*158380, *600516, *120290, *600493, *182310, #252010,
*182530, *186830, *601839, *142790, *159465, *118990,
*250790, *248600, #248250, *186845, *601153, *142600,
*116930, *114860, *171834, #303600, *186880, *600444,
*142871, *601852, *602602, *602607, *114207, *186910,
232220, 600880, *134635, *112203, #112100, *111680,
*231680, *311030, *111250, *111200, *134390, #226670,
145600, *226200, *602714, *171760, *133550, *602727,
*161555, *602744, *602746, #131705, *602835, *600423,
*176267, *602859, #600918, 277175, *602874, *601020,
*109770, *600170, *217070, *173515, *602893, *147280,
*154360, *171050, *108780, *176257, *600979, *600377,
*108360, *204500, *170260, *146880, *154582, *601011,
*600997, *602992, *201475, *603005, *190198, *147360,
*270400, *600238, *164970, *306250, #126600, *193065,
*181350, *106180, *602136, *600937, *603086, *603087,
*307030, *182099, *103320, *601683, *192430, *103180,
*102681, *192321, *600244, *191740, *191315, *603152,
*102642, *191305, #266140, *100500, *600867, *604585,

*604404, *604345, *603201, *605430, *603207, *603208, *605433, *604101, *603969, *605896, *604616, *605851, *605768, *604576, *605754, *605730, *605477, *603263, *605538, *603283, *604402, *605453, *605427, *603302, *605458, 603313, *604415, *603345, *605541, *603353, *605295, *603879, *605268, *605266, *605246, *603377, *603380, *605181, *604203, *603425, *603867, *605106, *605017, *603842, *604936, *603510, *604857, *605932, *605816, *603765, *603551, *605357, *605237, *604204, *603594, *605110, *604190, *603861, *604962, *603639, *603644, *605007, *605349, *604943, *604918, *604907, *603667, *603681, *605396, *605561, *603712, *603713, *605688, *605942, *604878, *604843, *604659, *604671, *603798, *604682, *604056, *604705, *603749, 602586, *603647, *602515, #602475, *603717, *602359, *602372, *602380, *602518, *603652, *602573, *603626, 602587, *603598, *602871, *603613, *603750, *603875, *602608, *602666, *602345, *602935, *603564, *603548, *603927, 601876, *602343, *603943, *603787, *601730, *601611, *602679, *603788, *602243, 603790, *601535, *603796, *601488, *601485, *602314, *601478, *604047, *604048, *602297, *604057, *602715, *602192, *601459, *601416, *603833, *602190, *604102, *602106, *604111, *602724, *603499, *602736, *601123, *601002, *600923, *601987, *604149, *601929, *600910, *600900, *600864, *604165, *600782, *602836, *600769, *600742, *602783, *601905, *600535, *604198, *601901, *600534, *602876, *603356, *600530, *604216, *604217, *602890, *602905, *600465, *600464, *600446, *602891, *603366, *601894, *604272, *603926, *603312, *600368, *602914, *600327, *603151, *603202, 602911, *602974, *603006, *601883, *603008, *600074, *603007, *603046, #603903, *604433, *600016, *603925, *516005, *516004, *516003, *601756, *604487, *516001, *313475, *313470, #307810, *604527, *604528, *601745, *604551, *604555, *603243, *603242, *603061, *603063, *603217, *300335, *300283, *300281, *604600, *300197, *603097, *603220, *601625, *604623, *603118, *601590, *604646, *300008, *601568, *300007, *275630, *601533, #275200, *270200, #261550, *604031, *604683, #254800, *251100, #242300, *604058, *604720, *240500, *233690, #232240, #226730, *223100, *222100, #220100, *216950, *604832, 212750, 212067, *604066, *193067, 601315, *193001, *604862, *604870, *191306, *600385, *604879, *191191, *601296, *604914, *190181, *604119, #188550, *604925, *188410, #601287, *604939, *188380, *604126, *604945, *604148, *188060, *604982, *186854, *604988, *186360, *186355, *185250, *600916, *605008, *605009, 185020, *600734, *605024, *182331, *605032, *605033, *182305, *180903, #179800, *179610, *605060, *179410, *178990, *176802, *605080, *176266, *176263, *176260, *600732, *173490, *604199, *173445, *173391, 172290, *605147, *605149, *171890, *600528, *171833, *605185, #170500, *605193, #168000, *605196, *167055, *605205, *605208, 166900, *605216, *162651, *162010, *600504, #161400, *604253, *160800, *159460, *154540, *605254, *605261, *153634, *600429, *153337, *600424, *605292, #604286, #152700, 152423, *152310, *151625, *600153, *604313, *151523, *150325, *150320, *150292, *603150, *150290, *150210, *605410, *605415, *605416, *605417, *605421, *603149, *604349, *147940, *600282, *147880, *146928, *146661, *600150, *146630, *142622, *600018, *605461, *138981, *138590, *600023, *138330, *605495, *138297, *605512, *138230, *136900, #301310, *516006, *605545, *605546, *136131, *134660, *134350, *516002, *605589, *131235, *130050, *605625, *126455, *126064, #125310, *605670, *604534, *125240, *123836, *123830, *123620, *605702, #122200, *120980, *120360,

*118510, *114835, *605710, *605716, *605722, *114217, *604561, *113810, *111740, #110800, *605748, *605752, *604564, *110600, *603160, *109610, *605784, #107480, *107273, *603192, *300169, *106195, *105210, *104615, *104614, *104210, *103850, 103581, *605876, *605877, *605879, *103220, *605887, *300150, *102910, *102670, *102576, *605916, *604629, *102575, *102573, *300132, *101800, *605947

3) Channel (Member of Membrane Protein)

361 Entries Found, Searching for "Channel"

*176266, *600724, *182390, *123825, *114208, *114206, *176267, *114205, *601784, *600937, *114204, *603415, *600053, *114207, *114209, *605427, *604527, *604528, *600760, *601011, *192500, *118425, *600228, *176261, *602235, *600761, *600359, *300008, *182389, *600877, *602232, *176263, *182391, *601328, *600054, *603939, *602208, *601534, *600504, *602323, *603208, *601958, *603537, *601012, *601327, *600734, *602780, *602781, *604433, *603220, *182392, *605874, *605873, *601745, *603888, *603219, *602604, *603796, *302910, *602866, *601013, *602905, *602906, *603967, *600163, #170500, *152427, *180901, *176260, #601462, *603951, *601141, *604492, *600702, *602023, *600308, *602754, *107776, *176257, *602024, *601949, *605222, *601142, *602983, *193245, *600681, *176265, *600235, *176262, *176258, *605206, *604427, *605411, *603305, *601219, *600150, *604065, *602343, *605223, *605720, *603906, *138249, *138253, *600843, *604385, *600003, *600935, *603940, *602727, *602158, 602911, *600397, *602726, *600845, *605080, *600580, *602872, *602106, *176264, *603953, *605722, *300110, *138252, *604111, *602717, *602420, *600570, 600844, *603493, *600932, *605716, *138254, *603652, *300138, *605410, *176268, *605214, *605696, *300334, *604660, *176256, *605879, *603749, *603583, *602345, *604661, *603787, 603313, *602982, *604337, *600846, *604662, *300328, *300281, *602566, *602836, *604003, *603788, *603651, *602421, *107777, #177200, *100725, #219700, *100690, *100710, *160800, #603830, #183086, *600509, #220400, *601144, *173910, *180902, *605692, #264350, *160900, *145600, #255700, *602076, *603061, *601313, *154275, *604233, *604532, *108500, #121201, #170400, *300225, *121014, *139311, #125800, #160120, *118503, 601439, *141500, #168300, *304040, #601887, *256450, *186945, *154276, #300009, #216900, *600040, *601014, *601042, *602512, *601383, *605445, *602368, *603831, #117000, *601218, *108745, *605248, #177735, *173900, *601212, *182139, *601059, *600039, *601485, *180903, *186360, *603319, #600101, *118509, *600109, #121200, *600170, *604187, *176975, *137163, #310468, #263800, #262300, *603750, *600229, *124030, *602251, *603829, *137143, *145500, *600669, *147450, *154050, *603353, *600516, *601157, *600855, *601154, *602522, *249210, *600968, #252650, *171060, *600919, *156490, #259700, *601678, *601764, #310500, *131244, *300041, *121011, *125950, *114180, *602974, *600637, *113730, *118504, *605145, *604669, *118800, *121013, *121015, *138491, *600421, *104610, *604045, *604594, *131230, *605487, *138247, *600467, *602485, *602481, *138251, *137192, *602403, 600851, *277900, *603785, *603152, *603199, *603475, #168600, #272120, *170280, *603852, *241200, *603053, *600465, *603034, *142461, *164920, *137164, *600884, *600442, *123885, *604001, *600232, *232200, *171050, *602103, *602014, *300211, *600983, *602887, *604415, *604418, *300242, #300071, *604471, *600837, 168350, *118511, 193007, *600300, *604654, #601820, *180297, *600046, *603853,

*604678, *604693, #604772, *118508, *603855, *605204, #254210, *182099, *182307, #130600, *601109, *114080, *300103, *182860, *605438, *601129, *603964, *600019, *516060, #185000, *138079, *104210, *605818, *603418, *305990, *305450

4) Extracellular Matrix

218 Entries Found, Searching for "Extracellular Matrix"
*605912, *603479, *602201, *604633, *601418, *601548, *115437, *154870, *600754, *602261, *602285, *602262, *134797, *120361, *604629, *604871, *603321, *603320, *601807, #154700, *116935, *185261, *120360, *185250, *605470, *603767, *253700, *190180, *128239, *308700, *276901, *193300, *120324, *188826, *602109, *155760, *600514, *600261, #177170, *600536, *147557, #116920, *150240, *601313, *120140, 601614, *605158, *120150, *120180, #200610, *605127, *193400, *192240, #173900, *152200, #136900,, *135821, #130070, *120320, *120220, *112260, *310200, *600900, *600262, *605670, *600985, *179590, #245150, *602574, *601463, 183850, *601211, *604241, *600758, *186745, *604710, *602369, *602090, *190182, *192975, *602178, *230740, *600065, *601652, *158106, *190181, *156790, #158810, *193210, *155120, *192977, *193065, *226700, *187380, *231050, *182120, *188060, *186355, 163200, *164010, #156550, *151510, *150370, *253800, *156225, *150325, #194050, *150290, *216550, *147620, *600215, *222600, *147559, *165380, *182888, *600491, *146650, *146640, *600564, *600596, *600616, *600700, *600742, *138297, *182889, *154705, *600930, *301870, *153619, *601050, *601090, *601105, *165070, *305370,, *135820, *130660, *310300, *601492, *128240, *601587, #126600, *601636, *600119, *601692, *601728, *125485, 601858, *601915, *602048, *175100, *602108, *121010, *600245, *120470, *120328, *120325, *602264, *120280, *602366, *600309, *602402, *602415, *602428, *602453, *602505, #166210, *602600, *602941, *603005, *603196, 603209, *603221, *603234, *603319, *120250, *120210, *120120, *603489, *603551, *118938, *603799, *603842, *603924, *603963, *604042, *604063, *604149, *604160, *601028, *604467, *604510, *604592, *116930, *116806, *601284, *604724, *604806, *604807, *604808, *107269, *605007, *605008, *605009, *600214, *600076, *605174, *605175, *605292, *605343, *605351, #600204, *605497, *605546, *605587, *605623, *600211, *605702, *103320

In addition to these, the various keywords shown in the above-mentioned categorization or others can be used for the OMIM search and the result may suggest the involvement thereof in diseases.

Further, the use of nucleotide sequences of cDNAs of the present invention enables analyzing the expression frequency of genes corresponding to the cDNAs. In addition, functions of the genes can be predicted based on the information obtained by the expression frequency analysis.

There are several methods for analyzing the expression levels of genes involved in diseases. Differences in gene expression levels between diseased and normal tissues are studied by the analytical methods using, for example, Northern hybridization, RT-PCR, DNA microarray, etc. (Experimental Medicine, Vol. 17, No. 8, 980–1056 (1999); Cell Engineering (additional volume) DNA Microarray and Advanced PCR Methods, Muramatsu & Nawa (eds.), Shujunsya (2000)). By computer analysis, in addition to these analysis methods, the nucleotide sequences of expressed genes can be compared to analyze the expression frequency. For example, there is a database called "BODYMAP"; gene clones are extracted at random from cDNA libraries of various tissues and/or cells, and the clones homologous to one another are assigned to a single cluster based on the information of nucleotide sequence homology at the 3'-end; genes are classified into any clusters, and the numbers of clones in the respective clusters are compared to gain the information on expression frequency.

When explicit difference in the expression levels between diseased tissues and normal tissues is observed for a gene by these analytical methods, it can be conclude that the gene is closely involved in a disease or disorder. Instead of diseased tissues, when gene expression is explicitly different between normal cells and cells reproducing disease-associated specific features, it can be concluded that the gene is closely involved in a disease or disorder.

From the 2443 clones whose full-length nucleotide sequences had been revealed, genes involved in particular pathology or functions were selected by the use of databases shown below (see Example 7; "Expression frequency analysis in silico"). The database used in the analyses of the present invention contains nucleotide sequences of 1,402,070 clones, and the population of the database is large enough for the analysis. The sequence information in the database was obtained by selecting cDNA clones at random from cDNA libraries derived from the various tissues and cells shown in Example 1 and determining the 5'-end sequences thereof.

Then, the nucleotide sequences of respective clones in this database were categorized (clustered) based on the nucleotide sequence homology determined with a search program; the number of clones belonging to every cluster of each library was determined and normalized; thus, the ratio of a certain gene in a cDNA library was determined. This analysis provided the information of the expression frequency of a gene in a tissue or cell that is the source of the cDNA library.

Then, in order to analyze the expression of genes corresponding to the nucleotide sequences of cDNAs of the present invention in tissues and cells, the libraries from the tissues or cells, which had been used in the large-scale cDNA analyses, were taken as subjects to compare the expression levels between different tissues or cells. Namely, the expression frequency was analyzed by comparing the previously normalized values between tissues or cells from which 600 or more cDNA clones whose nucleotide sequences had been analyzed were derived. The result of this analysis showed that the cDNA clones corresponded to the genes involved in the pathology and functions, which are indicated below. Each value in Tables 3 to 51 indicated below represents a relative expression frequency; the higher the value, the higher the expression level. osteoporosis-related genes Osteoporosis is a pathology in which bones are easily broken owing to overall decrease in components of bone. The onset correlates to the balance between the functions of osteoblast producing bone and osteoclast absorbing bone, namely bone metabolism. Thus, the genes involved in the increase of osteoclasts differentiating from precursor cells of monocyte/macrophage line (Molecular Medicine 38. 642–648. (2001)) are genes involved in osteoporosis relevant to bone metabolism.

A nucleotide sequence information-based analysis was carried out to identify the genes whose expression frequencies are higher or lower in CD34+ cell (cell expressing a glycoprotein CD34) treated with the osteoclast differentiation factor (Molecular Medicine 38. 642–648. (2001)) than in the untreated CD34+ cell, which is the precursor cell of monocyte/macrophage line. The result of comparative analysis for the frequency between the cDNA libraries prepared from the RNA of CD34+ cells (CD34C) and from the RNA of CD34+ cells treated with the osteoclast differentiation factor (D30ST, D60ST or D90ST) showed that the genes whose expression levels were different between the two were 56 clones indicated in Table 3. These clones are involved in osteoporosis.

Genes involved in Neural Cell Differentiation

Genes involved in neural cell differentiation are useful for treating neurological diseases. Genes with varying expression levels in response to induction of cellular differentiation in neural cells are thought to be involved in neurological diseases.

A survey was performed for genes whose expression levels are varied in response to induction of differentiation (stimulation by retinoic acid (RA) or growth inhibitor treatment after RA stimulation) in cultured cells of a neural strain, NT2. The result of comparative analysis of cDNA libraries derived from undifferentiated NT2 cells (NT2RM) and the cells subjected to the differentiation treatment (NT2RP, NT2RI or NT2NE) showed that the genes whose expression levels were different between the two were 288 clones indicated in Table 4. These genes are neurological disease-related genes.

Cancer-related Genes

It has been assumed that, distinct from normal tissues, cancer tissues express a distinct set of genes, and thus the expression thereof can contribute to the carcinogenesis in tissues and cells. Thus, genes whose expression patterns in cancer tissues are different from those in normal tissues are cancer-related genes. Search was carried out for the genes whose expression levels in cancer tissues were different from those in normal tissues.

The result of comparative analysis of cDNA libraries derived from breast tumor (TBAES) and normal breast (BEAST) showed that the genes whose expression levels were different between the two were 35 clones indicated in Table 5.

The result of comparative analysis of cDNA libraries derived cervical tumor (TCERX) and normal cervical duct (CERVX) showed that the genes whose expression levels were different between the two were 11 clones indicated in Table 6.

The result of comparative analysis of cDNA libraries derived from colon tumor (TCOLN) and normal colon (COLON) showed that the genes whose expression levels were different between the two were 25 clones indicated in Table 7.

The result of comparative analysis of cDNA libraries derived from esophageal tumor (TESOP) and normal esophagus (NESOP) showed that the genes whose expression levels were different between the two were 41 clones indicated in Table 8.

The result of comparative analysis of cDNA libraries derived from kidney tumor (TKIDN) and normal kidney (KIDNE) showed that the genes whose expression levels were different between the two were 175 clones indicated in Table 9.

The result of comparative analysis of cDNA libraries derived from liver tumor (TLIVE) and normal liver (LIVER) showed that the genes whose expression levels were different between the two were 47 clones indicated in Table 10.

The result of comparative analysis of cDNA libraries derived from lung tumor (TLUNG) and normal lung (HLUNG) showed that the genes whose expression levels were different between the two were 62 clones indicated in Table 11.

The result of comparative analysis of cDNA libraries derived from ovary tumor (TOVER) and normal ovary (NOVER) showed the genes whose expression levels were different between the two were 23 clones indicated in Table 12.

The result of comparative analysis of cDNA libraries derived from stomach tumor (TSTOM) and normal stomach (STOMA) showed that the genes whose expression levels were different between the two were 70 clones indicated in Table 13.

The result of comparative analysis of cDNA libraries derived from uterine tumor (TUTER) and normal uterus (UTERU) showed that the genes whose expression levels were different between the two were 236 clones indicated in Table 14.

The result of comparative analysis of cDNA libraries derived from tongue cancer (CTONG) and normal tongue (NTONG) showed that the genes whose expression levels were different between the two were 232 clones indicated in Table 15.

These genes are involved in cancers.

Further, there is a method to search for genes involved in development and differentiation, which is the expression frequency analysis in which the expression levels of genes are compared between developing and/or differentiating tissues and/or cells and adult tissues and/or cells. The genes involved in tissue development and/or differentiation are genes participating in tissue construction and expression of function, and thus are useful genes, which are available for regenerative medicine aiming at convenient regeneration of injured tissues.

By using the information of gene expression frequency gained from the database of 5'-end nucleotide sequences described above, genes involved in development or differentiation of particular tissues were selected from the 2443 clones whose full-length nucleotide sequence had been revealed (see Example 7).

The result of comparative analysis of cDNA libraries derived from fetal brain (FCBBF, FEBRA or OCBBF) and adult brain (BRACE, BRALZ, BRAMY, BRAWH, BRCAN, BRCOC, BRHIP, BRSSN, BRSTN or BRTHA) showed that the genes whose expression levels were different between the two were 1195 clones indicated in Tables 16 to 48.

The result of comparative analysis of cDNA libraries derived from fetal heart (FEHRT) and adult heart (HEART) showed that the genes whose expression levels were different between the two were 45 clones indicated in Table 49.

The result of comparative analysis of cDNA libraries derived from fetal kidney (FEKID) and adult kidney (KIDNE) showed that the genes whose expression levels were different between the two were 118 clones indicated in Table 50.

The result of comparative analysis of cDNA libraries derived from fetal lung (FELNG) and adult lung (HLUNG) showed that the genes whose expression levels were different between the two were 63 clones indicated in Table 51. These genes are involved in regeneration of tissues and/or cells.

The expression frequency or the like can be analyzed by PCR based on the nucleotide sequences of cDNAs of the present invention. There are some known methods for comparing the quantities of amplification products obtained by PCR. For example, the band intensities can be determined by ethidium bromide staining. With RI-labeled or fluorescently labeled primers, the RI signal or fluorescence intensity can be assayed for the quantity of labeled amplification products. Alternatively, the quantity of amplification products can also be determined by measuring the RI signal or the fluorescence intensity from the RI-labeled or fluorescently labeled probe hybridizing to the products. The assay results thus obtained are compared and then the clones exhibiting differences in the expression levels can be selected.

There are some quantitative PCR methods: a PCR method using internal standards; a competitive PCR, in which the quantification is achieved by adding, to a sample, a dilution series of a known quantity of a template RNA and by comparing the quantity of an amplification product derived from the RNA of interest with the quantity of an amplification product derived from the template RNA. These methods overcome the problems of errors in the amount of amplification products among tubes and of the plateau effect. ATAC-PCR (Adaptor-tagged competitive PCR) is a method of competitive PCR which is practiced by using multiple adapters of different sizes attached to a gene whose 3'-end nucleotide sequence has previously been determined. The ratio of expression frequency of a single mRNA species from a number of tissues (cells) can be assayed in a single step (Nucleic Acids Research 1997, 25(22): 4694–4696; "DNA Micro-array and Advanced PCR Techniques", Cell Technology, supplement, Eds., Muramatsu and Nawa (Shujunsha, 2000): 104–112).

If it is observed, by using these analytical methods, that the expression levels of genes are evidently varied during major cellular events (such as differentiation and apoptosis), the genes are involved in the cellular events and accordingly are candidates for disease- and/or disorder-related genes. Further, genes exhibiting tissue-specific expression are genes playing important parts in the tissue functions and, therefore, can be candidates for genes involved in diseases and/or disorders affecting the tissues.

For example, inflammation is an important biological response that is known to be involved in various diseases. The representative inflammation-inducing factors include TNF-α (Tumor Necrosis Factor-alpha). There exists a signaling cascade activated by TNF-α stimulations, wherein NF-κB is a transducing molecule (Cell 1995, 80:529–532). It has also been revealed that many inflammation-related genes, including IL-2, IL-6 and G-CSF, are varied in the expression levels thereof in response to the signal through the pathway (Trends Genet. 1999, 15(6): 229–235). It is assumed that genes whose expression levels are varied in response to the stimulation of TNF-α also participate in inflammation.

Further, the infection of *Helicobacter pylori* to the gastric epithelia is known to cause gastritis and gastroduodenal ulcer (Mebio 2000, July, 17(7): 16–33). Thus, the genes whose expression levels are altered depending on co-culturing cells with *Helicobacter pylori* may be involved in gastritis and gastroduodenal ulcer. A recent study has suggested that *Helicobacter pylori* strongly activates the NF-κB pathway(Gastroenterology 2000, 119: 97–108).

THP-1 cell, which is a human monocyte cell line, was cultured in the presence of TNF-α (Tumor Necrosis Factor-alpha) The genes whose expression levels were altered owing to the presence of TNF-α were searched for, and the result showed that the clones whose expression levels were increased owing to the presence of TNF-α were ASTRO20152140, BRACE20057620, BRACE20060720, BRACE20090440, BRACE20152870, BRACE20229280, BRAMY20002770, BRAMY20266850, BRAMY20280720, BRAWH20106180, BRAWH20122770, BRHIP20096170, BRHIP20111200, BRHIP20186120, BRHIP20194940, BRHIP20207430, BRSSN20152380, CTONG20095270, CTONG20100240, CTONG20158150, CTONG20265130, D30ST200 06540, D90ST20031370, FCBBF20071860, FCBBF30251420, FCBBF30252520, FCBBF40001420, FEBRA20017050, FEBRA20082100, HCHON20011160, KIDNE20141190, KIDNE20163880, KIDNE20182690, LIVER10004790, LIVER20038540, LIVER20085800, MESAN20130220, MESAN20174170, NT2NE20158600, NT2RI20005750, NT2RP70110860, NT2RP70169110, NT2RP70175670, NT2RP70188710, PERIC20002140, PLACE60155130, PROST20120160, PROST20149250, PROST20161950, PUAEN20015260, SKNSH20080430, SMINT20051610, SMINT20060780, SMINT20161220, SMINT20163960, SPLEN20101190, SPLEN20157300, SPLEN20163560, SPLEN20214580, SPLEN20279950, STOMA20048520, TESTI20076850, TESTI20087620, TESTI20108720, TESTI20220100, TESTI20239510, TESTI20266740, TESTI20342430, TESTI20370020, TESTI20391210, TESTI20401020, TESTI20415640, THYMU20130890, THYMU20286290, TRACH20060150, TRACH20099340, UTERU20004240, UTERU20068990, UTERU20119060.

On the other hand, the clones whose expression levels were decreased owing to the presence of TNF-α were ASTRO20032120, ASTRO20084250, ASTRO20181690, BRACE20062640, BRACE20067430, BRACE20235400, BRALZ20018340, BRALZ20069760, BRALZ20075450, BRAMY20163270, BRAMY20204450, BRAMY20218670, BRAMY20229800, BRAWH10000930, BRAWH20107540, BRAWH20132190, BRAWH20158530, BRCAN20273340, BRHIP20105710, BRHIP20186120, BRSSN20176820, CTONG20095290, DFNES20031920, FCBBF30033050, FCBBF30071520, FCBBF30083820, HCHON20008980, HCHON20022470, HHDPC20034390, KIDNE20028720, KIDNE20079440, KIDNE20127750, KIDNE20148900, LIVER20011130, MAMGL10000830, MESAN20127350, NT2NE20181650, NT2RI20023160, NT2RP70102350, NT2RP70157890, NTONG20029480, OCBBF20020830, OCBBF20024680, OCBBF20061720, OCBBF20127040, OCBBF20139260, OCBBF20178990, PEBLM20013120, PLACE60003480, PLACE60181070, PROST20151240, PUAEN20003740, PUAEN20011880, PUAEN20078980, PUAEN20085150, SKNSH20080430, SMINT20001760, SMINT20047810, SMINT20108530, SPLEN20158990, SPLEN20283650, STOMA20010250, STOMA20057820, TESTI20060400, TESTI20161970, TESTI20275620, TESTI20369690, TESTI20386230, TESTI20392250, TESTI20409440, TESTI20424730, THYMU20095960, THYMU20111180, THYMU20226600, THYMU20253250, THYMU20272490, TRACH20153810, UTERU20176130, UTERU20186740.

These clones are inflammation-related genes.

MKN45, which is a gastric cancer cell line, was co-cultured with *Helicobacter pylori*. The genes whose expression levels were altered owing to the presence of Helicobacter pylori were searched for, and the result showed that the clones whose expression levels were increased owing to the presence of *Helicobacter pylori* were ADRGL20067670, BLADE20004630, BRACE20039040, BRACE20151320, BRACE20229280, BRACE20235400, BRALZ20058880, BRAMY20060920, BRAMY20184670, BRAMY20218670, BRAMY20229800, BRCAN20147880, BRHIP20196410, BRHIP30004880, BRSSN20187310, CD34C30004940, CTONG20265130, DFNES20031920, FCBBF30278630, FCBBF40001420, HHDPC20095280, KIDNE20130450, LIVER20011130, LIVER20038540, NT2NE20172590, NT2RP70169110, OCBBF20085200, OCBBF20180840, PEBLM10000240, PLACE60003480, PROST20120160, PROST20151240, PUAEN20011880, SKMUS20031680, SKNSH20080430, SMINT20056210, SMINT20105000, SPLEN20019450, SPLEN20211570, STOMA20048520, TESTI20004890, TESTI20083940, TESTI20168480, TESTI20239510, TESTI20308600, TESTI20478010, UTERU20126880.

On the other hand, the clones whose expression levels were decreased owing to the presence of *Helicobacter pylori* were ASTRO20032120, BRACE20090440, BRACE20114780, BRALZ20064740, BRAMY20002770, BRAMY20210400, BRAMY20215230, BRAMY20247280, BRAMY20267130, BRAWH20029630, BRAWH20100690, BRAWH20118230, BRCOC20105100, BRHIP20218580, BRSSN20046570, CTONG20138030, CTONG20146970, CTONG20158150, D30ST20037970, FCBBF30001840, FCBBF30033050, FEBRA20082100, HCHON20035130, HCHON20043590, HCHON20067220, NT2NE20174920, NT2RI20009870, NT2RI20023160, NT2RP70062230, NT2RP70130020, NTONG20070340, OCBBF20020150, OCBBF20094240, OCBBF20107920, PROST20144220, PROST20149160, PROST20153320, PUAEN20003740, PUAEN20025680, PUAEN20040670, SMINT20014580, SPLEN20101190, STOMA20076800, TESTI20087620, TESTI20098530, TESTI20123080, TESTI20161970, TESTI20234140, TESTI20288110, TESTI20357960, TESTI20391210, TESTI20424730, THYMU20158250, THYMU20226600, TRACH20005020, TRACH20134950, TRACH20184490, TSTOM20001390, UTERU20119060, UTERU20134910, UTERU20176130.

These clones are involved in gastritis or gastroduodenal ulcer.

For example, if the polypeptide encoded by the cDNA of the present invention is a regulatory factor of cellular conditions such as growth and differentiation, it can be used for developing medicines as follows. The polypeptide or antibody provided by the invention is injected into a certain kind of cells by microinjection. Then, using the cells, it is possible to screen low molecular weight compounds, etc. by measuring the change in the cellular conditions, or the activation or inhibition of a particular gene. The screening can be performed as follows.

First, the polypeptide is expressed and purified as recombinant. The purified polypeptide is microinjected into cells such as various cell lines, or primary culture cells, and the cellular change such as growth and differentiation can be examined. Alternatively, the induction of genes whose expression is known to be involved in a particular change of cellular conditions may be detected by the amount of mRNA or polypeptide. Alternatively, the amount of intracellular molecules (low molecular weight compounds, etc.) that is changed by the function of the gene product (polypeptide) which is known to be involved in a particular change of cellular conditions may be detected. The compounds to be screened (both low and high molecular compounds are acceptable) can be added to the culture media and assessed for their activity by measuring the change of the cellular conditions.

Instead of microinjection, cell lines introduced with the gene obtained in the invention can be used for the screening. If the gene product is turn out to be involved in a particular change in the cellular conditions, the change of the product can be used as a measurement for screening. Once a compound is screened out which can activate or inhibit the function of the polypeptide of the invention, it can be applied for developing medicines.

If the polypeptide encoded by the cDNA of the present invention is a secretory protein, membrane protein, or protein involved in signal transduction, glycoprotein, transcription, or diseases, it can be used in functional assays for developing medicines.

In case of a membrane protein, it is most likely to be a polypeptide that functions as a receptor or ligand on- the cell surface. Therefore, it is possible to reveal a new relationship between a ligand and receptor by screening the membrane protein of the invention based on the binding activity with the known ligand or receptor. Screening can be performed according to the known methods.

For example, a ligand against the polypeptide of the invention can be screened in the following manner. Namely, a ligand that binds to a specific polypeptide can be screened by a method comprising the steps of: (a) contacting a test sample with the polypeptide of the invention or a partial peptide thereof, or cells expressing these, and (b) selecting a test sample that binds to said polypeptide, said partial peptide, or said cells.

On the other hand, for example, screening using cells expressing the polypeptide of the present invention that is a receptor protein can also be performed as follows. It is possible to screen receptors that is capable of binding to a specific polypeptide by using procedures (a) attaching the sample cells to the polypeptide of the invention or its partial peptide, and (b) selecting cells that can bind to the said polypeptide or its partial peptide.

In a following screening as an example, first the polypeptide of the invention is expressed, and the recombinant polypeptide is purified. Next, the purified polypeptide is labeled, binding assay is performed using a various cell lines or primary cultured cells, and cells that are expressing a receptor are selected (Growth and differentiation factors and their receptors, Shin-Seikagaku Jikken Kouza Vol. 7 (1991) Honjyo, Arai, Taniguchi, and Muramatsu edit, p 203–236, Tokyo-Kagaku-Doujin). A polypeptide of the invention can be labeled with RI such as $^{125}$I, and enzyme (alkaline phosphatase etc.).

Alternatively, a polypeptide of the invention may be used without labeling and then detected by using a labeled antibody against the polypeptide. The cells that are selected by the above screening methods, which express a receptor of the polypeptide of the invention, can be used for the further screening of an agonists or antagonists of the said receptor.

Once the ligand binding to the polypeptide of the invention, the receptor of the polypeptide of the invention or the cells expressing the receptor are obtained by screening, it is possible to screen a compound that binds to the ligand and receptor. Also it is possible to screen a compound that can inhibit both bindings (agonists or antagonists of the receptor, for example) by utilizing the binding activities.

When the polypeptide of the invention is a receptor, the screening method comprises the steps of (a) contacting the polypeptide of the invention or cells expressing the polypeptide of the invention with the ligand, in the presence of a test sample, (b) detecting the binding activity between said polypeptide or cells expressing said polypeptide and the ligand, and (c) selecting a compound that reduces said binding activity when compared to the activity in the absence of the test sample. Furthermore, when the polypeptide of the invention is a ligand, the screening method comprises the steps of (a) contacting the polypeptide of the invention with its receptor or cells expressing the receptor in the presence of samples, (b) detecting the binding activity between the polypeptide and its receptor or the cells expressing the receptor, and (c) selecting a compound that can potentially reduce the binding activity compared to the activity in the absence of the sample.

Samples to screen include cell extracts, expressed products from a gene library, synthesized low molecular compound, synthesized peptide, and natural compounds, for example, but are not construed to be listed here. A compound that is isolated by the above screening using a binding activity of the polypeptide of the invention can also be used as a sample.

A compound isolated by the screening may be a candidate to be an agonist or an antagonist of the receptor of the polypeptide. By utilizing an assay that monitors a change in the intracellular signaling such as phosphorylation which results from reduction of the binding between the polypeptide and its receptor, it is possible to identify whether the obtained compound is an agonist or antagonist of the receptor. Also, the compound may be a candidate of a molecule that can inhibit the interaction between the polypeptide and its associated proteins (including a receptor) in vivo. Such compounds can be used for developing drugs for precaution or cures of a disease in which the polypeptide is involved.

Secretory proteins may regulate cellular conditions such as growth and differentiation. It is possible to find out a novel factor that regulates cellular conditions by adding the secretory protein of the invention to a certain kind of cell, and performing a screening by utilizing the cellular changes in growth or differentiation, or activation of a particular gene.

The screening can be performed, for example, as follows. First, the polypeptide of the invention is expressed and purified in a recombinant form. Then, the purified polypeptide is added to a various kind of cell lines or primary cultured cells, and the change in the cell growth and differentiation is monitored. The induction of a particular gene that is known to be involved in a certain cellular change is detected by the amounts of mRNA and polypeptide. Alternatively, the amount of an intracellular molecule (low-molecular-weight compounds, etc.) that is changed by the function of a gene product (polypeptide) that is known to function in a certain cellular change is used for the detection.

Once the screening reveals that the polypeptide of the invention can regulate cellular conditions or the functions, it is possible to apply the polypeptide as a pharmaceutical and diagnostic medicine for related diseases by itself or by altering a part of it into an appropriate composition.

As is above described for membrane proteins, the secretory protein provided by the invention may be used to explore a novel ligand-receptor interaction using a screening based on the binding activity to a known ligand or receptor. A similar method can be used to identify an agonist or antagonist. The resulting compounds obtained by the methods can be a candidate of a compound that can inhibit the interaction between the polypeptide of the invention and an interacting molecule (including a receptor). The compounds may be able to use as a preventive, therapeutic, and diagnostic medicine for the diseases, in which the polypeptide may play a certain role.

Proteins involved in signal transduction or transcription may be a factor that affects a certain polypeptide or gene in response to intracellular/extracellular stimuli. It is possible to find out a novel factor that can affect a polypeptide or gene by expressing the polypeptide provided by the invention in a certain types of cells, and performing a screening utilizing the activation of a certain intracellular polypeptide or gene.

The screening may be performed as follows. First, a transformed cell line expressing the polypeptide is obtained. Then, the transformed cell line and the untransformed original cell line are compared for the changes in the expression of a certain gene by detecting the amount of its mRNA or polypeptide. Alternatively, the amount of an intracellular molecule (low molecular weight compounds, etc.) that is changed by the function of a certain gene product (polypeptide) may be used for the detection. Furthermore, the change of the expression of a certain gene can be detected by introducing a fusion gene that comprises a regulatory region of the gene and a marker gene (luciferase, P-galactosidase, etc.) into a cell, expressing the polypeptide provided by the invention into the cell, and estimating the activity of a marker gene product (polypeptide).

If the polypeptide or gene of the invention is involved in diseases, it is possible to screen a gene or compound that can regulate its expression and/or activity either directly or indirectly by utilizing the polypeptide of the present invention.

For example, the polypeptide of the invention is expressed and purified as a recombinant polypeptide. Then, the polypeptide or gene that interacts with the polypeptide of the invention is purified, and screened based on the binding. Alternatively, the screening can be performed by adding with a compound of a candidate of the inhibitor added in advance and monitoring the change of binding activity. In another method, a transcription regulatory region locating in the 5'-upstream of the gene encoding the polypeptide of the invention that is capable of regulating the expression of other genes is obtained, and fused with a marker gene. The fusion is introduced into a cell, and the cell is added with compounds to explore a regulatory factor of the expression of the said gene.

The compound obtained by the screening can be used for developing pharmaceutical and diagnostic medicines for the diseases in which the polypeptide of the present invention is involved. Similarly, if the regulatory factor obtained in the screening is turn out to be a polypeptide, compounds that can newly affect the expression or activity of the polypeptide may be used as a medicine for the diseases in which the polypeptide of the invention is involved.

If the polypeptide of the invention has an enzymatic activity, regardless as to whether it is a secretory protein, membrane protein, or proteins involved in signal transduction, glycoprotein, transcription, or diseases, a screening may be performed by adding a compound to the polypeptide of the invention and monitoring the change of the compound. The enzymatic activity may also be utilized to screen a compound that can inhibit the activity of the polypeptide.

In a screening given as an example, the polypeptide of the invention is expressed and the recombinant polypeptide is purified. Then, compounds are contacted with the purified polypeptide, and the amount of the compound and the reaction products is examined. Alternatively, compounds that are candidates of an inhibitor are pretreated, then a compound (substrate) that can react with the purified polypeptide is added, and the amount of the substrate and the reaction products is examined.

The compounds obtained in the screening may be used as a medicine for diseases in which the polypeptide of the invention is involved. Also they can be applied for tests that examine whether the polypeptide of the invention functions normally in vivo.

Whether the secretory protein, membrane protein, signal transduction-related protein, glycoprotein-related protein, or transcription-related protein of the present invention is a novel protein involved in diseases or not is determined in another method than described above, by obtaining a specific antibody against the polypeptide of the invention, and examining the relationship between the expression or activity of the polypeptide and a certain disease. In an alternative way, it may be analyzed referred to the methods in "Molecular Diagnosis of Genetic Diseases" (Elles R. edit, (1996) in the series of "Method in Molecular Biology" (Humana Press).

Proteins involved in diseases are targets of screening as mentioned, and thus are very useful in developing drugs which regulate their expression and activity. Also, the proteins are useful in the medicinal industry as a diagnostic marker of the related disease or a target of gene therapy.

Compounds isolated as mentioned above can be administered patients as it is, or after formulated into a pharmaceutical composition according to the known methods. For example, a pharmaceutically acceptable carrier or vehicle, specifically sterilized water, saline, plant oil, emulsifier, or suspending agent can be mixed with the compounds appropriately. The pharmaceutical compositions can be administered to patients by a method known to those skilled in the art, such as intraarterial, intravenous, or subcutaneous injections. The dosage may vary depending on the weight or age of a patient, or the method of administration, but those skilled in the art can choose an appropriate dosage properly. If the compound is encoded by polynucleotide, the polynucleotide can be cloned into a vector for gene therapy, and used for gene therapy. The dosage of the polynucleotide and the method of its administration may vary depending on the weight or age of a patient, or the symptoms, but those skilled in the art-can choose properly.

The present invention further relates to databases comprising at least a sequence of polynucleotide and/or polypeptide, or a medium recorded in such databases, selected from the sequence data of the nucleotide and/or the amino acids indicated in Table 1. The term "database" means a set of accumulated information as machine-searchable and readable information of nucleotide sequence. The databases of the present invention comprise at least one of the novel nucleotide sequences of polynucleotides provided by the present invention. The databases of the present invention can consist of only the sequence data of the novel polynucleotides provided by the present invention or can comprise other information on nucleotide sequences of known full-length cDNAs or ESTs. The databases of the present invention can be comprised of not only the information on the nucleotide sequences but also the information on the gene functions revealed by the present invention. Additional information such as names of DNA clones carrying the full-length cDNAs can be recorded or linked together with the sequence data in the databases.

The database of the present invention is useful for gaining complete gene sequence information from partial sequence information of a gene of interest. The database of the present invention comprises nucleotide sequence information of full-length cDNAs. Consequently, by comparing the information in this database with the nucleotide sequence of a partial gene fragment yielded by differential display method or subtraction method, the information on the full-length nucleotide sequence of interest can be gained from the sequence of the partial fragment as a starting clue.

The sequence information of the full-length cDNAs constituting the database of the present invention contains not only the information on the complete sequences but also extra information on expression frequency of the genes as well as homology of the genes to known genes and known polypeptides. Thus the extra information facilitates rapid functional analyses of partial gene fragments. Further, the information on human genes is accumulated in the database of the present invention, and therefore, the database is useful for isolating a human homologue of a gene originating from other species. The human homologue can be isolated based on the nucleotide sequence of the gene from the original species.

At present, information on a wide variety of gene fragments can be obtained by differential display method and subtraction method. In general, these gene fragments are utilized as tools for isolating the full-length sequences thereof. When the gene fragment corresponds to an already-known gene, the full-length sequence is easily obtained by comparing the partial sequence with the information in known databases. However, when there exists no information corresponding to the partial sequence of interest in the known databases, cDNA cloning should be carried out for the full-length cDNA. It is often difficult to obtain the full-length nucleotide sequence using the partial sequence information as an initial clue. If the full-length of the gene is not available, the amino acid sequence of the polypeptide encoded by the gene remains unidentified. Thus the database of the present invention can contribute to the identification of full-length cDNAs corresponding to gene fragments, which cannot be revealed by using databases of known genes.

The present invention has provided 2443 polynucleotides. As has not yet proceeded the isolation of full-length cDNA within the human, the invention has great significance. It is known that secretory proteins, membrane proteins, signal transduction-related proteins, glycoprotein-related proteins, transcription-related proteins, and so on are involved in many diseases. The genes and proteins involved in diseases are useful for developing a diagnostic marker or medicines for regulation of their expression and activity, or as a target of gene therapy.

In particular, cDNA assumed to encode secretory proteins, which were provided by this invention, are very important for the industry since the encoded proteins themselves are expected to be useful as pharmaceutical agents and many disease-related genes may be included in them. In addition, membrane proteins, signal transduction-related proteins, transcription-related proteins, disease-related proteins, and genes encoding them can be used as indicators for diseases, etc. These cDNA are also very important for the industry, which are expected to regulate the activity or expression of the encoded protein to treat diseases, etc.

Any patents, patent applications, and publications cited herein are incorporated by reference.

The invention is illustrated more specifically with reference to the following examples, but is not to be construed as being limited thereto.

EXAMPLE 1

Preparation of cDNA Library by Oligo-capping (1) Extraction and Purchase of mRNA Total RNAs as mRNA sources were extracted from human tissues (shown below) by the method as described in the reference (J. Sambrook, E. F. Fritsch & T. Maniatis, Molecular Cloning Second edition, Cold Spring harbor Laboratory Press, 1989). Further, by the method as described in the reference (J. Sambrook, E. F. Fritsch & T. Maniatis, Molecular Cloning Second edition, Cold Spring harbor Laboratory Press, 1989), total RNAs as mRNA sources were extracted from human culture cells and human primary culture cells (shown below) which had been cultivated by the methods described in the catalogs.

The library names and the origins are indicated below in the order of "Library name: Origin". When a library was prepared by the subtraction method, the item is followed by a description of how to prepare the subtracted library.

<Extraction of mRNA from Human Tissues>
NTONG: Normal tongue;
CTONG: Tongue cancer;
FCBBF: Fetal brain;
OCBBF: Fetal brain;
PLACE: Placenta;
SYNOV: Synovial membrane tissue (from rheumatioid arthritis);
CORDB: Cord blood.

<Extraction of mRNA from Culture Cells>
BNGH4: H4 cells (ATCC #HTB-148);
IMR32: IMR32 cells (ATCC #CCL-127);
SKNMC: SK-N-MC cells (ATCC #HTB-10);
3NB69: NB69 cells (RCB #RCB0480);
BGGI1: GI1 cells (RCB #RCB0763);
NB9N4: NB9 cells (RCB #RCB0477);
SKNSH: SK-N-SH cells (RCB #RCB0426);
AHMSC: Human mesenchymal (HMSC) cells;
CHONS: Chondrocytes;
ERLTF: TF-1 cells (erythroleukemia);
HELAC: HeLa cells;
JCMLC: Leukemia, myelogenous;
MESTC: Mesenchyme stem cells;
NLESE: Mesenchymal stem cells;
NCRRM: Embryonal carcinoma;
NCRRP: Embryonal carcinoma treated with retinoic acid (RA) to induce the differentiation;
T1ESE: Mesenchymal stem cells treated with trichostatin and 5-azacytidine to induce the differentiation;
NT2RM: NT2 cells (STARATAGENE #204101);
NT2RP: NT2 cells treated with retinoic acid (RA) for 5 weeks to induce the differentiation;
NT2RI: NT2 cells treated with RA for 5 weeks to induce the differentiation, followed by the treatment with the growth inhibitor for 2 weeks;
NT2NE: NT2 cells were treated with RA and the growth inhibitor for the neuronal differentiation, and the resultant neurons were concentrated and harvested (NT2 Neuron);
NTISM: NT2 cells (STARATAGENE #204101) were treated with RA for 5 weeks to induce the differentiation, and then treated with the growth inhibitor for 2 weeks; mRNA was prepared from the cells and a cDNA library was constructed from the mRNA; the cDNAs of the library whose nucleotide sequences were shared by those of mRNAs from undifferentiated NT2 cells were subtracted by using a Subtract Kit (Invitrogen #K4320-01); the subtracted library (NT2RI-NT2RM) was provided by this procedure.

RCB indicates that the cell was provided by the Cell Bank, RIKEN GENE BANK, The Institute of Physical and Chemical Research; ATCC indicates that the cell was provided by American Type Culture Collection.

<Extraction of mRNA from Primary Culture Cells>
ASTRO: Normal human astrocyte NHA5732, Takara Shuzo #CC2565;
DFNES: Normal human dermal fibroblast (neonatal skin); NHDF-Neo NHDF2564, Takara Shuzo #CC2509;
MESAN: Normal human mesangial cell NHMC56046-2, Takara Shuzo #CC2559;
NHNPC: Normal human neural progenitor cell NHNP5958, Takara Shuzo #CC2599;
PEBLM: Normal human peripheral blood mononuclear cell HPBMC5939, Takara Shuzo #CC2702;
HSYRA: Human synoviocyte HS-RA (from rheumatioid arthritis), Toyobo #T404K-05;
PUAEN: Normal human pulmonary artery endothelial cells, Toyobo #T302K-05;
UMVEN: Normal human umbilical vein endothelial cell HUVEC, Toyobo #T200K-05;
HCASM: Normal human coronary artery smooth muscle cell HCASMC, Toyobo #T305K-05;
HCHON: Normal human chondrocyte HC, Toyobo #T402K-05;
HHDPC: Normal human dermal papilla cell HDPC, Toyobo #THPCK-001;
CD34C: CD34+ cells (AllCells, LLC #CB14435M);
D30ST: CD34+ cells treated with the osteoclast differentiation factor (ODF) for 3 days to induce the differentiation;
D60ST: CD34+ cells treated with ODF for 6 days to induce the differentiation;
D90ST: CD34+ cells treated with ODF for 9 days to induce the differentiation;
ACTVT: Activated T-cells;
LYMPB: Lymphoblasts, EB virus transferred B cells;
NETRP: Neutrophils.

Then, total RNAs extracted from the following human tissues were purchased and used as mRNA sources. The library names and the origins are indicated below in the order of "Library name: Origin". When a library was prepared by the subtraction method, the item is followed by a description of how to prepare the subtracted library.

<Purchase of Total RNA Containing mRNA Extracted from Human Tissues>
ADRGL: Adrenal gland, CLONTECH #64016-1;
BRACE: Brain (cerebellum), CLONTECH #64035-1;
BRAWH: Whole brain, CLONTECH #64020-1;
FEBRA: Fetal brain, CLONTECH #64019-1;
FELIV: Fetal liver, CLONTECH #64018-1;
HEART: Heart, CLONTECH #64025-1;
HLUNG: Lung, CLONTECH #64023-1;
KIDNE: Kidney, CLONTECH #64030-1;
LIVER: Liver, CLONTECH #64022-1;
MAMGL: Mammary Gland, CLONTECH #64037-1;
PANCR: Pancreas, CLONTECH #64031-1;
PROST: Prostate, CLONTECH #64038-1;
SALGL: Salivary Gland, CLONTECH #64026-1;
SKMUS: Skeletal Muscle, CLONTECH #64033-1;
SMINT: Small Intestine, CLONTECH #64039-1;
SPLEN: Spleen, CLONTECH #64034-1;
STOMA: Stomach, CLONTECH #64090-1;
TBAES: Breast (Tumor), CLONTECH #64015-1;
TCERX: Cervix (Tumor), CLONTECH #64010-1;
TCOLN: Colon (Tumor), CLONTECH #64014-1;
TESTI: Testis, CLONTECH #64027-1;
THYMU: Thymus, CLONTECH #64028-1;
TLUNG: Lung (Tumor), CLONTECH #64013-1;
TOVAR: Ovary (Tumor), CLONTECH #64011-1;
TRACH: Trachea, CLONTECH #64091-1;

TUTER: Uterus (Tumor), CLONTECH #64008-1;
UTERU: Uterus, CLONTECH #64029-1;
ADIPS: Adipose, Invitrogen #D6005-01;
BLADE: Bladder, Invitrogen #D6020-01;
BRALZ: Cerebral cortex from an Alzheimer patient (Brain, cortex, Alzheimer), Invitrogen #D6830-01;
CERVX: Cervix-, Invitrogen #D6047-01;
COLON: Colon, Invitrogen #D6050-0;
NESOP: Esophagus, Invitrogen #D6060-01;
PERIC: Pericardium, Invitrogen #D6105-01;
RECTM: Rectum, Invitrogen #D6110-01;
TESOP: Esophageal (Tumor), Invitrogen #D6860-01;
TKIDN: Kidney (Tumor), Invitrogen #D6870-01;
TLIVE: Liver (Tumor), Invitrogen #D6880-01;
TSTOM: Stomach (Tumor), Invitrogen #D6920-01;
BEAST: Adult breast, STARATAGENE #735044;
FEHRT: Fetal heart, STARATAGENE #738012;
FEKID: Fetal kidney, STARATAGENE #738014;
FELNG: Fetal lung, STARATAGENE #738020;
NOVAR: Adult ovary, STARATAGENE #735260;
BRASW: subtracted library (BRALZ-BRAWH). A cDNA library was constructed from mRNA prepared from tissues of cerebral cortex obtained from an Alzheimer patient [BRALZ: Cerebral cortex from an Alzheimer patient (Brain, cortex, Alzheimer), Invitrogen #D6830-01]; the cDNAs of this library whose nucleotide sequences were shared by those of mRNAs from whole brain tissue [BRAWH: Whole brain, CLONTECH #64020-1] were subtracted by using a Subtract Kit (Invitrogen #K4320-01).

Further, mRNAs extracted and purified as poly A(+) RNAs from the human tissues shown below were purchased. A cDNA library was prepared from an RNA mixture in which the poly A(+) RNA from each tissue had been combined with poly A(-) RNA. The poly A(-) RNA was prepared by removing poly A(+) RNA from the total RNA of whole brain tissue (CLONTECH #64020-1) by using oligo dT cellulose. The library names and the origins are indicated below in the order of "Library name: Origin".

<Purchase of mRNAs of Human Tissues as Poly A(+) RNAs>
BRAMY: Brain (amygdala), CLONTECH #6574-1;
BRCAN: Brain (caudate nucleus), CLONTECH #6575-1;
BRCOC: Brain (corpus callosum), CLONTECH #6577-1;
BRHIP: Brain (hippocampus), CLONTECH #6578-1;
BRSSN: Brain (substantia nigra), CLONTECH #6580-1;
BRSTN: Brain (subthalamic nucleus), CLONTECH #6581-1;
BRTHA: Brain (thalamus), CLONTECH #6582-1.

(2) Preparation of cDNA Library cDNA library was prepared from each RNA by the improved method (WO 01/04286) of oligo capping [M. Maruyama and S. Sugano, Gene, 138: 171–174 (1994)]. A series of procedures, BAP (Bacterial Alkaline Phosphatase) treatment, TAP (Tobacco Acid Pyrophosphatase) treatment, RNA ligation, first strand cDNA synthesis and RNA removal, were carried out using the oligo-cap linker (SEQ ID NO: 5455) and oligo dT primer (SEQ ID NO: 5456) as described in WO 01/04286. Then, the single-stranded cDNA was converted to a double-stranded cDNA by PCR (polymerase chain reaction) using 5' (SEQ ID NO: 5457) and 3' (SEQ ID NO: 5458) PCR primers, and then digested with SfiI. Then, a fraction of cDNA fragments, typically 2-kb or longer (3-kb or longer in some cases), was unidirectionally cloned into a DraIII-digested pME18SFL3 vector (FIG. 1) (GenBank AB0D9864, Expression vector); the cDNA library was thus prepared.

The names of cDNA libraries, which were used in the analysis of full-length cDNA sequences, and their origins are shown in Table 2.

TABLE 2

| Library | Type | Origin, etc. |
|---|---|---|
| 3NB69 | Culture cell | NB69 cells (RCB #RCB0480) |
| ADIPS | Tissue | Adipose (Invitrogen #D6005-01) |
| ADRGL | Tissue | Adrenal gland (CLONTECH #64016-1) |
| ASTRO | Primary culture cell | Normal Human Astrocyte NHA5732 (Takara Shuzo #CC2565) |
| BEAST | Tissue | Adult Breast (STARATAGENE #735044) |
| BGGI1 | Culture cell | GI1 cells (RCB #RCB0763) |
| BLADE | Tissue | Bladder (Invitrogen #D6020-01) |
| BNGH4 | Culture cell | H4 cells (ATCC #HTB-148) |
| BRACE | Tissue | Brain, cerebellum (CLONTECH #64035-1) |
| BRALZ | Tissue | Brain, cortex, Alzheimer (Invitrogen #D6830-01) |
| BRAMY | Tissue | Brain, amygdala (CLONTECH #6574-1) |
| BRAWH | Tissue | Brain, whole (CLONTECH #64020-1) |
| BRCAN | Tissue | Brain, caudate nucleus (CLONTECH #6575-1) |
| BRCOC | Tissue | Brain, corpus callosum (CLONTECH #6577-1) |
| BRHIP | Tissue | Brain, hippocampus (CLONTECH #6578-1) |
| BRSSN | Tissue | Brain, substantia nigra (CLONTECH #6580-1) |
| BRSTN | Tissue | Brain, subthalamic nucleus (CLONTECH #6581-1) |
| BRTHA | Tissue | Brain, thalamus (CLONTECH #6582-1) |
| CD34C | Primary culture cell | CD34+ cells (AllCells, LLC #CB14435M) |
| COLON | Tissue | Colon (Invitrogen #D6050-0) |
| CTONG | Tissue | Tongue, Cancer |
| D3OST | Primary culture cell | CD34+ cells (ODF induction for 3 days) |
| D6OST | Primary culture cell | CD34+ cells (ODF induction for 6 days) |
| D9OST | Primary culture cell | CD34+ cells (ODF induction for 9 days) |
| DFNES | Primary culture cell | Normal Human Dermal Fibroblasts (Neonatal Skin); NHDF-Neo NHDF2564 (Takara Shuzo #CC2509) |
| FCBBF | Tissue | Brain, Fetal |
| FEBRA | Tissue | Brain, Fetal (CLONTECH #64019-1) |
| FEHRT | Tissue | Heart, Fetal (STARATAGENE #738012) |
| FELNG | Tissue | Lung, Fetal (STARATAGENE #738020) |
| HCASM | Primary culture cell | Human coronary artery smooth muscle cells HCASMC (Toyobo #T305K-05) |
| HCHON | Primary culture cell | Human Chondrocytes HC (Toyobo #T402K-05) |
| HEART | Tissue | Heart (CLONTECH #64025-1) |
| HHDPC | Primary culture cell | Human dermal papilla cells HDPC (Toyobo #THPCK-001) |
| HLUNG | Tissue | Lung (CLONTECH #64023-1) |
| IMR32 | Culture cell | IMR32 cells (ATCC #CCL-127) |
| KIDNE | Tissue | Kidney (CLONTECH #64030-1) |
| LIVER | Tissue | Liver (CLONTECH #64022-1) |
| MAMGL | Tissue | Mammary Gland (CLONTECH #64037-1) |

TABLE 2-continued

| Library | Type | Origin, etc. |
|---|---|---|
| MESAN | Primary culture cell | Normal human mesangial cells NHMC56046-2 (Takara Shuzo #CC2559) |
| NESOP | Tissue | Esophagus (Invitrogen #D6060-01) |
| NOVAR | Tissue | Adult Ovary (STARATAGENE #735260) |
| NT2NE | Culture cell | NT2 cells concentrated after differenciation (NT2 Neuron) |
| NT2RI | Culture cell | NT2 cells treated by growth inhibitor for 2 weeks after RA induction for 5 weeks |
| NT2RP | Culture cell | NT2 cells treated by RA for 5 weeks |
| NTONG | Tissue | Tongue |
| OCBBF | Tissue | Brain, Fetal |
| PANCR | Tissue | Pancreas (CLONTECH #64031-1) |
| PEBLM | Primary culture cell | Human peripheral blood mononuclear cells HPBMC5939 (Takara Shuzo #CC2702) |
| PERIC | Tissue | Pericardium (Invitrogen #D6105-01) |
| PLACE | Tissue | Placenta |
| PROST | Tissue | Prostate (CLONTECH #64038-1) |
| PUAEN | Primary culture cell | Human pulmonary artery endothelial cells (Toyobo #T302K-05) |
| RECTM | Tissue | Rectum (Invitrogen #D6110-01) |
| SALGL | Tissue | Salivary Gland (CLONTECH #64026-1) |
| SKMUS | Tissue | Skeletal Muscle (CLONTECH #64033-1) |
| SKNMC | Culture cell | SK-N-MC cells (ATCC #HTB-10) |
| SKNSH | Culture cell | SK-N-SH cells (RCB #RCB0426) |
| SMINT | Tissue | Small Intestine (CLONTECH #64039-1) |
| SPLEN | Tissue | Spleen (CLONTECH #64034-1) |
| STOMA | Tissue | Stomach (CLONTECH #64090-1) |
| SYNOV | Tissue | Synovial membrane tissue from rheumatioid arthritis |
| TBAES | Tissue | Breast, Tumor (CLONTECH #64015-1) |
| TCOLN | Tissue | Colon, Tumor (CLONTECH #64014-1) |
| TESOP | Tissue | Esophageal, Tumor (Invitrogen #D6860-01) |
| TESTI | Tissue | Testis (CLONTECH #64027-1) |
| THYMU | Tissue | Thymus (CLONTECH #64028-1) |
| TKIDN | Tissue | Kidney, Tumor (Invitrogen #D6870-01) |
| TOVAR | Tissue | Ovary, Tumor (CLONTECH #64011-1) |
| TRACH | Tissue | Trachea (CLONTECH #64091-1) |
| TSTOM | Tissue | Stomach, Tumor (Invitrogen #D6920-01) |
| TUTER | Tissue | Uterus, Tumor (CLONTECH #64008-1) |
| UMVEN | Primary culture cell | Human umbilical vein endothelial cells HUVEC (Toyobo #T200K-05) |
| UTERU | Tissue | Uterus (CLONTECH #64029-1) |

The cDNA library with the high fullness ratio (the fullness ratio of 5'-end, which was calculated for each cDNA library by using the protein coding region found in known mRNA species as an index, was 90% in average) prepared by the improved oligo-capping method was constructed by using a eukaryotic expression vector pME18SFL3. The vector contains SRα promoter and SV40 small t intron in the upstream of the cloning site, and SV40 polyA added signal sequence site in the downstream. As the cloning site of pME18SFL3 has asymmetrical DraIII sites, and the ends of cDNA fragments contain SfiI sites complementary to the DraIII sites, the cloned cDNA fragments can be inserted into the downstream of the SRa promoter unidirectionally. Therefore, clones containing full-length cDNA can be expressed transiently by introducing the obtained plasmid directly into COS cells, etc. Thus, the clones can be analyzed very easily in terms of the proteins that are the gene products of the clones, or in terms of the biological activities of the proteins.

(3) Assessment of the 5'-end Completeness of Clones Derived from the cDNA Library Prepared by Oligo-capping With respect to the plasmid DNAs of clones derived from the libraries, the nucleotide sequences of cDNA 5'-ends (3'-ends as well in some cases) were determined in a DNA sequencer (ABI PRISM 3700, PE Biosystems), after sequencing reaction was conducted by using a DNA sequencing reagent (BigDye Terminator Cycle Sequencing FS Ready Reaction Kit, PE Biosystems) according to the manual. A database was constructed based on the obtained data.

The 5'-end completeness of about 1110,000 clones derived from the human cDNA libraries prepared by the improved oligo-capping method was determined by the following method. The clones whose 5'-end sequences were consistent with those of known human mRNA in the public database were judged to be "full-length" if they had a longer 5'-end sequence than that of the known human mRNA; or even though the 5'-end sequence was shorter, if it contained the translation initiation codon it was judged to have the "full-length" sequence. Clones which did not contain the translation initiation codon were judged to be "not-full-length". The fullness ratio ((the number of full-length clones)/(the number of full-length and not-full-length clones)) at the 5'-end of the cDNA clones was determined by comparing with known human mRNA. As a result, the fullness ratio of the 5'-ends was 90%. The result indicates that the fullness ratio at the 5'-end sequence was extremely high in the human cDNA clones obtained by the oligo-capping method.

EXAMPLE 2

Sequencing Analysis of cDNA Ends and Selection of Full-length Clones

With respect to the plasmid DNAs of clones obtained from each cDNA library, the 5'-end nucleotide sequences of the cDNAs were determined in a DNA sequencer (ABI PRISM 3700, PE Biosystems), after sequencing reaction was conducted by using a DNA sequencing reagent (Dye Terminator Cycle Sequencing FS Ready Reaction Kit, dRhodamine Terminator Cycle Sequencing FS Ready Reaction Kit or BigDye Terminator Cycle Sequencing FS Ready Reaction Kit, PE Biosystems) according to the manual. A database was constructed using the data obtained.

For the analyzed 5'-end sequences of cDNA clones, the data with the annotation of "complete cds" in the GenBank and UniGene were searched by BLAST homology search. When identical to certain human mRNA sequences, such cDNA clones were excluded. Then, clustering was carried out. When the identity was 90% or higher, and the length of consensus sequence was 50 base pairs or longer, the cDNA clones were assumed to belong to an identical cluster, and thus clustered. cDNA clones longer in the 5' direction were selected from the members belonging to a cluster; if required, the 3'-end sequences of the selected clones were determined by the same analysis method as used to determine the 5'-end sequences. The data of the end sequences obtained were analyzed, and then the clones forming a sequence contig at 5'- and 3'-ends were excluded. Further, as mentioned above, the data was analyzed again by BLAST homology search; when identical to certain human mRNA sequences (including sequences patented and applied for), the cDNA clones were excluded. Thus, the cDNAs clones to be analyzed for their nucleotide sequence were obtained.

EXAMPLE 3

Analysis of the Full-length Nucleotide Sequences

The full-length nucleotide sequences of the selected clones were determined. The nucleotide sequence determination was mainly performed by primer walking method comprising the dideoxy terminator method using custom-made synthetic DNA primers. Namely, the nucleotide sequences of the DNAs were determined in a sequencer from PE Biosystems, after sequencing reaction was carried out with a DNA sequencing reagent from the same supplier using the custom-made synthetic DNA primers according to the manual. A part of the clones were analyzed with a DNA sequencer from Licor.

Further, the nucleotide sequences of a part of the clones were determined by the shotgun method where the plasmids containing the cDNAs were digested at random were used, instead of the use of custom-made primers, by the same method in the DNA sequencer. The full-length nucleotide sequences were finally determined by completely assembling the partial nucleotide sequences obtained by the above method.

Then, the regions translatable to proteins were deduced from the determined full-length nucleotide sequences, and thereby the amino acid sequences were determined. SEQ ID NOs corresponding to the respective sequences are shown in Table 1.

EXAMPLE 4

Functional Prediction by Homology Search

For the determined nucleotide sequences, GenBank, SwissProt, UniGene, and nr were searched by BLAST. The clones exhibiting higher homology, which were convenient to predict their functions based on the nucleotide sequences and deduced amino acid sequences, were selected based on the BLAST search hit data whose P value or E value was $10^{-4}$ or lower and for which the length of consensus sequence×homology=30 or higher in the amino acid database search. Further, from them, representative clones were selected, which are shown as Homology Search Result Data in the last part herein. Accordingly, the data shown herein are merely the representative data, and the molecule exhibiting homology to each clone is not limited thereto. Further, with respect to a part of clones, the BLAST search hit data that did not meet the criteria as described above are not shown herein.

EXAMPLE 5

Search for Signal Sequence, Transmembrane Domain and Other Functional Domains in the Deduced Amino Acid Sequences With respect to the amino acid sequences deduced from the full-length nucleotide sequences, the prediction was made for the presence of signal sequence at the amino terminus, the presence of transmembrane domain, and the presence of functional protein domains (motifs). The signal sequence at the amino terminus was searched for by PSORT [K. Nakai & M. Kanehisa, Genomics, 14: 897–911 (1992)]; the transmembrane domain, by SOSUI [T. Hirokawa et al., Bioinformatics, 14: 378–379 (1998)] (Mitsui Knowledge Industry); the function domain, by Pfam. The amino acid sequence in which the signal sequence at the amino terminus or transmembrane domain had been predicted to be present by PSORT or SOSUI were assumed to be a secretory or membrane protein. Further, when the amino acid sequence hit a certain functional domain by the Pfam functional domain search, the protein function can be predicted based on the hit data, for example, by referring to the function categories on the PROSITE. In addition, the functional domain search can also be carried out on the PROSITE.

The search results obtained with the respective programs are shown below.

The clones whose deduced amino acid sequences were detected to have the signal sequences by PSORT are as follows.

ADRGL20013520, ASTRO20005330, ASTRO20055750, BNGH420088500, BRACE20038000, BRACE20081720, BRACE20101710, BRACE20224480, BRACE20257100, BRACE20273890, BRALZ20013500, BRALZ20054710, BRALZ20077930, BRAMY20063970, BRAMY20284910, BRAWH20016860, BRAWH20064050, BRCOC10000870, BRCOC20078640, BRCOC20090520, BRCOC20101230, BRCOC20114180, BRCOC20121720, BRCOC20134480, BRCOC20136750, BRHIP20179200, BRHIP20198190, BRHIP20217620, BRSSN20003120, BRSSN20137020, COLON10001350, COLON20093370, CTONG20158660, CTONG20267700, D30ST20036070, D30ST20038560, D60ST20005070, FCBBF10001210, FCBBF10002430, FCBBF10003760, FCBBF10005740, FCBBF20042560, FCBBF30086440, FCBBF30095260, FCBBF30172550, FCBBF30238870, FEBRA20009090, FEBRA20029860, FEBRA20086620, FEBRA20092890, FEBRA20111460, FEBRA20130190, FEBRA20145780, FEBRA20235500, HCHON20064590, HCHON20067700, HCHON20086720, HEART20049410, HHDPC20001040, HHDPC20014320, KIDNE20011400, KIDNE20022620, KIDNE20126130, KIDNE20127450, LIVER20064690, MESAN10001260, MESAN20038510, MESAN20115970, MESAN20152770, MESAN20153910, NT2NE20118960, NT2NE20124480, NT2NE20183760, NT2RI20003480, NT2RI20023910, NT2RI20028470, NT2RI20040930, NT2RP70134990, NTONG20029700, NTONG20063010, OCBBF20019830, OCBBF20078920, OCBBF20086400, OCBBF20087010, OCBBF20116850, OCBBF20122620, OCBBF20130910, OCBBF20188730, PEBLM20075980, PLACE60086400, PROST20175290, SKNSH20028660, SMINT20009840, SMINT20022020, SMINT20073650, SMINT20095050, SMINT20105330, SMINT20127930, SMINT20153260, SMINT20157450, SMINT20173240, SMINT20178550, SMINT20191420, SMINT20192000, SPLEN20079510, SPLEN20095810, SPLEN20118300, SPLEN20141360, SPLEN20157880, SPLEN20171890, SPLEN20213830, STOMA20005390, STOMA20056640, STOMA20080500, STOMA20088380, SYNOV20001520, SYNOV20001730, SYNOV20002790, SYNOV20002970, SYNOV20004260, SYNOV20007000, SYNOV20008240, SYNOV20009230, SYNOV20010880, SYNOV20011110, SYNOV20013000, TESOP20005690, TESTI20123560, TESTI20208400, TESTI20211220, TESTI20272960, TESTI20309170, TESTI20316870, TESTI20385960, TESTI20390260, TESTI20391770, TESTI20396130, TESTI20415170, TESTI20421490, TESTI20441940, TESTI20444180, TESTI20463580, THYMU10005360, THYMU20027560, THYMU20032870, THYMU20039810, THYMU20066100, THYMU20106710, THYMU20111830, THYMU20161640, THYMU20162190, THYMU20194420, THYMU20222890, THYMU20241850, TKIDN20005210,

TRACH20029540, TRACH20034840, TRACH20050040, TRACH20069180, TRACH20085400, TRACH20136710, TRACH20145440, TRACH20180840, UTERU20158300, UTERU20158800, UTERU20161570

The clones whose deduced amino acid sequences were detected to have the transmembrane domains by SOSUI are as follows. Numerals indicate the numbers of transmembrane domains detected in the deduced amino acid sequences. Of the search result, the clone name and the number of transmembrane domains are demarcated by a double slash mark (//).

ADIPS10000640//3, ADRGL20018540//1, ADRGL20035850//2, ASTRO20001410//1, ASTRO20005330//3, ASTRO20058630//4, ASTRO20190390//1, BEAST20004540//1, BGGI110000240//2, BRACE20006400//1, BRACE20038470//1, BRACE20039040//1, BRACE20039540//1, BRACE20051380//1, BRACE20059370//1, BRACE20061050//1, BRACE20063630//2, BRACE20067430//1, BRACE20069090//2, BRACE20101700//2, BRACE20116110//2, BRACE20147800//1, BRACE20153680//5, BRACE20163350//1, BRACE20179340//6, BRACE20188470//4, BRACE20195100//1, BRACE20201570//1, BRACE20210140//1, BRACE20224480//1, BRACE20224500//1, BRACE20228480//1, BRACE20232840//1, BRACE20238000//2, BRACE20274080//1, BRALZ20013500//2, BRALZ20064740//1, BRALZ20069760//3, BRALZ20073760//3, BRAMY20000860//2, BRAMY20002770//2, BRAMY20025840//1, BRAMY20039260//3, BRAMY20060920//1, BRAMY20063970//3, BRAMY20111960//1, BRAMY20112800//2, BRAMY20134140//2, BRAMY20135900//1, BRAMY20136210//1, BRAMY20144620//3, BRAMY20152110//1, BRAMY20174550//4, BRAMY20181220//2, BRAMY20195090//1, BRAMY20211390//1, BRAMY20211420//10, BRAMY20215230//1, BRAMY20218250//10, BRAMY20218670//3, BRAMY20229800//1, BRAMY20231720//1, BRAMY20247280//1, BRAMY20252180//2, BRAMY20273960//1, BRAMY20277170//5, BRAWH20015350//1, BRAWH20015890//2, BRAWH20016860//3, BRAWH20018730//10, BRAWH20030250//4, BRAWH20110790//3, BRAWH20121640//11, BRAWH2-0122580//2, BRAWH20132190//2, BRCAN20064010//2, BRCAN20071190//1, BRCAN20091560//1, BRCAN20103740//1, BRCAN20224720//1, BRCAN20273550//5, BRCAN20280360//6, BRCAN20285450//2, BRCOC20004040//4, BRCOC20006370//2, BRCOC20041750//1, BRCOC20077690//2, BRCOC20090520//1, BRCOC20091960//2, BRCOC20101230//6, BRCOC20107300//1, BRCOC20114180//3, BRCOC20121720//7, BRCOC20134480//3, BRCOC20136750//2, BRHIP20000870//2, BRHIP20003120//3, BRHIP20111200//1, BRHIP20118380//1, BRHIP20118910//2, BRHIP20121410//3, BRHIP20135100//1, BRHIP20183690//9, BRHIP20191490//2, BRHIP20191770//1, BRHIP20207430//1, BRHIP20208270//1, BRHIP20208590//2, BRHIP20217620//1, BRHIP20233090//1, BRHIP20234380//1, BRHIP20238880//1, BRHIP20283030//1, BRSSN20043040//2, BRSSN20137020//2, BRSSN20146100//3, BRSSN20169050//2, BRTHA20046290//2, CTONG10000100//6, CTONG10001650//1, CTONG20092570//7, CTONG20095340//5, CTONG20103480//1, CTONG20114290//2, CTONG20119200//2, CTONG20124220//3, CTONG20131490//1, CTONG20133480//2, CTONG20149950//1, CTONG20158660//9, CTONG20267700//1, D30ST20036070//1, D30ST30002580//2, D90ST20015470//2, D90ST20040180//7, FCBBF10000240//8, FCBBF10001150//1, FCBBF10001550//1, FCBBF10003220//1, FCBBF20032970//1, FCBBF20051220//2, FCBBF30012350//1, FCBBF30078290//1, FCBBF30090690//1, FCBBF30123470//3, FCBBF30175310//9, FCBBF30215060//4, FCBBF30251420//1, FEBRA20002100//5, FEBRA20080810//5, FEBRA20095880//1, FEBRA20125070//1, FEBRA20140100//3, FEBRA20211710//1, FEBRA20235500//10, HCHON20007510//1, HCHON20016650//7, HCHON20040020//1, HCHON20068710//4, HEART20005410//1, HEART20049800//1, HHDPC10000830//3, HHDPC20014320//1, HHDPC20068620//1, HHDPC20091780//2, KIDNE20003940//10, KIDNE20021910//4, KIDNE20100070//2, KIDNE20109730//2, KIDNE20125630//2, KIDNE20130450//2, KIDNE20137340//4, LIVER20035110//1, LIVER20062510//1, LIVER20087060//1, MESAN20014500//6, MESAN20038510//1, MESAN20103120//5, MESAN20139360//1, BRSSN20003120//7, BRSSN20066110//2, BRSSN20142940//1, BRSSN20151990//2, BRSTN20002200//1, BRTHA20046420//5, CTONG10000940//1, CTONG20004690//5, CTONG20092580//2, CTONG20099380//2, CTONG20105080//9, CTONG20114740//3, CTONG20120770//1, CTONG20124730//1, CTONG20132220//1, CTONG20139340//2, CTONG20155400//1, CTONG20161850//2, D30ST10001090//5, D30ST20038560//1, D90ST20002780//2, D90ST20026730//1, DFNES20025880//1, FCBBF10000380//1, FCBBF10001210//1, FCBBF10002700//2, FCBBF10005460//1, FCBBF20042560//3, FCBBF30008470//2, FCBBF30024750//1, FCBBF30086440//3, FCBBF30095260//2, FCBBF30172550//1, FCBBF30190850//1, FCBBF30238870//1, FCBBF30279030//5, FEBRA20037260//1, FEBRA20093520//1, FEBRA20111460//1, FEBRA20130190//1, FEBRA20145780//2, FEBRA20229630//3, HCHON20000380//2, HCHON20008180//1, HCHON20035130//1, HCHON20067700//1, HEART20003060//1, HEART20034320//2, HEART20072310//2, HHDPC20001040//1, HHDPC20034720//1, HHDPC20084140//1, HLUNG10000550//2, KIDNE20007770//2, KIDNE20022620//1, KIDNE20101510//2, KIDNE20121880//5, KIDNE20126010//1, KIDNE20131580//7, KIDNE20181660//1, LIVER20045650//1, LIVER20075680//1, LIVER20091180//1, MESAN20027090//2, MESAN20089360//1, MESAN20115970//4, MESAN20153910//1,

NOVAR20000380//1, NT2NE20021620//1, NT2NE20131890//1, NT2NE20155110//1, NT2NE20159740//3, NT2RI20023910//2, NT2RI20054050//8, NT2RI20086220//4, NT2RI20244600//6, NT2RP70081610//6, NT2RP70125160//3, NT2RP70137290//1, NT2RP70188020//1, NTONG20048060//1, NTONG20051530//1, NTONG20067830//1, OCBBF10001750//2, OCBBF20023570//1, OCBBF20037440//1, OCBBF20059560//2, OCBBF20072320//1, OCBBF20086400//1, OCBBF20088140//1, OCBBF20107090//2, OCBBF20120390//12, OCBBF20132850//3, OCBBF20178880//1, OCBBF20180840//1, PEBLM20024320//2, PEBLM20074370//1, PLACE60121080//1, PLACE60177140//6, PROST20050670//1, PROST20116600//2, PROST20127800//3, PROST20164440//3, PROST20170980//1, PUAEN20003740//2, SALGL10001710//5, SKMUS20011640//3, SKMUS20028210//1, SKMUS20077400//1, SKNSH20051940//1, SMINT20011990//1, SMINT20029760//1, SMINT20049090//1, SMINT20095050//2, SMINT20105330//1, SMINT20157450//5, SMINT20178550//3, SPLEN20003070//2, SPLEN20026950//1, SPLEN20095810//1, SPLEN20118300//9, SPLEN20141990//1, SPLEN20152760//2, SPLEN20165310//1, SPLEN20169220//2, SPLEN20171890//4, SPLEN20186430//6, SPLEN20211940//3, SPLEN20273950//1, SPLEN20293800//4, SPLEN20329240//1, STOMA20008880//1, STOMA20056670//1, STOMA20077450//2, NT2NE20010050//1, NT2NE20118960//4, NT2NE20132170//9, NT2NE20156260//1, NT2NE20177520//2, NT2RI20025400//2, NT2RI20076290//8, NT2RI20091940//3,- NT2RP70072690//1, NT2RP70122910//2, NT2RP70133740//4, NT2RP70179710//1, NTONG20028070//1, NTONG20049910//1, NTONG20061870//1, NTONG20092330//2, OCBBF20013890//3, OCBBF20026630//1, OCBBF20050770//1, OCBBF20063320//1, OCBBF20080050//2, OCBBF20086910//1, OCBBF20091150//1, OCBBF20116850//2, OCBBF20130910//2, OCBBF20155060//2, OCBBF20180120//10, PANCR10000910//3, PEBLM20040150//2, PERIC20004220//4, PLACE60161600//2, PROST20005050//1, PROST20107820//4, PROST20120160//1, PROST20146010//3, PROST20169800//1, PROST20191640//1, PUAEN20030180//2, SKMUS20007800//7, SKMUS20020840//3, SKMUS20028400//1, SKNSH20031740//1, SKNSH20063040//3, SMINT20022020//4, SMINT20040860//7, SMINT20053870//1, SMINT20100680//1, SMINT20144890//1, SMINT20173240//3, SMINT20192000//1, SPLEN20008740//4, SPLEN20029310//3, SPLEN20097330//1, SPLEN20141360//1, SPLEN20144520//3, SPLEN20157880//1, SPLEN20167200//1, SPLEN20169720//1, SPLEN20172120//2, SPLEN20211570//2, SPLEN20213830//2, SPLEN20292950//7, SPLEN20304950//2, STOMA20006780//2, STOMA20051200//1, STOMA20062130//1, STOMA20080500//4, SYNOV20013560//1, SYNOV30001840//4, TBAES20003150//2, TESOP20005690//3, TESTI20001720//3, TESTI20036380//6, TESTI20037560//1, TESTI20082330//1, TESTI20094120//8, TESTI20110280//1, TESTI20123080//1, TESTI20123560//3, TESTI20128350//1, TESTI20136100//2, TESTI20136710//2, TESTI20143390//8, TESTI20148000//1, TESTI20164100//3, TESTI20193360//1, TESTI20209810//1, TESTI20209990//1, TESTI20214250//2, TESTI20230250//1, TESTI20231940//1, TESTI20237520//2, TESTI20242990//2, TESTI20254220//7, TESTI20254860//1, TESTI20265970//2, TESTI20271850//2, TESTI20272960//8, TESTI20284880//2, TESTI20291310//4, TESTI20291960//5, TESTI20303360//1, TESTI20303420//1, TESTI20307700//2, TESTI20316870//1, TESTI20333000//2, TESTI20347180//6, TESTI20347300//1, TESTI20355020//1, TESTI20357960//1, TESTI20370810//9, TESTI20373820//1, TESTI20383880//1, TESTI20390410//1, TESTI20391770//3, TESTI20393530//1, TESTI20397760//2, TESTI20401280//1, TESTI20422640//2, TESTI20441940//5, TESTI20444130//1, TESTI20449200//6, TESTI20463520//1, TESTI20463580//1, THYMU20027560//4, THYMU20032870//1, THYMU20039810//3, THYMU20100410//2, THYMU20106710//1, THYMU20111830//1, THYMU20141670//1, THYMU20147770//1, THYMU20159430//1, THYMU20161640//4, THYMU20162190//2, THYMU20173980//2, THYMU20208300//1, THYMU20216840//2, THYMU20229220//1, THYMU20241850//2, THYMU20277390//7, TRACH20002870//3, TRACH20003590//1, TRACH20016210//1, TRACH20029540//1, TRACH20033230//6, TRACH20042920//6, TRACH20050040//2, TRACH20068660//6, TRACH20076740//4, TRACH20085400//2, TRACH20085830//1, TRACH20109650//2, TRACH20111130//1, TRACH20128110//5, TRACH20134950//1, TRACH20140820//1, TRACH20145440//1, TRACH20168350//1, UMVEN20000690//1, UTERU20030570//5, UTERU20040610//1, UTERU20055480//2, UTERU20076390//4, UTERU20094350//1, UTERU20135860//2, UTERU20158300//3, UTERU20158800//2, UTERU20161570//6, UTERU20178100//1, UTERU20186740//1

The Names of clones whose deduced amino acid sequences were detected to have functional domains with Pfam, and the name of hit functional domains are as follows. The search result is indicated as "clone name//functional domain name". When the clone has multiple hit functional domains, they are listed and demarcated by a double slash mark (//). When the clone has multiple hits of an identical functional domain, each is listed without abridgment. 3NB6910001910//tRNA synthetases class II (A)// tRNA synthetases class II (A)// DHHA1 domain 3NB6920014590//Homeobox domain ADIPS20004250//Zinc finger, C2H2 type// DNA binding domain with preference for// Zinc finger, C2H2 type// Zinc finger, C2H2 type// Zinc finger, C2H2 type// Zinc finger, C2H2 type// TRAF-type zinc finger// Zinc finger, C2H2 type// UvrD/REP helicase// Zinc finger, C2H2 type// Zinc finger, C2H2 type// Zinc finger, C2H2 type ADRGL10001470//Cytochrome P450// Cytochrome P450

ADRGL20011190//Calponin homology (CH) domain// Calponin homology (CH) domain// Pou domain-N-terminal to homeobox domain ADRGL20018300//TPR Domain// TPR Domain// TPR Domain// TPR Domain// PPR repeat// TPR Domain ADRGL20035850//Cytochrome P450

ADRGL20048330//PHD-finger// Rabphilin-3A effector domain// C2 domain// C2 domain ASTRO20008010//Zinc finger, C2H2 type// Zinc finger, C2H2 type// Zinc finger, C2H2 type// Zinc finger, C2H2 type// Zinc finger, C2H2 type ASTRO20012490//Eukaryotic initiation factor 1A ASTRO20027430//Leucine Rich Repeat// Leucine Rich Repeat// Leucine Rich Repeat// Leucine Rich Repeat// Leucine Rich Repeat// Leucine Rich Repeat// Leucine Rich Repeat ASTRO20033160//Mitochondrial carrier proteins// Mitochondrial carrier proteins// Mitochondrial carrier proteins ASTRO20055750//Collagen triple helix repeat (20 copies)// Heavy-metal-associated domain ASTRO20058630//Vacuolar sorting protein 9 (VPS9) domain ASTRO20064750//Zinc finger, C2H2 type// Nuclear transition protein 2

ASTRO20072210//PDZ domain (Also known as DHR or GLGF).

ASTRO20084250//KH domain// Zinc finger, C3HC4 type (RING finger)

ASTRO20105820//FAD binding domain

ASTRO20106150//Calpain family cysteine protease// Calpain large subunit, domain III ASTRO20108190//Rap/ran-GAP ASTRO20125520//DnaJ domain ASTRO20130500//ThiF family// Repeat in ubiquitin-activating (UBA) pro ASTRO20143630//KH domain// Bacterial regulatory proteins, crp family ASTRO20155290//TPR Domain// TPR Domain// TPR Domain ASTRO20168470//Zinc finger, C2H2 type// Zinc finger, C2H2 type// Zinc finger, C2H2 type// Zinc finger, C2H2 type// Zinc finger, C2H2 type// Zinc finger, C2H2 type// TRAF-type zinc finger// Zinc finger, C2H2 type// Transcription factor S-II (TFIIS)// Zinc finger, C2H2 type// Zinc finger, C2H2 type BGGI110001930//UBX domain BGGI120006160//Fumarylacetoacetate (FAA) hydrolase fam BLADE20003400//Zinc finger, C2H2 type// Zinc finger, C2H2 type// Zinc finger, C2H2 type// PHD-finger// Zinc finger, C2H2 type// Zinc finger, C2H2 type BLADE20003890//KRAB box// Zinc finger, C2H2 type// Zinc finger, C2H2 type// Src homology domain 2// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Src homology domain 2// Zinc finger, C2H2 type// Zinc finger, C2H2 type// Zinc finger, C2H2 type// Zinc finger, C2H2 type// Zinc finger, C2H2 type BNGH420088500//SAM domain (Sterile alpha motif)

BRACE20003070//SAM domain (Sterile alpha motif)

BRACE20011070//F-box domain.

BRACE20027620//Dienelactone hydrolase family// Dienelactone hydrolase family

BRACE20038000//ATP synthase, Delta/Epsilon chain// Dual specificity phosphatase, catalytic d BRACE20039540//Immunoglobulin domain// Adenovirus E3 region protein CR2

BRACE20050900//TPR Domain// TPR Domain// TPR Domain// TPR Domain

BRACE20052160//SAM domain (Sterile alpha motif)

BRACE20053280//PDZ domain (Also known as DHR or GLGF).

BRACE20053480//Ribosomal protein L22p/L17e// Glycosyl hydrolases family 38

BRACE20053630//Plant thionins// Mitochondrial carrier proteins// Mitochondrial carrier proteins BRACE20057620//Eukaryotic initiation factor 4E BRACE20058580//L1 (late) protein BRACE20059370//FERM domain (Band 4.1 family)

BRACE20060550//Ank repeat// Ank repeat// Ank repeat// PEP-utilizing enzymes

BRACE20060720//WD domain, G-beta repeat// WD domain, G-beta repeat

BRACE20060890//Zinc finger, C2H2 type// Zinc finger, C2H2 type// Zinc finger, C2H2 type// TRAF-type zinc finger// Zinc finger, C2H2 type// Zinc finger, C2H2 type BRACE20062640//Alanine racemase// RNB-like proteins BRACE20063780//NOL1/NOP2/sun family BRACE20064880//KH domain// KH domain// KH domain BRACE20068590//KRAB box// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type BRACE20096200//Sir2 family// Sir2 family BRACE20107530//short chain dehydrogenase BRACE20115920//Spectrin repeat// Fes/CIP4 homology domain// Interleukin 10

BRACE20148240//Ras family

BRACE20151320//Zinc finger, C3HC4 type (RING finger)

BRACE20153680//Sir2 family// Ion transport protein

BRACE20163350//Immunoglobulin domain// Immunoglobulin domain

BRACE20177200//RanBP1 domain.

BRACE20188470//ABC transporter// Thymidylate kinase

BRACE20190040//Integrase DNA binding domain

BRACE20192440//Translation initiation factor IF-3

BRACE20223330//3'-5exonuclease// Adenylylsulfate kinase// Protein of unknown function DUF82

BRACE20232840//4Fe-4S binding domain// ABC transporter// ABC transporter// ATPases associated with various cellular act BRACE20240740//Ribosomal protein L36

BRACE20253330//PDZ domain (Also known as DHR or GLGF).

BRACE20269200//Heat-labile enterotoxin alpha chain

BRACE20273890//UBA domain

BRACE20284100//Polysaccharide lyase family 8

BRACE20286360//Alpha adapt in carboxyl-terminal domain

BRALZ20013500//Keratin, high sulfur B2 protein// u-PAR/Ly-6 domain

BRALZ20054710//Zinc finger, C3HC4 type (RING finger)// TRAF-type zinc finger

BRALZ20058880//STAT protein

BRALZ20077930//Ribosomal protein S27a

BRAMY20000520//RNA recognition motif. (a.k.a. RRM, RBD, or RNP domain)

BRAMY20002770//DB module

BRAMY20025840//Sec7 domain

BRAMY20045240//Flagellar L-ring protein

BRAMY20054880//Pou domain-N-terminal to homeobox domain

BRAMY20103570//DNA binding domain with preference for A/T r

BRAMY20104640//Eukaryotic protein kinase domain// Protein kinase C terminal domain BRAMY20111960//Ribosomal protein L36

BRAMY20121620//TPR Domain// TPR Domain// TPR Domain// TPR Domain// PPR repeat

BRAMY20124260//ZU5 domain// Death domain

BRAMY20148130//WD domain, G-beta repeat// WD domain, G-beta repeat// WD domain, G-beta repeat// WD domain, G-beta repeat// TBC domain BRAMY20153110//ACT domain// Biopterin-dependent aromatic amino acid hydroxylase BRAMY20157820//Kinesin motor domain BRAMY20162510//MAGE family BRAMY20167060//Collagen triple helix repeat (20 copies)

BRAMY20174550//ABC transporter transmembrane region.// Phosphoribulokinase// Adenylylsulfate kinase// FtsK/SpoIIIE family// ABC transporter BRAMY20211390//Zinc finger, C3HC4 type (RING finger)

BRAMY20211420//Transient receptor// GGL domain

BRAMY20213100//LIM domain containing proteins// GATA zinc finger// ' Paired box' domain BRAMY20215230//ribonuclease.

BRAMY20217460//EF hand// EF hand// EF hand

BRAMY20218250//Ion transport protein// Sir2 family// Ion transport protein

BRAMY20240040//Nuclear transition protein 2

BRAMY20245300//Fanconi anaemia group C protein// Metallo-beta-lactamase superfamily BRAMY20248490//Sodium:sulfate symporter transmembrane BRAMY20260910//Zinc finger, C2H2 type// PHD-finger// Zinc finger, C2H2 type// Zinc finger, C2H2 type// Zinc finger, C2H2 type BRAMY20270730//Zinc finger, C2H2 type// Zinc finger, C2H2 type// Transcription factor S-II (TFIIS)// Zinc finger, C2H2 type// Zinc finger, C2H2 type// PHD-finger// Zinc finger, C2H2 type// Zinc finger, C2H2 type// Zinc finger, C2H2 type// Zinc finger, C2H2 type// Zinc finger, C3HC4 type (RING finger)// Zinc finger, C2H2 type// Zinc finger, C2H2 type// Zinc finger, C2H2 type BRAMY20271400//Phorbol esters/diacylglycerol binding dom// PHD-finger BRAMY20277170//K+ channel tetramerisation domain// NADH- ubiquinone/plastoquinone oxidoreduc// Ion transport protein// Transmembrane region cyclic Nucleotide G BRAMY20285160//NTR/C345C module BRAWH20002320//Leucine Rich Repeat// Leucine Rich Repeat// Leucine Rich Repeat// Leucine Rich Repeat BRAWH20011710//Ank repeat// Ank repeat// Ank repeat// CAP-Gly domain// CAP-Gly domain BRAWH20012390//EF hand// EF hand// EF hand BRAWH20016620//Eukaryotic protein kinase domain// EIAV coat protein, gp90

BRAWH20018730//Sugar (and other) transporter

BRAWH20028110//4Fe-4S binding domain// LIM domain containing proteins// LIM domain containing proteins// LIM domain containing proteins// LIM domain containing proteins// Villin headpiece domain BRAWH20030250//jmjN domain BRAWH20064050//Sushi domain (SCR repeat)// EGF-like domain// Trypsin Inhibitor like cysteine rich domain// EGF-like domain// Granulins// Granulins// EGF-like domain BRAWH20075700//Zinc finger, C2H2 type// Zinc finger, C2H2 type// Zinc finger, C2H2 type// Transcription factor S-II (TFIIS)// Zinc finger, C2H2 type// Zinc finger, C2H2 type// Zinc finger, C2H2 type// Zinc finger, C2H2 type// Zinc finger, C2H2 type BRAWH20096780//KRAB box// Zinc finger, C2H2 type// Zinc finger, C2H2 type// PHD-finger// Zinc finger, C2H2 type// Zinc finger, C2H2 type// Zinc finger, C2H2 type// Zinc finger, C2H2 type// Transcription factor S-II (TFIIS)// Zinc finger, C2H2 type// Zinc finger, C2H2 type// Zinc finger, C2H2 type// Zinc finger, C2H2 type// Zinc finger, C2H2 type BRAWH20101360//Hexokinase BRAWH20103290//CRAL/TRIO domain.// Spectrin repeat// Extracellular link domain// RhoGEF domain// PH domain BRAWH20110960//PCI domain BRAWH20112940//Similarity to lectin domain of ricin beta-chain, 3 copies.

BRAWH20114000//Glutamate/Leucine/Phenylalanine/ Valine dehydrogenase

BRAWH20117950//Carboxylesterases

BRAWH20118230//Transforming growth factor beta like domain

BRAWH20121640//eubacterial secY protein// Transmembrane amino acid transporter protein BRAWH20132190//Acetyltransferase (GNAT) family BRAWH20137480//Villin headpiece domain BRAWH20138660//Adaptor complexes medium subunit family BRAWH20149340//IQ calmodulin-binding motif// RhoGEF domain BRAWH20164460//Sigma-54 interaction domain// ATPases associated with various cellular activities (AAA)

BRAWH20171030//Adenylate kinase// NB-ARC domain// ATPases associated with various cellu BRAWH20185060//Integrase core domain BRCAN10001490//chromo (CHRromatin Organization MOdifier)

BRCAN20003460//Thioredoxin

BRCAN20071190//Ubiquitin family// UBX domain

BRCAN20091560//Rieske [2Fe-2S] domain// Phosphoglucose isomerase// FAD binding domain// Pyridine nucleotide-disulphide oxidoreductase// Phytoene dehydrogenase related enzyme BRCAN20124080//WD domain, G-beta repeat// WD domain, G-beta repeat// WD domain, G-beta repeat// WD domain, G-beta repeat// WD domain, G-beta repeat// WD domain, G-beta repeat// WD domain, G-beta repeat// WD domain, G-beta repeat// WD domain, G-beta repeat BRCAN20273550//FATC domain BRCAN20273640//Formin Homology 2 Domain BRCAN20280210//Zinc finger, C2H2 type// Zinc finger, C2H2 type// Zinc finger, C2H2 type// Zinc finger, C2H2 type BRCAN20280360//PAP2 superfamily BRCOC20001860//FliP family// Glycosyl hydrolase family 47

BRCOC20004040//7 transmembrane receptor (rhodopsin family)// Neurohypophysial hormones, C-terminal Domain BRCOC20006370//Plexin repeat BRCOC20008160//Spectrin repeat// Spectrin repeat// Tropomyosins// Spectrin repeat// Adenylate cyclase// Spectrin repeat// FF domain// Spectrin repeat// Spectrin repeat// Spectrin repeat BRCOC20008500//Vacuolar sorting protein 9 (VPS9) domain// Ras association (RalGDS/AF-6) domain BRCOC20023230//Reverse transcriptase (RNA-dependent DNA polymerase)

BRCOC20026640//Gag P30 core shell protein

BRCOC20027510//Leucine Rich Repeat// Leucine Rich Repeat// Leucine Rich Repeat// Leucine Rich Repeat// Leucine Rich Repeat// Leucine Rich Repeat// Leucine Rich Repeat BRCOC20031250//Triosephosphate isomerase BRCOC20035130//14-3-3 proteins BRCOC20037320//Apolipoprotein A1/A4/E family BRCOC20055420//Helix-loop-helix DNA-binding domain// Myristoyl-CoA BRCOC20074760//Herpesvirus UL25 family// Beige/BEACH domain BRCOC20110100//Integrase core domain BRCOC20121720//PHD-finger BRCOC20144000//Helicases conserved C-terminal domain BRCOC20178270//Zinc finger, C2H2 type// Zinc finger, C2H2 type// Zinc finger, C2H2 type// Zinc finger, C2H2 type// Zinc finger, C2H2 type// Transcription factor S-I1 (TFIIS)// Zinc finger, C2H2 type// Zinc finger, C2H2 type// Zinc finger, C2H2 type BRCOC20178560//LIM domain containing proteins// LIM domain containing proteins// LIM domain containing proteins// Ribosomal protein L24e// LIM domain containing proteins BRHIP10001290//Ribosomal protein S3, C-terminal domai// Similarity to lectin domain of ricin b BRHIP20001630//Protein of unknown function DUF16

BRHIP20003120//Dehydrins// Reticulon

BRHIP20005530//ThiF family

BRHIP20096850//ICE-like protease (caspase) p20 domain// Aminotransferases class-I BRHIP20115080//PH domain BRHIP20118910//Fibronectin type I domain BRHIP20119330//KRAB box// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Transcription factor S-II (TFIIS)// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// TRAF-type zinc finger// Zinc finger, C2H2 type// Zinc finger, C2H2 type// Zinc finger, C2H2 type BRHIP20132860//PDZ domain (Also known as DHR or GLGF).

BRHIP20143730//MYND finger

BRHIP20153600//RNA recognition motif. (a.k.a. RRM, RBD, or

BRHIP20174040//GAF domain// GAF domain// Transposase, Mutator family// 3' 5'-cyclic nucleotide phosphodiesterase BRHIP20176420//RNA recognition motif. (a.k.a. RRM, RBD, or RNP domain)

BRHIP20183690//DEAD/DEAH box helicase// Integral membrane protein DUF6// Integral membrane protein DUF7

BRHIP20189980//bZIP transcription factor

BRHIP20191860//Helix-loop-helix DNA-binding domain

BRHIP20207990//Phorbol esters/diacylglycerol binding dom// Zinc finger, C3HC4 type (RING finger)// PHD-finger BRHIP20222280//Zinc finger, C2H2 type// Zinc finger, C2H2 type// Zinc finger, C2H2 type// Zinc finger, C2H2 type// Zinc finger, C2H2 type// Zinc finger, C2H2 type// Transcription factor S-II (TFIIS)// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type BRHIP20236950//Outer Capsid protein VP4 (Hemagglutinin)

BRHIP20238600//WD domain, G-beta repeat// WD domain, G-beta repeat// WD domain, G-beta repeat// WD domain, G-beta repeat BRHIP20238880//wnt family of developmental signaling protei BRHIP20249110//Hexokinase// Hexokinase BRHIP20252450//Spectrin repeat// Spectrin repeat// Spectrin repeat// Phosphoenolpyruvate carboxykinase// Spectrin repeat// Spectrin repeat// Spectrin repeat// eRF1-like proteins// Spectrin repeat BRHIP20253660//SH3 domain BRHIP20283030//Cadherin domain// Cadherin domain// Cadherin domain// Cadherin domain// Cadherin domain// Cadherin domain// Cadherin domain// Cadherin domain BRHIP20285830//Intermediate filament proteins BRHIP30004570//Sushi domain (SCR repeat)// Sushi domain (SCR repeat)// Sushi domain (SCR repeat)// Sushi domain (SCR repeat)

BRHIP30004880//Immunoglobulin domain// Immunoglobulin domain// Immunoglobulin domain// Immunoglobulin domain// Immunoglobulin domain// Immunoglobulin domain// Fibronectin type III domain// Fibronectin type III domain BRSSN20003120//7 transmembrane receptor (metabotropic gluta BRSSN20013420//Histone deacetylase family// Zn-finger in ubiquitin-hydrolases and o BRSSN20014260//Leucine Rich Repeat// Leucine Rich Repeat// Leucine Rich Repeat// Leucine Rich Repeat// Leucine Rich Repeat BRSSN20015790//Pyridoxal-dependent decarboxylase BRSSN20021600//BTB/POZ domain// Kelch motif// Kelch motif// Kelch motif// Kelch motif// Kelch motif// Kelch motif BRSSN20038200//Guanine nucleotide exchange factor for Ras-like GTPases; N-terminal motif// Initiator RepB protein// RasGEF domain BRSSN20039370//KRAB box// Zinc finger, C2H2 type// Zinc finger, C2H2 type BRSSN20046790//Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// PHD-finger// Zinc finger, C2H2 type BRSSN20101100//° Cold-shock DNA-binding domain BRSSN20105870//ATPases associated with various cellular activities (AAA)

BRSSN20117990//short chain dehydrogenase

BRSSN20120810//Trypsin

BRSSN20146100//Adenylate and Guanylate cyclase catalytic domain// Adenylate and Guanylate cyclase catalytic domain// Zinc finger, C4 type (two domains)// Adenylate and Guanylate cyclase catalytic domain BRSSN20176820//Wiskott Aldrich syndrome homology region 2

BRSSN20177570//Phosducin

BRSSN20187310//Ank repeat// Ank repeat// Ank repeat// Ank repeat// Ank repeat

BRSTN10000830//Kelch motif// Kelch motif// Kelch motif// Kelch motif

BRSTN20005360//TPR Domain// TPR Domain

BRTHA20000570/IReverse transcriptase (RNA-dependent DNA pol

BRTHA20004740//Phosphoglycerate kinases// lactate/malate dehydrogenase// Flavoprotein// short chain dehydrogenase// Zinc-binding dehydrogenases BRTHA20046290//Transmembrane 4 family CD34C30004240//RhoGAP domain COLON10001350//Immunoglobulin domain// Immunoglobulin domain// Immunoglobulin domain// Immunoglobulin domain// Immunoglobulin domain CTONG10000220//Leucine Rich Repeat// Leucine Rich Repeat// Leucine Rich Repeat CTONG10000620//Sec7 domain// PH domain// Josephin CTONG10000930//Armadillo/beta-catenin-like repeats CTONG10000940//Ank repeat// Ank repeat// Ank repeat CTONG10002770//Calponin homology (CH) domain// Calponin homology (CH) domain CTONG20009770//Proteasome/cyclosome repeat// Proteasome/cyclosome repeat// Proteasome/cyclosome repeat// Proteasome/cyclosome repeat// Proteasome/cyclosome repeat// Proteasome/cyclosome repeat// Proteasome/cyclosome repeat CTONG20014280//WD domain, G-beta repeat// WD domain, G-beta repeat// WD domain, G-beta repeat// WD domain, G-beta repeat// WD domain, G-beta repeat// WD domain, G-beta repeat// WD domain, G-beta repeat CTONG20027090//Glypican// Leucine Rich Repeat// Leucine Rich Repeat CTONG20050280//KRAB box// Zinc finger, C2H2 type// Zinc finger, C2H2 type// Zinc finger, C2H2 type// Zinc finger, C2H2 type// Zinc finger, C2H2 type// Zinc finger, C2H2 type// TRAF-type zinc finger// Zinc finger, C2H2 type// Zinc finger, C2H2 type// Zinc finger, C2H2 type// Zinc finger, C2H2 type// Zinc finger, C2H2 type CTONG20075860//Ribulose bisphosphate carboxylase, smal CTONG20076130//Hepatitis C virus non-structural protein NS2

CTONG20085950//SCAN domain// Zinc finger, C2H2 type// Zinc finger, C2H2 type// Zinc finger, C2H2 type// Zinc finger, C2H2 type// Zinc finger, C2H2 type// Zinc finger, C2H2 type CTONG20092570//Integral membrane protein DUF6// Uncharacterized protein family UPF0005

CTONG20092700//BTB/POZ domain

CTONG20093950//Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type CTONG20095340//El-E2 ATPase CTONG20096750//Disintegrin CTONG20098440//Acyltransferase CTONG20099550//GGL domain CTONG20105080//Integral membrane protein DUF6

CTONG20106520//Pyridoxal-phosphate dependent enzyme

CTONG20114290//Apolipoprotein Al/A4/E family

CTONG20118150//WD domain, G-beta repeat// WD domain, G-beta repeat// WD domain, G-beta repeat// WD domain, G-beta repeat// WD domain, G-beta repeat// WD domain, G-beta repeat// WD domain, G-beta repeat// WD domain, G-beta repeat// WD domain, G-beta repeat// WD domain, G-beta repeat// WD domain, G-beta repeat CTONG20118250//Eukaryotic-type carbonic anhydrase CTONG20121010//Zinc finger, C2H2 type// CONSTANS family zinc finger// Zinc finger, C2H2 type// Zinc finger, C2H2 type// Transcription factor S-II (TFIIS)// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type CTONG20121580//Kinesin motor domain// FHA domain// Histidine carboxylase PI chain CTONG20124010//WD domain, G-beta repeat// WD domain, G-beta repeat// WD domain, G-beta repeat// WD domain, G-beta repeat// WD domain, G-beta repeat CTONG20125640//Ribosomal protein L10//60s Acidic ribosomal protein CTONG20128430//Beta/Gamma crystallin// Beta/Gamma crystallin// Beta/Gamma crystallin// Beta/Gamma crystallin// Beta/Gamma crystallin// Similarity to tectin domain of ricin b CTONG20129960//F-box domain.// UvrD/REP helicase// UvrD/REP helicase// Viral (Superfamily 1) RNA helicase CTONG20131560//PDZ domain (Also known as DHR or GLGF).

CTONG20133390//Zinc finger, C2H2 type// Transcription factor S-II (TFIIS)// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C3HC4 type,(RING finger)// Zinc finger, C2H2 type// Zinc finger, C2H2 type CTONG20133520//KRAB box// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type CTONG20139860//Ank repeat// Ank repeat// Ank repeat CTONG20140580//Domain of unknown function DUF25// SNF2 and others N-terminal domain// SNF2 and others N-terminal domain// Small cytokines (intecrine/chemokine), inter CTONG20143690//MYND finger CTONG20146300//Reverse transcriptase (RNA-dependent DNA pol CTONG20149460//BTB/POZ domain// Kelch motif// Kelch motif// Kelch motif// Domain of unknown function// Kelch motif// Kelch motif// Kelch motif CTONG20153300//C. elegans Srg family integral membrane prote// TBC domain CTONG20153580//F-box domain.// Leucine Rich Repeat// Leucine Rich Repeat// Leucine Rich Repeat// Leucine Rich Repeat// Leucine Rich Repeat CTONG20155180//RNA helicase CTONG20156780//RNA recognition motif. (a.k.a. RRM, RBD, or RNP domain)

CTONG20158040//UTP--glucose-1-phosphate uridylyltransferase

CTONG20158660//Latrophilin/CL-1-like GPS domain// 7 transmembrane receptor (Secretin family)

CTONG20159530//Glypican

CTONG20160560//DNA binding domain with preference for A/T rich regions

CTONG20161850//Immunoglobulin domain

CTONG20165050//Keratin, high sulfur B2 protein

CTONG20186320//Kelch motif// Kelch motif// Kelch motif// Kelch motif

CTONG20200310//RNB-like proteins

D30ST20006180//Dual specificity phosphatase, catalytic domain

D30ST20036070//Leucine Rich Repeat

D90ST20023970//Glycosyl hydrolases family 18// Glycosyl hydrolases family 18

D90ST20026730//Leucine Rich Repeat// Leucine Rich Repeat// Leucine Rich Repeat// Leucine Rich Repeat// Leucine Rich Repeat// Leucine Rich Repeat// Leucine Rich Repeat D90ST20033970//KRAB box// Zinc finger, C2H2 type// Zinc finger, C2H2 type// PHD-finger// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Putative zinc finger in N-recognin// Zinc finger, C2H2 type// Zinc finger, C2H2 type D90ST20035940//Mitochondrial carrier proteins// Mitochondrial carrier proteins D90ST20040180//7 transmembrane receptor (rhodopsin family)

DFNES20037420//Elongation factor Tu family

DFNES20071130//Phosphotriesterase family// Phosphotriesterase family// Phosphotriesterase family FCBBF10000240//Phosphoenolpyruvate carboxylase// Bacterial Cytochrome Ubiquinol Oxidas// Glycosyl transferase FCBBF10000630//Molluscan rhodopsin C-terminal tail// WW domain FCBBF10001150//Cadherin domain// Cadherin domain// Cadherin domain// Cadherin domain// Cadherin domain FCBBF10001210//Immunoglobulin domain// Immunoglobulin domain FCBBF10001550//Glutamate/Leucine/Phenylalanine/Valine dehydrogenase FCBBF10001710//DM DNA binding domain// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type FCBBF10002800//Immunoglobulin domain// Immunoglobulin domain// Immunoglobulin domain// Immunoglobulin domain FCBBF10003670//Ubiquitin carboxyl-terminal hydrolases famil FCBBF10003770//PDZ domain (Also known as DHR or GLGF).// PDZ domain (Also known as DHR or GLGF).// pfkB family carbohydrate kinase// PDZ domain (Also known as DHR or GLGF).// ThiC family// PDZ domain (Also known as DHR or GLGF).// PDZ domain (Also known as DHR or GLGF).// PDZ domain (Also known as DHR or GLGF).// TIR domain FCBBF10004120//RNA recognition motif. (a.k.a. RRM, RBD, or FCBBF10004370//KRAB box// Zinc finger, C2H2 type// Ribosomal protein L37e// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type FCBBF10005060//CRAL/TRIO domain.

FCBBF10005460//Immunoglobulin domain// Immunoglobulin domain// Immunoglobulin domain// Fibronectin type III domain// Fibronectin type III domain FCBBF10005500//Keratin, high sulfur B2 protein FCBBF10005740//Mitochondrial carrier proteins// Mitochondrial carrier proteins FCBBF20014270//Acyl CoA binding protein FCBBF20042170//Fibrillar collagen C-terminal domain FCBBF20049300//Olfactomedin-like domain FCBBF20059090//Zinc finger, C2H2 type FCBBF20064520//RNA recognition motif. (a.k.a. RRM, RBD, or FCBBF20067810//Nerve growth factor family// GTP1/OBG family// GTP1/OBG family// GTPase of unknown function// ADP-ribosylation factor family// Ras family FCBBF20068820//Zinc finger, C2H2 type// Zinc finger, C2H2 type// Zinc finger, C2H2 type// Zinc finger, C2H2 type// Zinc finger, C2H2 type// Zinc finger, C2H2 type FCBBF30010810//KRAB box// Rieske [2Fe-2S] domain// Zinc finger, C2H2 type// Zinc finger, C2H2 type// PHD-finger// Zinc finger, C2H2 type// Zinc finger, C2H2 type// Zinc finger, C2H2 type// Zinc finger, C2H2 type// Zinc finger, C2H2 type// Zinc finger, C2H2 type FCBBF30012350//Eukaryotic protein kinase domain FCBBF30012810//Ubiquitin carboxyl-terminal hydrolases famil FCBBF30015940//Methyl-accepting chemotaxis protein (MCP) signaling domain FCBBF30016320//SecA protein, amino terminal region FCBBF30018550//Oxysterol-binding protein FCBBF30025560//Prolyl oligopeptidase family// Pou domain-N-terminal to homeobox doma// Homeobox domain FCBBF30033050//Sm protein FCBBF30039020//Herpesvirus UL6 like// Growth-Arrest-Specific Protein 2 Domain FCBBF30049550//Ank repeat// Ank repeat// Ank repeat// Ank repeat// Ank repeat// Ank repeat// Glutamine amidotransferases class-II// Ank repeat// Ank repeat// Ank repeat// Ank repeat// Ank repeat// Ank repeat// Ank repeat// Ank repeat// Ank repeat// Ank repeat// Ank repeat// Ank repeat// Ank repeat// Ank repeat// Ank repeat// Ank repeat// ZU5 domain FCBBF30054440//PLAT/LH2 domain FCBBF30057290//KRAB box// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type FCBBF30078290//DNA binding domain with preference for A/T r FCBBF30086440//Pilin (bacterial filament)

FCBBF30090690//Leucine rich repeat N-terminal domain// Leucine Rich Repeat// Leucine Rich Repeat// Leucine Rich Repeat// Leucine Rich Repeat// Leucine Rich Repeat// Leucine rich repeat C-terminal domain FCBBF30095260//DHHC zinc finger domain FCBBF30129630//Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type FCBBF30175310//Clq domain// CDP-alcohol phosphatidyltransferase FCBBF30190850//Sushi domain (SCR repeat)// Sushi domain (SCR repeat)// Sushi domain (SCR repeat)// Keratin, high sulfur B2 protein// Sushi domain (SCR repeat)// Phosphate transporter family FCBBF30195640//PHD-finger// CONSTANS family zinc finger// PHD-finger// PHD-finger // Hsp20/alpha crystallin family FCBBF30225660//Ank repeat// Ank repeat// Ank repeat// K+ channel tetramerisation domain// BTB/POZ domain FCBBF30233680//G10protein FCBBF30238870//Laminin G domain// Thrombospondin N-terminal -like domains// Laminin G domain// von Willebrand factor type C domain// von Willebrand factor type C domain// EGF-like domain// EB module// EGF-like domain// EGF-like domain// Trypsin Inhibitor like cysteine rich domain// Metallothionein// EGF-like domain// EGF-like domain// EGF-like domain FCBBF30240960//Zinc finger, C2H2 type// Zinc finger, C2H2 type// Zinc finger, C2H2 type// Zinc finger, C2H2 type// Zinc finger, C2H2 type// Zinc finger, C2H2 type// PHD-finger// Zinc finger, C2H2 type// Zinc finger, C2H2 type// Zinc finger, C2H2 type// Zinc finger, C2H2 type FCBBF30246630//Leucine Rich Repeat// Leucine Rich Repeat FCBBF30247930//Uncharacterized protein family UPF0004

FCBBF30262510//Ank repeat// Fibronectin type III domain

FCBBF30281880//Regulator of G protein signaling domain// PX domain

FCBBF30285280//Keratin, high sulfur B2 protein// Bacterial regulatory proteins, gntR family FCBBF40001730//WD domain, G-beta repeat// WD domain, G-beta repeat// WD domain, G-beta repeat// WD domain, G-beta repeat// WD domain, G-beta repeat// WD domain, G-beta repeat FEBRA10001880//Eukaryotic protein kinase domain// Eukaryotic protein kinase domain FEBRA10001900//Zinc finger, C2H2 type FEBRA20004620//Rap/ran-GAP FEBRA20007620//Bacterial type II secretion system protein// DEAD/DEAH box helicase// Helicases conserved C-terminal domain FEBRA20018690//Zinc finger, C2H2 type FEBRA20024100//Ank repeat// Ank repeat// Myosin head (motor domain)// Myosin head (motor domain)

FEBRA20025270//Sulfotransferase proteins

FEBRA20026110//Dictyostelium (slime mold) repeats// Zinc finger, C2H2 type// Dictyostelium (slime mold) repeats// Zinc finger, C2H2 type// Dictyostelium (slime mold) repeats// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Dictyostelium (slime mold) repeats// Zinc finger, C2H2 type// Zinc finger, C2H2 type// Zinc finger, C2H2 type// Zinc finger, C2H2 type// Dictyostelium (slime mold) repeats// Zinc finger, C2H2 type// Zinc finger, C2H2 type// Dictyostelium (slime mold) repeats// Zinc finger, C2H2 type FEBRA20034680//Zinc finger, C2H2 type// Zinc finger, C2H2 type// Zinc finger, C2H2 type// DnaJ central domain (4 repeats)// Zinc finger, C2H2 type// Zinc finger, C2H2 type// Zinc finger, C2H2 type// Zinc finger, C2H2 type/I Zinc finger, C2H2 type// Zinc finger, C2H2 type// Zinc finger, C2H2 type// PHD-finger// Zinc finger, C2H2 type FEBRA20040530//KRAB box// Zinc finger, C2H2 type// Transcription factor S-II (TFIIS)// Zinc finger, C2H2 type// Zinc finger, C2H2 type// Zinc finger, C2H2 type// Bacterial dnaA protein// Zinc finger, C2H2 type// Zinc finger, C2H2 type// Zinc finger, C2H2 type// Zinc finger, C2H2 type// Zinc finger, C2H2 type FEBRA20080810//POT family FEBRA20082010//KRAB box// Zinc finger, C2H2 type// PHD-finger// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type FEBRA20086620//Olfactomedin-like domain FEBRA20088360//Alpha adaptin carboxyl-terminal domai FEBRA20090290//Zinc finger, C3HC4 type (RING finger)

FEBRA20092890//Immunoglobulin domain// Immunoglobulin domain// Immunoglobulin domain// Immunoglobulin domain// Immunoglobulin domain// Immunoglobulin domain// Fibronectin type III domain FEBRA20097310//SAP domain// RNA recognition motif. (a.k.a. RRM, RBD, or FEBRA20111460//Hemagglutinin FEBRA20130190//Galactosyltransferase// Fringe-like FEBRA20132740//PH domain FEBRA20144170//Eukaryotic protein kinase domain// Protein kinase C terminal domain// Eukaryotic protein kinase domain FEBRA20167390//Sialyltransferase family FEBRA20171380//KRAB box// wnt family of developmental signaling protei// Zinc finger, C2H2 type// Zinc finger, C2H2 type// Zinc finger, C2H2 type// Zinc finger, C2H2 type// Zinc finger, C2H2 type// Transcription factor S-II (TFIIS)// Zinc finger, C2H2 type// Zinc finger, C2H2 type// Zinc finger, C2H2 type// PHD-finger// Zinc finger, C2H2 type// Putative zinc finger in N-recognin// Zinc finger, C2H2 type// Zinc finger, C2H2 type// Zinc finger, C2H2 type FEBRA20184330//PDZ domain (Also known as DHR or GLGF).

FEBRA20192420//Cyclin-dependent kinase inhibitor// IQ calmodulin-binding motif// IQ calmodulin-binding motif// IQ calmodulin-binding motif// IQ calmodulin-binding motif// IQ calmodulin-binding motif FEBRA20195820//Zinc finger, C2H2 type// Zinc finger, C2H2 type// Zinc finger, C2H2 type// TRAF-type zinc finger// Zinc finger, C2H2 type FEBRA20196370//Cyclin-dependent kinase inhibitor// IQ calmodulin-binding motif// IQ calmodulin-binding motif// IQ calmodulin-binding motif// IQ calmodulin-binding motif// IQ calmodulin-binding motif FEBRA20196630//DEAD/DEAH box helicase// Helicases conserved C-terminal domain FEBRA20214970//Reverse transcriptase (RNA-dependent DNA pol FEBRA20222040//bZIP transcription factor// K-box region FEBRA20223220//EGF-like domain// EGF-like domain// Cadherin domain FEBRA20229630//NADH-Ubiquinone/plastoquinone (complex I)

FEBRA20235500//Sodium Bile acid symporter family// ABC 3 transport family

FEBRA20237640//SAM domain (Sterile alpha motif)

FEHRT20003250//Phosphatidylinositol 3- and 4-kinases

HCASMl0000500//Ribonucleotide reductases// Nucleotidyltransferase domain

HCHON10001760//Histone deacetylase family
HCHON20000380//Glucose-6-phosphate dehydrogenase
HCHON20003220//Formyl transferase// Phosphopantetheine attachment site// Protein of unknown function DUF132// Aldehyde dehydrogenase family
HCHON20007510//Phosphotyrosine interaction domain (PTB/PID)// TBC domain
HCHON20008150//RNA recognition motif. (a.k.a. RRM, RBD, or
HCHON20008320//Glutamine synthetase// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Transcription factor S-Il (TFIIS)// Zinc finger, C2H2 type// Zinc finger, C2H2 type// PHD-finger// Zinc finger, C2H2 type
HCHON20009560//Zinc finger, C2H2 type// Zinc finger, C2H2 type// Zinc finger, C2H2 type// Zinc finger, C2H2 type
HCHON20010990//TPR Domain
HCHON20015350//FtsJ cell division protein
HCHON20015980//FG-GAP repeat// von Willebrand factor type A domain
HCHON20016040//Insulin-like growth factor binding proteins
HCHON20016650//Leucine rich repeat C-terminal domain// Immunoglobulin domain// Latrophilin/CL-1-like GPS domain// 7 transmembrane receptor (Secretin family)
HCHON20035130//Zinc finger, C2H2 type// Zinc finger, C2H2 type
HCHON20036420//Death effector domain
HCHON20040020//Syntaxin
HCHON20059870//Bromodomain// Bromodomain
HCHON20064590//Alpha-2-macroglobulin family N-terminal regi// Alpha-2-macroglobulin family N-terminal regi
HCHON2006841Q//IQ calmodulin-binding motif// IQ calmodulin-binding motif// IQ calmodulin-binding motif// IQ calmodulin-binding motif// IQ calmodulin-binding motif// IQ calmodulin-binding motif// IQ calmodulin-binding motif// IQ calmodulin-binding motif// IQ calmodulin-binding motif// IQ calmodulin-binding motif// IQ calmodulin-binding motif// IQ calmodulin-binding motif// IQ calmodulin-binding motif// IQ calmodulin-binding motif// IQ calmodulin-binding motif// IQ calmodulin-binding motif// IQ calmodulin-binding motif// IQ calmodulin-binding motif// IQ calmodulin-binding motif// IQ calmodulin-binding motif// IQ calmodulin-binding motif// IQ calmodulin-binding motif// IQ calmodulin-binding motif// IQ calmodulin-binding motif// IQ calmodulin-binding motif// IQ calmodulin-binding motif// IQ calmodulin-binding motif// IQ calmodulin-binding motif// IQ calmodulin-binding motif// IQ calmodulin-binding motif
HCHON20086720//Insulin-like growth factor binding pr// Thyroglobulin type-1 repeat
HCHON20100740//EGF-like domain// F5/8 type C domain// F5/8 type C domain
HEART20003060//Immunoglobulin domain// Immunoglobulin domain
HEART20005410//u-PAR/Ly-6 domain
HEART20017730//Ank repeat// Ank repeat// Ank repeat// Ank repeat// Ank repeat// Ank repeat// Ank repeat
HEART20025980//Calponin homology (CH) domain
HEART20034320//Glycosyl hydrolase family 9// Glycosyl hydrolase family 9
HEART20061950//PDZ domain (Also known as DHR or GLGF).
HEART20077670//Protein phosphatase 2A regulatory B subunit
HEART20083640//NAD-dependent DNA ligase
HEART20090000//Inositol polyphosphate phosphatase family, c
HHDPC10000830//Zinc finger, C3HC4 type (RING finger)
HHDPC20014320//Reprolysin family propeptide
HHDPC20031130//Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type
HHDPC20034390//Cereal trypsin/alpha-amylase inhibito
HHDPC20034720//Glutathione S-transferases.
HHDPC20068620//Immunoglobulin domain// Immunoglobulin domain
HHDPC20091780//CUB domain// F5/8 type C domain
HHDPC20092080//Thyroglobulin type-1 repeat
HLUNG20016330//Methyl-accepting chemotaxis protein (MCP) s/I PH domain// PH domain// Methanol dehydrogenase beta subunit
HLUNG20017120//Peptidyl-tRNA hydrolase domain
HLUNG20023340//KH domain
HLUNG20033780//Birnavirus VP3 protein// RhoGEF domain// PH domain// SH3 domain
IMR3220002430//WD domain, G-beta repeat// WD domain, G-beta repeat// WD domain, G-beta repeat// WD domain, G-beta repeat// WD domain, G-beta repeat
KIDNE20002520//tRNA synthetases class I (E and Q)// tRNA synthetases class I (K)// tRNA synthetases class I (E and Q)
KIDNE20003940//Phosphotransferase system, EIIC// FecCD transport family// ABC 3 transport family
KIDNE20007770//Immunoglobulin domain// Immunoglobulin domain// Immunoglobulin domain
KIDNE20008010//Dihydropyridine sensitive L-type calcium
KIDNE20009470//G-patch domain// Peptidase family MI
KIDNE20017130//MYND finger// DM DNA binding domain// Ribosomal protein L36
KIDNE20020150//Ribosomal protein S13/S18// Hsp70protein
KIDNE20021680//3-hydroxyacyl-CoA dehydrogenase
KIDNE20022620//Glycosyl transferase family 8
KIDNE20024830//C2 domain// C2 domain
KIDNE20027250//Zinc finger, C2H2 type// Zinc finger, C2H2 type// Zinc finger, C2H2 type// Zinc finger, C2H2 type
KIDNE20027950//KRAB box
KIDNE20028390//Galactose-1-phosphate uridyl transfer// Galactose-1-phosphate uridyl transfer
KIDNE20028720//ATP synthase (C/AC39) subunit
KIDNE20028830//K-box region
KIDNE20100070//AMP-binding enzyme
KIDNE20101510//EGF-like domain// Trypsin Inhibitor like cysteine rich d// EGF-like domain// Keratin, high sulfur B2 protein// Zona pellucida-like domain
KIDNE20102710//Ank repeat// Ank repeat// Ank repeat// Ank repeat// Ank repeat
KIDNE20107390//Histone-like transcription factor (CBF/// GHMP kinases putative ATP-binding prote
KIDNE20107620//Eukaryotic protein kinase domain// Dihydropyridine sensitive L-type calcium KIDNE20109730//Sodium
KIDNE20109890//WD domain, G-beta repeat// WD domain, G-beta repeat// WD domain, G-beta repeat// WD domain, G-beta repeat// WD domain, G-beta repeat// Zinc finger, C4 type (two domains)// WD domain, G-beta repeat// WD domain, G-beta repeat
KIDNE20121880//PMP-22/EMP/MP20/Claudin family
KIDNE20125630//ATPlG1/PLM/MAT8 family
KIDNE20127100//Kelch motif// Kelch motif// Kelch motif
KIDNE20127750//Bacterial regulatory proteins, tetR family
KIDNE20137340//Uncharacterized membrane protein family UPFO
KIDNE20182690//BAH domain// ELM2 domain
LIVER10004790//EF hand
LIVER20002160//Hsp70 protein
LIVER20035680//UvrD/REP helicase
LIVER20055440//RhoGAP domain
LIVER20064690//Serpins (serine protease inhibitors)
LIVER20080530//Ank repeat// Ank repeat// Ank repeat// SAM domain (Sterile alpha motif)
LIVER20087060//Guanylate-binding protein
LIVER20087510//PHD-finger
MAMGL10000830//LysM domain
MESAN10001260//von Willebrand factor type C domain// von Willebrand factor type C domain// von Willebrand factor type C domain// von Willebrand factor type C domain// TILa domain// von Willebrand factor type C domain// Keratin, high sulfur B2 protein// PEP-utilizing enzymes// von Willebrand factor type D domain// Plant PEC family metallothionein// Trypsin Inhibitor like cysteine rich
MESAN20029400//Zinc finger, C3HC4 type (RING finger)// RNA polymerases M/15 Kd subunits
MESAN20031900//Zinc finger, C3HC4 type (RING finger)// Peroxidase// Zinc finger, C3HC4 type (RING finger)// B-box zinc finger.// Fibronectin type III domain
MESAN20035290//FYVE zinc finger
MESAN20036460//Corticotropin-releasing factor family
MESAN20038510//Oxidoreductase molybdopterin binding d
MESAN20101140//LIM domain containing proteins
MESAN20103120//Sodium/calcium exchanger protein
MESAN20125860//Transferrin
MESAN20127350//Zinc knuckle
MESAN20130220//' chromo' (CHRromatin Organization MOdifier)// Enoyl-CoA hydratase/isomerase family
MESAN20136110//KH domain// KH domain// Zinc finger, C3HC4 type (RING finger)
MESAN20141920//Troponin// Tropomyosins// Borrelia ORF-A
MESAN20154010//Tryptophan synthase alpha chain// Ribulose-phosphate 3 epimerase family// Indole-3-glycerol phosphate synthases
MESAN20171520//PH domain
MESAN20174170//Regulator of G protein signaling domain
MESAN20186700//Hepatitis C virus RNA dependent RNA polymerase
NOVAR10000150//Cytosolic long-chain acyl-CoA thioester hydrolase
NT2NE20010490//Zinc finger, C2H2 type// Zinc finger, C2H2 type// Zinc finger// Zinc finger, C2H2 type// Zinc finger, C2H2 type// Zinc finger, C2H2 type// Zinc finger, C2H2 type// Zinc finger, C2H2 type// Zinc finger, C2H2 type// Transcription factor S-II (TFIIS)// Zinc finger, C2H2 type// Zinc finger, C2H2 type// DM DNA binding domain// Zinc finger, C2H2 type// PHD-finger// Zinc finger, C2H2 type// Zinc finger, C2H2 type
NT2NE20021620//Vacuolar sorting protein 9 (VPS9) domain
NT2NE20080170//CRAL/TRIO domain.
NT2NE20089970//KRAB box
NT2NE20118960//Gram-negative pili assembly chaperone
NT2NE20125050//Ezrin/radixin/moesin family
NT2NE20130190//Zinc finger, C2H2 type
NT2NE20132170//GNS1/SUR4 family// Transmembrane amino acid transporter protein
NT2NE20142210//PAS domain// PAS domain
NT2NE20157470//von Willebrand factor type A domain// Trypsin
NT2NE20158600//Ank repeat// Ank repeat
NT2NE20177520//Sushi domain (SCR repeat)// Sushi domain (SCR repeat)// Sushi domain (SCR repeat)// Sushi domain (SCR repeat)
NT2NE20181650//Src homology domain 2
NT2NE20183760//Calcitonin / CGRP / IAPP family
NT2NE20184900//FF domain
NT2RI20001330//Ank repeat// Ank repeat
NT2RI20003480//Glypican
NT2RI20005750//Cell division protein// Sigma-54 interaction domain// ADP-ribosylation factor family// ABC transporter// Ras family
NT2RI20009870//Fringe-like
NT2RI20025640//Reverse transcriptase (RNA-dependent DNA pol
NT2RI20040930//Mitochondrial carrier proteins// Mitochondrial carrier proteins
NT2RI20040990//Ank repeat// Ank repeat// Ank repeat// Ank repeat// Ank repeat// Ank repeat// Ank repeat
NT2RI20046080//recA bacterial DNA recombination proteins
NT2RI20048840//ADP-ribosylation factor family// G-protein alpha subunit
NT2RI20054050//HSF-type DNA-binding domain
NT2RI20056700//Spectrin repeat// Apolipoprotein Al/A4/E family// Olfactomedin-like domain
NT2RI20091730//Molluscan rhodopsin C-terminal tail
NT2RI20240080//TPR Domain// TPR Domain// TPR Domain
NT2RI20244600//PAP2 superfamily
NT2RI20273230//DEAD/DEAH box helicase
NT2RP60000770//Zinc finger, C2H2 type// Zinc finger, C2H2 type// TRAF-type zinc finger// Zinc finger, C2H2 type// Zinc finger, C2H2 type// Zinc finger, C2H2 type// Zinc finger, C2H2 type// Zinc finger, C2H2 type
NT2RP60000850//C2 domain
NT2RP70027380//PX domain// SH3 domain// RhoGAP domain
NT2RP70032610//Peptidase family M20/M25/M40// Enol-ase
NT2RP70036880//TBC domain
NT2RP70043480//KRAB box// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Transcription factor S-Il (TFIIS)// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// PHD-finger// Zinc finger,-C2H2 type// Zinc finger, C2H2 type
NT2RP70044280//RNA recognition motif. (a.k.a. RRM, RBD, or RNP domain)

NT2RP70062230//Zinc finger, C2H2 type// Zinc finger, C2H2 type// Pancreatic hormone peptides// Zinc finger, C2H2 type// Zinc finger, C2H2 type// Zinc finger, C2H2 type NT2RP70063950//RhoGEF domain// Extracellular link domain// PH domain NT2RP70078420//PH domain// Putative GTP-ase activating protein for Arf// Ank repeat// Ank repeat NT2RP70080850//SPRY domain// Adenovirus EB1 55K protein / large t-an NT2RP70102350//Viral methyltransferase// Helix-loop-helix DNA-binding domain NT2RP70105210//Myc amino-terminal region NT2RP70157890//KRAB box NT2RP70159960//PH domain NT2RP70179710//Zinc finger, C3HC4 type (RING finger)// PHD-finger NT2RP70188710//Yeast PIR proteins NT2RP70192730//alpha/beta hydrolase fold NT2RP70194450//Bacterial regulatory proteins, crp family NT2RP70195430//Zinc-binding dehydrogenases NT2RP70198350//PWWP domain NTONG20009770//Coronavirus S2 glycoprotein// Peptidase family M3

NTONG20013620//Sulfotransferase proteins

NTONG20015870//Transposase// Outer membrane efflux protein// Intermediate filament proteins NTONG20028070//von Willebrand factor type C domain NTONG20029480//NAD-dependent DNA ligase NTONG20029700//Laminin N-terminal (Domain VI)// Laminin EGF-like (Domains III and V)// Laminin EGF-like (Domains III and V)// Laminin EGF-like (Domains III and V)

NTONG20046140//Eukaryotic protein kinase domain// Aminoglycoside phosphotransferase NTONG20051530//Mov34/MPN/PAD-1 family// Extracellular link domain// Adhesin lipoprotein// Lectin C-type domain NTONG20056570//WD domain, G-beta repeat// WD domain, G-beta repeat NTONG20063010//EGF-like domain// Trypsin Inhibitor like cysteine rich domain// EGF-like domain// EGF-like domain// Keratin, high sulfur B2 protein// Chitin binding Peritrophin-A domain// Zona pellucida-like domain NTONG20064840//C2 domain// C2 domain NTONG20067830//Ank repeat// Ank repeat// Ank repeat// Ank repeat// Ank repeat NTONG20070200//Zinc finger, C2H2 type// Zinc finger, C2H2 type// Zinc finger, C2H2 type// Zinc finger, C2H2 type// Transcription factor S-II (TFIIS)// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type NTONG20070340//Collagen triple helix repeat (20 copies)// Collagen triple helix repeat (20 copies)// Collagen triple helix repeat (20 copies)

NTONG20075220//RyR domain

NTONG20076930//Alpha-2-macroglobulin family

NTONG20083650//TPR Domain// TPR Domain// TPR Domain// PPR repeat// TPR Domain// PPR repeat// TPR Domain NTONG20092290//Immunoglobulin domain// Immunoglobulin domain NTONG20092330//Putative membrane protein OCBBF10001850//KRAB box// Zinc finger, C2H2 type// Zinc finger, C2H2 type// Zinc finger, C2H2 type// Zinc finger, C2H2 type// Zinc finger, C2H2 type// Zinc finger, C2H2 type// PHD-finger// Zinc finger, C2H2 type// DM DNA binding domain// Zinc finger, C2H2 type// Zinc finger, C2H2 type// MYND finger// Zinc finger, C2H2 type// Zinc finger, C2H2 type// Zinc finger, C2H2 type OCBBF20019380//Sushi domain (SCR repeat)// CUB domain OCBBF20019830//Fibronectin type III domain// Fibronectin type III domain// EGF-like domain// Metallothionein family 5

OCBBF20020830//Pumilio-family RNA binding domains (aka PUM-HD, Pumilio homology domain)// Pumilio-family RNA binding domains (aka PUM-HD, Pumilio homology domain)// Pumilio-family RNA binding domains (aka PUM-HD, Pumilio homology domain)// Pumilio-family RNA binding domains (aka PUM-HD, Pumilio homology domain)// Pumilio-family RNA binding domains (aka PUM-HD, Pumilio homology domain)// Putative GTP-ase activating protein for Arf// Pumilio-family RNA binding domains (aka PUM-HD, Pumilio homology domain)// Pumilio-family RNA binding domains (aka PUM-HD, Pumilio homology domain)// Pumilio-family RNA binding domains (aka PUM-HD, Pumilio homology domain)

OCBBF20022900//IQ calmodulin-binding motif// Dishevelled specific domain// Kunitz/Bovine pancreatic trypsin inhibitor domain OCBBF20028050//Phorbol esters/diacylglycerol binding domain (C1 domain)// Zinc finger, C3HC4 type (RING finger)// PHD-finger OCBBF20028650//Ank repeat// Ank repeat// Helicases conserved C-terminal domain OCBBF20030280//Lipoprotein amino terminal region OCBBF20035930//NSF attachment protein OCBBF20037440//Zinc finger, C3HC4 type (RING finger)

OCBBF20046120//Zinc finger, C2H2 type// Zinc finger, C2H2 type// Zinc finger, C2H2 type// PHD-finger// Zinc finger, C2H2 type// Zinc finger, C2H2 type// Transcription factor S-II (TFIIS)// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type OCBBF20049300//KRAB box// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Putative zinc finger in N-recognin// Zinc finger, C2H2 type// DM DNA binding domain// Zinc finger, C2H2 type OCBBF20049840//PDZ domain (Also known as DHR or GLGF).

OCBBF20050770//Dehydrins// Carnitate acyltransferase

OCBBF20053430//Extracellular link domain// Eukaryotic protein kinase domain// Protein kinase C terminal domain OCBBF20053730//Ank repeat// Ank repeat// Ank repeat// Patatin OCBBF20054760//Death domain OCBBF20059560//UvrB/uvrC motif OCBBF20066390//Zinc finger, C2H2 type// Zinc finger, C2H2 type// Zinc finger, C2H2 type// Zinc finger, C2H2 type// Zinc finger, C2H2 type OCBBF20071210//Spectrin repeat OCBBF20071840//Zinc finger, C2H2 type// Transcription factor S-II (TFIIS)// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C3HC4 type (RING finger)// Zinc finger, C2H2 type// Zinc finger, C2H2 type OCBBF20079310//Acetyltransferase (GNAT) family OCBBF20080410//KRAB box// Zinc finger, C2H2 type// Zinc finger, C2H2 type// Zinc finger, C2H2 type// Zinc finger, C2H2 type// Transcription factor S-II (TFIIS)// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type OCBBF20082830//alpha/beta hydrolase fold OCBBF20086400//ADP-ribosylation factor family// ABC transporter// FtsK/SpoIIIE family// Ras family OCBBF20086910//HMG (high mobility group) box OCBBF20107090//Cadherin domain OCBBF20108190//Zinc finger, C2H2 type// Zinc finger, C2H2 type// IBR domain// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type OCBBF20108430//ADP-ribosylation factor family// G-protein alpha subunit OCBBF20108580//Caspase recruitment domain OCBBF20108630//ABC transporter OCBBF20109310//PH domain// Arrestin (or S-antigen)

OCBBF20116850//Leucine rich repeat N-terminal domain// Leucine Rich Repeat// Leucine Rich Repeat// Leucine Rich Repeat// Leucine Rich Repeat// Leucine Rich Repeat// Leucine rich repeat C-terminal domain// Immunoglobulin domain OCBBF20120390//Caveolin// Hepatitis C virus core protein// Sodium:neurotransmitter symporter family OCBBF20121390//BTB/POZ domain// Kelch motif// Kelch motif// Kelch motif// Kelch motif// Kelch motif OCBBF20124360//CNH domain OCBBF20125530//Vpu protein// Zinc finger, C3HC4 type (RING finger)

OCBBF20127040//Interleukin-6/G-CSF/MGF family

OCBBF20127140//WD domain, G-beta repeat// WD domain, G-beta repeat,

OCBBF20127550//Outer Capsid protein VP4 (Hemagglutinin)

OCBBF20128120//DnaJ domain// DnaJ central domain (4 repeats)// DnaJ C terminal region OCBBF20129360//PH domain// EF hand// Ribosomal RNA adenine dimethylases// EF hand// Sulfotransferase proteins// Somatotropin hormone family// Phosphatidylinositol-specific phospholi// Phosphatidylinositol-specific phospholi// C2 domain OCBBF20132850//Leucine rich repeat N-terminal domain// Leucine Rich Repeat// Leucine Rich Repeat// Leucine Rich Repeat// Leucine Rich Repeat// Leucine Rich Repeat// Leucine Rich Repeat// Leucine Rich Repeat// Leucine rich repeat C-terminal domain// Immunoglobulin domain// Fibronectin type III domain OCBBF20140640//Phosphotyrosine interaction domain (PTB/PID)

OCBBF20140890//Ribosomal protein L11

OCBBF20145760//Glypican

OCBBF20148280//Zinc finger, C2H2 type// PHD-finger// Zinc finger, C2H2 type// Zinc finger, C2H2 type// Zinc finger, C2H2 type// Zinc finger, C2H2 type OCBBF20148730//BTB/POZ domain// Kelch motif// Kelch motif// Kelch motif// Kelch motif OCBBF20155060//EGF-like domain// Laminin EGF-like (Domains III and V)// Laminin G domain// EGF-like domain// Laminin G domain// EGF-like domain OCBBF20173980//Regulator of chromosome condensation// Regulator of chromosome condensation// Regulator of chromosome condensation// Regulator of chromosome condensation// Regulator of chromosome condensation// BTB/POZ domain// Thymidylate synthase OCBBF20178880//Granulins OCBBF20180120//Sodium:sulfate symporter transmembrane// Sodium:sulfate symporter transmembrane// Sodium:sulfate symporter transmembrane PEBLM10000240//Domain found in Dishevelled, Egl-10, and Ple PEBLM20013120//PH domain PEBLM200243201/Cation efflux family PEBLM20042900//Chitin synthase PEBLM20044520//Ubiquitin carboxyl-terminal hydrolase fam// Exonuclease PEBLM20052820//Protein phosphatase 2C PEBLM20060310//IBR domain// Zinc finger, C3HC4 type (RING finger)

PEBLM20060360//KRAB box

PEBLM20075980//Immunoglobulin domain// Immunoglobulin domain// Immunoglobulin domain PEBLM20078320//Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// PHD-finger// Zinc finger, C2H2 type// Zinc finger, C2H2 type// Zinc finger, C2H2 type// DnaJ central domain (4 repeats)// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type PERIC10000250//Prokaryotic DNA topoisomerase PERIC20003870//Ribosomal L32p protein family// NAC domain// TS-N domain PERIC20004220//Domain of unknown function PERIC20004780//bZIP transcription factor PLACE60003480//Chorismate synthase PLACE60060420//Ribosomal protein L44

PLACE60079250//Bacterial flagellin N-terminus// Spectrin repeat// Spectrin repeat// Spectrin repeat// Caulimovirus movement protein// Spectrin repeat// Spectrin repeat// Spectrin repeat// UvrB/uvrC motif// Spectrin repeat// Spectrin repeat// Flagellar hook-associated protein 2// Spectrin repeat// KE2 family protein PLACE60136500//dUTPase PLACE60136720//Porphobilinogen deaminase// GHMP kinases putative ATP-binding prot PLACE60177140//7 transmembrane receptor (rhodopsin family)

PROST20047270//CRAL/TRIO domain.

PROST20047390//Zinc finger, C2H2 type// Zinc finger, C2H2 type// Zinc finger, C2H2 type// Zinc finger, C2H2 type// Zinc finger, C2H2 type// PHD-finger// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type PROST20050670//Endothelin family PROST20066880//Zinc finger, C2H2 type// Zinc finger, C2H2 type// Zinc finger, C2H2 type// Zinc finger, C2H2 type// Zinc finger, C2H2 type PROST20079500//Hepatitis C virus non-structural protein NS4b// Ras association (RalGDS/AF-6) domain
PROST20100460//Cystine-knot domain
PROST20112970//Sterile alpha motif (SAM)/Pointed domain// SAM domain (Sterile alpha motif)
PROST20114390//Integrase DNA binding domain
PROST20161950//RasGEF domain
PROST20169800//Cytochrome P450
PROST20170980//Immunoglobulin domain// Adenovirus E3 region protein CR1
PROST20171280//Zinc finger, C2H2 type// Zinc finger, C2H2 type// Zinc finger, C2H2 type
PROST20176170//LIM domain containing proteins// LIM domain containing proteins// LIM domain containing proteins
PROST20185830//GATA zinc finger
PROST20189770//KRAB box// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Transcription factor S-II (TFIIS)// Zinc finger, C2H2type// Zinc finger, C2H2 type// Zinc finger, C2H2 type
PROST20191640//Zinc finger, C3HC4 type (RING finger)// IBR domain// Keratin, high sulfur B2 protein// Zinc finger, C3HC4 type (RING finger)
PUAEN10000850//Uncharacterized protein family UPF0025// Sec1 family
PUAEN20011880//ZAP domain// Piwi domain
PUAEN20015860//PDZ domain (Also known as DHR or GLGF).// Regulator of G protein signaling domain
PUAEN20018820//Sterile alpha motif (SAM)/Pointed domain// Ets-domain
PUAEN20030180//Eukaryotic-type carbonic anhydrase
PUAEN20040670//FERM domain (Band 4.1 family)// FERM domain (Band 4.1 family)
PUAEN20055020//PH domain// START domain
PUAEN20078980//PH domain// FYVE zinc finger// Domain of unknown function -DUF123// PH domain
PUAEN20083140//EF hand// PH domain// Neuregulin family
PUAEN20108240//Ank repeat// Ank repeat// Ank repeat// .Ank repeat// Ank repeat
SALGL10001710//ENV polyprotein (coat polyprotein)
SKMUS20001980//Nebulin repeat// Nebulin repeat// Nebulin repeat// Nebulin repeat// Nebulin repeat// Nebulin repeat
SKMUS20003610//Syndecan domain// Mitochondrial carrier proteins// Mitochondrial carrier proteins// Mitochondrial carrier proteins
SKMUS20007800//Matrix protein (MA), p15// Prenyltransferase and squalene oxidase re
SKMUS20016220//Nebulin repeat// Nebulin repeat// Nebulin repeat// Nebulin repeat// Nebulin repeat// Nebulin repeat// Nebulin repeat// Nebulin repeat// Nebulin repeat
SKMUS20018230//Ank repeat
SKMUS20018500//Coronavirus S2 glycoprotein
SKMUS20024750//Leucine Rich Repeat// Leucine Rich Repeat// Leucine Rich Repeat// Leucine Rich Repeat// Leucine Rich Repeat// Leucine Rich Repeat// Leucine Rich Repeat// Leucine Rich Repeat
SKMUS20029200//Ank repeat// Respiratory-chain NADH dehydrogenase, 4// Ank repeat// Ank repeat// Ank repeat// Ank repeat
SKMUS20048970//Actin// Actin
SKMUS20049030//Nebulin repeat// Nebulin repeat// Nebulin repeat// Nebulin repeat// Nebulin repeat// Nebulin repeat
SKMUS20084740//Syndecan domain
SKNSH20008190//KRAB box// Zinc finger, C2H2 type// Zinc finger, C2H2 type// Zinc finger, C2H2 type//-Zinc finger, C2H2 type// Zinc finger, C2H2 type// Zinc finger, C2H2 type// ANI-like Zinc finger// Zinc finger, C2H2 type// Zinc finger, C2H2 type// PHD- finger// Zinc finger, C2H2 type// Zinc finger, C2H2 type// Zinc finger, C2H2 type// Zinc finger, C2H2 type
SKNSH20020540//Arginase family
SKNSH20063040//Transmembrane 4 family// Transmembrane 4 family
SMINT20001760//PHD-finger// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type
SMINT20009840//Immunoglobulin domain// Immunoglobulin domain
SMINT20013480//Metallo-beta-lactamase superfamily
SMINT20028820//Eukaryotic protein kinase domain
SMINT20035690//Ribosomal L29 protein
SMINT20049090//Eukaryotic protein kinase domain
SMINT20050750//Kazal-type serine protease inhibitor domain
SMINT20068010//Kinesin motor domain
SMINT20071400//NOL1/NOP2/sun family
SMINT20073650//Immunoglobulin domain// Immunoglobulin domain// Immunoglobulin domain// Immunoglobulin domain// Immunoglobulin domain
SMINT20102780//Quinolinate phosphoribosyl transferase
SMINT20106290//Formamidopyrimidine-DNA glycosylase
SMINT20106720//Immunoglobulin domain// Immunoglobulin domain// Immunoglobulin domain// Immunoglobulin domain
SMINT20110330//pKID domain
SMINT20112730//Immunoglobulin domain// Immunoglobulin domain// Immunoglobulin domain// Immunoglobulin domain// Immunoglobulin domain
SMINT20115880//Zinc finger, C2H2 type// Zinc finger, C2H2 type// Zinc finger, C2H2 type
SMINT20121220//Myosin tail
SMINT20121950//2Fe-2S iron-sulfur cluster binding domains
SMINT20122910//START domain
SMINT20127930//Immunoglobulin domain// Immunoglobulin domain// Immunoglobulin domain// Immunoglobulin domain// Immunoglobulin domain
SMINT20130320//NB-ARC domain// ATPases associated with various cellular act
SMINT20131810//ENV polyprotein (coat polyprotein)
SMINT20136130//Immunoglobulin domain
SMINT20138900//Hrl repeat motif// Apolipoprotein Al/A4/E family// Intermediate filament proteins
SMINT20144430//Immunoglobulin domain
SMINT20144800//KRAB box// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type
SMINT20152940//Sigma-54 interaction domain// ATPases associated with various cellular activities (AAA)
SMINT20154540//Glutathione S-transferases.
SMINT20163960//Immunoglobulin domain SMINT20168570//Fasciclin domain SMINT20174360//haloacid dehalogenase-like hydrolase SMINT20177360//RNA recognition motif. (a.k.a. RRM, RBD, or SMINT20179740//Immunoglobulin domain// Immunoglobulin domain// Immunoglobulin domain// Immunoglobulin domain// Immunoglobulin domain SMINT20183530//ABC transporter// ABC transporter SMINT20190170//Immunoglobulin domain// Immunoglobulin domain// Immunoglobulin domain// Immunoglobulin domain// Immunoglobulin domain SMINT20191530//DEAD/DEAH box helicase// Helicases conserved C-terminal domain SPLEN20006070//Ank repeat// Ank repeat// Ank repeat// Ank repeat// Ank repeat// Ank repeat// Ank repeat// Ank repeat// Ank repeat// Ank repeat// Ank repeat// Ank repeat// Ank repeat// Ank repeat// Ank repeat// Ank repeat// Ank repeat// Ank repeat// Ank repeat// Ank repeat// Ank repeat// Ank repeat SPLEN20008740//Importin beta binding domain// Armadillo/beta-catenin-like repeats// Armadillo/beta-catenin-like repeats SPLEN20011410//RhoGAP domain SPLEN20026950//SNF2 and others N-terminal domain// Bromodomain// Helicases conserved C-terminal domain// Bromodomain SPLEN20027440//Zinc finger present in dystrophin, CBP/p300// Ank repeat// Ank repeat// Ank repeat// Ank repeat// Ank repeat// Ank repeat// Ank repeat SPLEN20039240//Ribosomal protein S13/S18// Hsp70protein SPLEN20054290//Zinc finger, C2H2 type// Transcription factor S-II (TFIIS)// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type SPLEN20077500//PH domain// Transposase SPLEN20079260//Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type SPLEN20084600//BTB/POZ domain// Kelch motif// Kelch motif// Kelch motif// Kelch motif// Kelch motif SPLEN20095410//Zinc finger, C2H2 type// Zinc finger, C2H2 type// Zinc-finger, C2H2 type// Zinc finger, C2H2 type// Zinc finger, C2H2 type// Zinc finger, C2H2 type// Zinc finger, C2H2 type// Zinc finger, C2H2 type SPLEN20095550//bZIP transcription factor// bZIP transcription factor// Hpt domain SPLEN20099700//Sigma-54 interaction domain// ATPases associated with various cellular ac// Thymidine kinase from herpesvirus SPLEN20103950//Ribosomal S17

SPLEN20118300//Transmembrane amino acid transporter protein

SPLEN20119810//Reverse transcriptase (RNA-dependent DNA polymerase)

SPLEN20126190//Lipoate-protein ligase B

SPLEN20140800//KRAB box// Zinc finger, C2H2 type// Zinc finger, C2H2 type// Zinc finger, C2H2 type// Zinc finger, C2H2 type// Zinc finger, C2H2 type// Zinc finger, C2H2 type// PHD-finger// DnaJ central domain (4 repeats)// Zinc finger, C2H2 type// Zinc finger, C2H2 type// Zinc finger, C2H2 type// Zinc finger, C2H2 type// Zinc finger, C2H2 type SPLEN20142100//von Willebrand factor type A domain SPLEN20143180//Src homology domain 2

SPLEN20145720//PH domain

SPLEN20147110//HECT-domain (ubiquitin-transferase).

SPLEN20147390//KRAB box// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type SPLEN20149110//Dishevelled specific domain SPLEN20150940//Histone deacetylase family SPLEN20151210//FERM domain (Band 4.1 family)// FERM domain (Band 4.1 family)// Isocitrate lyase SPLEN20157880//Immunoglobulin domain SPLEN20163560//Kinesin motor domain SPLEN20165310//Immunoglobulin domain// Immunoglobulin domain// Immunoglobulin domain// Immunoglobulin domain SPLEN20170310//PH domain SPLEN20171470//Keratin, high sulfur B2 protein SPLEN20173510//TPR Domain// TPR Domain// TPR Domain// TPR Domain// TPR Domain// NADH-ubiquinone/plastoquinone oxidoreduct SPLEN20174260//Penicillin amidase// Bacterial regulatory proteins, laci f// Vacuolar sorting protein 9 (VPS9) dom SPLEN20179180//EF hand SPLEN20179810//S-adenosylmethionine synthetase SPLEN20181810//Phorbol esters/diacylglycerol binding domain (C1 domain)// FYVE zinc finger SPLEN20186430//7 transmembrane receptor (rhodopsin family)// 7 transmembrane receptor (rhodopsin family)

SPLEN20211220//Metalloenzyme superfamily

SPLEN20212730//Calpain large subunit, domain III// EF hand// EF hand// EF hand

SPLEN20222270//PTB domain (IRS-1 type)

SPLEN20245300//Pancreatic hormone peptides

SPLEN20250170//RhoGEF domain// PH domain// FYVE zinc finger// Domain of unknown function DUF123// PH domain SPLEN20250390//EF hand// EF hand SPLEN20252190//Zinc finger, C2H2 type// Zinc finger, C2H2 type// Zinc finger, C2H2 type// Transcription factor S-II (TFIIS)// Zinc finger, C2H2 type// Zinc finger, C2H2 type// PHD-finger// Zinc finger, C2H2 type// Zinc finger, C2H2 type// Zinc finger, C2H2 type// Zinc finger, C2H2 type// TRAF-type zinc finger// Zinc finger, C2H2 type SPLEN20267650//KRAB box// Zinc finger, C2H2 type// Zinc finger, C2H2 type// Zinc finger, C2H2 type// Zinc finger, C2H2 type// TRAF-type zinc finger// Zinc finger, C2H2 type// Zinc finger, C2H2 type SPLEN20292950//Phosphoribulokinase// ABC transporter// Aldehyde oxidase and xanthine dehydrogenase, C terminus SPLEN20304950//Transmembrane 4 family SPLEN20305620//Dihydroorotate dehydrogenase STOMA20001830//Immunoglobulin domain// Immunoglobulin domain// Immunoglobulin domain// Immunoglobulin domain// Immunoglobulin domain STOMA20005390//Sodium and potassium ATPases// Immunoglobulin domain// Immunoglobulin domain// Immunoglobulin domain// Immunoglobulin domain// Immunoglobulin domain STOMA20005670//Immunoglobulin domain// Immunoglobulin domain// Immunoglobulin domain// Immunoglobulin domain STOMA20006400//Immunoglobulin domain// Immunoglobulin domain// Immunoglobulin domain// Immunoglobulin domain STOMA20006780//Hepatitis C virus RNA dependent RNA polymera// Somatotropin hormone family STOMA20008880//Olfactomedin-like domain STOMA20032890//Zinc finger, C2H2 type// Transcription factor S-II (TFIIS)// Zinc finger, C2H2 type// Zinc finger, C2H2 type// Zinc finger, C2H2 type STOMA20034770//Immunoglobulin domain// Immunoglobulin domain// Immunoglobulin domain// Immunoglobulin domain// Immunoglobulin domain STOMA20046680//bZIP transcription factor STOMA20056640//Immunoglobulin domain STOMA20056670//Immunoglobulin domain// Immunoglobulin domain// Immunoglobulin domain// Immunoglobulin domain// Immunoglobulin domain STOMA20057820//Uncharacterized protein family UPF0024

STOMA20062130//Immunoglobulin domain

STOMA20063980//Collagen triple helix repeat (20 copies)

STOMA20064470//Leucine Rich Repeat// Leucine Rich Repeat// Leucine Rich Repeat// Leucine Rich Repeat// Leucine Rich Repeat// Leucine Rich Repeat STOMA20069040//Keratin, high sulfur B2 protein STOMA20077450//Repeat in ubiquitin-activating (UBA) pro// Repeat in ubiquitin-activating (UBA) pro STOMA20080500//ABC transporter STOMA20083610//Immunoglobulin domain// Immunoglobulin domain//Immunoglobulin domain// Immunoglobulin domain// Immunoglobulin domain STOMA20088380//Immunoglobulin domain// Immunoglobulin domain// Immunoglobulin domain// Immunoglobulin domain// Immunoglobulin domain STOMA20092530//Immunoglobulin domain// Immunoglobulin domain// Immunoglobulin domain// Immunoglobulin domain STOMA20092890//Myosin head (motor domain)

SYNOV20001520//Immunoglobulin domain// Immunoglobulin domain

SYNOV20001730//Immunoglobulin domain// Immunoglobulin domain// Immunoglobulin domain SYNOV20002510//Immunoglobulin domain// Immunoglobulin domain// Immunoglobulin domain// Immunoglobulin domain SYNOV20002790//Immunoglobulin domain// Immunoglobulin domain// Immunoglobulin domain// Immunoglobulin domain SYNOV20002970//Immunoglobulin domain// Immunoglobulin domain// Immunoglobulin domain// Immunoglobulin domain SYNOV20004260//Immunoglobulin domain// Immunoglobulin domain// Immunoglobulin domain// Immunoglobulin domain SYNOV20007000//Immunoglobulin domain// Immunoglobulin domain// Immunoglobulin domain// Immunoglobulin domain SYNOV20008240//Immunoglobulin domain// Immunoglobulin in domain// Immunoglobulin domain SYNOV20009230//Immunoglobulin domain// Immunoglobulin domain// Immunoglobulin domain// Immunoglobulin domain// Immunoglobulin domain SYNOV20010880//Immunoglobulin domain// Immunoglobulin domain// Immunoglobulin domain// Immunoglobulin domain SYNOV20011110//Immunoglobulin domain// Immunoglobulin domain// Immunoglobulin domain// Immunoglobulin domain SYNOV20013000//Immunoglobulin domain// Immunoglobulin domain// Immunoglobulin domain// Immunoglobulin domain SYNOV20013560//Immunoglobulin domain// Immunoglobulin domain// Immunoglobulin domain// Immunoglobulin domain SYNOV20013900//Immunoglobulin domain// Immunoglobulin domain// Immunoglobulin domain// Immunoglobulin domain SYNOV20017080//UBX domain SYNOV30001840//Asparagine synthase// AMP-binding enzyme TBAES20000590//Cytochrome P450// Cytochrome P450

TBAES20002550//Peptidase family M1// Sigma-70 factor (ECF subfamily)

TBAES20003150//Cytochrome P450

TESOP20004000//Papain family cysteine protease

TESOP20005270//Sulfotransferase proteins

TESTI20001000//Formamidopyrimidine-DNA glycosylase

TESTI20001170//HORMA domain

TESTI20002780//Leucine Rich Repeat// Leucine Rich Repeat// Leucine Rich Repeat// PEP-utilizing enzymes TESTI20017950//Regulator of G protein signaling domain TESTI20023510//Transcription termination factor nusG TESTI20031810//Bacterial luciferase// Domain of unknown function DUF28

TESTI20035960//Coproporphyrinogen III oxidase// WD domain, G-beta repeat// WD domain, G-beta repeat// WD domain, G-beta repeat// WD domain, G-beta repeat// WD domain, G-beta repeat// WD domain, G-beta repeat TESTI20036380//Sulfate transporter family// Sodium Bile acid symporter family// STAS domain TESTI20041690//Zinc finger, C3HC4 type (RING finger)// PHD-finger// IBR domain// Zinc finger, C3HC4 type (RING finger)// B-box zinc finger.// lactate/malate dehydrogenase// Fibronectin type III domain TESTI20044230//Nucleosome assembly protein (NAP)// Nucleosome assembly protein (NAP)// Nucleosome assembly protein (NAP)

TESTI20044310//Leucine Rich Repeat// Leucine Rich Repeat// Leucine Rich Repeat// Leucine Rich Repeat// Chorismate synthase// UvrB/uvrC motif TESTI20046750//Respiratory-chain NADH dehydrogenase, 4

TESTI20057750//RNase H// Integrase Zinc binding domain

TESTI20061110//Heavy-metal-associated domain// ATPases associated with various cellular act TESTI20063830//Transposase TESTI20066670//Acyl-CoA dehydrogenase TESTI20067200//K-box region// Homeobox domain TESTI20082330//Tudor domain TESTI20083200//Dual specificity phosphatase, catalytic doma TESTI20083940//Progesterone receptor TESTI20088220//KRAB box// Zinc finger, C2H2 type// Zinc finger, C2H2 type// PHD-finger// Zinc finger, C2H2 type// Zinc finger, C2H2 type// Zinc finger, C2H2 type// Zinc finger, C2H2 type// BolA-like protein// Zinc finger, C2H2 type// Zinc finger, C2H2 type// Snake toxin// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type TESTI20094470//Ets-domain TESTI20098350//VAT-Nn domain TESTI20108720//Protein phosphatase 2C TESTI20121550//Putative GTP-ase activating protein for Arf TESTI20127760//Cyclin// Calcitonin / CGRP / IAPP family TESTI20130010//Zinc finger, C2H2 type// Zinc finger, C2H2 type// Zinc finger, C2H2 type// Zinc finger, C2H2 type// Zinc finger, C2H2 type TESTI20136710//Glypican// PHD-finger TESTI20143390//Integral membrane protein DUF6// Integral membrane protein DUF6

TESTI20148000//Thioredoxin// Calsequestrin// Thioredoxin

TESTI20152460//Putative zinc finger in N-recognin// PHD-finger

TESTI20156100//Zinc finger, C2H2 type// Zinc finger, C2H2 type// Zinc finger, C2H2 type TESTI20157520//K+ channel tetramerisation domain// K+ channel tetramerisation domain TESTI20168480//Immunoglobulin domain// Immunoglobulin domain// Immunoglobulin domain// MAM domain.// Immunoglobulin domain TESTI20170350//Cystine-knot domain TESTI20184620//PH domain// Oxysterol-binding protein TESTI20185650//AN1-like Zinc finger TESTI20189410//PHD-finger TESTI20192800//HC03-transporter family// Ank repeat// Ank repeat// Ank repeat// Alpha-2-macroglobulin family TESTI20197940//Domain of unknown function DUF27// Aconitase family (aconitate hydratase)

TESTI20200710//PHD-finger// LIM domain containing proteins

TESTI20202650//Repeat in HS1/Cortactin

TESTI20204450//Zinc finger, C2H2 type// Zinc finger, C2H2 type// Homeobox domain TESTI20208400//NOL1/NOP2/sun family TESTI20208710//WD domain, G-beta repeat// WD domain, G-beta repeat TESTI20211160//Hydroxyethylthiazole kinase family TESTI20214250//Mitochondrial carrier proteins// Mitochondrial carrier proteins TESTI20215990//F-box domain.// Leucine Rich Repeat// Leucine Rich Repeat// Leucine Rich Repeat// Leucine Rich Repeat// Leucine Rich Repeat// Leucine Rich Repeat// Leucine Rich Repeat TESTI20216370//Carboxylesterases TESTI20226230//Adenylate kinase// Pou domain-N-terminal to homeobox d TESTI20229600//EGF-like domain// Metallothionein family 5// Replication protein// Laminin G domain// EGF-like domain// Laminin G domain// Insulin-like growth factor binding prot// EGF-like domain// Laminin G domain TESTI20230850//PAS domain TESTI20231920/-/Gag P30 core shell protein TESTI20232140//Phosphatidylinositol-specific phospholipase// Phosphatidylinositol-specific phospholipase TESTI20234140//EF hand// WD domain, G-beta repeat// WD domain, G-beta repeat// WD domain, G-beta repeat// WD domain, G-beta repeat TESTI20234360//WW domain// PPIC-type PPIASE domain.

TESTI20238610//MAGE family// Uncharacterized protein family UPF0057

TESTI20242830//E2 (early) protein, C terminal// Syndecan domain

TESTI20244190//Immunoglobulin domain// Immunoglobulin domain// Immunoglobulin domain// Immunoglobulin domain TESTI20254860//Immunoglobulin domain// Immunoglobulin domain// Immunoglobulin domain// Immunoglobulin domain// Reeler domain// Fibronectin type III domain// Fibronectin type III domain TESTI20255820//FERM domain (Band 4.1 family)// FERM domain (Band 4.1 family)// Isocitrate lyase TESTI20258460//PH domain TESTI20265970//Guanylate-binding protein TESTI20266740//Nucleotidyltransferase domain TESTI20272960//7 transmembrane receptor (rhodopsin family)

TESTI20275030//WD domain, G-beta repeat// WD domain, G-beta repeat

TESTI20288910//SH3 domain

TESTI20291960//Rhomboid family

TESTI20303220//Immunoglobulin domain// Immunoglobulin domain// Immunoglobulin domain// Immunoglobulin domain// Fibronectin type III domain// Alphaherpesvirus glycoprotein E// Fibronectin type III domain// Fibronectin type III domain// Fibronectin type III domain TESTI20303360//ENV polyprotein (coat polyprotein)

TESTI20305540//Hantavirus nucleocapsid protein// Troponin// Apolipoprotein A1/A4/E family TESTI20308600//Homeobox domain TESTI20309170//TPR Domain// Zinc finger, C3HC4 type (RING finger)// Aldo/keto reductase family// ATP-dependent protease La (LON) domain TESTI20314180//Trypsin// Trypsin TESTI20317600//Terpene synthase family TESTI20318090//Zinc finger, C2H2 type// Zinc finger, C2H2 type// Zinc finger, C2H2 type// Zinc finger, C2H2 type// Zinc finger, C2H2 type TESTI20320440//Thioredoxin TESTI20320670//RNA recognition motif. (a.k.a. RRM, RBD, or RNP domain)// RNA recognition motif. (a.k.a. RRM, RBD, or RNP domain)

TESTI20326810//RanBP1 domain.

TESTI20327680//EF hand// EF hand

TESTI20328280//KE2 family protein// Troponin

TESTI20333000//Immunoglobulin domain// Immunoglobulin domain

TESTI20334410//DEAD/DEAH box helicase// Helicases conserved C-terminal domain

TESTI20335050//Zinc finger, C3HC4 type (RING finger)

TESTI20335200//Immunoglobulin domain

TESTI20343070//Transcription factor E2F/dimerisation partner (TDP)

TESTI20351830//K-box region

TESTI20352620//Saposin A-type domain

TESTI20355020//Tudor domain

TESTI20358980//Homeobox domain// Collagen triple helix repeat (20 copies)

TESTI20366910//Pyridine nucleotide-disulphide oxidoreductase

TESTI20368330//Rhodanese-like domain

TESTI20369690//PHD-finger
TESTI20370020//Bleomycin resistance protein
TESTI20370810//Ion transport protein// Polysaccharide biosynthesis protein// Sugar (and other) transporter
TESTI20371030//Kelch motif// Kelch motif// Kelch motif// Kelch motif// Kelch motif
TESTI20375340//Phosphatidylinositol-specific phospholi// UvrD/REP helicase// Phosphatidylinositol-specific phospholi// C2 domain
TESTI20377230//Thymidylate synthase
TESTI20378190//KRAB box// Zinc finger, C2H2 type// Zinc finger, C2H2 type// Zinc finger, C2H2 type// Zinc finger, C2H2 type// Zinc finger, C2H2 type// Zinc finger, C2H2 type// Transcription factor S-II (TFIIS)// Zinc finger, C2H2 type// Zinc finger, C2H2 type// Zinc finger, C2H2 type
TESTI20381040//Putative zinc finger in N-recognin
TESTI20382750//Kinesin motor domain
TESTI20383880//DnaJ domain
TESTI20385960//Zinc finger, C3HC4 type (RING finger)// SPRY domain
TESTI20390410//Arsenical pump membrane protein
TESTI20391210//IQ calmodulin-binding motif
TESTI20391770//Domain of unknown function DUFI9// Thioredoxin
TESTI20392250//PH domain// Phorbol esters/diacylglycerol binding domain (Cl domain)
TESTI20392270//Cyclin
TESTI20392760//Leucine Rich Repeat// Leucine Rich Repeat// Leucine Rich Repeat// Leucine Rich Repeat// Leucine Rich Repeat// Leucine Rich Repeat// Leucine Rich Repeat
TESTI20393530//Mitochondrial carrier proteins
TESTI20397760//El-E2 ATPase
TESTI20400940//K-box region
TESTI20401020//Mitochondrial carrier proteins// Mitochondrial carrier proteins
TESTI20408150//Keratin, high sulfur B2 protein
TESTI20416640//Choline/ethanolamine kinase
TESTI20432750//Cytochrome C and Quinol oxidase polypeptide
TESTI20432820//Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Transcription factor S-II (TFIIS)// Zinc finger, C2H2 type// Zinc finger, C2H2 type// Zinc finger, C2H2 type
TESTI20436560//Spectrin repeat// Intermediatelfilament proteins// Intermediate filament tail domain
TESTI20442760//Immunoglobulin domain// Immunoglobulin domain// Immunoglobulin domain// Immunoglobulin domain
TESTI20443090//SAP domain// Zinc knuckle// Zinc finger, C3HC4 type (RING finger)
TESTI20444130//ENV polyprotein (coat polyprotein)
TESTI20449200//7 transmembrane receptor (metabotropic gluta
TESTI20451990//SAP domain
TESTI20455090//Intermediate filament proteins
TESTI20455620//Hsp70 protein
TESTI20456110//B-box zinc finger.// Spectrin repeat// SPRY domain
TESTI20463580//Ubiquitin carboxyl-terminal hydrolases famil// Immunoglobulin domain// Ubiquitin carboxyl-terminal hydrolase family
TESTI20467320//Wiskott Aldrich syndrome homology region 2
TESTI20467970//Neurohypophysial hormones, N-terminal Domain// Neurohypophysial hormones, N-terminal Domain// Neurohypophysial hormones, N-terminal Domain// Neurohypophysial hormones, N-terminal Domain// Neurohypophysial hormones, N-terminal Domain// Neurohypophysial hormones, N-terminal Domain// Neurohypophysial hormones, N-terminal Domain// Neurohypophysial hormones, N-terminal Domain// Neurohypophysial hormones, N-terminal Domain// Neurohypophysial hormones, N-terminal Domain
TESTI20471410//Protein phosphatase 2C
TESTI20478850//Herpesvirus Glycoprotein B
THYMU10005360//Immunoglobulin domain// Viral coat protein// Immunoglobulin domain
THYMU10005540//Immunoglobulin domain// Immunoglobulin domain// Immunoglobulin domain// Immunoglobulin domain
THYMU20023380//Copper/zinc superoxide dismutase (SODC)
THYMU20027560//Domain of unknown function
THYMU20039810//MAC/Perforin domain
THYMU20105190//Myosin head (motor domain)
THYMU20106710//Immunoglobulin domain
THYMU20111180//Domain of unknown function DUF27// Aconitase family (aconitate hydratase)
THYMU20115850//Reverse transcriptase (RNA-dependent DNA pol
THYMU20118520//Ubiquitin family
THYMU20122730//VHS domain
THYMU20126900//3-hydroxyacyl-CoA dehydrogenase// UDP-glucose/GDP-mannose dehydrogenase fa
THYMU20130890//Ribosomal protein S9/S16
THYMU20141670//Phorbol esters/diacylglycerol binding dom// PHD-finger// FYVE zinc finger
THYMU20142040//Wiskott Aldrich syndrome homology region 2
THYMU20143270//Cytochrome C oxidase subunit II
THYMU20147770//Immunoglobulin domain// Immunoglobulin domain// Immunoglobulin domain// Immunoglobulin domain
THYMU20159430//Immunoglobulin domain// Immunoglobulin domain// Immunoglobulin domain// Immunoglobulin domain// Immunoglobulin domain
THYMU20161640//PMP-22/EMP/MP20/Claudin family// Integral membrane protein DUF6
THYMU20169680//Ank repeat// Ank repeat
THYMU20172150//WD domain, G-beta repeat
THYMU20194360//Kelch motif
THYMU20201980//PH domain// Phorbol esters/diacylglycerol binding domain (C1 domain)// FYVE zinc finger// PH domain
THYMU20202890//Eukaryotic protein kinase domain
THYMU20209590//PH domain// Dynamin GTPase effector domain
THYMU20216840//PHD-finger
THYMU20229220//Closterovirus coat protein
THYMU20239000//Collagen triple helix repeat (20 copies)
THYMU20240710//tRNA synthetases class I (E and Q)
THYMU20241850//Class II histocompatibility antigen, beta// Immunoglobulin domain
THYMU20247480//KRAB box// Zinc finger, C2H2 type// Zinc finger, C2H2 type// Zinc finger, C2H2 type// Zinc finger, C2H2 type// Zinc finger, C2H2 type// Zinc finger, C2H2 type
THYMU20279750//Immunoglobulin domain
TKIDN10000010//Mitochondrial import inner membrane transloc TKIDN20004640//GHMP kinases putative ATP-binding protei TKIDN20047480//Eukaryotic protein kinase domain TOVAR20004760//Leucine Rich Repeat// Leucine Rich Repeat// Leucine Rich Repeat TRACH20002870//PMP-22/EMP/MP20/Claudin family TRACH20003590//Cytochrome P450

TRACH20005020//Ank repeat// MutT-like domain

TRACH20005400//ADP-ribosylation factor family// Ras family

TRACH20016210//Fucosyl transferase

TRACH20019960//Na+/K+ ATPase C-terminus

TRACH20028030//DnaJ domain// DnaJ central domain (4 repeats)// DnaJ C terminal region TRACH20033230//Nucleoside transporter// Sugar (and other) transporter// Influenza RNA-dependent RNA polymerase subunit PB2

TRACH20041830//Thioredoxin// Thioredoxin

TRACH20042920//Glutamine synthetase

TRACH20048450//Phospholipase D. Active site motif// Phospholipase D. Active site motif TRACH20050040//Plexin repeat TRACH20067620//Core-2/I-Branching enzyme TRACH20069180//Immunoglobulin domain// Immunoglobulin domain// Immunoglobulin domain// Immunoglobulin domain TRACH20076740//Reduced folate carrier TRACH20076760//Keratin, high sulfur B2 protein TRACH20077540//Zinc finger, C2H2 type// G-patch domain TRACH20079690//KRAB box// Zinc finger, C2H2 type// Zinc finger, C2H2 type// TRAF-type zinc finger// Zinc finger, C2H2 type// Zinc finger, C2H2 type// Zinc finger, C2H2 type// Zinc finger, C2H2 type// Transcription factor S-II (TFIIS)// Zinc finger, C2H2 type// Zinc finger, C2H2 type TRACH20084720//tRNA synthetases class I (C)// tRNA synthetases class I (I, L, M and V)

TRACH20085400//Immunoglobulin domain// Immunoglobulin domain// Immunoglobulin domain// Immunoglobulin domain// Immunoglobulin domain// Immunoglobulin domain TRACH20085830//Cytochrome P450

TRACH20096610//Intermediate filament proteins// Intermediate filament tail domain TRACH20105870//Regulatory subunit of type II PKA R-subunit// eIF4-gamma/eIF5/eIF2-epsilon TRACH20121380//Raf-like Ras-binding domain// Leptin// Raf-like Ras-binding domain// LGN motif, putative GEF specific for G-alpha GTPase TRACH20128230//Immunoglobulin domain// Chitin synthase// Immunoglobulin domain// Immunoglobulin domain// Immunoglobulin domain TRACH20135520//TBC domain// Rhodanese-like domain TRACH20136710//Immunoglobulin domain TRACH20141240//Granulins TRACH20145440//von Willebrand factor type D domain TRACH20154860//Squash family of serine protease inhibito// Zinc finger, C4 type (two domains)// T-box// Zinc finger, C4 type (two domains)// Ligand-binding domain of nuclear hormone TRACH20163170//Homeobox domain TRACH20164980//Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// PHD-finger// Transcription factor S-II (TFIIS)// Zinc finger, C2H2 type// Zinc finger, C2H2 type// Zinc finger, C2H2 type// Zinc finger, C2H2 type TRACH20167220//wnt family of developmental signaling protei// PLAT/LH2 domain// Fibroblast growth factor TRACH20184490//KRAB box// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type TRACH20190240//EGF-like domain// EGF-like domain// Trypsin Inhibitor like cysteine rich domain// EGF-like domain TSTOM20005690//BTB/POZ domain// Kelch motif// Kelch motif// Kelch motif TUTER20002830//RNA recognition motif. (a.k.a. RRM, RBD, or RNP domain)

UMVEN10001860//PH domain// RhoGAP domain// bZIP transcription factor

UMVEN20000690//F5/8 type C domain

UTERU20030570//ABC 3 transport family// Voltage gated chloride channels// CBS domain// CBS domain UTERU20046640//Rotavirus NS26

UTERU20046980//EB module// TNFR/NGFR cysteine-rich region// Furin-like cysteine rich region// Thrombospondin type 1 domain UTERU20050690//Androgen receptor UTERU20055330//Reverse transcriptase (RNA-dependent DNA polymerase)

UTERU20055480//AMP-binding enzyme

UTERU20055930//Helper component proteinase

UTERU20064000//Peptidase family M1

UTERU20065930//Hrl repeat motif// PDZ domain (Also known as DHR or GLGF).

UTERU20115740//KRAB box

UTERU20116570//Villin headpiece domain

UTERU20119060//ADP-ribosyl cyclase

UTERU20144640//Choloylglycine hydrolase

UTERU20145480//KRAB box// Zinc finger, C2H2 type// Transcription factor S-II (TFIIS)// Zinc finger, C2H2 type// TRAF-type zinc finger// Zinc finger, C2H2 type// Zinc finger, C2H2 type// wnt family of developmental signaling proteins// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type// Zinc finger, C2H2 type UTERU20146310//Diacylglycerol kinase accessory domain (pres UTERU20161570//7 transmembrane receptor (rhodopsin family)

UTERU20168220//Cell division protein// Integrase Zinc binding domain// GTPase of unknown function UTERU20176130//Putative GTP-ase activating protein for Arf UTERU20176320//SMC domain N terminal domain// Tropomyosins UTERU20178100//Aminotransferases class-III pyridoxal-pho UTERU20179880//TPR Domain// TPR Domain// TPR Domain// TPR Domain UTERU20183640//Immunoglobulin domain UTERU20185230//DUP family of yeast membrane proteins

EXAMPLE 6

Functional Categorization Based on the Full-length Nucleotide Sequences

The functional prediction and categorization of the proteins encoded by the clones were carried out based on the result of homology search of the databases of GenBank, Swiss-Prot, UniGene and nr (see the Homology Search Result Data) for the full-length nucleotide sequences and the result of domain search of the amino acid sequences deduced from the full-length nucleotide sequences (see Example 5).

The clone predicted to belong to the category of secretory protein/membrane protein means a clone having hit data with some annotation, such as growth factor, cytokine, hormone, signal, transmembrane, membrane, extracellular matrix, receptor, G-protein coupled receptor, ionic channel, voltage-gated channel, calcium channel, cell adhesion, collagen, connective tissue, etc., suggesting that it is a secretory or membrane protein, or means a clone in which the presence of nucleotide sequence encoding a signal sequence or transmembrane domain was suggested by the results of PSORT and SOSUI analyses for deduced ORF.

The clone predicted to belong to the category of glycoprotein-related protein means a clone having hit data with some annotation, such as glycoprotein, suggesting that the clone encodes a glycoprotein-related protein.

The clone predicted to belong to the category of signal transduction-related protein means a clone having hit data with some annotation, such as serine/threonine-protein kinase, tyrosine-protein kinase, SH3 domain, SH2 domain, etc., suggesting that the clone encodes a signal transduction-related protein.

The clone predicted to belong to the category of transcription-related protein means a clone having hit data with some annotation, such as transcription regulation, zinc finger, homeobox, etc., suggesting that the clone encodes a transcription-related protein.

The clone predicted to belong to the category of disease-related protein means a clone having hit data with some annotation, such as disease mutation, syndrome, etc., suggesting that the clone encodes a disease-related protein, or means a clone whose full-length nucleotide sequence has hit data for Swiss-Prot, GenBank, or UniGene, where the hit data corresponds to genes or proteins which have been deposited in the Online Mendelian Inheritance in Man (OMIM), which is the human gene and disease database.

The clone predicted to belong to the category of enzyme and/or metabolism-related protein means a clone having hit data with some annotation, such as metabolism, oxidoreductase, E. C. No. (Enzyme commission number), etc., suggesting that the clone encodes an enzyme and/or metabolism-related protein.

The clone predicted to belong to the category of cell division and/or cell proliferation-related protein means a clone having hit data with some annotation, such as cell division, cell cycle, mitosis, chromosomal protein, cell growth, apoptosis, etc., suggesting that the clone encodes a cell division and/or cell proliferation-related protein.

The clone predicted to belong to the category of cytoskeleton-related protein means a clone having hit data with some annotation, such as structural protein, cytoskeleton, actin-binding, microtubles, etc., suggesting that the clone encodes a cytoskeleton-related protein.

The clone which is predicted to belong to the category of nuclear protein and/or RNA synthesis-related protein means a clone having hit data with some annotation, such as nuclear protein, RNA splicing, RNA processing, RNA helicase, polyadenylation, etc., suggesting that the clone encodes a nuclear protein and/or RNA synthesis-related protein.

The clone predicted to belong to the category of protein synthesis and/or transport-related protein means a clone having hit data with some annotation, such as translation regulation, protein biosynthesis, amino-acid biosynthesis, ribosomal protein, protein transport, signal recognition particle, etc., suggesting that the clone encodes a protein synthesis and/or transport-related protein.

The clone predicted to belong to the category of cellular defense-related protein means a clone having hit data with some annotation, such as heat shock, DNA repair, DNA damage, etc., suggesting that the clone encodes a cellular defense-related protein.

The clone predicted to belong to the category of development and/or differentiation-related proteins means a clone having hit data with some annotation, such as developmental protein, etc., suggesting that the clone encodes a development and/or differentiation-related protein.

The clone predicted to belong to the category of DNA-binding and/or RNA-binding protein means a clone having hit data with some annotation, such as DNA-binding, RNA-binding, etc.

The clone predicted to belong to the category of ATP-binding and/or GTP-binding protein means a clone having hit data with some annotation, such as ATP-binding, GTP-binding, etc.

In this functional categorization, when a single clone corresponded to multiple categories of those shown above, the clone was assigned to the multiple categories. However, the function of a protein is not restricted to the functional category in this classification, and there is the possibility that other functions are newly assigned to the protein.

The clones predicted to belong to the category of secretory protein and/or membrane protein are the following 632 clones. ADIPS10000640, ADRGL10001470, ADRGL20013520, ADRGL20018540, ADRGL20035850, ASTRO20001410, ASTRO20005330, ASTRO20033160, ASTRO20055750, ASTRO20058630, ASTRO20190390, BEAST20004540, BGGI110000240, BNGH420088500, BRACE20006400, BRACE20038000, BRACE20038470, BRACE20039040, BRACE20039540, BRACE20051380, BRACE20053630, BRACE20059370, BRACE20060550, BRACE20061050, BRACE20063630, BRACE20067430, BRACE20069090, BRACE20081720, BRACE20101700, BRACE20101710, BRACE20116110, BRACE20147800, BRACE20153680, BRACE20163350, BRACE20179340, BRACE20188470, BRACE20195100, BRACE20201570, BRACE20210140, BRACE20224480, BRACE20224500, BRACE20228480, BRACE20232840, BRACE20238000, BRACE20273890, BRACE20274080, BRALZ20013500, BRALZ20054710, BRALZ20064740, BRALZ20069760, BRALZ20073760, BRALZ20077930, BRAMY20000860, BRAMY20002770, BRAMY20025840, BRAMY20039260, BRAMY20060920, BRAMY20063970, BRAMY20111960, BRAMY20112800, BRAMY20124260, BRAMY20134140, BRAMY20135900, BRAMY20136210, BRAMY20144620, BRAMY20152110, BRAMY20174550, BRAMY20181220, BRAMY20195090, BRAMY20211390, BRAMY20211420, BRAMY20215230, BRAMY20218250, BRAMY20218670, BRAMY20229800, BRAMY20231720, BRAMY20247280, BRAMY20252180, BRAMY20273960, BRAMY20277170, BRAMY20284910, BRAMY20285160, BRAWH20015350, BRAWH20015890, BRAWH20016860, BRAWH20018730, BRAWH20030250, BRAWH20064050, BRAWH20110790, BRAWH20112940, BRAWH20117950, BRAWH20118230, BRAWH20121640, BRAWH20122580, BRAWH20132190, BRCAN20064010, BRCAN20071190, BRCAN20091560, BRCAN20103740, BRCAN20224720, BRCAN20273550, BRCAN20280360, BRCAN20285450, BRCOC10000870, BRCOC20004040, BRCOC20006370, BRCOC20041750, BRCOC20077690, BRCOC20078640, BRCOC20090520, BRCOC20101230, BRCOC20107300, BRCOC20114180, BRCOC20121720, BRCOC20134480, BRCOC20136750, BRHIP10001290, BRHIP20000870, BRHIP20003120, BRHIP20103090, BRHIP20111200, BRHIP20118380, BRHIP20118910, BRHIP20121410, BRHIP20135100, BRHIP20174040, BRHIP20179200, BRHIP20183690, BRHIP20191490, BRHIP20191770, BRHIP20198190, BRHIP20207430, BRHIP20208270, BRHIP20208590, BRHIP20217620, BRHIP20233090, BRHIP20234380, BRHIP20238880, BRHIP20283030, BRHIP30004570, BRSSN20003120, BRSSN20043040, BRSSN20066110, BRSSN20120810, BRSSN20137020, BRSSN20142940, BRSSN20146100, BRSSN20151990, BRSSN20169050, BRSTN20002200, BRTHA20004740, BRTHA20046290, BRTHA20046420, COLON10001350, COLON20093370, CTONG10000100, CTONG10000940, CTONG10001650, CTONG20004690, CTONG20009770, CTONG20092570, CTONG20092580, CTONG20095340, CTONG20099380, CTONG20103480, CTONG20105080, CTONG20114740, CTONG20119200, CTONG20120770, CTONG20124730, CTONG20131490, CTONG20132220, CTONG20133480, CTONG20139340, CTONG20149950, CTONG20155400, CTONG20158660, CTONG20159530, CTONG20161850, CTONG20267700, D30ST10001090, D30ST20036070, D30ST20038560, .D30ST30002580, D60ST20005070, D90ST20002780, D90ST20015470, D90ST20023970, D90ST20026730, D90ST20035940, D90ST20040180, DFNES20025880, FCBBF10000240, FCBBF10000380, FCBBF10001150, FCBBF10001210, FCBBF10001550, FCBBF10002430, FCBBF10002700, FCBBF10003220, FCBBF10003760, FCBBF10005460, FCBBF10005740, FCBBF20032970, FCBBF20042560, FCBBF20049300, FCBBF20051220, FCBBF30008470, FCBBF30024750, FCBBF30078290, FCBBF30083620, FCBBF30086440, FCBBF30090690, FCBBF30095260, FCBBF30123470, FCBBF30172550, FCBBF30175310, FCBBF30190850, FCBBF30215060, FCBBF30238870, FCBBF30251420, FCBBF30279030, FEBRA20002100, FEBRA20004620, FEBRA20009090, FEBRA20029860, FEBRA20037260, FEBRA20080810, FEBRA20086620, FEBRA20092890, FEBRA20093520, FEBRA20095880, FEBRA20111460, FEBRA20125070, FEBRA20130190, FEBRA20140100, FEBRA20145780, FEBRA20211710, FEBRA20223220, FEBRA20229630, FEBRA20235500, HCHON20000380, HCHON20008180, HCHON20015980, HCHON20016040, HCHON20016650, HCHON20040020, HCHON20064590, HCHON20067700, HCHON20068710, HCHON20086720, HCHON20100740, HEART20003060, HEART20005410, HEART20034320, HEART20049410, HEART20049800, HEART20072310, HHDPC20001040, HHDPC20014320, HHDPC20034720, HHDPC20068620, HHDPC20084140, HHDPC20091780, HHDPC20092080, HLUNG10000550, KIDNE20003940, KIDNE20007770, KIDNE20011400, KIDNE20021910, KIDNE20022620, KIDNE20100070, KIDNE20101510, KIDNE20109730, KIDNE20121880, KIDNE20125630, KIDNE20126010, KIDNE20126130, KIDNE20127450, KIDNE20130450, KIDNE20131580, KIDNE20137340, KIDNE20181660, LIVER20035110, LIVER20045650, LIVER20055200, LIVER20062510, LIVER20064690, LIVER20075680, LIVER20087060, LIVER20091180, MESAN10001260, MESAN20014500, MESAN20027090, MESAN20038510, MESAN20089360, MESAN20103120, MESAN20115970, MESAN20125860, MESAN20139360, MESAN20152770, MESAN20153910, MESAN20174170, NOVAR20000380, NT2NE20010050, NT2NE20021620, NT2NE20068130, NT2NE20118960, NT2NE20124480, NT2NE20131890, NT2NE20132170, NT2NE20155110, NT2NE20156260, NT2NE20157470, NT2NE20159740, NT2NE20177520, NT2NE20183760, NT2RI20003480, NT2RI20023910, NT2RI20025400, NT2RI20028470, NT2RI20040930, NT2RI20054050, NT2RI20056700, NT2RI20076290, NT2RI20086220, NT2RI20091940, NT2RI20244600, NT2RP70072690, NT2RP70081610, NT2RP70122910, NT2RP70125160, NT2RP70133740, NT2RP70134990, NT2RP70137290, NT2RP70179710, NT2RP70188020, NT2RP70192730, NT2RP70198350, NTONG20028070, NTONG20029700, NTONG20048060, NTONG20049910, NTONG20051530, NTONG20061870, NTONG20063010, NTONG20067830, NTONG20076930, NTONG20092330, OCBBF10001750, OCBBF20013890, OCBBF20019830, OCBBF20023570, OCBBF20026630, OCBBF20046690, OCBBF20050770, OCBBF20059560, OCBBF20063320, OCBBF20071210, OCBBF20072320, OCBBF20080050, OCBBF20086400, OCBBF20086910, OCBBF20087010, OCBBF20088140, OCBBF20091150, OCBBF20107090, OCBBF20108630, OCBBF20116850, OCBBF20120390, OCBBF20122620, OCBBF20130910, OCBBF20132850, OCBBF20145760, OCBBF20155060, OCBBF20178880, OCBBF20180120, OCBBF20180840, OCBBF20188730, PANCR10000910, PEBLM10000710, PEBLM20024320, PEBLM20040150, PEBLM20074370, PEBLM20075980, PERIC20004220, PLACE60086400, PLACE60121080, PLACE60161600, PLACE60177140, PROST20005050, PROST20050670, PROST20107820, PROST20116600, PROST20120160, PROST20127800, PROST20146010, PROST20164440, PROST20169800, PROST20170980, PROST20175290, PUAEN20003740, PUAEN20030180, SALGL10001710, SKMUS20003610, SKMUS20007800, SKMUS20011640, SKMUS20020840, SKMUS20028210, SKMUS20028400, SKMUS20077400, SKNSH20028660, SKNSH20031740, SKNSH20051940, SKNSH20063040, SMINT20009840, SMINT20011990, SMINT20022020, SMINT20029760, SMINT20040860, SMINT20050750, SMINT20053870, SMINT20073650, SMINT20095050, SMINT20100680, SMINT20105330, SMINT20106720, SMINT20121950, SMINT20127930, SMINT20144430, SMINT20144890, SMINT20153260, SMINT20154540, SMINT20157450, SMINT20173240, SMINT20178550, SMINT20191420, SMINT20192000, SPLEN20003070, SPLEN20021660, SPLEN20029310, SPLEN20079510, SPLEN20095810, SPLEN20097330, SPLEN20118300, SPLEN20141360, SPLEN20141990, SPLEN20142100, SPLEN20144520, SPLEN20152760, SPLEN20157880, SPLEN20165310, SPLEN20167200, SPLEN20169220, SPLEN20169720, SPLEN20171890, SPLEN20172120, SPLEN20179810, SPLEN20186430, SPLEN20211570, SPLEN20211940, SPLEN20213830, SPLEN20273950, SPLEN20292950, SPLEN20293800, SPLEN20304950, SPLEN20329240, STOMA20005390, STOMA20005670, STOMA20006400, STOMA20006780, STOMA20008880, STOMA20051200, STOMA20056640, STOMA20056670, STOMA20062130, STOMA20077450, STOMA20080500, STOMA20088380, STOMA20092530, SYNOV20001520, SYNOV20001730, SYNOV20002510, SYNOV20002790, SYNOV20002970, SYNOV20004260, SYNOV20007000, SYNOV20008240, SYNOV20009230, SYNOV20010880, SYNOV20011110, SYNOV20013000, SYNOV20013560, SYNOV20013900, SYNOV30001840, TBAES20003150, TESOP20004000, TESOP20005690, TESTI20001720, TESTI20036380, TESTI20037560, TESTI20094120, TESTI20110280, TESTI20123080, TESTI20123560, TESTI20128350, TESTI20136100, TESTI20136710, TESTI20143390, TESTI20148000, TESTI20164100, TESTI20193360, TESTI20209810, TESTI20209990, TESTI20211220, TESTI20214250, TESTI20216370, TESTI20230250, TESTI20231940, TESTI20242990, TESTI20244190, TESTI20254220, TESTI20254860, TESTI20265970, TESTI20271850, TESTI20272960, TESTI20284880, TESTI20291310, TESTI20291960, TESTI20303220, TESTI20303360, TESTI20303420, TESTI20307700, TESTI20309170, TESTI20314180, TESTI20316870, TESTI20333000, TESTI20335200, TESTI20347180, TESTI20347300, TESTI20352620, TESTI20357960, TESTI20370810, TESTI20373820, TESTI20383880, TESTI20390260, TESTI20390410, TESTI20391770, TESTI20393530, TESTI20396130, TESTI20397760, TESTI20401020, TESTI20401280, TESTI20415170, TESTI20421490, TESTI20422640, TESTI20441940, TESTI20442760, TESTI20444130, TESTI20444180, TESTI20449200, TESTI20463520, TESTI20463580, TESTI20465350, THYMU10005360, THYMU10005540, THYMU20027560, THYMU20032870, THYMU20039810, THYMU20066100, THYMU20081490, THYMU20100410, THYMU20106710, THYMU20111830, THYMU20141670, THYMU20147770, THYMU20159430, THYMU20161640, THYMU20162190, THYMU20173980, THYMU20194420, THYMU20208300, THYMU20216840, THYMU20222890, THYMU20229220, THYMU20241850, THYMU20277390, TKIDN20005210, TRACH20002870, TRACH20003590, TRACH20016210, TRACH20019960, TRACH20029540, TRACH20033230, TRACH20034840, TRACH20042920, TRACH20050040, TRACH20067620, TRACH20068660, TRACH20069180, TRACH20076740, TRACH20085400, TRACH20085830, TRACH20109650, TRACH20111130, TRACH20121380, TRACH20128110, TRACH20128230, TRACH20134950, TRACH20136710, TRACH20139820, TRACH20140820, TRACH20145440, TRACH20168350, TRACH20180840, TRACH20190240, UMVEN20000690, UTERU20030570, UTERU20040610, UTERU20046980, UTERU20055480, UTERU20064860, UTERU20076390, UTERU20094350, UTERU20135860, UTERU20144640, UTERU20158300, UTERU20158800, UTERU20161570, UTERU20178100, UTERU20183640, UTERU20186740

The clones predicted to belong to the category of glycoprotein-related protein are the following 128 clones. ADIPS10000640, BRACE20059370, BRACE20163350, BRAMY20277170, BRAMY20285160, BRAWH20064050, BRAWH20112940, BRAWH20117950, BRAWH20118230, BRCAN20103740, BRCOC20004040, BRCOC20006370, BRHIP10001290, BRHIP20103090, BRHIP20283030, BRHIP30004570, BRSSN20003120, BRSSN20146100, BRTHA20046290, COLON10001350, CTONG20159530, D90ST20023970, D90ST20040180, FCBBF10001150, FCBBF20049300, FCBBF30024750, FCBBF30083620, FCBBF30190850, FCBBF30238870, FEBRA20086620, FEBRA20092890, HCHON20015980, HCHON20016040, HCHON20064590, HCHON20086720, HCHON20100740, HEART20003060, HHDPC20014320, HHDPC20068620, HHDPC20092080, KIDNE20003940, KIDNE20007770, KIDNE20101510, LIVER20064690, MESAN20125860, NT2NE20118960, NT2NE20157470, NT2NE20177520, NT2RI20003480, NT2RI20056700, NT2RP70192730, NTONG20051530, NTONG20076930, OCBBF20107090, OCBBF20108630, OCBBF20120390, OCBBF20145760, OCBBF20155060, PLACE60177140, SMINT20050750, SMINT20073650, SMINT20105330, SMINT20106720, SMINT20112730, SMINT20127930, SMINT20153260, SMINT20179740, SMINT20190170, SPLEN20021660, SPLEN20142100, SPLEN20157880, SPLEN20165310, SPLEN20179810, SPLEN20186430, STOMA20001830, STOMA20005390, STOMA20005670, STOMA20006400, STOMA20008880, STOMA20034770, STOMA20056640, STOMA20056670, STOMA20083610, STOMA20088380, STOMA20092530, SYNOV20001520, SYNOV20001730, SYNOV20002510, SYNOV20002790, SYNOV20002970, SYNOV20004260, SYNOV20007000, SYNOV20008240, SYNOV20009230, SYNOV20010880, SYNOV20011110, SYNOV20013000, SYNOV20013560, SYNOV20013900, TESOP20004000, TESTI20136100, TESTI20216370, TESTI20244190, TESTI20254860, TESTI20303220, TESTI20335200, TESTI20352620, TESTI20358980, TESTI20442760, TESTI20449200, TESTI20455090, THYMU10005360, THYMU10005540, THYMU20147770, THYMU20159430, THYMU20241850, TRACH20016210, TRACH20050040, TRACH20067620, TRACH20069180, TRACH20076740, TRACH20128230, UTERU20046980, UTERU20064860, UTERU20144640, UTERU20158800, UTERU20161570, UTERU20183640

The clones predicted to belong to the category of signal transduction-related protein are the following 84 clones. ASTRO20108190, BRACE20115920, BRACE20154120, BRACE20177200, BRACE20237270, BRAMY20104640, BRAMY20242470, BRAMY20271400, BRAWH20016620, BRAWH20103290, BRAWH20149340, BRCOC20021550, BRCOC20091960, BRHIP20189980, BRHIP20218580, BRHIP20238600, BRSSN20038200, CD34C30004240, CTONG20118150, CTONG20127450, CTONG20200310, FCBBF30012350, FCBBF40001730, FEBRA10001880, FEBRA20004620, FEBRA20132740, FEBRA20144170, FEHRT20003250, HCHON20007510, HLUNG20033780, IMR3220002430, KIDNE20008010, KIDNE20102710, KIDNE20107620, NT2NE20080170, NT2NE20181650, NT2RP70027380, NT2RP70036880, NT2RP70063950, NT2RP70078420, NT2RP70159960, NTONG20046140, NTONG20056570, OCBBF20028050, OCBBF20053430, OCBBF20054760, OCBBF20124360, OCBBF20127140, OCBBF20149280, OCBBF20173980, PEBLM20013120, PEBLM20085760, PROST20161950, PUAEN20015260, PUAEN20015860, PUAEN20083140, SMINT20028820, SMINT20049090, SMINT20110660, SPLEN20011410, SPLEN20121750, SPLEN20170310, SPLEN20181810, SPLEN20222270, SPLEN20250170, SPLEN20283650, TESTI20035960, TESTI20288910, TESTI20305540, TESTI20326810, TESTI20369650, TESTI20392250, TESTI20416640, TESTI20432750, TESTI20467320, THYMU20169680, THYMU20172150, THYMU20201980, THYMU20202890, TKIDN20004640, TKIDN20047480, TRACH20057690, UMVEN10001860, UTERU20146310

The clones predicted to belong to the category of transcription-related protein are the following 144 clones. 3NB6920014590, ADIPS20004250, ASTRO20008010, ASTRO20168470, BLADE20003400, BLADE20003890, BRACE20060890, BRACE20068590, BRACE20257100, BRAMY20210400, BRAMY20260910, BRAMY20270730, BRAWH20028110, BRAWH20075700, BRAWH20096780, BRCAN20280210, BRCOC20144000, BRCOC20178270, BRHIP20005340, BRHIP20096170, BRHIP20119330, BRHIP20191860, BRHIP20195890, BRHIP20222280, BRSSN20039370, BRSSN20046790, BRSSN20176820, CTONG20050280, CTONG20075860, CTONG20085950, CTONG20091080, CTONG20092700, CTONG20121010, CTONG20124220, CTONG20133390, CTONG20133520, D90ST20033970, FCBBF10001710, FCBBF10004370, FCBBF20059090, FCBBF20068820, FCBBF30007680, FCBBF30010810, FCBBF30018550, FCBBF30025560, FCBBF30057290, FCBBF30083820, FCBBF30129630, FCBBF30240960, FCBBF30246230, FEBRA20018690, FEBRA20026110, FEBRA20034680, FEBRA20040530, FEBRA20082010, FEBRA20171380, FEBRA20195820, FEBRA20233770, HCHON20008320, HCHON20009560, HCHON20035130, HHDPC10000830, HHDPC20030490, HHDPC20031130, KIDNE20027250, KIDNE20027950, KIDNE20182690, LIVER20055440, NT2NE20010490, NT2NE20089970, NT2NE20142210, NT2NE20184900, NT2RP60000770, NT2RP70043480, NT2RP70063950, NT2RP70102350, NT2RP70157890, NTONG20070200, OCBBF10001850, OCBBF20020830, OCBBF20037440, OCBBF20046120, OCBBF20049300, OCBBF20054200, OCBBF20066390, OCBBF20071840, OCBBF20080410, OCBBF20108190, OCBBF20125530, OCBBF20148280, PEBLM20060360, PEBLM20078320, PERIC20003870, PROST10003220, PROST20047390, PROST20066880, PROST20185830, PROST20189770, PROST20191640, SKNSH20008190, SMINT20001760, SMINT20028820, SMINT20130320, SMINT20144800, SPLEN20026950, SPLEN20054290, SPLEN20079260, SPLEN20095410, SPLEN20117660, SPLEN20140800, SPLEN20147390, SPLEN20160450, SPLEN20162680, SPLEN20243830, SPLEN20250170, SPLEN20252190, SPLEN20267650, STOMA20032890, STOMA20063250, TESTI20039400, TESTI20041690, TESTI20067200, TESTI20088220, TESTI20130010, TESTI20156100, TESTI20230850, TESTI20318090, TESTI20320670, TESTI20378190, TESTI20385960, TESTI20409890, TESTI20420620, TESTI20432820, TESTI20456110, THYMU20247480, TRACH20079690, TRACH20154860, TRACH20163170, TRACH20164980, TRACH20184490, UTERU20099720, UTERU20116570, UTERU20145480, UTERU20176130

The clones predicted to belong to the category of disease-related protein are the following 387 clones. ADIPS20004250, ADRGL10001470, ADRGL20011190, ADRGL20018300, ADRGL20035850, ADRGL20078100, ASTRO10001650, ASTRO20008010, ASTRO20027430, ASTRO20106150, ASTRO20108190, ASTRO20168470, BLADE20003400, BLADE20003890, BRACE20038480, BRACE20039540, BRACE20059370, BRACE20108130, BRACE20108880, BRACE20115920, BRACE20116460, BRACE20232840, BRACE20248260, BRACE20253330, BRACE20284100, BRALZ20013500, BRALZ20017430, BRALZ20018340, BRAMY20000520, BRAMY20025840, BRAMY20120910, BRAMY20134140, BRAMY20135900, BRAMY20162510, BRAMY20174550, BRAMY20210400, BRAMY20211390, BRAMY20242470, BRAMY20245300, BRAMY20266850, BRAMY20285160, BRAWH20016620, BRAWH20028110, BRAWH20064050, BRAWH20096780, BRAWH20110960, BRAWH20113430, BRAWH20114000, BRAWH20118230, BRAWH20121640, BRAWH20128270, BRAWH20137480, BRCAN20103740, BRCAN20224720, BRCAN20279700, BRCAN20280210, BRCAN20283190, BRCOC20001860, BRCOC20006370, BRCOC20027510, BRCOC20055420, BRCOC20099370, BRCOC20178270, BRCOC20178560, BRHIP20003120, BRHIP20005340, BRHIP20174040, BRHIP20176420, BRHIP20191490, BRHIP20191860, BRHIP20194940, BRHIP20195890, BRHIP20222280, BRHIP20249110, BRHIP20285930, BRHIP30004880, BRSSN20013420, BRSSN20038200, BRSSN20039370, BRSSN20046790, BRSSN20066110, BRSSN20101100, BRSSN20120810, BRSSN20187310, BRTHA20046290, CD34C30004240, COLON10001350, CTONG20004690, CTONG20052650, CTONG20099550, CTONG20124220, CTONG20125640, CTONG20128430, CTONG20131560, CTONG20133390, CTONG20153300, CTONG20153580, CTONG20158040, CTONG20159530, D60ST20003580, D90ST20023970, DFNES20001530, DFNES20037420, FCBBF10001210, FCBBF10001710, FCBBF10003770, FCBBF20059090, FCBBF20064520, FCBBF20068820, FCBBF30010810, FCBBF30024750, FCBBF30025560, FCBBF30039020, FCBBF30049550, FCBBF30057290, FCBBF30083620, FCBBF30129630, FCBBF30190850, FCBBF30238870, FCBBF30240960, FCBBF30243640, FCBBF30279030, FCBBF30281880, FCBBF40001730, FEBRA10001880, FEBRA20004620, FEBRA20010120, FEBRA20018690, FEBRA20082010, FEBRA20097310, FEBRA20130190, FEBRA20132740, FEBRA20144170, FEBRA20195820, FEBRA20223220, FEBRA20233770, FEBRA20235500, FEHRT20003250, HCHON10001760, HCHON20007380, HCHON20008320, HCHON20009560, HCHON20015230, HCHON20015980, HCHON20016040, HCHON20035130, HCHON20036420, HCHON20064590, HCHON20067700, HCHON20086720, HCHON20100740, HEART20003060, HEART20017730, HEART20025980, HEART20049410, HHDPC20014320, HHDPC20030490, HHDPC20084140, HHDPC20091140, HHDPC20091780, HHDPC20092080, HLUNG20033780, IMR3220002430, KIDNE20007770, KIDNE20020150, KIDNE20021680, KIDNE20022620, KIDNE20024830, KIDNE20027950, KIDNE20101370, KIDNE20101510, KIDNE20182690, LIVER20002160, LIVER20055200, LIVER20055440, LIVER20059810, LIVER20064690, MESAN20101140, MESAN20125860, MESAN20130220, MESAN20154010, MESAN20174170, NOVAR10000910, NT2NE20010490, NT2NE20118960, NT2NE20157470, NT2RI20040990, NT2RI20041880, NT2RI20048840, NT2RI20050960, NT2RI20240080, NT2RP60000770, NT2RP70027380, NT2RP70032610, NT2RP70037240, NT2RP70192730, NT2RP70198350, NTONG20013620, NTONG20015870, NTONG20028070, NTONG20067830, NTONG20070200, NTONG20090600, NTONG20092330, OCBBF20006770, OCBBF20037440, OCBBF20046120, OCBBF20049300, OCBBF20053490, OCBBF20053730, OCBBF20054760, OCBBF20071840,. OCBBF20072240, OCBBF20078920, OCBBF20108430, OCBBF2010858,0, OCBBF20127140, OCBBF20129360, OCBBF20145760, OCBBF20153350, OCBBF20173980, OCBBF20178880, PEBLM10000710, PEBLM20013120, PERIC10000250, PLACE60060420, PLACE60177140, PROST20100460, PROST20159240, PROST20169800, PROST20176170, PUAEN20018820, PUAEN20030180, PUAEN20055020, PUAEN20083140, SKMUS20018230, SKMUS20018500, SKMUS20021530, SKMUS20024750, SKMUS20029200, SKMUS20048970, SKMUS20049030, SKNSH20008190, SKNSH20089400, SMINT20001760, SMINT20026890, SMINT20028820, SMINT20050750, SMINT20073650, SMINT20105330, SMINT20112730, SMINT20121220, SMINT20127350, SMINT20127930, SMINT20136130, SMINT20138900, SMINT20153260, SMINT20155180, SMINT20179740, SMINT20190170, SMINT20191420, SPLEN20006070, SPLEN20011410, SPLEN20026950, SPLEN20027440, SPLEN20039240, SPLEN20079260, SPLEN20095410, SPLEN20146450, SPLEN20147390, SPLEN20151210, SPLEN20160450, SPLEN20170310, SPLEN20179180, SPLEN20186430, SPLEN20212730, SPLEN20243830, SPLEN20245300, SPLEN20250390, SPLEN20252190, SPLEN20267650, SPLEN20305620, STOMA20001830, STOMA20005390, STOMA20008880, STOMA20010250, STOMA20034770, STOMA20046680, STOMA20056670, STOMA20064470, STOMA20077450, STOMA20080500, STOMA20083610, STOMA20088380, SYNOV20001520, SYNOV20001730, SYNOV20002790, SYNOV20002970, SYNOV20007000, SYNOV20008240, SYNOV20009230, SYNOV20010880, SYNOV20011110, TBAES20003770, TESOP20004000, TESOP20005270, TESTI20031270, TESTI20036380, TESTI20044310, TESTI20067200, TESTI20116830, TESTI20121550, TESTI20156100, TESTI20168480, TESTI20208400, TESTI20215990, TESTI20231940, TESTI20234360, TESTI20237520, TESTI20238610, TESTI20239510, TESTI20249990, TESTI20266740, TESTI20316870, TESTI20318090, TESTI20335050, TESTI20335200, TESTI20343570, TESTI20352620, TESTI20368330, TESTI20369650, TESTI20385960, TESTI20392250, TESTI20400940, TESTI20404240, TESTI20420620, TESTI20436560, TESTI20438570, TESTI20441940, TESTI20442760, TESTI20443090, TESTI20449200, TESTI20455090, TESTI20455620, TESTI20456110, TESTI20463580, TESTI20465350, TESTI20465690, TESTI20467210, THYMU20122730, THYMU20126900, THYMU20130890, THYMU20159430, THYMU20169650, THYMU20172150, THYMU20180280, THYMU20193640, THYMU20209590, THYMU20232090, THYMU20247480, TKIDN10000010, TKIDN20004640, TKIDN20047480, TRACH20016210, TRACH20019960, TRACH20050040, TRACH20057690, TRACH20067620, TRACH20077540, TRACH20079690, TRACH20096610, TRACH20105870, TRACH20121380, TRACH20154860, TRACH20162860, TRACH20163170, TRACH20164980, TRACH20190240, TSTOM20005690, TUTER20002830, UTERU20003570, UTERU20116570, UTERU20144640, UTERU20151980, UTERU20158800, UTERU20183640, UTERU20185230

In particular, hit data of the following 386 clones for Swiss-Prot, or GenBank, UniGene, or nr corresponded to genes or proteins which had been deposited in the Online Mendelian Inheritance in Man (OMIM), which is the human gene and disease database, (the OMIM Number is shown in the parenthesis after the Clone Name). ADIPS20004250 (601505), ADRGL10001470 (202010;103900), ADRGL20011190 (182790), ADRGL20018300 (600025), ADRGL20035850 (202110), ADRGL20078100 (103270), ASTRO10001650 (126660), ASTRO20008010 (603899), ASTRO20027430 (179555), ASTRO20106150 (602537), ASTRO20108190 (191092), ASTRO20168470 (604077), BLADE20003400 (601276), BLADE20003890 (604077), BRACE20038480 (601504), BRACE20039540 (600169), BRACE20059370 (130500;266140), BRACE20108130 (605413), BRACE20108880 (603758), BRACE20115920 (300023), BRACE20116460 (603150), BRACE20232840 (601213), BRACE20248260 (600813), BRACE20253330 (604990), BRACE20284100 (602415), BRALZ20013500 (602470), BRALZ20017430 (600658), BRALZ20018340 (600547), BRAMY20000520 (164020), BRAMY20025840 (602327), BRAMY20120910 (600188), BRAMY20134140 (603931), BRAMY20135900 (601342), BRAMY20162510 (300098), BRAMY20174550 (605464), BRAMY20210400 (603809), BRAMY20211390 (602212), BRAMY20242470 (605000), BRAMY20245300 (605367), BRAMY20266850 (605609), BRAMY20285160 (120700), BRAWH20016620 (605762), BRAWH20028110 (602330), BRAWH20064050 (135820), BRAWH20096780 (602277), BRAWH20110960 (603481), BRAWH20113430 (602649), BRAWH20114000 (138130), BRAWH20118230 (112267), BRAWH20121640 (604437), BRAWH20128270 (601997), BRAWH20137480 (602330), BRCAN20103740 (602566), BRCAN20224720 (600923;176200), BRCAN20279700 (604205), BRCAN20280210 (194538), BRCAN20283190 (602118), BRCOC20001860 (604346), BRCOC20006370 (603784), BRCOC20027510 (179555), BRCOC20055420 (603801), BRCOC20099370 (606045), BRCOC20178270 (194558), BRCOC20178560 (602567), BRHIP20003120 (604249), BRHIP20005340 (147586), BRHIP20174040 (602658), BRHIP20176420 (164020), BRHIP20191490 (600009), BRHIP20191860 (602272), BRHIP20194940 (604696), BRHIP20195890 (602211), BRHIP20222280 (603899), BRHIP20249110 (142600), BRHIP20285930 (602626), BRHIP30004880 (188840), BRSSN20013420 (300272), BRSSN20038200 (602306), BRSSN20039370 (194531), BRSSN20046790 (604077), BRSSN20066110 (605248), BRSSN20101100 (600188), BRSSN20120810 (142440), BRSSN20187310 (182900), BRTHA20046290 (602644), COLON10001350 (146900), CTONG20004690 (600019), CTONG20052650 (603871), CTONG20099550 (190370), CTONG20124220 (184756), CTONG20125640 (180510), CTONG20128430 (601797), CTONG20131560 (103390), CTONG20133390 (604077), CTONG20153300 (604334), CTONG20153580 (605652), CTONG20158040 (602862), CTONG20159530 (600395), D60ST20003580 (602443), D90ST20023970 (601525), DFNES20001530 (164500), DFNES20037420 (139259), FCBBF10001210 (602461), FCBBF10001710 (194558), FCBBF10003770 (604597), FCBBF20059090 (194542), FCBBF20064520 (164020), FCBBF20068820 (194558), FCBBF30010810 (603899), FCBBF30024750 (603706), FCBBF30025560 (600494), FCBBF30039020 (602835), FCBBF30049550 (106410), FCBBF30057290 (194556), FCBBF30083620 (300022), FCBBF30129630 (603899), FCBBF30190850 (131210), FCBBF30238870 (602320), FCBBF30240960 (604078), FCBBF30243640 (601961), FCBBF30279030 (605208), FCBBF30281880 (602517), FCBBF40001730 (176981), FEBRA10001880 (605451), FEBRA20004620 (600278), FEBRA20010120 (600368), FEBRA20018690 (194542), FEBRA20082010 (602187), FEBRA20097310 (602895), FEBRA20130190 (605863), FEBRA20132740 (602654), FEBRA20144170 (601685), FEBRA20195820 (604074), FEBRA20223220 (604633), FEBRA20233770 (603347), FEBRA20235500 (312090), FEHRT20003250 (600286), HCHON10001760 (605315), HCHON20007380 (600833), HCHON20008320 (604077), HCHON20009560 (194548), HCHON20015230 (604646), HCHON20015980 (604789), HCHON20016040 (146732), HCHON20035130 (194529), HCHON20036420 (603434), HCHON20064590 (103950), HCHON20067700 (603054), HCHON20086720 (146732), HCHON20100740 (602281), HEART20003060 (109480), HEART20017730 (106410), HEART20025490 (602127), HEART20049410 (603777), HHDPC20014320 (602714), HHDPC20030490 (603795), HHDPC20084140 (605184), HHDPC20091140 (603054), HHDPC20091780 (227400), HHDPC20092080 (146732), HLUNG20033780 (600888), IMR3220002430 (602923), KIDNE20007770 (114890), KIDNE20020150 (140550;603012), KIDNE20021680 (601609), KIDNE20022620 (603590), KIDNE20024830 (604205), KIDNE20027950 (194531), KIDNE20101370 (602580), KIDNE20101510 (191845), KIDNE20182690 (605226), LIVER20002160 (600816), LIVER20055200 (604814), LIVER20055440 (605277), LIVER20059810 (230350), LIVER20064690 (601841), MESAN20101140 (602567), MESAN20125860 (155750), MESAN20130220 (603778), MESAN20154010 (180480), MESAN20174170 (602516), NOVAR10000910 (159350), NT2NE20010490 (603899), NT2NE20118960 (180490), NT2NE20157470 (217000), NT2RI20040990 (106410), NT2RI20041880 (160775), NT2RI20048840 (139360), NT2RI20050960 (606103), NT2RI20240080 (603419), NT2RP60000770 (603044), NT2RP70027380 (118423), NT2RP70032610 (172430), NT2RP70037240 (604108), NT2RP70192730 (278000), NT2RP70198350 (300043), NTONG20013620 (604125), NTONG20015870 (123940), NTONG20028070 (602369), NTONG20067830 (182900), NTONG20070200 (194558), NTONG20090600 (313440), NTONG20092330 (153700), OCBBF20006770 (154500), OCBBF20037440 (602290), OCBBF20046120 (601262), OCBBF20049300 (602277), OCBBF20053490 (154550;602579), OCBBF20053730 (603604), OCBBF20054760 (603453), OCBBF20071840 (604077), OCBBF20072240 (604331), OCBBF20078920 (602120), OCBBF20108430 (139360), OCBBF20108580 (300103), OCBBF20127140 (139380), OCBBF20129360 (602142), OCBBF20145760 (600395), OCBBF20153350 (601935), OCBBF20173980 (603524), OCBBF20178880 (601617), PEBLM10000710 (601007), PEBLM20013120 (602288), PERIC10000250 (603582), PLACE60060420 (180469), PLACE60177140 (600022), PROST20100460 (158374), PROST20159240 (606019), PROST20169800 (604426), PROST20176170 (605903), PUAEN20018820 (164740), PUAEN20030180 (603263), PUAEN20055020 (604677), PUAEN20083140 (604762), SKMUS20018230 (603768), SKMUS20018500 (601402), SKMUS20021530 (606045), SKMUS20024750 (179555), SKMUS20029200 (605758), SKMUS20048970 (102610), SKMUS20049030 (161650), SKNSH20008190 (604075), SKNSH20089400 (603070), SMINT20001760 (194558), SMINT20026890 (602127), SMINT20028820 (604719), SMINT20050750 (182120), SMINT20073650 (146900), SMINT20105330 (230500;230600;230650;253010), SMINT20112730 (146900), SMINT20121220 (160776), SMINT20127350 (180740), SMINT20127930 (146900), SMINT20136130 (147220), SMINT20138900 (125660;601419), SMINT20153260 (602201), SMINT20155180 (603004), SMINT20179740 (147020), SMINT20190170 (146900), SMINT20191420 (102770), SPLEN20006070 (182900), SPLEN20011410 (602732), SPLEN20026950 (600014), SPLEN20027440 (106410), SPLEN20039240 (140550;603012), SPLEN20079260 (604074), SPLEN20095410 (602277), SPLEN20146450 (602861), SPLEN20147390 (604078), SPLEN20151210 (600267), SPLEN20160450 (604375), SPLEN20170310 (605216), SPLEN20179180 (605890), SPLEN20186430 (600052), SPLEN20212730 (114230), SPLEN20243830 (601796), SPLEN20245300 (606004), SPLEN20250390 (114220), SPLEN20252190 (604077), SPLEN20267650 (602277), SPLEN20305620 (126064), STOMA20001830 (146900), STOMA20005390 (146900), STOMA20008880 (601652;137750), STOMA20010250 (605786), STOMA20034770 (146900), STOMA20046680 (164772), STOMA20056670 (146900), STOMA20064470 (173320), STOMA20077450 (314370), STOMA20080500 (605414), .STOMA20083610 (146900), STOMA20088380 (146900), SYNOV20001520 (147200), SYNOV20001730 (147120), SYNOV20002790 (147120), SYNOV20002970 (147120), SYNOV20007000 (147120), SYNOV20008240 (147120), SYNOV20009230 (146900), SYNOV20010880 (147120), SYNOV20011110 (147120), TBAES20003770 (118990), TESOP20004000 (116810), TESOP20005270 (600641), TESTI20031270 (191161), TESTI20036380 (126650;214700), TESTI20044310 (179555), TESTI20067200 (176312), TESTI20116830 (603142), TESTI20121550 (600862), TESTI20156100 (602253), TESTI20168480 (188840), TESTI20208400 (164031), TESTI20215990 (605652), TESTI20231940 (604200), TESTI20234360 (601052), TESTI20237520 (604212), TESTI20238610 (300097), TESTI20239510 (604334), TESTI20249990 (164500), TESTI20266740 (605198), TESTI20316870 (605497), TESTI20318090 (604077), TESTI20335050 (605209), TESTI20335200 (109770), TESTI20343570 (190470), TESTI20352620 (176801;249900), TESTI20368330 (157680), TESTI20369650 (602052), TESTI20385960 (605970), TESTI20392250 (605541), TESTI20400940 (117143), TESTI20404240 (602725), TESTI20420620 (602955), TESTI20436560 (150330), TESTI20438570 (603577), TESTI20441940 (604119), TESTI20442760 (603491), TES.TI20443090 (602954), TESTI20449200 (604101), TESTI20455090 (148070), TESTI20455620 (140560), TESTI20456110 (109092), TESTI20463580 (603486), TESTI20465350 (123830), TESTI20465690 (605468), TESTI20467210 (600833), THYMU20122730 (604700), THYMU20126900 (603370), THYMU20130890 (603675), THYMU20159430 (146900), THYMU20169680 (601441), THYMU20172150 (605000), THYMU20180280 (600549), THYMU20193640 (603083;164021), THYMU20209590 (602378), THYMU20232090 (601717), THYMU20247480 (604077), TKIDN10000010 (605034), TKIDN20004640 (137028), TKIDN20047480 (602399), TRACH20016210 (136836), TRACH20019960 (182310), TRACH20050040- (603784), TRACH20057690 (164731), TRACH20067620 (600429;110800), TRACH20077540 (300080), TRACH20079690 (604078), TRACH20096610 (150330), TRACH20105870 (600495), TRACH20121380 (602513), TRACH20154860 (180240), TRACH20162860 (603845), TRACH20163170 (601739), TRACH20164980 (602277), TRACH20190240 (604633), TSTOM20005690 (605775), TUTER20002830 (602719), UTERU20030570 (602023;241200), UTERU20116570 (602330), UTERU20144640 (228000), UTERU20151980 (602038), UTERU20158800 (600738), UTERU20183640 (601281), UTERU20185230 (605333)

The clones predicted to belong to the category of enzyme and/or metabolism-related protein are the following 206 clones. 3NB6910001910, ADRGL10001470, ADRGL20035850, ADRGL20078100, ASTRO20105820, ASTRO20106150, ASTRO20130500, ASTRO20145760, BRACE20027620, BRACE20038000, BRACE20062640, BRACE20096200, BRACE20107530, BRACE20108130, BRACE20108880, BRACE20116460, BRACE20148240, BRACE20185680, BRACE20253160, BRALZ20017430, BRALZ20018340, BRAMY20104640, BRAMY20134140, BRAMY20153110, BRAMY20213100, BRAMY20252720, BRAWH20016620, BRAWH20105840, BRAWH20112940, BRAWH20114000, BRAWH20117950, BRAWH20125380, BRAWH20132190, BRAWH20171030, BRCAN20054490, BRCAN20224720, BRCAN20280360, BRCAN20283190, BRCAN20283380, BRCOC20001860, BRCOC20031250, BRCOC20055420, BRCOC20091960, BRCOC20144000, BRHIP10001290, BRHIP20005530, BRHIP20096850, BRHIP20103090, BRHIP20174040, BRHIP20249110, BRSSN20013420, BRSSN20015790, BRSSN20120810, BRSSN20146100, CTONG20095340, CTONG20106520, CTONG20118250, CTONG20127450, CTONG20140580, CTONG20153300, CTONG20158040, D30ST20006180, D60ST20003580, DFNES20031920, DFNES20071130, FCBBF10001820, FCBBF10003670, FCBBF30012350, FCBBF30012810, FCBBF30175310, FCBBF30243640, FEBRA10001880, FEBRA20007620, FEBRA20130190, FEBRA20144170, FEBRA20167390, FEBRA20196630, FEHRT20003250, HCHON10001760, HCHON20003220, HCHON20015350, HEART20034320, HEART20090000, HHDPC20014320, KIDNE20002520, KIDNE20008010, KIDNE20021680, KIDNE20022620, KIDNE20028390, KIDNE20028720, KIDNE20107620, LIVER20059810, MESAN20154010, NT2NE20118960, NT2NE20157470, NT2RI20005750, NT2RI20244600, NT2RI20273230, NT2RP70032610, NT2RP70045590, NT2RP70192730, NT2RP70195430, NTONG20009770, NTONG20013620, NTONG20046140, OCBBF20028650, OCBBF20030910, OCBBF20046690, OCBBF20050770, OCBBF20053430, OCBBF20053490, OCBBF20053730, OCBBF20054760, OCBBF20078920, OCBBF20124360, OCBBF20129360, OCBBF20178880, PEBLM20044520, PEBLM20052820, PEBLM20060490, PERIC10000250, PLACE50000660, PROST20083600, PROST20169800, PUAEN20015260, PUAEN20030180, SKMUS20018230, SMINT20028820, SMINT20049090, SMINT20102780, SMINT20105330, SMINT20106290, SMINT20110660, SMINT20152940, SMINT20191420, SMINT20191530, SPLEN20021660, SPLEN20026950, SPLEN20121750, SPLEN20145720, SPLEN20149240, SPLEN20150940, SPLEN20151210, SPLEN20173510, SPLEN20212730, SPLEN20250390, SPLEN20305620, STOMA20006860, STOMA20077450, TBAES20002550, TBAES20003150, TESOP20004000, TESOP20005270, TESTI20001000, TESTI20002720, TESTI20002780, TESTI20060400, TESTI20066670, TESTI20082330, TESTI20083200, TESTI20108720, TESTI20116830, TESTI20143390, TESTI20148000, TESTI20216370, TESTI20232140, TESTI20234360, TESTI20237520, TESTI20239510, TESTI20266740, TESTI20314180, TESTI20334410, TESTI20343570, TESTI20352620, TESTI20355020, TESTI20366910, TESTI20368330, TESTI20369650, TESTI20375340, TESTI20397760, TESTI20416640, TESTI20432750, TESTI20463580, TESTI20465350, TESTI20471410, TESTI20473830, THYMU20023380, THYMU20111830, THYMU20126900, THYMU20169680, THYMU20202890, TKIDN20004640, TKIDN20047480, TRACH20003590, TRACH20016210, TRACH20019960, TRACH20041830, TRACH20057690, TRACH20067620, TRACH20084720, TRACH20085830, TRACH20162860, UTERU20064860, UTERU20144640, UTERU20146310, UTERU20151980

The clones predicted to belong to the category of cytoskeleton-related protein are the following 75 clones. ADRGL20011190, ADRGL20018300, ASTRO10001650, ASTRO20055750, BRACE20003070, BRACE20059370, BRACE20163350, BRAMY20121620, BRAMY20157820, BRAMY20242470, BRAWH20028110, BRAWH20137480, BRCAN20003460, BRCOC20008160, BRCOC20059510, BRHIP20115080, BRHIP20137230, BRHIP20167880, BRHIP20283030, BRHIP20285830, BRSSN20187310, CTONG10002770, CTONG20052900, CTONG20121580, FCBBF10001150, FCBBF30013770, FCBBF30015940, FCBBF30049550, FEBRA20024100, FEBRA20237640, HCHON20015980, HCHON20068410, HEART20017730, HEART20025980, HEART20061950, HEART20077670, HLUNG20016330, KIDNE20118580, MESAN20004570, NT2RI20040990, NT2RI20041880, NT2RP70037240, NT2RP70062230, NTONG20015870, NTONG20056570, NTONG20067830, NTONG20090600, OCBBF20107090, OCBBF20155060, PLACE60079250, PUAEN20040670, SKMUS20001980, SKMUS20016220, SKMUS20048970, SKMUS20049030, SMINT20024570, SMINT20026890, SMINT20121220, SMINT20138900, SPLEN20006070, SPLEN20027440, SPLEN20142100, TESTI20063830, TESTI20094230, TESTI20278400, TESTI20371030, TESTI20417300, TESTI20436560, TESTI20455090, THYMU20105190, THYMU20172150, THYMU20209590, TRACH20096610, UMVEN10001560, UTERU20116570

The clones predicted to belong to the category of nuclear protein and/or RNA synthesis-related protein are the following 65 clones. BRACE20057190, BRACE20064880, BRACE20248260, BRACE20253160, BRAMY20000520, BRAMY20120910, BRAWH20113430, BRAWH20171030, BRCAN10001490, BRCAN20283190, BRCOC20037320, BRCOC20178560, BRHIP20106100, BRHIP20176420, BRHIP20243470, BRSSN20101100, CTONG20114290, CTONG20125540, CTONG20131560, CTONG20140580, DFNES20001530, FCBBF20064520, FEBRA20007620, FEBRA20010120, FEBRA20097310, FEBRA20144170, FEBRA20174410, FEBRA20215500, IMR3220002430, MESAN20101140, NT2RI20273230, OCBBF20028650, OCBBF20030910, OCBBF20078920, PROST20104000, PUAEN20018820, SKMUS20007010, SMINT20127350, SMINT20177360, SMINT20191530, SPLEN20008740, SPLEN20146450, STOMA20046680, TESTI20082330, TESTI20094470, TESTI20121550, TESTI20208400, TESTI20234360, TESTI20237520, TESTI20249990, TESTI20334410, TESTI20355020, TESTI20368330, TESTI20392760, TESTI20408970, TESTI20436560, TESTI20438570, TESTI20443090, THYMU20193640, THYMU20202890, THYMU20241210, TRACH20096610, TUTER20002830, UTERU20151980, UTERU20176320

The clones predicted to belong to the category of protein synthesis and/or transport-related protein are the following 62 clones. 3NB6910001910, ASTRO20106150, ASTRO20130500, ASTRO20141350, BRACE20038480, BRACE20052160, BRACE20057620, BRACE20106840, BRACE20172980, BRACE20192440, BRAWH20110960, BRCOC20037320, BRHIP20005530, BRSSN20120810, BRSTN20005360, CTONG20009770, CTONG20114290, CTONG20125640, CTONG20153300, D60ST20003580, DFNES20037420, FCBBF30012810, FEBRA20080810, HCHON20064590, HHDPC20014320, HHDPC20084140, HLUNG20017120, LIVER20064690, NT2NE20132170, NT2NE20157470, NT2RP70133740, NTONG20009770, NTONG20075220, NTONG20076930, OCBBF20030910, OCBBF20035930, OCBBF20153340, PLACE60060420, SMINT20152940, SPLEN20008740, SPLEN20103950, SPLEN20118300, SPLEN20212730, SPLEN20250390, STOMA20077450, TBAES20002550, TESOP20004000, TESTI20239510, TESTI20278400, TESTI20314180, TESTI20463580, THYMU20111830, THYMU20122730, THYMU20130890, THYMU20232090, TKIDN10000010, TRACH20084720, TRACH20105870, TRACH20139820, TRACH20149970, UTERU20120310, UTERU20188110

The clones predicted to belong to the category of cellular defense-related protein are the following 15 clones. BRCOC20144000, CTONG20092680, KIDNE20020150, LIVER20002160, NT2RI20050960, NT2RP70045590, OCBBF20128120, PLACE60003480, SKNSH20089400, SMINT20106290, SPLEN20039240, TESTI20001000, TESTI20455620, TRACH20028030, UTERU20176320

The clones predicted to belong to the category of development and/or differentiation-related protein are the following 13 clones. 3NB6920014590, BRAMY20211390, CTONG20091080, CTONG20121010, FCBBF30024750, KIDNE20027250, NT2NE20142210, OCBBF20054200, PROST10003220, SKMUS20007010, SPLEN20179810, STOMA20063250, TESTI20291960

The clones predicted to belong to the category of DNA-binding and/or RNA-binding protein are the following 174 clones. 3NB6920014590, ADIPS20004250, ASTRO20008010, ASTRO20168470, BLADE20003400, BLADE20003890, BRACE20057620, BRACE20060890, BRACE20064880, BRACE20068590, BRACE20248260, BRACE20253160, BRAMY20000520, BRAMY20213100, BRAMY20260910, BRAMY20270730, BRAWH20028110, BRAWH20075700, BRAWH20096780, BRAWH20113430, BRCAN10001490, BRCAN20280210, BRCAN20283190, BRCOC20144000, BRCOC20178270, BRCOC20178560, BRHIP20005340, BRHIP20106100, BRHIP20119330, BRHIP20153600, BRHIP20176420, BRHIP20191860, BRHIP20195890, BRHIP20222280, BRSSN20039370, BRSSN20046790, BRSSN20176820, CTONG20050280, CTONG20075860, CTONG20085950, CTONG20091080, CTONG20092700, CTONG20121010, CTONG20124220, CTONG20125540, CTONG20133390, CTONG20133520, CTONG20140580, CTONG20156780, D90ST20033970, FCBBF10001710, FCBBF10004370, FCBBF20059090, FCBBF20064520, FCBBF20068820, FCBBF30007680, FCBBF30010810, FCBBF30018550, FCBBF30025560, FCBBF30057290, FCBBF30083820, FCBBF30129630, FCBBF30240960, FCBBF30246230, FEBRA20010120, FEBRA20018690, FEBRA20026110, FEBRA20034680, FEBRA20040530, FEBRA20082010, FEBRA20097310, FEBRA20171380, FEBRA20195820, FEBRA20196630, FEBRA20233770, HCHON20008320,. HCHON20009560, HCHON20035130, HHDPC10000830, HHDPC20031130, KIDNE20017130, KIDNE20027250, KIDNE20027950, KIDNE20107390, KIDNE20182690, LIVER20055440, MESAN20101140, NT2NE20010490, NT2NE20089970, NT2NE20142210, NT2NE20184900, NT2RP60000770, NT2RP70044280, NT2RP70102350, NT2RP70157890, NTONG20070200, OCBBF10001850, OCBBF20020830, OCBBF20037440, OCBBF20046120, OCBBF20049300, OCBBF20066390, OCBBF20071840, OCBBF20078920, OCBBF20080410, OCBBF20108190, OCBBF20125530, OCBBF20148280, PEBLM20060360, PEBLM20060490, PEBLM20078320, PERIC10000250, PROST10003220, PROST20047390, PROST20066880, PROST20185830, PROST20189770, PROST20191640, PUAEN20018820, SKNSH20008190, SKNSH20089400, SMINT20001760, SMINT20127350, SMINT20144800, SMINT20177360, SMINT20191530, SPLEN20054290, SPLEN20079260, SPLEN20095410, SPLEN20140800, SPLEN20147390, SPLEN20160450, SPLEN20252190, SPLEN20267650, STOMA20010250, STOMA20032890, STOMA20046680, STOMA20063250, TESTI20039400, TESTI20067200, TESTI20088220, TESTI20094470, TESTI20121550, TESTI20130010, TESTI20156100, TESTI20204450, TESTI20230850, TESTI20237520, TESTI20266740, TESTI20318090, TESTI20320670, TESTI20334410, TESTI20355020, TESTI20378190, TESTI20385960, TESTI20432820, TESTI20443090, TESTI20456110, THYMU20193640, THYMU20241210, THYMU20247480, TRACH20079690, TRACH20105870, TRACH20139820, TRACH20154860, TRACH20163170, TRACH20164980, TRACH20184490, TUTER20002830, UTERU20099720, UTERU20116570, UTERU20145480, UTERU20176130, UTERU20185230

The clones predicted to belong to the category of ATP binding and/or GTP-binding protein are the following 68 clones. 3NB6910001910, BRACE20108130, BRACE20148240, BRAMY20134140, BRAMY20157820, BRAMY20174550, BRAWH20164460, BRCAN20003460, BRCAN20054490, BRCAN20283190, BRCOC20059510, BRCOC20144000, BRHIP20103090, BRHIP20115080, BRHIP20167880, BRSTN20005360, CD34C30004240, CTONG20095340, CTONG20121580, CTONG20200310, DFNES20037420, FCBBF20067810, FCBBF30012350, FCBBF30015940, FEBRA20007620, FEBRA20024100, FEBRA20144170, KIDNE20020150, KIDNE20028720, LIVER20002160, LIVER20087060, NT2RI20005750, NT2RI20041880, NT2RI20048840, NT2RI20273230, OCBBF20028650, OCBBF20046690, OCBBF20054760, OCBBF20108430, OCBBF20108630, SMINT20121220, SMINT20183530, SMINT20191530, SPLEN20026950, SPLEN20039240, SPLEN20099700, SPLEN20145720, SPLEN20179180, STOMA20006860, TESTI20035960, TESTI20355020, TESTI20397760, TESTI20400940, TESTI20417300, TESTI20443090, TESTI20455620, THYMU20105190, THYMU20202890, THYMU20209590, TKIDN20004640, TKIDN20047480, TRACH20005400, TRACH20019960, TRACH20057690, TRACH20084720, UTERU20168220, UTERU20176320, UTERU20185230

Among the clones other than the ones shown above, BRAMY20248490, FCBBF10002800, NTONG20092290, OCBBF20127040, SMINT20163960, THYMU20279750, TRACH20167220, are clones which were predicted to highly possibly belong to the category of secretory protein and/or membrane protein based on the result of domain search by Pfam. FCBBF10002800, NTONG20092290, OCBBF20127040, SMINT20163960, TESTI20478850, THYMU20279750

The 6 clones shown above are clones which were predicted to highly possibly belong to the category of glycoprotein-related protein based on the result of domain search by Pfam. BRACE20060720, BRACE20223330, BRALZ20058880, BRAMY20148130, BRAWH20101360, BRCAN20124080, BRHIP20253660, CTONG10000620, CTONG20014280, CTONG20124010, KIDNE20109890, MESAN20171520, OCBBF20109310, OCBBF20140640, PROST20079500, PUAEN20078980, SPLEN20077500, SPLEN20143180, TESTI20017950, TESTI20184620, TESTI20208710, TESTI20211160, TESTI20226230, TESTI20234140, TESTI20258460, TESTI20275030

The 26 clones shown above are clones which were predicted to highly possibly belong to the category of signal transduction-related protein based on the result of domain search by Pfam. ADRGL20048330, ASTRO20064750, ASTRO20084250, BRACE20151320, BRALZ20058880, BRHIP20207990, CTONG20093950, FCBBF30195640, FEBRA10001900, FEBRA20090290, FEBRA20214970, FEBRA20222040, KIDNE20109890, LIVER20087510, MESAN20029400, MESAN20031900, MESAN20035290, MESAN20136110, NT2NE20130190, PEBLM20060310, PERIC20004780, PROST20171280, PUAEN20078980, SMINT20115880, SPLEN20095550, TESTI20023510, TESTI20083940, TESTI20152460, TESTI20185650, TESTI20189410, TESTI20200710, TESTI20308600, TESTI20343070, TESTI20369690, TESTI20381040, UTERU20050690

The 36 clones shown above are clones which were predicted to highly possibly belong to the category of transcription-related protein based on the result of domain search by Pfam. BGGI120006160, BRACE20053480, BRACE20190040, BRACE20223330, BRAWH20101360, BRAWH20185060, BRCOC20023230, BRHIP20252450, BRSSN20105870, BRSSN20117990, BRTHA20000570, CTONG20098440, CTONG20129960, CTONG20146300, CTONG20155180, FEBRA20025270, HEART20083640, KIDNE20009470, LIVER20035680, MESAN20029400, MESAN20031900, MESAN20186700, NOVAR10000150, NTONG20029480, OCBBF20079310, OCBBF20082830, PEBLM20042900, PLACE60136500, PLACE60136720, PROST20114390, SKNSH20020540, SMINT20013480, SMINT20174360, SPLEN20077500, SPLEN20119810, SPLEN20126190, SPLEN20174260, SPLEN20211220, TESTI20046750, TESTI20057750, TESTI20061110, TESTI20197940, TESTI20211160, TESTI20226230, TESTI20255820, TESTI20317600, TESTI20377230, THYMU20111180, THYMU20115850, THYMU20143270, THYMU20240710, UTERU20055330, UTERU20055930, UTERU20064000, UTERU20119060

The 55 clones shown above are clones which were predicted to highly possibly belong to the category of enzyme and/or metabolism-related protein based on the result of domain search by Pfam. TESTI20127760, TESTI20392270

The 2 clones shown above are clones which were predicted to highly possibly belong to the category of cell division and/or cell proliferation-related protein based on the result of domain search by Pfam. FCBBF30262510, MESAN20031900, NT2NE20125050, SMINT20068010, SPLEN20163560, STOMA20092890, TESTI20382750

The 7 clones shown above are clones which were predicted to highly possibly belong to the category of cytoskeleton-related protein based on the result of domain search by Pfam. THYMU20118520

The clone shown above is clone which were predicted to highly possibly belong to the category of nuclear protein and/or RNA synthesis-related protein based on the result of domain search by Pfam. BRACE20053480, BRACE20240740, KIDNE20009470, OCBBF20140890, SMINT20035690, UTERU20064000

The 6 clones shown above are clones which were predicted to highly possibly belong to the category of protein synthesis and/or transport-related protein based on the result of domain search by Pfam. ADRGL20048330, ASTRO20064750, ASTRO20084250, BRACE20151320, BRACE20190040, BRACE20223330, BRALZ20058880, BRAMY20103570, BRCOC20023230, BRHIP20207990, BRTHA20000570, CTONG20093950, CTONG20129960, CTONG20146300, CTONG20155180, CTONG20160560, FCBBF10004120, FCBBF30195640, FEBRA10001900, FEBRA20090290, FEBRA20214970, FEBRA20222040, HCHON20008150, HEART20083640, KIDNE20109890, LIVER20035680, LIVER20087510, MESAN20029400, MESAN20031900, MESAN20035290, MESAN20136110, MESAN20186700, NT2NE20130190, NT2RI20025640, NTONG20029480, PEBLM20060310, PERIC20004780, PROST20114390, PROST20171280, PUAEN20078980, SMINT20115880, SPLEN20095550, SPLEN20119810, TESTI20023510, TESTI20057750, TESTI20083940, TESTI20152460, TESTI20185650, TESTI20189410, TESTI20200710, TESTI20308600, TESTI20343070, TESTI20369690, TESTI20381040, THYMU20115850, UTERU20050690, UTERU20055330

The 57 clones shown above are clones which were predicted to highly possibly belong to the category of DNA-binding and/or RNA-binding protein based on the result of domain search by Pfam. PLACE60136720

The clone shown above is a clone which was predicted to highly possibly belong to the category of ATP-binding and/or GTP-binding protein based on the result of domain search by Pfam.

The 213 clones shown below are clones which were unassignable to any of the above-mentioned categories, but have been predicted to have some functions based on homology search for their full-length nucleotide sequences and motif search in their deduced ORFs. Clone Name, Definition in the result of homology search or Motif Name in the motif search, demarcated by a double slash mark (//), are shown below. ADRGL20028570//*Rattus norvegicus* MG87 mRNA, complete cds. ADRGL20061930//transposon-derived Busterl transposase-like protein ASTRO20012490//Eukaryotic initiation factor 1A ASTRO20072210//PERIAXIN. ASTRO20114370//*Mus musculus* SMARI mRNA, complete cds. ASTRO20125520// dnaj protein [Schizosaccharomyces pombe] ASTRO20143630//KH domain// Bacterial regulatory proteins, crp family ASTRO20155290//TPR Domain// TPR Domain// TPR Domain ASTRO20181690//oocyte-specific protein P100 BGGI110001930//UBX domain BRACE20011070//*Mus musculus* F-box protein FBX15 mRNA, partial cds. BRACE20039440//*Drosophila melanogaster* CHARYBDE (charybde) mRNA, complete cds. BRACE20050900//TPR Domain// TPR Domain// TPR Domain// TPR Domain BRACE20053280//*Mus musculus* Pdz-containing protein (Pdzx) mRNA, complete cds. BRACE20057730//toxin sensitivity protein KTI12 homolog BRACE20058580//*Homo sapiens* HCMOGT-1 mRNA for sperm antigen, complete cds. BRACE20063780//NOL1/NOP2/sun family BRACE20269200//Heat-labile enterotoxin alpha chain BRACE20276430//*Homo sapiens* retinoblastoma-associated protein RAP140 mRNA, complete cds. BRACE20286360//Alpha adaptin carboxyl-terminal domain BRAMY10001300//*Homo sapiens* MAGE-E1b mRNA, complete cds. BRAMY20045240//Flagellar L-ring protein BRAMY20054880//*Rattus norvegicus* KPL2 (Kpl2) mRNA, complete cds. BRAMY20167060//Collagen triple helix repeat (20 copies) BRAMY20184670//*Homo sapiens* mRNA for ALEXI, complete cds. BRAMY20217460// *Homo sapiens* cardiac voltage gated potassium channel modulatory subunit mRNA, complete cds, alternatively spliced. BRAMY20240040//*Homo sapiens* suppressor of white apricot homolog 2 (SWAP2) mRNA, complete cds. BRAMY20247110//*Mus musculus* semaphorin cytoplasmic domain-associated protein 3A (Semcap3) mRNA, complete cds. BRAWH20004600//*Mus musculus* mRNA for NAKAP95, complete cds. BRAWH20011710//cytoplasmic linker 2 BRAWH20012390//Trichomonas vaginalis mRNA for centrin (cel gene). BRAWH20017010//*Homo sapiens* testes development-related NYD-SP22 mRNA, complete cds. BRAWH20029630//*Homo sapiens* bet3 (BET3) mRNA, complete cds. BRAWH20138660//*Homo sapiens* stonin 2 mRNA, complete cds. BRCOC20008500//Human ras inhibitor mRNA, 3' end. BRCOC20026640//Gag P30 core shell protein BRCOC20035130//14-3-3 PROTEIN EPSILON (MITOCHONDRIAL IMPORT STIMULATION FACTOR L SUBUNIT) (PROTEIN KINASE C INHIBITOR PROTEIN-1) (KCIP-1) (14-3-3E). BRCOC20074760//CDC4-LIKE PROTEIN (FRAGMENT). BRCOC20110100//Integrase core domain BRCOC20176520//*Rattus norvegicus* mRNA for type II brain 4.1, complete cds. BRHIP20001630//Protein of unknown function DUF16 BRHIP20132860//*Homo sapiens* rhophilin-like protein mRNA, complete cds. BRHIP20143730//MYND finger BRHIP20175420//*Mus musculus* partial mRNA for stretch responsive protein 278 (sr278 gene). BRHIP20236950//Outer Capsid protein VP4 (Hemagglutinin) BRSSN20014260//RIBONUCLEASE INHIBITOR. BRSSN20018690//*Homo sapiens* NY-REN-25 antigen mRNA, partial cds. BRSSN20021600//RING CANAL PROTEIN (KELCH PROTEIN). BRSSN20177570//Phosducin BRSTN10000830//Kelch motif// Kelch motif// Kelch motif// Kelch motif CTONG10000220//*Mus musculus* cerebellar postnatal development protein-1 (Cpd1) mRNA, partial cds. CTONG10000930//Armadillo/beta-catenin-like repeats CTONG20027090//Glypican// Leucine Rich Repeat// Leucine Rich Repeat CTONG20076130//ZINC FINGER PROTEIN 185 (LIM-DOMAIN PROTEIN ZNF185) (P1-A). CTONG20096750//Disintegrin CTONG20100240//*Mus musculus* radial spokehead-L protein (Rshl1) mRNA, complete cds. CTONG20139860//*Homo sapiens* nasopharyngeal carcinoma susceptibility protein LZ16 mRNA, complete cds. CTONG20143690//MYND finger CTONG20149460//RING CANAL PROTEIN (KELCH PROTEIN). CTONG20165050//Keratin, high sulfur B2 protein CTONG20186320//RING CANAL PROTEIN (KELCH PROTEIN). D30ST20013280//ARP2/3 COMPLEX 16 KDA SUBUNIT (P16-ARC). D30ST20024360//*Homo sapiens* neuroendocrine differentiation factor mRNA, complete cds. D90ST20031370//*Homo sapiens* mRNA for partial putative TCPTP-interacting protein (ptpip5 gene). DFNES20014040//TRICHOHYALIN. FCBBF10000630//*Homo sapiens* huntingtin interacting protein HYPB mRNA, partial cds. FCBBF10000770//*Homo sapiens* REC8 mRNA, partial cds. FCBBF10005060//CELLULAR RETINALDEHYDE-BINDING PROTEIN (CRALBP). FCBBF10005500//Keratin, high sulfur B2 protein FCBBF20014270//ACYL-COA-BINDING PROTEIN (ACBP) (DIAZEPAM BINDING INHIBITOR) (DBI) (ENDOZEPINE) (EP). FCBBF20042170//*Homo sapiens* NIBAN mRNA, complete cds. FCBBF30016320//SecA protein, amino terminal region FCBBF30033050//Sm protein FCBBF30054440//PLAT/LH2 domain FCBBF30225660//Ank repeat// Ank repeat// Ank repeat// K+ channel tetramerisation domain// BTB/POZ domain FCBBF30233680//G10 protein FCBBF30246630//*H.sapiens* mRNA for ZYG homologue. FCBBF30250730//TRICHOHYALIN. FCBBF30252520//*Homo sapiens* bicaudal-D (BICD) mRNA, alternatively spliced, partial cds. FCBBF30252800//NDRG1 PROTEIN (DIFFERENTIATION-RELATED GENE 1 PROTEIN) (DRG1) (REDUCING AGENTS AND TUNICAMYCIN-RESPONSIVE PROTEIN) (RTP) (NICKEL-SPECIFIC INDUCTION PROTEIN CAP43). FCBBF30252850//*Mus musculus* peripherial benzodiazepine receptor associated protein (Pap7) mRNA, complete cds. FCBBF30285280//Keratin, high sulfur B2 protein// Bacterial regulatory proteins, gntR family FEBRA20088360//ALPHA-ADAPTIN C (CLATHRIN ASSEMBLY PROTEIN COMPLEX 2 ALPHA-C LARGE CHAIN) (100 KDA COATED VESICLE PROTEIN C) (PLASMA MEMBRANE ADAPTOR HA2/AP2 ADAPTIN ALPHA C SUBUNIT). FEBRA20184330//*Rattus norvegicus* glutamate receptor interacting protein 2 (GRIP2) mRNA, complete cds. FEBRA20192420//Cyclin-dependent kinase inhibitor// IQ calmodulin-binding motif// IQ calmodulin-binding motif// IQ calmodulin-binding motif// IQ calmodulin-binding motif// IQ calmodulin-binding motif FEBRA20196370//Cyclin-dependent kinase inhibitor// IQ calmodulin-binding motif// IQ calmodulin-binding motif// IQ calmodulin-binding motif// IQ calmodulin-binding motif// IQ calmodulin-binding motif FEBRA20225040//high-glucose-regulated protein 8 HCHON20001560//TRANSCRIPTION FACTOR-LIKE PROTEIN MORF4. HCHON20003440//*Homo sapiens* cyclin-D binding Myb-like protein mRNA, complete cds. HCHON20010990//TPR Domain HCHON20059870//Hypothetical protein. 1HHDPC20034390//Cereal trypsin/alpha-amylase inhibito HHDPC20057420//*Mus musculus* proline-rich protein (Bprp) mRNA, complete cds. HHDPC20064600//SUPPRESSOR PROTEIN SRP40. HLUNG20023340//*Mus musculus* SLM-1 (Slm1) mRNA, complete cds. KIDNE20007210//*Xenopus laevis* mRNA for RPA interacting protein alpha (ripalpha gene). KIDNE20028830//K-box region KIDNE20115080//*Homo sapiens* mRNA for hNBL4, complete cds. KIDNE20124400//*Homo sapiens* mRNA for ALEX1, complete cds. KIDNE20127100//*Drosophila melanogaster* Diablo (dbo) mRNA, complete cds. KIDNE20127750// *Homo sapiens* partial mRNA for transport-secretion protein 2.1 (TTS-2.1 gene). KIDNE20190740//*Rattus norvegicus* SNIP-b mRNA, complete cds. LIVER10004790//EF hand LIVER20011130//*Homo sapiens* F-box protein FBL9 mRNA, partial cds. LIVER20064100//Ciona intestinalis mRNA for myoplasmin-C1, complete cds. LIVER20080530//*Drosophila melanogaster* forked mRNA for large Forked protein, complete cds. MAMGL10000830// *Drosophila melanogaster* L82B (L82) mRNA, complete cds. MESAN20036460//Corticotropin-releasing factor family MESAN20127350//myelin expression factor-3 MESAN20141920//Human ovarian cancer downregulated myosin heavy chain homolog (Doc1) mRNA, complete cds. NT2NE20010400//*Homo sapiens* GL013 mRNA, complete cds. NT2NE20122430//GLYOXYLATE-INDUCED PROTEIN. NT2NE20158600//erythroid ankyrin-Synechocystis sp. (strain PCC 6803). NT2RI20001330//*Homo sapiens* KE03 protein mRNA, partial cds. NT2RI20009870//lunatic fringe precursor [Mus musculus] NT2RI20046080//recA bacterial DNA recombination proteins NT2RI20091730// Molluscan rhodopsin C-terminal tail NT2RP60000850//Bos taurus RPGR-interacting protein-1 (RPGRIP1) mRNA, complete cds. NT2RP70080850//SPRY domain// Adenovirus EBI 55K protein / large t-an NT2RP70105210//Myc amino-terminal region NT2RP70188710//Yeast PIR proteins NT2RP70194450//Bacterial regulatory proteins, crp family NTONG20052650//Gallus gallus Xin mRNA, complete cds. NTONG20064400//REPETIN. NTONG20064840//*Mus musculus* slpl mRNA for synaptotagmin-like protein 1, complete cds. NTONG20066460// *Mus musculus* Gd mRNA for gasdermin, complete cds. NTONG20067090//*Mus musculus* mRNA for Sh3yl1, complete cds. NTONG20070340//collagen alpha 1(IX) chain NTONG20083650//TPR Domain// TPR Domain// TPR Domain// PPR repeat// TPR Domain// PPR repeat// TPR Domain NTONG20088620//*Homo sapiens* genethonin 3 mRNA, partial cds. OCBBF10000540//*Mus musculus* rjs (ris) mRNA, complete cds. OCBBF20019380//seizure related gene 6 OCBBF20022900//*Homo sapiens* SCHIP-1 mRNA, complete cds. OCBBF20030280//*Rattus norvegicus* hfb2 mRNA, complete cds. OCBBF20046470//ARFAPTIN 1. OCBBF20049840//*Homo sapiens* mRNA for neurabin II protein. OCBBF20068490//*Mus musculus* RW1 protein mRNA, complete cds. OCBBF20071960//Coturnix coturnix japonica qMEF2D gene. OCBBF20073540//*Homo sapiens* p30 DBC mRNA, complete cds. OCBBF20121390//RING CANAL PROTEIN (KELCH PROTEIN). OCBBF20127550//Outer Capsid protein VP4 (Hemagglutinin) OCBBF20148730//RING CANAL PROTEIN (KELCH PROTEIN). OCBBF20178150//Plasmodium falciparum ADA2-like protein gene, partial cds. PEBLM10000240// Domain found in Dishevelled, Egl-10, and Ple PROST20047270//CRAL/TRI0 domain. PROST20112970//Sterile alpha motif (SAM)/Pointed domain// SAM domain (Sterile alpha motif) PUAEN10000850//Uncharacterized protein family UPF0025// Secl family PUAEN20011880//*Mus musculus* mRNA for MIWI (piwi), complete cds. PUAEN20051100//*Mus musculus* otogelin mRNA, complete cds. PUAEN20108240//*Drosophila melanogaster* ankyrin 2 (Ank2) mRNA, complete cds. SKMUS20084740//Syndecan domain SMINT20053300//*Homo sapiens* hepatocellular carcinoma-associated antigen 59 mRNA, complete cds. SMINT20071400//NOL1/NOP2/sun family SMINT20101440//Human cisplatin resistance associated alpha protein (hCRA alpha) mRNA, complete cds. SMINT20110330//pKID domain SMINT20122910//*Mus musculus* StAR-related protein 1-4E mRNA, partial cds. SMINT20131810//ENV polyprotein (coat polyprotein) SMINT20168570//*Homo sapiens* mRNA for stabilin-1 (stab1 gene). SPLEN20008390//Human placenta (Diff48) mRNA, complete cds. SPLEN20084600//RING CANAL PROTEIN (KELCH PROTEIN). SPLEN20128000//*Xenopus laevis* XMAB21 (Xmab-21) mRNA, complete cds. SPLEN20149110//Dishevelled specific domain SPLEN20171470//Keratin, high sulfur B2 protein SPLEN20194050//*Homo sapiens* HOTTL protein mRNA, complete cds. SPLEN20214580//*Mus musculus* mdgl-1 mRNA, complete cds. STOMA20057820//Uncharacterized protein family UPF0024 STOMA20063980//Collagen triple helix repeat (20 copies) STOMA20069040//Keratin, high sulfur B2 protein SYNOV20017080//UBX domain TBAES20000590//Cytochrome P450// Cytochrome P450 TESTI20001170//HORMA domain TESTI20031810//Bacterial luciferase// Domain of unknown function DUF28 TESTI20044230//*Mus musculus* testis-specific Y-encoded-like protein (Tspyl1) mRNA, complete cds. TESTI20098350//VAT-Nn domain TESTI20157520//K+ channel tetramerisation domain// K+ channel tetramerisation domain TESTI20170350//Cystine-knot domain TESTI20192800//*Homo sapiens* nasopharyngeal carcinoma susceptibility protein LZ16 mRA, complete cds. TESTI20199750//TRICHOHYALIN. TESTI20202650//Repeat in HS1/Cortactin TESTI20229600//Drosophila-melanogaster SP2353 mRNA, complete cds. TESTI20231920// Gag P30 core shell protein TESTI20242830//E2 (early) protein, C terminal// Syndecan domain TESTI20254540//*Homo sapiens* hepatocellular carcinoma-associated antigen 59 mRNA, complete cds. TESTI20320440//THIOREDOXIN. TESTI20327680//EF hand// EF hand TESTI20328280//KE2 family protein// Troponin TESTI20351830//K-box region TESTI20370020//Bleomycin resistance protein TESTI20391210//IQ calmodulin-binding motif TESTI20408150//Keratin,-high sulfur B2 protein TESTI20451990//SAP domain TESTI20467970// Neurohypophysial hormones, N-terminal Domain// Neurohypophysial hormones, N-terminal Domain// Neurohypophysial hormones, N-terminal Domain// Neurohypophysial hormones, N-terminal Domain// Neurohypophysial hormones, N-terminal Domain// Neurohypophysial hormones, N-terminal Domain// Neurohypophysial hormones, N-terminal Domain// Neurohypophysial hormones, N-terminal Domain// Neurohypophysial hormones, N-terminal Domain THYMU20108310//Mouse NCBP-29 mRNA for PW29, complete cds. THYMU20142040//WISKOTT-ALDRICH SYNDROME PROTEIN HOMOLOG (WASP). THYMU20194360//Kelch motif THYMU20239000//collagen alpha 1(XI) chain TOVAR20004760//Leucine Rich Repeat// Leucine Rich Repeat// Leucine Rich Repeat TRACH20005020//Ank repeat// MutT-like domain TRACH20007020//TRICHOHYALIN. TRACH20048450// PROTEIN K4 (PROTEIN K3). TRACH20068700//*Homo sapiens* adaptor protein CIKS mRNA, complete cds. TRACH20076760//Keratin, high sulfur B2 protein TRACH20135520//TBC domain// Rhodanese-like domain TRACH20141240//*Mus musculus* G21 protein mRNA, complete cds. TRACH20183170//*Rattus norvegicus* Sprague-Dawley SM-20 MRNA, complete cds. UTERU20000740//Human fusion protein mRNA, complete cds. UTERU20004240//CGI-96 protein UTERU20006960// endoplasmic reticulum resident protein 58 UTERU20022940//Human (p23) MRNA, complete cds. UTERU20046640//*Mus musculus* ld1Bp (LDLB) mRNA, complete cds. UTERU20065930//GTP-rHO BINDING PROTEIN 1 (RHOPHILIN). UTERU20115740//Human PMS2 related (hPMSR3) gene, complete cds. UTERU20179880//TPR Domain// TPR Domain// TPR Domain// TPR Domain With respect to the remaining 882 clones, there are so far no information available for estimating their functions. However, there is the possibility that the functions of these clones will be revealed in future. Their Clone Names are indicated below. 3NB6920014080, ADRGL20000640, ADRGL20012870, ADRGL20013010, ADRGL20044590, ADRGL20067670, ADRGL20068170, ADRGL20068460, ADRGL20073570, ADRGL20076360, ADRGL20083310, ASTRO20032120, ASTRO20100720, ASTRO20111490, ASTRO20114610, ASTRO20136710, ASTRO20138020, ASTRO20152140, ASTRO20166810, ASTRO20173480, BLADE20004630, BRACE20019540, BRACE20037660, BRACE20038850, BRACE20051690, BRACE20054500, BRACE20055180, BRACE20056810, BRACE20057420, BRACE20058810, BRACE20060840, BRACE20061740, BRACE20062400, BRACE20062740, BRACE20063800, BRACE20063930, BRACE20082950, BRACE20090440, BRACE20096540, BRACE20097320, BRACE20099570, BRACE20106690, BRACE20109370, BRACE20109830, BRACE20111830, BRACE20114780, BRACE20115450, BRACE20118380, BRACE20121850, BRACE20136240, BRACE20141080, BRACE20142320, BRACE20142570, BRACE20148210, BRACE20150310, BRACE20152870, BRACE20163150, BRACE20165830, BRACE20171240, BRACE20175870, BRACE20190440, BRACE20220300, BRACE20223280, BRACE20229280, BRACE20230700, BRACE20235400, BRACE20262930, BRACE20262940, BRACE20266750, BRACE20267250, BRACE20269710, BRACE20283920, BRACE20287410, BRALZ20014450, BRALZ20019660, BRALZ20059500, BRALZ20065600, BRALZ20075450, BRALZ20075760, BRALZ20080310, BRALZ20088690, BRAMY10001570, BRAMY20004110,
BRAMY20011140, BRAMY20071850,
BRAMY20102080, BRAMY20110640,
BRAMY20116790, BRAMY20121190,
BRAMY20137560, BRAMY20147540,
BRAMY20160700, BRAMY20163250,
BRAMY20163270, BRAMY20167710,
BRAMY20168920, BRAMY20170140,
BRAMY20178640, BRAMY20182730,
BRAMY20183080, BRAMY20196000,
BRAMY20204450, BRAMY20205740,
BRAMY20229840, BRAMY20230600,
BRAMY20250240, BRAMY20250320,
BRAMY20261680, BRAMY20267130,
BRAMY20268990, BRAMY20277140,
BRAMY20280720, BRAMY20285930,
BRAMY20286820, BRAWH10000930,
BRAWH20012410, BRAWH20014920,
BRAWH20016660, BRAWH20100690,
BRAWH20103180, BRAWH20106180,
BRAWH20107540, BRAWH20110660, BRAWH20111550,
BRAWH20122770, BRAWH20126190,
BRAWH20126980, BRAWH20139410,
BRAWH20142340, BRAWH20147290,
BRAWH20155950, BRAWH20158530,
BRAWH20160280, BRAWH20162690,
BRAWH20166790, BRAWH20173050,
BRAWH20182060, BRCAN20006200, BRCAN20006390,
BRCAN20060190, BRCAN20126130, BRCAN20143700,
BRCAN20147880, BRCAN20216690, BRCAN20237240,
BRCAN20263400, BRCAN20273100, BRCAN20273340,
BRCAN20275130, BRCAN20280400, BRCAN20284600,
BRCOC20004870, BRCOC20020850, BRCOC20031000,
BRCOC20031870, BRCOC20037400, BRCOC20093800,
BRCOC20105100, BRCOC20117690, BRCOC20119960,
BRCOC20122290, BRCOC20128130, BRCOC20135730,
BRCOC20147480, BRCOC20148330, BRCOC20155970,
BRCOC20158240, BRHIP10001740, BRHIP20104440,
BRHIP20105710, BRHIP20107440, BRHIP20110800,
BRHIP20115760, BRHIP20123140, BRHIP20129720,
BRHIP20139720, BRHIP20140630, BRHIP20142850,
BRHIP20143860, BRHIP20149540, BRHIP20153560,
BRHIP20169680, BRHIP20169900, BRHIP20170100,
BRHIP20173150, BRHIP20180140, BRHIP20186120,
BRHIP20186500, BRHIP20190070, BRHIP20196410,
BRHIP20205090, BRHIP20208420, BRHIP20214950,
BRHIP20227080, BRHIP20230710, BRHIP20232290,
BRHIP20238690, BRHIP20240460, BRHIP20254480,
BRHIP20277620, BRHIP20284800, BRHIP30001110,
BRSSN10000920, BRSSN20006340, BRSSN20015030,
BRSSN20028570, BRSSN20038410, BRSSN20046570,
BRSSN20046860, BRSSN20097020, BRSSN20105960,
BRSSN20108300, BRSSN20121030, BRSSN20152380,
BRSSN20159070, BRSSN20159820, BRSTN20000580,
BRTHA20046390, CD34C30001250, CD34C30003140,
CD34C30004940, COLON20043180, CTONG20002180,
CTONG20028410, CTONG20038890, CTONG20049410,
CTONG20077790, CTONG20082690, CTONG20091320,
CTONG20095270, CTONG20095290, CTONG20096430,
CTONG20097660, CTONG20099630, CTONG20101480,
CTONG20105660, CTONG20106230, CTONG20108210,
CTONG20124470, CTONG20126070, CTONG20128470,
CTONG20136300, CTONG20138030, CTONG20139070,
CTONG20140320, CTONG20141650, CTONG20146970,
CTONG20147050, CTONG20150910, CTONG20158150,
CTONG20162170, CTONG20163550, CTONG20164990,
CTONG20265130, CTONG20273610, D30ST10002670,
D30ST10002700, D30ST20006540, D30ST20007340,
D30ST20024170, D30ST20024520, D30ST20037970,
D30ST30002910, D60ST20004450, D90ST20000310,
D90ST20035800, DFNES10000030, DFNES10001850,
DFNES20010910, DFNES20055270, DFNES20082800,
FCBBF10003740, FCBBF20006780, FCBBF20023700,
FCBBF20035280, FCBBF20054280, FCBBF20056370,
FCBBF20071860, FCBBF20072650, FCBBF20075560,
FCBBF20076330, FCBBF30001840, FCBBF30016570,
FCBBF30019120, FCBBF30028180, FCBBF30052180,
FCBBF30062880, FCBBF30070770, FCBBF30071520,
FCBBF30170590, FCBBF30178730, FCBBF30189490,
FCBBF30199610, FCBBF30240020, FCBBF30242250,
FCBBF30262360, FCBBF30266780, FCBBF30266920,
FCBBF30278630, FCBBF30284720, FCBBF40001420,
FCBBF40005480, FEBRA20003210, FEBRA20017050,
FEBRA20018280, FEBRA20025520, FEBRA20026280,
FEBRA20027810, FEBRA20034360, FEBRA20037500,
FEBRA20042190, FEBRA20052910, FEBRA20060610,
FEBRA20072120, FEBRA20079310, FEBRA20082100,
FEBRA20095140, FEBRA20098460, FEBRA20161120,
FEBRA20166540, FEBRA20176800, FEBRA20197110,
FEBRA20204000, FEBRA20204060, FEBRA20216360,
FEBRA20226010, FEBRA20229560, FEBRA20232850,
FELNG20002410, HCHON20002260, HCHON20008980,
HCHON20009350, HCHON20011160, HCHON20014970,
HCHON20022470, HCHON20036760, HCHON20043590,
HCHON20067220, HCHON20074820, HCHON20076500,
HEART20021840, HEART20037810, HEART20049400,
HEART20063340, HEART20067870, HEART20067890,
HEART20074430, HEART20089940, HEART20095990,
HHDPC10000650, HHDPC20006920, HHDPC20057940,
HHDPC20095280, HLUNG20016770, HLUNG20084390,
KIDNE20006780, KIDNE20011170, KIDNE20013730,
KIDNE20018730, KIDNE20018970, KIDNE20021980,
KIDNE20029800, KIDNE20067330, KIDNE20079440,
KIDNE20096280, KIDNE20096470, KIDNE20100840,
KIDNE20102650, KIDNE20104300, KIDNE20106740,
KIDNE20107500, KIDNE20112000, KIDNE20120090,
KIDNE20122910, KIDNE20132180, KIDNE20138010,
KIDNE20141190, KIDNE20144890, KIDNE20148900,
KIDNE20163880, KIDNE20180710, KIDNE20186780,
LIVER10001260, LIVER20011910, LIVER20028420,
LIVER20038540, LIVER20084730, LIVER20085800,
MESAN20106640, MESAN20121130, MESAN20132110,
MESAN20138450, MESAN20157080, MESAN20161590,
MESAN20164090, MESAN20182090, NESOP10001080,
NOVAR1,0001020, NOVAR20003520, NT2NE20003740,
NT2NE20010210, NT2NE20015240, NT2NE20043780,
NT2NE20053580, NT2NE20072200, NT2NE20074250,
NT2NE20089610, NT2NE20108540, NT2NE20110360,
NT2NE20146810, NT2NE20152750, NT2NE20172590,
NT2NE20174800, NT2NE20174920, NT2NE20187390,
NT2RI20022600, NT2RI20023160, NT2RI20023590,
NT2RI20036670, NT2RI20055790, NT2RI20069730,
NT2RI20198260, NT2RI20203900, NT2RI20207030,
NT2RI20216250, NT2RI20244960, NT2RI20250750,
NT2RI20252550, NT2RP70010740, NT2RP70056750,
NT2RP70075240, NT2RP70077660, NT2RP70085440,
NT2RP70110860, NT2RP70111320, NT2RP70130020,
NT2RP70137640, NT2RP70143480, NT2RP70147210,
NT2RP70150800, NT2RP70169110, NT2RP70175670,
NT2RP70181970, NT2RP70190640, NT2RP70203790,
NTONG20050620, NTONG20050860, NTONG20065010,
NTONG20077560, NTONG20090680, OCBBF20005230,
OCBBF20020150, OCBBF20029800, OCBBF20032460,
OCBBF20041680, OCBBF20045330, OCBBF20047570, OCBBF20048660, OCBBF20051610, OCBBF20060300, OCBBF20061720, OCBBF20062140, OCBBF20062410, OCBBF20074140, OCBBF20076220, OCBBF20079460, OCBBF20081380, OCBBF20084660, OCBBF20085200, OCBBF20088220, OCBBF20094240, OCBBF20097720, OCBBF20100400, OCBBF20103130, OCBBF20104040, OCBBF20105570, OCBBF20107920, OCBBF20111770, OCBBF20118970, OCBBF20126780, OCBBF20130110, OCBBF20139260, OCBBF20151150, OCBBF20164050, OCBBF20164670, OCBBF20170690, OCBBF20173060, OCBBF20173250, OCBBF20178990, OCBBF20186870, OCBBF20189560, PEBLM20024550, PEBLM20071880, PEBLM20072960, PERIC20002140, PERIC20003860, PLACE60004630, PLACE60119750, PLACE60138830, PLACE60153220, PLACE60155130, PLACE60169420, PLACE60181070, PLACE60187690, PLACE60188340, PROST10004800, PROST20005670, PROST20021010, PROST20024890, PROST20029270, PROST20052280, PROST20057930, PROST20059040, PROST20087700, PROST20097950, PROST20111050, PROST20120050, PROST20121900, PROST20123530, PROST20127400, PROST20130530, PROST20132600, PROST20133270, PROST20144220, PROST20149160, PROST20149250, PROST20151240, PROST20152460, PROST20153320, PROST20166680, PROST20168290, PROST20178360, PUAEN20025680, PUAEN20027580, PUAEN20044000, PUAEN20045110, PUAEN20045250, PUAEN20052470, PUAEN20081230, PUAEN20085150, RECTM10001410, RECTM20003490, RECTM20005100, SKMUS20012010, SKMUS20031680, SKMUS20046670, SKNMC20006220, SKNSH20034660, SKNSH20062340, SKNSH20080430, SKNSH20087770, SKNSH20091970, SMINT20005410, SMINT20008240, SMINT20011140, SMINT20011580, SMINT20014580, SMINT20015590, SMINT20023280, SMINT20033170, SMINT20033400, SMINT20042990, SMINT20047810, SMINT20056210, SMINT20058000, SMINT20060780, SMINT20065960, SMINT20076470, SMINT20080540, SMINT20089170, SMINT20092330, SMINT20092720, SMINT20098320, SMINT20103690, SMINT20105000, SMINT20108530, SMINT20109970, SMINT20122850, SMINT20132280, SMINT20153530, SMINT20158100, SMINT20161220, SMINT20162860, SMINT20164400, SMINT20164770, SMINT20173190, SPLEN10000830, SPLEN20000640, SPLEN20002220, SPLEN20008820, SPLEN20013540, SPLEN20016260, SPLEN20019450, SPLEN20020070, SPLEN20022230, SPLEN20023140, SPLEN20031600, SPLEN20032040, SPLEN20032190, SPLEN20033960, SPLEN20040600, SPLEN20076530, SPLEN20101190, SPLEN20106250, SPLEN20129610, SPLEN20146690, SPLEN20149190, SPLEN20152610, SPLEN20157300, SPLEN20158900, SPLEN20158990, SPLEN20160690, SPLEN20160980, SPLEN20166270, SPLEN20171210, SPLEN20176200, SPLEN20193110, SPLEN20198110, SPLEN20204170, SPLEN20212950, SPLEN20214400, SPLEN20225220, SPLEN20242320, SPLEN20242730, SPLEN20249560, SPLEN20261440, SPLEN20264110, SPLEN20279950, SPLEN20280660, SPLEN20303970, STOMA20013890, STOMA20026880, STOMA20036460, STOMA20048520, STOMA20048840, STOMA20062290, STOMA20067800, STOMA20072690, STOMA20076800, STOMA20086140, STOMA20092560, SYNOV20003970, TCOLN20001390, TESOP20000900, TESOP20003120, TESTI10000940, TESTI20004890, TESTI20011200, TESTI20018230, TESTI20029930, TESTI20030310, TESTI20030890, TESTI20038270, TESTI20066770, TESTI20076850, TESTI20086210, TESTI20087620, TESTI20094020, TESTI20098530, TESTI20102800, TESTI20105720, TESTI20112940, TESTI20114070, TESTI20116650, TESTI20122310, TESTI20129150, TESTI20129220, TESTI20130120, TESTI20135660, TESTI20136990, TESTI20137370, TESTI20137670, TESTI20143240, TESTI20143620, TESTI20155900, TESTI20157100, TESTI20159140, TESTI20161970, TESTI20168630, TESTI20168960, TESTI20169960, TESTI20171020, TESTI20178160, TESTI20179320, TESTI20183370, TESTI20185810, TESTI20192280, TESTI20194300, TESTI20194810, TESTI20199170, TESTI20200260, TESTI20203440, TESTI20209460, TESTI20211240, TESTI20213150, TESTI20213580, TESTI20220100, TESTI20220650, TESTI20224620, TESTI20226490, TESTI20234270, TESTI20238000, TESTI20239470, TESTI20240090, TESTI20241530, TESTI20241920, TESTI20244760, TESTI20262330, TESTI20262910, TESTI20265250, TESTI20265370, TESTI20269570, TESTI20272060, TESTI20272390, TESTI20275620, TESTI20277360, TESTI20278200, TESTI20280980, TESTI20282540, TESTI20285830, TESTI20288110, TESTI20289850, TESTI20291620, TESTI20294700, TESTI20297850, TESTI20301360, TESTI20305560, TESTI20307540, TESTI20310070, TESTI20311290, TESTI20319190, TESTI20327740, TESTI20330310, TESTI20333950, TESTI20336410, TESTI20337100, TESTI20342430, TESTI20345060, TESTI20347740, TESTI20347770, TESTI20357750, TESTI20357930, TESTI20361140, TESTI20367360, TESTI20369130, TESTI20369220, TESTI20370550, TESTI20371060, TESTI20378450, TESTI20380650, TESTI20386230, TESTI20386440, TESTI20388580, TESTI20391130, TESTI20392090, TESTI20401430, TESTI20406420, TESTI20409440, TESTI20413300, TESTI20415640, TESTI20419560, TESTI20423020, TESTI20424000, TESTI20424730, TESTI20425070, TESTI20427830, TESTI20428060, TESTI20429280, TESTI20429580, TESTI20433130, TESTI20438660, TESTI20447540, TESTI20451710, TESTI20458190, TESTI20465520, TESTI20468630, TESTI20471470, TESTI20471530, TESTI20472120, TESTI20473420, TESTI20477920, TESTI20478010, TESTI20478180, TESTI20479300, THYMU20000570, THYMU20001950, THYMU20015210, THYMU20018190, THYMU20029100, THYMU20045120, THYMU20058070, THYMU20061700, THYMU20070360, THYMU20075320, THYMU20095960, THYMU20101610, THYMU20101920, THYMU20111420, THYMU20114470, THYMU20118060, THYMU20119390, THYMU20128070, THYMU20128260, THYMU20142970, THYMU20153160, THYMU20158250, THYMU20186390, THYMU20186730, THYMU20187720, THYMU20195990, THYMU20204160, THYMU20204990, THYMU20215090, THYMU20215970, THYMU20226600, THYMU20228540, THYMU20235760, THYMU20239430, THYMU20246840, THYMU20250420, THYMU20251890, THYMU20253250, THYMU20255570, THYMU20255720, THYMU20259090, THYMU20265300, THYMU20271250, THYMU20272490, THYMU20283790, THYMU20284120, THYMU20286290, THYMU20286320, TKIDN20030590, TKIDN20030620, TOVAR20005750, TRACH20027840, TRACH20032720, TRACH20037360, TRACH20056980, TRACH20060150, TRACH20082780, TRACH20091230, TRACH20092680, TRACH20099340, TRACH20107710, TRACH20115740, TRACH20118940, TRACH20147250, TRACH20153810, TRACH20169800, TRACH20187180, TSTOM10001860, TSTOM20001390, TSTOM20003150, UMVEN20003540, UTERU20006290, UTERU20020010, UTERU20054460, UTERU20056010, UTERU20059050, UTERU20061030, UTERU20067050, UTERU20068990, UTERU20070040, UTERU20070810, UTERU20081300, UTERU20084260, UTERU20095380, UTERU20095400, UTERU20101240, UTERU20114100, UTERU20118110, UTERU20118970, UTERU20119680, UTERU20124070, UTERU20126880, UTERU20134910, UTERU20143980, UTERU20146680, UTERU20150870, UTERU20164260, UTERU20188810

EXAMPLE 7

Expression Frequency Analysis in Silico

The cDNA libraries derived from various tissues and cells as indicated in Example 1 were prepared, and cDNA clones were selected from each library at random. The 5'-end sequences were determined and the database was constructed based on the data. The database was constructed based on the nucleotide sequences of 1,402,070 clones, and thus the population of the database is large enough for the analysis.

Then, clones having a homologous sequence are categorized into a single cluster (clustering) by searching the nucleotide sequences of respective clones in this database with the program of nucleotide sequence homology search; the number of clones belonging to each cluster was determined and normalized for every library; thus, the ratio of a certain gene in each cDNA library was determined. This analysis gave the information of the expression frequency of genes in tissues and cells which were sources of the cDNA libraries.

Then, in order to analyze the expression of a gene containing the nucleotide sequence of the cDNA of the present invention in tissues and cells, the library derived from a tissue or a cell used in the large-scale cDNA analysis was subjected to the comparison of the expression levels between tissues or cells. Namely, the expression frequency was analyzed by comparing the previously normalized values between tissues and/or cells for which the nucleotide sequences of 600 or more cDNA clones had been analyzed. By this analysis, some of the genes were revealed to be involved in the pathology and functions indicated below. Each value in Tables 3 to 51 shown below represents a relative expression frequency; the higher the value, the higher the expression level.

Osteoporosis-related Genes

Osteoporosis is a pathology in which bones are easily broken owing to overall decrease in components of bone. The onset involves the balance between the functions of osteoblast producing bone and osteoclast absorbing bone, namely bone metabolism. Thus, the genes involved in the increase of osteoclasts differentiating from precursor cells of monocyte/macrophage line (Molecular Medicine 38. 642–648. (2001)) are genes involved in osteoporosis relevant to bone metabolism.

A nucleotide sequence information-based analysis was carried out to identify the genes whose expression frequencies are higher or lower in CD34+ cell (cell expressing a glycoprotein CD34) treated with the osteoclast differentiation factor (Molecular Medicine 38. 642–648. (2001)) than in the untreated CD34+ cell, which is the precursor cell of monocyte/macrophage line. The result of comparative analysis for the frequency between the two cDNA libraries prepared from the RNA of CD34+ cells (CD34C) and from the RNA of CD34+ cells treated with the osteoclast differentiation factor (D30ST, D60ST or D90ST) showed that the genes whose expression levels were different between the two were the following clones (Table 3). ASTRO20001410, D30ST10001090, D30ST20036070, THYMU20039810, KIDNE20028720, BRAWH10000930, BRHIP20005340, CTONG20141650, D90ST20000310, D90ST20002780, D90ST20023970, D90ST20026730, D90ST20031370, D90ST20033970, D90ST20035800, D90ST20035940, D90ST20040180, FCBBF30018550, FCBBF30233680, KIDNE20102650, NT2RI20023160, PROST20107820, SKNSH20089400, SMINT20033400, CTONG20108210, D60ST20003580, D60ST20005070, ASTRO20155290, D30ST10002670, D30ST10002700, D30ST20006180, D30ST20006540, D30ST20007340, D30ST20013280, D30ST20024170, D30ST20024360, D30ST20037970, D30ST30002580, D30ST30002910, FCBBF10004120, NT2RI20001330, NTONG20009770, SPLEN20084600, SPLEN20140800, THYMU20169680, TRACH20141240, CD34C30001250, CD34C30003140, CD34C30004240, CD34C30004940, DFNES10001850, HHDPC20034390, NT2RI20091730, SKMUS20003610, SPLEN20225220, BRCOC20101230

These genes are involved in osteoporosis.

Genes Involved in Neural Cell Differentiation

Genes involved in neural cell differentiation are useful for treating neurological diseases. Genes with varying expression levels in response to induction of cellular differentiation in neural cells are thought to be involved in neurological diseases.

A survey was performed for genes whose expression levels are varied in response to induction of differentiation (stimulation by retinoic acid (RA) or growth inhibitor treatment after RA stimulation) in cultured cells of a neural strain, NT2. The result of comparative analysis of cDNA libraries derived from undifferentiated NT2 cells (NT2RM) and the cells subjected to the differentiation treatment (NT2RP, NT2RI or NT2NE) showed that the genes whose expression levels were different between the two were the following clones (Table 4). CTONG20027090, CTONG20160560, NT2RP70032610, OCBBF20188730, SPLEN20162680, BRCOC20101230, BRHIP20005340, BRHIP20238880, FCBBF30016320, FEBRA20080810, FEBRA20225040, HCHON20008320, HHDPC20034390, HLUNG10000550, NT2RI20028470, NT2RI20054050, NT2RI20091730, NT2RP70078420, PUAEN20003740, THYMU20271250, BRACE20003070, BRACE20039040, BRAWH20004600, BRAWH20011710, BRCOC20121720, BRHIP20005530, D30ST10002700, HCHON20007380, HEART20072310, KIDNE20121880, MESAN20121130, NT2RI20022600, NT2RI20023160, NT2RI20086220, NT2RI20216250, NT2RP60000850, NT2RP70036880, NT2RP70043480, NT2RP70062230, NT2RP70081610, NT2RP70102350, NT2RP70130020, NT2RP70190640, OCBBF10001850, OCBBF20097720, OCBBF20173980, PEBLM20044520, SPLEN20173510, TRACH20007020, UTERU20065930, HCHON20022470, NT2NE20010490, NT2NE20174800, NT2NE20177520, PROST20087700, PROST20107820, SMINT20028820, TESTI20063830, ASTRO20125520, BRHIP30001110, HCHON20002260, HCHON20008150, KIDNE20002520, NT2NE20130190, NT2NE20158600, NT2RI20001330, NT2RI20025400, NT2RI20036670, NT2RI20048840, SKMUS20020840, BRACE20057190, BRACE20060550, BRACE20267250, BRAWH20107540, BRAWH20118230, CTONG20075860, CTONG20095290, FEBRA20086620, FEBRA20144170, FEBRA20196370, HLUNG20023340, NT2NE20003740, NT2NE20010050, NT2NE20010210, NT2NE20010400, NT2NE20015240, NT2NE20021620, NT2NE20043780, NT2NE20053580, NT2NE20068130, NT2NE20072200, NT2NE20074250, NT2NE20080170, NT2NE20089610, NT2NE20089970, NT2NE20108540, NT2NE20110360, NT2NE20118960, NT2NE20122430, NT2NE20124480, NT2NE20125050, NT2NE20131890, NT2NE20132170, NT2NE20142210, NT2NE20146810, NT2NE20152750, NT2NE20155110, NT2NE20156260, NT2NE20157470, NT2NE20159740, NT2NE20172590, NT2NE20174920, NT2NE20181650, NT2NE20183760, NT2NE20184900, NT2NE20187390, OCBBF20108430, RECTM20005100, SMINT20001760, SPLEN20169720, TESTI20265250, ASTRO10001650, ASTRO20033160, BRACE20011070, BRACE20039440, BRACE20151320, BRAMY20104640, BRAMY20137560, BRAMY20167060, BRAWH20028110, BRCAN20280360, BRCOC20004870, BRHIP20207990, BRHIP20217620, BRHIP20249110, BRSTN10000830, CTONG10000940, CTONG20004690, CTONG20050280, CTONG20105660, CTONG20125640, CTONG20133520, CTONG20186320, FCBBF10000770, FCBBF10002800, FCBBF10003770, FCBBF30018550, FCBBF30123470, FCBBF30246230, FEBRA20018280, FEBRA20095140, FEBRA20192420, HCHON20064590, HHDPC10000830, HLUNG20016770, HLUNG20033780, IMR3220002430, KIDNE20104300, MESAN20004570, MESAN20089360, NOVAR10000910, NT2RI20003480, NT2RI20005750, NT2RI20009870, NT2RI20023590, NT2RI20023910, NT2RI20025640, NT2RI20040930, NT2RI20041880, NT2RI20046080, NT2RI20050960, NT2RI20055790, NT2RI20056700, NT2RI20069730, NT2RI20076290, NT2RI20091940, NT2RI20198260, NT2RI20203900, NT2RI20207030, NT2RI20240080, NT2RI20244600, NT2RI20244960, NT2RI20250750, NT2RI20252550, NT2RI20273230, NTONG20067090, OCBBF10001750, OCBBF20047570, OCBBF20054760, OCBBF20059560, OCBBF20073540, OCBBF20125530, OCBBF20126780, OCBBF20127040, OCBBF20140890, SKMUS20003610, SKNSH20008190, SKNSH20080430, SMINT20144800, SPLEN20027440, SPLEN20095550, SPLEN20140800, TESTI20094020, TESTI20369690, TESTI20391770, TESTI20442760, TRACH20084720, TRACH20107710, TRACH20118940, UTERU20022940, ASTRO20108190, BGGI120006160, BRAMY20136210, BRAWH20016620, BRAWH20164460, BRCOC20144000, BRHIP20132860, BRSSN20146100, CTONG10000100, CTONG20103480, CTONG20108210, CTONG20139070, FCBBF10000240, FCBBF10000630, FCBBF20067810, FCBBF30010810, FCBBF30012810, FCBBF30013770, FCBBF30039020, FCBBF40001420, FEBRA10001880, FEBRA20082010, HHDPC20001040, KIDNE20021910, NT2RP60000770, NT2RP70010740, NT2RP70027380, NT2RP70037240, NT2RP70044280,-NT2RP70045590, NT2RP70056750, NT2RP70063950, NT2RP70072690, NT2RP70077660, NT2RP70085440, NT2RP70105210, NT2RP70110860, NT2RP70111320, NT2RP70122910, NT2RP70125160, NT2RP70133740, NT2RP70134990, NT2RP70137290, NT2RP70137640, NT2RP70143480, NT2RP70147210, NT2RP70150800, NT2RP70157890, NT2RP70159960, NT2RP70169110, NT2RP70175670, NT2RP70179710, NT2RP70181970, NT2RP70188020, NT2RP70188710, NT2RP70192730, NT2RP70194450, NT2RP70195430, NT2RP70198350, NT2RP70203790, OCBBF20039250, OCBBF20080410, OCBBF20108190, OCBBF20108580, OCBBF20122620, OCBBF20130110, OCBBF20151150, OCBBF20189560, PROST10003220, TESTI20001720, TESTI20121550, TESTI20152460, TESTI20211240, TESTI20234140, UMVEN20003540, UTERU20006960, UTERU20094350, UTERU20164260

These genes are neurological disease-related genes.

Cancer-related Genes

It has been assumed that, distinct from normal tissues, cancer tissues express a distinct set of genes, and thus the expression can contribute to the carcinogenesis in tissues and cells. Thus, the genes whose expression patterns in cancer tissues are different from those in normal tissues are cancer-related genes. Search was carried out for the genes whose expression levels in cancer tissues were different from those in normal tissues.

The result of comparative analysis of cDNA libraries derived from breast tumor (TBAES) and normal breast (BEAST) showed that the genes whose expression levels were different between the two were the following clones (Table 5). BRACE20039040, BRAMY20163250, BRCOC20031250, BRHIP20005340, BRHIP20217620, BRHIP30001110, FCBBF10000770, FCBBF30010810, FEBRA20080810, FEBRA20144170, FEBRA20196630, FEBRA20197110, HCHON20002260, HCHON20040020, HHDPC20034390, HLUNG10000550, NOVAR10000910, NT2RI20023160, NT2RI20054050, NT2RI20091730, OCBBF20188730, SMINT20144800, SPLEN20128000, SPLEN20171210, SPLEN20264110, TBAES20000590, TBAES20002550, TBAES20003150, TESTI20334410, TESTI20432750, TRACH20003590, TRACH20084720, UTERU20046640, BEAST20004540, SPLEN20008740

The result of comparative analysis of cDNA libraries derived cervical tumor (TCERX) and normal cervical duct (CERVX) showed that the genes whose expression levels were different between the two were the following clones (Table 6). BGGI120006160, BRAMY20063970, BRHIP20218580, FEBRA20002100, SPLEN20162680, TESTI20214250, CTONG20105080, HCHON20015980, PROST20175290, TESTI20254220, THYMU20279750

The result of comparative analysis of cDNA libraries derived from colon tumor (TCOLN) and normal colon (COLON) showed that the genes whose expression levels were different between the two were the following clones (Table 7). ASTRO20001410, BRAWH20162690, CTONG20132220, HCHON20002260, NT2RI20001330, TCOLN20001390, 3NB6910001910, BRAMY20120910, BRAWH20004600, BRCOC20031250, BRCOC20031870, COLON10001350, COLON20043180, COLON20093370, FEBRA20002100, FEBRA20082010, FEBRA20197110, KIDNE20007770, KIDNE20013730, NT2RP70045590, OCBBF20078920, PROST20083600, SPLEN20011410, TRACH20084720, THYMU20271250

The result of comparative analysis of cDNA libraries derived from esophageal tumor (TESOP) and normal esophagus (NESOP) showed that the genes whose expression levels were different between the two were the following clones (Table 8). ASTRO20033160, ASTRO20125520, BRAMY20266850, BRAWH20164460, BRHIP20005340, BRHIP20191490, CTONG20095290, CTONG20143690, CTONG20161850, DFNES20001530, DFNES20071130, FCBBF30123470, FCBBF30175310, FEBRA20095140, HCHON20016650, MESAN20025190, NT2RI20028470, NT2RI20054050, NT2RP70036880, NTONG20009770, NTONG20064840, NTONG20076930, SMINT20042990, SPLEN20008820, SPLEN20128000, SPLEN20149110, STOMA20013890, TESOP20000900, TESOP20003120, TESOP20004000, TESOP20005270, TESOP20005690, TESTI20334410, THYMU20271250, TRACH20141240, UTERU20022940, NESOP10001080, NT2RI20023160, NTONG20013620, TRACH20077540, NTONG20015870

The result of comparative analysis of cDNA libraries derived from kidney tumor (TKIDN) and normal kidney (KIDNE) showed that the genes whose expression levels were different between the two were the following clones (Table 9). ASTRO20008010, ASTRO20181690, BRACE20111830, BRACE20152870, BRACE20237270, BRAMY20147540, BRAMY20286820, BRAWH20015350, BRAWH20096780, BRAWH20132190, BRAWH20182060, BRCAN20060190, BRCOC20004870, BRCOC20176520, BRHIP20000870, BRHIP20198190, BRHIP20233090, BRHIP30001110, BRSSN20015790, BRSTN20000580, CTONG10000940, CTONG20098440, CTONG20150910, CTONG20165050, DFNES20014040, DFNES20037420, FCBBF10000770, FCBBF30083820, FCBBF30247930, FEBRA20037500, FEBRA20072120, FEBRA20080810, FEBRA20086620, FEBRA20140100, FEBRA20144170, FEBRA20176800, HCHON20008320, HCHON20059870, HLUNG10000550, MESAN20106640, NT2RI20025400, NT2RI20076290, NT2RI20091940, OCBBF20019830, OCBBF20022900, OCBBF20039250, OCBBF20080050, OCBBF20097720, OCBBF20125530, OCBBF20130110, OCBBF20140640, OCBBF20173980, PANCR10000910, PROST20087700, PUAEN20044000, SPLEN20144520, SPLEN20160980, TKIDN10000010, TKIDN20004640, TKIDN20005210, TKIDN20030590, TKIDN20030620, TKIDN20047480, TRACH20003590, TRACH20028030, TRACH20183170, TRACH20184490, UMVEN20003540, UTERU20004240, UTERU20055930, ASTRO10001650, ASTRO20108190, BGGI120006160, BRACE20039040, BRAMY20102080, BRAWH20004600, BRAWH20125380, BRAWH20162690, BRHIP20115760, BRHIP20205090, CTONG20052650, CTONG20108210, CTONG20128470, CTONG20133480, CTONG20139070, D90ST20000310, DFNES20001530, FCBBF10001820, FEBRA20002100, HCHON20008980, HCHON20016650, HLUNG20033780, KIDNE20002520, KIDNE20003940, KIDNE20006780, KIDNE20007210, KIDNE20007770, KIDNE20008010, KIDNE20009470, KIDNE20011170, KIDNE20011400, KIDNE20013730, KIDNE20017130, KIDNE20018730, KIDNE20018970, KIDNE20020150, KIDNE20021680, KIDNE20021910, KIDNE20021980, KIDNE20022620, KIDNE20024830, KIDNE20027250, KIDNE20027950, KIDNE20028390, KIDNE20028720, KIDNE20028830, KIDNE20029800, KIDNE20067330, KIDNE20079440, KIDNE20096280, KIDNE20096470, KIDNE20100070, KIDNE20100840, KIDNE20101370, KIDNE20101510, KIDNE20102650, KIDNE20102710, KIDNE20104300, KIDNE20106740, KIDNE20107390, KIDNE20107500, KIDNE20107620, KIDNE20109730, KIDNE20109890, KIDNE20112000, KIDNE20115080, KIDNE20118580, KIDNE20120090, KIDNE20121880, KIDNE20122910, KIDNE20124400, KIDNE20125630, KIDNE20126010, KIDNE20126130, KIDNE20127100, KIDNE20127450, KIDNE20127750, KIDNE20130450, KIDNE20131580, KIDNE20132180, KIDNE20137340, KIDNE20138010, KIDNE20141190, KIDNE20144890, KIDNE20148900, KIDNE20163880, KIDNE20180710, KIDNE20181660, KIDNE20182690, KIDNE20186780, KIDNE20190740, LIVER20035110, MESAN20025190, NT2RP70043480, PROST20107820, PROST20123530, PROST20161950, PUAEN20030180, SKMUS20003610, SMINT20033400, TBAES20000590, TESTI20044310, TESTI20082330, TRACH20032720, UTERU20099720

The result of comparative analysis of cDNA libraries derived from liver tumor (TLIVE) and normal liver (LIVER) showed that the genes whose expression levels were different between the two were the following clones (Table 10). BRAWH20166790, CTONG20103480, HEART20005410, LIVER10001260, LIVER10004790, LIVER20002160, LIVER20011130, LIVER20011910, LIVER20028420, LIVER20035110, LIVER20035680, LIVER20038540, LIVER20045650, LIVER20055200, LIVER20055440, LIVER20059810, LIVER20062510, LIVER20064100, LIVER20064690, LIVER20075680, LIVER20080530, LIVER20084730, LIVER20085800, LIVER20087510, LIVER20091180, NTONG20063010, PROST20087700, PROST20107820, TRACH20005400, ASTRO20001410, ASTRO20125520, BRACE20152870, BRAMY20167060, BRAMY20181220, BRAMY20285160, BRCOC20001860, FEBRA20144170, HLUNG10000550, OCBBF20073540, OCBBF20088220, PLACE60169420, SMINT20152940, SPLEN20242320, THYMU20000570, TRACH20077540, UTERU20055930, UTERU20065930

The result of comparative analysis of cDNA libraries derived from lung tumor (TLUNG) and normal lung (HLUNG) showed that the genes whose expression levels were different between the two were the following clones (Table 11). BRACE20096200, BRAWH20004600, BRAWH20030250, BRCAN20006390, BRCAN20280360, BRHIP20238880, CTONG10000940, CTONG20103480, CTONG20129960, CTONG20155180, FCBBF10001210, FEBRA20144170, FEBRA20197110, HCHON20002260, HHDPC20034390, HLUNG10000550, HLUNG20016330, HLUNG20016770, HLUNG20017120, HLUNG20023340, HLUNG20033780, HLUNG20084390, IMR3220002430, LIVER20028420, NOVAR20000380, NT2RI20023910, NT2RI20054050, NT2RI20091730, NT2RP70044280, OCBBF20020830, OCBBF20125530, PLACE60004630, PROST20057930, PROST20107820, PROST20185830, PUAEN20030180, SMINT20121220, SPLEN20002220, SPLEN20008740, SPLEN20054290, SPLEN20128000, SPLEN20157300, SPLEN20176200, SPLEN20179180, SPLEN20211940, STOMA20013890, TBAES20000590, TESTI20094230, TESTI20184620, TESTI20334410, THYMU20000570, THYMU20039810, TRACH20007020, TRACH20141240, TRACH20183170, ASTRO20108190, ASTRO20155290, BRHIP20096850, FEBRA20080810, MESAN20014500, SMINT20028820, SPLEN20162680

The result of comparative analysis of cDNA libraries derived from ovary tumor (TOVER) and normal ovary (NOVER) showed the genes whose expression levels were different between the two were the following clones (Table 12). BGGI120006160, BRHIP20005340, BRHIP20191860, HHDPC20001040, NOVAR10000150, NOVAR10000910, NOVAR10001020, NOVAR20000380, NOVAR20003520, THYMU20271250, ASTRO20141350, BRAMY20157820, BRCOC20001860, HLUNG20016770, NT2RI20054050, NTONG20090600, PROST20087700, PUAEN20015860, SPLEN20029310, TOVAR20004760, TOVAR20005750, TRACH20079690, UTERU20004240

The result of comparative analysis of cDNA libraries derived from stomach tumor (TSTOM) and normal stomach (STOMA) showed that the genes whose expression levels were different between the two were the following clones (Table 13). BRACE20060840, FEBRA20052910, HCHON20002260, HLUNG10000550, NTONG20009770, PROST20107820, THYMU20039810, TSTOM10001860, TSTOM20001390, TSTOM20003150, TSTOM20005690, ASTRO20125520, BRACE20039040, BRAMY20124260, BRCOC20031870, BRHIP20191860, CTONG20128470, FEBRA20037500, HCHON20040020, HHDPC10000830, IMR3220002430, KIDNE20007770, NOVAR20000380, NT2RI20054050, NT2RI20091730, PROST20130530, SPLEN20149110, SPLEN20157880, STOMA20001830, STOMA20005390, STOMA20005670, STOMA20006400, STOMA20006780, STOMA20006860, STOMA20008880, STOMA20010250, STOMA20013890, STOMA20026880, STOMA20032890, STOMA20034770, STOMA20036460, STOMA20046680, STOMA20048520, STOMA20048840, STOMA20051200, STOMA20056640, STOMA20056670, STOMA20057820, STOMA20062130, STOMA20062290, STOMA20063250, STOMA20063980, STOMA20064470, STOMA20067800, STOMA20069040, STOMA20072690, STOMA20076800, STOMA20077450, STOMA20080500, STOMA20083610, STOMA20086140, STOMA20088380, STOMA20092530, STOMA20092560, STOMA20092890, TESTI20184620, TRACH20003590, TRACH20183170, PROST20083600, TRACH20068660

The result of comparative analysis of cDNA libraries derived from uterine tumor (TUTER) and normal uterus (UTERU) showed that the genes whose expression levels were different between the two were the following clones (Table 14). DFNES10001850, NT2RI20023910, SMINT20144800, SPLEN20162680, TOVAR20004760, TUTER20002830, ASTRO20008010, ASTRO20033160, ASTRO20058630, ASTRO20105820, ASTRO20108190, BRACE20039040, BRACE20057190, BRACE20060840, BRACE20111830, BRACE20223330, BRAMY20266850, BRAWH20113430, BRAWH20126980, BRCOC20031870, BRCOC20107300, BRCOC20121720, BRCOC20155970, BRHIP20105710, BRHIP20191490, BRHIP20207990, BRHIP20217620, BRHIP20222280, BRHIP20238880, BRHIP20249110, BRSSN20018690, BRTHA20000570, CTONG10000940, CTONG10002770, CTONG20095290, CTONG20099380, CTONG20103480, CTONG20108210, CTONG20118250, CTONG20129960, CTONG20131560, CTONG20139070, CTONG20139340, CTONG20143690, CTONG20160560, D30ST30002580, FCBBF10000240, FCBBF10001820, FCBBF10003670, FCBBF10004120, FCBBF10005740, FCBBF30175310, FCBBF30240020, FCBBF30246230, FCBBF40001420, FEBRA20002100, FEBRA20004620, FEBRA20018280, FEBRA20025270, FEBRA20034360, FEBRA20037500, FEBRA20080810, FEBRA20082100, FEBRA20144170, FEBRA20225040, HCHON20002260, HCHON20007380, HCHON20015980, HCHON20016650, HCHON20022470, HCHON20040020, HCHON20076500, HEART20072310, HHDPC20034390, HLUNG10000550, HLUNG20016770, KIDNE20131580, LIVER20028420, MAMGL10000830, MESAN20171520, NOVAR10000150, NOVAR10000910, NT2NE20053580, NT2NE20159740, NT2NE20174920, NT2RI20023160, NT2RI20041880, NT2RI20054050, NT2RI20076290, NT2RI20273230, NT2RP60000770, NT2RP60000850, NT2RP70036880, NT2RP70043480, NT2RP70045590, NT2RP70056750, NT2RP70062230, NT2RP70081610, OCBBF10001750, OCBBF20006770, OCBBF20032460, OCBBF20039250, OCBBF20047570, OCBBF20054760, OCBBF20059560, OCBBF20068490, OCBBF20080050, OCBBF20094240, OCBBF20097720, OCBBF20103130, OCBBF20105570, OCBBF20140640, OCBBF20173980, OCBBF20180120, OCBBF20188730, OCBBF20189560, PEBLM20044520, PLACE60060420, PROST20087700, PROST20107820, PROST20149160, PROST20159240, PROST20176170, PROST20189770, PUAEN20003740, PUAEN20015860, SKMUS20003610, SKNSH20008190, SKNSH20080430, SMINT20026890, SMINT20029760, SMINT20068010, SMINT20110330, SMINT20121220, SPLEN20008390, SPLEN20011410, SPLEN20054290, SPLEN20128000, SPLEN20140800, SPLEN20145720, SPLEN20169720, SPLEN20179180, SPLEN20193110, SPLEN20194050, SPLEN20211940, SPLEN20212730, SPLEN20225220, TBAES20000590, TESTI20061110, TESTI20116830, TESTI20184620, TESTI20208710, TESTI20211240, TESTI20213580, TESTI20214250, TESTI20334410, TESTI20369130, TESTI20369690, TESTI20391770, THYMU20039810, THYMU20216840, THYMU20240710, TRACH20003590, TRACH20032720, TRACH20033230, TRACH20141240, TRACH20149970, UMVEN10001860, UTERU20000740, UTERU20004240, UTERU20006290, UTERU20020010, UTERU20022940, UTERU20030570, UTERU20040610, UTERU20046640, UTERU20046980, UTERU20050690, UTERU20054460, UTERU20055330, UTERU20055930, UTERU20056010, UTERU20059050, UTERU20061030, UTERU20064000, UTERU20064860, UTERU20065930, UTERU20067050, UTERU20068990, UTERU20070040, UTERU20070810, UTERU20076390, UTERU20081300, UTERU20084260, UTERU20094350, UTERU20095380, UTERU20095400, UTERU20097760, UTERU20099720, UTERU20101240, UTERU20114100, UTERU20115740, UTERU20116570, UTERU20118110, UTERU20118970, UTERU20119060, UTERU20119680, UTERU20120310, UTERU20124070, UTERU20126880, UTERU20134910, UTERU20135860, UTERU20143980, UTERU20144640, UTERU20145480, UTERU20146310, UTERU20146680, UTERU20150870, UTERU20151980, UTERU20158300, UTERU20158800, UTERU20161570, UTERU20164260, UTERU20168220, UTERU20176130, UTERU20176320, UTERU20178100, UTERU20179880, UTERU20183640, UTERU20185230, UTERU20186740, UTERU20188110, UTERU20188810, BRAWH10000930, CTONG20128470, UTERU20006960

The result of comparative analysis of cDNA libraries derived from tongue cancer (CTONG) and normal tongue (NTONG) showed that the genes whose expression levels were different between the two were the following clones (Table 15). ADRGL20018300, ASTRO20058630, ASTRO20072210, ASTRO20108190, BRACE20003070, BRACE20039040, BRACE20060720, BRACE20061050, BRACE20210140, BRACE20276430, BRAMY20152110, BRAMY20266850, BRAMY20271400, BRAWH10000930, BRAWH20004600, BRCAN20280360, BRCOC20004870, BRHIP20005340, BRHIP20005530, BRHIP20238880, BRSSN20146100, CTONG10000100, CTONG10000220, CTONG10000620, CTONG10000930, CTONG10000940, CTONG10001650, CTONG10002770, CTONG20002180, CTONG20004690, CTONG20009770, CTONG20014280, CTONG20027090, CTONG20028410, CTONG20038890, CTONG20049410, CTONG20050280, CTONG20052650, CTONG20052900, CTONG20075860, CTONG20076130, CTONG20077790, CTONG20082690, CTONG20085950, CTONG20091080, CTONG20091320, CTONG20092570, CTONG20092580, CTONG20092680, CTONG20092700, CTONG20093950, CTONG20095270, CTONG20095290, CTONG20095340, CTONG20096430, CTONG20096750, CTONG20097660, CTONG20098440, CTONG20099380, CTONG20099550, CTONG20099630, CTONG20100240, CTONG20101480, CTONG20103480, CTONG20105080, CTONG20105660, CTONG20106230, CTONG20106520, CTONG20108210, CTONG20114290, CTONG20114740, CTONG20118150, CTONG20118250, CTONG20119200, CTONG20120770, CTONG20121010, CTONG20121580, CTONG20124010, CTONG20124220, CTONG20124470, CTONG20124730, CTONG20125540, CTONG20125640, CTONG20126070, CTONG20127450, CTONG20128470, CTONG20129960, CTONG20131490, CTONG20131560, CTONG20132220, CTONG20133390, CTONG20133480, CTONG20133520, CTONG20136300, CTONG20138030, CTONG20139070, CTONG20139340, CTONG20139860, CTONG20140320, CTONG20140580, CTONG20141650, CTONG20146300, CTONG20147050, CTONG20149460, CTONG20149950, CTONG20153300, CTONG20153580, CTONG20155180, CTONG20155400, CTONG20156780, CTONG20158040, CTONG20158150, CTONG20158660, CTONG20159530, CTONG20160560, CTONG20161850, CTONG20162170, CTONG20163550, CTONG20164990, CTONG20165050, CTONG20186320, CTONG20200310, CTONG20265130, CTONG20267700, CTONG20273610, FCBBF10000240, FCBBF10005740, FCBBF30123470, FCBBF30233680, FEBRA20025270, FEBRA20037500, HCHON20002260, HCHON20007380, HCHON20007510, HCHON20015350, HCHON20040020, HHDPC20034390, HLUNG10000550, KIDNE20002520, KIDNE20009470, KIDNE20115080, KIDNE20127100, LIVER20028420, MESAN20029400, NT2RI20023160, NT2RI20023910, NT2RI20091730, NT2RP70043480, NT2RP70078420, NT2RP70081610, OCBBF20006770, OCBBF20059560, OCBBF20073540, OCBBF20094240, OCBBF20108580, PEBLM20044520, PEBLM20071880, PROST20107820, PUAEN20030180, SKNSH20008190, SMINT20023280, SMINT20089170, SPLEN20179180, TESTI20094020, TESTI20094230, TESTI20152460, TESTI20184620, TESTI20211240, TESTI20442760, THYMU20039810, TRACH20028030, TRACH20141240, TSTOM20003150, UTERU20004240, UTERU20055930, UTERU20065930, UTERU20119060, UTERU20124070, BRACE20039440, BRACE20068590, FCBBF30018550, IMR3220002430, KIDNE20028830, NT2RI20028470, NT2RI20054050, NT2RI20086220, NTONG20009770, NTONG20013620, NTONG20028070, NTONG20029480, NTONG20029700, NTONG20046140, NTONG20048060, NTONG20049910, NTONG20050620, NTONG20050860, NTONG20051530, NTONG20052650, NTONG20056570, NTONG20061870, NTONG20063010, NTONG20064400, NTONG20064840, NTONG20065010, NTONG20066460, NTONG20067090, NTONG20067830, NTONG20070200, NTONG20070340, NTONG20075220, NTONG20076930, NTONG20077560, NTONG20083650, NTONG20088620, NTONG20090600, NTONG20090680, NTONG20092290, NTONG20092330, OCBBF20068490, SKMUS20001980, SMINT20138900, SPLEN20008390, SPLEN20162680, UTERU20134910, ASTRO20155290, FEBRA20080810, NT2RP70032610, NT2RP70036880, NTONG20015870, OCBBF20188730, SMINT20122910, SPLEN20099700

These genes are involved in cancers.

Further, there is a method to search for genes involved in development and differentiation: the expression frequency analysis in which the expression levels of genes are compared between developing or differentiating tissues and/or cells and adult tissues and/or cells. The genes involved in tissue development and/or differentiation are genes participating in tissue construction and expression of function, and thus are useful genes, which are available for regenerative medicine aiming at convenient regeneration of injured tissues.

Search was carried out for the genes whose expression frequencies were different between developing and/or differentiating tissues and/or cells, and adult tissues and/or cells, by using the information of gene expression frequency based on the database of the nucleotide sequences of 1,402,070 clones shown above.

The result of comparative analysis of cDNA libraries derived from fetal brain (FCBBF, FEBRA or OCBBF) and adult brain (BRACE, BRALZ, BRAMY, BRAWH, BRCAN, BRCOC, BRHIP, BRSSN, BRSTN or BRTHA) showed that the genes whose expression levels were different between the two were the following clones (Tables 16 to 48). 3NB6910001910, ADRGL20018300, ASTRO20001410, ASTRO20033160, ASTRO20058630, ASTRO20064750, ASTRO20100720, ASTRO20141350, ASTRO20145760, ASTRO20181690, BGGI120006160, BRACE20006400, BRACE20011070, BRACE20019540, BRACE20027620, BRACE20037660, BRACE20038000, BRACE20038470, BRACE20038480, BRACE20038850, BRACE20039440, BRACE20039540, BRACE20050900, BRACE20051380, BRACE20051690, BRACE20052160, BRACE20053280, BRACE20053480, BRACE20053630, BRACE20054500, BRACE20055180, BRACE20057420, BRACE20057620, BRACE20057730, BRACE20058580, BRACE20058810, BRACE20060840, BRACE20060890, BRACE20061050, BRACE20061740, BRACE20062400, BRACE20062740, BRACE20063630, BRACE20063780, BRACE20063800, BRACE20063930, BRACE20064880, BRACE20068590, BRACE20069090, BRACE20081720, BRACE20082950, BRACE20096200, BRACE20096540, BRACE20097320, BRACE20101700, BRACE20101710, BRACE20106840, BRACE20107530, BRACE20108130, BRACE20108880, BRACE20109370, BRACE20109830, BRACE20114780, BRACE20115450, BRACE20115920, BRACE20116110, BRACE20116460, BRACE20118380, BRACE20121850, BRACE20141080, BRACE20142320, BRACE20147800, BRACE20148210, BRACE20148240, BRACE20150310, BRACE20151320, BRACE20152870, BRACE20153680, BRACE20154120, B,RACE20163150, BRACE20163350, BRACE20165830, BRACE20171240, BRACE20172980, BRACE20175870, BRACE20177200, BRACE20179340, BRACE20185680, BRACE20188470, BRACE20190040, BRACE20190440, BRACE20192440, BRACE20195100, BRACE20201570, BRACE20220300, BRACE20223280, BRACE20223330, BRACE20224480, BRACE20224500, BRACE20228480, BRACE20229280, BRACE20230700, BRACE20232840, BRACE20235400, BRACE20237270, BRACE20238000, BRACE20240740, BRACE20248260, BRACE20253160, BRACE20253330, BRACE20257100, BRACE20262930, BRACE20262940, BRACE20266750, BRACE20267250, BRACE20269200, BRACE20269710, BRACE20273890, BRACE20274080, BRACE20283920, BRACE20284100, BRACE20286360, BRACE20287410, BRALZ20013500, BRALZ20014450, BRALZ20017430, BRALZ20018340, BRALZ20054710, BRALZ20058880, BRALZ20059500, BRALZ20064740, BRALZ20065600, BRALZ20069760, BRALZ20073760, BRALZ20075450, BRALZ20075760, BRALZ20077900, BRALZ20077930, BRALZ20080310, BRALZ20088690, BRAMY10001300, BRAMY10001570, BRAMY20000520, BRAMY20000860, BRAMY20002770, BRAMY20004110, BRAMY20011140, BRAMY20025840, BRAMY20039260, BRAMY20045240, BRAMY20054880, BRAMY20060920, BRAMY20063970, BRAMY20071850, BRAMY20102080, BRAMY20104640, BRAMY20110640, BRAMY20111960, BRAMY20116790, BRAMY20121190, BRAMY20121620, BRAMY20124260, BRCOC20021550, BRCOC20023230, BRCOC20026640,
BRAMY20134140, BRAMY20135900, BRCOC20027510, BRCOC20031000, BRCOC20031250,
BRAMY20136210, BRAMY20137560, BRCOC20031870, BRCOC20035130, BRCOC20037320,
BRAMY20144620, BRAMY20147540, BRCOC20037400, BRCOC20041750, BRCOC20055420,
BRAMY20148130, BRAMY20152110, BRCOC20059510, BRCOC20077690, BRCOC20090520,
BRAMY20153110, BRAMY20157820, BRCOC20091960, BRCOC20093800, BRCOC20099370,
BRAMY20160700, BRAMY20163250, BRCOC20101230, BRCOC20107300, BRCOC20110100,
BRAMY20163270, BRAMY20167060, BRCOC20114180, BRCOC20117690, BRCOC20119960,
BRAMY20167710, BRAMY20168920, BRCOC20121720, BRCOC20122290, BRCOC20128130,
BRAMY20170140, BRAMY20174550, BRCOC20134480, BRCOC20135730, BRCOC20136750,
BRAMY20178640, BRAMY20181220, BRCOC20144000, BRCOC20147480, BRCOC20148330,
BRAMY20182730, BRAMY20183080, BRCOC20155970, BRCOC20158240, BRCOC20176520,
BRAMY20184670, BRAMY20195090, BRCOC20178560, BRHIP10001290, BRHIP20000870,
BRAMY20204450, BRAMY20205740, BRHIP20001630, BRHIP20096170, BRHIP20096850,
BRAMY20210400, BRAMY20211390, BRHIP20103090, BRHIP20104440, BRHIP20105710,
BRAMY20211420, BRAMY20213100, BRHIP20106100, BRHIP20107440, BRHIP20111200,
BRAMY20215230, BRAMY20217460, BRHIP20115080, BRHIP20115760, BRHIP20118380,
BRAMY20218250, BRAMY20218670, BRHIP20118910, BRHIP20119330, BRHIP20121410,
BRAMY20229800, BRAMY20229840, BRHIP20123140, BRHIP20129720, BRHIP20132860,
BRAMY20230600, BRAMY20231720, BRHIP20135100, BRHIP20137230, BRHIP20139720,
BRAMY20240040, BRAMY20245300, BRHIP20140630, BRHIP20142850, BRHIP20143730,
BRAMY20247110, BRAMY20247280, BRHIP20143860, BRHIP20149540, BRHIP20153560,
BRAMY20248490, BRAMY20250240, BRHIP20153600, BRHIP20167880, BRHIP20169680,
BRAMY20250320, BRAMY20252180, BRHIP20169900, BRHIP20170100, BRHIP20173150,
BRAMY20252720, BRAMY20260910, BRHIP20174040, BRHIP20175420, BRHIP20180140,
BRAMY20261680, BRAMY20266850, BRHIP20183690, BRHIP20186120, BRHIP20186500,
BRAMY20267130, BRAMY20268990, BRHIP20189980, BRHIP20190070, BRHIP20191490,
BRAMY20270730, BRAMY20271400, BRHIP20191770, BRHIP20194940, BRHIP20195890,
BRAMY20273960, BRAMY20277140, BRHIP20196410, BRHIP20205090, BRHIP20207430,
BRAMY20277170, BRAMY20280720, BRHIP20207990, BRHIP20208420, BRHIP20208590,
BRAMY20284910, BRAMY20285160, BRHIP20227080, BRHIP20230710, BRHIP20232290,
BRAMY20285930, BRAMY20286820, BRHIP20233090, BRHIP20234380, BRHIP20236950,
BRAWH20002320, BRAWH20012390, BRHIP20238600, BRHIP20238690, BRHIP20240460,
BRAWH20014920, BRAWH20015350, BRHIP20243470, BRHIP20249110, BRHIP20252450,
BRAWH20015890, BRAWH20016660, BRHIP20253660, BRHIP20277620, BRHIP20283030,
BRAWH20016860, BRAWH20017010, BRHIP20284800, BRHIP20285830, BRHIP20285930,
BRAWH20018730, BRAWH20028110, BRHIP30004880, BRSSN10000920, BRSSN20013420,
BRAWH20029630, BRAWH20064050, BRSSN20014260, BRSSN20015030, BRSSN20015790,
BRAWH20075700, BRAWH20096780, BRSSN20018690, BRSSN20028570, BRSSN20038200,
BRAWH20100690, BRAWH20101360, BRSSN20038410, BRSSN20039370, BRSSN20043040,
BRAWH20103180, BRAWH20105840, BRSSN20046570, BRSSN20046790, BRSSN20046860,
BRAWH20106180, BRAWH20107540, BRSSN20066110, BRSSN20097020, BRSSN20101100,
BRAWH20110660, BRAWH20110790, BRAWH20110960, BRSSN20105870, BRSSN20105960, BRSSN20108300,
BRAWH20111550, BRAWH20112940, BRAWH20114000, BRSSN20120810, BRSSN20121030, BRSSN20137020,
BRAWH20117950, BRAWH20118230, BRSSN20142940, BRSSN20146100, BRSSN20151990,
BRAWH20122580, BRAWH20125380, BRSSN20159070, BRSSN20159820, BRSSN20169050,
BRAWH20126190, BRAWH20126980, BRSSN20176820, BRSSN20177570, BRSSN20187310,
BRAWH20132190, BRAWH20137480, BRSTN20000580, BRSTN20005360, BRTHA20000570,
BRAWH20138660, BRAWH20139410, BRTHA20004740, BRTHA20046290, BRTHA20046390,
BRAWH20142340, BRAWH20147290, BRTHA20046420, CD34C30001250, CD34C30004240,
BRAWH20149340, BRAWH20155950, CTONG10000100, CTONG20004690, CTONG20027090,
BRAWH20158530, BRAWH20160280, CTONG20050280, CTONG20076130, CTONG20077790,
BRAWH20162690, BRAWH20166790, CTONG20095290, CTONG20095340, CTONG20099380,
BRAWH20171030, BRAWH20173050, CTONG20106520, CTONG20118250, CTONG20121010,
BRAWH20182060, BRAWH20185060, BRCAN10001490, CTONG20127450, CTONG20128470, CTONG20141650,
BRCAN20003460, BRCAN20006200, BRCAN20006390, CTONG20143690, CTONG20153300, CTONG20155180,
BRCAN20054490, BRCAN20060190, BRCAN20064010, CTONG20158150, CTONG20161850, CTONG20164990,
BRCAN20071190, BRCAN20091560, BRCAN20103740, CTONG20186320, D30ST10002700, D60ST20003580,
BRCAN20124080, BRCAN20126130, BRCAN20143700, D90ST20000310, D90ST20035800, DFNES20010910,
BRCAN20147880, BRCAN20216690, BRCAN20224720, DFNES20071130, HCHON20002260, HCHON20003220,
BRCAN20237240, BRCAN20263400, BRCAN20273100, HCHON20010990, HCHON20015350, HCHON20022470,
BRCAN20273340, BRCAN20273550, BRCAN20275130, HCHON20067220, HCHON20067700, HEART20003060,
BRCAN20279700, BRCAN20280210, BRCAN20280400, HEART20005410, HEART20061950, HEART20090000,
BRCAN20283190, BRCAN20283380, BRCAN20284600, HHDPC10000650, HHDPC20057940, HLUNG20033780,
BRCAN20285450, BRCOC10000870, BRCOC20001860, KIDNE20011170, KIDNE20027250, KIDNE20104300,
BRCOC20004040, BRCOC20004870, BRCOC20006370, KIDNE20107500, KIDNE20122910, KIDNE20127100,
BRCOC20008160, BRCOC20008500, BRCOC20020850, KIDNE20180710, LIVER10001260, LIVER20064100, LIVER20087510, MAMGL10000830, MESAN20031900, MESAN20036460, MESAN20106640, MESAN20164090, NOVAR10000150, NOVAR20000380, NT2NE20010400, NT2NE20010490, NT2NE20021620, NT2NE20122430, NT2NE20125050, NT2NE20174920, NT2RI20001330, NT2RI20023590, NT2RI20041880, NT2RI20046080, NT2RI20216250, NT2RI20252550, NT2RP60000770, NT2RP70045590, NT2RP70063950, NT2RP70195430, NT2RP70198350, NTONG20028070, NTONG20046140, NTONG20064840, NTONG20067830, NTONG20077560, PANCR10000910, PEBLM20024550, PEBLM20052820, PEBLM20074370, PERIC20004780, PLACE50000660, PLACE60079250, PLACE60136720, PLACE60138830, PROST20005670, PROST20050670, PROST20107820, PROST20111050, PROST20116600, PROST20120160, PROST20123530, PROST20161950, PROST20171280, PROST20175290, PROST20185830, PROST20191640, PUAEN20015860, PUAEN20030180, PUAEN20044000, PUAEN20078980, PUAEN20085150, PUAEN20108240, SKMUS20012010, SKNSH20062340, SMINT20013480, SMINT20042990, SMINT20053300, SMINT20076470, SMINT20092330, SMINT20101440, SMINT20121220, SMINT20121950, SMINT20122910, SMINT20130230, SMINT20131810, SMINT20144800, SMINT20163960, SPLEN20002220, SPLEN20008740, SPLEN20011410, SPLEN20016260, SPLEN20027440, SPLEN20029310, SPLEN20033960, SPLEN20054290, SPLEN20126190, SPLEN20128000, SPLEN20145720, SPLEN20146450, SPLEN20147110, SPLEN20149110, SPLEN20157880, SPLEN20158900, SPLEN20171210, SPLEN20179180, SPLEN20186430, SPLEN20204170, SPLEN20212730, SPLEN20214580, SPLEN20250390, STOMA20051200, STOMA20062290, STOMA20092890, SYNOV20003970, TESOP20005270, TESTI10000940, TESTI20001720, TESTI20002720, TESTI20004890, TESTI20011200, TESTI20035960, TESTI20037560, TESTI20044310, TESTI20061110, TESTI20063830, TESTI20086210, TESTI20152460, TESTI20168960, TESTI20170350, TESTI20208400, TESTI20213580, TESTI20214250, TESTI20254220, TESTI20258460, TESTI20330310, TESTI20334410, TESTI20366910, TESTI20391770, TESTI20432750, TESTI20455620, THYMU20000570, THYMU20058070, THYMU20066100, THYMU20075320, THYMU20081490, THYMU20100410, THYMU20101920, THYMU20108310, THYMU20119390, THYMU20126900, THYMU20128260, THYMU20169680, THYMU20193640, THYMU20209590, THYMU20235760, THYMU20239430, THYMU20240710, THYMU20253250, THYMU20286290, TKIDN10000010, TKIDN20005210, TKIDN20030590, TRACH20005020, TRACH20005400, TRACH20007020, TRACH20019960, TRACH20034840, TRACH20079690, TRACH20128110, TRACH20149970, TRACH20183170, UMVEN10001860, UMVEN20003540, UTERU20000740, UTERU20030570, UTERU20054460, UTERU20055930, UTERU20056010, UTERU20064860, UTERU20065930, UTERU20070040, UTERU20081300, UTERU20084260, UTERU20094350, UTERU20120310, UTERU20124070, UTERU20164260, UTERU20168220, UTERU20183640, ASTRO20032120, ASTRO20125520, BRACE20039040, BRACE20060720, BRACE20062640, BRACE20090440, BRACE20099570, BRACE20111830, BRACE20142570, BRAWH20128270, BRCAN20280360, BRHIP20110800, BRHIP20176420, BRSSN20003120, CTONG20105660, CTONG20124010, CTONG20133480, CTONG20139070, CTONG20160560, FCBBF10001210, FCBBF10001550, FCBBF10001710, FCBBF10001820, FCBBF10002430, FCBBF10002700, FCBBF10002800, FCBBF10003220, FCBBF10003740, FCBBF10003760, FCBBF10005060, FCBBF10005460, FCBBF10005500, FCBBF20006780, FCBBF20014270, FCBBF20023700, FCBBF20032970, FCBBF20035280, FCBBF20042170, FCBBF20042560, FCBBF20051220, FCBBF20054280, FCBBF20056370, FCBBF20064520, FCBBF20067810, FCBBF20071860, FCBBF20072650, FCBBF20076330, FCBBF30008470, FCBBF30010810, FCBBF30012350, FCBBF30012810, FCBBF30015940, FCBBF30019120, FCBBF30024750, FCBBF30028180, FCBBF30033050, FCBBF30039020, FCBBF30052180, FCBBF30054440, FCBBF30057290, FCBBF30062880, FCBBF30070770, FCBBF30071520, FCBBF30078290, FCBBF30083620, FCBBF30123470, FCBBF30170590, FCBBF30172550, FCBBF30175310, FCBBF30178730, FCBBF30190850, FCBBF30195640, FCBBF30199610, FCBBF30215060, FCBBF30225660, FCBBF30240960, FCBBF30242250, FCBBF30243640, FCBBF30247930, FCBBF30252520, FCBBF30252800, FCBBF30252850, FCBBF30262510, FCBBF30266780, FCBBF30266920, FCBBF30278630, FCBBF30279030, FCBBF30281880, FCBBF30284720, FCBBF30285280, FCBBF40001730, FCBBF40005480, HCHON20007380, HEART20072310, HHDPC20068620, HLUNG20023340, KIDNE20017130, KIDNE20028830, MESAN20014500, NT2RP70072690, NT2RP70137640, NTONG20067090, PLACE60004630, PROST20083600, PROST20189770, RECTM20003490, SKNSH20008190, SMINT20115880, SPLEN20169720, SPLEN20194050, SPLEN20284240, TESTI20083940, TESTI20213150, TESTI20254540, TESTI20265250, TRACH20118940, UTERU20145480, UTERU20146680, ASTRO20155290, BRAWH20030250, BRAWH20113430, BRAWH20122770, BRHIP20005340, BRHIP30001110, BRSTN20002200, CTONG20052900, CTONG20108210, DFNES20031920, FEBRA10001900, FEBRA20003210, FEBRA20007620, FEBRA20009090, FEBRA20010120, FEBRA20017050, FEBRA20018280, FEBRA20025270, FEBRA20025520, FEBRA20026110, FEBRA20026280, FEBRA20029860, FEBRA20034680, FEBRA20037260, FEBRA20040530, FEBRA20042190, FEBRA20052910, FEBRA20060610, FEBRA20072120, FEBRA20079310, FEBRA20082010, FEBRA20088360, FEBRA20090290, FEBRA20092890, FEBRA20093520, FEBRA20097310, FEBRA20113560, FEBRA20125070, FEBRA20132740, FEBRA20140100, FEBRA20161120, FEBRA20166540, FEBRA20167390, FEBRA20171380, FEBRA20176800, FEBRA20184330, FEBRA20192420, FEBRA20195820, FEBRA20196370, FEBRA20196630, FEBRA20197110, FEBRA20211710, FEBRA20214970, FEBRA20215500, FEBRA20216360, FEBRA20222040, FEBRA20223220, FEBRA20225040, FEBRA20226010, FEBRA20229560, FEBRA20229630, FEBRA20232850, FEBRA20235500, HCHON20040020, KIDNE20102650, NT2RP70037240, PEBLM20072960, PLACE60169420, SKMUS20003610, SMINT20026890, SMINT20033400, SPLEN20020070, SPLEN20079510, TESTI20001000, TESTI20094020, THYMU20027560, THYMU20180280, THYMU20271250, TRACH20003590, UMVEN10001560, UTERU20022940, UTERU20046640, UTERU20119060, UTERU20144640, UTERU20176130, ASTRO20008010, BRACE20276430, BRAMY20103570, BRAMY20120910, BRAMY20162510, BRAMY20196000, BRAWH20164460, BRCAN20273640, BRCOC20105100, BRHIP20198190, BRHIP20222280, BRHIP20254480, BRHIP30004570, CTONG20028410, CTONG20091080, CTONG20103480, CTONG20126070, CTONG20139340, DFNES20001530, HCHON20008150, HHDPC20001040, HLUNG20016330, HLUNG20017120, IMR3220002430, KIDNE20007210, KIDNE20021910, KIDNE20124400, MESAN10001260, MESAN20029400, MESAN20121130, MESAN20153910, NT2NE20159740, NT2NE20177520, NT2RI20086220, NT2RI20250750, NT2RP60000850, NT2RP70044280, NT2RP70056750, NT2RP70081610, NTONG20009770, OCBBF10000540, OCBBF10001750, OCBBF20006770, OCBBF20013890, OCBBF20019830, OCBBF20020150, OCBBF20020830, OCBBF20023570, OCBBF20028050, OCBBF20028650, OCBBF20029800, OCBBF20030280, OCBBF20030910, OCBBF20035930, OCBBF20037440, OCBBF20041680, OCBBF20045330, OCBBF20046120, OCBBF20046470, OCBBF20046690, OCBBF20048660, OCBBF20050770, OCBBF20051610, OCBBF20053430, OCBBF20053490, OCBBF20053730, OCBBF20054200, OCBBF20054760, OCBBF20060300, OCBBF20062140, OCBBF20062410, OCBBF20066390, OCBBF20071210, OCBBF20071840, OCBBF20072240, OCBBF20073540, OCBBF20074140, OCBBF20076220, OCBBF20079310, OCBBF20079460, OCBBF20081380, OCBBF20082830, OCBBF20085200, OCBBF20086400, OCBBF20086910, OCBBF20088140, OCBBF20088220, OCBBF20091150, OCBBF20100400, OCBBF20103130, OCBBF20104040, OCBBF20105570, OCBBF20107090, OCBBF20107920, OCBBF20108580, OCBBF20108630, OCBBF20109310, OCBBF20111770, OCBBF20116850, OCBBF20118970, OCBBF20120390, OCBBF20121390, OCBBF20122620, OCBBF20124360, OCBBF20127040, OCBBF20127140, OCBBF20127550, OCBBF20128120, OCBBF20129360, OCBBF20130910, OCBBF20132850, OCBBF20140890, OCBBF20145760, OCBBF20148280, OCBBF20151150, OCBBF20153340, OCBBF20153350, OCBBF20155060, OCBBF20164670, OCBBF20170690, OCBBF20173060, OCBBF20173250, OCBBF20178150, OCBBF20180840, OCBBF20186870, OCBBF20189560, PEBLM20044520, PEBLM20071880, PLACE60060420, PROST20047390, PUAEN20003740, SMINT20029760, SPLEN20008820, SPLEN20084600, SPLEN20095550, SPLEN20099700, SPLEN20140800, SPLEN20173510, SPLEN20211220, SPLEN20250170, STOMA20067800, TESTI20031270, TESTI20116830, TESTI20121550, TESTI20234140, TESTI20442760, THYMU20039810, THYMU20070360, TRACH20033230, TRACH20084720, BRACE20067430, BRAWH10000930, BRHIP20003120, BRSSN20152380, FEBRA20024100, FEBRA20027810, FEBRA20037500, FEBRA20082100, FEBRA20098460, FEBRA20144170, FEBRA20145780, FEBRA20233770, HHDPC10000830, MESAN20025190, MESAN20089360, NT2RI20048840, NT2RP70043480, OCBBF20032460, OCBBF20039250, OCBBF20049300, OCBBF20061720, OCBBF20078920, OCBBF20084660, OCBBF20087010, PROST20087700, PROST20153320, TRACH20135520, ADIPS20004250, ASTRO10001650, BRACE20056810, BRACE20059370, BRACE20106690, BRACE20210140, BRAWH20103290, BRAWH20121640, BRHIP20005530, BRHIP20217620, BRHIP20218580, BRHIP20238880, CTONG20075860, CTONG20129960, FCBBF10000240, FCBBF10000630, FCBBF10001150, FCBBF10004120, FCBBF10005740, FCBBF20075560, FCBBF30018550, FCBBF30025560, FCBBF30086440, FCBBF30090690, FCBBF30189490, FCBBF30233680, FCBBF30240020, HCHON20007510, HCHON20016650, HHDPC20095280, KIDNE20002520, KIDNE20009470, NT2RI20003480, NT2RI20055790, NT2RP70027380, NT2RP70032610, NT2RP70062230, OCBBF10001850, OCBBF20022900, OCBBF20026630, OCBBF20049840, OCBBF20059560, OCBBF20068490, OCBBF20071960, OCBBF20080410, OCBBF20094240, OCBBF20097720, OCBBF20108190, OCBBF20108430, OCBBF20126780, OCBBF20130110, OCBBF20139260, OCBBF20148730, OCBBF20149280, OCBBF20164050, OCBBF20173980, OCBBF20178880, OCBBF20180120, OCBBF20188730, PROST20057930, SPLEN20162680, SPLEN20211940, TESTI20184620, TESTI20211240, TESTI20369690, THYMU20141670, TRACH20028030, UTERU20099720, UTERU20135860, BRACE20057190, BRHIP20191860, BRHIP20214950, FCBBF10003670, FCBBF10004370, FCBBF30013770, FCBBF30095260, FCBBF30246230, FEBRA20002100, FEBRA20034360, FEBRA20095140, FEBRA20130190, FEBRA20204060, HCHON20008320, LIVER20028420, TRACH20111130, ASTRO20108190, BRACE20003070, BRACE20060550, BRAWH20004600, BRAWH20011710, BRAWH20016620, BRHIP10001740, BRSTN10000830, CTONG10000940, CTONG20150910, D30ST10002670, FCBBF10000380, FCBBF10000770, FCBBF10003770, FCBBF20059090, FCBBF30016320, FCBBF30016570, FCBBF30049550, FCBBF30083820, FCBBF30238870, FCBBF40001420, FEBRA10001880, FEBRA20004620, FEBRA20080810, FEBRA20086620, FEBRA20095880, HHDPC20034390, HLUNG10000550, NT2RI20023160, NT2RI20023910, NT2RI20025400, NT2RI20028470, NT2RI20054050, NT2RI20076290, NT2RI20091730, NT2RI20091940, NT2RP70036880, NT2RP70078420, OCBBF20047570, OCBBF20080050, OCBBF20125530, OCBBF20140640, TRACH20032720, TRACH20141240, UTERU20004240

The result of comparative analysis of cDNA libraries derived from fetal heart (FEHRT) and adult heart (HEART) showed that the genes whose expression levels were different between the two were the following clones (Table 49). FEHRT20003250, OCBBF20189560, BRAWH20029630, CTONG20150910, HCHON20007510, HEART20003060, HEART20005410, HEART20021840, HEART20025980, HEART20034320, HEART20037810, HEART20049400, HEART20049410, HEART20049800, HEART20061950, HEART20063340, HEART20067870, HEART20067890, HEART20072310, HEART20074430, HEART20077670, HEART20089940, HEART20090000, HEART20095990, HLUNG10000550, HLUNG20017120, KIDNE20028390, KIDNE20028830, NTONG20029480, OCBBF10001750, PROST20127800, SKMUS20001980, SKMUS20003610, SMINT20026890, SMINT20121220, SMINT20122910, SMINT20183530, SPLEN20008740, SPLEN20027440, SPLEN20162680, STOMA20062290, TESTI20254220, THYMU20271250, TRACH20141240, UTERU20004240

The result of comparative analysis of cDNA libraries derived from fetal kidney (FEKID) and adult kidney (KIDNE) showed that the genes whose expression levels were different between the two were the following clones (Table 50). ASTRO10001650, ASTRO20108190, BGGI120006160, BRACE20039040, BRACE20060550, BRAMY20102080, BRAWH20004600, BRAWH20125380, BRAWH20162690, BRHIP20115760, BRHIP20205090, BRHIP20238880, CTONG20052650, CTONG20108210, CTONG20128470, CTONG20133480, CTONG20139070, D90ST20000310, DFNES20001530, FCBBF10001820, FEBRA20002100, HCHON20008980, HCHON20016650, HLUNG20033780, KIDNE20002520, KIDNE20003940, KIDNE20006780, KIDNE20007210, KIDNE20007770, KIDNE20008010, KIDNE20009470, KIDNE20011170, KIDNE20011400, KIDNE20013730, KIDNE20017130, KIDNE20018730, KIDNE20018970, KIDNE20020150, KIDNE20021680, KIDNE20021910, KIDNE20021980, KIDNE20022620, KIDNE20024830, KIDNE20027250, KIDNE20027950, KIDNE20028390, KIDNE20028830, KIDNE20029800, KIDNE20067330, KIDNE20079440, KIDNE20096280, KIDNE20096470, KIDNE20100070, KIDNE20100840, KIDNE20101370, KIDNE20101510, KIDNE20102650, KIDNE20102710, KIDNE20104300, KIDNE20106740, KIDNE20107390, KIDNE20107500, KIDNE20107620, KIDNE20109730, KIDNE20109890, KIDNE20112000, KIDNE20115080, KIDNE20118580, KIDNE20120090, KIDNE20121880, KIDNE20122910, KIDNE20124400, KIDNE20125630, KIDNE20126010, KIDNE20126130, KIDNE20127100, KIDNE20127450, KIDNE20127750, KIDNE20130450, KIDNE20131580, KIDNE20132180, KIDNE20137340, KIDNE20138010, KIDNE20141190, KIDNE20144890, KIDNE20148900, KIDNE20163880, KIDNE20180710, KIDNE20181660, KIDNE20182690, KIDNE20186780, KIDNE20190740, LIVER20035110, MESAN20025190, NOVAR20000380, NT2RI20054050, NT2RP70043480, PROST20107820, PROST20123530, PROST20161950, PUAEN20030180, SKMUS20003610, SMINT20033400, TBAES20000590, TESTI20044310, TESTI20082330, TRACH20032720, UTERU20099720, BRACE20003070, BRCOC20031870, CTONG20125640, FCBBF30016320, HCHON20002260, HLUNG10000550, PROST20130530, SPLEN20169720, SPLEN20194050, KIDNE20028720

The result of comparative analysis of cDNA libraries derived from fetal lung (FELNG) and adult lung (HLUNG) showed that the genes whose expression levels were different between the two were the following clones (Table 51). BRACE20096200, BRAWH20004600, BRAWH20030250, BRCAN20006390, BRCAN20280360, BRHIP20238880, CTONG10000940, CTONG20103480, CTONG20129960, CTONG20155180, FCBBF10001210, FEBRA20144170, FEBRA20197110, HHDPC20034390, HLUNG20016330, HLUNG20016770, HLUNG20017120, HLUNG20023340, HLUNG20033780, HLUNG20084390, IMR3220002430, LIVER20028420, NOVAR20000380, NT2RI20054050, NT2RI20091730, NT2RP70044280, OCBBF20020830, OCBBF20125530, PLACE60004630, PROST20057930, PROST20107820, PROST20185830, PUAEN20030180, SMINT20121220, SPLEN20002220, SPLEN20054290, SPLEN20128000, SPLEN20157300, SPLEN20176200, SPLEN20179180, SPLEN20211940, STOMA20013890, TBAES20000590, TESTI20094230, TESTI20184620, TESTI20334410, THYMU20000570, THYMU20039810, TRACH20007020, TRACH20141240, TRACH20183170, D90ST20033970, FELNG20002410, HCHON20016650, KIDNE20029800, OCBBF20145760, SPLEN20162680, TESTI20214250, TRACH20005400, HCHON20002260, HLUNG10000550, NT2RI20023910, SPLEN20008740

These genes are involved in regeneration of tissues and/or cells.

EXAMPLE 8

Expression Frequency Analysis by PCR

Specific PCR primers were prepared based on the full-length nucleotide sequences, and the expression frequency was analyzed by the ATAC-PCR method (Adaptor-tagged competitive PCR method: Nucleic Acids Research 1997, 25(22): 4694–4696; "DNA Micro-array and Advanced PCR Techniques", Cell Technology, supplement, Eds., Muramatsu and Nawa (Shujunsha, 2000): 104–112). Inflammation-related genes can be identified by revealing the genes whose expression levels are altered depending on the presence of an inflammation-inducing factor. Then, by using THP-1 cell line, which is a cell line of monocyte line, and TNF-α, which is inflammation-inducing factor, suitable for this system, the genes whose expression levels are altered depending on the presence of the factors were searched for by the system.

THP-1 cell line (purchased from DAINIPPON PHARMACEUTICAL) was cultured to be confluent in RPMI1640 medium (sigma) containing 5% fetal calf serum (GIBCO BRL). Then, the medium was changed with the medium containing 10 ng/ml TNF-α (human recombinant TNF-α; Pharmacia Biotech), and the culture was continued at 37° C. under 5% $CO_2$. After three hours, the cells were harvested, and total RNA was extracted from them by using ISOGEN reagent (Nippon Gene). The extraction was carried out according to the method in the document attached to ISOGEN reagent. In addition, total RNA was also extracted from the cells cultured without stimulation of TNF-α.

The genes involved in the onset of gastritis and gastroduodenal ulcer induced by the infection of *Helicobacter pylori* to the epithelia of stomach can be identified by revealing the genes whose expression levels are altered depending on co-culturing the cells with *Helicobacter pylori*. A recent study has suggested that various substances derived from *Helicobacter pylori* trigger the inflammation reaction. In particular, the members belonging to the family of genes called "cag pathogenicity island (cag PAI)" contribute to the activation of the NF-εB pathway (Gastroenterology 2000, 119: 97–108). Further, it has been found that cag PAI is involved in the onset of gastritis and the like by the study using an animal model (Journal of Experimental Medicine 2000, 192:1601–1610). Then, by using co-culture of a gastric cancer cell line with cag PAI-positive *Helicobacter pylori* (TN2), suitable for this system, the genes whose expression levels are altered depending on the presence of *Helicobacter pylori* were searched for by the system. Further, in order to study the involvement of cag PAI in the alterations of gene expression levels depending on the co-culture with *Helicobacter pylori*, the altered expression levels were compared between the cells co-cultured with a strain of *Helicobacter pylori* (TN2ΔcagE strain) having a mutation in cagE, which is one of the cag PAI genes, and the cag PAI-positive strain (TN2).

A gastric cancer cell line MKN45 (provided by the Cell Bank, RIKEN GENE BANK, The Institute of Physical and Chemical Research) was cultured to be confluent in RPMI1640 medium (sigma) containing 10% fetal calf serum (GIBCO BRL). Then, the medium was changed with the medium containing 100-fold excess (in terms of the number of cells or the number of colonies) of *Helicobacter pylori* (cag PAI positive strain (TN2) and cagE mutant (TN2ΔcagE): both were provided by Prof. Omata, Faculty of Medicine, The University of Tokyo), as compared with the number of the cancer cells. The culture was continued at 37° C. under 5% $CO_2$. After three hours, the cells were harvested, and total RNA was extracted from them by using ISOGEN reagent (Nippon Gene). The extraction was carried out according to the method in the document attached to ISOGEN reagent. In addition, total RNA was also extracted from the cells cultured without *Helicobacter pylori*.

The analysis by the ATAC-PCR method was carried out basically according to "DNA Micro-array and Advanced PCR Techniques", Cell Technology, supplement (Genome Science Series 1, Eds., Muramatsu and Nawa (Shujunsha, 2000): 104–112). Adapter ligation to the internal standard sample (sample to make the calibration curve for the clone of interest) and test sample was carried out in the two separate reaction systems indicated below. The combination of 6 types of adapters (AD-1, AD-2, AD-3, AD-4, AD-5 and AD-6: see the sequences indicated below) and the samples are as follows.

Reaction system A
AD1; internal standard, 10-fold
AD2; THP-1 cells, unstimulated
AD3; internal standard, 3-fold
AD4; THP-1 cells, TNF-α stimulation for one hour
AD5; THP-1 cells, TNF-α stimulation for three hours
AD6; internal standard, 1-fold Reaction system B
AD1; internal standard, 1-fold
AD2; MKN45 cells, unstimulated
AD3; internal standard, 3-fold
AD4; MKN45 cells, co-cultured with TN2(*Helicobacter pylori*)
AD5; internal standard, 10-fold
AD6; MKN45 cells, co-cultured with TN2ΔcagE(cagE gene mutant)

Adapter sequences:

```
//5'-GTACATATTGTCGTTAGAACGCG-3'              SEQ ID NO: 4887
//3'-CATGTATAACAGCAATCTTGCGCCTAG-5'          SEQ ID NO: 4888

AD2;
//5'-GTACATATTGTCGTTAGAACGCG-3'              SEQ ID NO: 4889
//3'-CATGTATAACAGCAATCTTGCGCTGACTAG-5'       SEQ ID NO: 4890

AD3;
//5'-GTACATATTGTCGTTAGAACGCGCATACT-3'        SEQ ID NO: 4891
//3'-CATGTATAACAGCAATCTTGCGCGTATGACTAG-5'    SEQ ID NO: 4892

AD4;
//5'-GTACATATTGTCGTTAGAACGCGATCCATACT-3'     SEQ ID NO: 4893
//3'-CATGTATAACAGCAATCTTGCGCTAGGTATGACTAG-5' SEQ ID NO: 4894

AD5;
//5'-GTACATATTGTCGTTAGAACGCGTCAATCCATACT-3'  SEQ ID NO: 4895
//3'-CATGTATAACAGCAATCTTGCGCAGTTAGGTATGACTAG-5' SEQ ID NO: 4896

AD6;
//5'-GTACATATTGTCGTTAGAACGCGTACTCAATCCATACT-3' SEQ ID NO: 4897
//3'-CATGTATAACAGCAATCTTGCGCATGAGTTAGGTATGACTAG-5' SEQ ID NO: 4898
```

The internal standard sample used for this assay was a mixture of total RNAs from tissues (or culture cells; all from UNITECH) of Fetal Brain, Testis, Trachea, and Spleen. RNA was prepared according to the standard method.

The sequences of primers specific to the genes and the names of clones of interest in the analysis are as follows. The gene specific primers were designed to produce the PCR products of 70 to 200 bp, which are derived from the adapter-containing cDNA. The sequence of adapter-specific primer (labeled with fluorescence (FAM)) used in the competitive PCR was GTACATATTGTCGTTAGAACGC (22 nucleotides; SEQ ID NO: 4899). PCR was basically carried out with a cycling profile of preheating at 94° C. for 3 minutes, and 35 or 40 cycles of denaturation at 94° C. for 30 seconds/annealing at 50° C. for 60 seconds/extension at 72° C. for 90 seconds.

The nucleotide sequences of clone specific primers used in the experiments

Clone name, primer sequence and SEQ ID NO are indicated below in this order. Each is demarcated by a double slash mark (//). For a clone for which a primer used in Reaction system A (THP-1 cells) was different from a primer used in Reaction system B (MKN45 cells), the sequence of each of the primers was shown.

| | | |
|---|---|---|
| 3NB6920014080 | //GTCCTGAAGGTAGATGCT// | SEQ ID NO: 4900 |
| ADRGL20013010 | //GGAGGATAGAGCTTGGAG// | SEQ ID NO: 4901 |
| ADRGL20067670 | //ATAAAACAGGACCAAGGA// | SEQ ID NO: 4902 |
| ADRGL20083310 | //AAATAAGGCTAAAATGGAACT// | SEQ ID NO: 4903 |
| ASTRO20032120 | //AGTGCTCCCAATTATCCG// | SEQ ID NO: 4904 |
| ASTRO20084250 | //TAGAAAATATGCTGGGTG// | SEQ ID NO: 4905 |
| ASTRO20152140 | //TCATTCTTCTCCCACAGC// | SEQ ID NO: 4906 |
| ASTRO20166810 | //AGTTTTATTTCCAGGCTATC// | SEQ ID NO: 4907 |

-continued

| | | |
|---|---|---|
| ASTRO20181690 | //ATGGAGAACAGGACAGCT// | SEQ ID NO: 4908 |
| BLADE20004630 | //CAAACATCAACCAGAGAA// | SEQ ID NO: 4909 |
| BRACE20006400 | //TCCCAATCAGCTAAGGTC// | SEQ ID NO: 4910 |
| BRACE20019540 | //CAGGTTATCGAGAGTTACAT// | SEQ ID NO: 4911 |
| BRACE20038480 | //TCTGGTTGGATTTTGTGC// | SEQ ID NO: 4912 |
| BRACE20039040 | //TGAACTTTGTGGTCTGGT// | SEQ ID NO: 4913 |
| BRACE20039440 | //TGAACAGTGACATTTTAGG// | SEQ ID NO: 4914 |
| BRACE20052160 | //AAGAATAAAAGGGACGAG// | SEQ ID NO: 4915 |
| BRACE20053630 | //GTTTGATACAGATGATTAGGTTA// | SEQ ID NO: 4916 |
| BRACE20057620 | //GGACAGGTAAGAACTAGGC// | SEQ ID NO: 4917 |
| BRACE20058810 | //ATCATCTTTCCAATCCAG// | SEQ ID NO: 4918 |
| BRACE20060720 | //GTACCACCTGACCTTCTG// | SEQ ID NO: 4919 |
| BRACE20060840 | //AGAAGTTTTATCCCACATTT// | SEQ ID NO: 4920 |
| BRACE20061740 //(Reaction system A) | //TAACATAACCCTCCCGTC// | SEQ ID NO: 4921 |
| //(Reaction system B) | //ATAGTGGTGACGTTCCCC// | SEQ ID NO: 4922 |
| BRACE20062640 | //TCTGTTGCTGAAGGAAAA// | SEQ ID NO: 4923 |
| BRACE20063780 | //TCCTGTGTGCTATTTGAA// | SEQ ID NO: 4924 |
| BRACE20067430 | //AATAACAGCAACTCCAGA// | SEQ ID NO: 4925 |
| BRACE20090440 | //CCCAACATTACCAAAAGT// | SEQ ID NO: 4926 |
| BRACE20101700 | //CAACATTTTCAAGCACTG// | SEQ ID NO: 4927 |
| BRACE20114780 | //GATGTTGGGGTTTGGAAG// | SEQ ID NO: 4928 |
| BRACE20151320 | //ACCAGCTGCCCATAGAAG// | SEQ ID NO: 4929 |
| BRACE20152870 | //GAAGGCAAGATGGTAAGT// | SEQ ID NO: 4930 |
| BRACE20163150 | //CATAGAGAAAGCGGGGAA// | SEQ ID NO: 4931 |
| BRACE20165830//(Reaction system A) | //TCTCCCTGTTCTCTCTTT// | SEQ ID NO: 4932 |
| //(Reaction system B) | //TATGACCCAAACGCCTAG// | SEQ ID NO: 4933 |
| BRACE20201570 | //CCTTCTCATCTAGCTTGC// | SEQ ID NO: 4934 |
| BRACE20210140 | //TACTGATTGGGAAGCACT// | SEQ ID NO: 4935 |
| BRACE20223330 | //GTTGAAATGCTTGAGCAC// | SEQ ID NO: 4936 |
| BRACE20224500 | //ATTTAGAGCGCCATCCTT// | SEQ ID NO: 4937 |
| BRACE20229280 | //CTGAGGGTAAAGGAAGGG// | SEQ ID NO: 4938 |
| BRACE20235400 | //TTTTACGATTGCCTTTGC// | SEQ ID NO: 4939 |
| BPACE20266750 | //TTAGGAGTGAAGACAGGA// | SEQ ID NO: 4940 |
| BRACE20267250 | //GTGCAGTGATAAGTGGCT// | SEQ ID NO: 4941 |
| BRACE20269710 | //AGGCAGGGAAAGTAGGGT// | SEQ ID NO: 4942 |
| BRALZ20018340 | //AGGAGAGGCTTGAGGACT// | SEQ ID NO: 4943 |
| BRALZ20058880 | //AAGGGACCAAAATGAGAG// | SEQ ID NO: 4944 |
| BRALZ20059500 | //AACAGCCCTCTAATGAAA// | SEQ ID NO: 4945 |
| BRALZ20064740 | //ACTCATGTTGCTCCACCT// | SEQ ID NO: 4946 |
| BRALZ20069760 | //TATGTATGGCTTTGAGCA// | SEQ ID NO: 4947 |

-continued

| | | |
|---|---|---|
| BPALZ20075450 | //GCTGAAGAAATGTGCTGC// | SEQ ID NO: 4948 |
| BRALZ20088690 | //ATCATAGTTGTACATACTTTGGG// | SEQ ID NO: 4949 |
| BRAMY20002770 | //TTCTTTCCTGTAATAGTTGG// | SEQ ID NO: 4950 |
| BRAMY20004110 | //AGCTATCTGTGAAAGTCCT// | SEQ ID NO: 4951 |
| BRAMY20060920//(Reaction system A) | //TGCTGTCTCGTGATAAAG// | SEQ ID NO: 4952 |
| //(Reaction system B) | //TTTCTAATGGTTTGGCAC// | SEQ ID NO: 4953 |
| BRAMY20103570//(Reaction system A) | //TCAACAGTGCTTTTCCTT// | SEQ ID NO: 4954 |
| //(Reaction system B) | //GACTCTTCTCCAGGGTGC// | SEQ ID NO: 4955 |
| BRAMY20144620 | //CACGCCATTCTGTTAAAA// | SEQ ID NO: 4956 |
| BRAMY20152110 | //AATGGGCTAAATATTGCT// | SEQ ID NO: 4957 |
| BRAMY20162510 | //GCAAATACAGGTAAATGACAG// | SEQ ID NO: 4958 |
| BRAMY20163250 | //CAAGAGAAATTAAAGAAGACC// | SEQ ID NO: 4959 |
| BRAMY20163270//(Reaction system A) | //TGCTTTCAACTGTCATTT// | SEQ ID NO: 4960 |
| //(Reaction system B) | //GAATGATGCCCGATGTAG// | SEQ ID NO: 4961 |
| BRAMY20168920 | //GAATATCCCTGTGGAGTC// | SEQ ID NO: 4962 |
| BRAMY20178640 | //AGTCTCACTCTATTGCCA// | SEQ ID NO: 4963 |
| BRAMY20184670 | //AACGAATAGCAGGGTAGC// | SEQ ID NO: 4964 |
| BRAMY20204450 | //GGTGAGTTACTGGCTGCA// | SEQ ID NO: 4965 |
| BRAMY20210400 | //AAGATTAACCATACAACAGAAA// | SEQ ID NO: 4966 |
| BRAMY20215230 | //TGAACAAGAAACACCAGT// | SEQ ID NO: 4967 |
| BRAMY20218670 | //AGGAGGCACGGTAACAAT// | SEQ ID NO: 4968 |
| BRAMY20229800 | //GTCTTCTGTCTCATGGGG// | SEQ ID NO: 4969 |
| BRAMY20229840 | //AAAGTTCATGAGGGGCTG// | SEQ ID NO: 4970 |
| BRAMY20231720 | //CAGCACAAAATCAGTTAAA// | SEQ ID NO: 4971 |
| BRAMY20247280 | //GGTTTAGATTTATGAGACAAGA// | SEQ ID NO: 4972 |
| BRAMY20261680 | //GTTACTGCAGGGCTTCAG// | SEQ ID NO: 4973 |
| BRAMY20266850 | //TGCATGGAATTAAGGAGT// | SEQ ID NO: 4974 |
| BRAMY20267130 | //AATCTGTAAAATGGGAATAAG// | SEQ ID NO: 4975 |
| BRAMY20277140//(Reaction system A) | //ATGAGATTGTGTTGTCCA// | SEQ ID NO: 4976 |
| //(Reaction system B) | //TTCCAGCATTTTCGTTTT// | SEQ ID NO: 4977 |
| BRAMY20280720//(Reaction system A) | //TTCCCAAGTCCAGATTTT// | SEQ ID NO: 4978 |
| //(Reaction system B) | //CTGAGGAGCAGTGACAAG// | SEQ ID NO: 4979 |
| BRAWH10000930 | //GGGAGAGAAGAGTCCTGC// | SEQ ID NO: 4980 |
| BRAWH20015350 | //GCTATGAAGACAACCAAACT// | SEQ ID NO: 4981 |
| BRAWH20017010 | //AGGAAGAGATGGGTCAGC// | SEQ ID NO: 4982 |
| BRAWH20029630 | //GGAGTATCACCATGTAAAGA// | SEQ ID NO: 4983 |
| BRAWH20100690//(Reaction system A) | //AAATGAGCACTCCATTCC// | SEQ ID NO: 4984 |
| //(Reaction system B) | //AATGAGCACTCCATTCCC// | SEQ ID NO: 4985 |
| BRAWH2010G180//(Reaction system A) | //CATTTTATTGTCACCCAC// | SEQ ID NO: 4986 |
| //(Reaction system B) | //CCTTTAACAGCATCTCTAGTG// | SEQ ID NO: 4987 |

-continued

| | | |
|---|---|---|
| BRAWH20107540 | //GTTGAGCTATTTGCAGAG// | SEQ ID NO: 4988 |
| BRAWH20110660 | //CTTAGCAACTTTCCACAC// | SEQ ID NO: 4989 |
| BRAWH20118230 | //GTCAGAAAACTCACACCA// | SEQ ID NO: 4990 |
| BRAWH20122770 | //AAGTTGATAGGGAAGGTTT// | SEQ ID NO: 4991 |
| BRAWH20126190 | //ACCATGTGCTCAGAATCA// | SEQ ID NO: 4992 |
| BRAWH20132190 | //TAAGATTCACAGGGTGGA// | SEQ ID NO: 4993 |
| BRAWH20138660 | //GATGGAAAATGTAAGGCT// | SEQ ID NO: 4994 |
| BRAWH20139410 | //CCATCCTCTACACAGCAG// | SEQ ID NO: 4995 |
| BRAWH20155950//(Reaction system A) | //CTCTCATTTTGGCTCTGC// | SEQ ID NO: 4996 |
| //(Reaction system B) | //CTACTCCACCTCTGCTGC// | SEQ ID NO: 4997 |
| BRAWH20158530 | //AGTTTTCTGATGGCCTTG// | SEQ ID NO: 4998 |
| BRCAN20060190 | //AGGTAGCCCCAGAGTCAC// | SEQ ID NO: 4999 |
| BRCAN20147880 | //ACTCAGCAATCAGGTCCA// | SEQ ID NO: 5000 |
| BRCAN20273340 | //AATTATGAGATAGGATGTTAGCT// | SEQ ID NO: 5001 |
| BRCAN20273640 | //CTGCACCGATTTTATAGC// | SEQ ID NO: 5002 |
| BRCAN20275130 | //CACTATCCAGACACACCT// | SEQ ID NO: 5003 |
| BRCAN20280210 | //CACTGGATTTTCTTCACTT// | SEQ ID NO: 5004 |
| BRCAN20280400 | //GGAAGGATAGCAGTTGAT// | SEQ ID NO: 5005 |
| BRCOC20021550 | //TCCAAGCAGAGTTTTCAC// | SEQ ID NO: 5006 |
| BRCOC20037400 | //CAAGTCTGTTCATCTGGT// | SEQ ID NO: 5007 |
| BRCOC20105100//(Reaction system A) | //ACTTGAGGTTTCTTGGCA// | SEQ ID NO: 5008 |
| //(Reaction system B) | //GATTCTTCCCCGACTCAG// | SEQ ID NO: 5009 |
| BRHIP10001740 | //GTACACACCTGCTCCCAC// | SEQ ID NO: 5010 |
| BRHIP20001630 | //GGTCAGTAAGTGGTTGTG// | SEQ ID NO: 5011 |
| BRHIP20096170 | //TTATTTTGGATGCCCCTG// | SEQ ID NO: 5012 |
| BRH1P20103090 | //ACTCCAACAACCTTCATT// | SEQ ID NO: 5013 |
| BRH1P20105710 | //TTTCAAGTATCCTCCCCA// | SEQ ID NO: 5014 |
| BRHIP20110800 | //TAGAACTGCCTCCAACCC// | SEQ ID NO: 5015 |
| BRHIP20111200 | //TACTGAACGGTGACTGGC// | SEQ ID NO: 5016 |
| BRHIP20118910 | //ACAGGAAGGGAAAGAGT// | SEQ ID NO: 5017 |
| BRHIP20129720 | //GAGGAGAGTGAGAAGGGG// | SEQ ID NO: 5018 |
| BRHIP20143860 | //AGGTCAGGAGAACAAGCC// | SEQ ID NO: 5019 |
| BRHIP20173150 | //CTTTTGCAGAGTTTTCCT// | SEQ ID NO: 5020 |
| BRHIP20175420 | //TCTCTAGGGCAAAACATT// | SEQ ID NO: 5021 |
| BRH1P20186120//(Reaction system A) | //AATTGATACGCAGGGGAG// | SEQ ID NO : 5022 |
| //(Reaction system B) | //AAGGTCAGTTGAAGTGCT// | SEQ ID NO: 5023 |
| BRH1P20194940 | //TAGAGAAGGTGAGGCCAG// | SEQ ID NO: 5024 |
| BRH1P20196410 | //GGCATAGAAGTAATCAGAGA// | SEQ ID NO: 5025 |
| BRHIP20207430 | //AAGCTGAACCCCAATAAA// | SEQ ID NO: 5026 |
| BRHIP20218580 | //GATTACCAGAACACAGCC// | SEQ ID NO: 5027 |

-continued

| | | |
|---|---|---|
| BRHIP20233090 | //GTCCATTTACCAACGGCT// | SEQ ID NO: 5028 |
| BRHIP20284800 | //CACATCTTTACATTTATTGCTATT// | SEQ ID NO: 5029 |
| BRHIP30004880 | //TCTTCTCGTAGGGCTTGA// | SEQ ID NO: 5030 |
| BRSSN20046570 | //AAACACGAAATGGATGAA// | SEQ ID NO: 5031 |
| BRSSN20142940 | //AGAATCAGAGAAGCCGGT// | SEQ ID NO: 5032 |
| BRSSN20152380 | //ATACCCATTTCAGTTCCT// | SEQ ID NO: 5033 |
| BRSSN20176820 | //CAGTCCCAATACAGCTCA// | SEQ ID NO: 5034 |
| BRSSN20187310//(Reaction system A) | //CAATGACTAGTTTGTGCA// | SEQ ID NO: 5035 |
| //(Reaction system B) | //AAAGAAGCCAGGAAGATT// | SEQ ID NO: 5036 |
| BRTHA20046390 | //ACATGGAGCCTGGTTTAG// | SEQ ID NO: 5037 |
| CD34C30004240 | //TGGAAGATACGGATAACTC// | SEQ ID NO: 5038 |
| CD34C30004940//(Reaction system A) | //ACCACTGTTCTCTGGTGC// | SEQ ID NO: 5039 |
| //(Reaction system B) | //CCACCACTGTTCTCTGGT// | SEQ ID NO: 5040 |
| COLON20043180 | //TCGGATTGGGTTAAGGTC// | SEQ ID NO: 5041 |
| CTONG10000620 | //CTCCATTCATCAGACCAC// | SEQ ID NO: 5042 |
| CTONG20014280 | //TCCAAAAGACAGAACAGC// | SEQ ID NO: 5043 |
| CTONG20095270 | //GTTTTGTTCCCTGCTCAC// | SEQ ID NO: 5044 |
| CTONG20095290 | //AACACAGCTCAACAACTC// | SEQ ID NO: 5045 |
| CTONG20096750 | //TGACTAAGCATGGAGACT// | SEQ ID NO: 5046 |
| CTONG20100240 | //AGTCATAATCATCTTCCTCA// | SEQ ID NO: 5047 |
| CTONG20103480 | //GGTGGAGTAATGTATATAACGTAA// | SEQ ID NO: 5048 |
| CTONG20105660 | //CCATTAACACAAACCAAA// | SEQ ID NO: 5049 |
| CTONG20121010 | //GGAAGATGGGACCTCAGT// | SEQ ID NO: 5050 |
| CTONG20128470 | //TTGGGGTATCTTGGAGCT// | SEQ ID NO: 5051 |
| CTONG20138030 | //GGCATAGAAGTAATCAGAGA// | SEQ ID NO: 5052 |
| CTONG20139070 | //TCAAACCTCCTATCTTCTG// | SEQ ID NO: 5053 |
| CTONG20146970 | //TTTTAATCCTCAGTACATTTTC// | SEQ ID NO: 5054 |
| CTONG20158150 | //AAATAGGTTGATGTTGGC// | SEQ ID NO: 5055 |
| CTONG20186320 | //TGACTTTGGCCCTTTACC// | SEQ ID NO: 5056 |
| CTONG20265130 | //GGGTAGGTGCTAGAAATC// | SEQ ID NO: 5057 |
| D3OST20006540 | //GGAGACCACACATAACAT// | SEQ ID NO: 5058 |
| D3OST20037970 | //CACTGACGAAAGGGAAGA// | SEQ ID NO: 5059 |
| D9OST20031370 | //CGACTTGCCAGACTCACT// | SEQ ID NO: 5060 |
| DFNES10001850 | //GTGGCTCAAAGTAGGATT// | SEQ ID NO: 5061 |
| DFNES20031920 | //CTTACTCCAACCCAGGCT// | SEQ ID NO: 5062 |
| FCBBF10005060 | //TGCATGTTTTCTTCCTCA// | SEQ ID NO: 5063 |
| FCBBF20032970 | //CCAGACACAACAATACCA// | SEQ ID NO: 5064 |
| FCBBF20035280//(Reaction system A) | //ATACAATTTGTGCCTGTTA// | SEQ ID NO: 5065 |
| //(Reaction system B) | //CGGTAAGTAGTCTTCATGTG// | SEQ ID NO: 5066 |
| FCBBF20054280 | //GGTGCATCTGTACTTGAA// | SEQ ID NO: 5067 |

-continued

| | | |
|---|---|---|
| FCBBF20071860 | //TGGAGGAGTAGTTATCAGTTG// | SEQ ID NO: 5068 |
| FCBBF30001840 | //AGTGCTCCCAATTATCCG// | SEQ ID NO: 5069 |
| FCBBF30016320 | //GGCTACTCAAGGACACAG// | SEQ ID NO: 5070 |
| FCBBF30016570 | //AGGGATAAGATGGCAGGT// | SEQ ID NO: 5071 |
| FCBBF30033050 | //TCCTGTACTCCTTTCCAT// | SEQ ID NO: 5072 |
| FCBBF30071520 | //CAGGCATAAGAGGTGGCT// | SEQ ID NO: 5073 |
| FCBBF30083820 | //CCTGTGTGATACCAAATACT// | SEQ ID NO: 5074 |
| FCBBF30215060 | //CAGCCCCAATTACTAGAA// | SEQ ID NO: 5075 |
| FCBBF30251420 | //AGCATGTACTGGGAAAGC// | SEQ ID NO: 5076 |
| FCBBF30252520 | //AGGGATAAAGAATGCAAA// | SEQ ID NO: 5077 |
| FCBBF30262360 | //GAGCTTCAGGGGCATTTA// | SEQ ID NO: 5078 |
| FCBBF30266920 | //ATACGCAATTTTCAGACC// | SEQ ID NO: 5079 |
| FCBBF30278630 | //AAAAGACAACGATGCCTG// | SEQ ID NO: 5080 |
| FCBBF30285280 | //AAAGCAAAGTGATATAGGAGT// | SEQ ID NO: 5081 |
| FCBBF40001420 | //ACATTTCAGTCCATTCAC// | SEQ ID NO: 5082 |
| FEBRA10001880 | //TTGTCATGGTGGTAATCC// | SEQ ID NO: 5083 |
| FEBRA20010120 | //GGACCAGACTCACAAATT// | SEQ ID NO: 5084 |
| FEBRA20017050 | //TATACTAAAACCCAGCCA// | SEQ ID NO: 5085 |
| FEBRA20034360 | //CGGCAGCTAGAAAACCTC// | SEQ ID NO: 5086 |
| FEBRA20037260 | //CGTTGGTTTTCTGGACAC// | SEQ ID NO: 5087 |
| FEBRA20037500 | //CTCGGGCAGGATTAACTC// | SEQ ID NO: 5088 |
| FEBRA20082100 | //AGAAGATGCTAGGTTTGC// | SEQ ID NO: 5089 |
| FEBRA20095880 | //AGCATGTACTGGGAAAGC// | SEQ ID NO: 5090 |
| FEBRA20167390 | //GCTTATGTTGCAGTTTCA// | SEQ ID NO: 5091 |
| FEBRA20176800 | //TCAGTTTCAGGGGTCAAG// | SEQ ID NO: 5092 |
| FEBRA20226010 | //TCAGGGTATCAGCTTTCC// | SEQ ID NO: 5093 |
| HCASM10000500 | //TGTGGTGACTTACTGCCT// | SEQ ID NO: 5094 |
| HCHON20002260 | //CTCTCCAACAAACTGCAC// | SEQ ID NO: 5095 |
| HCHON20008980 | //CTGCTGCCTTACACAACC// | SEQ ID NO: 5096 |
| HCHON20009350 | //AGGTAATGAGGAATGCAC// | SEQ ID NO: 5097 |
| HCHON20010990 | //GATTCCACCCTCAAGATT// | SEQ ID NO: 5098 |
| HCHON20011160 | //CTCCTCCACGCTTGTTTT// | SEQ ID NO: 5099 |
| HCHON20015230 | //CTTGGTCACAGTTTTCAT// | SEQ ID NO: 5100 |
| HCHON20022470 | //CACACTTTCAATCCGAGG// | SEQ ID NO: 5101 |
| HCHON20035130 | //GTGGAAGATGCTCGACTG// | SEQ ID NO: 5102 |
| HCHON20043590 | //AGGATTAGGTATTGCTTCTC// | SEQ ID NO: 5103 |
| HCHON20067220 | //TAAGGAAAACCCAACCAC// | SEQ ID NO: 5104 |
| HCHON20076500 | //GAAAGACACCTGGCACAC// | SEQ ID NO: 5105 |
| HEART20021840 | //GTACCCCAAAAGAAACAT// | SEQ ID NO: 5106 |
| HEART20067870 | //GAACTATCTAATCACATGGG// | SEQ ID NO: 5107 |

-continued

| | | |
|---|---|---|
| HEART20083640//(Reaction system A) | //TCTTGATGTCTCCTGCCT// | SEQ ID NO: 5108 |
| //(Reaction system B) | //CTCGGCTGGAAGGTAAAA// | SEQ ID NO: 5109 |
| HHDPC10000650 | //ACTGGTAAGATATGGGCA// | SEQ ID NO: 5110 |
| HHDPC20034390 | //CTCTCCCAAACTCAGGTC// | SEQ ID NO: 5111 |
| HHDPC20095280 | //TGACCCAAAGACATACTG// | SEQ ID NO: 5112 |
| HLUNG10000550 | //GATTTACTTCCGGTTTCG// | SEQ ID NO: 5113 |
| KIDNE20018970 | //AAGAGAATAAGGCTGGGC// | SEQ ID NO: 5114 |
| KIDNE20028720 | //AACAAAATAAGGGGCCAG// | SEQ ID NO: 5115 |
| KIDNE20079440 | //AAGTTCATCTGGGTGTGG// | SEQ ID NO: 5116 |
| KIDNE20096470 | //ATCACCTGGAGAGCTTTG// | SEQ ID NO: 5117 |
| KIDNE20106740 | //AGGGACACTGAGAACTGG// | SEQ ID NO: 5118 |
| KIDNE20120090 | //GAAGCAGGGAAGTGTGAG// | SEQ ID NO: 5119 |
| KIDNE20127750 | //GCTATTACACATTCTGCATT// | SEQ ID NO: 5120 |
| KIDNE20130450 | //CAGCTACTTGGGACAGGA// | SEQ ID NO: 5121 |
| KIDNE20132180//(Reaction system A) | //ACCAGCTCAGCAAGAACT// | SEQ ID NO: 5122 |
| //(Reaction system B) | //CTCTGACATGAACTGGTG// | SEQ ID NO: 5123 |
| KIDNE20141190 | //CACATTGCCTAGAGAAAG// | SEQ ID NO: 5124 |
| KIDNE20148900 | //ACAACAGCAGATGACTCG// | SEQ ID NO: 5125 |
| KIDNE20163880 | //CAGTCACATCTCCCTTTA// | SEQ ID NO: 5126 |
| K1DNE20182690 | //TCACTGTATCACCATCTG// | SEQ ID NO: 5127 |
| L1VER10004790 | //TCCCTGCTAAGATGTTGA// | SEQ ID NO: 5128 |
| LIVER20011130 | //GAGGTCAAGGACACACAG// | SEQ ID NO: 5129 |
| L1VER20038540//(Reaction system A) | //AAGCAATGTGGCAGACTC// | SEQ ID NO: 5130 |
| //(Reaction system B) | //AGTGGGTTCTTTATCATTTT// | SEQ ID NO: 5131 |
| LIVER20055440 | //GTTTGCCAGGGAATGTTT// | SEQ ID NO: 5132 |
| LIVER20062510 | //GTAACGTGCTCTGAATGA// | SEQ ID NO: 5133 |
| L1VER20085800 | //GCTCTGCTGTTTCTAATTT// | SEQ ID NO: 5134 |
| MAMGL10000830 | //TCGATACGTGGAAGAATT// | SEQ ID NO: 5135 |
| MESAN20031900 | //TCCCAAGGCTGTAGTTCA// | SEQ ID NO: 5136 |
| MESAN20121130 | //AGCTTGTATCTAAATTCGTG// | SEQ ID NO: 5137 |
| MESAN20127350 | //CAGAAGACAGGTTGCCAG// | SEQ ID NO: 5138 |
| MESAN20130220 | //CCTAAGATTGGTCGTCCT// | SEQ ID NO: 5139 |
| MESAN20154010 | //ATCCTGTCATCTTTTCGC// | SEQ ID NO: 5140 |
| MESAN20174170 | //TGGCTAAGGTTCTCAGGA// | SEQ ID NO: 5141 |
| NOVAR10001020 | //GGGTCAGTAAATCTAATGC// | SEQ ID NO: 5142 |
| NT2NE20053580 | //CAAAACACAGAGTTATCAGAA// | SEQ ID NO: 5143 |
| NT2NE20089610 | //TGCTGTCCTAGAAGAATAAA// | SEQ ID NO: 5144 |
| NT2NE20089970 | //ACAATTATACTGGAAAAGCA// | SEQ ID NO: 5145 |
| NT2NE20146810 | //GCTGAGACCTTTTGCTAG// | SEQ ID NO: 5146 |
| NT2NE20155110 | //AGCCGAGGTTTTGAGTTA// | SEQ ID NO: 5147 |

-continued

| | | |
|---|---|---|
| NT2NE20156260 | //ACATTTGCACTGGAACTG// | SEQ ID NO: 5148 |
| NT2NE20158600 | //CTCAGAAGCCCAGCAATT// | SEQ ID NO: 5149 |
| NT2NE20172590 | //ACATCATAATCAAGCAGTAAA// | SEQ ID NO: 5150 |
| NT2NE20174920 | //AGGACAGCAACAAGAGAG// | SEQ ID NO: 5151 |
| NT2NE20181650 | //AGAGCTGATTTATACGCA// | SEQ ID NO: 5152 |
| NT2RI20005750 | //AAGGAGTCTACGAAGCAC// | SEQ ID NO: 5153 |
| NT2RI20009870 | //AAGATGACCCCGAGTTTG// | SEQ ID NO: 5154 |
| NT2RI20023160 | //CATGCAAATAGAGGACTG// | SEQ ID NO: 5155 |
| NT2RI20040930 | //CCATACTGTTCTCTGCTG// | SEQ ID NO: 5156 |
| NT2RI20046080 | //CCGTAACTTTTATATGCCTG// | SEQ ID NO: 5157 |
| NT2RI20055790 | //GCAAGAGCTACAGACAAA// | SEQ ID NO: 5158 |
| NT2RI20069730 | //AGTGTGCAGAAATCCGTG// | SEQ ID NO: 5159 |
| NT2RI20203900 | //AGCAGTAGCACAGCCTTA// | SEQ ID NO: 5160 |
| NT2RP70062230//(Reaction system A) | //ACTCTAACACATTTGGCA// | SEQ ID NO: 5161 |
| //(Reaction system B) | //TATTAGTGTGAGCTGGCA// | SEQ ID NO: 5162 |
| NT2RP70102350//(Reaction system A) | //ATAGGAGGTGTCATGCCC// | SEQ ID NO: 5163 |
| //(Reaction system B) | //TCTTTTGACCTACACTGC// | SEQ ID NO: 5164 |
| NT2RP70110860 | //GGGGAAGGGAGTAAGGTC// | SEQ ID NO: 5165 |
| NT2RP70111320 | //ACTTAGCATCCAGACCTC// | SEQ ID NO: 5166 |
| NT2RP70130020 | //ATACTCTCTGCTCATGGA// | SEQ ID NO: 5167 |
| NT2RP70143480 | //TTCTTGGCATCCTTCATT// | SEQ ID NO: 5168 |
| NT2RP70150800//(Reaction system A) | //GAGGCTTGTCTAGGGAA// | SEQ ID NO: 5169 |
| //(Reaction system B) | //GAACAAGGGATGCAGGAT// | SEQ ID NO: 5170 |
| NT2RP70157890//(Reaction system A) | //TATGTGATGTTTTCCCCA// | SEQ ID NO: 5171 |
| //(Reaction system B) | //CTGCCTAAATAACACTGAAG// | SEQ ID NO: 5172 |
| NT2RP70169110 | //CTGTCCTCATCTGTGCAT// | SEQ ID NO: 5173 |
| NT2RP70175670 | //GGTAGAACGGGAAATCAT// | SEQ ID NO: 5174 |
| NT2RP70188020 | //AGGTTTGAGTAGAGGGAA// | SEQ ID NO: 5175 |
| NT2RP70188710 | //ATACAGCAGGGAAGAGGC// | SEQ ID NO: 5176 |
| NT2RP70190640 | //CAATGTGTCTTCAGTTTCC// | SEQ ID NO: 5177 |
| NTONG20029480 | //TCTTGATGTCTCCTGCCT// | SEQ ID NO: 5178 |
| NTONG20064840 | //AAAGCCATCGTACACCAT// | SEQ ID NO: 5179 |
| NTONG20067090 | //AATTCTTTAGCTCTGTTGC// | SEQ ID NO: 5180 |
| NTONG20070340 | //ATCCACTGCCCCTTATCA// | SEQ ID NO: 5181 |
| NTONG20077560 | //CTGCTAGAATACGCCTTA// | SEQ ID NO: 5182 |
| NTONG20083650 | //CTCATAGTTCAAGGCAGC// | SEQ ID NO: 5183 |
| NTONG20090680 | //GAGTAAGGTCGTAGTCAGTG// | SEQ ID NO: 5184 |
| OCBBF20005230 | //GCAAGAGCTACAGACAAA// | SEQ ID NO: 5185 |
| OCBBF20019380 | //GTGGTCAGTGGAAAATGG// | SEQ ID NO: 5186 |
| OCBBF20020150 | //GGGACAGTATGGCAGAGA// | SEQ ID NO: 5187 |

-continued

| | | |
|---|---|---|
| OCBBF20020830 | //GCTTGCCATAGGTGTACT// | SEQ ID NO: 5188 |
| OCBBF20039250 | //TTTCAGCAGTTAAGTGTTTT// | SEQ ID NO: 5189 |
| OCBBF20041680 | //TCAGAAGGTATGCCCACT// | SEQ ID NO: 5190 |
| OCBBF20047570 | //ACCCTTATGTCAAACTGC// | SEQ ID NO: 5191 |
| OCBBF20051610 | //TTTTCCTACCTGCAATGG// | SEQ ID NO: 5192 |
| OCBBF20054200 | //GTCAGAAGCCATACGTGC// | SEQ ID NO: 5193 |
| OCBBF20061720 | //CAAAGTGGCCTAAACCCT// | SEQ ID NO: 5194 |
| OCBBF20062140 | //CTGGGGAGATAAGAGCCT// | SEQ ID NO: 5195 |
| OCBBF20071960//(Reaction system A) | //CTCAGTCACGCAATAGAT// | SEQ ID NO: 5196 |
| //(Reaction system B) | //TCTCTGGAAGGGAAAATT// | SEQ ID NO: 5197 |
| OCBBF20072320 | //AAGAAGGAATGGGCACAC// | SEQ ID NO: 5198 |
| OCBBF20079310 | //CAGTAGCAAAACCAGAGC// | SEQ ID NO: 5199 |
| OCBBF20081380 | //GTGGAAGTGCCTGATGAG// | SEQ ID NO: 5200 |
| OCBBF20085200 | //TACAGGGTCAGTTGGCAG// | SEQ ID NO: 5201 |
| OCBBF20094240 | //ACACAATTCATCACTGCT// | SEQ ID NO: 5202 |
| OCBBF20107920 | //GGTTGCTGTGAGTGCATT// | SEQ ID NO: 5203 |
| OCBBF20127040 | //TAGAGGAGGCAGTAAGGG// | SEQ ID NO: 5204 |
| OCBBF20130110 | //AGTGTCTATGGCTCTTCC// | SEQ ID NO: 5205 |
| OCBBF20139260 | //GGGTGGTTCTGTTAGGAG// | SEQ ID NO: 5206 |
| OCBBF20164050 | //TGCTGGAAATAATCGCTT// | SEQ ID NO: 5207 |
| OCBBF20178990 | //TGAGTGTGGTGAAGATAGT// | SEQ ID NO: 5208 |
| OCBBF20180840 | //AGAAACCTGAACGATGTC// | SEQ ID NO: 5209 |
| PEBLM10000240 | //ATTACGATGCTTTGTTCA// | SEQ ID NO: 5210 |
| PEBLM20013120 | //TAAAATTCTTGTGGTTGG// | SEQ ID NO: 5211 |
| PEBLM20024550 | //TTGTGCCCTTAGAAAATC// | SEQ ID NO: 5212 |
| PEBLM20052820 | //CCTGATAACCATGAATTG// | SEQ ID NO: 5213 |
| PEBLM20074370 | //AGCATTTGGTTTTATACTGTTA// | SEQ ID NO: 5214 |
| PERIC20002140 | //CGTTACCATCACAATTTCA// | SEQ ID NO: 5215 |
| PERIC20004780 | //ACTTGAGCAGAGGAGAGC// | SEQ ID NO: 5216 |
| PLACE60003480 | //ACTGGTATTTGCTGTGAA// | SEQ ID NO: 5217 |
| PLACE60136720 | //AGGAACAGAGGCTACATC// | SEQ ID NO: 5218 |
| PLACE60155130 | //GTCTAGCTGGGATGATGG// | SEQ ID NO: 5219 |
| PLACE60169420 | //AAGACCCCGATAGAGAGC// | SEQ ID NO: 5220 |
| PLACE60181070 | //CCTTCTTCAGTCTTGCAC// | SEQ ID NO: 5221 |
| PROST10004800 | //AGTTTTGTTCACCCCTCC// | SEQ ID NO: 5222 |
| PROST20120160 | //TAGAATGGTGGGAAGTGG// | SEQ ID NO: 5223 |
| PROST20144220 | //TTAGTGGTCTGTTGATAGTTTT// | SEQ ID NO: 5224 |
| PROST20149160 | //TTGGGCTTAGGTGAGTCC// | SEQ ID NO: 5225 |
| PROST20149250 | //GGTACATAAGGAATCGCT// | SEQ ID NO: 5226 |
| PROST20151240//(Reaction system A) | //ACTCTCGCTTCCTGTCAC// | SEQ ID NO: 5227 |

-continued

| | | |
|---|---|---|
| //(Reaction system B) | //GACGGACCCTTGACATTA// | SEQ ID NO: 5228 |
| PROST20153320 | //ACTGTGGAGAAGGAGGGA// | SEQ ID NO: 5229 |
| PROST20161950 | //ATTTGACGTATCCATGCC// | SEQ ID NO: 5230 |
| PROST20189770 | //TGGTAAGTGGTGGAAGCT// | SEQ ID NO: 5231 |
| PUAEN20003740 | //CCAAAACAATAATCCAACAT// | SEQ ID NO: 5232 |
| PUAEN20011880 | //AGCCGTTGTCATCATAGA// | SEQ ID NO: 5233 |
| PUAEN20015260 | //ATTGGAAGTCCCTATGAT// | SEQ ID NO: 5234 |
| PUAEN20025680 | //CTCCTCTGAAGTAGCTGC// | SEQ ID NO: 5235 |
| PUAEN20040670 | //AATGGTTCTCTGGCTTGG// | SEQ ID NO: 5236 |
| PUAEN20045250 | //CAAAATGGTTAAACACAAA// | SEQ ID NO: 5237 |
| PUAEN20078980 | //AGAAAGGCACACAATAAA// | SEQ ID NO: 5238 |
| PUAEN20085150 | //AATTTAGGGGAACTGAGTAC// | SEQ ID NO: 5239 |
| SKMUS20018230 | //TTCGCTCTTATCACCCAG// | SEQ ID NO: 5240 |
| SKMUS20028210 | //ACTTGCCTTGGAATTGCT// | SEQ ID NO: 5241 |
| SKMUS20031680 | //CAGAAGAACAGGAGGCAC// | SEQ ID NO: 5242 |
| SKMUS20046670 | //GCAACGTCTTACTGTGAA// | SEQ ID NO: 5243 |
| SKNSH20062340 | //GACATTGACGTATTCTAACTG// | SEQ ID NO: 5244 |
| SKNSH20080430 | //TACCCTCCGCTGTGTTAG// | SEQ ID NO: 5245 |
| SMINT20001760 | //CTCCTCCAGCTCTTGTCC// | SEQ ID NO: 5246 |
| SMINT20013480 | //GGCACGTTTTAATATACCAC// | SEQ ID NO: 5247 |
| SMINT20014580 | //CCCTCCAGACAGTTCAAA// | SEQ ID NO: 5248 |
| SMINT20033400 | //CGATGGGTAGGACTTAAA// | SEQ ID NO: 5249 |
| SMINT20047810//(Reaction system A) | //CTCCTGACATTTCCTTTT// | SEQ ID NO: 5250 |
| //(Reaction system B) | //TAGGAAAAGAAGCAGGGC// | SEQ ID NO: 5251 |
| SMINT20051610 | //AGTGAGGTTAGGGAAATATC// | SEQ ID NO: 5252 |
| SMINT20056210 | //TATTCCTGTTTGATGGGG// | SEQ ID NO: 5253 |
| SMINT20060780 | //TCTGTAATAGGGAGGTGTC// | SEQ ID NO: 5254 |
| SMINT20080540 | //GAGGTACTTTTCAGACAGG// | SEQ ID NO: 5255 |
| SMINT20105000//(Reaction system A) | //AAAATGAGGTTCAGTCCC// | SEQ ID NO: 5256 |
| //(Reaction system B) | //TCACCTCCCCATTAACTG// | SEQ ID NO: 5257 |
| SMINT20108530 | //CACCCTCGTTTTCTTTAG// | SEQ ID NO: 5258 |
| SMINT20122850 | //AGCTAAATCCACTGAGGT// | SEQ ID NO: 5259 |
| SMINT20122910 | //GGACAGACTTGCAGAGAA// | SEQ ID NO: 5260 |
| SMINT20153530 | //GGGCCTAGAGTGGAAGTG// | SEQ ID NO: 5261 |
| SMINT20161220 | //AGAACCAGTCCAAGCCAT// | SEQ ID NO: 5262 |
| SMINT20163960 | //TTGATAAAATAGAGCCCA// | SEQ ID NO: 5263 |
| SMINT20164770 | //AGTGTGCAGAAATCCGTG// | SEQ ID NO: 5264 |
| SMINT20168570//(Reaction system A) | //TGGTCCTCATGGTACAGC// | SEQ ID NO: 5265 |
| //(Reaction system B) | //ATGGCTGCTAGCTTGTCA// | SEQ ID NO: 5266 |
| SPLEN20008820 | //CTGTCTGCCCTGAATCTT// | SEQ ID NO: 5267 |

-continued

| | | |
|---|---|---|
| SPLEN20011410 | //TTTTGGGACTGGAAGGAG// | SEQ ID NO: 5268 |
| SPLEN20013540 | //TCACTCACACCAATCCTG// | SEQ ID NO: 5269 |
| SPLEN20019450 | //TTCGTAAACATCTGGGCA// | SEQ ID NO: 5270 |
| SPLEN20022230 | //AAGTTGCACCCAGACATC// | SEQ ID NO: 5271 |
| SPLEN20040600 | //TCTTATTTCACAGTTTCCA// | SEQ ID NO: 5272 |
| SPLEN20076530 | //CCCCACAGAACACTTACT// | SEQ ID NO: 5273 |
| SPLEN20101190 | //AGACGTAGCAGCAACTCC// | SEQ ID NO: 5274 |
| SPLEN20126190 | //TAGACCCAACCCTCACAC// | SEQ ID NO: 5275 |
| SPLEN20152760 | //TGAGACGAATTGGTAAAA// | SEQ ID NO: 5276 |
| SPLEN20157300 | //CTTGACATTTGCTCTCCA// | SEQ ID NO: 5277 |
| SPLEN20158990 | //AAAACTGGGTCAAATAAAA// | SEQ ID NO: 5278 |
| SPLEN20163560 | //TGCCCAGATAGAAAAGTG// | SEQ ID NO: 5279 |
| SPLEN20174260 | //GGCCTTGTTGAATCTGAA// | SEQ ID NO: 5280 |
| SPLEN20211570 | //CTCAACACAACTCCAAGC// | SEQ ID NO: 5281 |
| SPLEN20214580 | //CCAAACGAATGTCAAGCT// | SEQ ID NO: 5282 |
| SPLEN20245300 | //ATCTGCTCTTCATCCCTT// | SEQ ID NO: 5283 |
| SPLEN20279950 | //CCTGTTCCTAGACCGCAT// | SEQ ID NO: 5284 |
| SPLEN20280660 | //GGCCAGACAGGAAGAGTT// | SEQ ID NO: 5285 |
| SPLEN20283650 | //AAGTTGATGCTCCTGTTG// | SEQ ID NO: 5286 |
| SPLEN20329240//(Reaction system A) | //TAACACATGGACTGCTGG// | SEQ ID NO: 5287 |
| //(Reaction system B) | //AAGGTAGGAAATGCCAGC// | SEQ ID NO: 5288 |
| STOMA20010250 | //TTTTGACCATAAGCTCCT// | SEQ ID NO: 5289 |
| STOMA20032890 | //CGAGAAATAACTAATACACCTG// | SEQ ID NO: 5290 |
| STOMA20048520 | //GAGGGTGAAGCAGGTAGG// | SEQ ID NO: 5291 |
| STOMA20057820 | //GGCATTTCCCTTGTATATT// | SEQ ID NO: 5292 |
| STOMA20062290 | //CCGTGTATTCAGCTCCCT// | SEQ ID NO: 5293 |
| STOMA20076800 | //TAAACGGGAATCAGGAAG// | SEQ ID NO: 5294 |
| TESTI20001170 | //TTTCAGACATATCAAGTTCA// | SEQ ID NO: 5295 |
| TESTI20002780 | //ATTCCAGCCATACGGTTA// | SEQ ID NO: 5296 |
| TESTI20004890 | //AAAACCACAGGAAGAAAG// | SEQ ID NO: 5297 |
| TESTI20011200 | //TACAAGTTCACCTGCATT// | SEQ ID NO: 5298 |
| TESTI20018230 | //AACCACTCAGCAGAAAGA// | SEQ ID NO: 5299 |
| TESTI20035960 | //TGTCCATAGAGCCAGTTA// | SEQ ID NO: 5300 |
| TESTI20038270 | //GTTCTGTTGGAGGTGCTG// | SEQ ID NO: 5301 |
| TESTI20044230 | //AGGTCTTTTGTGTGCTGA// | SEQ ID NO: 5302 |
| TESTI20046750 | //GTAGTTGTCCTGCATGGC// | SEQ ID NO: 5303 |
| TESTI20060400 | //GGCCAGGATACTACACTT// | SEQ ID NO: 5304 |
| TESTI20066770 | //AACTGGCATTGGAGACCT// | SEQ ID NO: 5305 |
| TESTI20076850 | //TTGGTTTGTGATGTTAAGT// | SEQ ID NO: 5306 |
| TESTI20083940 | //TTTGTCTTCCGGTAGTTA// | SEQ ID NO: 5307 |

-continued

| | | |
|---|---|---|
| TESTI20087620 | //TGCCACTCTTGAAAACTC// | SEQ ID NO: 5308 |
| TESTI20098530 | //TCCATTACACAACAGCCT// | SEQ ID NO: 5309 |
| TESTI20105720 | //GGCAGACTTGTTTGAGCT// | SEQ ID NO: 5310 |
| TESTI20108720 | //TAGTTCTGTTGAGGCCCC// | SEQ ID NO: 5311 |
| TESTI20123080//(Reaction system A) | //CCTGTTTCTCTTCCTGAA// | SEQ ID NO: 5312 |
| //(Reaction system B) | //CTAAGTCCAGAAGCCTCG// | SEQ ID NO: 5313 |
| TESTI20128350 | //ATACCATGCTCCAACACC// | SEQ ID NO: 5314 |
| TESTI20136100 | //TTCACTTTTGTTCTCCAG// | SEQ ID NO: 5315 |
| TESTI20137670 | //CCTCCACTCTTCCTGTTG// | SEQ ID NO: 5316 |
| TESTI20143240 | //CTAAGAAGTCCTGGTTGG// | SEQ ID NO: 5317 |
| TESTI20143620//(Reaction system A) | //TTTTGTCTGAATTTGGAA// | SEQ ID NO: 5318 |
| //(Reaction system B) | //TGTAGAAAGCCTAACCCC// | SEQ ID NO: 5319 |
| TESTI20156100 | //ACTGGGCACATTCATAAA// | SEQ ID NO: 5320 |
| TESTI20161970 | //GTTCTATGCCTTGAGCCT// | SEQ ID NO: 5321 |
| TESTI20168480 | //AACTCTGGGTACCAACTT// | SEQ ID NO: 5322 |
| TESTI20168960 | //CTCCCTCTCCTTTCCTCA// | SEQ ID NO: 5323 |
| TESTI20178160 | //CGTTTTCTCGATGTCCAG// | SEQ ID NO: 5324 |
| TESTI20185810 | //AACATTCCTTGCAGCTCA// | SEQ ID NO: 5325 |
| TESTI20199170 | //AGAGTGAGCTGTGCCTTG// | SEQ ID NO: 5326 |
| TESTI20200260 | //CCAAGACATACCCAGGCT// | SEQ ID NO: 5327 |
| TESTI20200710 | //AATTGTGACAAGCAGCAG// | SEQ ID NO: 5328 |
| TESTI20202650 | //TGTTCATGTCACTGGCTG// | SEQ ID NO: 5329 |
| TESTI20220100//(Reaction system A) | //CTTCATAGGGCAGACTCC// | SEQ ID NO: 5330 |
| //(Reaction system B) | //GCTGTGAACTAGAGGGGC// | SEQ ID NO: 5331 |
| TESTI20224620 | //GGAGAAACCGATGAAGAA// | SEQ ID NO: 5332 |
| TESTI20229600//(Reaction system A) | //TTTAATAGTGCCCTGTGG// | SEQ ID NO: 5333 |
| //(Reaction system B) | //CTCTGGAATTTGCATTGA// | SEQ ID NO: 5334 |
| TESTI20230850 | //CAAGACTATGGAGGGGAG// | SEQ ID NO: 5335 |
| TESTI20231920 | //CTCCTCTTGCATTCTCCC// | SEQ ID NO: 5336 |
| TESTI20234140 | //CCAGTTATATCCCCAAAA// | SEQ ID NO: 5337 |
| TESTI20234270 | //CATAAAACCGAATAACTGAG// | SEQ ID NO: 5338 |
| TESTI20238000 | //AGTGTTTGTGGGCATAGA// | SEQ ID NO: 5339 |
| TESTI20238610 | //ACTTCAGACCTCCCTAGA// | SEQ ID NO: 5340 |
| TESTI20239510 | //TTATTGAAGGAAAGCCGC// | SEQ ID NO: 5341 |
| TESTI20242990 | //CCCTGCCTTCCCTATAGA// | SEQ ID NO: 5342 |
| TESTI20265250 | //GGGAAATAGAGGAGTGAT// | SEQ ID NO: 5343 |
| TESTI20265370 | //TGGTTTCAGATGTGCCTT// | SEQ ID NO: 5344 |
| TESTI20266740 | //TGGAAGAACGAAAGAGCC// | SEQ ID NO: 5345 |
| TESTI20272390 | //TCCAGGGTGTCGTAGAAG// | SEQ ID NO: 5346 |
| TESTI20275030 | //GCACGTTAAGGACTGTTT// | SEQ ID NO: 5347 |

-continued

| | | |
|---|---|---|
| TESTI20275620//(Reaction system A) | //TGTGCCTGACTAGGTGAG// | SEQ ID NO: 5348 |
| //(Reaction system B) | //AAGGACAGGTGAGTGTGG// | SEQ ID NO: 5349 |
| TESTI20277360 | //TGGAGTACAACCTGCATC// | SEQ ID NO: 5350 |
| TESTI20282540 | //TGTCTGGTAGAGTTGCGG// | SEQ ID NO: 5351 |
| TESTI20284880 | //TGATTTAATGAGTGGAACC// | SEQ ID NO: 5352 |
| TESTI20285830//(Reaction system A) | //CATGTGACCTTCTCTGGC// | SEQ ID NO: 5353 |
| //(Reaction system B) | //CAGTTCTTTAGCCAGGGA// | SEQ ID NO: 5354 |
| TESTI20288110 | //CCTTTTGTCTGATTCGTC// | SEQ ID NO: 5355 |
| TESTI20289850 | //CCTTACCAAACTCATCCA// | SEQ ID NO: 5356 |
| TESTI20307540 | //CGTGCATGAAAGTGAGTC// | SEQ ID NO: 5357 |
| TESTI20308600 | //CTTCTCAATCATCAGGGA// | SEQ ID NO: 5358 |
| TESTI20311290 | //TTCTCTGCACTCCTTGAT// | SEQ ID NO: 5359 |
| TESTI20317600 | //GAGTGTCTGGCATGGTTA// | SEQ ID NO: 5360 |
| TESTI20319190 | //AAGCTGGGATGATAAGGG// | SEQ ID NO: 5361 |
| TESTI20332420//(Reaction system A) | //CTTCTTGGTGCTGCTTTT// | SEQ ID NO: 5362 |
| //(Reaction system B) | //GCAGATATGTTTGTGAGAG// | SEQ ID NO: 5363 |
| TESTI20335200 | //AATAAACTACACCAGGGC// | SEQ ID NO: 5364 |
| TESTI20342430 | //TCCTACGTTGAGTTGCCT// | SEQ ID NO: 5365 |
| TESTI20345060 | //GTCCACTAGAAGAGGGTC// | SEQ ID NO: 5366 |
| TESTI20347300 | //GAAAGCTGTCGTTAAGGT// | SEQ ID NO: 5367 |
| TESTI20357960 | //AATGACAGGTGAGTGGGT// | SEQ ID NO: 5368 |
| TESTI20361140 | //AATTCACCAGGCTGTGTG// | SEQ ID NO: 5369 |
| TESTI20369220//(Reaction system A) | //TGGATTTGGAAGAGACCT// | SEQ ID NO. 5370 |
| //(Reaction system B) | //TTTGGGTGGAAGTAGAGA// | SEQ ID NO: 5371 |
| TESTI20369690 | //GCTGGTTATTCACGTGGT// | SEQ ID NO: 5372 |
| TEST120370020//(Reaction system A) | //TGGTCATACTCACTGCCC// | SEQ ID NO: 5373 |
| //(Reaction system B) | //GACCTGGTCATACTCACTG// | SEQ ID NO: 5374 |
| TESTI20371030 | //CTAAAGTCCAAAATGTGTAAGT// | SEQ ID NO: 5375 |
| TESTI20386230//(Reaction system A) | //GCTAAGGTGCTATGAAGG// | SEQ ID NO: 5376 |
| //(Reaction system B) | //ACAGTAAAAGGGCAAGTG// | SEQ ID NO: 5377 |
| TESTI20391210 | //AATACTCACATGCCAAGC// | SEQ ID NO: 5378 |
| TESTI20392090 | //CTTGGTTACAGAGGACAG// | SEQ ID NO: 5379 |
| TESTI20392250 | //ATTCCACTCTGCTCAAAG// | SEQ ID NO: 5380 |
| TESTI20392270 | //CCTTGTTGTCCATGAGTC// | SEQ ID NO: 5381 |
| TESTI20401020 | //CGTACACCACATAGCTGA// | SEQ ID NO: 5382 |
| TESTI20401430 | //TGGTAGAAAGAGAGTCACAT// | SEQ ID NO: 5383 |
| TESTI20409440 | //TAGAGCACGTTTCCCTGA// | SEQ ID NO: 5384 |
| TESTI20415640 | //TCTGGAAAATGAGGGTTA// | SEQ ID NO: 5385 |
| TESTI20424000 | //CCAGCTTTCTTCATCATC// | SEQ ID NO: 5386 |
| TESTI20424730 | //AGGAGTGTGGCATAGTCA// | SEQ ID NO: 5387 |

-continued

| | | |
|---|---|---|
| TESTI20425070 | //AAAGCCATCAGACCTCAT// | SEQ ID NO: 5388 |
| TESTI20433130 | //GTCCCATGATTTAGAACTC// | SEQ ID NO: 5389 |
| TESTI20438570 | //CTGCACTAGCCTTTTCCA// | SEQ ID NO: 5390 |
| TESTI20443090 | //GGAAGACAGGACCCAAGT// | SEQ ID NO: 5391 |
| TESTI20463520 | //TGTTGGACTAGAGGGGAA// | SEQ ID NO: 5392 |
| TESTI20465520 | //TCCAGGTCTCATTCTCTC// | SEQ ID NO: 5393 |
| TESTI20478010 | //TCCCTATCAGACGACCAG// | SEQ ID NO: 5394 |
| TESTI20478180 | //AAATCACCCTGCTTGTCA// | SEQ ID NO: 5395 |
| THYMU20029100 | //AGAAGCCAGGGAAGAGGT// | SEQ ID NO: 5396 |
| THYMU20061700 | //CTAGCTCTGAAGTGGCAT// | SEQ ID NO: 5397 |
| THYMU20095960//(Reaction system A) | //TGAAGAGATTACCCAGGT// | SEQ ID NO: 5398 |
| //(Reaction system B) | //GGACTCTGTAGATGTAACTGA// | SEQ ID NO: 5399 |
| THYMU20111180//(Reaction system A) | //TTCTGGGTAAGCCTGATT// | SEQ ID NO: 5400 |
| //(Reaction system B) | //CAAAGAATACCACAAATAGC// | SEQ ID NO: 5401 |
| THYMU20118060 | //CCAAGGCTAAAGAGAGAG// | SEQ ID NO: 5402 |
| THYMU20130890//(Reaction system A) | //AATCTCAAGGACCAGTTT// | SEQ ID NO: 5403 |
| //(Reaction system B) | //GACACAATGGACTCAAAA// | SEQ ID NO: 5404 |
| THYMU20142040 | //ACAGAAGGCCACAGTCAG// | SEQ ID NO: 5405 |
| THYMU20142970 | //CAAGGATACTGTGATGAAA// | SEQ ID NO: 5406 |
| THYMU20153160 | //GGTGGTTAGGACATTTCTC// | SEQ ID NO: 5407 |
| THYMU20158250 | //AAGGAGTGGATAGATGAATAG// | SEQ ID NO: 5408 |
| THYMU20187720 | //TGGTTACAAAGTCACAGG// | SEQ ID NO: 5409 |
| THYMU20194360 | //TTCACTTTTGTTTCCCAG// | SEQ ID NO: 5410 |
| THYMU20208300 | //ATACCACTAAGGCCCAGG// | SEQ ID NO: 5411 |
| THYMU20226600 | //GACTCTTTCAGCTGCTGC// | SEQ ID NO: 5412 |
| THYMU20239000 | //CAAATGGACAGGAACTTA// | SEQ ID NO: 5413 |
| THYMU20253250//(Reaction system A) | //AGAAAACCAGATAGGGCC// | SEQ ID NO: 5414 |
| //(Reaction system B) | //TAATGCAGGGAATGGAGT// | SEQ ID NO: 5415 |
| THYMU20272490 | //CATTATACACACGACGAA// | SEQ ID NO: 5416 |
| THYMU20284120 | //AAACCCACAGTGCTTCAT// | SEQ ID NO: 5417 |
| THYMU20286290 | //AGTCCCTCTCATTTCCAG// | SEQ ID NO: 5418 |
| TKIDN10000010 | //TGCCATAATTCTCCTTTT// | SEQ ID NO: 5419 |
| TRACH20005020 | //GCTTTTCTCCTTCCATGA// | SEQ ID NO: 5420 |
| TRACH20032720 | //CTACGCCCACTATATTCA// | SEQ ID NO: 5421 |
| TRACH20041830//(Reaction system A) | //AGATACTGAGAATGAGCCT// | SEQ ID NO: 5422 |
| //(Reaction system B) | //TTTCCATGCCTACCCTTT// | SEQ ID NO: 5423 |
| TRACH20060150//(Reaction system A) | //AGTCTCCTGCTGGCTAAG// | SEQ ID NO: 5424 |
| //(Reaction system B) | //GTCCCTTCTGTCTCCTGA// | SEQ ID NO: 5425 |
| TRACH20076760 | //GTGGAAGTGCCTGATGAG// | SEQ ID NO: 5426 |
| TRACH20082780 | //CTTTCACCTGGGATGGAT// | SEQ ID NO: 5427 |

-continued

| | | |
|---|---|---|
| TRACH20091230 | //AACATAGTCATTTCGTTCA// | SEQ ID NO: 5428 |
| TRACH20099340 | //GAGCACTGTAAGAGCCAT// | SEQ ID NO: 5429 |
| TRACH20109650 | //AAACATACCACGGAGAGA// | SEQ ID NO: 5430 |
| TRACH20115740 | //TATGAGCACACGAGGTCC// | SEQ ID NO: 5431 |
| TRACH20134950 | //AAGAGGGAACATCAGGCT// | SEQ ID NO: 5432 |
| TRACH20135520 | //TTCTTGGGCTTTATGTGG// | SEQ ID NO: 5433 |
| TRACH20153810//(Reaction system A) | //GCAGTGAGTCGTAGATGA// | SEQ ID NO: 5434 |
| //(Reaction system B) | //CTGCCTAGCCCTCTCACT// | SEQ ID NO: 5435 |
| TRACH20184490 | //ACTGTGAAGAGCCTGTTG// | SEQ ID NO: 5436 |
| TSTOM20001390 | //GGAATAGTAAGGACATAATGACA// | SEQ ID NO: 5437 |
| TSTOM20005690 | //GGAACCTTTTGTAACCCT// | SEQ ID NO: 5438 |
| UMVEN10001560 | //GCCACAACATCATTTTACTT// | SEQ ID NO: 5439 |
| UMVEN20003540 | //AAGTAAAAGACATCGGCA// | SEQ ID NO: 5440 |
| UTERU20004240 | //TACCTCCAGACTTTTGTG// | SEQ ID NO: 5441 |
| UTERU20046980 | //AGGATGGGAAGAAGGTTT// | SEQ ID NO: 5442 |
| UTERU20055930 | //GGATGAGTTGTGTGAAAA// | SEQ ID NO: 5443 |
| UTERU20068990 | //CCAAGGCTAAAGAGAGAG// | SEQ ID NO: 5444 |
| UTERU20070810 | //AAGTAGAGAATCCCAGCT// | SEQ ID NO: 5445 |
| UTERU20115740 | //TTTATGATTGAGGGGACC// | SEQ ID NO: 5446 |
| UTERU20119060 | //ACAGCATCCAATCAAAGA// | SEQ ID NO: 5447 |
| UTERU20124070 | //ACATCTGGTGGAAGCATC// | SEQ ID NO: 5448 |
| UTERU20126880 | //ACCTTAACCCCTCTTCCC// | SEQ ID NO: 5449 |
| UTERU20134910 | //AAGGAAGCCAACTCATGC// | SEQ ID NO: 5450 |
| UTERU20146680 | //ACCTTAACCCCTCTTCCC// | SEQ ID NO: 5451 |
| UTERU20176130 | //TAGAAAGGGGTGGTGAGA// | SEQ ID NO: 5452 |
| UTERU20185230 | //CGTTGAGAGCTTTTACAG// | SEQ ID NO: 5453 |
| UTERU20186740 | //CCACTTTGAGAGAACCCT// | SEQ ID NO: 5454 |

The result of expression frequency analysis is shown in Table 52. The clones not shown in the table contain clones whose expression levels could not be measured because the levels were too low or the sizes of the PCR products were different from the expected. It was confirmed that the expression levels of IL-8 genes used as positive control genes were elevated.

The result obtained by the search for the genes whose expression levels were altered depending on the presence of TNF-α in culturing THP-1 cell, which is a human monocyte cell line, showed that the clones whose expression levels were elevated by twofold or more one or three hours after the stimulation (the clones whose expression levels were 0.1 or lower both before and after the stimulation were excluded), were ASTRO20152140, BRACE20057620, BRACE20060720, BRACE20090440, BRACE20152870, BRACE20229280, BRAMY20002770, BRAMY20266850, BRAMY20280720, BRAWH20106180, BRAWH20122770, BRHIP20096170, BRHIP20111200, BRHIP20186120, BRHIP20194940, BRHIP20207430, BRSSN20152380, CTONG20095270, CTONG20100240, CTONG20158150, CTONG20265130, D30ST20006540, D90ST20031370, FCBBF20071860, FCBBF30251420, FCBBF30252520, FCBBF40001420, FEBRA20017050, FEBRA20082100, HCHON20011160, KIDNE20141190, KIDNE20163880, KIDNE20182690, LIVER10004790, LIVER20038540, LIVER20085800, MESAN20130220, MESAN20174170, NT2NE20158600, NT2RI20005750, NT2RP70110860, NT2RP70169110, NT2RP70175670, NT2RP70188710, PERIC20002140, PLACE60155130, PROST20120160, PROST20149250, PROST20161950, PUAEN20015260, SKNSH20080430, SMINT20051610, SMINT20060780, SMINT20161220, SMINT20163960, SPLEN20101190, SPLEN20157300, SPLEN20163560, SPLEN20214580, SPLEN20279950, STOMA20048520, TESTI20076850, TESTI20087620, TESTI20108720, TESTI20220100, TESTI20239510, TESTI20266740, TESTI20342430, TESTI20370020, TESTI20391210, TESTI20401020, TESTI20415640, THYMU20130890, THYMU20286290, TRACH20060150, TRACH20099340, UTERU20004240, UTERU20068990, UTERU20119060.

On the other hand, in particular cases where the expression levels were relatively high in the unstimulated cells (the relative value was 1 or higher), the clones whose expression levels were decreased by twofold or more by the TNF-α stimulation (the clones whose expression levels were increased 1 or 3 hours after the stimulation were excluded) were ASTRO20032120, ASTRO20084250, ASTRO20181690, BRACE20062640, BRACE20067430, BRACE20235400, BRALZ20018340, BRALZ20069760, BRALZ20075450, BRAMY20163270, BRAMY20204450, BRAMY20218670, BRAMY20229800, BRAWH10000930, BRAWH20107540, BRAWH20132190, BRAWH20158530, BRCAN20273340, BRHIP20105710, BRHIP20186120, BRSSN20176820, CTONG20095290, DFNES20031920, FCBBF30033050, FCBBF30071520, FCBBF30083820, HCHON20008980, HCHON20022470, HHDPC20034390, KIDNE20028720, KIDNE20079440, KIDNE20127750, KIDNE20148900, LIVER20011130, MAMGL10000830, MESAN20127350, NT2NE20181650, NT2RI20023160, NT2RP70102350, NT2RP70157890, NTONG20029480, OCBBF20020830, OCBBF20041680, OCBBF20061720, OCBBF20127040, OCBBF20139260, OCBBF20178990, PEBLM20013120, PLACE60003480, PLACE60181070, PROST20151240, PUAEN20003740, PUAEN20011880, PUAEN20078980, PUAEN20085150, SKNSH20080430, SMINT20001760, SMINT20047810, SMINT20108530, SPLEN20158990, SPLEN20283650, STOMA20010250, STOMA20057820, TESTI20060400, TESTI20161970, TESTI20275620, TESTI20369690, TESTI20386230, TESTI20392250, TESTI20409440, TESTI20424730, THYMU20095960, THYMU20111180, THYMU20226600, THYMU20253250, THYMU20272490, TRACH20153810, UTERU20176130, UTERU20186740.

These clones were thus revealed to be involved in the inflammation reaction induced by TNF-α.

The result obtained by the search for the genes whose expression levels were altered depending on co-culturing gastric cancer cell line MKN45 with cag PAI positive *Helicobacter pylori* (TN2), showed that the clones whose expression levels were elevated by twofold or more (the clones whose expression levels were 0.1 or lower both before and after the stimulation were excluded), were ADRGL20067670, BLADE20004630, BRACE20039040, BRACE20151320, BRACE20229280, BRACE20235400, BRALZ20058880, BRAMY20060920, BRAMY20184670, BRAMY20218670, BRAMY20229800, BRCAN20147880, BRHIP20196410, BRHIP30004880, BRSSN20187310, CD34C30004940, CTONG20265130, DFNES20031920, FCBBF30278630, FCBBF40001420, HHDPC20095280, KIDNE20130450, LIVER20011130, LIVER20038540, NT2NE20172590, NT2RP70169110, OCBBF20085200, OCBBF20180840, PEBLM10000240, PLACE60003480, PROST20120160, PROST20151240, PUAEN20011880, SKMUS20031680, SKNSH20080430, SMINT20056210, SMINT20105000, SPLEN20019450, SPLEN20211570, STOMA20048520, TESTI20004890, TESTI20083940, TESTI20168480, TESTI20239510, TESTI20308600, TESTI20478010, UTERU20126880.

Of these clones, the expression levels of ADRGL20067670, BLADE20004630, BRACE20151320, BRACE20229280, BRACE20235400, BRALZ20058880, BRAMY20218670, BRAMY20229800, BRHIP20196410, BRHIP30004880, CD34C30004940, DFNES20031920, FCBBF30278630, FCBBF40001420, HHDPC20095280, KIDNE20130450, LIVER20011130, LIVER20038540, NT2NE20172590, NT2RP70169110, PEBLM10000240, PROST20151240, PUAEN20011880, SKMUS20031680, SKNSH20080430, SMINT20056210, SMINT20105000, SPLEN20019450, SPLEN20211570, STOMA20048520, TESTI20168480, TESTI20308600, TESTI20478010, UTERU20126880 were not increased by the co-culture with the cage mutant (TN2ΔcagE). There may be the possibility that the expression levels of the 34 clones are altered via the NF-κB pathway. Among them, the expression levels of BRACE20229280, FCBBF40001420, LIVER20038540, NT2RP70169110, SKNSH20080430, STOMA20048520 were also increased when human monocyte cell line THP-1 was stimulated with TNF-α.

On the other hand, in particular cases where the expression levels were relatively high in the unstimulated cells (the relative value was 1 or higher), the clones whose expression levels were decreased by twofold or more in the presence of *Helicobacter pylori* were ASTRO20032120, BRACE20090440, BRACE20114780, BRALZ20064740, BRAMY20002770, BRAMY20210400, BRAMY20215230, BRAMY20247280, BRAMY20267130, BRAWH20029630, BRAWH20100690, BRAWH20118230, BRCOC20105100, BRHIP20218580, BRSSN20046570, CTONG20138030, CTONG20146970, CTONG2–0158150, D30ST20037970, FCBBF30001840, FCBBF30033050, FEBRA20082100, HCHON20035130, HCHON20043590, HCHON20067220, NT2NE20174920, NT2RI20009870, NT2RI20023160, NT2RP70062230, NT2RP70130020, NTONG20070340, OCBBF20020150, OCBBF20094240, OCBBF20107920, PROST20144220, PROST20149160, PROST20153320, PUAEN20003740, PUAEN20025680, PUAEN20040670, SMINT20014580, SPLEN20101190, STOMA20076800, TESTI20087620, TESTI20098530, TESTI20123080, TESTI20161970, TESTI20234140, TESTI20288110, TESTI20357960, TESTI20391210, TESTI20424730, THYMU20158250, THYMU20226600, TRACH20005020, TRACH20134950, TRACH20184490, TSTOM20001390, UTERU20119060, UTERU20134910, UTERU20176130.

These clones are involved in gastritis or gastroduodenal ulcer.

TABLE 3

| CloneID | CD34C | D3OST | D6OST | D9OST |
|---|---|---|---|---|
| ASTRO20001410 | 0 | 17.731 | 0 | 20.479 |
| D3OST10001090 | 0 | 62.515 | 0 | 24.068 |
| D3OST20036070 | 0 | 46.404 | 0 | 53.596 |
| THYMU20039810 | 0 | 18.291 | 0 | 21.126 |
| KIDNE20028720 | 0 | 0 | 38.385 | 46.259 |
| BRAWH10000930 | 0 | 0 | 0 | 6.219 |
| BRHIP20005340 | 0 | 0 | 0 | 4.615 |
| CTONG20141650 | 0 | 0 | 0 | 64.925 |
| D9OST20000310 | 0 | 0 | 0 | 63.705 |
| D9OST20002780 | 0 | 0 | 0 | 100 |
| D9OST20023970 | 0 | 0 | 0 | 37.837 |
| D9OST20026730 | 0 | 0 | 0 | 19.695 |
| D9OST20031370 | 0 | 0 | 0 | 100 |
| D9OST20033970 | 0 | 0 | 0 | 38.536 |
| D9OST20035800 | 0 | 0 | 0 | 93.047 |
| D9OST20035940 | 0 | 0 | 0 | 100 |
| D9OST20040180 | 0 | 0 | 0 | 100 |
| FCBBF30018550 | 0 | 0 | 0 | 37.763 |
| FCBBF30233680 | 0 | 0 | 0 | 33.084 |
| KIDNE20102650 | 0 | 0 | 0 | 63.715 |
| NT2RI20023160 | 0 | 0 | 0 | 10.811 |
| PROST20107820 | 0 | 0 | 0 | 3.279 |
| SKNSH20089400 | 0 | 0 | 0 | 25.857 |
| SMINT20033400 | 0 | 0 | 0 | 39.619 |

TABLE 3-continued

| CloneID | CD34C | D3OST | D6OST | D9OST |
|---|---|---|---|---|
| CTONG20108210 | 0 | 0 | 47.973 | 0 |
| D6OST20003580 | 0 | 0 | 95.4 | 0 |
| D6OST20005070 | 0 | 0 | 100 | 0 |
| ASTRO20155290 | 0 | 21.631 | 0 | 0 |
| D3OST10002670 | 0 | 50.415 | 0 | 0 |
| D3OST10002700 | 0 | 30.165 | 0 | 0 |
| D3OST20006180 | 0 | 100 | 0 | 0 |
| D3OST20006540 | 0 | 100 | 0 | 0 |
| D3OST20007340 | 0 | 93.334 | 0 | 0 |
| D3OST20013280 | 0 | 100 | 0 | 0 |
| D3OST20024170 | 0 | 100 | 0 | 0 |
| D3OST20024360 | 0 | 100 | 0 | 0 |
| D3OST20037970 | 0 | 100 | 0 | 0 |
| D3OST30002580 | 0 | 72.574 | 0 | 0 |
| D3OST30002910 | 0 | 93.334 | 0 | 0 |
| FCBBF10004120 | 0 | 22.594 | 0 | 0 |
| NT2RI20001330 | 0 | 29.915 | 0 | 0 |
| NTONG20009770 | 0 | 11.477 | 0 | 0 |
| SPLEN20084600 | 0 | 30.589 | 0 | 0 |
| SPLEN20140800 | 0 | 55.315 | 0 | 0 |
| THYMU20169680 | 0 | 86.295 | 0 | 0 |
| TRACH20141240 | 0 | 12.051 | 0 | 0 |
| CD34C30001250 | 97.628 | 0 | 0 | 0 |
| CD34C30003140 | 100 | 0 | 0 | 0 |
| CD34C30004240 | 96.167 | 0 | 0 | 0 |
| CD34C30004940 | 100 | 0 | 0 | 0 |
| DFNES10001850 | 55.393 | 0 | 0 | 0 |
| HHDPC20034390 | 21.364 | 0 | 0 | 0 |
| NT2RI20091730 | 46.845 | 0 | 0 | 0 |
| SKMUS20003610 | 44.913 | 0 | 0 | 0 |
| SPLEN20225220 | 59.537 | 0 | 0 | 0 |
| BRCOC20101230 | 46.01 | 0 | 0 | 14.772 |

TABLE 4

| CloneID | NT2RM | NT2RP | NT2RI | NT2NE |
|---|---|---|---|---|
| CTONG20027090 | 62.349 | 0 | 0 | 0 |
| CTONG20160560 | 57.22 | 0 | 0 | 0 |
| NT2RP70032610 | 39.095 | 3.274 | 0 | 0 |
| OCBBF20188730 | 39.876 | 0 | 0 | 0 |
| SPLEN20162680 | 12.432 | 0 | 2.355 | 6.263 |
| BRCOC20101230 | 0 | 2.64 | 3.981 | 3.97 |
| BRHIP20005340 | 0 | 0.825 | 1.244 | 1.24 |
| BRHIP20238880 | 0 | 2.66 | 7.355 | 2.667 |
| FCBBF30016320 | 0 | 7.441 | 2.805 | 5.595 |
| FEBRA20080810 | 0 | 6.827 | 5.147 | 2.566 |
| FEBRA20225040 | 0 | 3.958 | 2.985 | 5.952 |
| HCHON20008320 | 0 | 17.053 | 19.287 | 12.822 |
| HHDPC20034390 | 0 | 0.613 | 1.387 | 0.922 |
| HLUNG10000550 | 0 | 2.609 | 0.984 | 1.962 |
| NT2RI20028470 | 0 | 9.076 | 6.843 | 4.549 |
| NT2RI20054050 | 0 | 2.03 | 1.02 | 4.069 |
| NT2RI20091730 | 0 | 2.688 | 2.027 | 4.042 |
| NT2RP70078420 | 0 | 4.623 | 3.485 | 13.902 |
| PUAEN20003740 | 0 | 2.314 | 0.582 | 1.16 |
| THYMU20271250 | 0 | 0.431 | 0.651 | 1.297 |
| BRACE20003070 | 0 | 8.516 | 4.281 | 0 |
| BRACE20039040 | 0 | 6.248 | 4.711 | 0 |
| BRAWH20004600 | 0 | 1.471 | 5.545 | 0 |
| BRAWH20011710 | 0 | 8.931 | 2.245 | 0 |
| BRCOC20121720 | 0 | 13.559 | 5.112 | 0 |
| BRHIP20005530 | 0 | 12.387 | 9.34 | 0 |
| D3OST10002700 | 0 | 6.227 | 4.695 | 0 |
| HCHON20007380 | 0 | 7.176 | 5.411 | 0 |
| HEART20072310 | 0 | 11.675 | 17.605 | 0 |
| KIDNE20121880 | 0 | 21.519 | 16.225 | 0 |
| MESAN20121130 | 0 | 14.219 | 10.721 | 0 |
| NT2RI20022600 | 0 | 57.012 | 42.988 | 0 |
| NT2RI20023160 | 0 | 1.932 | 1.457 | 0 |
| NT2RI20086220 | 0 | 7.606 | 5.735 | 0 |
| NT2RI20216250 | 0 | 45.928 | 34.63 | 0 |
| NT2RP6000850 | 0 | 11.147 | 16.809 | 0 |
| NT2RP70036880 | 0 | 1.78 | 5.367 | 0 |
| NT2RP70043480 | 0 | 10.893 | 4.107 | 0 |
| NT2RP70062230 | 0 | 10.183 | 7.678 | 0 |
| NT2RP70081610 | 0 | 15.131 | 22.818 | 0 |
| NT2RP70102350 | 0 | 84.14 | 15.86 | 0 |
| NT2RP70130020 | 0 | 57.012 | 42.988 | 0 |
| NT2RP70190640 | 0 | 30.952 | 23.338 | 0 |
| OCBBF10001850 | 0 | 20.293 | 7.65 | 0 |
| OCBBF20097720 | 0 | 5.676 | 4.28 | 0 |
| OCBBF20173980 | 0 | 3.1 | 2.338 | 0 |
| PEBLM20044520 | 0 | 3.253 | 2.453 | 0 |
| SPLEN20173510 | 0 | 7.249 | 10.932 | 0 |
| TRACH20007020 | 0 | 9.462 | 7.134 | 0 |
| UTERU20065930 | 0 | 10.676 | 8.05 | 0 |
| HCHON20022470 | 0 | 6.766 | 0 | 10.174 |
| NT2NE20010490 | 0 | 21.179 | 0 | 31.847 |
| NT2NE20174800 | 0 | 39.941 | 0 | 60.059 |
| NT2NE20177520 | 0 | 28.292 | 0 | 42.542 |
| PROST20087700 | 0 | 1.88 | 0 | 14.135 |
| PROST20107820 | 0 | 0.586 | 0 | 2.644 |
| SMINT20028820 | 0 | 6.998 | 0 | 10.523 |
| TESTI20063830 | 0 | 9.768 | 0 | 14.689 |
| ASTRO20125520 | 0 | 0 | 2.686 | 5.357 |
| BRHIP30001110 | 0 | 0 | 1.86 | 3.71 |
| HCHON20002260 | 0 | 0 | 0.733 | 1.461 |
| HCHON20008150 | 0 | 0 | 5.075 | 20.242 |
| KIDNE20002520 | 0 | 0 | 1.553 | 6.195 |
| NT2NE20130190 | 0 | 0 | 33.397 | 66.603 |
| NT2NE20158600 | 0 | 0 | 33.397 | 66.603 |
| NT2RI20001330 | 0 | 0 | 4.656 | 9.286 |
| NT2RI20025400 | 0 | 0 | 3.141 | 6.265 |
| NT2RI20036670 | 0 | 0 | 33.397 | 66.603 |
| NT2RI20048840 | 0 | 0 | 1.404 | 5.6 |
| SKMUS20020840 | 0 | 0 | 11.346 | 22.628 |
| BRACE20057190 | 0 | 0 | 0 | 10.763 |
| BRACE20060550 | 0 | 0 | 0 | 14.499 |
| BRACE20267250 | 0 | 0 | 0 | 66.449 |
| BRAWH20107540 | 0 | 0 | 0 | 40.54 |
| BRAWH20118230 | 0 | 0 | 0 | 78.374 |
| CTONG20075860 | 0 | 0 | 0 | 21.782 |
| CTONG20095290 | 0 | 0 | 0 | 22.915 |
| FEBRA20086620 | 0 | 0 | 0 | 11.505 |
| FEBRA20144170 | 0 | 0 | 0 | 1.957 |
| FEBRA20196370 | 0 | 0 | 0 | 59.247 |
| HLUNG20023340 | 0 | 0 | 0 | 33.313 |
| NT2NE20003740 | 0 | 0 | 0 | 100 |
| NT2NE20010050 | 0 | 0 | 0 | 84.719 |
| NT2NE20010210 | 0 | 0 | 0 | 100 |
| NT2NE20010400 | 0 | 0 | 0 | 56.184 |
| NT2NE20015240 | 0 | 0 | 0 | 100 |
| NT2NE20021620 | 0 | 0 | 0 | 44.305 |
| NT2NE20043780 | 0 | 0 | 0 | 100 |
| NT2NE20053580 | 0 | 0 | 0 | 75.239 |
| NT2NE20068130 | 0 | 0 | 0 | 100 |
| NT2NE20072200 | 0 | 0 | 0 | 100 |
| NT2NE20074250 | 0 | 0 | 0 | 100 |
| NT2NE20080170 | 0 | 0 | 0 | 100 |
| NT2NE20089610 | 0 | 0 | 0 | 100 |
| NT2NE20089970 | 0 | 0 | 0 | 100 |
| NT2NE20108540 | 0 | 0 | 0 | 84.719 |
| NT2NE20110360 | 0 | 0 | 0 | 100 |
| NT2NE20118960 | 0 | 0 | 0 | 100 |
| NT2NE20122430 | 0 | 0 | 0 | 76.57 |
| NT2NE20124480 | 0 | 0 | 0 | 100 |
| NT2NE20125050 | 0 | 0 | 0 | 66.449 |
| NT2NE20131890 | 0 | 0 | 0 | 100 |
| NT2NE20132170 | 0 | 0 | 0 | 100 |
| NT2NE20142210 | 0 | 0 | 0 | 100 |
| NT2NE20146810 | 0 | 0 | 0 | 100 |
| NT2NE20152750 | 0 | 0 | 0 | 100 |
| NT2NE20155110 | 0 | 0 | 0 | 100 |
| NT2NE20156260 | 0 | 0 | 0 | 100 |
| NT2NE20157470 | 0 | 0 | 0 | 100 |
| NT2NE20159740 | 0 | 0 | 0 | 27.684 |
| NT2NE20172590 | 0 | 0 | 0 | 100 |
| NT2NE20174920 | 0 | 0 | 0 | 61.159 |
| NT2NE20181650 | 0 | 0 | 0 | 100 |
| NT2NE20183760 | 0 | 0 | 0 | 100 |

TABLE 4-continued

| CloneID | NT2RM | NT2RP | NT2RI | NT2NE |
|---|---|---|---|---|
| NT2NE20184900 | 0 | 0 | 0 | 84.719 |
| NT2NE20187390 | 0 | 0 | 0 | 100 |
| OCBBF20108430 | 0 | 0 | 0 | 53.98 |
| RECTM20005100 | 0 | 0 | 0 | 10.923 |
| SMINT20001760 | 0 | 0 | 0 | 50.667 |
| SPLEN20169720 | 0 | 0 | 0 | 7.349 |
| TESTI20265250 | 0 | 0 | 0 | 15.768 |
| ASTRO10001650 | 0 | 0 | 8.055 | 0 |
| ASTRO20033160 | 0 | 0 | 10.721 | 0 |
| BRACE20011070 | 0 | 0 | 26.748 | 0 |
| BRACE20039440 | 0 | 0 | 0.941 | 0 |
| BRACE20151320 | 0 | 0 | 29.94 | 0 |
| BRAMY20104640 | 0 | 0 | 40.041 | 0 |
| BRAMY20137560 | 0 | 0 | 68.63 | 0 |
| BRAMY20167060 | 0 | 0 | 9.007 | 0 |
| BRAWH20028110 | 0 | 0 | 15.672 | 0 |
| BRCAN20280360 | 0 | 0 | 4.387 | 0 |
| BRCOC20004870 | 0 | 0 | 0.526 | 0 |
| BRHIP20207990 | 0 | 0 | 9.197 | 0 |
| BRHIP20217620 | 0 | 0 | 5.063 | 0 |
| BRHIP20249110 | 0 | 0 | 67.372 | 0 |
| BRSTN10000830 | 0 | 0 | 3.481 | 0 |
| CTONG10000940 | 0 | 0 | 1.415 | 0 |
| CTONG20004690 | 0 | 0 | 5.307 | 0 |
| CTONG20050280 | 0 | 0 | 12.439 | 0 |
| CTONG20105660 | 0 | 0 | 24.642 | 0 |
| CTONG20125640 | 0 | 0 | 7.18 | 0 |
| CTONG20133520 | 0 | 0 | 49.384 | 0 |
| CTONG20186320 | 0 | 0 | 29.069 | 0 |
| FCBBF10000770 | 0 | 0 | 1.472 | 0 |
| FCBBF10002800 | 0 | 0 | 10.265 | 0 |
| FCBBF10003770 | 0 | 0 | 19.652 | 0 |
| FCBBF30018550 | 0 | 0 | 5.089 | 0 |
| FCBBF30123470 | 0 | 0 | 3.989 | 0 |
| FCBBF30246230 | 0 | 0 | 5.091 | 0 |
| FEBRA20018280 | 0 | 0 | 9.887 | 0 |
| FEBRA20095140 | 0 | 0 | 6.019 | 0 |
| FEBRA20192420 | 0 | 0 | 58.974 | 0 |
| HCHON20064590 | 0 | 0 | 19.64 | 0 |
| HHDPC10000830 | 0 | 0 | 1.779 | 0 |
| HLUNG20016770 | 0 | 0 | 6.385 | 0 |
| HLUNG20033780 | 0 | 0 | 16.824 | 0 |
| IMR3220002430 | 0 | 0 | 3.118 | 0 |
| KIDNE20104300 | 0 | 0 | 17.33 | 0 |
| MESAN20004570 | 0 | 0 | 7.197 | 0 |
| MESAN20089360 | 0 | 0 | 14.459 | 0 |
| NOVAR10000910 | 0 | 0 | 3.519 | 0 |
| NT2RI20003480 | 0 | 0 | 32.207 | 0 |
| NT2RI20005750 | 0 | 0 | 100 | 0 |
| NT2RI20009870 | 0 | 0 | 100 | 0 |
| NT2RI20023590 | 0 | 0 | 29.911 | 0 |
| NT2RI20023910 | 0 | 0 | 11.79 | 0 |
| NT2RI20025640 | 0 | 0 | 100 | 0 |
| NT2RI20040930 | 0 | 0 | 100 | 0 |
| NT2RI20041880 | 0 | 0 | 10.436 | 0 |
| NT2RI20046080 | 0 | 0 | 6.723 | 0 |
| NT2RI20050960 | 0 | 0 | 73.545 | 0 |
| NT2RI20055790 | 0 | 0 | 17.054 | 0 |
| NT2RI20056700 | 0 | 0 | 100 | 0 |
| NT2RI20069730 | 0 | 0 | 100 | 0 |
| NT2RI20076290 | 0 | 0 | 14.653 | 0 |
| NT2RI20091940 | 0 | 0 | 5.358 | 0 |
| NT2RI20198260 | 0 | 0 | 100 | 0 |
| NT2RI20203900 | 0 | 0 | 100 | 0 |
| NT2RI20207030 | 0 | 0 | 100 | 0 |
| NT2RI20240080 | 0 | 0 | 61.866 | 0 |
| NT2RI20244600 | 0 | 0 | 100 | 0 |
| NT2RI20244960 | 0 | 0 | 100 | 0 |
| NT2RI20250750 | 0 | 0 | 30.809 | 0 |
| NT2RI20252550 | 0 | 0 | 62.102 | 0 |
| NT2RI20273230 | 0 | 0 | 60.375 | 0 |
| NTONG20067090 | 0 | 0 | 16.469 | 0 |
| OCBBF10001750 | 0 | 0 | 13.09 | 0 |
| OCBBF20047570 | 0 | 0 | 4.504 | 0 |
| OCBBF20054760 | 0 | 0 | 8.495 | 0 |
| OCBBF20059560 | 0 | 0 | 10.318 | 0 |
| OCBBF20073540 | 0 | 0 | 3.651 | 0 |
| OCBBF20125530 | 0 | 0 | 2.131 | 0 |
| OCBBF20126780 | 0 | 0 | 12.535 | 0 |
| OCBBF20127040 | 0 | 0 | 37.942 | 0 |
| OCBBF20140890 | 0 | 0 | 35.863 | 0 |
| SKMUS20003610 | 0 | 0 | 1.943 | 0 |
| SKNSH20008190 | 0 | 0 | 4.523 | 0 |
| SKNSH20080430 | 0 | 0 | 18.4 | 0 |
| SMINT20144800 | 0 | 0 | 2.887 | 0 |
| SPLEN20027440 | 0 | 0 | 4.053 | 0 |
| SPLEN20095550 | 0 | 0 | 15.436 | 0 |
| SPLEN20140800 | 0 | 0 | 8.61 | 0 |
| TESTI20094020 | 0 | 0 | 16.66 | 0 |
| TESTI20369690 | 0 | 0 | 6.529 | 0 |
| TESTI20391770 | 0 | 0 | 7.531 | 0 |
| TESTI20442760 | 0 | 0 | 17.235 | 0 |
| TRACH20084720 | 0 | 0 | 5.703 | 0 |
| TRACH20107710 | 0 | 0 | 61.866 | 0 |
| TRACH20118940 | 0 | 0 | 16.16 | 0 |
| UTERU20022940 | 0 | 0 | 9.896 | 0 |
| ASTRO20108190 | 0 | 1.622 | 0 | 0 |
| BGGI120006160 | 0 | 2.155 | 0 | 0 |
| BRAMY20136210 | 0 | 70.518 | 0 | 0 |
| BRAWH20016620 | 0 | 22.162 | 0 | 0 |
| BRAWH20164460 | 0 | 20.968 | 0 | 0 |
| BRCOC20144000 | 0 | 40.488 | 0 | 0 |
| BRHIP20132860 | 0 | 82.532 | 0 | 0 |
| BRSSN20146100 | 0 | 17.209 | 0 | 0 |
| CTONG10000100 | 0 | 15.625 | 0 | 0 |
| CTONG20103480 | 0 | 4.268 | 0 | 0 |
| CTONG20108210 | 0 | 1.722 | 0 | 0 |
| CTONG20139070 | 0 | 10.392 | 0 | 0 |
| FCBBF10000240 | 0 | 10.583 | 0 | 0 |
| FCBBF10000630 | 0 | 14.415 | 0 | 0 |
| FCBBF20067810 | 0 | 30.502 | 0 | 0 |
| FCBBF30010810 | 0 | 6.328 | 0 | 0 |
| FCBBF30012810 | 0 | 49.073 | 0 | 0 |
| FCBBF30013770 | 0 | 24.817 | 0 | 0 |
| FCBBF30039020 | 0 | 56.608 | 0 | 0 |
| FCBBF40001420 | 0 | 8.811 | 0 | 0 |
| FEBRA10001880 | 0 | 5.044 | 0 | 0 |
| FEBRA20082010 | 0 | 17.339 | 0 | 0 |
| HHDPC20001040 | 0 | 4.459 | 0 | 0 |
| KIDNE20021910 | 0 | 34.358 | 0 | 0 |
| NT2RP60000770 | 0 | 15.492 | 0 | 0 |
| NT2RP70010740 | 0 | 100 | 0 | 0 |
| NT2RP70027380 | 0 | 27.748 | 0 | 0 |
| NT2RP70037240 | 0 | 22.256 | 0 | 0 |
| NT2RP70044280 | 0 | 16.256 | 0 | 0 |
| NT2RP70045590 | 0 | 20.543 | 0 | 0 |
| NT2RP70056750 | 0 | 7.009 | 0 | 0 |
| NT2RP70063950 | 0 | 82.532 | 0 | 0 |
| NT2RP70072690 | 0 | 56.608 | 0 | 0 |
| NT2RP70077660 | 0 | 74.295 | 0 | 0 |
| NT2RP70085440 | 0 | 100 | 0 | 0 |
| NT2RP70105210 | 0 | 100 | 0 | 0 |
| NT2RP70110860 | 0 | 100 | 0 | 0 |
| NT2RP70111320 | 0 | 100 | 0 | 0 |
| NT2RP70122910 | 0 | 100 | 0 | 0 |
| NT2RP70125160 | 0 | 100 | 0 | 0 |
| NT2RP70133740 | 0 | 100 | 0 | 0 |
| NT2RP70134990 | 0 | 100 | 0 | 0 |
| NT2RP70137290 | 0 | 100 | 0 | 0 |
| NT2RP70137640 | 0 | 54.725 | 0 | 0 |
| NT2RP70143480 | 0 | 100 | 0 | 0 |
| NT2RP70147210 | 0 | 100 | 0 | 0 |
| NT2RP70150800 | 0 | 100 | 0 | 0 |
| NT2RP70157890 | 0 | 100 | 0 | 0 |
| NT2RP70159960 | 0 | 100 | 0 | 0 |
| NT2RP70169110 | 0 | 100 | 0 | 0 |
| NT2RP70175670 | 0 | 100 | 0 | 0 |
| NT2RP70179710 | 0 | 100 | 0 | 0 |
| NT2RP70181970 | 0 | 100 | 0 | 0 |
| NT2RP70188020 | 0 | 100 | 0 | 0 |
| NT2RP70188710 | 0 | 100 | 0 | 0 |
| NT2RP70192730 | 0 | 100 | 0 | 0 |
| NT2RP70194450 | 0 | 100 | 0 | 0 |
| NT2RP70195430 | 0 | 50.987 | 0 | 0 |

TABLE 4-continued

| CloneID | NT2RM | NT2RP | NT2RI | NT2NE |
|---|---|---|---|---|
| NT2RP70198350 | 0 | 2.512 | 0 | 0 |
| NT2RP70203790 | 0 | 100 | 0 | 0 |
| OCBBF20039250 | 0 | 4.016 | 0 | 0 |
| OCBBF20080410 | 0 | 5.038 | 0 | 0 |
| OCBBF20108190 | 0 | 30.231 | 0 | 0 |
| OCBBF20108580 | 0 | 16.054 | 0 | 0 |
| OCBBF20122620 | 0 | 34.956 | 0 | 0 |
| OCBBF20130110 | 0 | 18.197 | 0 | 0 |
| OCBBF20151150 | 0 | 43.004 | 0 | 0 |
| OCBBF20189560 | 0 | 4.079 | 0 | 0 |
| PROST10003220 | 0 | 57.613 | 0 | 0 |
| TESTI20001720 | 0 | 20.618 | 0 | 0 |
| TESTI20121550 | 0 | 15.444 | 0 | 0 |
| TESTI20152460 | 0 | 28.533 | 0 | 0 |
| TESTI20211240 | 0 | 13.774 | 0 | 0 |
| TESTI20234140 | 0 | 39.241 | 0 | 0 |
| UMVEN20003540 | 0 | 1.985 | 0 | 0 |
| UTERU20006960 | 0 | 6.858 | 0 | 0 |
| UTERU20094350 | 0 | 12.888 | 0 | 0 |
| UTERU20164260 | 0 | 30.63 | 0 | 0 |

TABLE 5

| CloneID | BEAST | TBAES |
|---|---|---|
| BRACE20039040 | 0 | 18.237 |
| BRAMY20163250 | 0 | 26.506 |
| BRCOC20031250 | 0 | 39.975 |
| BRHIP20005340 | 0 | 2.408 |
| BRHIP20217620 | 0 | 19.598 |
| BRHIP30001110 | 0 | 7.202 |
| FCBBF10000770 | 0 | 5.697 |
| FCBBF30010810 | 0 | 18.471 |
| FEBRA20080810 | 0 | 9.963 |
| FEBRA20144170 | 0 | 3.798 |
| FEBRA20196630 | 0 | 61.269 |
| FEBRA20197110 | 0 | 14.875 |
| HCHON20002260 | 0 | 11.347 |
| HCHON20040020 | 0 | 5.523 |
| HHDPC20034390 | 0 | 1.789 |
| HLUNG10000550 | 0 | 3.808 |
| NOVAR10000910 | 0 | 27.245 |
| NT2RI20023160 | 0 | 11.28 |
| NT2RI20054050 | 0 | 1.975 |
| NT2RI20091730 | 0 | 7.846 |
| OCBBF20188730 | 0 | 9.748 |
| SMINT20144800 | 0 | 22.352 |
| SPLEN20128000 | 0 | 2.403 |
| SPLEN20171210 | 0 | 54.539 |
| SPLEN20264110 | 0 | 80.173 |
| TBAES20000590 | 0 | 84.801 |
| TBAES20002550 | 0 | 100 |
| TBAES20003150 | 0 | 100 |
| TESTI20334410 | 0 | 15.439 |
| TESTI20432750 | 0 | 62.244 |
| TRACH20003590 | 0 | 20.978 |
| TRACH20084720 | 0 | 11.037 |
| UTERU20046640 | 0 | 11.937 |
| BEAST20004540 | 100 | 0 |
| SPLEN20008740 | 10.632 | 0 |

TABLE 6

| CloneID | CERVX | TCERX |
|---|---|---|
| BGGI120006160 | 0 | 18.869 |
| BRAMY20063970 | 0 | 59.264 |
| BRHIP20218580 | 0 | 70.621 |
| FEBRA20002100 | 0 | 14.918 |
| SPLEN20162680 | 0 | 9.118 |
| TESTI20214250 | 0 | 36.333 |
| CTONG20105080 | 84.727 | 0 |

TABLE 6-continued

| CloneID | CERVX | TCERX |
|---|---|---|
| HCHON20015980 | 50.212 | 0 |
| PROST20175290 | 52.453 | 0 |
| TESTI20254220 | 51.293 | 0 |
| THYMU20279750 | 82.6 | 0 |

TABLE 7

| CloneID | COLON | TCOLN |
|---|---|---|
| ASTRO20001410 | 0 | 32.199 |
| BRAWH20162690 | 0 | 27.951 |
| CTONG20132220 | 0 | 79.674 |
| HCHON20002260 | 0 | 17.098 |
| NT2RI20001330 | 0 | 54.324 |
| TCOLN20001390 | 0 | 100 |
| 3NB6910001910 | 42.978 | 0 |
| BRAMY20120910 | 41.689 | 0 |
| BRAWH20004600 | 4.285 | 0 |
| BRCOC20031250 | 39.895 | 0 |
| BRCOC20031870 | 11.042 | 0 |
| COLON10001350 | 100 | 0 |
| COLON20043180 | 100 | 0 |
| COLON20093370 | 100 | 0 |
| FEBRA20002100 | 4.963 | 0 |
| FEBRA20082010 | 16.836 | 0 |
| FEBRA20197110 | 29.691 | 0 |
| KIDNE20007770 | 53.588 | 0 |
| KIDNE20013730 | 50.02 | 0 |
| NT2RP70045590 | 59.84 | 0 |
| OCBBF20078920 | 29.908 | 0 |
| PROST20083600 | 12.636 | 0 |
| SPLEN20011410 | 6.63 | 0 |
| TRACH20084720 | 11.015 | 0 |
| THYMU20271250 | 1.257 | 15.18 |

TABLE 8

| CloneID | NESOP | TESOP |
|---|---|---|
| ASTRO20033160 | 0 | 20.183 |
| ASTRO20125520 | 0 | 10.113 |
| BRAMY20266850 | 0 | 16.957 |
| BRAWH20164460 | 0 | 59.524 |
| BRHIP20005340 | 0 | 9.367 |
| BRHIP20191490 | 0 | 75.561 |
| CTONG20095290 | 0 | 43.261 |
| CTONG20143690 | 0 | 28.473 |
| CTONG20161850 | 0 | 17.787 |
| DFNES20001530 | 0 | 21.906 |
| DFNES20071130 | 0 | 45.721 |
| FCBBF30123470 | 0 | 15.017 |
| FCBBF30175310 | 0 | 10.97 |
| FEBRA20095140 | 0 | 45.326 |
| HCHON20016650 | 0 | 10.558 |
| MESAN20025190 | 0 | 31.731 |
| NT2RI20028470 | 0 | 8.588 |
| NT2RI20054050 | 0 | 1.921 |
| NT2RP70036880 | 0 | 5.052 |
| NTONG20009770 | 0 | 6.726 |
| NTONG20064840 | 0 | 29.574 |
| NTONG20076930 | 0 | 48.142 |
| SMINT20042990 | 0 | 61.748 |
| SPLEN20008820 | 0 | 12.019 |
| SPLEN20128000 | 0 | 2.337 |
| SPLEN20149110 | 0 | 7.218 |
| STOMA20013890 | 0 | 39.515 |
| TESOP20000900 | 0 | 100 |
| TESOP20003120 | 0 | 66.097 |
| TESOP20004000 | 0 | 100 |
| TESOP20005270 | 0 | 70.604 |
| TESOP20005690 | 0 | 100 |
| TESTI20334410 | 0 | 7.508 |

TABLE 8-continued

| CloneID | NESOP | TESOP |
|---|---|---|
| THYMU20271250 | 0 | 2.449 |
| TRACH20141240 | 0 | 7.062 |
| UTERU20022940 | 0 | 12.42 |
| NESOP10001080 | 100 | 0 |
| NT2RI20023160 | 17.058 | 0 |
| NTONG20013620 | 74.273 | 0 |
| TRACH20077540 | 31.967 | 0 |
| NTONG20015870 | 69.673 | 12.221 |

TABLE 9

| CloneID | KIDNE | TKIDN |
|---|---|---|
| ASTRO20008010 | 0 | 3.776 |
| ASTRO20181690 | 0 | 3.496 |
| BRACE20111830 | 0 | 23.795 |
| BRACE20152870 | 0 | 8.501 |
| BRACE20237270 | 0 | 73.082 |
| BRAMY20147540 | 0 | 5.185 |
| BRAMY20286820 | 0 | 78.604 |
| BRAWH20015350 | 0 | 12.794 |
| BRAWH20096780 | 0 | 78.731 |
| BRAWH20132190 | 0 | 35.86 |
| BRAWH20182060 | 0 | 40.908 |
| BRCAN20060190 | 0 | 13.906 |
| BRCOC20004870 | 0 | 1.072 |
| BRCOC20176520 | 0 | 51.098 |
| BRHIP20000870 | 0 | 24.363 |
| BRHIP20198190 | 0 | 32.096 |
| BRHIP20233090 | 0 | 43.183 |
| BRHIP30001110 | 0 | 3.79 |
| BRSSN20015790 | 0 | 49.863 |
| BRSTN20000580 | 0 | 8.929 |
| CTONG10000940 | 0 | 1.442 |
| CTONG20098440 | 0 | 66.526 |
| CTONG20150910 | 0 | 6.012 |
| CTONG20165050 | 0 | 66.526 |
| DFNES20014040 | 0 | 38.579 |
| DFNES20037420 | 0 | 38.579 |
| FCBBF10000770 | 0 | 2.998 |
| FCBBF30083820 | 0 | 39.87 |
| FCBBF30247930 | 0 | 59.143 |
| FEBRA20037500 | 0 | 6.758 |
| FEBRA20072120 | 0 | 14.531 |
| FEBRA20080810 | 0 | 2.621 |
| FEBRA20086620 | 0 | 17.626 |
| FEBRA20140100 | 0 | 59.757 |
| FEBRA20144170 | 0 | 1.999 |
| FEBRA20176800 | 0 | 35.198 |
| HCHON20008320 | 0 | 13.096 |
| HCHON20059870 | 0 | 36.909 |
| HLUNG10000550 | 0 | 2.004 |
| MESAN20106640 | 0 | 32.125 |
| NT2RI20025400 | 0 | 6.399 |
| NT2RI20076290 | 0 | 7.462 |
| NT2RI20091940 | 0 | 3.638 |
| OCBBF20019830 | 0 | 26.741 |
| OCBBF20022900 | 0 | 37.332 |
| OCBBF20039250 | 0 | 3.084 |
| OCBBF20080050 | 0 | 11.755 |
| OCBBF20097720 | 0 | 8.718 |
| OCBBF20125530 | 0 | 4.341 |
| OCBBF20130110 | 0 | 27.949 |
| OCBBF20140640 | 0 | 5.056 |
| OCBBF20173980 | 0 | 9.523 |
| PANCR10000910 | 0 | 1.114 |
| PROST20087700 | 0 | 2.887 |
| PUAEN20044000 | 0 | 26.668 |
| SPLEN20144520 | 0 | 68.029 |
| SPLEN20160980 | 0 | 68.029 |
| TKIDN10000010 | 0 | 41.198 |
| TKIDN20004640 | 0 | 68.029 |
| TKIDN20005210 | 0 | 55.069 |
| TKIDN20030590 | 0 | 78.393 |

TABLE 9-continued

| CloneID | KIDNE | TKIDN |
|---|---|---|
| TKIDN20030620 | 0 | 100 |
| TKIDN20047480 | 0 | 35.796 |
| TRACH20003590 | 0 | 11.039 |
| TRACH20028030 | 0 | 7.714 |
| TRACH20183170 | 0 | 10.844 |
| TRACH20184490 | 0 | 56.123 |
| UMVEN20003540 | 0 | 3.049 |
| UTERU20004240 | 0 | 3.144 |
| UTERU20055930 | 0 | 12.464 |
| ASTRO10001650 | 7.727 | 0 |
| ASTRO20108190 | 2.346 | 0 |
| BGGI120006160 | 3.117 | 0 |
| BRACE20039040 | 9.038 | 0 |
| BRAMY20102080 | 63.37 | 0 |
| BRAWH20004600 | 2.128 | 0 |
| BRAWH20125380 | 35.37 | 0 |
| BRAWH20162690 | 4.596 | 0 |
| BRHIP20115760 | 66.835 | 0 |
| BRHIP20205090 | 65.282 | 0 |
| CTONG20052650 | 65.178 | 0 |
| CTONG20108210 | 2.491 | 0 |
| CTONG20128470 | 6.004 | 0 |
| CTONG20133480 | 19.179 | 0 |
| CTONG20139070 | 7.516 | 0 |
| D9OST20000310 | 16.47 | 0 |
| DFNES20001530 | 11.162 | 0 |
| FCBBF10001820 | 59.128 | 0 |
| FEBRA20002100 | 4.929 | 0 |
| HCHON20008980 | 35.524 | 0 |
| HCHON20016650 | 5.38 | 0 |
| HLUNG20033780 | 32.277 | 0 |
| KIDNE20002520 | 2.979 | 0 |
| KIDNE20003940 | 100 | 0 |
| KIDNE20006780 | 100 | 0 |
| KIDNE20007270 | 73.728 | 0 |
| KIDNE20007770 | 19.958 | 0 |
| KIDNE20008010 | 100 | 0 |
| KIDNE20009470 | 8.811 | 0 |
| KIDNE20011170 | 77.71 | 0 |
| KIDNE20011400 | 100 | 0 |
| KIDNE20013730 | 24.839 | 0 |
| KIDNE20017130 | 54.019 | 0 |
| KIDNE20018730 | 100 | 0 |
| KIDNE20018970 | 100 | 0 |
| KIDNE20020150 | 100 | 0 |
| KIDNE20021680 | 100 | 0 |
| KIDNE20021910 | 24.85 | 0 |
| KIDNE20021980 | 100 | 0 |
| KIDNE20022620 | 100 | 0 |
| KIDNE20024830 | 100 | 0 |
| KIDNE20027250 | 35.87 | 0 |
| KIDNE20027950 | 100 | 0 |
| KIDNE20028390 | 25.593 | 0 |
| KIDNE20028720 | 1.993 | 0 |
| KIDNE20028830 | 7.907 | 0 |
| KIDNE20029800 | 10.988 | 0 |
| KIDNE20067330 | 100 | 0 |
| KIDNE20079440 | 35.045 | 0 |
| KIDNE20096280 | 100 | 0 |
| KIDNE20096470 | 100 | 0 |
| KIDNE20100070 | 100 | 0 |
| KIDNE20100840 | 100 | 0 |
| KIDNE20101370 | 100 | 0 |
| KIDNE20101510 | 100 | 0 |
| KIDNE20102650 | 8.237 | 0 |
| KIDNE20102710 | 100 | 0 |
| KIDNE20104300 | 33.246 | 0 |
| KIDNE20106740 | 100 | 0 |
| KIDNE20107390 | 100 | 0 |
| KIDNE20107500 | 74.264 | 0 |
| KIDNE20107620 | 100 | 0 |
| KIDNE20109730 | 100 | 0 |
| KIDNE20109890 | 100 | 0 |
| KIDNE20112000 | 100 | 0 |
| KIDNE20115080 | 65.178 | 0 |
| KIDNE20118580 | 100 | 0 |
| KIDNE20120090 | 33.186 | 0 |

TABLE 9-continued

| CloneID | KIDNE | TKIDN |
|---|---|---|
| KIDNE20121880 | 62.256 | 0 |
| KIDNE20122910 | 83.085 | 0 |
| KIDNE20124400 | 6.171 | 0 |
| KIDNE20125630 | 100 | 0 |
| KIDNE20126010 | 100 | 0 |
| KIDNE20126130 | 100 | 0 |
| KIDNE20127100 | 33.012 | 0 |
| KIDNE20127450 | 100 | 0 |
| KIDNE20127750 | 100 | 0 |
| KIDNE20130450 | 100 | 0 |
| KIDNE20131580 | 63.24 | 0 |
| KIDNE20132180 | 100 | 0 |
| KIDNE20137340 | 100 | 0 |
| KIDNE20138010 | 100 | 0 |
| KIDNE20141190 | 49.697 | 0 |
| KIDNE20144890 | 100 | 0 |
| KIDNE20148900 | 100 | 0 |
| KIDNE20163880 | 100 | 0 |
| KIDNE20180710 | 49.105 | 0 |
| KIDNE20181660 | 100 | 0 |
| KIDNE20182690 | 100 | 0 |
| KIDNE20186780 | 100 | 0 |
| KIDNE20190740 | 100 | 0 |
| LIVER20035110 | 28.683 | 0 |
| MESAN20025190 | 16.169 | 0 |
| NT2RP70043480 | 7.879 | 0 |
| PROST20107820 | 1.696 | 0 |
| PROST20123530 | 32.771 | 0 |
| PROST20161950 | 20.387 | 0 |
| PUAEN20030180 | 46.744 | 0 |
| SKMUS20003610 | 3.728 | 0 |
| SMINT20033400 | 10.243 | 0 |
| TBAES20000590 | 5.253 | 0 |
| TESTI20044310 | 29.162 | 0 |
| TESTI20082330 | 45.847 | 0 |
| TRACH20032720 | 12.917 | 0 |
| UTERU20099720 | 12.351 | 0 |

TABLE 10

| CloneID | LIVER | TLIVE |
|---|---|---|
| BRAWH20166790 | 83.525 | 0 |
| CTONG20103480 | 15.35 | 0 |
| HEART20005410 | 11.598 | 0 |
| LIVER10001260 | 66.455 | 0 |
| LIVER10004790 | 100 | 0 |
| LIVER20002160 | 100 | 0 |
| LIVER20011130 | 92.988 | 0 |
| LIVER20011910 | 100 | 0 |
| LIVER20028420 | 16.548 | 0 |
| LIVER20035110 | 71.317 | 0 |
| LIVER20035680 | 100 | 0 |
| LIVER20038540 | 100 | 0 |
| LIVER20045650 | 100 | 0 |
| LIVER20055200 | 100 | 0 |
| LIVER20055440 | 100 | 0 |
| LIVER20059810 | 24.82 | 0 |
| LIVER20062510 | 100 | 0 |
| LIVER20064100 | 88.658 | 0 |
| LIVER20064690 | 100 | 0 |
| LIVER20075680 | 100 | 0 |
| LIVER20080530 | 100 | 0 |
| LIVER20084730 | 100 | 0 |
| LIVER20085800 | 100 | 0 |
| LIVER20087510 | 75.266 | 0 |
| LIVER20091180 | 100 | 0 |
| NTONG20063010 | 47.641 | 0 |
| PROST20087700 | 6.762 | 0 |
| PROST20107820 | 2.108 | 0 |
| TRACH20005400 | 12.349 | 0 |
| ASTRO20001410 | 0 | 10.441 |
| ASTRO20125520 | 0 | 10.162 |
| BRACE20152870 | 0 | 15.788 |

TABLE 10-continued

| CloneID | LIVER | TLIVE |
|---|---|---|
| BRAMY20167060 | 0 | 34.076 |
| BRAMY20181220 | 0 | 87.217 |
| BRAMY20285160 | 0 | 81.346 |
| BRCOC20001860 | 0 | 20.45 |
| FEBRA20144170 | 0 | 3.712 |
| HLUNG10000550 | 0 | 3.721 |
| OCBBF20073540 | 0 | 6.907 |
| OCBBF20088220 | 0 | 16.388 |
| PLACE60169420 | 0 | 26.895 |
| SMINT20152940 | 0 | 54.735 |
| SPLEN20242320 | 0 | 45.601 |
| THYMU20000570 | 0 | 18.649 |
| TRACH20077540 | 0 | 30.987 |
| UTERU20055930 | 0 | 15.433 |
| UTERU20065930 | 0 | 10.151 |

TABLE 11

| CloneID | HLUNG | TLUNG |
|---|---|---|
| BRACE20096200 | 70.38 | 0 |
| BRAWH20004600 | 2.238 | 0 |
| BRAWH20030250 | 11.121 | 0 |
| BRCAN20006390 | 61.519 | 0 |
| BRCAN20280360 | 8.855 | 0 |
| BRHIP20238880 | 1.35 | 0 |
| CTONG10000940 | 1.428 | 0 |
| CTONG20103480 | 6.495 | 0 |
| CTONG20129960 | 10.709 | 0 |
| CTONG20155180 | 48.707 | 0 |
| FCBBF10001210 | 36.439 | 0 |
| FEBRA20144170 | 1.98 | 0 |
| FEBRA20197110 | 7.756 | 0 |
| HCHON20002260 | 2.958 | 0 |
| HHDPC20034390 | 0.933 | 0 |
| HLUNG10000550 | 3.971 | 0 |
| HLUNG20016330 | 29.367 | o |
| HLUNG20016770 | 12.888 | 0 |
| HLUNG20017120 | 12.093 | 0 |
| HLUNG20023340 | 33.714 | 0 |
| HLUNG20033780 | 33.957 | 0 |
| HLUNG20084390 | 100 | 0 |
| IMR3220002430 | 3.147 | 0 |
| LIVER20028420 | 14.004 | 0 |
| NOVAR20000380 | 2.278 | 0 |
| NT2RI20023910 | 8.923 | 0 |
| NT2RI20054050 | 2.059 | 0 |
| NT2RI20091730 | 4.091 | 0 |
| NT2RP70044280 | 12.369 | 0 |
| OCBBF20020830 | 40.304 | 0 |
| OCBBF20125530 | 4.302 | 0 |
| PLACE60004630 | 28.618 | 0 |
| PROST20057930 | 14.383 | 0 |
| PROST20107820 | 0.892 | 0 |
| PROST20185830 | 33.898 | 0 |
| PUAEN20030180 | 12.294 | 0 |
| SMINT20121220 | 12.822 | 0 |
| SPLEN20002220 | 44.799 | 0 |
| SPLEN20008740 | 1.788 | 0 |
| SPLEN20054290 | 26.875 | 0 |
| SPLEN20128000 | 1.253 | 0 |
| SPLEN20157300 | 51.319 | 0 |
| SPLEN20176200 | 18.8 | 0 |
| SPLEN20179180 | 3.344 | 0 |
| SPLEN20211940 | 12.373 | 0 |
| STOMA20013890 | 21.183 | 0 |
| TBAES20000590 | 5.527 | 0 |
| TESTI20094230 | 59.311 | 0 |
| TESTI20184620 | 10.365 | 0 |
| TESTI20334410 | 8.049 | 0 |
| THYMU20000570 | 4.974 | 0 |
| THYMU20039810 | 1.915 | 0 |
| TRACH20007020 | 14.4 | 0 |
| TRACH20141240 | 3.786 | 0 |

TABLE 11-continued

| CloneID | HLUNG | TLUNG |
|---|---|---|
| TRACH20183170 | 10.745 | 0 |
| ASTRO20108190 | 0 | 13.924 |
| ASTRO20155290 | 0 | 38.341 |
| BRHIP20096850 | 0 | 73.716 |
| FEBRA20080810 | 0 | 14.654 |
| MESAN20014500 | 0 | 59.68 |
| SMINT20028820 | 0 | 60.089 |
| SPLEN20162680 | 0 | 8.941 |

TABLE 12

| CloneID | NOVAR | TOVAR |
|---|---|---|
| BGGI120006160 | 21.31 | 0 |
| BRHIP20005340 | 8.158 | 0 |
| BRHIP20191860 | 47.038 | 0 |
| HHDPC20001040 | 44.094 | 0 |
| NOVAR10000150 | 72.374 | 0 |
| NOVAR10000910 | 46.155 | 0 |
| NOVAR10001020 | 99.094 | 0 |
| NOVAR20000380 | 14.805 | 0 |
| NOVAR20003520 | 100 | 0 |
| THYMU20271250 | 4.266 | 0 |
| ASTRO20141350 | 0 | 75.66 |
| BRAMY20157820 | 0 | 85.296 |
| BRCOC20001860 | 0 | 64.79 |
| HLUNG20016770 | 0 | 76.536 |
| NT2RI20054050 | 0 | 12.229 |
| NTONG20090600 | 0 | 60.694 |
| PROST20087700 | 0 | 16.991 |
| PUAEN20015860 | 0 | 62.197 |
| SPLEN20029310 | 0 | 88.828 |
| TOVAR20004760 | 0 | 49.428 |
| TOVAR20005750 | 0 | 96.313 |
| TRACH20079690 | 0 | 55.276 |
| UTERU20004240 | 0 | 18.499 |

TABLE 13

| CloneID | STOMA | TSTOM |
|---|---|---|
| BRACE20060840 | 0 | 65.917 |
| FEBRA20052910 | 0 | 77.883 |
| HCHON20002260 | 0 | 8.66 |
| HLUNG10000550 | 0 | 11.625 |
| NTONG20009770 | 0 | 21.112 |
| PROST20107820 | 0 | 5.223 |
| THYMU20039810 | 0 | 11.216 |
| TSTOM10001860 | 0 | 100 |
| TSTOM20001390 | 0 | 89.823 |
| TSTOM20003150 | 0 | 48.943 |
| TSTOM20005690 | 0 | 100 |
| ASTRO20125520 | 10.059 | 0 |
| BRACE20039040 | 17.642 | 0 |
| BRAMY20124260 | 42.064 | 0 |
| BRCOC20031870 | 10.704 | 0 |
| BRHIP20191860 | 13.43 | 0 |
| CTONG20128470 | 11.719 | 0 |
| FEBRA20037500 | 12.423 | 0 |
| HCHON20040020 | 5.343 | 0 |
| HHDPC10000830 | 6.661 | 0 |
| IMR3220002430 | 5.838 | 0 |
| KIDNE20007770 | 12.986 | 0 |
| NOVAR20000380 | 4.227 | 0 |
| NT2RI20054050 | 1.91 | 0 |
| NT2RI20091730 | 7.59 | 0 |
| PROST20130530 | 20.156 | 0 |
| SPLEN20149110 | 7.179 | 0 |
| SPLEN20157880 | 32.942 | 0 |
| STOMA20001830 | 100 | 0 |
| STOMA20005390 | 100 | 0 |
| STOMA20005670 | 100 | 0 |

TABLE 13-continued

| CloneID | STOMA | TSTOM |
|---|---|---|
| STOMA20006400 | 100 | 0 |
| STOMA20006780 | 100 | 0 |
| STOMA20006860 | 100 | 0 |
| STOMA20008880 | 100 | 0 |
| STOMA20010250 | 100 | 0 |
| STOMA20013890 | 39.303 | 0 |
| STOMA20026880 | 100 | 0 |
| STOMA20032890 | 100 | 0 |
| STOMA20034770 | 100 | 0 |
| STOMA20036460 | 100 | 0 |
| STOMA20046680 | 100 | 0 |
| STOMA20048520 | 100 | 0 |
| STOMA20048840 | 100 | 0 |
| STOMA20051200 | 85.988 | 0 |
| STOMA20056640 | 100 | 0 |
| STOMA20056670 | 100 | 0 |
| STOMA20057820 | 91.236 | 0 |
| STOMA20062130 | 100 | 0 |
| STOMA20062290 | 40.913 | 0 |
| STOMA20063250 | 100 | 0 |
| STOMA20063980 | 100 | 0 |
| STOMA20064470 | 100 | 0 |
| STOMA20067800 | 59.113 | 0 |
| STOMA20069040 | 100 | 0 |
| STOMA20072690 | 100 | 0 |
| STOMA20076800 | 100 | 0 |
| STOMA20077450 | 100 | 0 |
| STOMA20080500 | 100 | 0 |
| STOMA20083610 | 100 | 0 |
| STOMA20086140 | 100 | 0 |
| STOMA20088380 | 100 | 0 |
| STOMA20092530 | 100 | 0 |
| STOMA20092560 | 100 | 0 |
| STOMA20092890 | 39.042 | 0 |
| TESTI20184620 | 19.231 | 0 |
| TRACH20003590 | 40.588 | 0 |
| TRACH20183170 | 19.936 | 0 |
| PROST20083600 | 12.248 | 38.653 |
| TRACH20068660 | 6.753 | 21.311 |

TABLE 14

| CloneID | UTERU | TUTER |
|---|---|---|
| DFNES10001850 | 0 | 29.393 |
| NT2RI20023910 | 0 | 18.073 |
| SMINT20144800 | 0 | 35.406 |
| SPLEN20162680 | 0 | 9.628 |
| TOVAR20004760 | 0 | 50.572 |
| TUTER20002830 | 0 | 100 |
| ASTRO20008010 | 1.217 | 0 |
| ASTRO20033160 | 10.555 | 0 |
| ASTRO20058630 | 4.534 | 0 |
| ASTRO20105820 | 20.644 | 0 |
| ASTRO20108190 | 3.21 | 0 |
| BRACE20039040 | 3.092 | 0 |
| BRACE20057190 | 3.542 | 0 |
| BRACE20060840 | 3.661 | 0 |
| BRACE20111830 | 7.667 | 0 |
| BRACE20223330 | 10.589 | 0 |
| BRAMY20266850 | 2.956 | 0 |
| BRAWH20113430 | 8.367 | 0 |
| BRAWH20126980 | 22.868 | 0 |
| BRCOC20031870 | 0.938 | 0 |
| BRCOC20107300 | 12.892 | 0 |
| BRCOC20121720 | 6.71 | 0 |
| BRCOC20155970 | 25.187 | 0 |
| BRHIP20105710 | 18.366 | 0. |
| BRHIP20191490 | 13.172 | 0 |
| BRHIP20207990 | 12.072 | 0 |
| BRHIP20217620 | 6.646 | 0 |
| BRHIP20222280 | 10.898 | 0 |
| BRHIP20238880 | 0.439 | 0 |
| BRHIP20249110 | 11.054 | 0 |

TABLE 14-continued

| CloneID | UTERU | TUTER |
|---|---|---|
| BRSSN20018690 | 3.6 | 0 |
| BRTHA20000570 | 51.819 | 0 |
| CTONG10000940 | 0.464 | 0 |
| CTONG10002770 | 24.668 | 0 |
| CTONG20095290 | 7.541 | 0 |
| CTONG20099380 | 23.863 | 0 |
| CTONG20103480 | 6.336 | 0 |
| CTONG20108210 | 2.557 | 0 |
| CTONG20118250 | 10.239 | 0 |
| CTONG20129960 | 3.482 | 0 |
| CTONG20131560 | 24.668 | 0 |
| CTONG20139070 | 2.571 | 0 |
| CTONG20139340 | 8.273 | 0 |
| CTONG20143690 | 4.963 | 0 |
| CTONG20160560 | 2.372 | 0 |
| D3OST30002580 | 22.242 | 0 |
| FCBBF10000240 | 5.237 | 0 |
| FCBBF10001820 | 10.114 | 0 |
| FCBBF10003670 | 1.812 | 0 |
| FCBBF10004120 | 2.308 | 0 |
| FCBBF10005740 | 4.952 | 0 |
| FCBBF30175310 | 1.912 | 0 |
| FCBBF30240020 | 6.769 | 0 |
| FCBBF30246230 | 6.682 | 0 |
| FCBBF40001420 | 4.36 | 0 |
| FEBRA20002100 | 0.843 | 0 |
| FEBRA20004620 | 6.733 | 0 |
| FEBRA20018280 | 6.489 | 0 |
| FEBRA20025270 | 3.416 | 0 |
| FEBRA20034360 | 6.63 | 0 |
| FEBRA20037500 | 19.596 | 0 |
| FEBRA20080810 | 0.845 | 0 |
| FEBRA20082100 | 15.999 | 0 |
| FEBRA20144170 | 1.288 | 0 |
| FEBRA20225040 | 1.959 | 0 |
| HCHON20002260 | 0.962 | 0 |
| HCHON20007380 | 3.551 | 0 |
| HCHON20015980 | 5.796 | 0 |
| HCHON20016650 | 1.84 | 0 |
| HCHON20022470 | 3.348 | 0 |
| HCHON20040020 | 0.936 | 0 |
| HCHON20076500 | 7.263 | 0 |
| HEART20072310 | 11.555 | 0 |
| HHDPC20034390 | 1.517 | 0 |
| HLUNG10000550 | 1.937 | 0 |
| HLUNG20016770 | 4.191 | 0 |
| KIDNE20131580 | 21.635 | 0 |
| LIVER20028420 | 9.107 | 0 |
| MAMGL10000830 | 0.346 | 0 |
| MESAN20171520 | 24.337 | 0 |
| NOVAR10000150 | 3.622 | 0 |
| NOVAR10000910 | 2.31 | 0 |
| NT2NE20053580 | 24.761 | 0 |
| NT2NE20159740 | 9.111 | 0 |
| NT2NE20174920 | 20.127 | 0 |
| NT2RI20023160 | 0.956 | 0 |
| NT2RI20041880 | 3.425 | 0 |
| NT2RI20054050 | 1.004 | 0 |
| NT2RI20076290 | 2.404 | 0 |
| NT2RI20273230 | 39.625 | 0 |
| NT2RP60000770 | 30.666 | 0 |
| NT2RP60000850 | 11.032 | 0 |
| NT2RP70036880 | 0.881 | 0 |
| NT2RP70043480 | 2.695 | 0 |
| NT2RP70045590 | 10.166 | 0 |
| NT2RP70056750 | 10.406 | 0 |
| NT2RP70062230 | 5.039 | 0 |
| NT2RP70081610 | 7.488 | 0 |
| OCBBF10001750 | 8.591 | 0 |
| OCBBF20006770 | 19.428 | 0 |
| OCBBF20032460 | 11.672 | 0 |
| OCBBF20039250 | 0.994 | 0 |
| OCBBF20047570 | 2.956 | 0 |
| OCBBF20054760 | 16.727 | 0 |
| OCBBF20059560 | 3.386 | 0 |
| OCBBF20068490 | 2.41 | 0 |
| OCBBF20080050 | 3.787 | 0 |
| OCBBF20094240 | 8.655 | 0 |
| OCBBF20097720 | 1.404 | 0 |
| OCBBF20103130 | 16.359 | 0 |
| OCBBF20105570 | 43.708 | 0 |
| OCBBF20140640 | 3.258 | 0 |
| OCBBF20173980 | 3.068 | 0 |
| OCBBF20180120 | 10.043 | 0 |
| OCBBF20188730 | 6.611 | 0 |
| OCBBF20189560 | 2.019 | 0 |
| PEBLM20044520 | 6.439 | 0 |
| PLACE60060420 | 6.493 | 0 |
| PROST20087700 | 0.93 | 0 |
| PROST20107820 | 0.29 | 0 |
| PROST20149160 | 4.345 | 0 |
| PROST20159240 | 8.082 | 0 |
| PROST20176170 | 25.167 | 0 |
| PROST20189770 | 15.499 | 0 |
| PUAEN20003740 | 1.145 | 0 |
| PUAEN20015860 | 3.406 | 0 |
| SKMUS20003610 | 1.275 | 0 |
| SKNSH20008190 | 5.937 | 0 |
| SKNSH20080430 | 12.076 | 0 |
| SMINT20026890 | 51.875 | 0 |
| SMINT20029760 | 6.221 | 0 |
| SMINT20068010 | 19.209 | 0 |
| SMINT20110330 | 25.261 | 0 |
| SMINT20121220 | 4.169 | 0 |
| SPLEN20008390 | 10.886 | 0 |
| SPLEN20011410 | 2.253 | 0 |
| SPLEN20054290 | 17.478 | 0 |
| SPLEN20128000 | 0.407 | 0 |
| SPLEN20140800 | 5.651 | 0 |
| SPLEN20145720 | 7.423 | 0 |
| SPLEN20169720 | 4.837 | 0 |
| SPLEN20179180 | 3.262 | 0 |
| SPLEN20193110 | 57.827 | 0 |
| SPLEN20194050 | 3.416 | 0 |
| SPLEN20211940 | 8.047 | 0 |
| SPLEN20212730 | 17.589 | 0 |
| SPLEN20225220 | 1.691 | 0 |
| TBAES20000590 | 1.797 | 0 |
| TESTI20061110 | 24.59 | 0 |
| TESTI20116830 | 38.615 | 0 |
| TESTI20184620 | 3.37 | 0 |
| TESTI20208710 | 64.596 | 0 |
| TESTI20211240 | 6.816 | 0 |
| TESTI20213580 | 40.357 | 0 |
| TESTI20214250 | 4.107 | 0 |
| TESTI20334410 | 2.618 | 0 |
| TESTI20369130 | 24.204 | 0 |
| TESTI20369690 | 4.285 | 0 |
| TESTI20391770 | 4.943 | 0 |
| THYMU20039810 | 2.491 | 0 |
| THYMU20216840 | 58.853 | 0 |
| THYMU20240710 | 39.309 | 0 |
| TRACH20003590 | 3.557 | 0 |
| TRACH20032720 | 4.419 | 0 |
| TRACH20033230 | 2.123 | 0 |
| TRACH20141240 | 3.693 | 0 |
| TRACH20149270 | 25.316 | 0 |
| UMVEN10001860 | 0.63 | 0 |
| UTERU20000740 | 62.692 | 0 |
| UTERU20004240 | 1.013 | 0 |
| UTERU20006290 | 100 | 0 |
| UTERU20020010 | 40.126 | 0 |
| UTERU20022940 | 2.165 | 0 |
| UTERU20030570 | 3.085 | 0 |
| UTERU20040610 | 100 | 0 |
| UTERU20046640 | 4.048 | 0 |
| UTERU20046980 | 100 | 0 |
| UTERU20050690 | 64.596 | 0 |
| UTERU20054460 | 24.816 | 0 |
| UTERU20055330 | 100 | 0 |
| UTERU20055930 | 4.016 | 0 |
| UTERU20056010 | 3.04 | 0 |
| UTERU20059050 | 100 | 0 |
| UTERU20061030 | 100 | 0 |

TABLE 14-continued

| CloneID | UTERU | TUTER |
|---|---|---|
| UTERU20064000 | 15.228 | 0 |
| UTERU20064860 | 51.819 | 0 |
| UTERU20065930 | 3.522 | 0 |
| UTERU20067050 | 100 | 0 |
| UTERU20068990 | 100 | 0 |
| UTERU20070040 | 24.856 | 0 |
| UTERU20070810 | 17.449 | 0 |
| UTERU20076390 | 100 | 0 |
| UTERU20081300 | 53.896 | 0 |
| UTERU20084260 | 26.26 | 0 |
| UTERU20094350 | 12.756 | 0 |
| UTERU20095380 | 40.674 | 0 |
| UTERU20095400 | 100 | 0 |
| UTERU20097760 | 100 | 0 |
| UTERU20099720 | 16.901 | 0 |
| UTERU20101240 | 100 | 0 |
| UTERU20114100 | 100 | 0 |
| UTERU20115740 | 100 | 0 |
| UTERU20116570 | 100 | 0 |
| UTERU20118110 | 100 | 0 |
| UTERU20118970 | 100 | 0 |
| UTERU20119060 | 16.267 | 0 |
| UTERU20119680 | 100 | 0 |
| UTERU20120310 | 53.896 | 0 |
| UTERU20124070 | 29.356 | 0 |
| UTERU20126880 | 51.568 | 0 |
| UTERU20134910 | 13.929 | 0 |
| UTERU20135860 | 7.858 | 0 |
| UTERU20143980 | 100 | 0 |
| UTERU20144640 | 16.101 | 0 |
| UTERU20145480 | 39.231 | 0 |
| UTERU20146310 | 100 | 0 |
| UTERU20146680 | 39.231 | 0 |
| UTERU20150870 | 100 | 0 |
| UTERU20151980 | 100 | 0 |
| UTERU20158300 | 58.853 | 0 |
| UTERU20158800 | 100 | 0 |
| UTERU20161570 | 100 | 0 |
| UTERU20164260 | 15.158 | 0 |
| UTERU20168220 | 19.178 | 0 |
| UTERU20176130 | 12.264 | 0 |
| UTERU20176320 | 64.596 | 0 |
| UTERU20178100 | 100 | 0 |
| UTERU20179880 | 100 | 0 |
| UTERU20183640 | 53.896 | 0 |
| UTERU20185230 | 40.126 | 0 |
| UTERU20186740 | 100 | 0 |
| UTERU20188110 | 100 | 0 |
| UTERU20188810 | 100 | 0 |
| BRAWH10000930 | 2.2 | 10.279 |
| CTONG20128470 | 2.054 | 38.378 |
| UTERU20006960 | 3.394 | 63.416 |

TABLE 15

| CloneID | NTONG | CTONG |
|---|---|---|
| ADRGL20018300 | 0 | 22.262 |
| ASTRO20058630 | 0 | 14.161 |
| ASTRO20072210 | 0 | 34.963 |
| ASTRO20108190 | 0 | 5.013 |
| BRACE20003070 | 0 | 2.194 |
| BRACE20039040 | 0 | 4.829 |
| BRACE20060720 | 0 | 36.712 |
| BRACE20061050 | 0 | 39.515 |
| BRACE20210140 | 0 | 11.034 |
| BRACE20276430 | 0 | 26.828 |
| BRAMY20152110 | 0 | 24.194 |
| BRAMY20266850 | 0 | 4.616 |
| BRAMY20271400 | 0 | 48.032 |
| BRAWH10000930 | 0 | 3.436 |
| BRAWH20004600 | 0 | 1.137 |
| BRCAN20280360 | 0 | 4.497 |
| BRCOC20004870 | 0 | 0.54 |

TABLE 15-continued

| CloneID | NTONG | CTONG |
|---|---|---|
| BRHIP20005340 | 0 | 5.1 |
| BRHIP20005530 | 0 | 4.786 |
| BRHIP20238880 | 0 | 2.741 |
| BRSSN20146100 | 0 | 6.65 |
| CTONG10000100 | 0 | 12.075 |
| CTONG10000220 | 0 | 100 |
| CTONG10000620 | 0 | 100 |
| CTONG10000930 | 0 | 74.021 |
| CTONG10000940 | 0 | 0.725 |
| CTONG10001650 | 0 | 100 |
| CTONG10002770 | 0 | 38.523 |
| CTONG20002180 | 0 | 100 |
| CTONG20004690 | 0 | 5.439 |
| CTONG20009770 | 0 | 100 |
| CTONG20014280 | 0 | 62.446 |
| CTONG20027090 | 0 | 4.036 |
| CTONG20028410 | 0 | 19.729 |
| CTONG20038890 | 0 | 100 |
| CTONG20049410 | 0 | 100 |
| CTONG20050280 | 0 | 25.499 |
| CTONG20052650 | 0 | 34.822 |
| CTONG20052900 | 0 | 42.764 |
| CTONG20075860 | 0 | 11.194 |
| CTONG20076130 | 0 | 16.303 |
| CTONG20077790 | 0 | 62.68 |
| CTONG20082690 | 0 | 12.672 |
| CTONG20085950 | 0 | 100 |
| CTONG20091080 | 0 | 44.201 |
| CTONG20091320 | 0 | 100 |
| CTONG20092570 | 0 | 100 |
| CTONG20092580 | 0 | 100 |
| CTONG20092680 | 0 | 100 |
| CTONG20092700 | 0 | 100 |
| CTONG20093950 | 0 | 100 |
| CTONG20095270 | 0 | 100 |
| CTONG20095290 | 0 | 11.777 |
| CTONG20095340 | 0 | 14.323 |
| CTONG20096430 | 0 | 100 |
| CTONG20096750 | 0 | 100 |
| CTONG20097660 | 0 | 100 |
| CTONG20098440 | 0 | 33.474 |
| CTONG20099380 | 0 | 37.266 |
| CTONG20099550 | 0 | 100 |
| CTONG20099630 | 0 | 38.502 |
| CTONG20100240 | 0 | 100 |
| CTONG20101480 | 0 | 100 |
| CTONG20103480 | 0 | 13.193 |
| CTONG20105080 | 0 | 15.273 |
| CTONG20105660 | 0 | 25.256 |
| CTONG20106230 | 0 | 100 |
| CTONG20106520 | 0 | 29.937 |
| CTONG20108210 | 0 | 2.662 |
| CTONG20114290 | 0 | 100 |
| CTONG20114740 | 0 | 100 |
| CTONG20118150 | 0 | 100 |
| CTONG20118250 | 0 | 15.991 |
| CTONG20119200 | 0 | 100 |
| CTONG20120770 | 0 | 100 |
| CTONG20121010 | 0 | 29.404 |
| CTONG20121580 | 0 | 33.983 |
| CTONG20124010 | 0 | 7.835 |
| CTONG20124220 | 0 | 69.076 |
| CTONG20124470 | 0 | 100 |
| CTONG20124730 | 0 | 100 |
| CTONG20125540 | 0 | 100 |
| CTONG20125640 | 0 | 7.359 |
| CTONG20126070 | 0 | 3.221 |
| CTONG20127450 | 0 | 10.331 |
| CTONG20128470 | 0 | 9.622 |
| CTONG20129960 | 0 | 32.63 |
| CTONG20131490 | 0 | 24.817 |
| CTONG20131560 | 0 | 38.523 |
| CTONG20132220 | 0 | 6.999 |
| CTONG20133390 | 0 | 100 |
| CTONG20133480 | 0 | 10.246 |
| CTONG20133520 | 0 | 50.616 |
| CTONG20136300 | 0 | 100 |

TABLE 15-continued

| CloneID | NTONG | CTONG |
|---|---|---|
| CTONG20138030 | 0 | 100 |
| CTONG20139070 | 0 | 8.031 |
| CTONG20139340 | 0 | 12.919 |
| CTONG20139860 | 0 | 100 |
| CTONG20140320 | 0 | 100 |
| CTONG20140580 | 0 | 100 |
| CTONG20141650 | 0 | 8.968 |
| CTONG20146300 | 0 | 100 |
| CTONG20147050 | 0 | 34.963 |
| CTONG20149460 | 0 | 100 |
| CTONG20149950 | 0 | 100 |
| CTONG20153300 | 0 | 52.97 |
| CTONG20153580 | 0 | 74.021 |
| CTONG20155180 | 0 | 24.734 |
| CTONG20155400 | 0 | 100 |
| CTONG20156780 | 0 | 62.446 |
| CTONG20158040 | 0 | 100 |
| CTONG20158150 | 0 | 16.385 |
| CTONG20158660 | 0 | 100 |
| CTONG20159530 | 0 | 100 |
| CTONG20160560 | 0 | 3.704 |
| CTONG20161850 | 0 | 19.368 |
| CTONG20162170 | 0 | 100 |
| CTONG20163550 | 0 | 100 |
| CTONG20164990 | 0 | 65.066 |
| CTONG20165050 | 0 | 33.474 |
| CTONG20186320 | 0 | 14.897 |
| CTONG20200310 | 0 | 100 |
| CTONG20265130 | 0 | 100 |
| CTONG20267700 | 0 | 100 |
| CTONG20273610 | 0 | 100 |
| FCBBF10000240 | 0 | 12.268 |
| FCBBF10005740 | 0 | 3.866 |
| FCBBF30123470 | 0 | 4.088 |
| FCBBF30233680 | 0 | 9.14 |
| FEBRA20025270 | 0 | 5.334 |
| FEBRA20037500 | 0 | 6.8 |
| HCHON20002260 | 0 | 1.502 |
| HCHON20007380 | 0 | 5.546 |
| HCHON20007510 | 0 | 6.65 |
| HCHON20015350 | 0 | 17.176 |
| HCHON20040020 | 0 | 1.462 |
| HHDPC20034390 | 0 | 0.474 |
| HLUNG10000550 | 0 | 2.016 |
| KIDNE20002520 | 0 | 3.184 |
| KIDNE20009470 | 0 | 9.415 |
| KIDNE20115080 | 0 | 34.822 |
| KIDNE20127100 | 0 | 35.274 |
| LIVER20028420 | 0 | 3.556 |
| MESAN20029400 | 0 | 5.924 |
| NT2RI20023160 | 0 | 1.493 |
| NT2RI20023910 | 0 | 1.51 |
| NT2RI20091730 | 0 | 4.155 |
| NT2RP70043480 | 0 | 4.209 |
| NT2RP70078420 | 0 | 3.572 |
| NT2RP70081610 | 0 | 11.694 |
| OCBBF20006770 | 0 | 30.34 |
| OCBBF20059560 | 0 | 5.287 |
| OCBBF20073540 | 0 | 1.871 |
| OCBBF20094240 | 0 | 13.516 |
| OCBBF20108580 | 0 | 12.407 |
| PEBLM20044520 | 0 | 15.083 |
| PEBLM20071880 | 0 | 16.259 |
| PROST20107820 | 0 | 0.453 |
| PUAEN20030180 | 0 | 6.243 |
| SKNSH20008190 | 0 | 4.636 |
| SMINT20023280 | 0 | 34.547 |
| SMINT20089170 | 0 | 20.839 |
| SPLEN20179180 | 0 | 5.094 |
| TESTI20094020 | 0 | 17.075 |
| TESTI20094230 | 0 | 30.119 |
| TESTI20152460 | 0 | 22.051 |
| TESTI20184620 | 0 | 5.263 |
| TESTI20211240 | 0 | 10.645 |
| TESTI20442760 | 0 | 8.832 |
| THYMU20039810 | 0 | 0.973 |
| TRACH20028030 | 0 | 11.644 |
| TRACH20141240 | 0 | 1.923 |
| TSTOM20003150 | 0 | 4.245 |
| UTERU20004240 | 0 | 1.582 |
| UTERU20055930 | 0 | 2.091 |
| UTERU20065930 | 0 | 2.75 |
| UTERU20119060 | 0 | 12.702 |
| UTERU20124070 | 0 | 45.844 |
| BRACE20039440 | 34.336 | 0 |
| BRACE20068590 | 74.88 | 0 |
| FCBBF30018550 | 20.639 | 0 |
| IMR3220002430 | 6.323 | 0 |
| KIDNE20028830 | 16.715 | 0 |
| NT2RI20028470 | 9.251 | 0 |
| NT2RI20054050 | 2.069 | 0 |
| NT2RI20086220 | 23.258 | 0 |
| NTONG20009770 | 7.245 | 0 |
| NTONG20013620 | 25.727 | 0 |
| NTONG20028070 | 86.921 | 0 |
| NTONG20029480 | 32.729 | 0 |
| NTONG20029700 | 100 | 0 |
| NTONG20046140 | 43.643 | 0 |
| NTONG20048060 | 51.123 | 0 |
| NTONG20049910 | 100 | 0 |
| NTONG20050620 | 100 | 0 |
| NTONG20050860 | 100 | 0 |
| NTONG20051530 | 58.314 | 0 |
| NTONG20052650 | 100 | 0 |
| NTONG20056570 | 100 | 0 |
| NTONG20061870 | 100 | 0 |
| NTONG20063010 | 40.505 | 0 |
| NTONG20064400 | 100 | 0 |
| NTONG20064840 | 31.857 | 0 |
| NTONG20065010 | 100 | 0 |
| NTONG20066460 | 100 | 0 |
| NTONG20067090 | 66.789 | 0 |
| NTONG20067830 | 20.865 | 0 |
| NTONG20070200 | 100 | 0 |
| NTONG20070340 | 52.247 | 0 |
| NTONG20075220 | 100 | 0 |
| NTONG20076930 | 51.858 | 0 |
| NTONG20077560 | 49.744 | 0 |
| NTONG20083650 | 100 | 0 |
| NTONG20088620 | 100 | 0 |
| NTONG20090600 | 20.536 | 0 |
| NTONG20090680 | 100 | 0 |
| NTONG20092290 | 100 | 0 |
| NTONG20092330 | 100 | 0 |
| OCBBF20068490 | 14.895 | 0 |
| SKMUS20001980 | 23.281 | 0 |
| SMINT20138900 | 67.622 | 0 |
| SPLEN20008390 | 67.269 | 0 |
| SPLEN20162680 | 3.184 | 0 |
| UTERU20134910 | 86.071 | 0 |
| ASTRO20155290 | 13.655 | 3.451 |
| FEBRA20080810 | 10.438 | 1.319 |
| NT2RP70032610 | 10.013 | 27.835 |
| NT2RP70036880 | 5.442 | 16.504 |
| NTONG20015870 | 17.552 | 0.554 |
| OCBBF20188730 | 10.213 | 2.581 |
| SMINT20122910 | 33.985 | 8.589 |
| SPLEN20099700 | 37.585 | 9.499 |

TABLE 16

| Clone ID | FC-BBF | FEBRA | OCBBF | BRACE | BRALZ | BRAMY | BRAWH | BRCAN | BRCOC | BRHIP | BRSSN | BRSTN | BRTHA |
|---|---|---|---|---|---|---|---|---|---|---|---|---|---|
| 3NB6910001910 | 0 | 0 | 0 | 0 | 0 | 0 | 6.122 | 0 | 0 | 6.246 | 0 | 0 | 0 |
| ADRGL20018300 | 0 | 0 | 0 | 8.483 | 0 | 0 | 0 | 0 | 0 | 0 | 0 | 0 | 0 |
| ASTRO20001410 | 0 | 0 | 0 | 0 | 0 | 3.06 | 0 | 0 | 0 | 0 | 0 | 0 | 0 |
| ASTRO20033160 | 0 | 0 | 0 | 2.094 | 0 | 0 | 2.95 | 0 | 0 | 0 | 0 | 0 | 0 |
| ASTRO20058630 | 0 | 0 | 0 | 0 | 0 | 0 | 7.603 | 0 | 0 | 0 | 0 | 0 | 0 |
| ASTRO20064750 | 0 | 0 | 0 | 0 | 0 | 7.505 | 0 | 0 | 0 | 0 | 0 | 0 | 16.519 |
| ASTRO20100720 | 0 | 0 | 0 | 0 | 0 | 0 | 0 | 39.838 | 0 | 0 | 0 | 0 | 0 |
| ASTRO20141350 | 0 | 0 | 0 | 0 | 0 | 0 | 0 | 0 | 12.305 | 0 | 0 | 0 | 0 |
| ASTRO20145760 | 0 | 0 | 0 | 0 | 0 | 11.388 | 0 | 0 | 0 | 0 | 42.066 | 0 | 0 |
| ASTRO20181690 | 0 | 0 | 0 | 0 | 0 | 0.952 | 0 | 2.167 | 0 | 1.927 | 0 | 0 | 0 |
| BGGI120006160 | 0 | 0 | 0 | 1.269 | 0 | 0.901 | 0 | 2.051 | 0 | 0 | 0 | 3.224 | 0.991 |
| BRACE20006400 | 0 | 0 | 0 | 100 | 0 | 0 | 0 | 0 | 0 | 0 | 0 | 0 | 0 |
| BRACE20011070 | 0 | 0 | 0 | 10.447 | 53.184 | 0 | 0 | 0 | 0 | 0 | 0 | 0 | 0 |
| BRACE20019540 | 0 | 0 | 0 | 100 | 0 | 0 | 0 | 0 | 0 | 0 | 0 | 0 | 0 |
| BRACE20027620 | 0 | 0 | 0 | 100 | 0 | 0 | 0 | 0 | 0 | 0 | 0 | 0 | 0 |
| BRACE20037660 | 0 | 0 | 0 | 100 | 0 | 0 | 0 | 0 | 0 | 0 | 0 | 0 | 0 |
| BRACE20038000 | 0 | 0 | 0 | 38.906 | 0 | 0 | 0 | 0 | 0 | 0 | 0 | 0 | 30.394 |
| BRACE20038470 | 0 | 0 | 0 | 100 | 0 | 0 | 0 | 0 | 0 | 0 | 0 | 0 | 0 |
| BRACE20038480 | 0 | 0 | 0 | 38.787 | 0 | 0 | 0 | 0 | 0 | 0 | 0 | 0 | 0 |
| BRACE20038850 | 0 | 0 | 0 | 100 | 0 | 0 | 0 | 0 | 0 | 0 | 0 | 0 | 0 |
| BRACE20039440 | 0 | 0 | 0 | 0.367 | 0 | 2.086 | 0.518 | 1.188 | 1.834 | 0 | 1.927 | 1.867 | 0 |
| BRACE20039540 | 0 | 0 | 0 | 16.746 | 0 | 0 | 0 | 0 | 0 | 0 | 0 | 0 | 0 |
| BRACE20050900 | 0 | 0 | 0 | 52.057 | 0 | 0 | 0 | 0 | 0 | 0 | 0 | 0 | 0 |
| BRACE20051380 | 0 | 0 | 0 | 100 | 0 | 0 | 0 | 0 | 0 | 0 | 0 | 0 | 0 |
| BRACE20051690 | 0 | 0 | 0 | 100 | 0 | 0 | 0 | 0 | 0 | 0 | 0 | 0 | 0 |
| BRACE20052160 | 0 | 0 | 0 | 100 | 0 | 0 | 0 | 0 | 0 | 0 | 0 | 0 | 0 |
| BRACE20053280 | 0 | 0 | 0 | 100 | 0 | 0 | 0 | 0 | 0 | 0 | 0 | 0 | 0 |
| BRACE20053480 | 0 | 0 | 0 | 100 | 0 | 0 | 0 | 0 | 0 | 0 | 0 | 0 | 0 |
| BRACE20053630 | 0 | 0 | 0 | 10.086 | 0 | 0 | 0 | 0 | 0 | 0 | 0 | 0 | 0 |
| BRACE20054500 | 0 | 0 | 0 | 100 | 0 | 0 | 0 | 0 | 0 | 0 | 0 | 0 | 0 |
| BRACE20055180 | 0 | 0 | 0 | 100 | 0 | 0 | 0 | 0 | 0 | 0 | 0 | 0 | 0 |
| BRACE20057420 | 0 | 0 | 0 | 100 | 0 | 0 | 0 | 0 | 0 | 0 | 0 | 0 | 0 |
| BRACE20057620 | 0 | 0 | 0 | 100 | 0 | 0 | 0 | 0 | 0 | 0 | 0 | 0 | 0 |
| BRACE20057730 | 0 | 0 | 0 | 100 | 0 | 0 | 0 | 0 | 0 | 0 | 0 | 0 | 0 |
| BRACE20058580 | 0 | 0 | 0 | 14.668 | 0 | 0 | 41.331 | 0 | 0 | 21.084 | 0 | 0 | 22.917 |
| BRACE20058810 | 0 | 0 | 0 | 100 | 0 | 0 | 0 | 0 | 0 | 0 | 0 | 0 | 0 |

TABLE 17

| Clone ID | FC-BBF | FEBRA | OCBBF | BRACE | BRALZ | BRAMY | BRAWH | BRCAN | BRCOC | BRHIP | BRSSN | BRSTN | BRTHA |
|---|---|---|---|---|---|---|---|---|---|---|---|---|---|
| BRACE20060840 | 0 | 0 | 0 | 2.179 | 0 | 3.093 | 0 | 14.084 | 0 | 0 | 0 | 11.067 | 0 |
| BRACE20060890 | 0 | 0 | 0 | 54.983 | 0 | 0 | 16.309 | 0 | 0 | 0 | 0 | 0 | 0 |
| BRACE20061050 | 0 | 0 | 0 | 15.058 | 0 | 0 | 0 | 0 | 0 | 0 | 0 | 0 | 0 |
| BRACE20061740 | 0 | 0 | 0 | 100 | 0 | 0 | 0 | 0 | 0 | 0 | 0 | 0 | 0 |
| BRACE20062400 | 0 | 0 | 0 | 100 | 0 | 0 | 0 | 0 | 0 | 0 | 0 | 0 | 0 |
| BRACE20062740 | 0 | 0 | 0 | 41.329 | 0 | 58.671 | 0 | 0 | 0 | 0 | 0 | 0 | 0 |
| BRACE20063630 | 0 | 0 | 0 | 26.312 | 0 | 9.338 | 0 | 21.263 | 0 | 0 | 0 | 0 | 0 |
| BRACE20063780 | 0 | 0 | 0 | 38.787 | 0 | 0 | 0 | 0 | 0 | 0 | 0 | 0 | 0 |
| BRACE20063800 | 0 | 0 | 0 | 58.183 | 0 | 0 | 0 | 0 | 41.817 | 0 | 0 | 0 | 0 |
| BRACE20063930 | 0 | 0 | 0 | 100 | 0 | 0 | 0 | 0 | 0 | 0 | 0 | 0 | 0 |
| BRACE20064880 | 0 | 0 | 0 | 100 | 0 | 0 | 0 | 0 | 0 | 0 | 0 | 0 | 0 |
| BRACE20068590 | 0 | 0 | 0 | 7.211 | 0 | 0 | 0 | 0 | 0 | 0 | 0 | 11.267 | 0 |
| BRACE20069090 | 0 | 0 | 0 | 100 | 0 | 0 | 0 | 0 | 0 | 0 | 0 | 0 | 0 |
| BRACE20081720 | 0 | 0 | 0 | 100 | 0 | 0 | 0 | 0 | 0 | 0 | 0 | 0 | 0 |
| BRACE20082950 | 0 | 0 | 0 | 100 | 0 | 0 | 0 | 0 | 0 | 0 | 0 | 0 | 0 |
| BRACE20096200 | 0 | 0 | 0 | 13.619 | 0 | 0 | 0 | 0 | 0 | 0 | 0 | 0 | 0 |
| BRACE20096540 | 0 | 0 | 0 | 100 | 0 | 0 | 0 | 0 | 0 | 0 | 0 | 0 | 0 |
| BRACE20097320 | 0 | 0 | 0 | 100 | 0 | 0 | 0 | 0 | 0 | 0 | 0 | 0 | 0 |
| BRACE20101700 | 0 | 0 | 0 | 100 | 0 | 0 | 0 | 0 | 0 | 0 | 0 | 0 | 0 |
| BRACE20101710 | 0 | 0 | 0 | 100 | 0 | 0 | 0 | 0 | 0 | 0 | 0 | 0 | 0 |
| BRACE20106840 | 0 | 0 | 0 | 38.787 | 0 | 0 | 0 | 0 | 0 | 0 | 0 | 0 | 0 |
| BRACE20107530 | 0 | 0 | 0 | 13.239 | 0 | 0 | 0 | 66.077 | 0 | 0 | 0 | 20.684 | 0 |
| BRACE20108130 | 0 | 0 | 0 | 100 | 0 | 0 | 0 | 0 | 0 | 0 | 0 | 0 | 0 |
| BRACE20108880 | 0 | 0 | 0 | 100 | 0 | 0 | 0 | 0 | 0 | 0 | 0 | 0 | 0 |
| BRACE20109370 | 0 | 0 | 0 | 100 | 0 | 0 | 0 | 0 | 0 | 0 | 0 | 0 | 0 |
| BRACE20109830 | 0 | 0 | 0 | 100 | 0 | 0 | 0 | 0 | 0 | 0 | 0 | 0 | 0 |
| BRACE20114780 | 0 | 0 | 0 | 100 | 0 | 0 | 0 | 0 | 0 | 0 | 0 | 0 | 0 |
| BRACE20115450 | 0 | 0 | 0 | 100 | 0 | 0 | 0 | 0 | 0 | 0 | 0 | 0 | 0 |
| BRACE20115920 | 0 | 0 | 0 | 100 | 0 | 0 | 0 | 0 | 0 | 0 | 0 | 0 | 0 |
| BRACE20116110 | 0 | 0 | 0 | 100 | 0 | 0 | 0 | 0 | 0 | 0 | 0 | 0 | 0 |
| BRACE20116460 | 0 | 0 | 0 | 100 | 0 | 0 | 0 | 0 | 0 | 0 | 0 | 0 | 0 |
| BRACE20118380 | 0 | 0 | 0 | 100 | 0 | 0 | 0 | 0 | 0 | 0 | 0 | 0 | 0 |
| BRACE20121850 | 0 | 0 | 0 | 100 | 0 | 0 | 0 | 0 | 0 | 0 | 0 | 0 | 0 |
| BRACE20141080 | 0 | 0 | 0 | 100 | 0 | 0 | 0 | 0 | 0 | 0 | 0 | 0 | 0 |

TABLE 17-continued

| | | | | | | | | | | | | | |
|---|---|---|---|---|---|---|---|---|---|---|---|---|---|
| BRACE20142320 | 0 | 0 | 0 | 100 | 0 | 0 | 0 | 0 | 0 | 0 | 0 | 0 | 0 |
| BRACE20147800 | 0 | 0 | 0 | 100 | 0 | 0 | 0 | 0 | 0 | 0 | 0 | 0 | 0 |
| BRACE20148210 | 0 | 0 | 0 | 100 | 0 | 0 | 0 | 0 | 0 | 0 | 0 | 0 | 0 |

TABLE 18

| | | | | | | | | | | | | | |
|---|---|---|---|---|---|---|---|---|---|---|---|---|---|
| BRACE20148240 | 0 | 0 | 0 | 100 | 0 | 0 | 0 | 0 | 0 | 0 | 0 | 0 | 0 |
| BRACE20150310 | 0 | 0 | 0 | 100 | 0 | 0 | 0 | 0 | 0 | 0 | 0 | 0 | 0 |
| BRACE20151320 | 0 | 0 | 0 | 11.694 | 0 | 0 | 0 | 0 | 58.366 | 0 | 0 | 0 | 0 |
| BRACE20152870 | 0 | 0 | 0 | 1.63 | 0 | 0 | 0 | 0 | 8.135 | 0 | 0 | 0 | 2.547 |
| BRACE20153680 | 0 | 0 | 0 | 41.512 | 0 | 0 | 58.488 | 0 | 0 | 0 | 0 | 0 | 0 |
| BRACE20154120 | 0 | 0 | 0 | 17.282 | 0 | 0 | 12.174 | 0 | 0 | 0 | 0 | 0 | 0 |
| BRACE20163150 | 0 | 0 | 0 | 100 | 0 | 0 | 0 | 0 | 0 | 0 | 0 | 0 | 0 |
| BRACE20163350 | 0 | 0 | 0 | 9.897 | 0 | 0 | 0 | 0 | 0 | 0 | 0 | 0 | 0 |
| BRACE20165830 | 0 | 0 | 0 | 100 | 0 | 0 | 0 | 0 | 0 | 0 | 0 | 0 | 0 |
| BRACE20171240 | 0 | 0 | 0 | 100 | 0 | 0 | 0 | 0 | 0 | 0 | 0 | 0 | 0 |
| BRACE20172980 | 0 | 0 | 0 | 100 | 0 | 0 | 0 | 0 | 0 | 0 | 0 | 0 | 0 |
| BRACE20175870 | 0 | 0 | 0 | 100 | 0 | 0 | 0 | 0 | 0 | 0 | 0 | 0 | 0 |
| BRACE20177200 | 0 | 0 | 0 | 100 | 0 | 0 | 0 | 0 | 0 | 0 | 0 | 0 | 0 |
| BRACE20179340 | 0 | 0 | 0 | 13.12 | 0 | 0 | 0 | 0 | 0 | 0 | 0 | 33.326 | 0 |
| BRACE20185680 | 0 | 0 | 0 | 100 | 0 | 0 | 0 | 0 | 0 | 0 | 0 | 0 | 0 |
| BRACE20188470 | 0 | 0 | 0 | 13.846 | 0 | 0 | 39.016 | 0 | 0 | 0 | 0 | 0 | 21.634 |
| BRACE20190040 | 0 | 0 | 0 | 39.025 | 0 | 0 | 0 | 0 | 0 | 0 | 0 | 0 | 60.975 |
| BRACE20190440 | 0 | 0 | 0 | 100 | 0 | 0 | 0 | 0 | 0 | 0 | 0 | 0 | 0 |
| BRACE20192440 | 0 | 0 | 0 | 28.977 | 0 | 0 | 0 | 0 | 0 | 0 | 0 | 0 | 0 |
| BRACE20195100 | 0 | 0 | 0 | 100 | 0 | 0 | 0 | 0 | 0 | 0 | 0 | 0 | 0 |
| BRACE20201570 | 0 | 0 | 0 | 100 | 0 | 0 | 0 | 0 | 0 | 0 | 0 | 0 | 0 |
| BRACE20220300 | 0 | 0 | 0 | 100 | 0 | 0 | 0 | 0 | 0 | 0 | 0 | 0 | 0 |
| BRACE20223280 | 0 | 0 | 0 | 100 | 0 | 0 | 0 | 0 | 0 | 0 | 0 | 0 | 0 |
| BRACE20223330 | 0 | 0 | 0 | 12.602 | 0 | 0 | 17.756 | 0 | 0 | 18.115 | 0 | 0 | 19.69 |
| BRACE20224480 | 0 | 0 | 0 | 100 | 0 | 0 | 0 | 0 | 0 | 0 | 0 | 0 | 0 |
| BRACE20224500 | 0 | 0 | 0 | 100 | 0 | 0 | 0 | 0 | 0 | 0 | 0 | 0 | 0 |
| BRACE20228480 | 0 | 0 | 0 | 100 | 0 | 0 | 0 | 0 | 0 | 0 | 0 | 0 | 0 |
| BRACE20229280 | 0 | 0 | 0 | 100 | 0 | 0 | 0 | 0 | 0 | 0 | 0 | 0 | 0 |
| BRACE20230700 | 0 | 0 | 0 | 100 | 0 | 0 | 0 | 0 | 0 | 0 | 0 | 0 | 0 |
| BRACE20232840 | 0 | 0 | 0 | 100 | 0 | 0 | 0 | 0 | 0 | 0 | 0 | 0 | 0 |
| BRACE20235400 | 0 | 0 | 0 | 100 | 0 | 0 | 0 | 0 | 0 | 0 | 0 | 0 | 0 |
| BRACE20237270 | 0 | 0 | 0 | 14.013 | 0 | 0 | 0 | 0 | 0 | 0 | 0 | 0 | 0 |
| BRACE20238000 | 0 | 0 | 0 | 100 | 0 | 0 | 0 | 0 | 0 | 0 | 0 | 0 | 0 |
| BRACE20240740 | 0 | 0 | 0 | 45.981 | 0 | 0 | 0 | 0 | 0 | 0 | 0 | 0 | 0 |
| BRACE20248260 | 0 | 0 | 0 | 100 | 0 | 0 | 0 | 0 | 0 | 0 | 0 | 0 | 0 |
| BRACE20253160 | 0 | 0 | 0 | 100 | 0 | 0 | 0 | 0 | 0 | 0 | 0 | 0 | 0 |
| BRACE20253330 | 0 | 0 | 0 | 100 | 0 | 0 | 0 | 0 | 0 | 0 | 0 | 0 | 0 |

TABLE 19

| | | | | | | | | | | | | | |
|---|---|---|---|---|---|---|---|---|---|---|---|---|---|
| BRACE20257100 | 0 | 0 | 0 | 100 | 0 | 0 | 0 | 0 | 0 | 0 | 0 | 0 | 0 |
| BRACE20262930 | 0 | 0 | 0 | 100 | 0 | 0 | 0 | 0 | 0 | 0 | 0 | 0 | 0 |
| BRACE20262940 | 0 | 0 | 0 | 100 | 0 | 0 | 0 | 0 | 0 | 0 | 0 | 0 | 0 |
| BRACE20266750 | 0 | 0 | 0 | 100 | 0 | 0 | 0 | 0 | 0 | 0 | 0 | 0 | 0 |
| BRACE20267250 | 0 | 0 | 0 | 13.014 | 0 | 0 | 0 | 0 | 0 | 0 | 0 | 0 | 0 |
| BRACE20269200 | 0 | 0 | 0 | 100 | 0 | 0 | 0 | 0 | 0 | 0 | 0 | 0 | 0 |
| BRACE20269710 | 0 | 0 | 0 | 100 | 0 | 0 | 0 | 0 | 0 | 0 | 0 | 0 | 0 |
| BRACE20273890 | 0 | 0 | 0 | 100 | 0 | 0 | 0 | 0 | 0 | 0 | 0 | 0 | 0 |
| BRACE20274080 | 0 | 0 | 0 | 100 | 0 | 0 | 0 | 0 | 0 | 0 | 0 | 0 | 0 |
| BRACE20283920 | 0 | 0 | 0 | 7.236 | 0 | 0 | 0 | 0 | 18.058 | 0 | 37.945 | 36.76 | 0 |
| BRACE20284100 | 0 | 0 | 0 | 100 | 0 | 0 | 0 | 0 | 0 | 0 | 0 | 0 | 0 |
| BRACE20286360 | 0 | 0 | 0 | 37.993 | 48.354 | 0 | 0 | 0 | 0 | 13.653 | 0 | 0 | 0 |
| BRACE20287410 | 0 | 0 | 0 | 100 | 0 | 0 | 0 | 0 | 0 | 0 | 0 | 0 | 0 |
| BRALZ20013500 | 0 | 0 | 0 | 0 | 100 | 0 | 0 | 0 | 0 | 0 | 0 | 0 | 0 |
| BRALZ20014450 | 0 | 0 | 0 | 0 | 100 | 0 | 0 | 0 | 0 | 0 | 0 | 0 | 0 |
| BRALZ20017430 | 0 | 0 | 0 | 0 | 100 | 0 | 0 | 0 | 0 | 0 | 0 | 0 | 0 |
| BRALZ20018340 | 0 | 0 | 0 | 0 | 76.517 | 0 | 0 | 0 | 0 | 0 | 0 | 0 | 23.483 |
| BRALZ20054710 | 0 | 0 | 0 | 0 | 100 | 0 | 0 | 0 | 0 | 0 | 0 | 0 | 0 |
| BRALZ20058880 | 0 | 0 | 0 | 0 | 100 | 0 | 0 | 0 | 0 | 0 | 0 | 0 | 0 |
| BRALZ20059500 | 0 | 0 | 0 | 0 | 100 | 0 | 0 | 0 | 0 | 0 | 0 | 0 | 0 |
| BRALZ20064740 | 0 | 0 | 0 | 0 | 100 | 0 | 0 | 0 | 0 | 0 | 0 | 0 | 0 |
| BRALZ20065600 | 0 | 0 | 0 | 0 | 100 | 0 | 0 | 0 | 0 | 0 | 0 | 0 | 0 |
| BRALZ20069760 | 0 | 0 | 0 | 0 | 100 | 0 | 0 | 0 | 0 | 0 | 0 | 0 | 0 |
| BRALZ20073760 | 0 | 0 | 0 | 0 | 100 | 0 | 0 | 0 | 0 | 0 | 0 | 0 | 0 |
| BRALZ20075450 | 0 | 0 | 0 | 0 | 100 | 0 | 0 | 0 | 0 | 0 | 0 | 0 | 0 |
| BRALZ20075760 | 0 | 0 | 0 | 0 | 100 | 0 | 0 | 0 | 0 | 0 | 0 | 0 | 0 |
| BRALZ20077900 | 0 | 0 | 0 | 0 | 100 | 0 | 0 | 0 | 0 | 0 | 0 | 0 | 0 |
| BRALZ20077930 | 0 | 0 | 0 | 0 | 100 | 0 | 0 | 0 | 0 | 0 | 0 | 0 | 0 |

TABLE 19-continued

| | | | | | | | | | | | | |
|---|---|---|---|---|---|---|---|---|---|---|---|---|
| BRALZ20080310 | 0 | 0 | 0 | 0 | 100 | 0 | 0 | 0 | 0 | 0 | 0 | 0 |
| BRALZ20088690 | 0 | 0 | 0 | 0 | 100 | 0 | 0 | 0 | 0 | 0 | 0 | 0 |
| BRAMY10001300 | 0 | 0 | 0 | 0 | 0 | 12.137 | 0 | 0 | 0 | 0 | 0 | 0 |
| BRAMY10001570 | 0 | 0 | 0 | 0 | 0 | 100 | 0 | 0 | 0 | 0 | 0 | 0 |
| BRAMY20000520 | 0 | 0 | 0 | 0 | 39.13 | 21.823 | 0 | 0 | 0 | 0 | 39.047 | 0 |
| BRAMY20000860 | 0 | 0 | 0 | 0 | 0 | 100 | 0 | 0 | 0 | 0 | 0 | 0 |
| BRAMY20002770 | 0 | 0 | 0 | 0 | 0 | 100 | 0 | 0 | 0 | 0 | 0 | 0 |
| BRAMY20004110 | 0 | 0 | 0 | 4.399 | 0 | 18.735 | 0 | 0 | 0 | 12.647 | 23.069 | 0 | 0 |
| BRAMY20011140 | 0 | 0 | 0 | 0 | 0 | 100 | 0 | 0 | 0 | 0 | 0 | 0 |

TABLE 20

| | | | | | | | | | | | | |
|---|---|---|---|---|---|---|---|---|---|---|---|---|
| BRAMY20025840 | 0 | 0 | 0 | 0 | 0 | 100 | 0 | 0 | 0 | 0 | 0 | 0 | 0 |
| BRAMY20039260 | 0 | 0 | 0 | 0 | 0 | 100 | 0 | 0 | 0 | 0 | 0 | 0 | 0 |
| BRAMY20045240 | 0 | 0 | 0 | 0 | 0 | 21.841 | 0 | 0 | 0 | 0 | 0 | 78.159 | 0 |
| BRAMY20054880 | 0 | 0 | 0 | 8.088 | 0 | 22.964 | 0 | 0 | 40.37 | 11.626 | 0 | 0 | 0 |
| BRAMY20060920 | 0 | 0 | 0 | 0 | 0 | 100 | 0 | 0 | 0 | 0 | 0 | 0 | 0 |
| BRAMY20063970 | 0 | 0 | 0 | 0 | 0 | 2.83 | 0 | 6.443 | 0 | 2.865 | 10.452 | 0 | 0 |
| BRAMY20071850 | 0 | 0 | 0 | 0 | 0 | 100 | 0 | 0 | 0 | 0 | 0 | 0 | 0 |
| BRAMY20102080 | 0 | 0 | 0 | 0 | 0 | 36.63 | 0 | 0 | 0 | 0 | 0 | 0 | 0 |
| BRAMY20104640 | 0 | 0 | 0 | 15.639 | 0 | 33.302 | 11.017 | 0 | 0 | 0 | 0 | 0 | 0 |
| BRAMY20110640 | 0 | 0 | 0 | 0 | 0 | 100 | 0 | 0 | 0 | 0 | 0 | 0 | 0 |
| BRAMY20111960 | 0 | 0 | 0 | 0 | 0 | 100 | 0 | 0 | 0 | 0 | 0 | 0 | 0 |
| BRAMY20116790 | 0 | 0 | 0 | 0 | 0 | 100 | 0 | 0 | 0 | 0 | 0 | 0 | 0 |
| BRAMY20121190 | 0 | 0 | 0 | 0 | 0 | 100 | 0 | 0 | 0 | 0 | 0 | 0 | 0 |
| BRAMY20121620 | 0 | 0 | 0 | 0 | 0 | 100 | 0 | 0 | 0 | 0 | 0 | 0 | 0 |
| BRAMY20124260 | 0 | 0 | 0 | 0 | 0 | 6.228 | 0 | 0 | 0 | 0 | 0 | 0 | 0 |
| BRAMY20134140 | 0 | 0 | 0 | 0 | 0 | 100 | 0 | 0 | 0 | 0 | 0 | 0 | 0 |
| BRAMY20135900 | 0 | 0 | 0 | 0 | 0 | 43.537 | 0 | 0 | 0 | 0 | 0 | 0 | 0 |
| BRAMY20136210 | 0 | 0 | 0 | 0 | 0 | 29.482 | 0 | 0 | 0 | 0 | 0 | 0 | 0 |
| BRAMY20137560 | 0 | 0 | 0 | 0 | 0 | 19.026 | 0 | 0 | 0 | 0 | 0 | 0 | 0 |
| BRAMY20144620 | 0 | 0 | 0 | 0 | 0 | 49.688 | 0 | 0 | 0 | 50.312 | 0 | 0 | 0 |
| BRAMY20147540 | 0 | 0 | 0 | 5.965 | 5.061 | 4.234 | 5.603 | 12.854 | 9.924 | 27.152 | 10.427 | 0 | 12.427 |
| BRAMY20148130 | 0 | 0 | 0 | 0 | 0 | 19.441 | 0 | 0 | 0 | 0 | 0 | 0 | 0 |
| BRAMY20152110 | 0 | 0 | 0 | 0 | 0 | 13.088 | 0 | 0 | 0 | 0 | 0 | 0 | 0 |
| BRAMY20153110 | 0 | 0 | 0 | 0 | 0 | 100 | 0 | 0 | 0 | 0 | 0 | 0 | 0 |
| BRAMY20157820 | 0 | 0 | 0 | 0 | 0 | 7.891 | 0 | 0 | 0 | 0 | 0 | 0 | 0 |
| BRAMY20160700 | 0 | 0 | 0 | 0 | 0 | 100 | 0 | 0 | 0 | 0 | 0 | 0 | 0 |
| BRAMY20163250 | 0 | 0 | 0 | 0 | 0 | 3.796 | 11.304 | 0 | 0 | 3.844 | 0 | 0 | 4.178 |
| BRAMY20163270 | 0 | 0 | 0 | 0 | 0 | 100 | 0 | 0 | 0 | 0 | 0 | 0 | 0 |
| BRAMY20167060 | 0 | 0 | 0 | 0 | 0 | 4.994 | 0 | 0 | 0 | 0 | 0 | 0 | 0 |
| BRAMY20167710 | 0 | 0 | 0 | 0 | 0 | 100 | 0 | 0 | 0 | 0 | 0 | 0 | 0 |
| BRAMY20168920 | 0 | 0 | 0 | 10.306 | 0 | 14.63 | 14.52 | 0 | 0 | 44.442 | 0 | 0 | 16.102 |
| BRAMY20170140 | 0 | 0 | 0 | 0 | 0 | 100 | 0 | 0 | 0 | 0 | 0 | 0 | 0 |
| BRAMY20174550 | 0 | 0 | 0 | 0 | 0 | 100 | 0 | 0 | 0 | 0 | 0 | 0 | 0 |
| BRAMY20178640 | 0 | 0 | 0 | 0 | 0 | 13.922 | 0 | 0 | 0 | 14.097 | 51.427 | 0 | 0 |
| BRAMY20181220 | 0 | 0 | 0 | 0 | 0 | 12.783 | 0 | 0 | 0 | 0 | 0 | 0 | 0 |
| BRAMY20182730 | 0 | 0 | 0 | 0 | 0 | 100 | 0 | 0 | 0 | 0 | 0 | 0 | 0 |
| BRAMY20183080 | 0 | 0 | 0 | 0 | 0 | 100 | 0 | 0 | 0 | 0 | 0 | 0 | 0 |

TABLE 21

| | | | | | | | | | | | | |
|---|---|---|---|---|---|---|---|---|---|---|---|---|
| BRAMY20184670 | 0 | 0 | 0 | 0 | 0 | 100 | 0 | 0 | 0 | 0 | 0 | 0 | 0 |
| BRAMY20195090 | 0 | 0 | 0 | 0 | 0 | 100 | 0 | 0 | 0 | 0 | 0 | 0 | 0 |
| BRAMY20204450 | 0 | 0 | 0 | 0 | 0 | 100 | 0 | 0 | 0 | 0 | 0 | 0 | 0 |
| BRAMY20205740 | 0 | 0 | 0 | 0 | 0 | 100 | 0 | 0 | 0 | 0 | 0 | 0 | 0 |
| BRAMY20210400 | 0 | 0 | 0 | 0 | 0 | 100 | 0 | 0 | 0 | 0 | 0 | 0 | 0 |
| BRAMY20211390 | 0 | 0 | 0 | 0 | 0 | 25.787 | 0 | 0 | 0 | 0 | 0 | 0 | 0 |
| BRAMY20211420 | 0 | 0 | 0 | 38.011 | 0 | 26.981 | 0 | 0 | 0 | 0 | 0 | 0 | 0 |
| BRAMY20213100 | 0 | 0 | 0 | 0 | 0 | 12.518 | 0 | 0 | 0 | 0 | 0 | 0 | 0 |
| BRAMY20215230 | 0 | 0 | 0 | 0 | 0 | 21.367 | 0 | 0 | 0 | 0 | 0 | 0 | 0 |
| BRAMY20217460 | 0 | 0 | 0 | 0 | 0 | 100 | 0 | 0 | 0 | 0 | 0 | 0 | 0 |
| BRAMY20218250 | 0 | 0 | 0 | 0 | 0 | 66.389 | 0 | 0 | 0 | 33.611 | 0 | 0 | 0 |
| BRAMY20218670 | 0 | 0 | 0 | 25.113 | 0 | 35.65 | 0 | 0 | 0 | 0 | 0 | 0 | 39.237 |
| BRAMY20229800 | 0 | 0 | 0 | 0 | 0 | 15.383 | 30.533 | 0 | 54.084 | 0 | 0 | 0 | 0 |
| BRAMY20229840 | 0 | 0 | 0 | 0 | 0 | 100 | 0 | 0 | 0 | 0 | 0 | 0 | 0 |
| BRAMY20230600 | 0 | 0 | 0 | 0 | 0 | 100 | 0 | 0 | 0 | 0 | 0 | 0 | 0 |
| BRAMY20231720 | 0 | 0 | 0 | 0 | 0 | 100 | 0 | 0 | 0 | 0 | 0 | 0 | 0 |
| BRAMY20240040 | 0 | 0 | 0 | 1.963 | 0 | 2.787 | 0 | 6.346 | 9.799 | 0 | 0 | 0 | 3.067 |
| BRAMY20245300 | 0 | 0 | 0 | 0 | 0 | 100 | 0 | 0 | 0 | 0 | 0 | 0 | 0 |
| BRAMY20247110 | 0 | 0 | 0 | 0 | 0 | 12.354 | 0 | 0 | 43.436 | 0 | 0 | 44.21 | 0 |
| BRAMY20247280 | 0 | 0 | 0 | 0 | 0 | 100 | 0 | 0 | 0 | 0 | 0 | 0 | 0 |
| BRAMY20248490 | 0 | 0 | 0 | 0 | 0 | 100 | 0 | 0 | 0 | 0 | 0 | 0 | 0 |
| BRAMY20250240 | 0 | 0 | 0 | 0 | 0 | 100 | 0 | 0 | 0 | 0 | 0 | 0 | 0 |

TABLE 21-continued

| | | | | | | | | | | | | | |
|---|---|---|---|---|---|---|---|---|---|---|---|---|---|
| BRAMY20250320 | 0 | 0 | 0 | 0 | 0 | 100 | 0 | 0 | 0 | 0 | 0 | 0 | 0 |
| BRAMY20252180 | 0 | 0 | 0 | 0 | 0 | 100 | 0 | 0 | 0 | 0 | 0 | 0 | 0 |
| BRAMY20252720 | 0 | 0 | 0 | 0 | 0 | 47.605 | 0 | 0 | 0 | 0 | 0 | 0 | 52.395 |
| BRAMY20260910 | 0 | 0 | 0 | 0 | 0 | 100 | 0 | 0 | 0 | 0 | 0 | 0 | 0 |
| BRAMY20261680 | 0 | 0 | 0 | 0 | 0 | 32.33 | 32.087 | 0 | 0 | 0 | 0 | 0 | 35.583 |
| BRAMY20266850 | 0 | 0 | 0 | 0 | 0 | 2.497 | 0 | 0 | 0 | 0 | 0 | 0 | 0 |
| BRAMY20267130 | 0 | 0 | 0 | 0 | 0 | 100 | 0 | 0 | 0 | 0 | 0 | 0 | 0 |
| BRAMY20268990 | 0 | 0 | 0 | 0 | 0 | 100 | 0 | 0 | 0 | 0 | 0 | 0 | 0 |
| BRAMY20270730 | 0 | 0 | 0 | 0 | 0 | 100 | 0 | 0 | 0 | 0 | 0 | 0 | 0 |
| BRAMY20271400 | 0 | 0 | 0 | 0 | 0 | 51.968 | 0 | 0 | 0 | 0 | 0 | 0 | 0 |
| BRAMY20273960 | 0 | 0 | 0 | 0 | 0 | 100 | 0 | 0 | 0 | 0 | 0 | 0 | 0 |
| BRAMY20277140 | 0 | 0 | 0 | 0 | 0 | 100 | 0 | 0 | 0 | 0 | 0 | 0 | 0 |
| BRAMY20277170 | 0 | 0 | 0 | 0 | 0 | 16.593 | 20.585 | 0 | 0 | 12.601 | 0 | 0 | 50.221 |
| BRAMY20280720 | 0 | 0 | 0 | 0 | 0 | 100 | 0 | 0 | 0 | 0 | 0 | 0 | 0 |
| BRAMY20284910 | 0 | 0 | 0 | 0 | 0 | 36.15 | 0 | 0 | 0 | 0 | 0 | 0 | 0 |

TABLE 22

| | | | | | | | | | | | | | |
|---|---|---|---|---|---|---|---|---|---|---|---|---|---|
| BRAMY20285160 | 0 | 0 | 0 | 0 | 0 | 3.974 | 0 | 0 | 0 | 0 | 14.68 | 0 | 0 |
| BRAMY20285930 | 0 | 0 | 0 | 0 | 0 | 100 | 0 | 0 | 0 | 0 | 0 | 0 | 0 |
| BRAMY20286820 | 0 | 0 | 0 | 0 | 0 | 21.396 | 0 | 0 | 0 | 0 | 0 | 0 | 0 |
| BRAWH20002320 | 0 | 0 | 0 | 0 | 0 | 0 | 100 | 0 | 0 | 0 | 0 | 0 | 0 |
| BRAWH20012390 | 0 | 0 | 0 | 0 | 0 | 0 | 7.296 | 0 | 0 | 0 | 27.156 | 0 | 8.091 |
| BRAWH20014920 | 0 | 0 | 0 | 0 | 0 | 0 | 100 | 0 | 0 | 0 | 0 | 0 | 0 |
| BRAWH20015350 | 0 | 0 | 0 | 0 | 5.352 | 6.965 | 1.975 | 15.859 | 5.247 | 10.075 | 16.539 | 14.243 | 10.951 |
| BRAWH20015890 | 0 | 0 | 0 | 0 | 0 | 0 | 100 | 0 | 0 | 0 | 0 | 0 | 0 |
| BRAWH20016660 | 0 | 0 | 0 | 0 | 0 | 0 | 100 | 0 | 0 | 0 | 0 | 0 | 0 |
| BRAWH20016860 | 0 | 0 | 0 | 0 | 0 | 0 | 100 | 0 | 0 | 0 | 0 | 0 | 0 |
| BRAWH20017010 | 0 | 0 | 0 | 0 | 0 | 0 | 100 | 0 | 0 | 0 | 0 | 0 | 0 |
| BRAWH20018730 | 0 | 0 | 0 | 0 | 0 | 0 | 100 | 0 | 0 | 0 | 0 | 0 | 0 |
| BRAWH20028110 | 0 | 0 | 0 | 0 | 31.162 | 17.379 | 8.624 | 0 | 0 | 17.598 | 0 | 0 | 9.564 |
| BRAWH20029630 | 0 | 0 | 0 | 8.469 | 0 | 0 | 11.932 | 0 | 0 | 0 | 0 | 0 | 0 |
| BRAWH20064050 | 0 | 0 | 0 | 0 | 0 | 0 | 12.977 | 0 | 0 | 13.24 | 0 | 0 | 0 |
| BRAWH20075700 | 0 | 0 | 0 | 0 | 0 | 0 | 100 | 0 | 0 | 0 | 0 | 0 | 0 |
| BRAWH20096780 | 0 | 0 | 0 | 0 | 0 | 0 | 21.269 | 0 | 0 | 0 | 0 | 0 | 0 |
| BRAWH20100690 | 0 | 0 | 0 | 0 | 0 | 0 | 100 | 0 | 0 | 0 | 0 | 0 | 0 |
| BRAWH20101360 | 0 | 0 | 0 | 0 | 0 | 26.605 | 26.404 | 0 | 0 | 0 | 0 | 0 | 0 |
| BRAWH20103180 | 0 | 0 | 0 | 0 | 0 | 0 | 100 | 0 | 0 | 0 | 0 | 0 | 0 |
| BRAWH20105840 | 0 | 0 | 0 | 0 | 0 | 0 | 30.356 | 69.644 | 0 | 0 | 0 | 0 | 0 |
| BRAWH20106180 | 0 | 0 | 0 | 0 | 0 | 0 | 100 | 0 | 0 | 0 | 0 | 0 | 0 |
| BRAWH20107540 | 0 | 0 | 0 | 7.94 | 0 | 0 | 11.186 | 0 | 0 | 0 | 0 | 40.334 | 0 |
| BRAWH20110660 | 0 | 0 | 0 | 0 | 0 | 0 | 21.178 | 0 | 0 | 0 | 78.822 | 0 | 0 |
| BRAWH20110790 | 0 | 0 | 0 | 0 | 0 | 0 | 100 | 0 | 0 | 0 | 0 | 0 | 0 |
| BRAWH20110960 | 0 | 0 | 0 | 0 | 0 | 0 | 54.53 | 0 | 0 | 0 | 0 | 0 | 0 |
| BRAWH20111550 | 0 | 0 | 0 | 0 | 0 | 0 | 100 | 0 | 0 | 0 | 0 | 0 | 0 |
| BRAWH20112940 | 0 | 0 | 0 | 0 | 0 | 0 | 100 | 0 | 0 | 0 | 0 | 0 | 0 |
| BRAWH20114000 | 0 | 0 | 0 | 0 | 0 | 0 | 100 | 0 | 0 | 0 | 0 | 0 | 0 |
| BRAWH20117950 | 0 | 0 | 0 | 0 | 0 | 0 | 100 | 0 | 0 | 0 | 0 | 0 | 0 |
| BRAWH20118230 | 0 | 0 | 0 | 0 | 0 | 0 | 21.626 | 0 | 0 | 0 | 0 | 0 | 0 |
| BRAWH20122580 | 0 | 0 | 0 | 0 | 0 | 0 | 100 | 0 | 0 | 0 | 0 | 0 | 0 |
| BRAWH20125380 | 0 | 0 | 0 | 0 | 0 | 0 | 10.145 | 0 | 0 | 0 | 18.88 | 0 | 0 |
| BRAWH20126190 | 0 | 0 | 0 | 0 | 0 | 0 | 100 | 0 | 0 | 0 | 0 | 0 | 0 |
| BRAWH20126980 | 0 | 0 | 0 | 0 | 0 | 57.958 | 19.174 | 0 | 0 | 0 | 0 | 0 | 0 |
| BRAWH20132190 | 0 | 0 | 0 | 0 | 35.004 | 9.761 | 19.375 | 0 | 0 | 0 | 0 | 0 | 0 |
| BRAWH20137480 | 0 | 0 | 0 | 0 | 0 | 8.068 | 2.669 | 6.123 | 9.455 | 2.723 | 9.934 | 0 | 2.96 |

TABLE 23

| | | | | | | | | | | | | | |
|---|---|---|---|---|---|---|---|---|---|---|---|---|---|
| BRAWH20138660 | 0 | 0 | 0 | 0 | 0 | 0 | 100 | 0 | 0 | 0 | 0 | 0 | 0 |
| BRAWH20139410 | 0 | 0 | 0 | 0 | 0 | 0 | 100 | 0 | 0 | 0 | 0 | 0 | 0 |
| BRAWH20142340 | 0 | 0 | 0 | 0 | 0 | 0 | 100 | 0 | 0 | 0 | 0 | 0 | 0 |
| BRAWH20147290 | 0 | 0 | 0 | 0 | 0 | 0 | 100 | 0 | 0 | 0 | 0 | 0 | 0 |
| BRAWH20149340 | 0 | 0 | 0 | 0 | 0 | 0 | 35.975 | 0 | 0 | 0 | 0 | 0 | 0 |
| BRAWH20155950 | 0 | 0 | 0 | 0 | 0 | 0 | 100 | 0 | 0 | 0 | 0 | 0 | 0 |
| BRAWH20158530 | 0 | 0 | 0 | 0 | 0 | 0 | 100 | 0 | 0 | 0 | 0 | 0 | 0 |
| BRAWH20160280 | 0 | 0 | 0 | 0 | 0 | 50.189 | 49.811 | 0 | 0 | 0 | 0 | 0 | 0 |
| BRAWH20162690 | 0 | 0 | 0 | 0.936 | 0 | 1.328 | 1.318 | 3.025 | 4.67 | 0 | 4.907 | 0 | 0 |
| BRAWH20166790 | 0 | 0 | 0 | 6.839 | 0 | 0 | 9.636 | 0 | 0 | 0 | 0 | 0 | 0 |
| BRAWH20171030 | 0 | 0 | 0 | 0 | 0 | 0 | 100 | 0 | 0 | 0 | 0 | 0 | 0 |
| BRAWH20173050 | 0 | 0 | 0 | 0 | 0 | 0 | 100 | 0 | 0 | 0 | 0 | 0 | 0 |
| BRAWH20182060 | 0 | 0 | 0 | 0 | 0 | 0 | 11.051 | 0 | 0 | 11.275 | 0 | 0 | 36.766 |
| BRAWH20185060 | 0 | 0 | 0 | 0 | 0 | 0 | 100 | 0 | 0 | 0 | 0 | 0 | 0 |
| BRCAN10001490 | 0 | 0 | 0 | 0 | 0 | 0 | 0 | 56.874 | 0 | 0 | 0 | 0 | 0 |
| BRCAN20003460 | 0 | 0 | 0 | 0 | 0 | 0 | 0 | 100 | 0 | 0 | 0 | 0 | 0 |

TABLE 23-continued

| | | | | | | | | | | | | | |
|---|---|---|---|---|---|---|---|---|---|---|---|---|---|
| BRCAN20006200 | 0 | 0 | 0 | 0 | 0 | 0 | 0 | 100 | 0 | 0 | 0 | 0 | 0 |
| BRCAN20006390 | 0 | 0 | 0 | 0 | 0 | 0 | 0 | 38.481 | 0 | 0 | 0 | 0 | 0 |
| BRCAN20054490 | 0 | 0 | 0 | 0 | 0 | 0 | 0 | 100 | 0 | 0 | 0 | 0 | 0 |
| BRCAN20060190 | 0 | 0 | 0 | 2.666 | 13.575 | 0 | 0 | 25.857 | 26.617 | 3.833 | 0 | 13.546 | 0 |
| BRCAN20064010 | 0 | 0 | 0 | 0 | 0 | 22.844 | 0 | 52.014 | 0 | 0 | 0 | 0 | 25.142 |
| BRCAN20071190 | 0 | 0 | 0 | 0 | 0 | 0 | 0 | 38.885 | 0 | 0 | 0 | 61.115 | 0 |
| BRCAN20091560 | 0 | 0 | 0 | 0 | 0 | 0 | 0 | 100 | 0 | 0 | 0 | 0 | 0 |
| BRCAN20103740 | 0 | 0 | 0 | 0 | 0 | 30.516 | 0 | 69.484 | 0 | 0 | 0 | 0 | 0 |
| BRCAN20124080 | 0 | 0 | 0 | 0 | 0 | 0 | 0 | 100 | 0 | 0 | 0 | 0 | 0 |
| BRCAN20126130 | 0 | 0 | 0 | 0 | 0 | 0 | 0 | 100 | 0 | 0 | 0 | 0 | 0 |
| BRCAN20143700 | 0 | 0 | 0 | 0 | 0 | 0 | 0 | 100 | 0 | 0 | 0 | 0 | 0 |
| BRCAN20147880 | 0 | 0 | 0 | 0 | 0 | 0 | 0 | 100 | 0 | 0 | 0 | 0 | 0 |
| BRCAN20216690 | 0 | 0 | 0 | 0 | 0 | 0 | 0 | 100 | 0 | 0 | 0 | 0 | 0 |
| BRCAN20224720 | 0 | 0 | 0 | 0 | 0 | 0 | 0 | 100 | 0 | 0 | 0 | 0 | 0 |
| BRCAN20237240 | 0 | 0 | 0 | 0 | 0 | 0 | 0 | 100 | 0 | 0 | 0 | 0 | 0 |
| BRCAN20263400 | 0 | 0 | 0 | 10.726 | 54.604 | 0 | 0 | 34.67 | 0 | 0 | 0 | 0 | 0 |
| BRCAN20273100 | 0 | 0 | 0 | 0 | 0 | 0 | 0 | 100 | 0 | 0 | 0 | 0 | 0 |
| BRCAN20273340 | 0 | 0 | 0 | 0 | 0 | 30.516 | 0 | 69.484 | 0 | 0 | 0 | 0 | 0 |
| BRCAN20273550 | 0 | 0 | 0 | 0 | 0 | 0 | 0 | 100 | 0 | 0 | 0 | 0 | 0 |
| BRCAN20275130 | 0 | 0 | 0 | 0 | 0 | 0 | 0 | 100 | 0 | 0 | 0 | 0 | 0 |
| BRCAN20279700 | 0 | 0 | 0 | 0 | 0 | 0 | 0 | 100 | 0 | 0 | 0 | 0 | 0 |

TABLE 24

| | | | | | | | | | | | | | |
|---|---|---|---|---|---|---|---|---|---|---|---|---|---|
| BRCAN20280210 | 0 | 0 | 0 | 0 | 0 | 0 | 0 | 100 | 0 | 0 | 0 | 0 | 0 |
| BRCAN20280400 | 0 | 0 | 0 | 0 | 0 | 0 | 0 | 60.666 | 0 | 0 | 0 | 0 | 0 |
| BRCAN20283190 | 0 | 0 | 0 | 0 | 0 | 0 | 0 | 29.858 | 0 | 0 | 48.439 | 0 | 0 |
| BRCAN20283380 | 0 | 0 | 0 | 0 | 0 | 0 | 0 | 100 | 0 | 0 | 0 | 0 | 0 |
| BRCAN20284600 | 0 | 0 | 0 | 0 | 0 | 0 | 0 | 100 | 0 | 0 | 0 | 0 | 0 |
| BRCAN20285450 | 0 | 0 | 0 | 0 | 0 | 0 | 0 | 38.885 | 0 | 0 | 0 | 61.115 | 0 |
| BRCOC10000870 | 0 | 0 | 0 | 0 | 0 | 0 | 0 | 0 | 100 | 0 | 0 | 0 | 0 |
| BRCOC20001860 | 0 | 0 | 0 | 4.222 | 0 | 0 | 0 | 0 | 10.537 | 0 | 0 | 0 | 0 |
| BRCOC20004040 | 0 | 0 | 0 | 0 | 0 | 0 | 0 | 0 | 100 | 0 | 0 | 0 | 0 |
| BRCOC20004870 | 0 | 0 | 0 | 0 | 0 | 0 | 0 | 0.665 | 1.026 | 0 | 0 | 0 | 0.643 |
| BRCOC20006370 | 0 | 0 | 0 | 0 | 0 | 0 | 0 | 0 | 100 | 0 | 0 | 0 | 0 |
| BRCOC20008160 | 0 | 0 | 0 | 0 | 0 | 0 | 22.014 | 0 | 77.986 | 0 | 0 | 0 | 0 |
| BRCOC20008500 | 0 | 0 | 0 | 0 | 0 | 0 | 0 | 0 | 100 | 0 | 0 | 0 | 0 |
| BRCOC20020850 | 0 | 0 | 0 | 0 | 0 | 0 | 0 | 0 | 100 | 0 | 0 | 0 | 0 |
| BRCOC20021550 | 0 | 0 | 0 | 0 | 0 | 0 | 0 | 0 | 75.977 | 0 | 0 | 0 | 0 |
| BRCOC20023230 | 0 | 0 | 0 | 0 | 0 | 0 | 0 | 0 | 100 | 0 | 0 | 0 | 0 |
| BRCOC20026640 | 0 | 0 | 0 | 0 | 0 | 0 | 0 | 0 | 100 | 0 | 0 | 0 | 0 |
| BRCOC20027510 | 0 | 0 | 0 | 0 | 0 | 0 | 0 | 0 | 100 | 0 | 0 | 0 | 0 |
| BRCOC20031000 | 0 | 0 | 0 | 16.691 | 0 | 0 | 0 | 0 | 83.309 | 0 | 0 | 0 | 0 |
| BRCOC20031250 | 0 | 0 | 0 | 0 | 0 | 0 | 0 | 0 | 20.131 | 0 | 0 | 0 | 0 |
| BRCOC20031870 | 0 | 0 | 0 | 0.558 | 0 | 0 | 0.786 | 1.804 | 2.786 | 0 | 5.854 | 2.836 | 0 |
| BRCOC20035130 | 0 | 0 | 0 | 0 | 0 | 0 | 0 | 0 | 100 | 0 | 0 | 0 | 0 |
| BRCOC20037320 | 0 | 0 | 0 | 0 | 0 | 0 | 0 | 0 | 75.977 | 0 | 0 | 0 | 0 |
| BRCOC20037400 | 0 | 0 | 0 | 0 | 0 | 0 | 0 | 0 | 100 | 0 | 0 | 0 | 0 |
| BRCOC20041750 | 0 | 0 | 0 | 0 | 0 | 0 | 0 | 0 | 34.465 | 0 | 0 | 0 | 0 |
| BRCOC20055420 | 0 | 0 | 0 | 0 | 0 | 17.805 | 0 | 0 | 62.599 | 0 | 0 | 0 | 19.596 |
| BRCOC20059510 | 0 | 0 | 0 | 0 | 0 | 0 | 0 | 0 | 100 | 0 | 0 | 0 | 0 |
| BRCOC20077690 | 0 | 0 | 0 | 0 | 0 | 0 | 0 | 0 | 100 | 0 | 0 | 0 | 0 |
| BRCOC20090520 | 0 | 0 | 0 | 0 | 0 | 0 | 0 | 0 | 100 | 0 | 0 | 0 | 0 |
| BRCOC20091960 | 0 | 0 | 0 | 0 | 0 | 0 | 0 | 0 | 100 | 0 | 0 | 0 | 0 |
| BRCOC20093800 | 0 | 0 | 0 | 0 | 0 | 0 | 0 | 0 | 100 | 0 | 0 | 0 | 0 |
| BRCOC20099370 | 0 | 0 | 0 | 0 | 0 | 16.189 | 0 | 0 | 56.917 | 16.392 | 0 | 0 | 0 |
| BRCOC20101230 | 0 | 0 | 0 | 0 | 0 | 0 | 0 | 2.513 | 3.881 | 0 | 0 | 0 | 0 |
| BRCOC20107300 | 0 | 0 | 0 | 0 | 0 | 0 | 0 | 0 | 38.292 | 0 | 0 | 0 | 11.987 |
| BRCOC20110100 | 0 | 0 | 0 | 0 | 0 | 0 | 0 | 0 | 100 | 0 | 0 | 0 | 0 |
| BRCOC20114180 | 0 | 0 | 0 | 0 | 0 | 0 | 0 | 0 | 100 | 0 | 0 | 0 | 0 |
| BRCOC20117690 | 0 | 0 | 0 | 0 | 0 | 0 | 0 | 0 | 100 | 0 | 0 | 0 | 0 |

TABLE 25

| | | | | | | | | | | | | | |
|---|---|---|---|---|---|---|---|---|---|---|---|---|---|
| BRCOC20119960 | 0 | 0 | 0 | 0 | 0 | 0 | 0 | 0 | 100 | 0 | 0 | 0 | 0 |
| BRCOC20121720 | 0 | 0 | 0 | 1.996 | 0 | 0 | 0 | 0 | 9.965 | 2.87 | 0 | 0 | 3.119 |
| BRCOC20122290 | 0 | 0 | 0 | 0 | 0 | 0 | 0 | 0 | 100 | 0 | 0 | 0 | 0 |
| BRCOC20128130 | 0 | 0 | 0 | 0 | 0 | 0 | 0 | 39.306 | 60.694 | 0 | 0 | 0 | 0 |
| BRCOC20134480 | 0 | 0 | 0 | 0 | 0 | 0 | 0 | 0 | 100 | 0 | 0 | 0 | 0 |
| BRCOC20135730 | 0 | 0 | 0 | 0 | 0 | 0 | 0 | 0 | 100 | 0 | 0 | 0 | 0 |
| BRCOC20136750 | 0 | 0 | 0 | 0 | 0 | 0 | 0 | 0 | 100 | 0 | 0 | 0 | 0 |
| BRCOC20144000 | 0 | 0 | 0 | 0 | 0 | 0 | 0 | 0 | 59.512 | 0 | 0 | 0 | 0 |
| BRCOC20147480 | 0 | 0 | 0 | 0 | 0 | 0 | 0 | 0 | 100 | 0 | 0 | 0 | 0 |
| BRCOC20148330 | 0 | 0 | 0 | 0 | 0 | 0 | 0 | 0 | 100 | 0 | 0 | 0 | 0 |

TABLE 25-continued

| | | | | | | | | | | | | | |
|---|---|---|---|---|---|---|---|---|---|---|---|---|---|
| BRCOC20155970 | 0 | 0 | 0 | 0 | 0 | 0 | 0 | 0 | 74.813 | 0 | 0 | 0 | 0 |
| BRCOC20158240 | 0 | 0 | 0 | 0 | 0 | 0 | 0 | 0 | 100 | 0 | 0 | 0 | 0 |
| BRCOC20176520 | 0 | 0 | 0 | 0 | 0 | 0 | 0 | 0 | 48.902 | 0 | 0 | 0 | 0 |
| BRCOC20178560 | 0 | 0 | 0 | 0 | 0 | 0 | 0 | 0 | 100 | 0 | 0 | 0 | 0 |
| BRHIP10001290 | 0 | 0 | 0 | 0 | 0 | 49.688 | 0 | 0 | 0 | 50.312 | 0 | 0 | 0 |
| BRHIP20000870 | 0 | 0 | 0 | 0 | 23.781 | 6.632 | 0 | 0 | 0 | 13.429 | 24.496 | 0 | 7.299 |
| BRHIP20001630 | 0 | 0 | 0 | 0 | 0 | 0 | 37.398 | 0 | 0 | 38.155 | 0 | 0 | 0 |
| BRHIP20096170 | 0 | 0 | 0 | 0 | 0 | 0 | 0 | 0 | 0 | 100 | 0 | 0 | 0 |
| BRHIP20096850 | 0 | 0 | 0 | 0 | 0 | 0 | 7.124 | 0 | 0 | 7.269 | 0 | 0 | 7.901 |
| BRHIP20103090 | 0 | 0 | 0 | 0 | 0 | 0 | 0 | 0 | 0 | 100 | 0 | 0 | 0 |
| BRHIP20104440 | 0 | 0 | 0 | 0 | 0 | 0 | 0 | 0 | 0 | 47.917 | 0 | 0 | 52.083 |
| BRHIP20105710 | 0 | 0 | 0 | 21.859 | 0 | 15.515 | 0 | 0 | 0 | 31.42 | 0 | 0 | 0 |
| BRHIP20106100 | 0 | 0 | 0 | 0 | 0 | 0 | 0 | 0 | 0 | 100 | 0 | 0 | 0 |
| BRHIP20107440 | 0 | 0 | 0 | 0 | 0 | 0 | 0 | 0 | 0 | 100 | 0 | 0 | 0 |
| BRHIP20111200 | 0 | 0 | 0 | 32.686 | 0 | 7.734 | 15.351 | 0 | 0 | 15.661 | 28.568 | 0 | 0 |
| BRHIP20115080 | 0 | 0 | 0 | 0 | 0 | 0 | 0 | 0 | 0 | 22.032 | 0 | 0 | 23.948 |
| BRHIP20115760 | 0 | 0 | 0 | 13.607 | 0 | 0 | 0 | 0 | 0 | 19.559 | 0 | 0 | 0 |
| BRHIP20118380 | 0 | 0 | 0 | 0 | 0 | 0 | 0 | 0 | 0 | 100 | 0 | 0 | 0 |
| BRHIP20118910 | 0 | 0 | 0 | 0 | 0 | 0 | 0 | 0 | 0 | 60.949 | 0 | 0 | 0 |
| BRHIP20119330 | 0 | 0 | 0 | 0 | 0 | 0 | 0 | 0 | 0 | 100 | 0 | 0 | 0 |
| BRHIP20121410 | 0 | 0 | 0 | 0 | 0 | 0 | 0 | 0 | 0 | 47.917 | 0 | 0 | 52.083 |
| BRHIP20123140 | 0 | 0 | 0 | 0 | 0 | 0 | 0 | 0 | 0 | 100 | 0 | 0 | 0 |
| BRHIP20129720 | 0 | 0 | 0 | 0 | 0 | 0 | 0 | 0 | 0 | 47.917 | 0 | 0 | 52.083 |
| BRHIP20132860 | 0 | 0 | 0 | 0 | 0 | 0 | 0 | 0 | 0 | 17.468 | 0 | 0 | 0 |
| BRHIP20135100 | 0 | 0 | 0 | 0 | 0 | 0 | 0 | 0 | 0 | 100 | 0 | 0 | 0 |
| BRHIP20137230 | 0 | 0 | 0 | 0 | 0 | 0 | 0 | 0 | 0 | 100 | 0 | 0 | 0 |
| BRHIP20139720 | 0 | 0 | 0 | 0 | 0 | 0 | 0 | 0 | 0 | 100 | 0 | 0 | 0 |

TABLE 26

| | | | | | | | | | | | | | |
|---|---|---|---|---|---|---|---|---|---|---|---|---|---|
| BRHIP20140630 | 0 | 0 | 0 | 0 | 0 | 0 | 0 | 0 | 0 | 36.967 | 0 | 0 | 0 |
| BRHIP20142850 | 0 | 0 | 0 | 0 | 0 | 0 | 0 | 0 | 0 | 100 | 0 | 0 | 0 |
| BRHIP20143730 | 0 | 0 | 0 | 0 | 0 | 0 | 0 | 0 | 0 | 34.432 | 0 | 0 | 37.426 |
| BRHIP20143860 | 0 | 0 | 0 | 0 | 0 | 0 | 0 | 0 | 0 | 55.026 | 0 | 0 | 0 |
| BRHIP20149540 | 0 | 0 | 0 | 0 | 0 | 0 | 0 | 0 | 0 | 100 | 0 | 0 | 0 |
| BRHIP20153560 | 0 | 0 | 0 | 0 | 0 | 0 | 0 | 0 | 0 | 100 | 0 | 0 | 0 |
| BRHIP20153600 | 0 | 0 | 0 | 0 | 0 | 0 | 0 | 0 | 0 | 100 | 0 | 0 | 0 |
| BRHIP20167880 | 0 | 0 | 0 | 0 | 0 | 0 | 0 | 0 | 0 | 100 | 0 | 0 | 0 |
| BRHIP20169680 | 0 | 0 | 0 | 0 | 0 | 0 | 0 | 0 | 0 | 100 | 0 | 0 | 0 |
| BRHIP20169900 | 0 | 0 | 0 | 0 | 0 | 0 | 0 | 0 | 0 | 100 | 0 | 0 | 0 |
| BRHIP20170100 | 0 | 0 | 0 | 0 | 0 | 0 | 0 | 0 | 0 | 14.025 | 0 | 0 | 0 |
| BRHIP20173150 | 0 | 0 | 0 | 0 | 0 | 0 | 0 | 0 | 0 | 100 | 0 | 0 | 0 |
| BRHIP20174040 | 0 | 0 | 0 | 0 | 0 | 0 | 0 | 0 | 0 | 100 | 0 | 0 | 0 |
| BRHIP20175420 | 0 | 0 | 0 | 0 | 0 | 0 | 0 | 0 | 0 | 100 | 0 | 0 | 0 |
| BRHIP20180140 | 0 | 0 | 0 | 0 | 0 | 0 | 0 | 0 | 0 | 100 | 0 | 0 | 0 |
| BRHIP20183690 | 0 | 0 | 0 | 0 | 0 | 0 | 0 | 0 | 0 | 100 | 0 | 0 | 0 |
| BRHIP20186120 | 0 | 0 | 0 | 0 | 0 | 0 | 0 | 0 | 0 | 100 | 0 | 0 | 0 |
| BRHIP20186500 | 0 | 0 | 0 | 0 | 0 | 0 | 0 | 0 | 0 | 100 | 0 | 0 | 0 |
| BRHIP20189980 | 0 | 0 | 0 | 0 | 0 | 0 | 0 | 0 | 0 | 100 | 0 | 0 | 0 |
| BRHIP20190070 | 0 | 0 | 0 | 0 | 0 | 0 | 0 | 0 | 0 | 100 | 0 | 0 | 0 |
| BRHIP20191490 | 0 | 0 | 0 | 0 | 0 | 0 | 0 | 0 | 0 | 11.267 | 0 | 0 | 0 |
| BRHIP20191770 | 0 | 0 | 0 | 0 | 0 | 0 | 0 | 0 | 0 | 100 | 0 | 0 | 0 |
| BRHIP20194940 | 0 | 0 | 0 | 25.807 | 0 | 0 | 0 | 0 | 0 | 74.193 | 0 | 0 | 0 |
| BRHIP20195890 | 0 | 0 | 0 | 0 | 0 | 0 | 0 | 0 | 0 | 100 | 0 | 0 | 0 |
| BRHIP20196410 | 0 | 0 | 0 | 0 | 0 | 0 | 0 | 0 | 0 | 100 | 0 | 0 | 0 |
| BRHIP20205090 | 0 | 0 | 0 | 0 | 0 | 0 | 0 | 0 | 0 | 19.104 | 0 | 0 | 0 |
| BRHIP20207430 | 0 | 0 | 0 | 0 | 0 | 0 | 0 | 0 | 0 | 100 | 0 | 0 | 0 |
| BRHIP20207990 | 0 | 0 | 0 | 3.592 | 0 | 15.298 | 5.061 | 0 | 0 | 36.143 | 0 | 0 | 5.612 |
| BRHIP20208420 | 0 | 0 | 0 | 0 | 0 | 0 | 0 | 0 | 0 | 100 | 0 | 0 | 0 |
| BRHIP20208590 | 0 | 0 | 0 | 0 | 0 | 0 | 0 | 0 | 0 | 100 | 0 | 0 | 0 |
| BRHIP20227080 | 0 | 0 | 0 | 0 | 0 | 0 | 0 | 0 | 0 | 100 | 0 | 0 | 0 |
| BRHIP20230710 | 0 | 0 | 0 | 0 | 0 | 49.688 | 0 | 0 | 0 | 50.312 | 0 | 0 | 0 |
| BRHIP20232290 | 0 | 0 | 0 | 0 | 0 | 0 | 0 | 0 | 0 | 15.312 | 0 | 0 | 0 |
| BRHIP20233090 | 0 | 0 | 0 | 8.28 | 0 | 0 | 11.666 | 0 | 0 | 23.804 | 0 | 0 | 0 |
| BRHIP20234380 | 0 | 0 | 0 | 0 | 0 | 0 | 0 | 0 | 0 | 26.026 | 0 | 0 | 0 |
| BRHIP20236950 | 0 | 0 | 0 | 0 | 0 | 0 | 0 | 0 | 0 | 36.438 | 0 | 0 | 0 |
| BRHIP20238600 | 0 | 0 | 0 | 0 | 0 | 0 | 0 | 0 | 0 | 100 | 0 | 0 | 0 |

TABLE 27

| | | | | | | | | | | | | | |
|---|---|---|---|---|---|---|---|---|---|---|---|---|---|
| BRHIP20238690 | 0 | 0 | 0 | 0 | 0 | 0 | 0 | 0 | 0 | 36.661 | 0 | 0 | 39.849 |
| BRHIP20240460 | 0 | 0 | 0 | 0 | 0 | 0 | 0 | 0 | 0 | 31.291 | 0 | 0 | 0 |
| BRHIP20243470 | 0 | 0 | 0 | 0 | 0 | 0 | 0 | 0 | 0 | 100 | 0 | 0 | 0 |
| BRHIP20249110 | 0 | 0 | 0 | 0 | 0 | 0 | 0 | 0 | 0 | 9.456 | 0 | 0 | 0 |

TABLE 27-continued

| | | | | | | | | | | | | | |
|---|---|---|---|---|---|---|---|---|---|---|---|---|---|
| BRHIP20252450 | 0 | 0 | 0 | 0 | 0 | 0 | 0 | 0 | 0 | 47.666 | 0 | 0 | 0 |
| BRHIP20253660 | 0 | 0 | 0 | 0 | 0 | 0 | 0 | 0 | 0 | 100 | 0 | 0 | 0 |
| BRHIP20277620 | 0 | 0 | 0 | 0 | 0 | 0 | 0 | 0 | 0 | 100 | 0 | 0 | 0 |
| BRHIP20283030 | 0 | 0 | 0 | 0 | 0 | 0 | 0 | 0 | 0 | 100 | 0 | 0 | 0 |
| BRHIP20284800 | 0 | 0 | 0 | 0 | 0 | 0 | 0 | 0 | 0 | 100 | 0 | 0 | 0 |
| BRHIP20285830 | 0 | 0 | 0 | 0 | 0 | 0 | 0 | 0 | 0 | 12.691 | 0 | 0 | 0 |
| BRHIP20285930 | 0 | 0 | 0 | 0 | 0 | 0 | 0 | 0 | 0 | 100 | 0 | 0 | 0 |
| BRHIP30004880 | 0 | 0 | 0 | 0 | 0 | 0 | 0 | 0 | 0 | 100 | 0 | 0 | 0 |
| BRSSN10000920 | 0 | 0 | 0 | 0 | 0 | 0 | 0 | 0 | 0 | 0 | 100 | 0 | 0 |
| BRSSN20013420 | 0 | 0 | 0 | 0 | 0 | 0 | 0 | 0 | 0 | 0 | 100 | 0 | 0 |
| BRSSN20014260 | 0 | 0 | 0 | 0 | 0 | 0 | 0 | 0 | 0 | 0 | 100 | 0 | 0 |
| BRSSN20015030 | 0 | 0 | 0 | 0 | 0 | 0 | 0 | 0 | 0 | 0 | 100 | 0 | 0 |
| BRSSN20015790 | 0 | 0 | 0 | 0 | 0 | 0 | 0 | 0 | 0 | 0 | 50.137 | 0 | 0 |
| BRSSN20018690 | 0 | 0 | 0 | 2.142 | 0 | 0 | 0 | 6.925 | 0 | 0 | 11.235 | 0 | 6.695 |
| BRSSN20028570 | 0 | 0 | 0 | 0 | 0 | 0 | 0 | 0 | 0 | 0 | 100 | 0 | 0 |
| BRSSN20038200 | 0 | 0 | 0 | 0 | 0 | 0 | 0 | 0 | 0 | 0 | 100 | 0 | 0 |
| BRSSN20038410 | 0 | 0 | 0 | 0 | 0 | 0 | 0 | 0 | 0 | 0 | 100 | 0 | 0 |
| BRSSN20039370 | 0 | 0 | 0 | 0 | 0 | 0 | 0 | 0 | 0 | 0 | 100 | 0 | 0 |
| BRSSN20043040 | 0 | 0 | 0 | 0 | 0 | 0 | 0 | 0 | 0 | 0 | 100 | 0 | 0 |
| BRSSN20046570 | 0 | 0 | 0 | 0 | 0 | 0 | 0 | 0 | 0 | 0 | 85.061 | 0 | 0 |
| BRSSN20046790 | 0 | 0 | 0 | 0 | 0 | 0 | 0 | 0 | 0 | 0 | 56.646 | 0 | 16.878 |
| BRSSN20046860 | 0 | 0 | 0 | 0 | 0 | 0 | 0 | 0 | 0 | 0 | 100 | 0 | 0 |
| BRSSN20066110 | 0 | 0 | 0 | 0 | 0 | 21.304 | 0 | 0 | 0 | 0 | 78.696 | 0 | 0 |
| BRSSN20097020 | 0 | 0 | 0 | 0 | 0 | 0 | 0 | 0 | 0 | 0 | 100 | 0 | 0 |
| BRSSN20101100 | 0 | 0 | 0 | 0 | 0 | 0 | 0 | 0 | 0 | 0 | 100 | 0 | 0 |
| BRSSN20105870 | 0 | 0 | 0 | 16.015 | 0 | 0 | 0 | 0 | 0 | 0 | 83.985 | 0 | 0 |
| BRSSN20105960 | 0 | 0 | 0 | 0 | 43.31 | 12.077 | 0 | 0 | 0 | 0 | 44.612 | 0 | 0 |
| BRSSN20108300 | 0 | 0 | 0 | 0 | 0 | 0 | 0 | 0 | 0 | 0 | 100 | 0 | 0 |
| BRSSN20120810 | 0 | 0 | 0 | 0 | 0 | 0 | 0 | 0 | 0 | 0 | 100 | 0 | 0 |
| BRSSN20121030 | 0 | 0 | 0 | 0 | 0 | 0 | 0 | 0 | 0 | 0 | 100 | 0 | 0 |
| BRSSN20137020 | 0 | 0 | 0 | 0 | 0 | 0 | 0 | 0 | 33.606 | 0 | 35.308 | 0 | 0 |
| BRSSN20142940 | 0 | 0 | 0 | 0 | 0 | 0 | 0 | 0 | 0 | 0 | 34.652 | 0 | 0 |
| BRSSN20146100 | 0 | 0 | 0 | 5.068 | 0 | 3.597 | 0 | 0 | 0 | 10.927 | 13.288 | 0 | 11.878 |

TABLE 28

| | | | | | | | | | | | | | |
|---|---|---|---|---|---|---|---|---|---|---|---|---|---|
| BRSSN20151990 | 0 | 0 | 0 | 16.015 | 0 | 0 | 0 | 0 | 0 | 0 | 83.985 | 0 | 0 |
| BRSSN20159070 | 0 | 0 | 0 | 0 | 0 | 0 | 0 | 0 | 0 | 0 | 100 | 0 | 0 |
| BRSSN20159820 | 0 | 0 | 0 | 0 | 0 | 0 | 0 | 0 | 0 | 0 | 60.467 | 0 | 0 |
| BRSSN20169050 | 0 | 0 | 0 | 0 | 0 | 0 | 0 | 0 | 0 | 0 | 100 | 0 | 0 |
| BRSSN20176820 | 0 | 0 | 0 | 0 | 0 | 0 | 0 | 0 | 0 | 0 | 100 | 0 | 0 |
| BRSSN20177570 | 0 | 0 | 0 | 0 | 0 | 0 | 0 | 0 | 0 | 0 | 100 | 0 | 0 |
| BRSSN20187310 | 0 | 0 | 0 | 0 | 0 | 0 | 0 | 0 | 0 | 0 | 100 | 0 | 0 |
| BRSTN20000580 | 0 | 0 | 0 | 3.424 | 0 | 2.431 | 0 | 33.205 | 25.637 | 0 | 8.978 | 17.396 | 0 |
| BRSTN20005360 | 0 | 0 | 0 | 0 | 0 | 0 | 0 | 0 | 0 | 22.055 | 0 | 77.945 | 0 |
| BRTHA20000570 | 0 | 0 | 0 | 0 | 0 | 0 | 0 | 0 | 0 | 0 | 0 | 0 | 48.181 |
| BRTHA20004740 | 0 | 0 | 0 | 0 | 0 | 0 | 0 | 0 | 0 | 0 | 0 | 0 | 100 |
| BRTHA20046290 | 0 | 0 | 0 | 0 | 0 | 0 | 0 | 0 | 0 | 0 | 0 | 0 | 100 |
| BRTHA20046390 | 0 | 0 | 0 | 0 | 0 | 0 | 0 | 0 | 0 | 0 | 0 | 0 | 100 |
| BRTHA20046420 | 0 | 0 | 0 | 0 | 0 | 0 | 0 | 0 | 0 | 0 | 0 | 0 | 100 |
| CD34C30001250 | 0 | 0 | 0 | 0 | 0 | 0 | 0 | 0 | 0 | 2.372 | 0 | 0 | 0 |
| CD34C30004240 | 0 | 0 | 0 | 0 | 0 | 0 | 0 | 0 | 0 | 2.336 | 0 | 0 | 0 |
| CTONG10000100 | 0 | 0 | 0 | 0 | 0 | 6.532 | 0 | 0 | 0 | 0 | 0 | 0 | 7.19 |
| CTONG20004690 | 0 | 0 | 0 | 0 | 0 | 0 | 0 | 0 | 10.345 | 0 | 0 | 0 | 0 |
| CTONG20027090 | 0 | 0 | 0 | 1.538 | 0 | 0 | 0 | 0 | 0 | 0 | 0 | 0 | 0 |
| CTONG20050280 | 0 | 0 | 0 | 14.575 | 0 | 0 | 6.845 | 0 | 0 | 0 | 0 | 0 | 7.591 |
| CTONG20076130 | 0 | 0 | 0 | 0 | 0 | 0 | 0 | 0 | 0 | 0 | 0 | 0 | 9.707 |
| CTONG20077790 | 0 | 0 | 0 | 0 | 0 | 0 | 0 | 0 | 0 | 0 | 0 | 0 | 37.32 |
| CTONG20095290 | 0 | 0 | 0 | 0 | 0 | 0 | 0 | 14.506 | 0 | 0 | 0 | 0 | 0 |
| CTONG20095340 | 0 | 0 | 0 | 16.375 | 0 | 0 | 0 | 0 | 0 | 23.537 | 28.623 | 0 | 8.528 |
| CTONG20099380 | 0 | 0 | 0 | 0 | 0 | 0 | 0 | 0 | 0 | 0 | 0 | 0 | 22.188 |
| CTONG20106520 | 0 | 0 | 0 | 0 | 0 | 0 | 0 | 0 | 0 | 0 | 0 | 0 | 35.648 |
| CTONG20118250 | 0 | 0 | 0 | 6.093 | 0 | 0 | 0 | 0 | 0 | 0 | 0 | 0 | 0 |
| CTONG20121010 | 0 | 0 | 0 | 0 | 0 | 15.907 | 0 | 0 | 0 | 0 | 0 | 0 | 0 |
| CTONG20127450 | 0 | 0 | 0 | 0 | 0 | 0 | 0 | 0 | 0 | 5.659 | 0 | 0 | 0 |
| CTONG20128470 | 0 | 0 | 0 | 1.222 | 0 | 0 | 3.444 | 0 | 0 | 0 | 0 | 0 | 1.91 |
| CTONG20141650 | 0 | 0 | 0 | 0 | 0 | 0 | 0 | 0 | 0 | 0 | 0 | 0 | 5.339 |
| CTONG20143690 | 0 | 0 | 0 | 2.954 | 0 | 0 | 0 | 0 | 0 | 4.246 | 0 | 0 | 0 |
| CTONG20153300 | 0 | 0 | 0 | 0 | 0 | 0 | 28.439 | 0 | 0 | 0 | 0 | 0 | 0 |
| CTONG20155180 | 0 | 0 | 0 | 0 | 0 | 0 | 26.559 | 0 | 0 | 0 | 0 | 0 | 0 |
| CTONG20158150 | 0 | 0 | 0 | 6.244 | 0 | 0 | 8.797 | 0 | 0 | 0 | 0 | 0 | 0 |
| CTONG20161850 | 0 | 0 | 0 | 3.69 | 0 | 2.619 | 0 | 0 | 0 | 0 | 0 | 0 | 0 |
| CTONG20164990 | 0 | 0 | 0 | 0 | 0 | 0 | 34.934 | 0 | 0 | 0 | 0 | 0 | 0 |

TABLE 29

| | | | | | | | | | | | | | |
|---|---|---|---|---|---|---|---|---|---|---|---|---|---|
| CTONG20186320 | 0 | 0 | 0 | 5.677 | 0 | 0 | 0 | 0 | 0 | 0 | 0 | 0 | 0 |
| D30ST10002700 | 0 | 0 | 0 | 0 | 0 | 7.81 | 0 | 0 | 9.153 | 0 | 0 | 0 | 0 |
| D60ST20003580 | 0 | 0 | 0 | 0 | 0 | 1.432 | 0 | 0 | 0 | 0 | 0 | 0 | 1.576 |
| D90ST20000310 | 0 | 0 | 0 | 0 | 0 | 0 | 0 | 0 | 16.736 | 0 | 0 | 0 | 0 |
| D90ST20035800 | 0 | 0 | 0 | 0 | 0 | 6.953 | 0 | 0 | 0 | 0 | 0 | 0 | 0 |
| DFNES20010910 | 0 | 0 | 0 | 0 | 0 | 0 | 0 | 19.689 | 0 | 0 | 0 | 0 | 0 |
| DFNES20071130 | 0 | 0 | 0 | 0 | 0 | 0 | 0 | 0 | 0 | 0 | 0 | 0 | 7.411 |
| HCHON20002260 | 0 | 0 | 0 | 1.431 | 0 | 0 | 0.403 | 0.925 | 2.857 | 0.411 | 0 | 1.454 | 0 |
| HCHON20003220 | 0 | 0 | 0 | 0 | 0 | 0 | 10.98 | 0 | 0 | 0 | 0 | 0 | 0 |
| HCHON20010990 | 0 | 0 | 0 | 0 | 0 | 0 | 0 | 0 | 0 | 2.783 | 0 | 0 | 3.025 |
| HCHON20015350 | 0 | 0 | 0 | 0 | 0 | 18.444 | 0 | 0 | 0 | 0 | 0 | 0 | 0 |
| HCHON20022470 | 0 | 0 | 0 | 1.993 | 10.144 | 0 | 5.615 | 0 | 9.945 | 2.864 | 0 | 0 | 9.34 |
| HCHON20067220 | 0 | 0 | 0 | 0 | 0 | 0 | 0 | 0 | 35.892 | 0 | 0 | 0 | 0 |
| HCHON20067700 | 0 | 0 | 0 | 0 | 0 | 2.822 | 0 | 0 | 0 | 0 | 0 | 0 | 0 |
| HEART20003060 | 0 | 0 | 0 | 9.616 | 0 | 0 | 0 | 0 | 0 | 0 | 0 | 0 | 0 |
| HEART20005410 | 0 | 0 | 0 | 0 | 0 | 0 | 0 | 3.07 | 4.74 | 0 | 0 | 0 | 0 |
| HEART20061950 | 0 | 0 | 0 | 0 | 0 | 0 | 0 | 0 | 0 | 9.669 | 0 | 0 | 0 |
| HEART20090000 | 0 | 0 | 0 | 7.336 | 0 | 0 | 0 | 23.712 | 0 | 0 | 0 | 0 | 0 |
| HHDPC10000650 | 0 | 0 | 0 | 0 | 0 | 0 | 0 | 0 | 0 | 27.988 | 0 | 0 | 0 |
| HHDPC20057940 | 0 | 0 | 0 | 0 | 0 | 8.015 | 0 | 0 | 0 | 8.116 | 0 | 0 | 8.821 |
| HLUNG20033780 | 0 | 0 | 0 | 6.571 | 0 | 0 | 0 | 0 | 0 | 0 | 0 | 0 | 0 |
| KIDNE20011170 | 0 | 0 | 0 | 0 | 0 | 0 | 22.29 | 0 | 0 | 0 | 0 | 0 | 0 |
| KIDNE20027250 | 0 | 0 | 0 | 7.303 | 0 | 0 | 10.289 | 23.605 | 0 | 0 | 0 | 0 | 11.41 |
| KIDNE20104300 | 0 | 0 | 0 | 0 | 0 | 0 | 0 | 21.878 | 0 | 0 | 0 | 0 | 10.575 |
| KIDNE20107500 | 0 | 0 | 0 | 0 | 0 | 0 | 0 | 0 | 0 | 0 | 0 | 0 | 11.811 |
| KIDNE20122910 | 0 | 0 | 0 | 16.915 | 0 | 0 | 0 | 0 | 0 | 0 | 0 | 0 | 0 |
| KIDNE20127100 | 0 | 0 | 0 | 0 | 0 | 0 | 0 | 0 | 0 | 0 | 0 | 0 | 10.501 |
| KIDNE20180710 | 0 | 0 | 0 | 0 | 50.895 | 0 | 0 | 0 | 0 | 0 | 0 | 0 | 0 |
| LIVER10001260 | 0 | 0 | 0 | 0 | 0 | 0 | 0 | 0 | 0 | 0 | 28.534 | 0 | 0 |
| LIVER20064100 | 0 | 0 | 0 | 0 | 0 | 0 | 0 | 0 | 0 | 0 | 0 | 0 | 11.342 |
| LIVER20087510 | 0 | 0 | 0 | 0 | 0 | 0 | 0 | 0 | 0 | 0 | 0 | 0 | 9.629 |
| MAMGL10000830 | 0 | 0 | 0 | 0.206 | 0 | 0 | 0 | 0 | 0 | 0.296 | 0 | 0 | 0.321 |
| MESAN20031900 | 0 | 0 | 0 | 0 | 0 | 0 | 0 | 0 | 0 | 0 | 0 | 0 | 19.624 |
| MESAN20036460 | 0 | 0 | 0 | 0 | 0 | 0 | 0 | 0 | 0 | 0 | 0 | 0 | 23.021 |
| MESAN20106640 | 0 | 0 | 0 | 6.16 | 0 | 0 | 0 | 19.91 | 0 | 0 | 0 | 0 | 9.624 |
| MESAN20164090 | 0 | 0 | 0 | 0 | 0 | 0 | 0 | 38.222 | 0 | 0 | 0 | 0 | 0 |
| NOVAR10000150 | 0 | 0 | 0 | 0 | 0 | 0 | 0 | 0 | 10.757 | 0 | 0 | 0 | 0 |

TABLE 30

| | | | | | | | | | | | | | |
|---|---|---|---|---|---|---|---|---|---|---|---|---|---|
| NOVAR20000380 | 0 | 0 | 0 | 3.968 | 15.711 | 0.626 | 1.242 | 4.275 | 6.602 | 0 | 9.248 | 17.918 | 0 |
| NT2NE20010400 | 0 | 0 | 0 | 11.003 | 0 | 15.621 | 0 | 0 | 0 | 0 | 0 | 0 | 17.192 |
| NT2NE20010490 | 0 | 0 | 0 | 0 | 0 | 0 | 0 | 0 | 0 | 0 | 0 | 31.686 | 0 |
| NT2NE20021620 | 0 | 0 | 0 | 0 | 0 | 0 | 0 | 0 | 0 | 0 | 45.501 | 0 | 0 |
| NT2NE20122430 | 0 | 0 | 0 | 0 | 0 | 0 | 0 | 0 | 0 | 0 | 0 | 0 | 23.43 |
| NT2NE20125050 | 0 | 0 | 0 | 13.014 | 0 | 0 | 0 | 0 | 0 | 0 | 0 | 0 | 0 |
| NT2NE20174920 | 0 | 0 | 0 | 0 | 0 | 0 | 0 | 0 | 0 | 0 | 0 | 0 | 18.714 |
| NT2RI20001330 | 0 | 0 | 0 | 1.819 | 0 | 0 | 0 | 0 | 0 | 0 | 0 | 0 | 0 |
| NT2RI20023590 | 0 | 0 | 0 | 0 | 0 | 0 | 8.23 | 0 | 0 | 0 | 0 | 0 | 0 |
| NT2RI20041880 | 0 | 0 | 0 | 0 | 0 | 0 | 0 | 0 | 0 | 0 | 0 | 10.353 | 0 |
| NT2RI20046080 | 0 | 0 | 0 | 0 | 0 | 0 | 8.488 | 0 | 0 | 0 | 0 | 0 | 0 |
| NT2RI20216250 | 0 | 0 | 0 | 0 | 0 | 0 | 0 | 0 | 19.442 | 0 | 0 | 0 | 0 |
| NT2RI20252550 | 0 | 0 | 0 | 0 | 0 | 0 | 0 | 0 | 0 | 0 | 0 | 0 | 37.898 |
| NT2RP60000770 | 0 | 0 | 0 | 0 | 0 | 0 | 0 | 0 | 0 | 0 | 0 | 0 | 7.128 |
| NT2RP70045590 | 0 | 0 | 0 | 0 | 0 | 0 | 0 | 0 | 0 | 0 | 0 | 0 | 9.452 |
| NT2RP70063950 | 0 | 0 | 0 | 0 | 0 | 0 | 0 | 0 | 17.468 | 0 | 0 | 0 | 0 |
| NT2RP70195430 | 0 | 0 | 0 | 0 | 38.221 | 0 | 0 | 0 | 10.792 | 0 | 0 | 0 | 0 |
| NT2RP70198350 | 0 | 0 | 0 | 0 | 0 | 0 | 1.042 | 0 | 0 | 0 | 0 | 3.758 | 0 |
| NTONG20028070 | 0 | 0 | 0 | 0 | 0 | 0 | 0 | 0 | 0 | 0 | 0 | 0 | 13.079 |
| NTON620046140 | 0 | 0 | 0 | 0 | 0 | 0 | 0 | 0 | 0 | 0 | 0 | 0 | 6.567 |
| NTONG20064840 | 0 | 0 | 0 | 3.068 | 0 | 0 | 0 | 0 | 0 | 0 | 0 | 0 | 0 |
| NTONG20067830 | 0 | 0 | 0 | 0 | 0 | 2.853 | 0 | 0 | 0 | 0 | 0 | 0 | 0 |
| NTONG20077560 | 0 | 0 | 0 | 4.791 | 0 | 0 | 0 | 0 | 0 | 0 | 0 | 0 | 0 |
| PANCR10000910 | 0 | 0 | 0 | 0.214 | 0 | 0 | 0 | 0 | 0 | 0 | 0 | 0 | 0 |
| PEBLM20024550 | 0 | 0 | 0 | 0 | 0 | 0 | 0 | 0 | 0 | 0 | 33.118 | 0 | 0 |
| PEBLM20052820 | 0 | 0 | 0 | 0 | 0 | 11.82 | 0 | 0 | 0 | 0 | 0 | 0 | 0 |
| PEBLM20074370 | 0 | 0 | 0 | 0 | 21.543 | 0 | 0 | 0 | 0 | 0 | 0 | 0 | 0 |
| PERIC20004780 | 0 | 0 | 0 | 7.727 | 0 | 0 | 0 | 0 | 0 | 0 | 0 | 0 | 0 |
| PLACE50000660 | 0 | 0 | 0 | 0 | 0 | 18.438 | 0 | 0 | 0 | 0 | 0 | 32.991 | 0 |
| PLACE60079250 | 0 | 0 | 0 | 0 | 0 | 0 | 0 | 23.248 | 0 | 0 | 0 | 0 | 0 |
| PLACE60136720 | 0 | 0 | 0 | 0 | 0 | 27.825 | 0 | 0 | 0 | 0 | 0 | 0 | 0 |
| PLACE60138830 | 0 | 0 | 0 | 0 | 0 | 0 | 0 | 0 | 0 | 0 | 0 | 0 | 38.39 |
| PROST20005670 | 0 | 0 | 0 | 0 | 0 | 14.432 | 0 | 0 | 0 | 0 | 0 | 0 | 0 |
| PROST20050670 | 0 | 0 | 0 | 11.45 | 0 | 0 | 0 | 0 | 0 | 0 | 0 | 0 | 17.889 |

TABLE 30-continued

| | | | | | | | | | | | | | |
|---|---|---|---|---|---|---|---|---|---|---|---|---|---|
| PROST20107820 | 0 | 0 | 0 | 0 | 0 | 0 | 0.243 | 0 | 0 | 0 | 0 | 0 | 0 |
| PROST20111050 | 0 | 0 | 0 | 25.26 | 0 | 0 | 0 | 0 | 0 | 0 | 0 | 0 | 0 |
| PR0ST20116600 | 0 | 0 | 0 | 16.676 | 0 | 0 | 0 | 0 | 0 | 0 | 0 | 0 | 0 |

TABLE 31

| | | | | | | | | | | | | | |
|---|---|---|---|---|---|---|---|---|---|---|---|---|---|
| PROST20120160 | 0 | 0 | 0 | 0 | 0 | 22.126 | 0 | 0 | 0 | 0 | 0 | 0 | 0 |
| PROST20123530 | 0 | 0 | 0 | 0 | 0 | 0 | 0 | 0 | 0 | 0 | 0 | 33.893 | 0 |
| PROST20161950 | 0 | 0 | 0 | 0 | 0 | 0 | 0 | 0 | 0 | 0 | 0 | 21.086 | 0 |
| PROST20171280 | 0 | 0 | 0 | 0 | 0 | 8.119 | 0 | 0 | 0 | 0 | 0 | 0 | 0 |
| PROST20175290 | 0 | 0 | 0 | 1.802 | 0 | 0 | 0 | 0 | 0 | 0 | 0 | 0 | 2.815 |
| PROST20185830 | 0 | 0 | 0 | 0 | 0 | 0 | 0 | 0 | 0 | 0 | 0 | 33.325 | 0 |
| PROST20191640 | 0 | 0 | 0 | 0 | 0 | 0 | 3.687 | 0 | 0 | 0 | 0 | 0 | 0 |
| PUAEN20015860 | 0 | 0 | 0 | 2.027 | 0 | 0 | 0 | 0 | 0 | 2.913 | 0 | 0 | 0 |
| PUAEN20030180 | 0 | 0 | 0 | 0 | 0 | 0 | 0 | 0 | 0 | 0 | 0 | 12.086 | 3.717 |
| PUAEN20044000 | 0 | 0 | 0 | 0 | 0 | 7.259 | 0 | 0 | 0 | 0 | 0 | 0 | 0 |
| PUAEN20078980 | 0 | 0 | 0 | 0 | 39.038 | 0 | 0 | 0 | 0 | 0 | 0 | 0 | 0 |
| PUAEN20085150 | 0 | 0 | 0 | 13.781 | 0 | 0 | 0 | 0 | 0 | 9.905 | 0 | 0 | 21.533 |
| PUAEN20108240 | 0 | 0 | 0 | 11.155 | 0 | 26.393 | 5.239 | 0 | 0 | 16.034 | 0 | 0 | 11.619 |
| SKMUS20012010 | 0 | 0 | 0 | 0 | 0 | 1.795 | 0 | 0 | 0 | 0 | 0 | 0 | 0 |
| SKNSH20062340 | 0 | 0 | 0 | 0 | 0 | 3.527 | 0 | 0 | 0 | 0 | 0 | 0 | 0 |
| SMINT20013480 | 0 | 0 | 0 | 0 | 0 | 0 | 0 | 0 | 32.864 | 0 | 0 | 0 | 0 |
| SMINT20042990 | 0 | 0 | 0 | 6.406 | 0 | 0 | 0 | 0 | 0 | 0 | 0 | 0 | 0 |
| SMINT20053300 | 0 | 0 | 0 | 0 | 0 | 0 | 0 | 0 | 0 | 0 | 51.332 | 0 | 0 |
| SMINT20076470 | 0 | 0 | 0 | 0 | 0 | 22.212 | 0 | 0 | 0 | 0 | 0 | 0 | 0 |
| SMINT20092330 | 0 | 0 | 0 | 16.746 | 0 | 0 | 0 | 0 | 0 | 0 | 0 | 0 | 0 |
| SMINT20101440 | 0 | 0 | 0 | 0 | 0 | 0 | 0 | 0 | 0 | 0 | 0 | 0 | 23.912 |
| SMINT20121220 | 0 | 0 | 0 | 0 | 0 | 0 | 0 | 0 | 12.384 | 0 | 0 | 0 | 3.877 |
| SMINT20121950 | 0 | 0 | 0 | 16.746 | 0 | 0 | 0 | 0 | 0 | 0 | 0 | 0 | 0 |
| SMINT20122910 | 0 | 0 | 0 | 6.546 | 0 | 0 | 0 | 0 | 0 | 0 | 0 | 0 | 0 |
| SMINT20130320 | 0 | 0 | 0 | 0 | 0 | 12.051 | 0 | 0 | 0 | 0 | 0 | 0 | 0 |
| SMINT20131810 | 0 | 0 | 0 | 0 | 0 | 22.212 | 0 | 0 | 0 | 0 | 0 | 0 | 0 |
| SMINT20144800 | 0 | 0 | 0 | 0 | 0 | 0 | 0 | 0 | 5.628 | 0 | 5.913 | 0 | 0 |
| SMINT20163960 | 0 | 0 | 0 | 0 | 0 | 0 | 0 | 0 | 50.098 | 0 | 0 | 0 | 0 |
| SPLEN20002220 | 0 | 0 | 0 | 0 | 0 | 0 | 12.214 | 0 | 0 | 0 | 0 | 0 | 0 |
| SPLEN20008740 | 0 | 0 | 0 | 0 | 1.761 | 0 | 0.487 | 0 | 0 | 0 | 0 | 0 | 0 |
| SPLEN20011410 | 0 | 0 | 0 | 0.67 | 0 | 0 | 0 | 0 | 0 | 0.963 | 0 | 0 | 2.094 |
| SPLEN20016260 | 0 | 0 | 0 | 0 | 0 | 0 | 0 | 0 | 0 | 0 | 0 | 67.455 | 0 |
| SPLEN20027440 | 0 | 0 | 0 | 0 | 0 | 0 | 2.23 | 0 | 7.901 | 0 | 0 | 0 | 0 |
| SPLEN20029310 | 0 | 0 | 0 | 0 | 0 | 0 | 4.078 | 0 | 0 | 0 | 0 | 0 | 0 |
| SPLEN20033960 | 0 | 0 | 0 | 0 | 0 | 0 | 0 | 0 | 0 | 0 | 0 | 67.455 | 0 |
| SPLEN20054290 | 0 | 0 | 0 | 5.201 | 0 | 0 | 0 | 0 | 0 | 3.738 | 0 | 0 | 4.063 |
| SPLEN20126190 | 0 | 0 | 0 | 0 | 0 | 0 | 36.501 | 0 | 0 | 0 | 0 | 0 | 0 |

TABLE 32

| | | | | | | | | | | | | | |
|---|---|---|---|---|---|---|---|---|---|---|---|---|---|
| SPLEN20128000 | 0 | 0 | 0 | 0 | 0 | 0 | 0 | 0.784 | 0 | 0 | 0 | 0 | 0.379 |
| SPLEN20145720 | 0 | 0 | 0 | 0 | 0 | 0 | 0 | 0 | 22.047 | 0 | 0 | 0 | 6.902 |
| SPLEN20146450 | 0 | 0 | 0 | 0 | 0 | 0 | 0 | 0 | 0 | 0 | 68.148 | 0 | 0 |
| SPLEN20147110 | 0 | 0 | 0 | 0 | 0 | 0 | 2.652 | 0 | 0 | 0 | 0 | 0 | 0 |
| SPLEN20149110 | 0 | 0 | 0 | 0.749 | 0 | 0 | 0 | 0 | 0 | 0 | 0 | 0 | 2.34 |
| SPLEN20157880 | 0 | 0 | 0 | 3.436 | 0 | 0 | 0 | 0 | 0 | 0 | 0 | 0 | 5.368 |
| SPLEN20158900 | 0 | 0 | 0 | 28.977 | 0 | 0 | 0 | 0 | 0 | 0 | 0 | 0 | 0 |
| SPLEN20171210 | 0 | 0 | 0 | 0 | 0 | 15.624 | 7.753 | 0 | 0 | 0 | 0 | 0 | 8.598 |
| SPLEN20179180 | 0 | 0 | 0 | 0 | 0 | 0 | 0 | 0 | 3.23 | 0 | 0 | 0 | 0 |
| SPLEN20186430 | 0 | 0 | 0 | 0 | 0 | 0 | 36.501 | 0 | 0 | 0 | 0 | 0 | 0 |
| SPLEN20204170 | 0 | 0 | 0 | 9.907 | 0 | 0 | 0 | 0 | 0 | 0 | 0 | 50.331 | 15.479 |
| SPLEN20212730 | 0 | 0 | 0 | 0 | 0 | 0 | 14.747 | 0 | 0 | 0 | 0 | 0 | 16.354 |
| SPLEN20214580 | 0 | 0 | 0 | 0 | 0 | 0 | 0 | 0 | 0 | 0 | 0 | 0 | 38.93 |
| SPLEN20250390 | 0 | 0 | 0 | 28.977 | 0 | 0 | 0 | 0 | 0 | 0 | 0 | 0 | 0 |
| STOMA20051200 | 0 | 0 | 0 | 0 | 0 | 0 | 0 | 0 | 0 | 0 | 0 | 0 | 14.012 |
| STOMA20062290 | 0 | 0 | 0 | 0 | 0 | 0 | 6.012 | 0 | 0 | 0 | 0 | 0 | 0 |
| STOMA20092890 | 0 | 0 | 0 | 4.072 | 0 | 0 | 5.737 | 0 | 0 | 0 | 0 | 0 | 0 |
| SYNOV20003970 | 0 | 0 | 0 | 0 | 0 | 0 | 0 | 0 | 0 | 48.614 | 0 | 0 | 0 |
| TESOP20005270 | 0 | 0 | 0 | 0 | 0 | 0 | 0 | 0 | 0 | 0 | 0 | 0 | 11.444 |
| TESTI10000940 | 0 | 0 | 0 | 0 | 0 | 0 | 0 | 22.629 | 0 | 0 | 0 | 0 | 0 |
| TESTI20001720 | 0 | 0 | 0 | 0 | 0 | 0 | 0 | 0 | 0 | 0 | 0 | 0 | 9.487 |
| TESTI20002720 | 0 | 0 | 0 | 6.872 | 0 | 0 | 0 | 0 | 0 | 0 | 0 | 0 | 0 |
| TESTI20004890 | 0 | 0 | 0 | 0 | 0 | 0 | 0 | 0 | 0 | 0 | 0 | 57.966 | 0 |
| TESTI20011200 | 0 | 0 | 0 | 0 | 0 | 0 | 0 | 0 | 0 | 0.986 | 0 | 0 | 0 |
| TESTI20035960 | 0 | 0 | 0 | 0 | 0 | 0 | 0 | 0 | 14.759 | 0 | 0 | 0 | 0 |
| TESTI20037560 | 0 | 0 | 0 | 0 | 0 | 0 | 0 | 0 | 0 | 0 | 0 | 0 | 11.634 |
| TESTI20044310 | 0 | 0 | 0 | 0 | 0 | 8.365 | 0 | 0 | 0 | 0 | 0 | 0 | 0 |
| TESTI20061110 | 0 | 0 | 0 | 14.633 | 0 | 0 | 0 | 47.3 | 0 | 0 | 0 | 0 | 0 |

TABLE 32-continued

| | | | | | | | | | | | | | |
|---|---|---|---|---|---|---|---|---|---|---|---|---|---|
| TESTI20063830 | 0 | 0 | 0 | 0 | 0 | 4.084 | 0 | 0 | 0 | 4.135 | 0 | 0 | 0 |
| TESTI20086210 | 0 | 0 | 0 | 0 | 0 | 0 | 0 | 0 | 35.791 | 0 | 0 | 0 | 0 |
| TESTI20152460 | 0 | 0 | 0 | 8.403 | 0 | 0 | 0 | 0 | 0 | 0 | 0 | 0 | 0 |
| TESTI20168960 | 0 | 0 | 0 | 0 | 0 | 0 | 0 | 0 | 0 | 43.832 | 0 | 0 | 0 |
| TESTI20170350 | 0 | 0 | 0 | 29.776 | 0 | 0 | 0 | 0 | 0 | 42.801 | 0 | 0 | 0 |
| TESTI20208400 | 0 | 0 | 0 | 11.599 | 0 | 0 | 0 | 0 | 0 | 0 | 0 | 0 | 0 |
| TESTI20213580 | 0 | 0 | 0 | 0 | 0 | 0 | 0 | 0 | 0 | 0 | 0 | 0 | 37.524 |
| TESTI20214250 | 0 | 0 | 0 | 1.222 | 0 | 0 | 1.722 | 0 | 0 | 0 | 0 | 0 | 1.909 |
| TESTI20254220 | 0 | 0 | 0 | 1.762 | 0 | 0 | 0 | 0 | 0 | 0 | 0 | 0 | 0 |

TABLE 33

| | | | | | | | | | | | | | |
|---|---|---|---|---|---|---|---|---|---|---|---|---|---|
| TESTI20258460 | 0 | 0 | 0 | 43.347 | 0 | 0 | 0 | 0 | 0 | 20.77 | 0 | 0 | 22.576 |
| TESTI20330310 | 0 | 0 | 0 | 0 | 0 | 0 | 0 | 0 | 0 | 0 | 0 | 0 | 34.12 |
| TESTI20334410 | 0 | 0 | 0 | 0 | 0 | 0 | 0 | 0 | 0 | 0 | 0 | 0 | 2.434 |
| TESTI20366910 | 0 | 0 | 0 | 0 | 0 | 0 | 0 | 0 | 0 | 0 | 0 | 84.653 | 0 |
| TESTI20391770 | 0 | 0 | 0 | 5.883 | 0 | 0 | 16.578 | 0 | 0 | 21.141 | 0 | 0 | 18.384 |
| TESTI20432750 | 0 | 0 | 0 | 0 | 31.972 | 0 | 0 | 0 | 0 | 0 | 0 | 0 | 0 |
| TESTI20455620 | 0 | 0 | 0 | 0 | 0 | 0 | 0 | 0 | 0 | 0 | 0 | 84.653 | 0 |
| THYMU20000570 | 0 | 0 | 0 | 0 | 0 | 0 | 0 | 0 | 0 | 0 | 0 | 0 | 1.504 |
| THYMU20058070 | 0 | 0 | 0 | 45.981 | 0 | 0 | 0 | 0 | 0 | 0 | 0 | 0 | 0 |
| THYMU20066100 | 0 | 0 | 0 | 0 | 0 | 0 | 0 | 0 | 0 | 0 | 0 | 0 | 30.115 |
| THYMU20075320 | 0 | 0 | 0 | 0 | 56.448 | 0 | 0 | 0 | 0 | 0 | 0 | 0 | 0 |
| THYMU20081490 | 0 | 0 | 0 | 0 | 0 | 0 | 0 | 0 | 0 | 0 | 0 | 0 | 6.532 |
| THYMU20100410 | 0 | 0 | 0 | 0 | 0 | 18.787 | 0 | 0 | 0 | 19.023 | 0 | 0 | 0 |
| THYMU20101920 | 0 | 0 | 0 | 0 | 0 | 0 | 0 | 0 | 0 | 0 | 0 | 0 | 57.08 |
| THYMU20108310 | 0 | 0 | 0 | 0 | 0 | 0 | 54.53 | 0 | 0 | 0 | 0 | 0 | 0 |
| THYMU20119390 | 0 | 0 | 0 | 45.981 | 0 | 0 | 0 | 0 | 0 | 0 | 0 | 0 | 0 |
| THYMU20126900 | 0 | 0 | 0 | 0 | 0 | 3.915 | 0 | 0 | 0 | 0 | 0 | 0 | 0 |
| THYMU20128260 | 0 | 0 | 0 | 0 | 22.315 | 22.147 | 0 | 0 | 22.595 | 0 | 0 | 0 | 0 |
| THYMU20169680 | 0 | 0 | 0 | 0 | 0 | 0 | 0 | 0 | 0 | 7.541 | 0 | 0 | 0 |
| THYMU20193640 | 0 | 0 | 0 | 29.854 | 0 | 0 | 0 | 0 | 0 | 0 | 0 | 0 | 0 |
| THYMU20209590 | 0 | 0 | 0 | 7.868 | 0 | 0 | 11.085 | 25.432 | 0 | 0 | 0 | 0 | 12.293 |
| THYMU20235760 | 0 | 0 | 0 | 0 | 0 | 0 | 15.94 | 0 | 0 | 0 | 0 | 57.476 | 0 |
| THYMU20239430 | 0 | 0 | 0 | 0 | 0 | 0 | 54.53 | 0 | 0 | 0 | 0 | 0 | 0 |
| THYMU20240710 | 0 | 0 | 0 | 0 | 0 | 33.209 | 0 | 0 | 0 | 0 | 0 | 0 | 0 |
| THYMU20253250 | 0 | 0 | 0 | 0 | 0 | 13.123 | 0 | 29.879 | 46.138 | 0 | 0 | 0 | 0 |
| THYMU20286290 | 0 | 0 | 0 | 0 | 0 | 0 | 0 | 0 | 0 | 0 | 0 | 0 | 20.303 |
| TKIDN10000010 | 0 | 0 | 0 | 7.899 | 0 | 0 | 0 | 0 | 0 | 0 | 0 | 0 | 12.342 |
| TKIDN20005210 | 0 | 0 | 0 | 0 | 0 | 0 | 29.753 | 0 | 0 | 15.178 | 0 | 0 | 0 |
| TKIDN20030590 | 0 | 0 | 0 | 0 | 0 | 0 | 0 | 0 | 0 | 21.607 | 0 | 0 | 0 |
| TRACH20005020 | 0 | 0 | 0 | 0 | 0 | 0 | 47.167 | 0 | 0 | 0 | 0 | 0 | 0 |
| TRACH20005400 | 0 | 0 | 0 | 0 | 0 | 0 | 0 | 0 | 0 | 0 | 0 | 0 | 3.16 |
| TRACH20007020 | 0 | 0 | 0 | 5.573 | 0 | 0 | 0 | 0 | 0 | 0 | 0 | 0 | 0 |
| TRACH20019960 | 0 | 0 | 0 | 0 | 0 | 0 | 0 | 67.193 | 0 | 0 | 0 | 0 | 0 |
| TRACH20034840 | 0 | 0 | 0 | 38.787 | 0 | 0 | 0 | 0 | 0 | 0 | 0 | 0 | 0 |
| TRACH20079690 | 0 | 0 | 0 | 0 | 0 | 0 | 2.538 | 0 | 0 | 0 | 0 | 0 | 0 |
| TRACH20128110 | 0 | 0 | 0 | 5.533 | 28.17 | 0 | 0 | 17.886 | 0 | 0 | 0 | 0 | 34.582 |
| TRACH20149970 | 0 | 0 | 0 | 12.555 | 0 | 0 | 14.151 | 0 | 0 | 7.219 | 0 | 0 | 0 |

TABLE 34

| | | | | | | | | | | | | | |
|---|---|---|---|---|---|---|---|---|---|---|---|---|---|
| TRACH20183170 | 0 | 0 | 0 | 0 | 0 | 0 | 2.93 | 0 | 0 | 0 | 0 | 0 | 0 |
| UMVEN10001860 | 0 | 0 | 0 | 0 | 0 | 0 | 0 | 0.606 | 0 | 0 | 0 | 0 | 0 |
| UMVEN20003540 | 0 | 0 | 0 | 0 | 0 | 0 | 0 | 1.89 | 2.918 | 0 | 0 | 2.97 | 0.913 |
| UTERU20000740 | 0 | 0 | 0 | 37.308 | 0 | 0 | 0 | 0 | 0 | 0 | 0 | 0 | 0 |
| UTERU20030570 | 0 | 0 | 0 | 1.836 | 0 | 0 | 0 | 0 | 0 | 0 | 0 | 9.326 | 0 |
| UTERU20054460 | 0 | 0 | 0 | 0 | 75.184 | 0 | 0 | 0 | 0 | 0 | 0 | 0 | 0 |
| UTERU20055930 | 0 | 0 | 0 | 1.593 | 0 | 3.393 | 4.49 | 0 | 0 | 0 | 4.178 | 4.047 | 4.979 |
| UTERU20056010 | 0 | 0 | 0 | 0 | 0 | 0 | 0 | 5.848 | 0 | 2.601 | 0 | 0 | 0 |
| UTERU20064860 | 0 | 0 | 0 | 0 | 0 | 0 | 0 | 0 | 0 | 0 | 0 | 0 | 48.181 |
| UTERU20065930 | 0 | 0 | 0 | 1.048 | 0 | 5.951 | 2.953 | 0 | 0 | 1.506 | 0 | 0 | 3.275 |
| UTERU20070040 | 0 | 0 | 0 | 0 | 0 | 0 | 0 | 0 | 0 | 0 | 0 | 75.144 | 0 |
| UTERU20081300 | 0 | 0 | 0 | 0 | 0 | 0 | 0 | 0 | 0 | 46.104 | 0 | 0 | 0 |
| UTERU20084260 | 0 | 0 | 0 | 0 | 0 | 0 | 0 | 0 | 0 | 0 | 0 | 0 | 24.416 |
| UTERU20094350 | 0 | 0 | 0 | 0 | 0 | 5.388 | 26.737 | 0 | 0 | 16.367 | 0 | 0 | 5.93 |
| UTERU20120310 | 0 | 0 | 0 | 0 | 0 | 0 | 0 | 0 | 0 | 46.104 | 0 | 0 | 0 |
| UTERU20124070 | 0 | 0 | 0 | 0 | 0 | 24.8 | 0 | 0 | 0 | 0 | 0 | 0 | 0 |
| UTERU20164260 | 0 | 0 | 0 | 0 | 0 | 0 | 12.709 | 0 | 0 | 0 | 0 | 0 | 14.093 |
| UTERU20168220 | 0 | 0 | 0 | 0 | 0 | 4.05 | 10.05 | 0 | 0 | 6.152 | 0 | 0 | 0 |
| UTERU20183640 | 0 | 0 | 0 | 0 | 0 | 0 | 0 | 0 | 0 | 46.104 | 0 | 0 | 0 |
| ASTRO20032120 | 27.675 | 0 | 0 | 10.632 | 0 | 0 | 0 | 0 | 0 | 0 | 0 | 0 | 0 |
| ASTRO20125520 | 2.731 | 0 | 0 | 1.049 | 0 | 0 | 0 | 0 | 0 | 0 | 0 | 0 | 1.639 |
| BRACE20039040 | 4.789 | 0 | 0 | 3.68 | 9.367 | 0 | 0 | 0 | 0 | 0 | 0 | 9.348 | 0 |

TABLE 34-continued

| | | | | | | | | | | | | |
|---|---|---|---|---|---|---|---|---|---|---|---|---|
| BRACE20060720 | 36.414 | 0 | 0 | 13.99 | 0 | 0 | 0 | 0 | 0 | 0 | 0 | 0 |
| BRACE20062640 | 15.593 | 0 | 0 | 5.99 | 0 | 0 | 0 | 0 | 29.9 | 0 | 0 | 0 | 9.36 |
| BRACE20090440 | 18.536 | 0 | 0 | 7.121 | 0 | 0 | 0 | 0 | 0 | 0 | 0 | 0 |
| BRACE20099570 | 72.245 | 0 | 0 | 27.755 | 0 | 0 | 0 | 0 | 0 | 0 | 0 | 0 |
| BRACE20111830 | 11.876 | 0 | 0 | 22.812 | 0 | 6.477 | 0 | 0 | 0 | 13.116 | 0 | 0 | 14.257 |
| BRACE20142570 | 22.91 | 0 | 0 | 44.008 | 0 | 0 | 12.401 | 0 | 0 | 0 | 0 | 0 | 0 |
| BRAWH20128270 | 16.614 | 0 | 0 | 0 | 0 | 9.061 | 8.993 | 0 | 31.859 | 0 | 33.472 | 0 | 0 |
| BRCAN20280360 | 4.46 | 0 | 0 | 0 | 8.724 | 4.865 | 0 | 5.539 | 0 | 2.463 | 0 | 0 | 0 |
| BRHIP20110800 | 64.423 | 0 | 0 | 0 | 0 | 0 | 0 | 0 | 0 | 35.577 | 0 | 0 | 0 |
| BRHIP20176420 | 47.719 | 0 | 0 | 0 | 0 | 13.013 | 12.915 | 0 | 0 | 26.353 | 0 | 0 | 0 |
| BRSSN20003120 | 19.877 | 0 | 0 | 7.636 | 0 | 21.682 | 10.759 | 0 | 0 | 0 | 40.045 | 0 | 0 |
| CTONG20105660 | 50.102 | 0 | 0 | 0 | 0 | 0 | 0 | 0 | 0 | 0 | 0 | 0 | 0 |
| CTONG20124010 | 15.543 | 0 | 0 | 0 | 0 | 4.239 | 0 | 0 | 0 | 0 | 0 | 0 | 0 |
| CTONG20133480 | 10.163 | 0 | 0 | 0 | 0 | 5.543 | 5.501 | 0 | 0 | 0 | 0 | 0 | 12.201 |
| CT0NG20139070 | 7.966 | 0 | 0 | 4.591 | 0 | 2.172 | 2.156 | 0 | 0 | 0 | 0 | 0 | 2.391 |

TABLE 35

| | | | | | | | | | | | | | |
|---|---|---|---|---|---|---|---|---|---|---|---|---|---|
| CTONG20160560 | 3.674 | 0 | 0 | 0 | 0 | 0 | 3.977 | 0 | 0 | 0 | 0 | 0 | 0 |
| FCBBF10001210 | 18.354 | 0 | 0 | 0 | 0 | 10.01 | 0 | 0 | 35.196 | 0 | 0 | 0 | 0 |
| FCBBF10001550 | 100 | 0 | 0 | 0 | 0 | 0 | 0 | 0 | 0 | 0 | 0 | 0 | 0 |
| FCBBF10001710 | 100 | 0 | 0 | 0 | 0 | 0 | 0 | 0 | 0 | 0 | 0 | 0 | 0 |
| FCBBF10001820 | 15.666 | 0 | 0 | 0 | 0 | 0 | 0 | 0 | 0 | 0 | 0 | 0 | 0 |
| FCBBF10002430 | 100 | 0 | 0 | 0 | 0 | 0 | 0 | 0 | 0 | 0 | 0 | 0 | 0 |
| FCBBF10002700 | 10 | 0 | 0 | 0 | 0 | 0 | 0 | 0 | 0 | 0 | 0 | 0 | 0 |
| FCBBF10002800 | 10.435 | 0 | 0 | 0 | 0 | 0 | 0 | 0 | 0 | 0 | 0 | 0 | 0 |
| FCBBF10003220 | 100 | 0 | 0 | 0 | 0 | 0 | 0 | 0 | 0 | 0 | 0 | 0 | 0 |
| FCB8F10003740 | 73.865 | 0 | 0 | 0 | 0 | 0 | 0 | 0 | 0 | 0 | 0 | 0 | 0 |
| FCBBF10003760 | 78.7 | 0 | 0 | 0 | 0 | 0 | 21.3 | 0 | 0 | 0 | 0 | 0 | 0 |
| FCBBF10005060 | 34.365 | 0 | 0 | 0 | 0 | 0 | 0 | 0 | 0 | 0 | 0 | 0 | 0 |
| FCBBF10005460 | 100 | 0 | 0 | 0 | 0 | 0 | 0 | 0 | 0 | 0 | 0 | 0 | 0 |
| FCBBF10005500 | 100 | 0 | 0 | 0 | 0 | 0 | 0 | 0 | 0 | 0 | 0 | 0 | 0 |
| FCB5F20006780 | 100 | 0 | 0 | 0 | 0 | 0 | 0 | 0 | 0 | 0 | 0 | 0 | 0 |
| FCBBF20014270 | 100 | 0 | 0 | 0 | 0 | 0 | 0 | 0 | 0 | 0 | 0 | 0 | 0 |
| FCB8F20023700 | 100 | 0 | 0 | 0 | 0 | 0 | 0 | 0 | 0 | 0 | 0 | 0 | 0 |
| FCBBF20032970 | 100 | 0 | 0 | 0 | 0 | 0 | 0 | 0 | 0 | 0 | 0 | 0 | 0 |
| FCBBF20035280 | 100 | 0 | 0 | 0 | 0 | 0 | 0 | 0 | 0 | 0 | 0 | 0 | 0 |
| FCBBF20042170 | 100 | 0 | 0 | 0 | 0 | 0 | 0 | 0 | 0 | 0 | 0 | 0 | 0 |
| FCBBF20042560 | 100 | 0 | 0 | 0 | 0 | 0 | 0 | 0 | 0 | 0 | 0 | 0 | 0 |
| FCBBF20051220 | 100 | 0 | 0 | 0 | 0 | 0 | 0 | 0 | 0 | 0 | 0 | 0 | 0 |
| FCBBF20054280 | 72.245 | 0 | 0 | 27.755 | 0 | 0 | 0 | 0 | 0 | 0 | 0 | 0 | 0 |
| FCBBF20056370 | 5.134 | 0 | 0 | 0 | 0 | 0 | 0 | 0 | 0 | 0 | 0 | 0 | 0 |
| FCBBF20064520 | 100 | 0 | 0 | 0 | 0 | 0 | 0 | 0 | 0 | 0 | 0 | 0 | 0 |
| FCBBF20067810 | 11.69 | 0 | 0 | 0 | 0 | 6.376 | 0 | 0 | 0 | 0 | 0 | 0 | 7.017 |
| FCBBF20071860 | 100 | 0 | 0 | 0 | 0 | 0 | 0 | 0 | 0 | 0 | 0 | 0 | 0 |
| FCBBF20072650 | 100 | 0 | 0 | 0 | 0 | 0 | 0 | 0 | 0 | 0 | 0 | 0 | 0 |
| FCBBF20076330 | 100 | 0 | 0 | 0 | 0 | 0 | 0 | 0 | 0 | 0 | 0 | 0 | 0 |
| FCBBF30008470 | 100 | 0 | 0 | 0 | 0 | 0 | 0 | 0 | 0 | 0 | 0 | 0 | 0 |
| FCBBF30010810 | 9.702 | 0 | 0 | 1.864 | 9.488 | 2.646 | 0 | 0 | 0 | 0 | 0 | 0 | 5.824 |
| FCBBF30012350 | 100 | 0 | 0 | 0 | 0 | 0 | 0 | 0 | 0 | 0 | 0 | 0 | 0 |
| FCBBF30012810 | 37.617 | 0 | 0 | 0 | 0 | 0 | 0 | 0 | 0 | 0 | 0 | 0 | 0 |
| FCBBF30015940 | 100 | 0 | 0 | 0 | 0 | 0 | 0 | 0 | 0 | 0 | 0 | 0 | 0 |
| FCBBF30019120 | 100 | 0 | 0 | 0 | 0 | 0 | 0 | 0 | 0 | 0 | 0 | 0 | 0 |
| FCBBF30024750 | 100 | 0 | 0 | 0 | 0 | 0 | 0 | 0 | 0 | 0 | 0 | 0 | 0 |
| FCBBF30028180 | 64.881 | 0 | 0 | 0 | 0 | 0 | 35.119 | 0 | 0 | 0 | 0 | 0 | 0 |

TABLE 36

| | | | | | | | | | | | | | |
|---|---|---|---|---|---|---|---|---|---|---|---|---|---|
| FCBBF30033050 | 100 | 0 | 0 | 0 | 0 | 0 | 0 | 0 | 0 | 0 | 0 | 0 | 0 |
| FCBBF30039020 | 43.392 | 0 | 0 | 0 | 0 | 0 | 0 | 0 | 0 | 0 | 0 | 0 | 0 |
| FCBBF30052180 | 100 | 0 | 0 | 0 | 0 | 0 | 0 | 0 | 0 | 0 | 0 | 0 | 0 |
| FCBBF30054440 | 100 | 0 | 0 | 0 | 0 | 0 | 0 | 0 | 0 | 0 | 0 | 0 | 0 |
| FCBBF30057290 | 100 | 0 | 0 | 0 | 0 | 0 | 0 | 0 | 0 | 0 | 0 | 0 | 0 |
| FCBBF30062880 | 100 | 0 | 0 | 0 | 0 | 0 | 0 | 0 | 0 | 0 | 0 | 0 | 0 |
| FCBBF30070770 | 100 | 0 | 0 | 0 | 0 | 0 | 0 | 0 | 0 | 0 | 0 | 0 | 0 |
| FCBBF30071520 | 100 | 0 | 0 | 0 | 0 | 0 | 0 | 0 | 0 | 0 | 0 | 0 | 0 |
| FCBBF30078290 | 20.784 | 0 | 0 | 0 | 0 | 0 | 0 | 0 | 0 | 0 | 0 | 0 | 0 |
| FCBBF30083620 | 100 | 0 | 0 | 0 | 0 | 0 | 0 | 0 | 0 | 0 | 0 | 0 | 0 |
| FCBBF30123470 | 4.055 | 0 | 0 | 0 | 0 | 0 | 0 | 0 | 7.775 | 0 | 8.169 | 0 | 2.434 |
| FCBBF30170590 | 100 | 0 | 0 | 0 | 0 | 0 | 0 | 0 | 0 | 0 | 0 | 0 | 0 |
| FCBBF30172550 | 64.423 | 0 | 0 | 0 | 0 | 0 | 0 | 0 | 0 | 35.577 | 0 | 0 | 0 |
| FCBBF30175310 | 2.962 | 0 | 0 | 0 | 5.793 | 0 | 3.207 | 3.678 | 0 | 0 | 0 | 0 | 3.556 |
| FCBBF30178730 | 100 | 0 | 0 | 0 | 0 | 0 | 0 | 0 | 0 | 0 | 0 | 0 | 0 |
| FCBBF30190850 | 100 | 0 | 0 | 0 | 0 | 0 | 0 | 0 | 0 | 0 | 0 | 0 | 0 |

TABLE 36-continued

| | | | | | | | | | | | | | |
|---|---|---|---|---|---|---|---|---|---|---|---|---|---|
| FCBBF30195640 | 100 | 0 | 0 | 0 | 0 | 0 | 0 | 0 | 0 | 0 | 0 | 0 | 0 |
| FCBBF30199610 | 100 | 0 | 0 | 0 | 0 | 0 | 0 | 0 | 0 | 0 | 0 | 0 | 0 |
| FCBBF30215060 | 100 | 0 | 0 | 0 | 0 | 0 | 0 | 0 | 0 | 0 | 0 | 0 | 0 |
| FCBBF30225660 | 64.881 | 0 | 0 | 0 | 0 | 0 | 35.119 | 0 | 0 | 0 | 0 | 0 | 0 |
| FCBBF30240960 | 100 | 0 | 0 | 0 | 0 | 0 | 0 | 0 | 0 | 0 | 0 | 0 | 0 |
| FCBBF30242250 | 100 | 0 | 0 | 0 | 0 | 0 | 0 | 0 | 0 | 0 | 0 | 0 | 0 |
| FCBBF30243640 | 100 | 0 | 0 | 0 | 0 | 0 | 0 | 0 | 0 | 0 | 0 | 0 | 0 |
| FCBBF30247930 | 29.517 | 0 | 0 | 11.34 | 0 | 0 | 0 | 0 | 0 | 0 | 0 | 0 | 0 |
| FCBBF30252520 | 100 | 0 | 0 | 0 | 0 | 0 | 0 | 0 | 0 | 0 | 0 | 0 | 0 |
| FCBBF30252800 | 100 | 0 | 0 | 0 | 0 | 0 | 0 | 0 | 0 | 0 | 0 | 0 | 0 |
| FCBBF30252850 | 44.606 | 0 | 0 | 0 | 0 | 0 | 0 | 55.394 | 0 | 0 | 0 | 0 | 0 |
| FCBBF30262510 | 100 | 0 | 0 | 0 | 0 | 0 | 0 | 0 | 0 | 0 | 0 | 0 | 0 |
| FCBBF30266780 | 100 | 0 | 0 | 0 | 0 | 0 | 0 | 0 | 0 | 0 | 0 | 0 | 0 |
| FCBBF30266920 | 29.977 | 0 | 0 | 11.517 | 0 | 0 | 0 | 0 | 0 | 0 | 58.507 | 0 | 0 |
| FCBBF30278630 | 100 | 0 | 0 | 0 | 0 | 0 | 0 | 0 | 0 | 0 | 0 | 0 | 0 |
| FCBBF30279030 | 100 | 0 | 0 | 0 | 0 | 0 | 0 | 0 | 0 | 0 | 0 | 0 | 0 |
| FCBBF30281880 | 100 | 0 | 0 | 0 | 0 | 0 | 0 | 0 | 0 | 0 | 0 | 0 | 0 |
| FCBBF30284720 | 100 | 0 | 0 | 0 | 0 | 0 | 0 | 0 | 0 | 0 | 0 | 0 | 0 |
| FCBBF30285280 | 100 | 0 | 0 | 0 | 0 | 0 | 0 | 0 | 0 | 0 | 0 | 0 | 0 |
| FCBBF40001730 | 100 | 0 | 0 | 0 | 0 | 0 | 0 | 0 | 0 | 0 | 0 | 0 | 0 |
| FCBBF40005480 | 27.002 | 0 | 0 | 10.374 | 0 | 14.727 | 0 | 0 | 0 | 0 | 0 | 0 | 0 |

TABLE 37

| | | | | | | | | | | | | | |
|---|---|---|---|---|---|---|---|---|---|---|---|---|---|
| HCHON20007380 | 5.501 | 0 | 0 | 0 | 0 | 0 | 0 | 0 | 0 | 0 | 11.082 | 0 | 0 |
| HEART20072310 | 8.949 | 0 | 0 | 0 | 0 | 4.881 | 0 | 0 | 0 | 4.942 | 0 | 0 | 0 |
| HHDPC20068620 | 13.827 | 0 | 0 | 0 | 0 | 7.541 | 0 | 0 | 0 | 0 | 0 | 0 | 0 |
| HLUNG20023340 | 16.982 | 0 | 0 | 0 | 0 | 0 | 0 | 0 | 0 | 0 | 0 | 0 | 0 |
| KIDNE20017130 | 28.625 | 0 | 0 | 0 | 0 | 0 | 0 | 0 | 0 | 0 | 0 | 0 | 0 |
| KIDNE20028830 | 8.38 | 0 | 0 | 0 | 0 | 0 | 0 | 5.203 | 0 | 0 | 8.442 | 8.178 | 0 |
| MESAN20014500 | 5.328 | 0 | 0 | 6.141 | 0 | 0 | 0 | 0 | 0 | 0 | 0 | 0 | 0 |
| NT2RP70072690 | 43.392 | 0 | 0 | 0 | 0 | 0 | 0 | 0 | 0 | 0 | 0 | 0 | 0 |
| NT2RP70137640 | 20.975 | 0 | 0 | 0 | 0 | 0 | 0 | 0 | 0 | 11.583 | 0 | 0 | 0 |
| NTONG20067090 | 16.742 | 0 | 0 | 0 | 0 | 0 | 0 | 0 | 0 | 0 | 0 | 0 | 0 |
| PLACE60004630 | 14.415 | 0 | 0 | 0 | 0 | 0 | 0 | 17.901 | 0 | 0 | 0 | 0 | 0 |
| PROST20083600 | 3.325 | 0 | 0 | 2.555 | 0 | 0 | 1.8 | 0 | 0 | 1.836 | 0 | 0 | 3.992 |
| PROST20189770 | 24.007 | 0 | 0 | 0 | 0 | 0 | 0 | 0 | 0 | 0 | 0 | 0 | 14.411 |
| RECTM20003490 | 7.826 | 0 | 0 | 0 | 0 | 0 | 0 | 0 | 0 | 0 | 0 | 0 | 0 |
| SKNSH20008190 | 4.598 | 0 | 0 | 1.767 | 8.994 | 12.539 | 2.489 | 0 | 0 | 0 | 0 | 0 | 8.28 |
| SMINT20115880 | 34.363 | 0 | 0 | 0 | 0 | 0 | 0 | 0 | 0 | 0 | 0 | 0 | 0 |
| SPLEN20169720 | 3.746 | 0 | 0 | 2.878 | 0 | 0 | 0 | 0 | 0 | 2.069 | 0 | 0 | 0 |
| SPLEN20194050 | 2.646 | 0 | 0 | 1.016 | 0 | 7.215 | 1.432 | 6.571 | 5.073 | 1.461 | 0 | 0 | 1.588 |
| SPLEN20284240 | 51.503 | 0 | 0 | 0 | 0 | 0 | 0 | 0 | 0 | 0 | 0 | 0 | 0 |
| TESTI20083940 | 73.865 | 0 | 0 | 0 | 0 | 0 | 0 | 0 | 0 | 0 | 0 | 0 | 0 |
| TESTI20213150 | 37.439 | 0 | 0 | 0 | 0 | 0 | 0 | 0 | 0 | 0 | 0 | 0 | 0 |
| TESTI20254540 | 20.808 | 0 | 0 | 0 | 0 | 0 | 0 | 0 | 0 | 0 | 0 | 0 | 12.49 |
| TESTI20265250 | 16.076 | 0 | 0 | 3.088 | 0 | 0 | 0 | 0 | 0 | 0 | 16.193 | 0 | 0 |
| TRACH20118940 | 32.856 | 0 | 0 | 0 | 0 | 8.96 | 0 | 0 | 0 | 0 | 0 | 32.063 | 0 |
| UTERU20145480 | 60.769 | 0 | 0 | 0 | 0 | 0 | 0 | 0 | 0 | 0 | 0 | 0 | 0 |
| UTERU20146680 | 60.769 | 0 | 0 | 0 | 0 | 0 | 0 | 0 | 0 | 0 | 0 | 0 | 0 |
| ASTR020155290 | 0 | 9.237 | 0 | 0 | 0 | 0 | 0 | 0 | 0 | 0 | 0 | 0 | 0 |
| BRAWH20030250 | 0 | 7.559 | 0 | 0 | 10.956 | 3.055 | 6.064 | 0 | 0 | 0 | 11.285 | 0 | 0 |
| BRAWH20113430 | 0 | 17.488 | 0 | 9.958 | 0 | 0 | 7.015 | 0 | 0 | 7.157 | 0 | 0 | 7.779 |
| BRAWH20122770 | 0 | 71.37 | 0 | 0 | 0 | 0 | 28.63 | 0 | 0 | 0 | 0 | 0 | 0 |
| BRHIP20005340 | 0 | 0.853 | 0 | 0 | 0 | 0 | 0.342 | 0 | 0 | 0.349 | 0 | 0 | 0 |
| BRHIP30001110 | 0 | 2.552 | 0 | 0.727 | 3.699 | 2.063 | 0 | 2.349 | 3.627 | 3.133 | 3.81 | 3.691 | 3.406 |
| BRSTN20002200 | 0 | 8.553 | 0 | 0 | 0 | 20.742 | 0 | 7.871 | 0 | 10.501 | 0 | 37.113 | 15.219 |
| CTONG20052900 | 0 | 57.236 | 0 | 0 | 0 | 0 | 0 | 0 | 0 | 0 | 0 | 0 | 0 |
| CTONG20108210 | 0 | 3.563 | 0 | 3.55 | 0 | 1.44 | 1.429 | 0 | 0 | 2.187 | 0 | 0 | 3.17 |
| DFNES20031920 | 0 | 7.467 | 0 | 0 | 0 | 3.018 | 0 | 0 | 0 | 0 | 0 | 0 | 0 |
| FEBRA10001900 | 0 | 19.812 | 0 | 0 | 0 | 0 | 0 | 18.233 | 0 | 0 | 0 | 0 | 0 |

TABLE 38

| | | | | | | | | | | | | | |
|---|---|---|---|---|---|---|---|---|---|---|---|---|---|
| FEBRA20003210 | 0 | 100 | 0 | 0 | 0 | 0 | 0 | 0 | 0 | 0 | 0 | 0 | 0 |
| FEBRA20007620 | 0 | 15.507 | 0 | 0 | 0 | 0 | 0 | 0 | 0 | 0 | 0 | 22.43 | 0 |
| FEBRA20009090 | 0 | 100 | 0 | 0 | 0 | 0 | 0 | 0 | 0 | 0 | 0 | 0 | 0 |
| FEBRA20010120 | 0 | 100 | 0 | 0 | 0 | 0 | 0 | 0 | 0 | 0 | 0 | 0 | 0 |
| FEBRA20017050 | 0 | 100 | 0 | 0 | 0 | 0 | 0 | 0 | 0 | 0 | 0 | 0 | 0 |
| FEBRA20018280 | 0 | 27.125 | 0 | 3.861 | 0 | 0 | 0 | 0 | 0 | 0 | 0 | 0 | 0 |
| FEBRA20025270 | 0 | 7.139 | 0 | 0 | 0 | 2.886 | 0 | 0 | 0 | 0 | 0 | 0 | 0 |
| FEBRA20025520 | 0 | 100 | 0 | 0 | 0 | 0 | 0 | 0 | 0 | 0 | 0 | 0 | 0 |
| FEBRA20026110 | 0 | 54.171 | 0 | 0 | 0 | 0 | 21.73 | 0 | 0 | 0 | 0 | 24.098 | 0 |
| FEBRA20026280 | 0 | 100 | 0 | 0 | 0 | 0 | 0 | 0 | 0 | 0 | 0 | 0 | 0 |

TABLE 38-continued

| | | | | | | | | | | | | | |
|---|---|---|---|---|---|---|---|---|---|---|---|---|---|
| FEBRA20029860 | 0 | 100 | 0 | 0 | 0 | 0 | 0 | 0 | 0 | 0 | 0 | 0 | 0 |
| FEBRA20034680 | 0 | 100 | 0 | 0 | 0 | 0 | 0 | 0 | 0 | 0 | 0 | 0 | 0 |
| FEBRA20037260 | 0 | 2.482 | 0 | 0.707 | 3.598 | 1.003 | 0 | 2.285 | 0 | 0 | 0 | 0 | 1.104 |
| FEBRA20040530 | 0 | 100 | 0 | 0 | 0 | 0 | 0 | 0 | 0 | 0 | 0 | 0 | 0 |
| FEBRA20042190 | 0 | 70.959 | 0 | 0 | 0 | 0 | 0 | 0 | 0 | 29.041 | 0 | 0 | 0 |
| FEBRA20052910 | 0 | 9.04 | 0 | 0 | 0 | 0 | 0 | 0 | 0 | 0 | 0 | 13.076 | 0 |
| FEBRA20060610 | 0 | 100 | 0 | 0 | 0 | 0 | 0 | 0 | 0 | 0 | 0 | 0 | 0 |
| FEBRA20072120 | 0 | 9.786 | 0 | 11.144 | 0 | 0 | 0 | 0 | 0 | 16.019 | 0 | 0 | 4.353 |
| FEBRA20079310 | 0 | 100 | 0 | 0 | 0 | 0 | 0 | 0 | 0 | 0 | 0 | 0 | 0 |
| FEBRA20082010 | 0 | 5.978 | 0 | 0 | 0 | 0 | 2.398 | 0 | 0 | 0 | 0 | 0 | 2.659 |
| FEBRA20088360 | 0 | 79.225 | 0 | 0 | 0 | 0 | 0 | 0 | 0 | 0 | 0 | 0 | 0 |
| FEBRA20090290 | 0 | 100 | 0 | 0 | 0 | 0 | 0 | 0 | 0 | 0 | 0 | 0 | 0 |
| FEBRA20092890 | 0 | 34.98 | 0 | 0 | 50.703 | 0 | 0 | 0 | 0 | 14.316 | 0 | 0 | 0 |
| FEBRA20093520 | 0 | 70.959 | 0 | 0 | 0 | 0 | 0 | 0 | 0 | 29.041 | 0 | 0 | 0 |
| FEBRA20097310 | 0 | 100 | 0 | 0 | 0 | 0 | 0 | 0 | 0 | 0 | 0 | 0 | 0 |
| FEBRA20113560 | 0 | 100 | 0 | 0 | 0 | 0 | 0 | 0 | 0 | 0 | 0 | 0 | 0 |
| FEBRA20125070 | 0 | 18.603 | 0 | 0 | 26.964 | 0 | 0 | 0 | 0 | 0 | 0 | 0 | 0 |
| FEBRA20132740 | 0 | 100 | 0 | 0 | 0 | 0 | 0 | 0 | 0 | 0 | 0 | 0 | 0 |
| FEBRA20140100 | 0 | 40.243 | 0 | 0 | 0 | 0 | 0 | 0 | 0 | 0 | 0 | 0 | 0 |
| FEBRA20161120 | 0 | 100 | 0 | 0 | 0 | 0 | 0 | 0 | 0 | 0 | 0 | 0 | 0 |
| FEBRA20166540 | 0 | 100 | 0 | 0 | 0 | 0 | 0 | 0 | 0 | 0 | 0 | 0 | 0 |
| FEBRA20167390 | 0 | 100 | 0 | 0 | 0 | 0 | 0 | 0 | 0 | 0 | 0 | 0 | 0 |
| FEBRA20171380 | 0 | 100 | 0 | 0 | 0 | 0 | 0 | 0 | 0 | 0 | 0 | 0 | 0 |
| FEBRA20176800 | 0 | 23.704 | 0 | 0 | 0 | 9.581 | 0 | 21.815 | 0 | 9.701 | 0 | 0 | 0 |
| FEBRA20184330 | 0 | 77.838 | 0 | 22.162 | 0 | 0 | 0 | 0 | 0 | 0 | 0 | 0 | 0 |
| FEBRA20192420 | 0 | 20.225 | 0 | 5.758 | 0 | 0 | 0 | 0 | 0 | 8.277 | 0 | 0 | 0 |
| FEBRA20195820 | 0 | 100 | 0 | 0 | 0 | 0 | 0 | 0 | 0 | 0 | 0 | 0 | 0 |

TABLE 39

| | | | | | | | | | | | | | |
|---|---|---|---|---|---|---|---|---|---|---|---|---|---|
| FEBRA20196370 | 0 | 40.753 | 0 | 0 | 0 | 0 | 0 | 0 | 0 | 0 | 0 | 0 | 0 |
| FEBRA20196630 | 0 | 21.712 | 0 | 0 | 0 | 0 | 0 | 0 | 0 | 0 | 0 | 0 | 0 |
| FEBRA20197110 | 0 | 5.271 | 0 | 0 | 0 | 0 | 0 | 4.851 | 0 | 0 | 0 | 0 | 2.345 |
| FEBRA20211710 | 0 | 26.519 | 0 | 0 | 0 | 10.719 | 0 | 24.406 | 0 | 0 | 0 | 38.357 | 0 |
| FEBRA20214970 | 0 | 100 | 0 | 0 | 0 | 0 | 0 | 0 | 0 | 0 | 0 | 0 | 0 |
| FEBRA20215500 | 0 | 77.838 | 0 | 22.162 | 0 | 0 | 0 | 0 | 0 | 0 | 0 | 0 | 0 |
| FEBRA20216360 | 0 | 50.44 | 0 | 14.361 | 0 | 0 | 0 | 0 | 0 | 0 | 0 | 0 | 0 |
| FEBRA20222040 | 0 | 100 | 0 | 0 | 0 | 0 | 0 | 0 | 0 | 0 | 0 | 0 | 0 |
| FEBRA20223220 | 0 | 100 | 0 | 0 | 0 | 0 | 0 | 0 | 0 | 0 | 0 | 0 | 0 |
| FEBRA20225040 | 0 | 4.094 | 0 | 0 | 0 | 0 | 0 | 3.768 | 11.636 | 0 | 0 | 0 | 0 |
| FEBRA20226010 | 0 | 77.838 | 0 | 22.162 | 0 | 0 | 0 | 0 | 0 | 0 | 0 | 0 | 0 |
| FEBRA20229560 | 0 | 100 | 0 | 0 | 0 | 0 | 0 | 0 | 0 | 0 | 0 | 0 | 0 |
| FEBRA20229630 | 0 | 100 | 0 | 0 | 0 | 0 | 0 | 0 | 0 | 0 | 0 | 0 | 0 |
| FEBRA20232850 | 0 | 100 | 0 | 0 | 0 | 0 | 0 | 0 | 0 | 0 | 0 | 0 | 0 |
| FEBRA20235500 | 0 | 40.825 | 0 | 0 | 59.175 | 0 | 0 | 0 | 0 | 0 | 0 | 0 | 0 |
| HCHON20040020 | 0 | 1.957 | 0 | 0 | 0 | 1.582 | 0 | 0 | 0 | 0 | 0 | 0 | 1.741 |
| KIDNE20102650 | 0 | 5.89 | 0 | 0 | 0 | 0 | 2.363 | 0 | 0 | 0 | 0 | 0 | 0 |
| NT2RP70037240 | 0 | 23.02 | 0 | 26.217 | 0 | 0 | 0 | 0 | 0 | 0 | 0 | 0 | 0 |
| PEBLM20072960 | 0 | 4.311 | 0 | 0 | 0 | 0 | 0 | 0 | 0 | 0 | 0 | 0 | 0 |
| PLACE60169420 | 0 | 9.752 | 0 | 0 | 0 | 3.942 | 3.912 | 8.975 | 13.858 | 0 | 14.56 | 0 | 4.338 |
| SKMUS20003610 | 0 | 2.666 | 0 | 0 | 0 | 1.077 | 0 | 2.453 | 0 | 0 | 0 | 0 | 0 |
| SMINT20026890 | 0 | 2.93 | 0 | 10.012 | 0 | 1.184 | 4.702 | 0 | 0 | 0 | 0 | 0 | 1.304 |
| SMINT20033400 | 0 | 7.324 | 0 | 0 | 0 | 2.96 | 0 | 0 | 0 | 0 | 0 | 0 | 0 |
| SPLEN20020070 | 0 | 47.573 | 0 | 0 | 0 | 19.229 | 0 | 0 | 0 | 0 | 0 | 0 | 0 |
| SPLEN20079510 | 0 | 58.898 | 0 | 0 | 0 | 0 | 0 | 0 | 0 | 0 | 0 | 0 | 0 |
| TESTI20001000 | 0 | 48.295 | 0 | 0 | 0 | 39.041 | 0 | 0 | 0 | 0 | 0 | 0 | 0 |
| TESTI20094020 | 0 | 22.853 | 0 | 0 | 0 | 9.237 | 0 | 0 | 0 | 0 | 0 | 0 | 0 |
| THYMU20027560 | 0 | 18.25 | 0 | 0 | 0 | 0 | 0 | 0 | 0 | 0 | 0 | 0 | 0 |
| THYMU20180280 | 0 | 74.935 | 0 | 0 | 0 | 0 | 0 | 0 | 0 | 0 | 0 | 0 | 0 |
| THYMU20271250 | 0 | 0.446 | 0 | 2.287 | 2.587 | 0.902 | 0.179 | 0.411 | 0 | 0 | 0 | 4.518 | 0.198 |
| TRACH20003590 | 0 | 7.434 | 0 | 0 | 0 | 0 | 0 | 0 | 0 | 3.042 | 0 | 0 | 0 |
| UMVEN10001560 | 0 | 2.576 | 0 | 0 | 0 | 0 | 0 | 0 | 0 | 0 | 0 | 0 | 0 |
| UTERU20022940 | 0 | 13.576 | 0 | 0 | 0 | 0 | 1.815 | 0 | 0 | 0 | 0 | 0 | 4.026 |
| UTERU20046640 | 0 | 4.23 | 0 | 0 | 0 | 1.71 | 1.697 | 0 | 0 | 0 | 0 | 0 | 1.882 |
| UTERU20119060 | 0 | 17 | 0 | 0 | 0 | 13.742 | 13.639 | 0 | 0 | 0 | 0 | 0 | 0 |
| UTERU20144640 | 0 | 33.653 | 0 | 0 | 0 | 0 | 0 | 0 | 0 | 0 | 50.246 | 0 | 0 |
| UTERU20176130 | 0 | 51.268 | 0 | 0 | 0 | 0 | 0 | 0 | 0 | 0 | 0 | 0 | 0 |

TABLE 40

| | | | | | | | | | | | | | |
|---|---|---|---|---|---|---|---|---|---|---|---|---|---|
| ASTRO20008010 | 0 | 0 | 1.267 | 0 | 0 | 0 | 0 | 0 | 0 | 0 | 0 | 0 | 0 |
| BRACE20276430 | 0 | 0 | 17.893 | 10.223 | 0 | 0 | 0 | 33.045 | 0 | 0 | 0 | 0 | 0 |
| BRAMY20103570 | 0 | 0 | 18.549 | 21.196 | 0 | 30.09 | 14.931 | 0 | 0 | 15.234 | 0 | 0 | 0 |
| BRAMY20120910 | 0 | 0 | 7.377 | 0 | 0 | 5.983 | 0 | 0 | 0 | 0 | 0 | 0 | 0 |

TABLE 40-continued

| | | | | | | | | | | | | | |
|---|---|---|---|---|---|---|---|---|---|---|---|---|---|
| BRAMY20162510 | 0 | 0 | 8.934 | 5.104 | 25.986 | 43.477 | 0 | 16.499 | 0 | 0 | 0 | 0 | 0 |
| BRAMY20196000 | 0 | 0 | 30.091 | 0 | 0 | 8.135 | 16.148 | 0 | 0 | 0 | 0 | 0 | 8.954 |
| BRAWH20164460 | 0 | 0 | 10.808 | 0 | 0 | 0 | 8.7 | 0 | 0 | 0 | 0 | 0 | 0 |
| BRCAN20273640 | 0 | 0 | 7.379 | 0 | 10.731 | 5.985 | 2.97 | 20.44 | 21.042 | 0 | 11.054 | 0 | 13.174 |
| BRC0C20105100 | 0 | 0 | 14.918 | 0 | 0 | 0 | 0 | 0 | 85.082 | 0 | 0 | 0 | 0 |
| BRHIP20198190 | 0 | 0 | 10.771 | 30.77 | 0 | 0 | 8.671 | 0 | 0 | 17.692 | 0 | 0 | 0 |
| BRHIP20222280 | 0 | 0 | 11.352 | 0 | 0 | 0 | 9.138 | 20.964 | 0 | 9.323 | 0 | 0 | 0 |
| BRHIP20254480 | 0 | 0 | 37.989 | 0 | 0 | 30.812 | 0 | 0 | 0 | 31.199 | 0 | 0 | 0 |
| BRHIP30004570 | 0 | 0 | 33.739 | 38.553 | 0 | 0 | 0 | 0 | 0 | 27.708 | 0 | 0 | 0 |
| CT0NG20028410 | 0 | 0 | 26.318 | 15.036 | 0 | 0 | 21.185 | 0 | 0 | 10.807 | 0 | 0 | 0 |
| CT0NG20091080 | 0 | 0 | 29.481 | 0 | 0 | 0 | 0 | 0 | 0 | 0 | 0 | 0 | 26.317 |
| CT0NG20103480 | 0 | 0 | 2.2 | 7.541 | 0 | 1.784 | 3.542 | 4.063 | 0 | 1.807 | 6.591 | 0 | 3.927 |
| CT0NG20126070 | 0 | 0 | 2.148 | 0 | 0 | 0 | 0 | 0 | 0 | 0 | 0 | 0 | 5.754 |
| CT0NG20139340 | 0 | 0 | 8.617 | 24.615 | 0 | 0 | 6.936 | 0 | 0 | 7.077 | 0 | 0 | 7.692 |
| DFNES20001530 | 0 | 0 | 3.977 | 0 | 0 | 0 | 0 | 0 | 0 | 0 | 0 | 0 | 3.551 |
| HCHON20008150 | 0 | 0 | 3.469 | 0 | 0 | 2.814 | 2.793 | 0 | 0 | 0 | 10.394 | 0 | 0 |
| HHDPC20001040 | 0 | 0 | 4.596 | 1.313 | 0 | 0 | 0 | 0 | 0 | 0 | 0 | 0 | 2.052 |
| HLUNG20016330 | 0 | 0 | 9.947 | 0 | 0 | 0 | 0 | 0 | 0 | 0 | 0 | 0 | 0 |
| HLUNG20017120 | 0 | 0 | 4.096 | 0 | 35.74 | 0 | 0 | 0 | 0 | 0 | 0 | 0 | 0 |
| IMR3220002430 | 0 | 0 | 2.132 | 1.218 | 0 | 1.729 | 0 | 0 | 0 | 2.626 | 0 | 0 | 0.951 |
| KIDNE20007210 | 0 | 0 | 26.272 | 0 | 0 | 0 | 0 | 0 | 0 | 0 | 0 | 0 | 0 |
| KIDNE20021910 | 0 | 0 | 17.71 | 15.177 | 0 | 0 | 0 | 0 | 0 | 0 | 0 | 0 | 7.905 |
| KIDNE20124400 | 0 | 0 | 2.199 | 2.513 | 0 | 0 | 0 | 0 | 0 | 3.612 | 6.588 | 0 | 3.926 |
| MESAN10001260 | 0 | 0 | 2.218 | 7.605 | 0 | 0 | 1.786 | 0 | 0 | 3.644 | 0 | 0 | 1.98 |
| MESAN20029400 | 0 | 0 | 3.951 | 0 | 0 | 0 | 3.18 | 0 | 0 | 0 | 0 | 0 | 0 |
| MESAN20121130 | 0 | 0 | 7.329 | 0 | 0 | 0 | 0 | 0 | 0 | 6.019 | 0 | 0 | 6.543 |
| MESAN20153910 | 0 | 0 | 25.095 | 0 | 0 | 0 | 0 | 0 | 0 | 0 | 0 | 0 | 0 |
| NT2NE20159740 | 0 | 0 | 18.979 | 21.687 | 0 | 7.697 | 0 | 0 | 0 | 0 | 0 | 0 | 8.471 |
| NT2NE20177520 | 0 | 0 | 29.166 | 0 | 0 | 0 | 0 | 0 | 0 | 0 | 0 | 0 | 0 |
| NT2RI20086220 | 0 | 0 | 3.92 | 0 | 0 | 0 | 0 | 0 | 0 | 0 | 0 | 0 | 6.999 |
| NT2RI20250750 | 0 | 0 | 21.061 | 12.033 | 0 | 0 | 0 | 0 | 0 | 17.297 | 0 | 0 | 18.801 |
| NT2RP6000850 | 0 | 0 | 5.745 | 3.283 | 0 | 4.66 | 4.625 | 0 | 0 | 0 | 0 | 0 | 5.129 |
| NT2RP70044280 | 0 | 0 | 12.569 | 7.181 | 0 | 6.796 | 16.862 | 0 | 0 | 6.881 | 0 | 0 | 0 |

TABLE 41

| | | | | | | | | | | | | | |
|---|---|---|---|---|---|---|---|---|---|---|---|---|---|
| NT2RP70056750 | 0 | 0 | 7.226 | 8.256 | 0 | 5.861 | 11.633 | 0 | 0 | 8.901 | 0 | 0 | 3.225 |
| NT2RP70081610 | 0 | 0 | 15.599 | 4.456 | 0 | 0 | 0 | 0 | 6.405 | 0 | 0 | 0 | 0 |
| NT0NG20009770 | 0 | 0 | 2.442 | 0 | 0 | 0 | 0 | 2.255 | 3.482 | 0 | 0 | 0 | 0 |
| OCBBF10000540 | 0 | 0 | 100 | 0 | 0 | 0 | 0 | 0 | 0 | 0 | 0 | 0 | 0 |
| OCBBF10001750 | 0 | 0 | 17.896 | 5.112 | 0 | 7.258 | 0 | 0 | 0 | 0 | 0 | 0 | 0 |
| OCBBF20006770 | 0 | 0 | 20.236 | 0 | 0 | 16.413 | 0 | 0 | 0 | 0 | 0 | 0 | 0 |
| OCBBF20013890 | 0 | 0 | 100 | 0 | 0 | 0 | 0 | 0 | 0 | 0 | 0 | 0 | 0 |
| OCBBF20019830 | 0 | 0 | 8.974 | 0 | 0 | 0 | 0 | 0 | 0 | 0 | 0 | 0 | 0 |
| OCBBF20020150 | 0 | 0 | 17.182 | 9.817 | 0 | 0 | 0 | 0 | 0 | 0 | 0 | 0 | 15.338 |
| OCBBF20020830 | 0 | 0 | 27.302 | 0 | 0 | 0 | 0 | 25.211 | 0 | 0 | 0 | 0 | 0 |
| OCBBF20023570 | 0 | 0 | 100 | 0 | 0 | 0 | 0 | 0 | 0 | 0 | 0 | 0 | 0 |
| OCBBF20028050 | 0 | 0 | 100 | 0 | 0 | 0 | 0 | 0 | 0 | 0 | 0 | 0 | 0 |
| OCBBF20028650 | 0 | 0 | 65.522 | 0 | 0 | 0 | 0 | 0 | 0 | 0 | 0 | 0 | 0 |
| OCBBF20029800 | 0 | 0 | 54.907 | 0 | 0 | 0 | 0 | 0 | 0 | 45.093 | 0 | 0 | 0 |
| OCBBF20030280 | 0 | 0 | 100 | 0 | 0 | 0 | 0 | 0 | 0 | 0 | 0 | 0 | 0 |
| OCBBF20030910 | 0 | 0 | 100 | 0 | 0 | 0 | 0 | 0 | 0 | 0 | 0 | 0 | 0 |
| OCBBF20035930 | 0 | 0 | 55.403 | 0 | 0 | 0 | 44.597 | 0 | 0 | 0 | 0 | 0 | 0 |
| OCBBF20037440 | 0 | 0 | 52.585 | 0 | 0 | 0 | 0 | 0 | 0 | 0 | 0 | 0 | 0 |
| OCBBF20041680 | 0 | 0 | 100 | 0 | 0 | 0 | 0 | 0 | 0 | 0 | 0 | 0 | 0 |
| OCBBF20045330 | 0 | 0 | 25.025 | 0 | 0 | 0 | 0 | 0 | 0 | 0 | 74.975 | 0 | 0 |
| OCBBF20046120 | 0 | 0 | 100 | 0 | 0 | 0 | 0 | 0 | 0 | 0 | 0 | 0 | 0 |
| OCBBF20046470 | 0 | 0 | 100 | 0 | 0 | 0 | 0 | 0 | 0 | 0 | 0 | 0 | 0 |
| OCBBF20046690 | 0 | 0 | 54.907 | 0 | 0 | 0 | 0 | 0 | 0 | 45.093 | 0 | 0 | 0 |
| OCBBF20048660 | 0 | 0 | 100 | 0 | 0 | 0 | 0 | 0 | 0 | 0 | 0 | 0 | 0 |
| OCBBF20050770 | 0 | 0 | 100 | 0 | 0 | 0 | 0 | 0 | 0 | 0 | 0 | 0 | 0 |
| OCBBF20051610 | 0 | 0 | 54.907 | 0 | 0 | 0 | 0 | 0 | 0 | 45.093 | 0 | 0 | 0 |
| OCBBF20053430 | 0 | 0 | 100 | 0 | 0 | 0 | 0 | 0 | 0 | 0 | 0 | 0 | 0 |
| OCBBF20053490 | 0 | 0 | 100 | 0 | 0 | 0 | 0 | 0 | 0 | 0 | 0 | 0 | 0 |
| OCBBF20053730 | 0 | 0 | 100 | 0 | 0 | 0 | 0 | 0 | 0 | 0 | 0 | 0 | 0 |
| OCBBF20054200 | 0 | 0 | 78.844 | 0 | 0 | 0 | 21.156 | 0 | 0 | 0 | 0 | 0 | 0 |
| OCBBF20054760 | 0 | 0 | 5.808 | 0 | 0 | 4.71 | 0 | 0 | 0 | 0 | 0 | 0 | 0 |
| OCBBF20060300 | 0 | 0 | 100 | 0 | 0 | 0 | 0 | 0 | 0 | 0 | 0 | 0 | 0 |
| OCBBF20062140 | 0 | 0 | 100 | 0 | 0 | 0 | 0 | 0 | 0 | 0 | 0 | 0 | 0 |
| OCBBF20062410 | 0 | 0 | 100 | 0 | 0 | 0 | 0 | 0 | 0 | 0 | 0 | 0 | 0 |
| OCBBF20066390 | 0 | 0 | 100 | 0 | 0 | 0 | 0 | 0 | 0 | 0 | 0 | 0 | 0 |
| OCBBF20071210 | 0 | 0 | 52.585 | 0 | 0 | 0 | 0 | 0 | 0 | 0 | 0 | 0 | 0 |
| OCBBF20071840 | 0 | 0 | 100 | 0 | 0 | 0 | 0 | 0 | 0 | 0 | 0 | 0 | 0 |

TABLE 42

| OCBBF20072240 | 0 | 0 | 11.73 | 6.702 | 0 | 0 | 9.442 | 0 | 0 | 0 | 0 | 0 | 0 |
|---|---|---|---|---|---|---|---|---|---|---|---|---|---|
| OCBBF20073540 | 0 | 0 | 1.248 | 0.713 | 0 | 1.012 | 3.014 | 2.305 | 0 | 0 | 0 | 0 | 1.114 |
| OCBBF20074140 | 0 | 0 | 59.836 | 0 | 0 | 0 | 0 | 0 | 0 | 0 | 0 | 0 | 0 |
| OCBBF20076220 | 0 | 0 | 4.561 | 2.606 | 0 | 0 | 0 | 0 | 0 | 0 | 0 | 0 | 0 |
| OCBBF20079310 | 0 | 0 | 100 | 0 | 0 | 0 | 0 | 0 | 0 | 0 | 0 | 0 | 0 |
| OCBBF20079460 | 0 | 0 | 100 | 0 | 0 | 0 | 0 | 0 | 0 | 0 | 0 | 0 | 0 |
| OCBBF20081380 | 0 | 0 | 100 | 0 | 0 | 0 | 0 | 0 | 0 | 0 | 0 | 0 | 0 |
| OCBBF20082830 | 0 | 0 | 100 | 0 | 0 | 0 | 0 | 0 | 0 | 0 | 0 | 0 | 0 |
| OCBBF20085200 | 0 | 0 | 100 | 0 | 0 | 0 | 0 | 0 | 0 | 0 | 0 | 0 | 0 |
| OCBBF20086400 | 0 | 0 | 100 | 0 | 0 | 0 | 0 | 0 | 0 | 0 | 0 | 0 | 0 |
| OCBBF20086910 | 0 | 0 | 100 | 0 | 0 | 0 | 0 | 0 | 0 | 0 | 0 | 0 | 0 |
| OCBBF20088140 | 0 | 0 | 100 | 0 | 0 | 0 | 0 | 0 | 0 | 0 | 0 | 0 | 0 |
| OCBBF20088220 | 0 | 0 | 2.961 | 0 | 0 | 0 | 0 | 0 | 0 | 0 | 0 | 0 | 0 |
| OCBBF20091150 | 0 | 0 | 100 | 0 | 0 | 0 | 0 | 0 | 0 | 0 | 0 | 0 | 0 |
| OCBBF20100400 | 0 | 0 | 100 | 0 | 0 | 0 | 0 | 0 | 0 | 0 | 0 | 0 | 0 |
| OCBBF20103130 | 0 | 0 | 34.079 | 0 | 49.562 | 0 | 0 | 0 | 0 | 0 | 0 | 0 | 0 |
| OCBBF20104040 | 0 | 0 | 100 | 0 | 0 | 0 | 0 | 0 | 0 | 0 | 0 | 0 | 0 |
| OCBBF20105570 | 0 | 0 | 22.763 | 13.005 | 0 | 0 | 0 | 0 | 0 | 0 | 0 | 0 | 0 |
| OCBBF20107090 | 0 | 0 | 100 | 0 | 0 | 0 | 0 | 0 | 0 | 0 | 0 | 0 | 0 |
| OCBBF20107920 | 0 | 0 | 100 | 0 | 0 | 0 | 0 | 0 | 0 | 0 | 0 | 0 | 0 |
| OCBBF20108580 | 0 | 0 | 33.1 | 4.728 | 0 | 0 | 13.322 | 0 | 0 | 20.388 | 0 | 0 | 0 |
| OCBBF20108630 | 0 | 0 | 55.216 | 0 | 0 | 44.784 | 0 | 0 | 0 | 0 | 0 | 0 | 0 |
| OCBBF20109310 | 0 | 0 | 100 | 0 | 0 | 0 | 0 | 0 | 0 | 0 | 0 | 0 | 0 |
| OCBBF20111770 | 0 | 0 | 100 | 0 | 0 | 0 | 0 | 0 | 0 | 0 | 0 | 0 | 0 |
| OCBBF20116850 | 0 | 0 | 100 | 0 | 0 | 0 | 0 | 0 | 0 | 0 | 0 | 0 | 0 |
| OCBBF20118970 | 0 | 0 | 21.447 | 0 | 0 | 17.395 | 0 | 0 | 61.158 | 0 | 0 | 0 | 0 |
| OCBBF20120390 | 0 | 0 | 9.527 | 3.266 | 0 | 7.727 | 26.074 | 0 | 0 | 31.296 | 0 | 0 | 22.111 |
| OCBBF20121390 | 0 | 0 | 100 | 0 | 0 | 0 | 0 | 0 | 0 | 0 | 0 | 0 | 0 |
| OCBBF20122620 | 0 | 0 | 36.036 | 0 | 0 | 0 | 29.008 | 0 | 0 | 0 | 0 | 0 | 0 |
| OCBBF20124360 | 0 | 0 | 59.836 | 0 | 0 | 0 | 0 | 0 | 0 | 0 | 0 | 0 | 0 |
| OCBBF20127040 | 0 | 0 | 25.938 | 14.819 | 0 | 0 | 0 | 0 | 0 | 21.301 | 0 | 0 | 0 |
| OCBBF20127140 | 0 | 0 | 7.211 | 4.12 | 0 | 0 | 0 | 0 | 0 | 0 | 0 | 0 | 0 |
| OCBBF20127550 | 0 | 0 | 100 | 0 | 0 | 0 | 0 | 0 | 0 | 0 | 0 | 0 | 0 |
| OCBBF20128120 | 0 | 0 | 25.584 | 0 | 74.416 | 0 | 0 | 0 | 0 | 0 | 0 | 0 | 0 |
| OCBBF20129360 | 0 | 0 | 55.403 | 0 | 0 | 0 | 44.597 | 0 | 0 | 0 | 0 | 0 | 0 |
| OCBBF20130910 | 0 | 0 | 100 | 0 | 0 | 0 | 0 | 0 | 0 | 0 | 0 | 0 | 0 |
| OCBBF20132850 | 0 | 0 | 63.64 | 36.36 | 0 | 0 | 0 | 0 | 0 | 0 | 0 | 0 | 0 |

TABLE 43

| OCBBF20140890 | 0 | 0 | 24.517 | 0 | 0 | 19.885 | 19.735 | 0 | 0 | 0 | 0 | 0 | 0 |
|---|---|---|---|---|---|---|---|---|---|---|---|---|---|
| OCBBF20145760 | 0 | 0 | 4.539 | 2.593 | 0 | 0 | 0 | 0 | 0 | 3.728 | 0 | 0 | 4.052 |
| OCBBF20148280 | 0 | 0 | 100 | 0 | 0 | 0 | 0 | 0 | 0 | 0 | 0 | 0 | 0 |
| OCBBF20151150 | 0 | 0 | 44.332 | 12.664 | 0 | 0 | 0 | 0 | 0 | 0 | 0 | 0 | 0 |
| OCBBF20153340 | 0 | 0 | 65.522 | 0 | 0 | 0 | 0 | 0 | 0 | 0 | 0 | 0 | 0 |
| OCBBF20153350 | 0 | 0 | 100 | 0 | 0 | 0 | 0 | 0 | 0 | 0 | 0 | 0 | 0 |
| OCBBF20155060 | 0 | 0 | 100 | 0 | 0 | 0 | 0 | 0 | 0 | 0 | 0 | 0 | 0 |
| OCBBF20164670 | 0 | 0 | 100 | 0 | 0 | 0 | 0 | 0 | 0 | 0 | 0 | 0 | 0 |
| OCBBF20170690 | 0 | 0 | 100 | 0 | 0 | 0 | 0 | 0 | 0 | 0 | 0 | 0 | 0 |
| OCBBF20173060 | 0 | 0 | 55.403 | 0 | 0 | 0 | 44.597 | 0 | 0 | 0 | 0 | 0 | 0 |
| OCBBF20173250 | 0 | 0 | 100 | 0 | 0 | 0 | 0 | 0 | 0 | 0 | 0 | 0 | 0 |
| OCBBF20178150 | 0 | 0 | 65.522 | 0 | 0 | 0 | 0 | 0 | 0 | 0 | 0 | 0 | 0 |
| OCBBF20180840 | 0 | 0 | 16.434 | 9.389 | 0 | 4.443 | 4.41 | 0 | 0 | 0 | 0 | 0 | 0 |
| OCBBF20186870 | 0 | 0 | 100 | 0 | 0 | 0 | 0 | 0 | 0 | 0 | 0 | 0 | 0 |
| OCBBF20189560 | 0 | 0 | 2.102 | 3.604 | 0 | 1.705 | 0 | 0 | 0 | 0 | 0 | 0 | 1.877 |
| PEBLM20044520 | 0 | 0 | 5.03 | 1.916 | 0 | 2.72 | 10.797 | 0 | 0 | 12.393 | 0 | 0 | 5.987 |
| PEBLM20071880 | 0 | 0 | 10.845 | 0 | 0 | 0 | 0 | 0 | 0 | 0 | 0 | 0 | 0 |
| PLACE60060420 | 0 | 0 | 6.763 | 0 | 0 | 0 | 0 | 0 | 0 | 0 | 0 | 0 | 0 |
| PROST20047390 | 0 | 0 | 27.713 | 10.556 | 0 | 0 | 0 | 0 | 0 | 7.587 | 0 | 0 | 0 |
| PUAEN20003740 | 0 | 0 | 1.59 | 0.909 | 1.156 | 0.322 | 2.24 | 0 | 0 | 0.653 | 0 | 0 | 1.775 |
| SMINT20029760 | 0 | 0 | 6.48 | 0 | 0 | 0 | 10.432 | 0 | 0 | 5.322 | 0 | 0 | 0 |
| SPLEN20008820 | 0 | 0 | 2.182 | 0 | 0 | 0 | 0 | 0 | 0 | 0 | 0 | 0 | 1.948 |
| SPLEN20084600 | 0 | 0 | 1.627 | 0 | 0 | 0 | 0 | 0 | 0 | 2.673 | 0 | 0 | 0 |
| SPLEN20095550 | 0 | 0 | 10.552 | 0 | 0 | 0 | 0 | 0 | 0 | 0 | 0 | 0 | 9.419 |
| SPLEN20099700 | 0 | 0 | 12.671 | 0 | 0 | 0 | 0 | 0 | 0 | 5.203 | 0 | 0 | 0 |
| SPLEN20140800 | 0 | 0 | 11.772 | 3.363 | 0 | 0 | 0 | 0 | 0 | 0 | 0 | 0 | 0 |
| SPLEN20173510 | 0 | 0 | 7.473 | 2.135 | 0 | 0 | 9.023 | 0 | 0 | 0 | 11.195 | 0 | 6.671 |
| SPLEN20211220 | 0 | 0 | 20.261 | 0 | 0 | 0 | 0 | 0 | 0 | 33.279 | 0 | 0 | 18.087 |
| SPLEN20250170 | 0 | 0 | 41.66 | 0 | 0 | 0 | 0 | 0 | 0 | 0 | 0 | 0 | 0 |
| STOMA20067800 | 0 | 0 | 10.791 | 0 | 0 | 0 | 0 | 0 | 0 | 0 | 0 | 0 | 0 |
| TESTI20031270 | 0 | 0 | 13.265 | 0 | 0 | 10.759 | 0 | 0 | 0 | 0 | 0 | 0 | 0 |
| TESTI20116830 | 0 | 0 | 40.221 | 0 | 0 | 0 | 0 | 0 | 0 | 0 | 0 | 0 | 0 |
| TESTI20121550 | 0 | 0 | 7.961 | 0 | 0 | 0 | 6.408 | 0 | 0 | 6.538 | 0 | 0 | 7.106 |
| TESTI20234140 | 0 | 0 | 5.057 | 2.889 | 0 | 0 | 0 | 0 | 0 | 0 | 0 | 0 | 0 |

TABLE 43-continued

| | | | | | | | | | | | | | |
|---|---|---|---|---|---|---|---|---|---|---|---|---|---|
| TESTI20442760 | 0 | 0 | 11.782 | 0 | 0 | 0 | 0 | 10.879 | 0 | 0 | 0 | 0 | 10.517 |
| THYMU20039810 | 0 | 0 | 0.649 | 0 | 0 | 0 | 0.522 | 0 | 1.85 | 2.664 | 0 | 0 | 0.579 |
| THYMU20070360 | 0 | 0 | 19.184 | 0 | 0 | 7.78 | 0 | 0 | 0 | 0 | 0 | 0 | 8.562 |

TABLE 44

| | | | | | | | | | | | | | |
|---|---|---|---|---|---|---|---|---|---|---|---|---|---|
| TRACH20033230 | 0 | 0 | 4.422 | 0 | 0 | 7.173 | 7.119 | 0 | 0 | 9.079 | 0 | 0 | 3.947 |
| TRACH20084720 | 0 | 0 | 3.898 | 1.114 | 0 | 0 | 0 | 0 | 0 | 5.558 | 0 | 0 | 8.7 |
| BRACE20067430 | 0 | 22.168 | 11.047 | 15.779 | 0 | 4.48 | 8.892 | 0 | 0 | 4.536 | 33.098 | 0 | 0 |
| BRAWH10000930 | 0 | 1.15 | 2.292 | 0.655 | 0 | 0 | 0.461 | 0 | 0 | 0 | 1.717 | 0 | 0.511 |
| BRHIP20003120 | 0 | 16.166 | 8.056 | 9.205 | 0 | 6.534 | 32.424 | 0 | 0 | 13.232 | 0 | 0 | 14.383 |
| BRSSN20152380 | 0 | 8.534 | 8.505 | 4.859 | 0 | 0 | 10.27 | 0 | 0 | 6.985 | 12.742 | 0 | 0 |
| FEBRA20024100 | 0 | 66.741 | 33.259 | 0 | 0 | 0 | 0 | 0 | 0 | 0 | 0 | 0 | 0 |
| FEBRA20027810 | 0 | 17.057 | 25.5 | 43.707 | 0 | 6.894 | 6.842 | 0 | 0 | 0 | 0 | 0 | 0 |
| FEBRA20037500 | 0 | 9.102 | 2.268 | 2.591 | 0 | 1.839 | 0 | 0 | 0 | 12.934 | 1.862 | 0 | 6.073 |
| FEBRA20082100 | 0 | 16.72 | 8.332 | 4.761 | 0 | 6.758 | 0 | 0 | 0 | 23.761 | 0 | 0 | 0 |
| FEBRA20098460 | 0 | 51.462 | 25.645 | 0 | 0 | 0 | 0 | 0 | 0 | 0 | 0 | 0 | 22.893 |
| FEBRA20144170 | 0 | 4.038 | 2.012 | 0.766 | 0 | 3.264 | 7.559 | 6.194 | 3.826 | 3.856 | 4.019 | 5.841 | 1.198 |
| FEBRA20145780 | 0 | 54.561 | 27.189 | 0 | 0 | 0 | 0 | 0 | 0 | 0 | 0 | 0 | 0 |
| FEBRA20233770 | 0 | 19.338 | 9.637 | 0 | 28.03 | 0 | 15.515 | 0 | 0 | 27.481 | 0 | 0 | 0 |
| HHDPC10000830 | 0 | 2.44 | 2.432 | 1.389 | 0 | 1.972 | 0 | 2.246 | 0 | 0 | 0 | 3.643 | 2.171 |
| MESAN20025190 | 0 | 11.561 | 5.761 | 0 | 0 | 4.673 | 0 | 0 | 0 | 4.732 | 0 | 0 | 5.143 |
| MESAN20089360 | 0 | 9.917 | 4.942 | 5.647 | 0 | 12.025 | 3.978 | 0 | 0 | 4.059 | 0 | 0 | 0 |
| NT2RI20048840 | 0 | 11.556 | 0.96 | 0 | 0 | 0 | 0 | 0 | 0 | 0.788 | 2.876 | 0 | 0 |
| NT2RP70043480 | 0 | 5.634 | 16.844 | 0 | 0 | 0 | 0 | 0 | 0 | 8.006 | 0 | 0 | 0 |
| OCBBF20032460 | 0 | 24.396 | 24.315 | 0 | 0 | 9.861 | 9.786 | 0 | 0 | 19.969 | 0 | 0 | 0 |
| OCBBF20039250 | 0 | 2.077 | 1.035 | 0 | 3.011 | 1.679 | 0 | 0 | 0 | 0 | 0 | 3.004 | 0 |
| OCBBF20049300 | 0 | 25.873 | 12.893 | 0 | 0 | 0 | 0 | 23.811 | 0 | 0 | 0 | 37.423 | 0 |
| OCBBF20061720 | 0 | 13.071 | 13.027 | 0 | 0 | 5.283 | 0 | 12.029 | 18.574 | 0 | 19.515 | 0 | 0 |
| OCBBF20078920 | 0 | 21.239 | 5.292 | 0 | 0 | 0 | 0 | 0 | 0 | 0 | 0 | 15.36 | 0 |
| OCBBF20084660 | 0 | 42.651 | 10.627 | 0 | 0 | 0 | 0 | 0 | 0 | 0 | 31.84 | 0 | 0 |
| OCBBF20087010 | 0 | 27.016 | 40.389 | 0 | 0 | 10.92 | 21.675 | 0 | 0 | 0 | 0 | 0 | 0 |
| PROST20087700 | 0 | 1.945 | 2.907 | 7.197 | 0 | 3.93 | 4.68 | 0 | 0 | 6.367 | 2.903 | 2.813 | 3.46 |
| PROST20153320 | 0 | 6.425 | 3.202 | 27.441 | 0 | 2.597 | 10.31 | 0 | 18.262 | 5.259 | 0 | 0 | 0 |
| TRACH20135520 | 0 | 25.898 | 12.906 | 7.374 | 0 | 0 | 10.389 | 0 | 0 | 31.797 | 0 | 0 | 0 |
| ADIPS20004250 | 1.434 | 0 | 0.964 | 0 | 0 | 0 | 1.553 | 0 | 0 | 1.584 | 0 | 0 | 0 |
| ASTRO10001650 | 4.095 | 0 | 11.014 | 0 | 0 | 0 | 0 | 0 | 0 | 0 | 0 | 0 | 0 |
| BRACE20056810 | 3.689 | 0 | 4.961 | 14.879 | 0 | 13.076 | 16.971 | 4.581 | 0 | 20.37 | 7.431 | 7.199 | 3.321 |
| BRACE20059370 | 22.318 | 0 | 7.504 | 8.574 | 0 | 0 | 0 | 0 | 0 | 0 | 0 | 0 | 0 |
| BRACE20106690 | 11.777 | 0 | 31.677 | 9.049 | 0 | 0 | 19.124 | 0 | 0 | 6.504 | 0 | 0 | 7.069 |
| BRACE20210140 | 10.945 | 0 | 14.719 | 4.205 | 0 | 0 | 17.772 | 0 | 0 | 18.132 | 0 | 0 | 0 |
| BRAWH20103290 | 13.868 | 0 | 6.217 | 21.311 | 0 | 10.085 | 20.017 | 0 | 0 | 15.317 | 0 | 0 | 11.099 |
| BRAWH20121640 | 38.493 | 0 | 25.884 | 14.788 | 0 | 0 | 20.835 | 0 | 0 | 0 | 0 | 0 | 0 |

TABLE 45

| | | | | | | | | | | | | | |
|---|---|---|---|---|---|---|---|---|---|---|---|---|---|
| BRHIP20005530 | 4.747 | 0 | 12.769 | 1.824 | 0 | 2.589 | 2.57 | 0 | 0 | 5.243 | 0 | 0 | 2.85 |
| BRHIP20217620 | 5.147 | 0 | 3.461 | 7.91 | 0 | 0 | 8.358 | 0 | 0 | 11.369 | 0 | 0 | 3.09 |
| BRHIP20218580 | 6.182 | 0 | 8.314 | 4.75 | 0 | 3.372 | 3.346 | 0 | 0 | 3.414 | 0 | 0 | 0 |
| BRHIP20238880 | 0.68 | 0 | 3.2 | 2.089 | 0 | 1.854 | 2.208 | 1.688 | 1.303 | 0.751 | 1.369 | 2.653 | 4.488 |
| CTONG20075860 | 11.104 | 0 | 14.933 | 0 | 0 | 0 | 0 | 0 | 21.292 | 0 | 0 | 0 | 0 |
| CTONG20129960 | 5.394 | 0 | 7.255 | 0 | 0 | 0 | 2.92 | 0 | 0 | 0 | 0 | 0 | 6.476 |
| FCBBF10000240 | 8.112 | 0 | 10.91 | 0 | 0 | 6.637 | 6.587 | 0 | 0 | 6.72 | 0 | 7.916 | 0 |
| FCBBF10000630 | 11.049 | 0 | 7.43 | 0 | 0 | 6.026 | 11.962 | 0 | 0 | 6.102 | 0 | 0 | 0 |
| FCBBF10001150 | 37.553 | 0 | 25.252 | 14.427 | 0 | 0 | 0 | 0 | 0 | 0 | 0 | 0 | 0 |
| FCBBF10004120 | 3.575 | 0 | 7.212 | 0 | 0 | 0 | 5.806 | 0 | 0 | 0 | 0 | 0 | 2.146 |
| FCBBF10005740 | 7.67 | 0 | 15.473 | 2.947 | 0 | 10.458 | 8.303 | 0 | 7.354 | 6.353 | 0 | 0 | 4.604 |
| FCBBF20075560 | 16.883 | 0 | 11.353 | 0 | 0 | 0 | 0 | 0 | 0 | 0 | 0 | 0 | 0 |
| FCBBF30018550 | 31.042 | 0 | 3.479 | 1.988 | 0 | 0 | 0 | 0 | 0 | 0 | 0 | 0 | 0 |
| FCBBF30025560 | 59.793 | 0 | 40.207 | 0 | 0 | 0 | 0 | 0 | 0 | 0 | 0 | 0 | 0 |
| FCBBF30086440 | 15.918 | 0 | 10.704 | 0 | 0 | 0 | 8.616 | 0 | 0 | 0 | 0 | 0 | 0 |
| FCBBF30090690 | 8.273 | 0 | 5.563 | 6.357 | 0 | 22.561 | 17.913 | 0 | 0 | 4.569 | 0 | 0 | 34.763 |
| FCBBF30189490 | 52.288 | 0 | 17.58 | 0 | 0 | 0 | 0 | 0 | 0 | 14.438 | 0 | 0 | 15.693 |
| FCBBF30233680 | 4.533 | 0 | 6.096 | 0 | 0 | 0 | 7.361 | 0 | 0 | 2.503 | 0 | 0 | 2.721 |
| FCBBF30240020 | 10.485 | 0 | 28.201 | 16.112 | 0 | 5.718 | 5.675 | 0 | 0 | 0 | 0 | 0 | 0 |
| HCHON20007510 | 6.596 | 0 | 4.435 | 0 | 0 | 0 | 3.57 | 0 | 0 | 0 | 0 | 0 | 3.959 |
| HCHON20016650 | 2.851 | 0 | 5.751 | 2.191 | 0 | 9.329 | 0 | 0 | 0 | 6.297 | 0 | 0 | 0 |
| HHDPC20095280 | 12.007 | 0 | 8.074 | 4.613 | 0 | 0 | 0 | 0 | 0 | 6.631 | 0 | 0 | 14.415 |
| KIDNE20002520 | 1.579 | 0 | 6.37 | 1.213 | 0 | 3.444 | 6.837 | 0 | 6.055 | 3.488 | 0 | 3.082 | 2.843 |
| KIDNE20009470 | 9.338 | 0 | 9.419 | 0 | 9.132 | 0 | 2.527 | 0 | 0 | 0 | 0 | 0 | 2.803 |
| NT2RI20003480 | 16.371 | 0 | 44.033 | 0 | 0 | 0 | 0 | 0 | 0 | 0 | 0 | 0 | 0 |
| NT2RI20055790 | 17.338 | 0 | 11.659 | 0 | 0 | 0 | 0 | 0 | 0 | 19.149 | 0 | 0 | 0 |
| NT2RP70027380 | 10.635 | 0 | 35.756 | 4.086 | 0 | 0 | 5.756 | 0 | 0 | 5.873 | 0 | 0 | 6.384 |
| NT2RP70032610 | 2.51 | 0 | 3.376 | 0 | 0 | 0 | 0 | 0 | 0 | 0 | 0 | 0 | 0 |

TABLE 45-continued

| ID | 1 | 2 | 3 | 4 | 5 | 6 | 7 | 8 | 9 | 10 | 11 | 12 |
|---|---|---|---|---|---|---|---|---|---|---|---|---|
| NT2RP70062230 | 7.806 | 0 | 10.498 | 17.994 | 0 | 0 | 4.225 | 0 | 0 | 8.622 | 15.726 | 0 | 0 |
| OCBBF10001850 | 15.555 | 0 | 31.379 | 0 | 0 | 0 | 4.21 | 0 | 0 | 0 | 0 | 0 | 0 |
| OCBBF20022900 | 18.632 | 0 | 12.529 | 0 | 0 | 20.324 | 0 | 0 | 0 | 0 | 0 | 0 | 11.184 |
| OCBBF20026630 | 59.793 | 0 | 40.207 | 0 | 0 | 0 | 0 | 0 | 0 | 0 | 0 | 0 | 0 |
| OCBBF20049840 | 44.001 | 0 | 29.587 | 0 | 0 | 0 | 0 | 0 | 0 | 0 | 0 | 0 | 26.412 |
| OCBBF20059560 | 5.245 | 0 | 3.527 | 6.045 | 10.258 | 5.721 | 0 | 6.513 | 0 | 0 | 10.566 | 0 | 3.148 |
| OCBBF20068490 | 3.734 | 0 | 7.532 | 0 | 0 | 0 | 0 | 0 | 0 | 0 | 0 | 0 | 0 |
| OCBBF20071960 | 33.142 | 0 | 66.858 | 0 | 0 | 0 | 0 | 0 | 0 | 0 | 0 | 0 | 0 |
| OCBBF20080410 | 7.723 | 0 | 2.597 | 0 | 0 | 0 | 4.18 | 0 | 0 | 0 | 0 | 0 | 0 |

TABLE 46

| ID | 1 | 2 | 3 | 4 | 5 | 6 | 7 | 8 | 9 | 10 | 11 | 12 |
|---|---|---|---|---|---|---|---|---|---|---|---|---|
| OCBBF20094240 | 13.407 | 0 | 9.015 | 0 | 0 | 0 | 0 | 0 | 0 | 0 | 0 | 0 | 0 |
| OCBBF20097720 | 4.351 | 0 | 5.851 | 6.686 | 0 | 7.119 | 9.42 | 2.702 | 4.172 | 12.014 | 0 | 4.246 | 1.306 |
| OCBBF20108190 | 23.173 | 0 | 15.583 | 8.903 | 0 | 0 | 0 | 0 | 0 | 0 | 0 | 0 | 13.91 |
| OCBBF20108430 | 27.517 | 0 | 18.503 | 0 | 0 | 0 | 0 | 0 | 0 | 0 | 0 | 0 | 0 |
| OCBBF20126780 | 25.486 | 0 | 25.707 | 29.374 | 0 | 0 | 6.898 | 0 | 0 | 0 | 0 | 0 | 0 |
| OCBBF20130110 | 13.949 | 0 | 9.38 | 0 | 0 | 22.823 | 0 | 0 | 0 | 7.703 | 0 | 0 | 0 |
| OCBBF20139260 | 22.924 | 0 | 77.076 | 0 | 0 | 0 | 0 | 0 | 0 | 0 | 0 | 0 | 0 |
| OCBBF20148730 | 26.202 | 0 | 17.619 | 0 | 0 | 0 | 28.366 | 0 | 0 | 0 | 0 | 0 | 0 |
| OCBBF20149280 | 59.793 | 0 | 40.207 | 0 | 0 | 0 | 0 | 0 | 0 | 0 | 0 | 0 | 0 |
| OCBBF20164050 | 71.253 | 0 | 28.747 | 0 | 0 | 0 | 0 | 0 | 0 | 0 | 0 | 0 | 0 |
| OCBBF20173980 | 2.376 | 0 | 9.588 | 1.826 | 0 | 3.888 | 9.005 | 0 | 4.557 | 6.562 | 4.788 | 0 | 4.28 |
| OCBBF20178880 | 31.476 | 0 | 21.165 | 0 | 0 | 0 | 17.037 | 0 | 0 | 0 | 0 | 0 | 0 |
| OCBBF20180120 | 5.185 | 0 | 3.487 | 0 | 0 | 0 | 2.828 | 0 | 0 | 0 | 0 | 0 | 0 |
| OCBBF20188730 | 5.12 | 0 | 5.164 | 0 | 0 | 0 | 1.386 | 0 | 0 | 2.828 | 0 | 0 | 4.61 |
| PROST20057930 | 7.245 | 0 | 4.872 | 0 | 0 | 0 | 0 | 0 | 0 | 0 | 0 | 0 | 4.349 |
| SPLEN20162680 | 3.991 | 0 | 2.147 | 0.307 | 0 | 0.435 | 0 | 0 | 3.373 | 0 | 0 | 1.558 | 0.479 |
| SPLEN20211940 | 12.464 | 0 | 4.191 | 0 | 0 | 0 | 3.373 | 0 | 0 | 0 | 0 | 0 | 0 |
| TESTI20184620 | 5.221 | 0 | 7.021 | 0 | 0 | 5.695 | 2.826 | 0 | 0 | 0 | 0 | 0 | 9.401 |
| TESTI20211240 | 10.559 | 0 | 7.1 | 0 | 0 | 5.759 | 17.146 | 0 | 0 | 11.662 | 0 | 0 | 0 |
| TESTI20369690 | 19.913 | 0 | 8.927 | 2.55 | 0 | 0 | 7.186 | 0 | 0 | 3.666 | 0 | 0 | 3.984 |
| THYMU20141670 | 10.152 | 0 | 20.48 | 0 | 0 | 0 | 0 | 0 | 0 | 0 | 0 | 19.814 | 6.094 |
| TRACH20028030 | 7.7 | 0 | 2.589 | 2.958 | 0 | 4.199 | 0 | 0 | 0 | 0 | 23.268 | 7.514 | 0 |
| UTERU20099720 | 13.09 | 0 | 39.61 | 0 | 0 | 0 | 3.543 | 0 | 0 | 3.614 | 0 | 0 | 0 |
| UTERU20135860 | 24.344 | 0 | 8.185 | 0 | 0 | 0 | 0 | 0 | 23.341 | 13.444 | 0 | 0 | 0 |
| BRACE20057190 | 5.487 | 14.807 | 0 | 6.324 | 32.194 | 5.985 | 0 | 6.814 | 0 | 3.03 | 11.054 | 0 | 0 |
| BRHIP20191860 | 7.292 | 9.84 | 0 | 0 | 0 | 3.977 | 0 | 0 | 0 | 4.027 | 0 | 0 | 0 |
| BRHIP20214950 | 11.849 | 15.989 | 0 | 4.552 | 46.351 | 0 | 0 | 14.715 | 0 | 6.544 | 0 | 0 | 0 |
| FCBBF10003670 | 5.613 | 3.787 | 0 | 0 | 0 | 1.531 | 0 | 0 | 0 | 1.55 | 0 | 0 | 0 |
| FCBBF10004370 | 23.626 | 31.88 | 0 | 0 | 0 | 0 | 0 | 0 | 0 | 0 | 0 | 0 | 0 |
| FCBBF30013770 | 19.023 | 25.669 | 0 | 0 | 0 | 0 | 10.297 | 0 | 0 | 0 | 0 | 0 | 0 |
| FCBBF30095260 | 21.826 | 29.451 | 0 | 0 | 0 | 23.808 | 11.814 | 0 | 0 | 0 | 0 | 0 | 13.101 |
| FCBBF30246230 | 41.402 | 13.966 | 0 | 0 | 0 | 0 | 0 | 0 | 0 | 0 | 0 | 0 | 12.426 |
| FEBRA20002100 | 1.306 | 3.524 | 0 | 0 | 0 | 0 | 0.707 | 0 | 0 | 0.721 | 0 | 0 | 0 |
| FEBRA20034360 | 10.27 | 13.858 | 0 | 0 | 0 | 5.601 | 0 | 0 | 39.387 | 0 | 0 | 0 | 0 |
| FEBRA20095140 | 12.239 | 24.772 | 0 | 0 | 0 | 3.338 | 0 | 0 | 0 | 3.379 | 0 | 0 | 0 |
| FEBRA20130190 | 42.565 | 57.435 | 0 | 0 | 0 | 0 | 0 | 0 | 0 | 0 | 0 | 0 | 0 |
| FEBRA20204060 | 42.565 | 57.435 | 0 | 0 | 0 | 0 | 0 | 0 | 0 | 0 | 0 | 0 | 0 |

TABLE 47

| ID | 1 | 2 | 3 | 4 | 5 | 6 | 7 | 8 | 9 | 10 | 11 | 12 |
|---|---|---|---|---|---|---|---|---|---|---|---|---|
| HCHON20008320 | 6.536 | 8.819 | 0 | 0 | 0 | 0 | 0 | 0 | 0 | 0 | 0 | 0 | 0 |
| LIVER20028420 | 3.527 | 9.518 | 0 | 0 | 0 | 1.924 | 0 | 4.38 | 0 | 0 | 0 | 0 | 6.351 |
| TRACH20111130 | 8.722 | 23.539 | 0 | 3.351 | 0 | 0 | 0 | 0 | 0 | 4.817 | 0 | 0 | 5.236 |
| ASTRO20108190 | 6.215 | 3.355 | 6.687 | 6.686 | 0 | 3.39 | 4.037 | 0 | 2.384 | 4.119 | 0 | 0 | 0 |
| BRACE20003070 | 6.528 | 2.936 | 10.243 | 20.064 | 0 | 0 | 1.178 | 2.702 | 0 | 2.403 | 0 | 0 | 1.306 |
| BRACE20060550 | 7.391 | 4.987 | 2.485 | 4.259 | 0 | 2.016 | 4.001 | 0 | 0 | 0 | 0 | 0 | 2.218 |
| BRAWH20004600 | 2.255 | 1.521 | 1.516 | 9.097 | 0 | 1.23 | 1.831 | 1.4 | 2.162 | 1.245 | 4.543 | 0 | 4.061 |
| BRAWH20011710 | 3.423 | 4.619 | 15.345 | 9.644 | 0 | 9.334 | 6.176 | 1.417 | 0 | 1.89 | 2.299 | 0 | 4.794 |
| BRAWH20016620 | 8.494 | 34.385 | 5.712 | 3.263 | 0 | 0 | 4.598 | 0 | 16.288 | 0 | 0 | 0 | 5.099 |
| BRHIP10001740 | 9.366 | 25.278 | 6.298 | 3.598 | 0 | 5.108 | 0 | 0 | 17.961 | 5.173 | 0 | 18.281 | 5.622 |
| BRSTN10000830 | 4.718 | 1.592 | 4.759 | 1.36 | 0 | 1.93 | 0.638 | 0 | 2.262 | 1.303 | 0 | 2.302 | 0 |
| CTONG10000940 | 10.792 | 16.505 | 4.354 | 1.106 | 1.407 | 2.747 | 0 | 1.787 | 4.139 | 2.781 | 1.45 | 0 | 0.864 |
| CTONG20150910 | 3.001 | 2.024 | 2.018 | 0.576 | 0 | 0 | 0 | 0 | 0 | 0 | 0 | 0 | 1.801 |
| D3OST10002670 | 7.978 | 10.765 | 5.365 | 0 | 0 | 0 | 0 | 9.907 | 0 | 0 | 0 | 15.57 | 0 |
| FCBBF10000380 | 20.755 | 28.007 | 41.87 | 0 | 0 | 0 | 0 | 0 | 0 | 0 | 0 | 0 | 0 |
| FCBBF10000770 | 19.451 | 22.208 | 13.079 | 0 | 0 | 0.816 | 0 | 0 | 0 | 0 | 0 | 0 | 0.898 |
| FCBBF10003770 | 39.957 | 26.958 | 13.434 | 0 | 0 | 0 | 0 | 0 | 0 | 0 | 0 | 0 | 0 |
| FCBBF20059090 | 11.53 | 15.558 | 31.013 | 4.43 | 0 | 0 | 6.241 | 0 | 0 | 19.102 | 0 | 0 | 6.921 |
| FCBBF30016320 | 2.852 | 3.848 | 13.424 | 1.096 | 0 | 0 | 0 | 3.542 | 0 | 0 | 0 | 0 | 0 |
| FCBBF30016570 | 8.716 | 11.762 | 11.722 | 11.72 | 0 | 4.754 | 11.795 | 0 | 0 | 9.627 | 8.78 | 0 | 5.232 |
| FCBBF30049550 | 28.476 | 19.212 | 28.723 | 0 | 0 | 0 | 0 | 0 | 0 | 23.589 | 0 | 0 | 0 |
| FCBBF30083820 | 19.899 | 26.851 | 13.381 | 0 | 0 | 0 | 0 | 0 | 0 | 0 | 0 | 0 | 0 |

TABLE 47-continued

| | | | | | | | | | | | | | |
|---|---|---|---|---|---|---|---|---|---|---|---|---|---|
| FCBBF30238870 | 17.508 | 23.625 | 58.866 | 0 | 0 | 0 | 0 | 0 | 0 | 0 | 0 | 0 | 0 |
| FCBBF40001420 | 13.508 | 18.228 | 18.167 | 18.164 | 0 | 11.051 | 3.656 | 0 | 0 | 0 | 0 | 0 | 4.054 |
| FEBRA10001880 | 38.663 | 15.651 | 36.398 | 0 | 0 | 2.109 | 0 | 0 | 0 | 2.135 | 0 | 0 | 0 |
| FEBRA20004620 | 5.215 | 7.037 | 7.013 | 28.049 | 0 | 0 | 31.051 | 0 | 0 | 8.64 | 0 | 0 | 6.261 |
| FEBRA20080810 | 1.308 | 3.531 | 4.399 | 1.508 | 0 | 2.141 | 2.124 | 3.249 | 0 | 0.722 | 2.636 | 0 | 0 |
| FEBRA20086620 | 5.865 | 11.87 | 1.972 | 5.633 | 0 | 6.397 | 11.11 | 0 | 0 | 3.239 | 0 | 11.446 | 1.76 |
| FEBRA20095880 | 8.952 | 24.158 | 42.136 | 0 | 0 | 0 | 19.382 | 0 | 0 | 0 | 0 | 0 | 5.373 |
| HHDPC20034390 | 2.819 | 1.268 | 5.371 | 1.625 | 0 | 0.513 | 1.78 | 0 | 0 | 1.816 | 0.947 | 0 | 0.846 |
| HLUNG10000550 | 1 | 1.349 | 4.035 | 0 | 0 | 0 | 0 | 0 | 1.918 | 1.105 | 4.029 | 1.952 | 1.201 |
| NT2RI20023160 | 1.481 | 1.999 | 0.996 | 0.569 | 0 | 0 | 0 | 0 | 2.84 | 0.818 | 0 | 0 | 0.889 |
| NT2RI20023910 | 4.495 | 4.043 | 1.007 | 0 | 0 | 4.086 | 0 | 1.86 | 0 | 0 | 0 | 0 | 1.799 |
| NT2RI20025400 | 3.194 | 17.238 | 2.148 | 1.227 | 0 | 6.967 | 6.915 | 7.932 | 0 | 5.291 | 6.434 | 24.933 | 1.917 |
| NT2RI20028470 | 6.957 | 9.388 | 7.797 | 0 | 0 | 1.265 | 0 | 0 | 0 | 1.281 | 0 | 0 | 2.784 |
| NT2RI20054050 | 0.519 | 1.4 | 0.349 | 0.199 | 0 | 0 | 0.561 | 0 | 0 | 0.573 | 3.134 | 0 | 1.245 |
| NT2RI20076290 | 3.724 | 5.025 | 5.008 | 1.431 | 0 | 4.062 | 0 | 0 | 0 | 0 | 0 | 0 | 0 |

TABLE 48

| | | | | | | | | | | | | | |
|---|---|---|---|---|---|---|---|---|---|---|---|---|---|
| NT2RI20091730 | 2.061 | 5.561 | 1.386 | 0 | 0 | 1.124 | 0 | 0 | 0 | 1.138 | 0 | 0 | 1.237 |
| NT2RI20091940 | 1.816 | 9.799 | 9.767 | 0 | 0 | 0.99 | 1.965 | 0 | 0 | 1.003 | 0 | 0 | 0 |
| NT2RP70036880 | 2.728 | 1.841 | 8.256 | 4.193 | 0 | 6.696 | 3.692 | 0 | 0 | 0 | 0 | 0 | 4.913 |
| NT2RP70078420 | 3.543 | 4.781 | 2.383 | 4.084 | 6.93 | 0 | 0 | 0 | 0 | 1.957 | 7.139 | 0 | 2.127 |
| OCBBF20047570 | 18.314 | 30.89 | 12.315 | 3.518 | 8.955 | 0 | 2.497 | 0 | 5.686 | 0 | 0 | 0 | 0 |
| OCBBF20080050 | 11.733 | 7.916 | 21.697 | 6.762 | 0 | 6.399 | 0 | 0 | 0 | 1.62 | 0 | 0 | 0 |
| OCBBF20125530 | 4.333 | 11.695 | 4.371 | 0 | 4.238 | 1.182 | 0 | 2.691 | 0 | 2.393 | 4.365 | 4.229 | 0 |
| OCBBF20140640 | 2.523 | 10.215 | 3.394 | 0 | 0 | 1.376 | 0 | 0 | 0 | 4.18 | 10.167 | 4.925 | 0 |
| TRACH20032720 | 6.845 | 9.236 | 9.205 | 2.63 | 0 | 11.2 | 3.705 | 8.5 | 13.125 | 3.78 | 0 | 0 | 4.109 |
| TRACH20141240 | 3.814 | 5.146 | 2.565 | 1.465 | 0 | 4.16 | 2.064 | 0 | 3.657 | 0 | 0 | 0 | 3.434 |
| UTERU20004240 | 3.138 | 4.234 | 1.055 | 3.014 | 3.069 | 0.856 | 1.699 | 3.897 | 3.009 | 0 | 0 | 3.062 | 0 |

TABLE 49

| CloneID | FEHRT | HEART |
|---|---|---|
| FEHRT20003250 | 100 | 0 |
| OCBBF20189560 | 35.243 | 0 |
| BRAWH20029630 | 0 | 79.6 |
| CTONG20150910 | 0 | 5.418 |
| HCHON20007510 | 0 | 23.818 |
| HEART20003060 | 0 | 90.384 |
| HEART20005410 | 0 | 53.555 |
| HEART20021840 | 0 | 100 |
| HEART20025980 | 0 | 100 |
| HEART20034320 | 0 | 100 |
| HEART20037810 | 0 | 100 |
| HEART20049400 | 0 | 100 |
| HEART20049410 | 0 | 63.375 |
| HEART20049800 | 0 | 100 |
| HEART20061950 | 0 | 63.227 |
| HEART20063340 | 0 | 100 |
| HEART20067870 | 0 | 100 |
| HEART20067890 | 0 | 100 |
| HEART20072310 | 0 | 32.316 |
| HEART20074430 | 0 | 100 |
| HEART20077670 | 0 | 100 |
| HEART20089940 | 0 | 100 |
| HEART20090000 | 0 | 68.952 |
| HEART20095990 | 0 | 100 |
| HLUNG10000550 | 0 | 3.611 |
| HLUNG20017120 | 0 | 21.996 |
| KIDNE20028390 | 0 | 48.974 |
| KIDNE20028830 | 0 | 15.131 |
| NTONG20029480 | 0 | 44.44 |
| OCBBF10001750 | 0 | 48.053 |
| PROST20127800 | 0 | 48.531 |
| SKMUS20001980 | 0 | 21.074 |
| SKMUS20003610 | 0 | 7.134 |
| SMINT20026890 | 0 | 7.842 |
| SMINT20121220 | 0 | 23.322 |
| SMINT20122910 | 0 | 30.763 |
| SMINT20183530 | 0 | 65.405 |
| SPLEN20008740 | 0 | 3.252 |
| SPLEN20027440 | 0 | 14.879 |

TABLE 49-continued

| CloneID | FEHRT | HEART |
|---|---|---|
| SPLEN20162680 | 0 | 2.882 |
| STOMA20062290 | 0 | 40.108 |
| TESTI20254220 | 0 | 16.559 |
| THYMU20271250 | 0 | 3.582 |
| TRACH20141240 | 0 | 6.886 |
| UTERU20004240 | 0 | 5.666 |

TABLE 50

| CloneID | FEKID | KIDNE |
|---|---|---|
| ASTRO10001650 | 0 | 7.727 |
| ASTRO20108190 | 0 | 2.346 |
| BGGI120006160 | 0 | 3.117 |
| BRACE20039040 | 0 | 9.038 |
| BRACE20060550 | 0 | 6.974 |
| BRAMY20102080 | 0 | 63.37 |
| BRAWH20004600 | 0 | 2.128 |
| BRAWH20125380 | 0 | 35.37 |
| BRAWH20162690 | 0 | 4.596 |
| BRHIP20115760 | 0 | 66.835 |
| BRHIP20205090 | 0 | 65.282 |
| BRHIP20238880 | 0 | 1.283 |
| CTONG20052650 | 0 | 65.178 |
| CTONG20108210 | 0 | 2.491 |
| CTONG20128470 | 0 | 6.004 |
| CTONG20133480 | 0 | 19.179 |
| CTONG20139070 | 0 | 7.516 |
| D9OST20000310 | 0 | 16.47 |
| DFNES20001530 | 0 | 11.162 |
| FCBBF10001820 | 0 | 59.128 |
| FEBRA20002100 | 0 | 4.929 |
| HCHON20008980 | 0 | 35.524 |
| HCHON20016650 | 0 | 5.38 |
| HLUNG20033780 | 0 | 32.277 |
| KIDNE20002520 | 0 | 2.979 |
| KIDNE20003940 | 0 | 100 |

TABLE 50-continued

| CloneID | FEKID | KIDNE |
|---|---|---|
| KIDNE20006780 | 0 | 100 |
| KIDNE20007210 | 0 | 73.728 |
| KIDNE20007770 | 0 | 19.958 |
| KIDNE20008010 | 0 | 100 |
| KIDNE20009470 | 0 | 8.811 |
| KIDNE20011170 | 0 | 77.71 |
| KIDNE20011400 | 0 | 100 |
| KIDNE20013730 | 0 | 24.839 |
| KIDNE20017130 | 0 | 54.019 |
| KIDNE20018730 | 0 | 100 |
| KIDNE20018970 | 0 | 100 |
| KIDNE20020150 | 0 | 100 |
| KIDNE20021680 | 0 | 100 |
| KIDNE20021910 | 0 | 24.85 |
| KIDNE20021980 | 0 | 100 |
| KIDNE20022620 | 0 | 100 |
| KIDNE20024830 | 0 | 100 |
| KIDNE20027250 | 0 | 35.87 |
| KIDNE20027950 | 0 | 100 |
| KIDNE20028390 | 0 | 25.593 |
| KIDNE20028830 | 0 | 7.907 |
| KIDNE20029800 | 0 | 10.988 |
| KIDNE20067330 | 0 | 100 |
| KIDNE20079440 | 0 | 35.045 |
| KIDNE20096280 | 0 | 100 |
| KIDNE20096470 | 0 | 100 |
| KIDNE20100070 | 0 | 100 |
| KIDNE20100840 | 0 | 100 |
| KIDNE20101370 | 0 | 100 |
| KIDNE20101510 | 0 | 100 |
| KIDNE20102650 | 0 | 8.237 |
| KIDNE20102710 | 0 | 100 |
| KIDNE20104300 | 0 | 33.246 |
| KIDNE20106740 | 0 | 100 |
| KIDNE20107390 | 0 | 100 |
| KIDNE20107500 | 0 | 74.264 |
| KIDNE20107620 | 0 | 100 |
| KIDNE20109730 | 0 | 100 |
| KIDNE20109890 | 0 | 100 |
| KIDNE20112000 | 0 | 100 |
| KIDNE20115080 | 0 | 65.178 |
| KIDNE20118580 | 0 | 100 |
| KIDNE20120090 | 0 | 33.186 |
| KIDNE20121880 | 0 | 62.256 |
| KIDNE20122910 | 0 | 83.085 |
| KIDNE20124400 | 0 | 6.171 |
| KIDNE20125630 | 0 | 100 |
| KIDNE20126010 | 0 | 100 |
| KIDNE20126130 | 0 | 100 |
| KIDNE20127100 | 0 | 33.012 |
| KIDNE20127450 | 0 | 100 |
| KIDNE20127750 | 0 | 100 |
| KIDNE20130450 | 0 | 100 |
| KIDNE20131580 | 0 | 63.24 |
| KIDNE20132180 | 0 | 100 |
| KIDNE20137340 | 0 | 100 |
| KIDNE20138010 | 0 | 100 |
| KIDNE20141190 | 0 | 49.697 |
| KIDNE20144890 | 0 | 100 |
| KIDNE20148900 | 0 | 100 |
| KIDNE20163880 | 0 | 100 |
| KIDNE20180710 | 0 | 49.105 |
| KIDNE20181660 | 0 | 100 |
| KIDNE20182690 | 0 | 100 |
| KIDNE20186780 | 0 | 100 |
| KIDNE20190740 | 0 | 100 |
| LIVER20035110 | 0 | 28.683 |
| MESAN20025190 | 0 | 16.169 |
| NOVAR20000380 | 0 | 2.166 |
| NT2RI20054050 | 0 | 2.936 |
| NT2RP70043480 | 0 | 7.879 |
| PROST20107820 | 0 | 1.696 |
| PROST20123530 | 0 | 32.771 |
| PROST20161950 | 0 | 20.387 |
| PUAEN20030180 | 0 | 46.744 |
| SKMUS20003610 | 0 | 3.728 |
| SMINT20033400 | 0 | 10.243 |

TABLE 50-continued

| CloneID | FEKID | KIDNE |
|---|---|---|
| TBAES20000590 | 0 | 5.253 |
| TESTI20044310 | 0 | 29.162 |
| TESTI20082330 | 0 | 45.847 |
| TRACH20032720 | 0 | 12.917 |
| UTERU20099720 | 0 | 12.351 |
| BRACE20003070 | 25.479 | 0 |
| BRCOC20031870 | 34.023 | 0 |
| CTONG20125640 | 85.462 | 0 |
| FCBBF30016320 | 33.393 | 0 |
| HCHON20002260 | 8.723 | 0 |
| HLUNG10000550 | 11.709 | 0 |
| PROST20130530 | 64.069 | 0 |
| SPLEN20169720 | 43.864 | 0 |
| SPLEN20194050 | 30.978 | 0 |
| KIDNE20028720 | 12.368 | 1.993 |

TABLE 51

| CloneID | FELNG | HLUNG |
|---|---|---|
| BRACE20096200 | 0 | 70.38 |
| BRAWH20004600 | 0 | 2.238 |
| BRAWH20030250 | 0 | 11.121 |
| BRCAN20006390 | 0 | 61.519 |
| BRCAN20280360 | 0 | 8.855 |
| BRHIP20238880 | 0 | 1.35 |
| CTONG10000940 | 0 | 1.428 |
| CTONG20103480 | 0 | 6.495 |
| CTONG20129960 | 0 | 10.709 |
| CTONG20155180 | 0 | 48.707 |
| FCBBF10001210 | 0 | 36.439 |
| FEBRA20144170 | 0 | 1.98 |
| FEBRA20197110 | 0 | 7.756 |
| HHDPC20034390 | 0 | 0.933 |
| HLUNG20016330 | 0 | 29.367 |
| HLUNG20016770 | 0 | 12.888 |
| HLUNG20017120 | 0 | 12.093 |
| HLUNG20023340 | 0 | 33.714 |
| HLUNG20033780 | 0 | 33.957 |
| HLUNG20084390 | 0 | 100 |
| IMR3220002430 | 0 | 3.147 |
| LIVER20028420 | 0 | 14.004 |
| NOVAR20000380 | 0 | 2.278 |
| NT2RI20054050 | 0 | 2.059 |
| NT2RI20091730 | 0 | 4.091 |
| NT2RP70044280 | 0 | 12.369 |
| OCBBF20020830 | 0 | 40.304 |
| OCBBF20125530 | 0 | 4.302 |
| PLACE60004630 | 0 | 28.618 |
| PROST20057930 | 0 | 14.383 |
| PROST20107820 | 0 | 0.892 |
| PROST20185830 | 0 | 33.898 |
| PUAEN20030180 | 0 | 12.294 |
| SMINT20121220 | 0 | 12.822 |
| SPLEN20002220 | 0 | 44.799 |
| SPLEN20054290 | 0 | 26.875 |
| SPLEN20128000 | 0 | 1.253 |
| SPLEN20157300 | 0 | 51.319 |
| SPLEN20176200 | 0 | 18.8 |
| SPLEN20179180 | 0 | 3.344 |
| SPLEN20211940 | 0 | 12.373 |
| STOMA20013890 | 0 | 21.183 |
| TBAES20000590 | 0 | 5.527 |
| TESTI20094230 | 0 | 59.311 |
| TESTI20184620 | 0 | 10.365 |
| TESTI20334410 | 0 | 8.049 |
| THYMU20000570 | 0 | 4.974 |
| THYMU20039810 | 0 | 1.915 |
| TRACH20007020 | 0 | 14.4 |
| TRACH20141240 | 0 | 3.786 |
| TRACH20183170 | 0 | 10.745 |
| D9OST20033970 | 61.464 | 0 |
| FELNG20002410 | 100 | 0 |
| HCHON20016650 | 33.188 | 0 |

TABLE 51-continued

| CloneID | FELNG | HLUNG |
|---|---|---|
| KIDNE20029800 | 67.783 | 0 |
| OCBBF20145760 | 78.585 | 0 |
| SPLEN20162680 | 9.292 | 0 |
| TESTI20214250 | 37.027 | 0 |
| TRACH20005400 | 30.64 | 0 |
| HCHON20002260 | 8.672 | 2.958 |
| HLUNG10000550 | 11.642 | 3.971 |
| NT2RI20023910 | 34.882 | 8.923 |
| SPLEN20008740 | 10.483 | 1.788 |

Table 52

Alteration of the expression level of each clone due to TNF-α stimulation to human monocyte cell line THP-1 and alteration of the expression level of each clone due to co-culture of gastric cancer cell line MKN45 with *Helicobacter pylori*. ctl, TNF__1h, and TNF__3h in the column of THP-1, respectively, indicate the relative mRNA expression levels in unstimulated THP-1, in the cell stimulated with 10 ng/mL TNF-α for 1 hour, and in the cell stimulated with 10 ng/mL TNF-α for 3 hours; ctl, Hp, and ΔcagE in the column of MKN45 indicate the relative mRNA expression levels in MKN45 cultured without *Helicobacter pylori*, in the cells co-cultured with cag PAI-positive *Helicobacter pylori* (TN2) (at a ratio of MKN45: TN2=1:100 cells (colonies)) for 3 hours, and in the cells co-cultured with the cagE mutant (TN2ΔcagE) (at a ratio of MKN45: TN2ΔcagE=1:100 cells (colonies)) for 3 hours, respectively.

| Clone Name | THP-1 ctl | TNF__ 1h | TNF__ 3h | MKN45 ctl | Hp | ΔcagE |
|---|---|---|---|---|---|---|
| 3NB6920014080 | 4 | 4 | 4.1 | | | |
| ADRGL20013010 | 0.1 | 0.1 | 0.1 | 0.04 | 0.04 | 0.04 |
| ADRGL20067670 | | | | 0 | 2.6 | 0 |
| ADRGL20083310 | 0.3 | 0.3 | 0.3 | | | |
| ASTRO20032120 | 1.4 | 1.7 | 0.6 | 1.2 | 0 | 1 |
| ASTRO20084250 | 1.2 | 1.1 | 0.4 | 0.1 | 0.04 | 0.1 |
| ASTRO20152140 | 0.1 | 0.9 | 0.4 | 1.6 | 1.8 | 1.6 |
| ASTRO20166810 | 0.7 | 0.7 | 0.2 | 4.3 | 3.5 | 4.4 |
| ASTRO20181690 | 1.5 | 1.9 | 0.2 | 1.8 | 2.2 | 0.2 |
| BLADE20004630 | 3.3 | 2.9 | 2.2 | 0.3 | 0.8 | 0 |
| BRACE20006400 | 3.6 | 3.5 | 3.6 | | | |
| BRACE20019540 | 0.7 | 0 | 0 | | | |
| BRACE20038480 | 0.5 | 0.6 | 0.3 | 0.2 | 0.2 | 0.2 |
| BRACE20039040 | 2.5 | 2.2 | 2.3 | 0.1 | 0.7 | 1.1 |
| BRACE20039440 | 0.3 | 0.3 | 0.2 | | | |
| BRACE20052160 | 2.7 | 2.3 | 1.9 | 1.3 | 0.8 | 1 |
| BRACE20053630 | 0.2 | 0.2 | 0 | 3.4 | 3 | 2.6 |
| BRACE20057620 | 0 | 3.7 | 0.5 | 0 | 0 | 0.3 |
| BRACE20058810 | 3.8 | 2 | 2.8 | 0.6 | 0 | 0.9 |
| BRACE20060720 | 0 | 1.3 | 0 | 0 | 0 | 0.04 |
| BRACE20060840 | 2.2 | 1.7 | 1.6 | 3.9 | 3.8 | 1.6 |
| BRACE20061740 | 1.9 | 2.1 | 2.7 | | | |
| BRACE20062640 | 1.9 | 0.2 | 2.4 | 2.3 | 1.2 | 1 |
| BRACE20063780 | 0 | 0.1 | 0 | 0.4 | 0.2 | 0.2 |
| BRACE20067430 | 2.4 | 0 | 1.7 | 0.04 | 0 | 0 |
| BRACE20090440 | 1.1 | 1.8 | 2.2 | 1 | 0.5 | 1.3 |
| BRACE20101700 | 3.1 | 1.8 | 1.7 | 0.5 | 0.4 | 1 |
| BRACE20114780 | 1 | 1.5 | 0.6 | 1.2 | 0.4 | 0.2 |
| BRACE20151320 | 0 | 0 | 0.1 | 0.1 | 0.2 | 0 |
| BRACE20152870 | 0.6 | 1.3 | 1.5 | 0.4 | 0.3 | 0.3 |
| BRACE20163150 | 1.5 | 1.7 | 0.9 | 1.4 | 1.4 | 1.7 |
| BRACE20165830 | 2.6 | 4.9 | 3.3 | | | |
| BRACE20201570 | 0 | 0 | 0 | 0 | 0 | 0 |
| BRACE20210140 | 1.7 | 1.4 | 1 | 1 | 0.6 | 0.5 |
| BRACE20223330 | 0.1 | 0 | 0 | 0 | 0.1 | 0 |
| BRACE20224500 | 0.2 | 0 | 0.2 | 0 | 0 | 0.1 |
| BRACE20229280 | 0.2 | 0.04 | 0.4 | 0 | 2.1 | 0 |
| BRACE20235400 | 1.8 | 0.6 | 1 | 0.3 | 0.6 | 0.1 |
| BRACE20266750 | 1.8 | 2.1 | 1 | 1.3 | 1.1 | 0.9 |
| BRACE20267250 | | | | 0.8 | 0.8 | 0 |
| BRACE20269710 | 0.9 | 0.9 | 0.7 | 0.4 | 0.2 | 0.1 |
| BRALZ20018340 | 1.1 | 1 | 0.5 | 0.3 | 0.4 | 0 |
| BRALZ20058880 | | | | 1 | 3.1 | 2.5 |
| BRALZ20059500 | 1.7 | 1.5 | 2.3 | | | |
| BRALZ20064740 | 1.9 | 2.8 | 1.2 | 8.9 | 0 | 0 |
| BRALZ20069760 | 1.3 | 0.4 | 0 | 0.04 | 0.04 | 0.04 |
| BRALZ20075450 | 1.3 | 0 | 0 | 0.04 | 0.04 | 0.04 |
| BRALZ20088690 | 1.8 | 1.4 | 1.5 | 0 | 0 | 1.6 |
| BRAMY20002770 | 0.8 | 2.4 | 0.3 | 1.2 | 0 | 0 |
| BRAMY20004110 | | | | 0.8 | 0 | 0 |
| BRAMY20060920 | | | | 0.3 | 11.8 | 12.2 |
| BRAMY20103570 | | 0.1 | 0.1 | 0.6 | 0 | 0 |
| BRAMY20144620 | 0.7 | 0 | 0.9 | | | |
| BRAMY20152110 | 1.8 | 1.7 | 1.2 | 2.5 | 2.3 | 0.8 |
| BRAMY20162510 | 0.1 | 0 | 0 | 0.7 | 0.7 | 0 |
| BRAMY20163250 | 3.4 | 4.2 | 2.4 | 2.2 | 1.5 | 0.9 |
| BRAMY20163270 | 3.8 | 0.7 | 4.5 | | | |
| BRAMY20168920 | 2.4 | 2.5 | 2.2 | 0.2 | 0.04 | 0.1 |
| BRAMY20178640 | 1.7 | 1.6 | 1.9 | 0.9 | 1 | 0.5 |
| BRAMY20184670 | 0.4 | 0.3 | 0.2 | 0.04 | 0.2 | 0.6 |
| BRAMY20204450 | 3.6 | 3.6 | 1.6 | 0 | 0 | 0 |
| BRAMY20210400 | 0.5 | 0.5 | 0.5 | 1 | 0.2 | 0.9 |
| BRAMY20215230 | 1 | 0.7 | 1.1 | 1.9 | 0.8 | 1 |
| BRAMY20218670 | 1.6 | 0 | 1.5 | 0.2 | 2.6 | 0.1 |
| BRAMY20229800 | 5 | 3.9 | 0.5 | 1.4 | 4 | 1 |
| BRAMY20229840 | 0.04 | 0 | 0.04 | 0.3 | 0 | 0.2 |
| BRAMY20231720 | 1.1 | 1.3 | 1.6 | | | |
| BRAMY20247280 | 3.5 | 2.2 | 1.9 | 2 | 0.7 | 0.5 |
| BRAMY20261680 | 5.2 | 4 | 3 | 3.5 | 3.2 | 2.5 |
| BRAMY20266850 | 0.4 | 4.4 | 6.9 | 2.2 | 2.9 | 2.7 |
| BRAMY20267130 | | | | 13.7 | 0 | 0 |
| BRAMY20277140 | 3.3 | 2.5 | 3 | 0.7 | 0.8 | 0 |
| BRAMY20280720 | 0 | 9.8 | 1.1 | | | |
| BRAWH10000930 | 2.6 | 1.3 | 1.9 | 0 | 0 | 0 |
| BRAWH20015350 | | | | 0 | 0 | 0 |
| BRAWH20017010 | 0.9 | 0 | 0 | 0.6 | 0.2 | 0.9 |
| BRAWH20029630 | 1.9 | 2.4 | 1.8 | 1.4 | 0.2 | 0.04 |
| BRAWH20100690 | | | | 3.2 | 0.9 | 0.8 |
| BRAWH20106180 | 0 | 2.7 | 0.5 | | | |
| BRAWH20107540 | 2.1 | 1.3 | 0.8 | 1.1 | 1.1 | 0.6 |
| BRAWH20110660 | 1.7 | 2.1 | 2.4 | 1.4 | 1.4 | 0.9 |
| BRAWH20118230 | 0 | 0 | 0.04 | 2.3 | 0.9 | 1.9 |
| BRAWH20122770 | 0 | 0 | 0.8 | | | |
| BRAWH20126190 | 0 | 0 | 0 | 0 | 0 | 0 |
| BRAWH20132190 | 2.2 | 2.2 | 1 | 1.8 | 1.5 | 0.4 |
| BRAWH20138660 | 3.3 | 2.2 | 2.1 | | | |
| BRAWH20139410 | 0.9 | 1.7 | 0.2 | 2.1 | 1.9 | 0.7 |
| BRAWH20155950 | 1.5 | 1.8 | 1.5 | 0.9 | 0 | 0 |
| BRAWH20158530 | 58.9 | 19.3 | 41.1 | | | |
| BRCAN20060190 | | | | 0.2 | 0 | 0.2 |
| BRCAN20147880 | 0.3 | 0.3 | 0 | 0.5 | 1 | 1.3 |
| BRCAN20273340 | 2.8 | 3.5 | 0 | 0.3 | 0.3 | 0.3 |
| BRCAN20273640 | 0.3 | 0.4 | 0.2 | 0.7 | 0.8 | 0.3 |
| BRCAN20275130 | 3.9 | 3.6 | 2.3 | 0.2 | 0 | 0 |
| BRCAN20280210 | 0 | 0 | 0 | 0.8 | 0 | 0 |
| BRCAN20280400 | 3 | 3.6 | 2.6 | 1.8 | 1.7 | 1 |
| BRCOC20021550 | 0.7 | 0 | 0.2 | 0.3 | 0.3 | 0 |
| BRCOC20037400 | 1.5 | 1 | 1.2 | 0.1 | 0 | 0.2 |
| BRCOC20105100 | | | | 3.8 | 1 | 1.5 |
| BRHIP10001740 | 0.8 | 0.7 | 0.9 | 0.4 | 0 | 0 |
| BRHIP20001630 | 0.5 | 0 | 0 | | | |
| BRHIP20096170 | 0 | 0.4 | 0.3 | | | |
| BRHIP20103090 | 1 | 1 | 1.3 | 0.9 | 0 | 0.7 |
| BRHIP20105710 | 1.5 | 0 | 1.9 | 0.7 | 0.7 | 0.9 |
| BRHIP20110800 | 1.9 | 2.7 | 2.2 | 0.8 | 0 | 0 |
| BRHIP20111200 | 0.3 | 0.9 | 1.1 | | | |
| BRHIP20118910 | | | | 0 | 0 | 0 |

-continued

| Clone Name | THP-1 ctl | THP-1 TNF 1h | THP-1 TNF 3h | MKN45 ctl | MKN45 Hp | MKN45 ΔcagE |
|---|---|---|---|---|---|---|
| BRHIP20129720 | 0 | 0.1 | 0 | 0 | 0 | 0 |
| BRHIP20143860 | 6.2 | 5.3 | 6.7 | 3.6 | 2.7 | 2.4 |
| BRHIP20173150 | 0 | 0.04 | 0 | 0.9 | 1.6 | 2.8 |
| BRHIP20175420 | 2.4 | 2.4 | 2.5 | 0.6 | 0 | 0 |
| BRHIP20186120 | 1.2 | 2.9 | 0 | | | |
| BRHIP20194940 | 0.04 | 0.7 | 0.3 | | | |
| BRHIP20196410 | 1.7 | 2.6 | 1.8 | 0.9 | 2 | 1 |
| BRHIP20207430 | 0 | 0 | 0.2 | 0 | 0 | 0.1 |
| BRHIP20218580 | 1.1 | 1.8 | 0.9 | 1.2 | 0.6 | 0.3 |
| BRHIP20233090 | 2.8 | 1.5 | 1.8 | 0.5 | 0 | 0.4 |
| BRHIP20284800 | 2.3 | 1.5 | 1.7 | | | |
| BRHIP30004880 | | | | 0.04 | 0.2 | 0.04 |
| BRSSN20046570 | 2.5 | 2 | 1.7 | 2.6 | 1 | 1.2 |
| BRSSN20142940 | 0 | 0 | 0.04 | 1.2 | 1.3 | 1.2 |
| BRSSN20152380 | 0.5 | 1 | 0.7 | 0.04 | 0.04 | 0.04 |
| BRSSN20176820 | 1.2 | 0.5 | 0.04 | 1.5 | 1 | 1.4 |
| BRSSN20187310 | | | | 2.5 | 9.6 | 27.6 |
| BRTHA20046390 | 2 | 2.1 | 2 | 3.2 | 3.2 | 2.4 |
| CD34C30004240 | 1 | 1.3 | 1.8 | 2 | 1.7 | 1.3 |
| CD34C30004940 | | | | 0 | 2.9 | 0 |
| COLON20043180 | | | | 7.2 | 6.6 | 7.2 |
| CTONG10000620 | 0.04 | 0.04 | 0.04 | | | |
| CTONG20014280 | 0.4 | 0.5 | 0 | | | |
| CTONG20095270 | 0 | 1.9 | 1.6 | 0 | 0 | 0 |
| CTONG20095290 | 1.5 | 0.5 | 0.8 | 0 | 0 | 0 |
| CTONG20096750 | 0 | 0.1 | 0 | 0 | 0 | 0 |
| CTONG20100240 | 0.2 | 0 | 0.04 | 0.2 | 0.04 | 0.04 |
| CTONG20103480 | 2.7 | 2.9 | 3.7 | 0 | 0.1 | 0 |
| CTONG20105660 | 7.2 | 4.3 | 3.7 | 3.1 | 2.8 | 3.1 |
| CTONG20121010 | 0 | 0 | 0 | 1.7 | 1.6 | 0 |
| CTONG20128470 | 0.8 | 1 | 1 | 0.2 | 0.3 | 0.2 |
| CTONG20138030 | 2.7 | 2.1 | 1.9 | 2.2 | 0.8 | 1.8 |
| CTONG20139070 | 2.4 | 2.3 | 2.2 | 0.9 | 0.4 | 1.1 |
| CTONG20146970 | 7 | 6.9 | 5.4 | 7.3 | 2.7 | 6.8 |
| CTONG20158150 | 0.2 | 3 | 0.4 | 1.6 | 0 | 1 |
| CTONG20186320 | 3.6 | 2.5 | 3.8 | 1.8 | 1.8 | 0.6 |
| CTONG20265130 | 1.2 | 2.2 | 6.3 | 0.8 | 6 | 20.3 |
| D3OST20006540 | 0.7 | 1.7 | 0.4 | 0.7 | 0.2 | 0.9 |
| D3OST20037970 | 2.7 | 2.7 | 1.7 | 1.9 | 0.6 | 1.3 |
| D9OST20031370 | 0.8 | 2.9 | 1.1 | 0.04 | 0.04 | 0.04 |
| DFNES10001850 | | | | 0 | 0 | 0 |
| DFNES20031920 | 2.1 | 2.2 | 0.8 | 1.2 | 2.9 | 0.8 |
| FCBBF10005060 | | | | 0.9 | 0 | 1 |
| FCBBF20032970 | 3.1 | 3.6 | 3.6 | 1.6 | 0.9 | 2 |
| FCBBF20035280 | | | | 0 | 0 | 0 |
| FCBBF20054280 | 2 | 2 | 2.4 | | | |
| FCBBF20071860 | 0.9 | 1.1 | 1.9 | 0 | 0 | 0.04 |
| FCBBF30001840 | 1 | 1.6 | 1.5 | 2.5 | 0 | 0 |
| FCBBF30016320 | 1 | 1.9 | 0.6 | 1.3 | 1.5 | 0.3 |
| FCBBF30016570 | 2.4 | 1.8 | 1.7 | 0.4 | 0.2 | 0.4 |
| FCBBF30033050 | 4.1 | 0 | 3.2 | 1 | 0 | 0.3 |
| FCBBF30071520 | 2 | 0 | 1.2 | | | |
| FCBBF30083820 | 2.9 | 3.5 | 1.4 | 2.2 | 1.6 | 0.5 |
| FCBBF30215060 | | | | 0.5 | 0.5 | 0.5 |
| FCBBF30251420 | 0 | 2.6 | 0 | 0.3 | 0.1 | 0.6 |
| FCBBF30252520 | 1 | 3.8 | 2.4 | 0.4 | 0 | 0 |
| FCBBF30262360 | | | | 0.0 | 0.04 | 0.04 |
| FCBBF30266920 | | | | 0.3 | 0.4 | 2 |
| FCBBF30278630 | | | | 1.3 | 3.6 | 0 |
| FCBBF30285280 | 0 | 0 | 0 | 0 | 0 | 0 |
| FCBBF40001420 | 0.3 | 0.7 | 0.3 | 0.1 | 0.7 | 0.1 |
| FEBRA10001880 | 0.5 | 0.4 | 0.4 | 0.4 | 0.4 | 0.5 |
| FEBRA20010120 | 4.2 | 6.4 | 3.5 | 0.7 | 0 | 0 |
| FEBRA20017050 | 0 | 0.8 | 0.8 | 0.04 | 0 | 0 |
| FEBRA20034360 | 0.8 | 0.9 | 0.7 | 0.1 | 0.1 | 0.1 |
| FEBRA20037260 | 1.2 | 1.4 | 0.9 | | | |
| FEBRA20037500 | 0.04 | 0 | 0.1 | 4.4 | 4 | 3.4 |
| FEBRA20082100 | 0.2 | 0.3 | 0.5 | 2.1 | 0.7 | 0.5 |
| FEBRA20095880 | 0.9 | 0 | 0.5 | 0.7 | 0.3 | 0.7 |
| FEBRA20167390 | 0.3 | 0 | 0 | 0.9 | 0.3 | 0.6 |
| FEBRA20176800 | 0.9 | 0 | 0 | 0.04 | 0 | 0 |
| FEBRA20226010 | 0.9 | 0.2 | 0.2 | 0 | 0 | 0 |
| HCASM10000500 | 2.7 | 2.7 | 3.1 | 0.9 | 0.8 | 0.4 |
| HCHON20002260 | 0.1 | 0 | 0 | 0.8 | 0.6 | 0.9 |
| HCHON20008980 | 1.8 | 2.4 | 0.2 | | | |
| HCHON20009350 | 0 | 0 | 0 | | | |
| HCHON20010990 | | | | 0.3 | 0.3 | 0.3 |
| HCHON20011160 | 0.04 | 0.2 | 0.04 | | | |
| HCHON20015230 | 2.6 | 2.3 | 2.4 | 1.2 | 1.7 | 0.6 |
| HCHON20022470 | 2 | 1.2 | 0.7 | 1.6 | 1.1 | 1.1 |
| HCHON20035130 | 1.9 | 2 | 2.4 | 1.3 | 0 | 2 |
| HCHON20043590 | 2.6 | 2.4 | 1.8 | 1.5 | 0.3 | 0.6 |
| HCHON20067220 | 1.5 | 2.1 | 2.3 | 2.1 | 0 | 0.9 |
| HCHON20076500 | 2.1 | 2.4 | 2.1 | 0 | 0.1 | 0 |
| HEART20021840 | 0.6 | 0.4 | 0 | | | |
| HEART20067870 | 0 | 0 | 0 | 0 | 0 | 0 |
| HEART20083640 | 0.8 | 0.2 | 0.2 | | | |
| HHDPC10000650 | 1.4 | 1.4 | 1.1 | 0.7 | 0.4 | 0.3 |
| HHDPC20034390 | 1.1 | 0.5 | 1.2 | 0.3 | 0.04 | 0.04 |
| HHDPC20095280 | 0.8 | 0.7 | 0.5 | 0 | 0.5 | 0 |
| HLUNG10000550 | 7.6 | 7 | 6.9 | 2.1 | 1.4 | 1 |
| KIDNE20018970 | 1.5 | 1.2 | 0.9 | 1.4 | 0.9 | 0.9 |
| KIDNE20028720 | 1.5 | 1.2 | 0 | | | |
| KIDNE20079440 | 1.4 | 1.8 | 0 | | | |
| KIDNE20096470 | 2.1 | 2.6 | 2.3 | 1.3 | 1 | 0.7 |
| KIDNE20106740 | 0.2 | 0.1 | 0 | 0 | 0 | 0 |
| KIDNE20120090 | 0.2 | 0 | 0 | | | |
| KIDNE20127750 | 1.9 | 0.6 | 0.4 | | | |
| KIDNE20130450 | 0.9 | 0.9 | 1.3 | 0.1 | 0.8 | 0.4 |
| KIDNE20132180 | | | | 0.7 | 0 | 0 |
| KIDNE20141190 | 0.1 | 0.2 | 0 | 0.4 | 0.3 | 0 |
| KIDNE20148900 | 4.6 | 0 | 4.7 | | | |
| KIDNE20163880 | 0.6 | 1.5 | 0 | 2.2 | 1.8 | 1.2 |
| KIDNE20182690 | 0.5 | 0.4 | 3.9 | 2.5 | 3.1 | 3.1 |
| LIVER10004790 | 1.5 | 3.3 | 1.6 | 0 | 0 | 0 |
| LIVER20011130 | 2.4 | 0.8 | 0 | 0.2 | 1.9 | 0.2 |
| LIVER20038540 | 0 | 5.1 | 0 | 1.2 | 4.9 | 0 |
| LIVER20055440 | 0.5 | 0.5 | 0.4 | 0.3 | 0.1 | 0.1 |
| LIVER20062510 | 1 | 1.1 | 1.2 | 0 | 0 | 0.9 |
| LIVER20085800 | 0 | 0.8 | 0.5 | | | |
| MAMGL10000830 | 5.4 | 4.3 | 0.1 | 0.6 | 0.6 | 0.7 |
| MESAN20031900 | 0.7 | 0.3 | 0.4 | 0.1 | 0.1 | 0.1 |
| MESAN20121130 | 2.6 | 2.8 | 2.2 | 0.1 | 0.04 | 0.04 |
| MESAN20127350 | 1.6 | 0.7 | 0.3 | | | |
| MESAN20130220 | 0.9 | 2.3 | 2.2 | | | |
| MESAN20154010 | 2.6 | 2.2 | 2 | 2.9 | 2.4 | 2.5 |
| MESAN20174170 | 0 | 0 | 0.7 | | | |
| NOVAR10001020 | | | | 0.3 | 0.04 | 0.04 |
| NT2NE20053580 | | | | 0.8 | 0 | 0 |
| NT2NE20089610 | 0.9 | 1.3 | 1.5 | 0.1 | 0.04 | 0.04 |
| NT2NE20089970 | 0.7 | 0 | 0 | 0 | 0 | 0 |
| NT2NE20146810 | | | | 2.8 | 2.3 | 1.9 |
| NT2NE20155110 | 2.5 | 2.6 | 2.9 | | | |
| NT2NE20156260 | 1.3 | 1.3 | 1.7 | 0.3 | 0.1 | 1 |
| NT2NE20158600 | 0.8 | 3.4 | 3 | | | |
| NT2NE20172590 | | | | 0 | 0.8 | 0 |
| NT2NE20174920 | 1.8 | 1 | 1.1 | 1.4 | 0 | 0 |
| NT2NE20181650 | 1 | 1.1 | 0.5 | 0.2 | 0.1 | 0.04 |
| NT2RI20005750 | 0 | 0.4 | 0 | 0.6 | 0.04 | 0 |
| NT2RI20009870 | 3 | 2.3 | 2.3 | 7.3 | 2.1 | 3.4 |
| NT2RI20023160 | 3.5 | 1.1 | 2.8 | 1.7 | 0.4 | 1.8 |
| NT2RI20040930 | 0.7 | 0.6 | 0.5 | 0.3 | 0.1 | 0.1 |
| NT2RI20046080 | 1.8 | 1.8 | 1.5 | 1.2 | 0.8 | 0.9 |
| NT2RI20055790 | 0.9 | 0.9 | 0.9 | 0.8 | 0.6 | 1 |
| NT2RI20069730 | 2.4 | 2.1 | 1.7 | 2.1 | 1.4 | 1.4 |
| NT2RI20203900 | 0 | 0 | 0 | 0 | 0 | 0 |
| NT2RP70062230 | | | | 1.8 | 0 | 1.5 |
| NT2RP70102350 | 1.7 | 0.04 | 0.04 | | | |
| NT2RP70110860 | 0 | 0 | 0.6 | 0 | 0 | 0 |
| NT2RP70111320 | | | | 3.2 | 4.4 | 2.8 |
| NT2RP70130020 | 0 | 0 | 0 | 1 | 0 | 0.1 |
| NT2RP70143480 | 1.2 | 2 | 1.7 | 0.8 | 1.1 | 0.6 |
| NT2RP70150800 | | | | 0.8 | 0.3 | 0.3 |
| NT2RP70157890 | 4.6 | 1.1 | 0.3 | 2.2 | 1.8 | 0 |
| NT2RP70169110 | 0.5 | 1.3 | 1.7 | 1 | 3.3 | 2.5 |
| NT2RP70175670 | 0.3 | 0.1 | 1.4 | 4.3 | 3.3 | 3.3 |

| Clone Name | THP-1 TNF ct1 | THP-1 TNF 1h | TNF 3h | MKN45 ct1 | MKN45 Hp | MKN45 ΔcagE |
|---|---|---|---|---|---|---|
| NT2RP70188020 | 2.5 | 2.8 | 2.6 | 0 | 0 | 0 |
| NT2RP70188710 | 0 | 0.1 | 0.2 | 4.3 | 2.8 | 2.9 |
| NT2RP70190640 | | | | 0.4 | 0.4 | 0.9 |
| NTONG20029480 | 3.1 | 0.7 | 2.2 | | | |
| NTONG20064840 | | | | 1.5 | 1 | 1 |
| NTONG20067090 | 2.5 | 2.1 | 2.3 | 0.4 | 0.1 | 0.2 |
| NTONG20070340 | 0.1 | 0 | 0 | 6.3 | 1.3 | 0.7 |
| NTONG20077560 | | | | 0.5 | 0.5 | 0.5 |
| NTONG20083650 | 2.9 | 2.9 | 2.7 | 2.5 | 2.5 | 1.9 |
| NTONG20090680 | 2.1 | 2 | 2.4 | 2 | 1.3 | 1.6 |
| OCBBF20005230 | 1.7 | 1.3 | 2.3 | 0.9 | 0.7 | 0.7 |
| OCBBF20019380 | 0.6 | 0.6 | 0.5 | 0 | 0 | 0 |
| OCBBF20020150 | 4.2 | 3.2 | 3 | 1 | 0 | 0.6 |
| OCBBF20020830 | 2.7 | 2.7 | 1.3 | 4.4 | 2.3 | 2.1 |
| OCBBF20039250 | 1 | 1.2 | 0.9 | 0.4 | 0.1 | 0.5 |
| OCBBF20041680 | 1.4 | 0 | 0 | | | |
| OCBBF20047570 | 0.04 | 0 | 0 | 0.3 | 0.2 | 0.6 |
| OCBBF20051610 | 0 | 0.04 | 0.04 | 0 | 0 | 0 |
| OCBBF20054200 | 0.4 | 0.3 | 0 | 0.04 | 0.04 | 0.04 |
| OCBBF20061720 | 1.3 | 2 | 0.2 | 0.7 | 1.2 | 0 |
| OCBBF20062140 | 3.3 | 3.1 | 5 | | | |
| OCBBF20071960 | | | | 0.1 | 0 | 0 |
| OCBBF20072320 | 0.04 | 0 | 0.04 | 0.04 | 0.04 | 0.04 |
| OCBBF20079310 | 0.04 | 0 | 0 | 0 | 0.04 | 1 |
| OCBBF20081380 | 6.3 | 6.1 | 5.1 | 0.8 | 0.4 | 0.6 |
| OCBBF20085200 | | | | 0.1 | 0.5 | 1.3 |
| OCBBF20094240 | 0.9 | 1.5 | 1.6 | 1.1 | 0.3 | 0 |
| OCBBF20107920 | 2.9 | 2.9 | 2.6 | 2.6 | 0.7 | 0.3 |
| OCBBF20127040 | 1.4 | 1.3 | 0.5 | 0.2 | 0.04 | 0 |
| OCBBF20130110 | | | | 3.2 | 2.4 | 1.8 |
| OCBBF20139260 | 2.1 | 0.7 | 0.2 | | | |
| OCBBF20164050 | 0.3 | 0.3 | 0.2 | 0.2 | 0 | 0.04 |
| OCBBF20178990 | 2.1 | 0.7 | 0.2 | 0.9 | 0 | 0 |
| OCBBF20180840 | 3.7 | 2.7 | 3.1 | 0.1 | 0.3 | 0.3 |
| PEBLM10000240 | 2.1 | 2.2 | 1.6 | 0 | 0.3 | 0 |
| PEBLM20013120 | 3.3 | 0.5 | 3 | | | |
| PEBLM20024550 | 0.1 | 0 | 0 | 3 | 2.2 | 0.7 |
| PEBLM20052820 | 1.9 | 2.1 | 2.2 | 1 | 0.6 | 0.8 |
| PEBLM20074370 | 0.9 | 0.9 | 1.7 | 3.7 | 3.1 | 3 |
| PERIC20002140 | 0.04 | 0.9 | 0.4 | 0.7 | 0.3 | 0.8 |
| PERIC20004780 | 0 | 0.04 | 0.1 | 0.04 | 0 | 0.04 |
| PLACE60003480 | 4.1 | 1.5 | 4.8 | 0.6 | 1.6 | 5.1 |
| PLACE60136720 | 0.5 | 0.7 | 0.7 | 0.6 | 0.7 | 0.2 |
| PLACE60155130 | 0.7 | 2.3 | 0 | | | |
| PLACE60169420 | 1.2 | 1.4 | 1.6 | 0.6 | 0 | 0.8 |
| PLACE60181070 | 42.3 | 10 | 28.2 | | | |
| PROST10004800 | 3.1 | 3.2 | 1.8 | | | |
| PROST20120160 | 0 | 0.6 | 0 | 0 | 0.3 | 0.9 |
| PROST20144220 | 2.5 | 2.8 | 2.4 | 1.6 | 0.5 | 0.2 |
| PROST20149160 | 0.7 | 0 | 0.4 | 1.6 | 0.6 | 0.6 |
| PROST20149250 | 0 | 0.9 | 0.4 | 0 | 0 | 0 |
| PROST20151240 | 1.3 | 0.7 | 0 | 0 | 1.2 | 0 |
| PROST20153320 | 1.4 | 1.2 | 1.8 | 1.4 | 0.3 | 1.2 |
| PROST20161950 | 0 | 0 | 0.6 | 2.2 | 1.4 | 1.2 |
| PROST20189770 | 1.1 | 1.4 | 0.8 | 2.8 | 2.8 | 2.1 |
| PUAEN20003740 | 3.1 | 0.5 | 2.8 | 1.4 | 0.5 | 2.4 |
| PUAEN20011880 | 1.3 | 2.4 | 0.4 | 0.1 | 0.3 | 0 |
| PUAEN20015260 | 0.04 | 0.04 | 7.4 | | | |
| PUAEN20025680 | 1.9 | 1 | 2.3 | 3.1 | 0.9 | 1.1 |
| PUAEN20040670 | 0.3 | 0.5 | 0.2 | 1.3 | 0.5 | 1 |
| PUAEN20045250 | 1.8 | 1.6 | 1.6 | 1.9 | 1.6 | 1.1 |
| PUAEN20078980 | 1.1 | 0.3 | 0.7 | 0.5 | 0 | 0.1 |
| PUAEN20085150 | 2 | 1 | 2.3 | 1.6 | 1.1 | 0.2 |
| SKMUS20018230 | 1.9 | 2.2 | 1.8 | 0.8 | 0.5 | 0.6 |
| SKMUS20028210 | 1.6 | 2.7 | 2.2 | 0 | 0 | 1.3 |
| SKMUS20031680 | 0.9 | 0 | 0 | 1.2 | 2.4 | 0.3 |
| SKMUS20046670 | 0.3 | 0.3 | 0.3 | | | |
| SKNSH20062340 | | | | 0.6 | 0.5 | 0 |
| SKNSH20080430 | 1.1 | 2.6 | 0.5 | 0 | 1.3 | 0 |
| SMINT20001760 | 1.8 | 1.5 | 0.7 | 0.3 | 0.1 | 0.3 |
| SMINT20013480 | 1.3 | 2.1 | 0.9 | | | |
| SMINT20014580 | 2.7 | 2.1 | 1.4 | 1.2 | 0 | 0.6 |
| SMINT20033400 | 2.6 | 1.7 | 1.4 | | | |
| SMINT20047810 | 2.2 | 0.7 | 0.5 | | | |
| SMINT20051610 | 0.1 | 0.1 | 0.3 | 0.4 | 0.1 | 0.5 |
| SMINT20056210 | | | | 0.9 | 1.8 | 0 |
| SMINT20060780 | 0.2 | 0.6 | 0.5 | 0.04 | 0.04 | 0.04 |
| SMINT20080540 | | | | 0 | 0 | 0 |
| SMINT20105000 | | | | 0 | 1.1 | 0.3 |
| SMINT20108530 | 1.3 | 1.5 | 0 | 0.04 | 0.04 | 0.04 |
| SMINT20122850 | 0.04 | 0.04 | 0.04 | 0.04 | 0.04 | 0.04 |
| SMINT20122910 | | | | 0.3 | 0.3 | 0.3 |
| SMINT20153530 | 4.8 | 4.6 | 5.6 | 2.7 | 1.5 | 1.8 |
| SMINT20161220 | 8.5 | 6.2 | 19.5 | 2 | 1.1 | 1 |
| SMINT20163960 | 0.6 | 0.5 | 1.4 | 0 | 0 | 0 |
| SMINT20164770 | 2.4 | 2.1 | 1.6 | 1.8 | 1.2 | 1 |
| SMINT20168570 | 0 | 0 | 0 | | | |
| SPLEN20008820 | 2.5 | 2.3 | 2.7 | 1.6 | 1.3 | 0.8 |
| SPLEN20011410 | 0.4 | 0.4 | 0.1 | | | |
| SPLEN20013540 | 1.6 | 0.9 | 1.1 | 2.4 | 1.4 | 1.8 |
| SPLEN20019450 | 1 | 1.8 | 1.2 | 0.2 | 0.6 | 0.4 |
| SPLEN20022230 | 4.5 | 6.2 | 3.9 | 1.4 | 1.1 | 1.6 |
| SPLEN20040600 | 3.2 | 4.5 | 3.6 | 0 | 0 | 0 |
| SPLEN20076530 | 0.04 | 0.04 | 0.04 | 0 | 0 | 0 |
| SPLEN20101190 | 0.3 | 0.2 | 0.6 | 1.6 | 0 | 0 |
| SPLEN20126190 | 2.5 | 3.4 | 2.8 | 5.2 | 3.5 | 3.1 |
| SPLEN20152760 | 4.2 | 3 | 3.2 | 1.2 | 0.8 | 1.6 |
| SPLEN20157300 | 0.4 | 0.5 | 2.5 | | | |
| SPLEN20158990 | 1.9 | 0.9 | 2.6 | 1.1 | 1.1 | 1.3 |
| SPLEN20163560 | 0.3 | 0.6 | 0.3 | 0 | 0 | 0 |
| SPLEN20174260 | 0.4 | 0 | 0 | 0.3 | 0.1 | 0.1 |
| SPLEN20211570 | 2.3 | 2.3 | 2.2 | 1 | 2.1 | 1.4 |
| SPLEN20214580 | 0.04 | 0.6 | 0.9 | 1.4 | 1.3 | 2.6 |
| SPLEN20245300 | 3.1 | 2.6 | 1.9 | 0.6 | 0 | 0.2 |
| SPLEN20279950 | 0.8 | 2.1 | 0.3 | | | |
| SPLEN20280660 | 0.6 | 0.5 | 1 | 0 | 0 | 0 |
| SPLEN20283650 | 1.8 | 1 | 0.8 | 0.8 | 0 | 0 |
| SPLEN20329240 | | | | 0.2 | 0 | 0 |
| STOMA20010250 | 2 | 0.9 | 1 | 0 | 0 | 0.7 |
| STOMA20032890 | 0.9 | 1.5 | 0.4 | | | |
| STOMA20048520 | 0.04 | 2 | 0.4 | 0 | 0.9 | 0 |
| STOMA20057820 | 1.3 | 1 | 0 | 4.3 | 4.1 | 0 |
| STOMA20062290 | 0.4 | 0.6 | 0.4 | 0.3 | 0.3 | 0.2 |
| STOMA20076800 | 1.1 | 0.7 | 0.6 | 1.2 | 0.6 | 0.3 |
| TESTI20001170 | 0 | 0 | 0 | 0.8 | 0.6 | 0.7 |
| TESTI20002780 | | | | 0 | 0 | 0 |
| TESTI20004890 | 1.1 | 0.7 | 0.6 | 0 | 0.2 | 0.4 |
| TESTI20011200 | 6.3 | 3.7 | 5.9 | 0.5 | 0.04 | 0.2 |
| TESTI20018230 | 0 | 0 | 0 | 0.04 | 0.04 | 0.04 |
| TESTI20035960 | 0.1 | 0 | 0 | 0.04 | 0.04 | 0.04 |
| TESTI20038270 | | | | 0 | 0 | 0 |
| TESTI20044230 | 0 | 0 | 0 | 0.6 | 0.2 | 0.2 |
| TESTI20046750 | 0.4 | 0.04 | 0.04 | 1 | 0.8 | 0 |
| TESTI20060400 | 1.2 | 2 | 0.2 | 0.7 | 0.5 | 0.04 |
| TESTI20066770 | 0 | 0 | 0 | 0.04 | 0.04 | 0.04 |
| TESTI20076850 | 0 | 0.6 | 0 | 0.04 | 0.04 | 0.04 |
| TESTI20083940 | 0.9 | 1.5 | 1.4 | 0 | 1.2 | 1.3 |
| TESTI20087620 | 0.8 | 2.3 | 0.8 | 1.1 | 0.04 | 0.1 |
| TESTI20098530 | | | | 5.3 | 1.2 | 0 |
| TESTI20105720 | 2.7 | 3.5 | 2.5 | 0.04 | 0.1 | 0.04 |
| TESTI20108720 | 0.04 | 1.5 | 1.1 | 2.5 | 2.1 | 1.8 |
| TESTI20123080 | | | | 6 | 0 | 0 |
| TESTI20128350 | | | | 1.4 | 1.6 | 0 |
| TESTI20136100 | 3.1 | 1.9 | 2.1 | | | |
| TESTI20137670 | | | | 0.4 | 0.4 | 0.4 |
| TESTI20143240 | 0.2 | 0.1 | 0.1 | 0.3 | 0.04 | 0.3 |
| TESTI20143620 | 0.04 | 0 | 0 | | | |
| TESTI20156100 | 0.1 | 0.04 | 0.1 | | | |
| TESTI20161970 | 1.2 | 0.7 | 0 | 1.1 | 0.4 | 1 |
| TESTI20168480 | | | | 0.5 | 5.7 | 0.5 |
| TESTI20168960 | | | | 0.5 | 0.5 | 0.5 |
| TESTI20178160 | 0.04 | 0.04 | 0.04 | 0.04 | 0.04 | 0.04 |
| TESTI20185810 | | | | 0.9 | 0 | 0 |
| TESTI20199170 | 0.7 | 0 | 0 | 0.9 | 0.8 | 0 |
| TESTI20200260 | | | | 0.3 | 0 | 0 |
| TESTI20200710 | 3.9 | 2.6 | 2.4 | 2.5 | 3.5 | 2.9 |

-continued

| Clone Name | THP-1 ct1 | TNF 1h | TNF 3h | MKN45 ct1 | Hp | ΔcagE |
|---|---|---|---|---|---|---|
| TESTI20202650 | 0.04 | 0.04 | 0.04 | 1 | 1.2 | 0.3 |
| TESTI20220100 | 0 | 5.7 | 0 | | | |
| TESTI20224620 | | | | 0 | 0 | 1.5 |
| TESTI20229600 | 0 | 0 | 0 | | | |
| TESTI20230850 | 0.04 | 0.04 | 0 | 0.04 | 0.04 | 0.04 |
| TESTI20231920 | | | | 0.5 | 0.5 | 0.5 |
| TESTI20234140 | | | | 1.8 | 0.3 | 0.3 |
| TESTI20234270 | 2.6 | 2.8 | 2.9 | 0.5 | 0.04 | 0.3 |
| TESTI20238000 | 0.2 | 0 | 0.04 | 0.04 | 0.04 | 0.04 |
| TESTI20238610 | | | | 0.04 | 0.04 | 0.04 |
| TESTI20239510 | 0 | 0.2 | 0 | 0.04 | 0.2 | 1 |
| TESTI20242990 | 1.8 | 2.1 | 1.8 | 0 | 0 | 0 |
| TESTI20265250 | 2.1 | 1.6 | 1.9 | 1.5 | 0.8 | 0.4 |
| TESTI20265370 | 0.04 | 0.04 | 0.04 | 0.04 | 0.04 | 0.04 |
| TESTI20266740 | 0.2 | 0 | 0.7 | 0.04 | 0.04 | 0.04 |
| TESTI20272390 | 1.3 | 1.2 | 0.8 | 0.2 | 0.2 | 0.4 |
| TESTI20275030 | 0 | 0 | 0 | 0 | 0 | 0.3 |
| TESTI20275620 | 1.3 | 0.04 | 0.7 | | | |
| TESTI20277360 | 0 | 0 | 0 | | | |
| TESTI20282540 | 0.04 | 0 | 0.1 | 0.2 | 0.04 | 0.3 |
| TESTI20284880 | 0.4 | 0.2 | 0.1 | 0.04 | 0 | 0.1 |
| TESTI20285830 | 0.04 | 0.04 | 0.04 | | | |
| TESTI20288110 | | | | 1.2 | 0 | 0 |
| TESTI20289850 | 0.04 | 0 | 0 | 0.04 | 0.04 | 0.04 |
| TESTI20307540 | | | | 0.6 | 0.8 | 0 |
| TESTI20308600 | | | | 0.5 | 1.2 | 0.5 |
| TESTI20311290 | 0 | 0 | 0 | 0 | 0 | 0.7 |
| TESTI20317600 | 0 | 0 | 0 | 0.04 | 0.04 | 0.04 |
| TESTI20319190 | 0.2 | 0 | 0 | 0.04 | 0.04 | 0.3 |
| TESTI20332420 | 0.6 | 0.1 | 0.9 | | | |
| TESTI20335200 | | | | 0.9 | 1.4 | 0.9 |
| TESTI20342430 | 0 | 2.8 | 0 | 0.6 | 0.6 | 0.5 |
| TESTI20345060 | | | | 0.1 | 0 | 0.04 |
| TESTI20347300 | 0.9 | 0.6 | 1.4 | 0.04 | 0 | 0 |
| TESTI20357960 | 1 | 1 | 1.7 | 2.7 | 1.3 | 1.7 |
| TESTI20361140 | 0.04 | 0.04 | 0.04 | 0.2 | 0 | 0 |
| TESTI20369220 | 0.04 | 0.04 | 0.04 | | | |
| TESTI20369690 | 1.5 | 0 | 1.3 | 1.3 | 1.4 | 1 |
| TESTI20370020 | 0.4 | 1.7 | 0.1 | | | |
| TESTI20371030 | 1.3 | 1.3 | 1 | 0.8 | 0.5 | 0.5 |
| TESTI20386230 | 2 | 0.2 | 0.3 | | | |
| TESTI20391210 | 0.6 | 2.3 | 4.9 | 3.1 | 0 | 2.4 |
| TESTI20392090 | 0 | 0 | 0.04 | 0.04 | 0.04 | 0.7 |
| TESTI20392250 | 9.3 | 7.8 | 3.8 | | | |
| TESTI20392270 | 1.8 | 1.4 | 1.6 | 1.1 | 1.6 | 1.1 |
| TESTI20401020 | 0.2 | 0.5 | 0.8 | 0 | 0 | 0 |
| TESTI20401430 | 4.3 | 4.8 | 4.3 | | | |
| TESTI20409440 | 1.4 | 0.5 | 0.3 | 0.5 | 0 | 0.3 |
| TESTI20415640 | 0.8 | 2.5 | 1 | 0 | 0 | 0 |
| TESTI20424000 | 0.2 | 0.04 | 0.04 | 0 | 0 | 0 |
| TESTI20424730 | 1.8 | 0.7 | 2.9 | 3.8 | 0 | 3.3 |
| TESTI20425070 | 2.3 | 2.4 | 2.6 | 1.9 | 1.4 | 1.2 |
| TESTI20433130 | | | | 0 | 0 | 0 |
| TESTI20438570 | 0.8 | 0.6 | 0.6 | 0.8 | 0.6 | 1.2 |
| TESTI20443090 | 0.1 | 0.1 | 0.1 | 0.3 | 0.5 | 0.6 |
| TESTI20463520 | | | | 0 | 0 | 0 |
| TESTI20465520 | 0.6 | 0.6 | 0.5 | 0.2 | 0 | 0.1 |
| TESTI20478010 | 0.9 | 1.7 | 0.7 | 0 | 0.3 | 0 |
| TESTI20478180 | 0.04 | 0.04 | 0.04 | 0.04 | 0 | 0 |
| THYMU20029100 | 1.9 | 1.2 | 2.3 | 2 | 2.9 | 2.5 |
| THYMU20061700 | 0 | 0 | 0 | 0.7 | 0.2 | 0.2 |
| THYMU20095960 | 2.9 | 2.4 | 0.5 | | | |
| THYMU20111180 | 1.1 | 0.6 | 0.5 | 0 | 0 | 0 |
| THYMU20118060 | 0.2 | 0 | 0.2 | 0.04 | 0.04 | 0.04 |
| THYMU20130890 | 0.6 | 1.3 | 3.3 | | | |
| THYMU20142040 | 1 | 1.1 | 0.7 | 1.3 | 1.1 | 1 |
| THYMU20142970 | 4 | 3.5 | 3.8 | 1.6 | 2 | 0.6 |
| THYMU20153160 | 1 | 0.7 | 1 | 0.1 | 0.1 | 0.04 |
| THYMU20158250 | 10.4 | 7 | 5.5 | 1.1 | 0 | 0 |
| THYMU20187720 | 3.2 | 3.2 | 2.8 | 2.4 | 2.2 | 2.3 |
| THYMU20194360 | 1.8 | 2.1 | 1.7 | 0.4 | 0.3 | 1.3 |
| THYMU20208300 | 1.9 | 1.9 | 1.6 | 0.3 | 0.2 | 0.3 |
| THYMU20226600 | 3 | 0 | 1.4 | 1.1 | 0.3 | 2.6 |
| THYMU20239000 | 2.1 | 2.3 | 2.8 | 1.4 | 0.8 | 1.1 |
| THYMU20253250 | 1.1 | 0.3 | 0.3 | | | |
| THYMU20272490 | 2.7 | 1.4 | 0.6 | 0.04 | 0.04 | 0.04 |
| THYMU20284120 | 3.8 | 4.1 | 4 | 0.4 | 0.04 | 0.5 |
| THYMU20286290 | 0 | 2.1 | 0.4 | 3.1 | 2.5 | 1.7 |
| TKIDN10000010 | 2.2 | 2.2 | 2.5 | 1.2 | 1 | 1.1 |
| TRACH20005020 | 0 | 0 | 0 | 2.8 | 0.9 | 0.5 |
| TRACH20032720 | 0.1 | 0 | 0 | 0.6 | 0.04 | 0.1 |
| TRACH20041830 | | | | 0.8 | 0.2 | 0.9 |
| TRACH20060150 | 0.2 | 0.9 | 2 | | | |
| TRACH20076760 | 5.1 | 4.9 | 4.5 | 0.6 | 0.5 | 0.4 |
| TRACH20082780 | | | | 0 | 0 | 0 |
| TRACH20091230 | 0.4 | 0 | 0.2 | 2.1 | 1.1 | 1.2 |
| TRACH20099340 | 1.8 | 3.8 | 4.9 | 1.9 | 2.5 | 0.9 |
| TRACH20109650 | 3.5 | 3.3 | 3.5 | 3.7 | 3.7 | 3.4 |
| TRACH20115740 | 0.04 | 0.04 | 0.04 | | | |
| TRACH20134950 | 5.6 | 5 | 4 | 3.5 | 1.2 | 1.9 |
| TRACH20135520 | 1 | 0.9 | 0.6 | 0.9 | 0.9 | 0.5 |
| TRACH20153810 | 2.1 | 0 | 0 | | | |
| TRACH20184490 | 2.2 | 3.2 | 2.8 | 1.6 | 0 | 0 |
| TSTOM20001390 | 1.5 | 2.1 | 1.8 | 2.5 | 0.4 | 2.5 |
| TSTOM20005690 | 1.3 | 0.8 | 1.1 | 0.3 | 0 | 0.1 |
| UMVEN10001560 | 2.4 | 2.6 | 3.3 | 0.6 | 0 | 0.04 |
| UMVEN20003540 | 5.2 | 3.9 | 4.9 | 3.1 | 2.4 | 2.8 |
| UTERU20004240 | 0.04 | 0.2 | 0.1 | 0.04 | 0 | 0.04 |
| UTERU20046980 | | | | 0 | 0 | 0 |
| UTERU20055930 | 2.5 | 3.6 | 2.9 | 2.3 | 1.6 | 2.5 |
| UTERU20068990 | 0.04 | 1.3 | 0.04 | 0.1 | 0 | 0 |
| UTERU20070810 | 2.7 | 1.9 | 2.4 | 1.9 | 1.3 | 1.1 |
| UTERU20115740 | 3.1 | 3.2 | 5 | 2.3 | 1.9 | 0 |
| UTERU20119060 | 0.8 | 1.9 | 0 | 1.9 | 0.3 | 1.6 |
| UTERU20124070 | 2 | 2.7 | 1.8 | 2.8 | 2.1 | 1.8 |
| UTERU20126880 | | | | 0 | 2.2 | 0.1 |
| UTERU20134910 | 2.5 | 2.7 | 2.3 | 2.9 | 1.4 | 1.3 |
| UTERU20146680 | 0 | 0.1 | 0 | 0.5 | 0 | 0.04 |
| UTERU20176130 | 2.9 | 1.3 | 1.6 | 1.9 | 0.6 | 0.8 |
| UTERU20185230 | 3.1 | 3.2 | 1.8 | 1.6 | 1.1 | 0.6 |
| UTERU20186740 | 1.9 | 1.4 | 0.7 | 0.04 | 0 | 0 |

Homology Search Result Data

Data obtained by the homology search for full-length nucleotide sequences and deduced amino acid sequences.

In the result of the search shown below, both units, aa and bp, are used as length units for the sequences to be compared.

Each data includes Clone name, Definition in hit data, P value, Length of sequence to be compared, Homology, and Accession number (No.) of hit data. These items are shown in this order and separated by a double-slash mark, //. 3NB6910001910//ALANYL-TRNA SYNTHETASE (EC 6.1.1.7) (ALANINE--TRNA LIGASE) (ALARS).//3. 10E-20//392aa//24%//067323 3NB6920014080 3NB6920014590//HOMEOBOX PROTEIN DLX-6.// 1.00E-91//226aa//78%//Q98877 ADIPS10000640//*Homo sapiens* synaptic glycoprotein SC2 (SC2) mRNA, complete cds.//1.60E-169//303aa//100%//AF222742 ADIPS20004250//ZINC FINGER PROTEIN OZF.//6.60E-27//223aa//32%//Q15072 ADRGL10001470//CYTOCHROME P450 11B1 PRECURSOR (EC 1.14.15.4) (CYPXIB1) (P450C11) (STEROID 11-BETA-HYDROXYLASE).//1.60E-38//84aa//98%//P15538 ADRGL20000640 ADRGL20011190//spectrin, beta, non-erythrocytic 1 [*Homo sapiens*].//1.00E-36//250aa//38%//NP_003119 ADRGL20012870 ADRGL20013010 ADRGL20013520 ADRGL20018300//KINESIN LIGHT CHAIN (KLC).// 1.20E-207//566aa//70%//Q07866 ADRGL20018540

ADRGL20028570//*Rattus norvegicus* MG87 mRNA, complete cds.//2.90E-69//250aa//53%//AF095741 ADRGL20035850//CYTOCHROME P450 17 (EC 1.14.99.9) (CYPXVII) (P450-C17) (STEROID 17-ALPHA-HYDROXYLASE/17,20 LYASE).//7.30E-52//99aa//100%// P05093 ADRGL20044590 ADRGL20048330//*Mus musculus* mRNA for granuphilin-a, complete cds.//0//673aa//89%// AB025258 ADRGL20061930//transposon-derived Buster1 transposase-like protein//6.00E-65//500aa//33%//NP_067034 ADRGL20067670 ADRGL20068170 ADRGL20068460 ADRGL20073570 ADRGL20076360 ADRGL20078100//NADPH:ADRENODOXIN OXIDOREDUCTASE PRECURSOR (EC 1.18.1.2) (ADRENODOXIN REDUCTASE) (FERREDOXIN-NADP(+) REDUCTASE).//3.10E-147//276aa//99%//P22570 ADRGL20083310 ASTRO10001650//DREBRIN E.// 4.80E-293//540aa//99%//Q16643 ASTRO20001410 ASTRO20005330 ASTRO20008010//ZINC FINGER PROTEIN 85 (ZINC FINGER PROTEIN HPF4) (HTF1).// 6.00E-57//143aa//70%//Q03923 ASTRO20012490 ASTRO20027430//RAS SUPPRESSOR PROTEIN 1 (RSU-1) (RSP-1 PROTEIN) (RSP-1).//2.20E-18//178aa//34%// Q15404 ASTRO20032120 ASTRO20033160//BRAIN MITOCHONDRIAL CARRIER PROTEIN-1.//2.70E-125// 291aa//80%//O95258 ASTRO20055750//Human elastin gene, exon 1.//2.70E-293//654aa//88%//M17282 ASTRO20058630 ASTRO20064750//*Homo sapiens* BM-003 mRNA, complete cds.//6.10E-69//214aa//64%// AF208845 ASTRO20072210//PERIAXIN.//2.10E-25// 87aa//56%//Q63425 ASTRO20084250//*Ciona savignyi* mRNA for PEM-3, complete cds.//3.50E-56//154aa//64%// AB001769 ASTRO20100720 ASTRO20105820//ACTIN INTERACTING PROTEIN 2.//2.60E-111//392aa//56%// P46681 ASTRO20106150//*H.sapiens* mRNA for calpain-like protease.//1.80E-291//473aa//98%//Y10552 ASTRO20108190//TUBERIN (TUBEROUS SCLEROSIS 2 PROTEIN).//5.30E-278//513aa//100%//P49815 ASTRO20111490 ASTRO20114370//*Mus musculus* SMAR1 mRNA, complete cds.//1.30E-213//461aa//89%// AF235503 ASTRO20114610 ASTRO20125520//dnaj protein [Schizosaccharomyces pombe]//7.80E-37//260aa// 38%//CAB59885 ASTRO20130500//UBIQUITIN-ACTIVATING ENZYME E1. //2. 70E-157//815aa//42%// Q29504 ASTRO20136710 ASTRO20138020 ASTRO20141350//*Mus musculus* mRNA for granuphilin-b, complete cds.//7.40E-12//169aa//30%//AB025259 ASTRO20143630 ASTRO20145760//TUBULIN--TYROSINE LIGASE (EC 6.3.2.25) (TTL).//1.60E-14//233aa// 27%//P38584 ASTRO20152140 ASTRO20155290 ASTRO20166810 ASTRO20168470//ZINC FINGER PROTEIN 135.//4.80E-103//289aa//59%//P52742 ASTRO20173480 ASTRO20181690//oocyte-specific protein P100//1.60E-70//554aa//36%//S23468 ASTRO20190390 BEAST20004540 BGGI110000240 BGGI110001930 BGGI120006160//isomerase-like protein [Arabidopsis thaliana].//1.00E-52//187aa//47%//BAB00076 BLADE20003400//ZINC FINGER PROTEIN 177.//2.50E-33//205aa//38%//Q13360 BLADE20003890//ZINC FINGER PROTEIN 135.//1.50E-264//471aa//95%//P52742 BLADE20004630 BNGH420088500 BRACE20003070// *Rattus norvegicus* neurabin mRNA, complete cds.//2.30E-40//172aa//46%//U72994 BRACE20006400 BRACE20011070//*Mus musculus* F-box protein FBX15 mRNA, partial cds.//9.60E-142//471aa//56%//AF176530 BRACE20019540 BRACE20027620//CYTOSOLIC ACYL COENZYME A THIOESTER HYDROLASE, INDUCIBLE (EC 3.1.2.2)X (LONG CHAIN ACYL-COA THIOESTER HYDROLASE) (LONG CHAIN ACYL-COA HYDROLASE) (CTE-I) (LACH2) (ACH2).//2.70E-148// 423aa//65%//O88267 BRACE20037660 BRACE20038000// MAP kinase phosphatase [*Drosophila melanogaster*].// 3.80E-83//426aa//42%//BAA89534 BRACE20038470// *Rattus norvegicus* neurexophilin 4 (Nph4) mRNA, complete cds.//1.70E-57//109aa//98%//AF042714 BRACE20038480//Human SEC14L mRNA, complete cds.// 2.60E-93//179aa//99%//D67029 BRACE20038850 BRACE20039040 BRACE20039440//*Drosophila melanogaster* CHARYBDE (charybde) mRNA, complete cds.// 6.50E-17//142aa//35%//AF221109 BRACE20039540// MHC class I chain-related gene A protein [*Homo sapiens*]// 2.00E-116//246aa//90%//NP_000238 BRACE20050900 BRACE20051380 BRACE20051690 BRACE20052160// *Xenopus laevis* bicaudal-C (Bic-C) mRNA, complete cds.// 2.10E-13//208aa//30%//AF224746 BRACE20053280//*Mus musculus* Pdz-containing protein (Pdzx) mRNA, complete cds.//5.20E-63//223aa//64%//AF229645 BRACE20053480//*Mus musculus* erythroblast macrophage protein EMP mRNA, complete cds.//1.70E-133//145aa// 97%//AF263247 BRACE20053630//BRITTLE-1 PROTEIN PRECURSOR.//1.20E-24//208aa//31%//P29518 BRACE20054500 BRACE20055180 BRACE20056810 BRACE20057190//NUCLEOPLASMIN.//5.20E-42// 215aa//45%//P05221 BRACE20057420 BRACE20057620//EUKARYOTIC TRANSLATION INITIATION FACTOR 4E (EIF-4E) (EIF4E) (MRNA CAP-BINDING PROTEIN) (EIF-4F 25 KDA SUBUNIT).// 1.00E-22//60aa//73%//P48597 BRACE20057730//toxin sensitivity protein KTI12 homolog//1.10E-10//173aa//26%// A64492 BRACE20058580//*Homo sapiens* HCMOGT-1 mRNA for sperm antigen, complete cds.//2.10E-178// 358aa//96%//AB041533 BRACE20058810 BRACE20059370//PROTEIN 4.1 (BAND 4.1) (P4.1).// 6.70E-52//400aa//32%//P1171 BRACE20060550// ANKYRIN HOMOLOG PRECURSOR.//1.30E-14//139aa// 44%//Q06527 BRACE20060720 BRACE20060840 BRACE20060890//ZINC FINGER PROTEIN ZIC4 (ZINC FINGER PROTEIN OF THE CEREBELLUM 4).//4.00E-131//264aa//87%//Q61467 BRACE20061050 BRACE20061740 BRACE20062400 BRACE20062640// HYPOTHETICAL 93.7 KDA PROTEIN F48E8.6 IN CHROMOSOME III.//9.10E-90//343aa//45%//Q09568 BRACE20062740 BRACE20063630 BRACE20063780 BRACE20063800 BRACE20063930 BRACE20064880// POLY(RC) BINDING PROTEIN 2 (PUTATIVE HETEROGENEOUS NUCLEAR RIBONUCLEOPROTEIN X) (HNRNP X) (CTBP) (CBP).//1.80E-129//207aa//81%// Q61990 BRACE20067430 BRACE20068590//HYPOTHETICAL ZINC FINGER PROTEIN KIAA0961.//2.70E-155//504aa//56%//Q9Y2G7 BRACE20069090 BRACE20081720 BRACE20082950 BRACE20090440 BRACE20096200//*Homo sapiens* sir2-related protein type 7 (SIRT7) mRNA, complete cds.//1.00E-162//305aa//99%// AF233395 BRACE20096540 BRACE20097320 BRACE20099570 BRACE20101700 BRACE20101710 BRACE20106690 BRACE20106840//*Rattus norvegicus* partial mRNA for CRM1 protein.//9.00E-59//120aa//100%// AJ238278 BRACE20107530//*Rattus norvegicus* putative peroxisomal 2,4-dienoyl-CoA reductase (DCR-AKL) mRNA, complete cds.//1.70E-48//108aa//91%//AF044574 BRACE20108130//*Homo sapiens* RAB-like protein 2B (RABL2B) mRNA, complete cds.//1.60E-43//92aa//100%// AF095352 BRACE20108880//MALEYLACETOACETATE ISOMERASE (EC 5.2.1.2) (MAAI) (GLUTATHIONE TRANSFERASE ZETA 1) (EC 2.5.1.18).//

5.90E-ll//27aa//100%//043708 BRACE20109370 BRACE20109830 BRACE20111830 BRACE20114780 BRACE20115450 BRACE20115920//RHO-GTPASE-ACTIVATING PROTEIN 4 (RHO-GAP HEMATOPOIETIC PROTEIN C1) (P115) (KIAA0131).//9.70E-73//291aa// 52%//P98171 BRACE20116110 BRACE20116460//ATP SYNTHASE DELTA CHAIN, MITOCHONDRIAL PRECURSOR (EC 3.6.1.34). //1.00E-20//48aa//100%//P30049 BRACE20118380 BRACE20121850 BRACE20136240 BRACE20141080 BRACE20142320 BRACE20142570 BRACE20147800 BRACE20148210 BRACE20148240// Gsplp [Saccharomyces cerevisiae].//1.00E-05//75aa//35%// NP_013396 BRACE20150310 BRACE20151320//*Drosophila melanogaster* Oregon R cytoplasmic basic protein (deltex) mRNA, complete cds.//6.10E-35//202aa//41%// U09789 BRACE20152870 BRACE20153680//*Rattus norvegicus* putative four repeat ion channel mRNA, complete cds.//4.10E-107//209aa//99%//AF078779 BRACE20154120//Shb=Src homology 2 protein//2.60E-23//79aa//48%//AAB29780 BRACE20163150 BRACE20163350//MYELIN P0 PROTEIN PRECURSOR.//8.20E-08//92aa//33%//P20938 BRACE20165830 BRACE20171240 BRACE20172980//translation initiation factor eIF3 [*Schizosaccharomyces pombe*]//5.60E-06// 136aa//30%//CAB11250 BRACE20175870 BRACE20177200//RAN-SPECIFIC GTPASE-ACTIVATING PROTEIN (RAN BINDING PROTEIN 1) (RANBP1) .//9.90E-32//63aa//100%//P34022 BRACE20179340 BRACE20185680//ACETYL-COENZYME A SYNTHETASE (EC 6.2.1.1) (ACETATE--COA LIGASE) (ACYL- ACTIVATING ENZYME).//1.40E-16//94aa// 40%//Q01576 BRACE20188470//ATP-binding cassette, sub-family A member 8//1.70E-115//457aa//50%//NP_009099 BRACE20190040 BRACE20190440 BRACE20192440//TRANSLATION INITIATION FACTOR IF-3.//1.20E-09//161aa//26%//P47438 BRACE20195100 BRACE20201570 BRACE20210140 BRACE20220300 BRACE20223280 BRACE20223330 BRACE20224480 BRACE20224500 BRACE20228480 BRACE20229280 BRACE20230700 BRACE20232840// ATP-binding cassette, sub-family E, member 1//0//560aa// 75%//NP_002931 BRACE20235400 BRACE20237270// Human WW domain binding protein-2 mRNA, complete cds.//6.10E-21//50aa//88%//U79458 BRACE20238000 BRACE20240740 BRACE20248260//*H.sapiens* PR264 mRNA.//1.50E-13//78aa//48%//X62447 BRACE20253160//putative trna-splicing endonuclease subunit [Schizosaccharomyces pombe]//1.10E-11//148aa// 32%//CAA21061 BRACE20253330//*Homo sapiens* Na+/H+ exchange regulatory co-factor (NHERF) mRNA, complete cds.//5.50E-88//157aa//99%//AF036241 BRACE20257100//transcription factor (SMIF gene)// 2.00E-37//110aa//94%//NP_060873 BRACE20262930 BRACE20262940 BRACE20266750 BRACE20267250 BRACE20269200 BRACE20269710 BRACE20273890// Human phosphotyrosine independent ligand p62B B-cell isoform for the Lck SH2 domain mRNA, partial cds.//5.70E-25//100aa//65%//U46752 BRACE20274080 BRACE20276430//*Homo sapiens* retinoblastoma-associated protein RAP140 mRNA, complete cds.//4.70E-106// 203aa//100%//AF180425 BRACE20283920 BRACE20284100//*Homo sapiens* beta-dystrobrevin (BDTN) mRNA, complete cds.//7.20E-121//237aa//100%// AF022728 BRACE20286360 BRACE20287410 BRALZ20013500//*Homo sapiens* prostate stem cell antigen (PSCA) mRNA, complete cds.//3.30E-06//122aa//32%// AF043498 BRALZ20014450 BRALZ20017430//*H.sapiens* mRNA for protein phosphatase 5.//1.70E-41//99aa//87%// X89416 BRALZ20018340//*H.sapiens* mRNA for glutamine transaminase K.//4.70E-93//114aa//98%//X82224 BRALZ20019660 BRALZ20054710//*Mus musculus* mRNA for cysteine and histidine-rich protein (Chrp gene).//1.70E-163//280aa//99%//AJ251516 BRALZ20058880 BRALZ20059500 BRALZ20064740 BRALZ20065600 BRALZ20069760 BRALZ20073760//MONOCYTE TO MACROPHAGE DIFFERENTIATION PROTEIN.//8.40E-41//76aa//69%//Q15546 BRALZ20075450 BRALZ20075760 BRALZ20077900//anaphase-promoting complex 1; meiotic checkpoint regulator//3.00E-91//190aa// 92%//NP_073153 BRALZ20077930//*Xenopus laevis* 4g2 mRNA, complete cds.//1.20E-191//501aa//71%//AF182319 BRALZ20080310 BRALZ20088690 BRAMY10001300// *Homo sapiens* MAGE-E1b mRNA, complete cds.//5.40E-78//140aa//97%//AB040528 BRAMY10001570 BRAMY20000520//HETEROGENEOUS NUCLEAR RIBONUCLEOPROTEINS C1/C2 (HNRNP C1 AND HNRNP C2). //7.10E-70//293aa//53%//P07910 BRAMY20000860 BRAMY20002770 BRAMY20004110 BRAMY20011140 BRAMY20025840//*H.sapiens* mRNA from TYL gene.//7.10E-103//198aa//98%//X99688 BRAMY20039260 BRAMY20045240 BRAMY20054880// *Rattus norvegicus* KPL2 (Kpl2) mRNA, complete cds.// 1.40E-43//155aa//59%//AF102129 BRAMY20060920//reduced in osteosclerosis transporter//1.50E-09//60aa//53%// NP_112471 BRAMY20063970 BRAMY20071850 BRAMY20102080 BRAMY20103570 BRAMY20104640// *Mus musculus* mRNA for serine/threonine protein kinase.// 1.80E-140//345aa//75%//AJ250840 BRAMY20110640 BRAMY20111960 BRAMY20112800 BRAMY20116790 BRAMY20120910//GRG PROTEIN,(ESPI PROTEIN) (AMINO ENHANCER OF SPLIT) (AES-1/AES-2).// 1.60E-97//188aa//100%//Q08117 BRAMY20121190 BRAMY20121620//*Mus musculus* kinesin light chain 2 (Klc2) mRNA, complete cds.//1.80E-256//500aa//85%// AF055666 BRAMY20124260//*Rattus norvegicus* transmembrane receptor Unc5H2 mRNA, complete cds.//2.80E-286//554aa//92%//U87306 BRAMY20134140//ATPase, H+ transporting, lysosomal (vacuolar proton pump) 9kD// 4.60E-29//52aa//59%//NP_003936 BRAMY20135900// CELLULAR APOPTOSIS SUSCEPTIBILITY PROTEIN.// 2.00E-07//146aa//23%//P55060 BRAMY20136210 BRAMY20137560 BRAMY20144620 BRAMY20147540 BRAMY20148130 BRAMY20152110 BRAMY20153110// TRYPTOPHAN 5-MONOOXYGENASE (EC 1.14.16.4) (TRYPTOPHAN 5-HYDROXYLASE).//8.50E-58//201aa// 58%//Q92142 BRAMY20157820//PUTATIVE KINESIN-LIKE PROTEIN C2F12.13.//1.10E-90//341aa//50%// 014343 BRAMY20160700 BRAMY20162510// MELANOMA-ASSOCIATED ANTIGEN B2 (MAGE-B2 ANTIGEN) (DAM6).//1.30E-33//209aa//35%//015479 BRAMY20163250 BRAMY20163270 BRAMY20167060 BRAMY20167710 BRAMY20168920 BRAMY20170140 BRAMY20174550//*Homo sapiens* ATP-binding cassette protein M-ABC1 mRNA, nuclear gene encoding mitochondrial protein, complete cds.//0//648aa//98%//AF047690 BRAMY20178640 BRAMY20181220 BRAMY20182730 BRAMY20183080 BRAMY20184670//*Homo sapiens* mRNA for ALEX1, complete cds.//6.40E-14//139aa//27%// AB039670 BRAMY20195090 BRAMY20196000 BRAMY20204450 BRAMY20205740 BRAMY20210400// *Homo sapiens* thyroid hormone receptor-associated protein complex component TRAP150 mRNA, complete cds.// 2.80E-16//141aa//39%//AF117756 BRAMY20211390// seven in absentia (Drosophila) homolog 1 [*Homo sapiens*]//

3.70E-156//282aa//99%//NP_003022 BRAMY20211420//*Homo sapiens* mRNA for LAK-4p, complete cds.//3.00E-31//224aa//33%//AB002405 BRAMY20213100//*Xenopus laevis* Mi-2 histone deacetylase complex protein 66 mRNA, complete cds.//2.10E-66//394aa//44%//AF171099 BRAMY20215230 BRAMY20217460//*Homo sapiens* cardiac voltage gated potassium channel modulatory subunit mRNA, complete cds, alternatively spliced.//3.70E-81//158aa//98%//AF295530 BRAMY20218250//putative four repeat ion channel [*Rattus norvegicus*]//0//588aa//99%//AF078779 BRAMY20218670 BRAMY20229800 BRAMY20229840 BRAMY20230600 BRAMY20231720 BRAMY20240040//*Homo sapiens* suppressor of white apricot homolog 2 (SWAP2) mRNA, complete cds.//3.20E-301//642aa//90%//AF042800 BRAMY20242470//CORONIN-LIKE PROTEIN P57 (CORONIN 1A).//1.60E-70//210aa//66%//P31146 BRAMY20245300//*Homo sapiens* putative prostate cancer susceptibility protein HPC2/ELAC2 mRNA, complete cds.//0//737aa//99%//AF304370 BRAMY20247110//*Mus musculus* semaphorin cytoplasmic domain-associated protein 3A (Semcap3) mRNA, complete cds.//6.00E-117//366aa//63%//AF127084 BRAMY20247280 BRAMY20248490 BRAMY20250240 BRAMY20250320 BRAMY20252180 BRAMY20252720//*Homo sapiens* mRNA for thioredoxin reductase II alpha, partial cds.//1.60E-84//161aa//99%//AB019694 BRAMY20260910//*Homo sapiens* zinc finger DNA binding protein 99 (ZNF281) mRNA, complete cds.//0//811aa//99%//AF125158 BRAMY20261680 BRAMY20266850//*Homo sapiens* oxidation protection protein (OXR1) mRNA, complete cds.//4.50E-57//193aa//56%//AF309387 BRAMY20267130 BRAMY20268990 BRAMY20270730//Fugu rubripes zinc finger protein, isotocin, fatty acid binding protein, sepiapterin reductase and vasotocin genes, complete cds.//7.80E-155//398aa//66%//U90880 BRAMY20271400//RHO-GUANINE NUCLEOTIDE EXCHANGE FACTOR (RHOGEF) (RIP2).//0//946aa//80%//P97433 BRAMY20273960 BRAMY20277140 BRAMY20277170//VOLTAGE-GATED POTASSIUM CHANNEL PROTEIN KV3.2 (KSHIIIA).//1.00E-290//538aa//97%//P22462 BRAMY20280720 BRAMY20284910 BRAMY20285160//COMPLEMENT C3 PRECURSOR [CONTAINS: C3A ANAPHYLATOXIN].//1.90E-79//148aa//100%//P01024 BRAMY20285930 BRAMY20286820 BRAWH10000930 BRAWH20002320//Manduca sexta death-associated small cytoplasmic leucine-rich protein SCLP mRNA, complete cds.//3.50E-18//167aa//31%//AF250910
BRAWH20004600//*Mus musculus* mRNA for NAKAP95, complete cds.//8.40E-184//336aa//84%//AB028921 BRAWH20011710//cytoplasmic linker 2//1.60E-96//316aa//59%//NP_034120 BRAWH20012390//Trichomonas vaginalis mRNA for centrin (cel gene).//4.70E-14//153aa//28%//AJ249457 BRAWH20012410 BRAWH20014920 BRAWH20015350 BRAWH20015890 BRAWH20016620//*Homo sapiens* mRNA for MOK protein kinase, complete cds.//3.40E-82//160aa//99%//AB022694 BRAWH20016660 BRAWH20016860 BRAWH20017010//*Homo sapiens* testes development-related NYD-SP22 mRNA, complete cds.//1.00E-23//56aa//92%//AF367474 BRAWH20018730//HYPOTHETICAL 56.4 KDA PROTEIN IN SRS2-SIP4 INTERGENIC REGION.//1.90E-46//503aa//31%//P47026 BRAWH20028110//*Homo sapiens* actin-binding double-zinc-finger protein (abLIM) mRNA, complete cds.//9.40E-168//416aa//61%//AF005654 BRAWH20029630//*Homo sapiens* bet3 (BET3) mRNA, complete cds.//2.40E-47//96aa//100%//AF041432 BRAWH20030250 BRAWH20064050//FIBULIN-1, ISOFORM C PRECURSOR.//6.30E-42//337aa//33%//P23144 BRAWH20075700//ZINC FINGER PROTEIN ZFP-1 (MKR1 PROTEIN).//1.60E-159//332aa//84%//P08042 BRAWH20096780//ZINC FINGER PROTEIN 184 (FRAGMENT).//5.00E-140//514aa//52%//Q99676 BRAWH20100690 BRAWH20101360 BRAWH20103180 BRAWH20103290//GUANINE NUCLEOTIDE EXCHANGE FACTOR DBS (DBL'S BIG SISTER) (MCF2 TRANSFORMING SEQUENCE-LIKE PROTEIN) (KIAA0362) (FRAGMENT).//0//756aa//99%//015068 BRAWH20105840//HYPOTHETICAL 27.0 KDA PROTEIN IN SPOOA-MMGA INTERGENIC REGION.//1.70E-21//156aa//32%//P54527 BRAWH20106180 BRAWH20107540 BRAWH20110660 BRAWH20110790 BRAWH20110960//*Homo sapiens* mRNA for 26S proteasome subunit p40.5, complete cds.//1.50E-175//378aa//90%//AB009398 BRAWH20111550 BRAWH20112940//POLYPEPTIDE N-ACETYLGALACTOSAMINYLTRANSFERASE (EC 2.4.1.41) (PROTEIN-UDP ACETYLGALACTOSAMINYLTRANSFERASE) (UDP-GALNAC:POLYPEPTIDE, N-ACETYLGALACTOSAMINYLTRANSFERASE) (GALNAC-T1).//1.10E-59//369aa//36%//Q07537 BRAWH20113430//COLD-INDUCIBLE RNA-BINDING PROTEIN (GLYCINE-RICH RNA-BINDING PROTEIN CIRP) (A18 HNRNP).//9.30E-52//104aa//96%//Q14011 BRAWH20114000//GLUTAMATE DEHYDROGENASE 1 PRECURSOR (EC 1.4.1.3) (GDH).//5.90E-233//426aa//98%//P00367 BRAWH20117950//LIVER CARBOXYLESTERASE PRECURSOR (EC 3.1.1.1) (PROLINE-BETA-NAPHTHYLAMIDASE).//1.80E-78//364aa//42%//Q29550 BRAWH20118230//BONE MORPHOGENETIC PROTEIN 7 PRECURSOR (BMP-7) (OSTEOGENIC PROTEIN 1) (OP-1).//7.60E-74//85aa//98%//P18075 BRAWH20121640//transporter protein; system Ni Na+ and H+-coupled glutamine transporter//1.00E-106//450aa//61%//NP_006832 BRAWH20122580 BRAWH20122770 BRAWH20125380//DIHYDRODIPICOLINATE SYNTHASE (EC 4.2.1.52) (DHDPS).//6.40E-15//121aa//35%//Q57695 BRAWH20126190 BRAWH20126980 BRAWH20128270//BH3 INTERACTING DOMAIN DEATH AGONIST (BID).//2.70E-100//195aa//99%//P55957 BRAWH20132190//*Homo sapiens* putative N-acetyltransferase Camello 2 (CML2) mRNA, complete cds.//1.80E-17//110aa//44%//AF185571 BRAWH20137480//actin binding LIM protein 1//2.80E-70//181aa//55%//NP_006710 BRAWH20138660//*Homo sapiens* stonin 2 mRNA, complete cds.//1.50E-171//322aa//99%//AF255309 BRAWH20139410 BRAWH20142340 BRAWH20147290 BRAWH20149340//GUANINE NUCLEOTIDE RELEASING PROTEIN (GNRP) (P140 RAS-GRF).//4.10E-129//290aa//83%//P28818 BRAWH20155950 BRAWH20158530 BRAWH20160280 BRAWH20162690 BRAWH20164460//TAT-BINDING HOMOLOG 7.//1.60E-95//366aa//54%//P54816 BRAWH20166790 BRAWH20171030//*Homo sapiens* putative helicase RUVBL mRNA, complete cds.//2.80E-209//324aa//100%//AF218313 BRAWH20173050 BRAWH20182060 BRAWH20185060 BRCAN10001490//chromobox homolog 6//2.10E-40//82aa//100%//NP_055107 BRCAN20003460//outer arm dynein intermediate chain 1//5.60E-57//159aa//49%//T02761 BRCAN20006200 BRCAN20006390 BRCAN20054490//Sus scrofa mRNA for 54 kDa vacuolar H(+)-ATPase subunit, beta isoform.//1.00E-117//229aa//96%//AJ223758 BRCAN20060190 BRCAN20064010 BRCAN20071190//FAF1 PROTEIN (FAS-ASSOCIATED FACTOR 1).//4.00E-225//433aa//96%//P54731 BRCAN20091560//*Xenopus laevis* mRNA for Nfrl, complete cds.//1.20E-256//605aa//77%//D86491 BRCAN20103740//P2X PURINOCEPTOR 7 (ATP RECEPTOR) (P2X7) (PURINERGIC RECEPTOR) (P2Z RECEPTOR).//2.20E-18//60aa//78%//Q99572 BRCAN20124080 BRCAN20126130 BRCAN20143700 BRCAN20147880 BRCAN20216690 BRCAN20224720// PROTOPORPHYRINOGEN OXIDASE (EC 1.3.3.4) (PPO).//4.40E-132//254aa//100%//P50336 BRCAN20237240 BRCAN20263400 BRCAN20273100 BRCAN20273340 BRCAN20273550 BRCAN20273640// lymphocyte specific formin related protein//3.00E-80// 350aa//56%//NP_062653 BRCAN20275130 BRCAN20279700//*Homo sapiens* copine I mRNA, complete cds.//2.10E-32//82aa//68%//U83246 BRCAN20280210//*H.sapiens* HZF10mRNA for zinc finger protein.//3.30E-54//219aa//49%//X78933 BRCAN20280360//*Homo sapiens* phosphatidic acid phosphohydrolase type-2c mRNA, complete cds.//8.20E-22// 213aa//28%//AF047760 BRCAN20280400 BRCAN20283190//CHROMODOMAIN-HELICASE-DNA-BINDING PROTEIN 1 (CHD-1).//1.20E-131// 235aa//99%//O14646 BRCAN20283380//*Mus musculus* mRNA for serine hydrolase protein, isoform 2 (serhl gene) .//6.50E-45//103aa//80%//AJ245737 BRCAN20284600 BRCAN20285450 BRCOC10000870 BRCOC20001860// *Homo sapiens*' endoplasmic reticulum alpha-mannosidase-I mRNA, complete cds.//6.30E-154//282aa//99%//AF145732 BRCOC20004040//*Rattus norvegicus* sphingosine I-phosphate receptor Edg-8 (Edg-8) mRNA, complete cds.//4.80E-108//265aa//81%//AF233649 BRCOC20004870 BRCOC20006370//PUTATIVE SURFACE GLYCOPROTEIN C21ORF1 PRECURSOR (C21ORF3).//4.00E-67// 144aa//88%//P53801 BRCOC20008160//*Homo sapiens* mRNA for actin binding protein ABP620, complete cds.// 4.20E-155//777aa//40%//AB029290 BRCOC20008500// Human ras inhibitor mRNA, 3' end.//4.60E-229//428aa// 100%//M37190 BRCOC20020850 BRCOC20021550// *Rattus norvegicus* mRNA for Nadrin, complete cds.//1.90E-56//47aa//55%//AB042827 BRCOC20023230 BRCOC20026640 BRCOC20027510//RAS SUPPRESSOR PROTEIN 1 (RSU-1) (RSP-1 PROTEIN) (RSP-1).//2.20E-18//178aa//34%//Q15404 BRCOC20031000 BRCOC20031250//TRIOSEPHOSPHATE ISOMERASE (EC 5.3.1.1) (TIM).//7.10E-38//92aa//82%//P48500 BRCOC20031870 BRCOC20035130//14-3-3 PROTEIN EPSILON (MITOCHONDRIAL IMPORT STIMULATION FACTOR L SUBUNIT) (PROTEIN KINASE C INHIBITOR PROTEIN-1) (KCIP-1) (14-3-3E).//1.00E-29//71aa// 88%//P42655 BRCOC20037320//PUTATIVE IMPORTIN BETA-4 SUBUNIT (KARYOPHERIN BETA-4 SUBUNIT) .//5.00E-75//937aa//26%//O60100 BRCOC20037400 BRCOC20041750 BRCOC20055420//GLYCYLPEPTIDE N-TETRADECANOYLTRANSFERASE 2 (EC 2.3.1.97) (PEPTIDE N-MYRISTOYLTRANSFERASE 2) (MYRISTOYL-COA:PROTEIN N-MYRISTOYLTRANSFERASE 2) (NMT 2).//7.90E-229//421aa//99%//O60551 BRCOC20059510//B.taurus myosin IB mRNA, complete CDS.//1.40E-29//117aa//53%//Z22852 BRCOC20074760// CDC4-LIKE PROTEIN (FRAGMENT).//4.50E-90//366aa// 48%//P50851 BRCOC20077690 BRCOC20078640 BRCOC20090520 BRCOC20091960//CDC42-binding protein kinase beta (DMPK-like) [*Homo sapiens*]//1.50E-71// 140aa//100%//NP_006026 BRCOC20093800 BRCOC20099370//*Homo sapiens* SPG protein (SPG) mRNA, complete cds. //0//576aa//97%//AF302154 BRCOC20101230////7.40E-32//227aa//35%// BRCOC20105100 BRCOC20107300//*Homo sapiens* GTT1 mRNA, complete cds.//3.60E-44//90aa//98%//AF270647 BRCOC20110100 BRCOC20114180 BRCOC20117690 BRCOC20119960 BRCOC20121720 BRCOC20122290 BRCOC20128130 BRCOC20134480 BRCOC20135730 BRCOC20136750 BRCOC20144000//DNA REPAIR PROTEIN RAD8.//5.50E-14//111aa//36%//P36607 BRCOC20147480 BRCOC20148330 BRCOC20155970 BRCOC20158240 BRCOC20176520//*Rattus norvegicus* mRNA for type II brain 4.1, complete cds.//2.30E-127// 269aa//79%//AB032827 BRCOC20178270//ZINC FINGER PROTEIN 83 (ZINC FINGER PROTEIN HPF1).// 4.90E-101//272aa//64%//P51522 BRCOC20178560// PINCH PROTEIN (PARTICULARY INTERESTING NEW CYS-HIS PROTEIN).//9.50E-130//247aa//85%//P48059 BRHIP10001290//*Homo sapiens* GalNAc-T9 mRNA for UDP-GalNAc:polypeptide N-acetylgalactosaminyltransferase, complete cds.//1.10E-108//299aa//63%//ABO40672 BRHIP10001740 BRHIP20000870 BRHIP20001630 BRHIP20003120//*Homo sapiens* reticulon gene family protein (RTN3) mRNA, complete cds.//2.20E-92//190aa//98%// AF059524 BRHIP20005340//GAMMA-INTERFERON-INDUCIBLE PROTEIN IFI-16 (INTERFERON-INDUCIBLE MYELOID DIFFERENTIATION TRANSCRIPTIONAL ACTIVATOR).//2.10E-157//407aa// 77%//Q16666 BRHIP20005530//UBIQUITIN-ACTIVATING ENZYME E1 1.//1.00E-59//318aa//41%//Q02053 BRHIP20096170//*Homo sapiens* cellular repressor of E1A-stimulated genes CREG mRNA, complete cds.//9.70E-35// 174aa//39%//AF084523 BRHIP20096850//ALANINE AMINOTRANSFERASE (EC 2.6.1.2) (GLUTAMIC-PYRUVIC TRANSAMINASE) (GPT) (GLUTAMIC--ALANINE TRANSAMINASE).//1.60E-166//423aa//69%// P25409 BRHIP20103090//VACUOLAR ATP SYNTHASE SUBUNIT AC45 PRECURSOR (EC 3.6.1.34) (V-ATPASE AC45 SUBUNIT).//2.00E-12//82aa//47%//P40682 BRHIP20104440 BRHIP20105710 BRHIP20106100// GAR2 PROTEIN.//1.50E-19//199aa//31%//P41891 BRHIP20107440 BRHIP20110800 BRHIP20111200 BRHIP20115080//DYNAMIN 2 (DYNAMIN UDNM).// 4.80E-63//123aa//95%//P39054 BRHIP20115760 BRHIP20118380 BRHIP20118910 BRHIP20119330// ZINC FINGER PROTEIN 91 (ZINC FINGER PROTEIN HTF10) (HPF7).//6.80E-207//651aa//54%//Q05481 BRHIP20121410 BRHIP20123140 BRHIP20129720 BRHIP20132860//*Homo sapiens* rhophilin-like protein mRNA, complete cds.//5.40E-144//298aa//93%//AF268032 BRHIP20135100 BRHIP20137230//*Homo sapiens* mRNA for paralemin. //1. 70E-37//352aa//35%//Y16278 BRHIP20139720 BRHIP20140630 BRHIP20142850 BRHIP20143730 BRHIP20143860 BRHIP20149540 BRHIP20153560 BRHIP20153600//*Xenopus laevis* RRM-containing protein SEB-4 mRNA, complete cds.//1.50E-72// 148aa//93%//AF223427 BRHIP20167880//*Mus musculus* left-right dynein (Lrd) mRNA, complete cds.//8.10E-22// 119aa//54%//AF183144 BRHIP20169680 BRHIP20169900 BRHIP20170100 BRHIP20173150 BRHIP20174040// CGMP-DEPENDENT 3', 5'-CYCLIC PHOSPHODIESTERASE (EC 3.1.4.17) (CYCLIC GMP STIMULATED PHOSPHODIESTERASE) (CGS-PDE).//0//857aa//99%// 000408 BRHIP20175420//*Mus musculus* partial mRNA for stretch responsive protein 278 (sr278 gene).//6.60E-36// 170aa//50%//AJ250191 BRHIP20176420//HETEROGENEOUS NUCLEAR RIBONUCLEOPROTEINS C1/C2 (HNRNP C1 AND HNRNP C2).//9.30E-68//292aa//52%// P07910 BRHIP20179200 BRHIP20180140 BRHIP20183690 BRHIP20186120 BRHIP20186500 BRHIP20189980//FLAGELLAR WD-REPEAT PROTEIN PF20.//2.90E-41//210aa//46%//P93107 BRHIP20190070 BRHIP20191490//interferon, alpha-inducible protein 27//2.60E-36//92aa//95%//NP_005523 BRHIP20191770 BRHIP20191860//TRANSCRIPTJON FACTOR 4 (IMMUNOGLOBULIN TRANSCRIPTION FACTOR 2) (ITF-2) (SL3-3 ENHANCER FACTOR 2) (SEF-2).//0//569aa//99%//P15884 BRHIP20194940//*Homo sapiens* A-kinase anchoring protein 220 mRNA, complete cds.//1.30E-23//190aa//37%//AF176555 BRHIP20195890//FORKHEAD BOX PROTEIN D2 (FORKHEAD-RELATED PROTEIN FKHL17) (FORKHEAD- RELATED TRANSCRIPTION FACTOR 9) (FREAC-9).//9.10E-07//104aa//31%//060548 BRHIP20196410 BRHIP20198190 BRHIP20205090 BRHIP20207430 BRHIP20207990 BRHIP20208270 BRHIP20208420 BRHIP20208590 BRHIP20214950 BRHIP20217620 BRHIP20218580//*Mus musculus* betaPix-b mRNA, complete cds.//5.10E-100//196aa//94%//AF247654 BRHIP20222280//ZINC FINGER PROTEIN 85 (ZINC FINGER PROTEIN HPF4) (HTF1).//1.70E-217//505aa//75%//Q03923 BRHIP20227080 BRHIP20230710 BRHIP20232290 BRHIP20233090 BRHIP20234380 BRHIP20236950 BRHIP20238600//WD-REPEAT PROTEIN SAZD.//3.30E-95//182aa//99%//Ql2788 BRHIP20238690 BRHIP20238880 BRHIP20240460 BRHIP20243470//GALECTIN-3 (GALACTOSE-SPECIFIC LECTIN 3) (MAC-2 ANTIGEN) (IGE-BINDING PROTEIN) (35 KDA LECTIN) (CARBOHYDRATE BINDING PROTEIN 35) (CBP 35) (LAMININ-BINDING PROTEIN) (LECTIN L-29).//1.10E-16//114aa//42%//P38486 BRHIP20249110//hexokinase 1//0//912aa//71%//NP_000179 BRHIP20252450//*Mus musculus* Syne-IB mRNA, partial cds.//1.40E- 159//980aa//33%//AF281870 BRHIP20253660//*Rattus norvegicus* mRNA for Proline Rich Synapse Associated Protein 1A (ProSAP1A gene).//1.90E-120//239aa//92%//AJ249562 BRHIP20254480 BRHIP20277620 BRHIP20283030//CADHERIN-RELATED TUMOR SUPPRESSOR PRECURSOR (FAT PROTEIN).//1.40E-88//881aa//29%//P33450
BRHIP20284800 BRHIP20285830//TYPE III INTERMEDIATE FILAMENT.//8.20E-10//88aa//35%//P23729 BRHIP20285930//*Homo sapiens* IL-1 receptor accessory protein mRNA, complete cds.//3.30E-08//104aa//32%//AF029213 BRHIP30001110 BRHIP30004570//P-SELECTIN PRECURSOR (GRANULE MEMBRANE PROTEIN 140) (GMP-140) (PADGEM) (CD62P) (LEUKOCYTE-ENDOTHELIAL CELL ADHESION MOLECULE 3) (LECAM3).//3.60E-32//281aa//31%//Q01102
BRHIP30004880//*H.sapiens* mRNA for titin protein (clone hhl-hh54).//9.60E-85//812aa//26%//X90568
BRSSN10000920 BRSSN20003120//METABOTROPIC GLUTAMATE RECEPTOR PRECURSOR.//7.00E-08//257aa//22%//P91685 BRSSN20006340 BRSSN20013420//histone deacetylase 6 [*Homo sapiens*] //0//811aa//99%//NP_006035 BRSSN20014260//RIBONUCLEASE INHIBITOR.//1.70E-10//195aa//29%//P29315
BRSSN20015030 BRSSN20015790//ORNITHINE DECARBOXYLASE (EC 4.1.1.17) (ODC).//9.00E-102//352aa//53%//P00860 BRSSN20018690//*Homo sapiens* NY-REN-25 antigen mRNA, partial cds.//9.30E-41//88aa//100%//AF155103 BRSSN20021600//RING CANAL PROTEIN (KELCH PROTEIN).//3.60E-59//510aa//31%//Q04652 BRSSN20028570 BRSSN20038200//RAL GUANINE NUCLEOTIDE DISSOCIATION STIMULATOR-LIKE 2 (RALGDS-LIKE FACTOR) (RAS-ASSOCIATED PROTEIN RAB2L).//3.90E-18//458aa//25%//015211 BRSSN20038410 BRSSN20039370//ZINC FINGER PROTEIN 7 (ZINC FINGER PROTEIN KOX4) (ZINC FINGER PROTEIN HF.16).//2.50E-38//94aa//52%//P17097 BRSSN20043040 BRSSN20046570 BRSSN20046790//ZINC FINGER PROTEIN 135.//8.60E-81//231aa//60%//P52742 BRSSN20046860 BRSSN20066110//*Homo sapiens* mRNA for mucolipidin, short form (ML4 gene).//1.70E-26//121aa//49%//AJ293659 BRSSN20097020 BRSSN20101100//GRG PROTEIN (ESP1 PROTEIN) (AMINO ENHANCER OF SPLIT) (AES-1/AES-2).//2.50E-10//70aa//51%//Q08117 BRSSN20105870 BRSSN20105960 BRSSN20108300 BRSSN20117990 BRSSN20120810//SERINE PROTEASE HEPSIN (EC 3.4.21.-) (TRANSMEMBRANE PROTEASE, SERINE 1).//9.80E-144//254aa//100%//P05981 BRSSN20121030 BRSSN20137020 BRSSN20142940 BRSSN20146100//ADENYLATE CYCLASE, OLFACTIVE TYPE (EC 4.6.1.1) (ADENYLATE CYCLASE TYPE III) (ATP PYROPHOSPHATE-LYASE) (ADENYLYL CYCLASE).//0//389aa//90%//P21932 BRSSN20151990 BRSSN20152380 BRSSN20159070 BRSSN20159820 BRSSN20169050 BRSSN20176820//*Mus musculus* p300 transcriptional cofactor JMY mRNA, complete cds.//8.50E-297//640aa//89%//AF201390 BRSSN20177570 BRSSN20187310//ANKYRIN 1 (ERYTHROCYTE ANKYRIN) (ANKYRIN R) (ANKYRINS 2.1 AND 2.2).//3.20E-26//306aa//30%//P16157 BRSTN10000830 BRSTN20000580 BRSTN20002200 BRSTN20005360//TRANSLATION INITIATION FACTOR IF-2.//1.20E-07//205aa//26%//060841 BRTHA20000570 BRTHA20004740//HYPOTHETICAL 41.6 KDA PROTEIN IN IMP1-HLJ1 INTERGENIC REGION (RF1095).//1.60E-16//310aa//27%//P28625 BRTHA20046290//NOVEL ANTIGEN 2 (NAG-2) (TSPAN-4).//7.30E-84//153aa//100%//014817
BRTHA20046390 BRTHA20046420 CD34C30001250 CD34C30003140 CD34C30004240//*H.sapiens* graf gene.//1.10E-140//270aa//100%//Y10388 CD34C30004940 COLON10001350//IG ALPHA-1 CHAIN C REGION.//1.70E-196//353aa//99%//P01876 COLON20043180 COLON20093370 CTONG10000100//GUFA PROTEIN.//2.10E-31//156aa//45%//Q06916 CTONG10000220//*Mus musculus* cerebellar postnatal development protein-1 (Cpd1) mRNA, partial cds.//1.80E-101//220aa//90%//U89345 CTONG10000620 CTONG10000930 CTONG10000940//CYCLIN-DEPENDENT KINASE 6 INHIBITOR (P18-INK6) (CYCLIN-DEPENDENT KINASE 4 INHIBITOR C) (P18-INK4C).//7.20E-13//131aa//35%//Q60772 CTONG10001650 CTONG10002770//PLECTIN.//2.00E-49//284aa//28%//P30427 CTONG20002180 CTONG20004690//CYTOCHROME B561 (CYTOCHROME B-561).//2.80E-50//101aa//100%//P49447 CTONG20009770//26S PROTEASOME REGULATORY SUBUNIT S2 (P97) (TUMOR NECROSIS FACTOR TYPE 1 RECEPTOR ASSOCIATED PROTEIN 2) (55.11 PROTEIN).//0//908aa//99%//Q13200 CTONG20014280//*Xenopus laevis* fizzyl mRNA, complete cds.//2.00E-82//479aa//38%//AF034578 CTONG20027090 CTONG20028410 CTONG20038890 CTONG20049410 CTONG20050280//ZINC FINGER PROTEIN ZFP-36 (FRAGMENT).//8.00E-149//490aa//55%//P16415 CTONG20052650//BYSTIN.//5.10E-60//120aa//99%//Q13895 CTONG20052900//FASCIN (ACTIN BUNDLING PROTEIN).//7.30E-257//437aa//98%//Q16658 CTONG20075860//*Homo sapiens* mRNA for SPIN protein.//3.90E-123//204aa//69%//Y14946 CTONG20076130//ZINC FINGER PROTEIN 185 (LIM-DOMAIN PROTEIN ZNF185) (P1-A).//1.10E-158//327aa//89%//015231 CTONG20077790 CTONG20082690 CTONG20085950//ZINC FINGER PROTEIN 191.//5.80E-91//346aa//53%//014754 CTONG20091080//HOMEOBOX PROTEIN DLX-1.//1.00E-54//134aa//84%//Q64317 CTONG20091320 CTONG20092570//*Rattus norvegicus* neural membrane protein 35 mRNA, complete cds.//1.00E-55//300aa//49%//AF044201 CTONG20092580 CTONG20092680//*Rattus norvegicus* protein associating with small stress protein PASS1 (Pass1) mRNA, complete cds.//1.40E-11//98aa//40%//AF168362 CTONG20092700//*Mus musculus* transcriptional repressor RP58 (rp58) mRNA, complete cds.//6.60E-18//162aa//35%//AF140224 CTONG20093950//*Mus musculus* zfh-4 mRNA for zinc-finger homeodomain protein 4, complete cds.//0//473aa//90%//AB024499 CTONG20095270 CTONG20095290 CTONG20095340//PROBABLE CATION-TRANSPORTING ATPASE W08D2.5 IN CHROMOSOME IV (EC 3.6.1.-).//3.90E-134//500aa//37%//Q27533 CTONG20096430 CTONG20096750 CTONG20097660 CTONG20098440 CTONG20099380 CTONG20099550//TRICHOHYALIN.//4.20E-16//534aa//25%//Q07283 CTONG20099630 CTONG20100240//*Mus musculus* radial spokehead-L protein (Rshl1) mRNA, complete cds.//1.60E-185//520aa//63%//AF329192 CTONG20101480 CTONG20103480 CTONG20105080 CTONG20105660 CTONG20106230 CTONG20106520//THREONINE SYNTHASE (EC 4.2.99.2).//6.70E-77//347aa//40%//Q42598 CTONG20108210 CTONG20114290//PUTATIVE IMPORTIN BETA-4 SUBUNIT (KARYOPHERIN BETA-4 SUBUNIT).//1.30E-75//937aa//27%//O60100 CTONG20114740//*Homo sapiens* NY-REN-57 antigen mRNA, partial cds.//1.70E-37//72aa//100%//AF155114 CTONG20118150//HYPOTHETICAL 100.6 KDA TRP-ASP REPEATS CONTAINING PROTEIN C1672.07 IN CHROMOSOME III.//2.10E-150//910aa//36%//O14053 CTONG20118250//CARBONIC ANHYDRASE (EC 4.2.1.1) (CARBONATE DEHYDRATASE).//3.30E-88//257aa//62%//Q92051 CTONG20119200//*Homo sapiens* NY-REN-57 antigen mRNA, partial cds.//1.00E-18//41aa//100%//AF155114 CTONG20120770 CTONG20121010//ZINC FINGER PROTEIN 29 (ZFP-29).//7.80E-131//380aa//58%//Q07230 CTONG20121580//KINESIN-LIKE PROTEIN KIF1A.//3.50E-148//395aa//59%//P33173 CTONG20124010 CTONG20124220//STEROL REGULATORY ELEMENT BINDING PROTEIN-1 (SREBP-1) (STEROL REGULATORY ELEMENT-BINDING TRANSCRIPTION FACTOR 1).//0//691aa//98%//P36956 CTONG20124470 CTONG20124730 CTONG20125540//PTB-ASSOCIATED SPLICING FACTOR (PSF).//6.90E-07//144aa//29%//P23246 CTONG20125640//60S ACIDIC RIBOSOMAL PROTEIN P0 (L10E).//7.50E-137//306aa//89%//P05388 CTONG20126070 CTONG20127450//*H.sapiens* mRNA for Ndr protein kinase.//4.50E-11//37aa//89%//Z35102 CTONG20128430//Human non-lens beta gamma-crystallin like protein (AIM1) mRNA, partial cds.//8.40E-127//616aa//40%//U83115 CTONG20128470 CTONG20129960//*Mus musculus* F-box protein FBX18 mRNA, partial cds.//0//905aa//92%//AF184275 CTONG20131490 CTONG20131560//NEUROBLAST DIFFERENTIATION ASSOCIATED PROTEIN AHNAK (DESMOYOKIN) (FRAGMENTS).//0//632aa//99%//Q09666 CTONG20132220 CTONG20133390//ZINC FINGER PROTEIN 135.//1.00E-139//416aa//57%//P52742 CTONG20133480 CTONG20133520//ZINC FINGER PROTEIN 228.//1.50E-163//670aa//50%//Q9UJU3 CTONG20136300 CTONG20138030 CTONG20139070 CTONG20139340 CTONG20139860//*Homo sapiens* nasopharyngeal carcinoma susceptibility protein LZ16 mRNA, complete cds.//3.50E-17//162aa//36%//AF121775 CTONG20140320 CTONG20140580//HepA-related protein//8.80E-61//345aa//42%//NP_054859 CTONG20141650 CTONG20143690 CTONG20146300 CTONG20146970 CTONG20147050 CTONG20149460//RING CANAL PROTEIN (KELCH PROTEIN).//1.20E-56//556aa//27%//Q04652 CTONG20149950 CTONG20150910 CTONG20153300//*H.sapiens* mRNA for tre oncogene (clone 210).//4.80E-214//259aa//78%//X63546 CTONG20153580//*Homo sapiens* leucine-rich repeats containing F-box protein FBL3 mRNA, complete cds.//4.80E-37//326aa//28%//AF186273 CTONG20155180 CTONG20155400 CTONG20156780//*Rattus norvegicus* PGC1 mRNA for PPAR gamma coactivator, complete cds.//1.80E-72//176aa//46%//AB025784 CTONG20158040//UDP-N-ACETYLGLUCOSAMINE PYROPHOSPHORYLASE (EC 2.7.7.23) (ANTIGEN X) (AGX) (AGX-1) (SPERM-ASSOCIATED ANTIGEN 2).//4.90E-126//376aa//61%//Q16222 CTONG20158150 CTONG20158660//*Rattus norvegicus* mRNA for seven transmembrane receptor, complete cds.//5.90E-99//632aa//36%//AB019120 CTONG20159530//GLYPICAN-1 PRECURSOR.//3.40E-118//222aa//100%//P35052 CTONG20160560 CTONG20161850 CTONG20162170 CTONG20163550 CTONG20164990 CTONG20165050 CTONG20186320//RING CANAL PROTEIN (KELCH PROTEIN).//3.70E-19//290aa//26%//Q04652 CTONG20200310//mitotic control protein dis3 homolog //1.20E-113//655aa//36%//JE0110 CTONG20265130 CTONG20267700 CTONG20273610 D30ST10001090 D30ST10002670 D30ST10002700 D30ST20006180//*Drosophila melanogaster* slingshot mRNA, complete cds.//9.20E-114//358aa//56%//AB036834 D30ST20006540 D30ST20007340 D30ST20013280//ARP2/3 COMPLEX 16 KDA SUBUNIT (P16-ARC).//1.10E-48//103aa//99%//O15511 D30ST20024170 D30ST20024360//*Homo sapiens* neuroendocrine differentiation factor mRNA, complete cds.//4.70E-35//80aa//100%//AF219226 D30ST20024520 D30ST20036070 D30ST20037970 D30ST20038560 D30ST30002580 D30ST30002910 D60ST20003580//*H.sapiens* mRNA for aminopeptidase P-like.//7.40E-70//103aa//99%//X95762 D60ST20004450 D60ST20005070 D90ST20000310 D90ST20002780 D90ST20015470//*Mus musculus* MPS1 gene and mRNA, 3' end.//4.60E-147//329aa//79%//L20315 D90ST20023970//CARTILAGE GLYCOPROTEIN-39 PRECURSOR (GP-39) (39 KDA SYNOVIAL PROTEIN) (YKL-40) (CHITINASE-3 LIKE 1).//1.30E-17//44aa//90%//P36222 D90ST20026730//*Homo sapiens* caspase recruitment domain protein 7 mRNA, complete cds.//2.40E-141//524aa//40%//AF298548 D90ST20031370//*Homo sapiens* mRNA for partial putative TCPTP-interacting protein (ptpip5 gene).//3.40E-39//176aa//48%//AJ242719 D90ST20033970//ZINC FINGER PROTEIN 91 (ZINC FINGER PROTEIN HTF10) (HPF7).//2.50E-152//541aa//52%//Q05481 D90ST20035800 D90ST20035940//BRAIN MITOCHONDRIAL CARRIER PROTEIN-i.//9.10E-93//216aa//80%//O95258 D90ST20040180//OLFACTORY RECEPTOR-LIKE PROTEIN OLF4.//1.20E-106//301aa//64%//Q95157 DFNES10000030 DFNES10001850 DFNES20001530//ATAXIN 7 (SPINOCEREBELLAR ATAXIA TYPE 7 PROTEIN).//2.30E-25//98aa//57%//O15265 DFNES20010910 DFNES20014040//TRICHOHYALIN.//1.70E-17//380aa//26%//P37709 DFNES20025880 DFNES20031920//*Drosophila melanogaster* mRNA for fucosyltransferase homologue (FucTB gene).//8.40E-18//133aa//36%//AJ302046 DFNES20037420//G1 TO S PHASE TRANSITION PROTEIN 1 HOMOLOG (GTP-BINDING PROTEIN GST1-HS).//1.00E-274//499aa//99%//P15170 DFNES20055270

DFNES20071130//PHOSPHOTRIESTERASE RELATED PROTEIN (PARATHION HYDROLASE-RELATED PROTEIN).//4.40E-141//233aa//86%//Q60866
DFNES20082800 FCBBF10000240 FCBBF10000380 FCBBF10000630//*Homo sapiens* huntingtin interacting protein HYPB mRNA, partial cds.//3.70E-16//36aa//100%// AF049610 FCBBF10000770//*Homo sapiens* REC8 mRNA, partial cds.//6.10E-266//528aa//96%//AF132734 FCBBF10001150//*Homo sapiens* protocadherin beta 14 (PCDH-betal4) mRNA, complete cds.//4.10E-308//717aa// 79%//AF152493 FCBBF10001210//*Homo sapiens* mRNA for SHPS-1, complete cds.//6.90E-22//135aa//43%//D86043 FCBBF10001550 FCBBF10001710//ZINC FINGER PROTEIN 83 (ZINC FINGER PROTEIN HPF1).//1.90E-131// 397aa//59%//P51522 FCBBF10001820//CITRATE LYASE BETA CHAIN (EC 4.1.3.6) (CITRASE) (CITRYL-COA LYASE SUBUNIT) (EC 4.1.3.34).//3.70E-32//294aa//27%// 053078 FCBBF10002430 FCBBF10002700 FCBBF10002800 FCBBF10003220 FCBBF10003670// QUEUINE TRNA-RIBOSYLTRANSFERASE (EC 2.4.2.29) (TRNA-GUANINE TRANSGLYCOSYLASE) (GUANINE INSERTION ENZYME).//2.60E-195//308aa// 100%//P54578 FCBBF10003740 FCBBF10003760 FCBBF10003770//*Homo sapiens* mRNA for GRIP1 protein.//0//572aa//99%//AJ133439 FCBBF10004120 FCBBF10004370//ZINC FINGER PROTEIN 33A (ZINC FINGER PROTEIN KOX31) (KIAA0065) (HA0946) (FRAGMENT).//3.30E-96//292aa//52%//Q06730
FCBBF10005060//CELLULAR RETINALDEHYDE-BINDING PROTEIN (CRALBP).//8.40E-51//260aa//41%// P10123 FCBBF10005460//*Mus musculus* putative neuronal cell adhesion molecule (Punc) mRNA, complete cds.// 9.20E-275//484aa//94%//AF026465 FCBBF10005500 FCBBF10005740//MITOCHONDRIAL CARRIER PROTEIN YMC2 PRECURSOR.//1.10E-27//194aa//38%// P38087 FCBBF20006780 FCBBF20014270//ACYL-COA-BINDING PROTEIN (ACBP) (DIAZEPAM BINDING INHIBITOR) (DBI) (ENDOZEPINE) (EP).//1.40E-34// 85aa//81%//P45882 FCBBF20023700 FCBBF20032970 FCBBF26035280 FCBBF20042170//*Homo sapiens* NIBAN mRNA, complete cds.//1.90E-177//345aa//100%// AB050477 FCBBF20042560 FCBBF20049300//NEURONAL OLFACTOMEDIN-RELATED ER LOCALIZED PROTEIN PRECURSOR (NOEL) (1B426B).//7.70E-64// 187aa//63%//Q62609 FCBBF20051220 FCBBF20054280 FCBBF20056370 FCBBF20059090//ZINC FINGER PROTEIN 44 (ZINC FINGER PROTEIN KOX7) (FRAGMENT).//2.00E-08//96aa//34%//P15621 FCBBF20064520// HETEROGENEOUS NUCLEAR RIBONUCLEOPROTEINS C1/C2 (HNRNP C1 AND HNRNP C2).//5.50E-70//293aa//53%//P07910 FCBBF20067810//SPOOB-ASSOCIATED GTP-BINDING PROTEIN.//1.30E-51//275aa//42%//P20964
FCBBF20068820//ZINC FINGER PROTEIN 83 (ZINC FINGER PROTEIN HPF1).//1.50E-74//216aa//62%// P51522 FCBBF20071860 FCBBF20072650 FCBBF20075560 FCBBF20076330 FCBBF30001840 FCBBF30007680//*Homo sapiens* general transcription factor 2-I (GTF2I) mRNA, alternatively spliced product, complete cds.//4.80E-56//141aa//72%//AF038968 FCBBF30008470 FCBBF30010810//ZINC FINGER PROTEIN 85 (ZINC FINGER PROTEIN HPF4) (HTF1).// 7.10E-173//436aa//70%//Q03923 FCBBF30012350//CALCIUM/CALMODULIN-DEPENDENT PROTEIN KINASE TYPE II GAMMA CHAIN (CAM- KINASE II GAMMA CHAIN) (EC 2.7.1.123) (CAMK-II, GAMMA SUBUNIT).//8.80E-143//291aa//92%//P11730

FCBBF30012810//*Homo sapiens* ubiquitin-specific processing protease mRNA, complete cds.//1.10E-123//450aa// 49%//AF229438 FCBBF30013770//*Rattus norvegicus* dnchc2 mRNA for cytoplasmic dynein heavy chain, complete cds.//0//806aa//93%//AB041881 FCBBF30015940// Chlamydomonas reinhardtii dhcl gene for 1-alpha dynein heavy chain.//4.90E-228//831aa//52%//AJ243806 FCBBF30016320 FCBBF30016570 FCBBF30018550// *Homo sapiens* putative zinc finger protein mRNA, complete cds.//9.40E-90//560aa//35%//AF251039 FCBBF30019120 FCBBF30024750//SEMAPHORIN 4F PRECURSOR (SEMAPHORIN W) (SEMA W).//2.00E-73//129aa//100%// 095754 FCBBF30025560//NERVOUS-SYSTEM SPECIFIC OCTAMER-BINDING TRANSCRIPTION FACTOR N-OCT 3 (BRAIN-SPECIFIC HOMEOBOX/POU DOMAIN PROTEIN 2) (BRN-2 PROTEIN) [CONTAINS: N-OCT 5A; N-OCT 5B].//4.30E-171//203aa//100%// P20265 FCBBF30028180 FCBBF30033050 FCBBF30039020//GROWTH-ARREST-SPECIFIC PROTEIN 2.//1.80E-68//194aa//64%//043903 FCBBF30049550//ANKYRIN 2 (BRAIN ANKYRIN) (ANKYRIN B) (ANKYRIN, NONERYTHROID).//0// 1016aa//99%//Q01484 FCBBF30052180 FCBBF30054440 FCBBF30057290//*Homo sapiens* GIOT-4 mRNA for gonadotropin inducible transcription repressor-4, complete cds.// 8.90E-258//642aa//68%//AB021644 FCBBF30062880 FCBBF30070770 FCBBF30071520 FCBBF30078290 FCBBF30083620//PLEXIN 4 PRECURSOR (TRANSMEMBRANE PROTEIN SEX).//5.80E-146//344aa//77%// P51805, FCBBF30083820//*Homo sapiens* C2H2 (Kruppel-type) zinc finger protein mRNA, complete cds.//1.50E-14// 142aa//38%//AF159567 FCBBF30086440 FCBBF30090690//*Homo sapiens* HT017 mRNA, complete cds.//8.60E-54//311aa//38%//AF225421 FCBBF30095260 FCBBF30123470 FCBBF30129630//ZINC FINGER PROTEIN 85 (ZINC FINGER PROTEIN HPF4) (HTF1).// 9.50E-98//228aa//73%//Q03923 FCBBF30170590 FCBBF30172550 FCBBF30175310//ETHANOLAMINE-PHOSPHOTRANSFERASE (EC 2.7.8.1) (ETHPT).// 2.10E-38//401aa//28%//P22140 FCBBF30178730 FCBBF30189490 FCBBF30190850//E-SELECTIN PRECURSOR (ENDOTHELIAL LEUKOCYTE ADHESION MOLECULE 1) (ELAM-1) (LEUKOCYTE-ENDOTHELIAL CELL ADHESION MOLECULE 2) (LECAM2) (CD62E).//6.10E-30//275aa//31%//P16581
FCBBF30195640//*Homo sapiens* ALR-like protein mRNA, complete cds.//9.10E-188//331aa//99%//AF264750 FCBBF30199610 FCBBF30215060 FCBBF30225660 FCBBF30233680 FCBBF30238870//PROTEIN KINASE C-BINDING PROTEIN NELL2 PRECURSOR (NEL-LIKE PROTEIN 2).//0//641aa//99%//Q99435 FCBBF30240020 FCBBF30240960//ZINC FINGER PROTEIN 136.//8.30E-131//338aa//65%//P52737 FCBBF30242250 FCBBF30243640//PROTEIN ARGININE N-METHYLTRANSFERASE 2 (EC 2.1.1.-).//6.40E-53//102aa//100%//P55345 FCBBF30246230//*Homo sapiens* C2H2 (Kruppel-type) zinc finger protein mRNA, complete cds.//7.10E-17//141aa//40%//AF159567 FCBBF30246630// *H.sapiens* mRNA for ZYG homologue.//4.80E-60//562aa// 29%//X99802 FCBBF30247930//*Rattus norvegicus* clone C42 CDK5 activator-binding protein mRNA, complete cds.//2.70E-73//162aa//87%//AF177477 FCBBF30250730// TRICHOHYALIN.//1.30E-10//240aa//27%//P22793
FCBBF30251420 FCBBF30252520//*Homo sapiens* bicaudal-D (BICD) mRNA, alternatively spliced, partial cds.// 2.50E-47//103aa//98%//U90030 FCBBF30252800// NDRG1 PROTEIN (DIFFERENTIATION-RELATED GENE 1 PROTEIN) (DRG1) (REDUCING AGENTS AND TUNICAMYCIN-RESPONSIVE PROTEIN) (RTP) (NICKEL-SPECIFIC INDUCTION PROTEIN CAP43).//1.30E-134//260aa//97%//Q92597 FCBBF30252850//*Mus musculus* peripherial benzodiazepine receptor associated protein (Pap7) mRNA, complete cds.//2.90E-46//185aa//50%//AF022770 FCBBF30262360 FCBBF30262510 FCBBF30266780 FCBBF30266920 FCBBF30278630 FCBBF30279030//*Homo sapiens* BNPI mRNA for brain-specific Na-dependent inorganic phosphate cotransporter, complete cds.//2.40E-120//222aa//100%//AB032436 FCBBF30281880//regulator of G-protein signalling 7 [*Homo sapiens*].//2.00E-05//100aa//33%//NP_002915 FCBBF30284720 FCBBF30285280 FCBBF40001420 FCBBF40001730//GUANINE NUCLEOTIDE-BINDING PROTEIN BETA SUBUNIT-LIKE PROTEIN 12.3 (P205) (RECEPTOR OF ACTIVATED PROTEIN KINASE C 1) (RACK1).//4.20E-120//265aa//84%//P25388 FCBBF40005480 FEBRA10001880//*Homo sapiens* serine/threonine kinase mRNA, complete cds.//4.60E-106//344aa//53%//AF005046 FEBRA10001900 FEBRA20002100//D-XYLOSE-PROTON SYMPORTER (D-XYLOSE TRANSPORTER).//2.00E-13//159aa//27%//052733 FEBRA20003210 FEBRA20004620//RAP1 GTPASE ACTIVATING PROTEIN 1 (RAPIGAP).//1.50E-46//208aa//43%//P47736 FEBRA20007620//PUTATIVE PRE-MRNA SPLICING FACTOR ATP-DEPENDENT RNA HELICASE SPBC16H5.10C.//2.30E-126//692aa//39%//042945 FEBRA20009090 FEBRA20010120//CLEAVAGE STIMULATION FACTOR, 64 KDA SUBUNIT (CSTF 64 KDA SUBUNIT) (CF-164 KDA SUBUNIT).//1.10E-73//137aa//97%//P33240 FEBRA20017050 FEBRA20018280 FEBRA20018690//ZINC FINGER PROTEIN 44 (ZINC FINGER PROTEIN KOX7) (FRAGMENT).//2.00E-08//96aa//34%//P15621 FEBRA20024100//*Rattus norvegicus* myosin heavy chain Myr 8 mRNA, complete cds.//0//863aa//78%//AF209114 FEBRA20025270 FEBRA20025520 FEBRA20026110//ZINC FINGER PROTEIN 91 (ZINC FINGER PROTEIN HTF10) (HPF7).//1.10E-217//810aa//48%//Q05481 FEBRA20026280 FEBRA20027810 FEBRA20029860 FEBRA20034360 FEBRA20034680//ZINC FINGER PROTEIN 84 (ZINC FINGER PROTEIN HPF2).//5.60E-93//481aa//35%//P51523 FEBRA20037260 FEBRA20037500 FEBRA20040530//ZINC FINGER PROTEIN 84 (ZINC FINGER PROTEIN HPF2).//3.30E-115//335aa//54%//P51523 FEBRA20042190 FEBRA20052910 FEBRA20060610 FEBRA20072120 FEBRA20079310 FEBRA20080810//*Rattus norvegicus* mRNA for peptide/histidine transporter, complete cds.//1.30E-107//239aa//87%//AB000280 FEBRA20082010//ZINC FINGER PROTEIN 195.//0//482aa//99%//014628 FEBRA20082100 FEBRA20086620//NEURONAL OLFACTOMEDIN-RELATED ER LOCALIZED PROTEIN PRECURSOR (NOEL) (1B426B).//3.80E-165//453aa//65%//Q62609 FEBRA20088360//ALPHA-ADAPTIN C (CLATHRIN ASSEMBLY PROTEIN COMPLEX 2 ALPHA-C LARGE CHAIN) (100 KDA COATED VESICLE PROTEIN C) (PLASMA MEMBRANE ADAPTOR HA2/AP2 ADAPTIN ALPHA C SUBUNIT).//5.60E-05//58aa//53%//P17427 FEBRA20090290 FEBRA20092890//*Rattus norvegicus* neural cell adhesion protein BIG-2 precursor (BIG-2) mRNA, complete cds.//0//697aa//93%//U35371 FEBRA20093280 FEBRA20095140 FEBRA20095880 FEBRA20097310//Human Hsp27 ERE-TATA-binding protein (HET) mRNA, complete cds.//0//597aa//97%//U72355 FEBRA20098460 FEBRA20111460 FEBRA20113560// R.norvegicus mRNA for DRM protein.//5.10E-65//157aa//80%//Y10019 FEBRA20125070 FEBRA20130190//UDP-GlcNAc:betaGal beta-1,3-N-acetylglucosaminyltransferase 3//8.20E-65//345aa//42%//NP_055071 FEBRA20132740//*Homo sapiens* mRNA for CDEP, complete cds.//3.70E-16//40aa//92%//AB008430 FEBRA20140100//RER1 PROTEIN.//3.20E-106//196aa//99%//015258 FEBRA20144170//RIBOSOMAL PROTEIN S6 KINASE II ALPHA 2 (EC 2.7.1.-) (S6KII-ALPHA 2) (P90-rSK 2) (RIBOSOMAL S6 KINASE 3) (RSK3) (PP90RSK3).//1.30E-269//495aa//99%//Q15349 FEBRA20145780 FEBRA20161120 FEBRA20166540 FEBRA20167390//*Mus musculus* ST6GalNAc V mRNA for GD1 alpha synthase, complete cds.//9.40E-64//134aa//91%//AB030836 FEBRA20171380//ZINC FINGER PROTEIN 33A (ZINC FINGER PROTEIN KOX31) (KIAA0065) (HA0946) (FRAGMENT).//6.30E-127//415aa//48%//Q06730 FEBRA20174410//*Mus musculus* mRNA for nuclear protein ZAP, complete cds.//2.30E-193//543aa//69%//AB033168 FEBRA20176800 FEBRA20184330//*Rattus norvegicus* glutamate receptor interacting protein 2 (GRIP2) mRNA, complete cds.//8.10E-72//161aa//88%//AF072509 FEBRA20192420 FEBRA20195820//ZINC FINGER PROTEIN 132.//2.60E-47//134aa//63%//P52740 FEBRA20196370 FEBRA20196630//RNA helicase-related protein//0//317aa//100%//NP_031398 FEBRA20197110 FEBRA20204000 FEBRA20204060 FEBRA20211710 FEBRA20214970 FEBRA20215500//*Mus musculus* Nulp1 (nulp1) mRNA, complete cds.//1.80E-38//146aa//64%//U94988 FEBRA20216360 FEBRA20222040 FEBRA20223220//*Homo sapiens* mRNA for fibulin-4.//9.20E-110//202aa//100%//AJ132819 FEBRA20225040//high-glucose-regulated protein 8//1.40E-110//514aa//51%//NP_057342 FEBRA20226010 FEBRA20229560 FEBRA20229630 FEBRA20232850 FEBRA20233770//NEURONAL PAS DOMAIN PROTEIN 2 (NEURONAL PAS2) (MEMBER OF PAS PROTEIN 4) (MOP4).//6.30E-62//164aa//81%//Q99743 FEBRA20235500//P3 PROTEIN.//5.20E-74//391aa//39%//P09131 FEBRA20237640//*Rattus norvegicus* neurabin mRNA, complete cds.//9.10E-29//172aa//46%//U72994 FEHRT20003250//PHOSPHATIDYLINOSITOL 4-KINASE ALPHA (EC 2.7.1.67) (PI4-KINASE) (PTDINS-4-KINASE) (PI4K-ALPHA).//2.20E-146//269aa//100%//P42356 FELNG20002410 HCASM10000500//TOPOISOMERASE 1-RELATED PROTEIN TRF5.//3.70E-09//193aa//22%//P48561 HCHON10001760//histone deacetylase 5//1.00E-133//320aa//67%//NP_005465 HCHON20000380 HCHON20001560//TRANSCRIPTION FACTOR-LIKE PROTEIN MORF4.//7.20E-116//235aa//93%//Q9Y690 HCHON20002260 HCHON20003220//10-FORMYLTETRAHYDROFOLATE DEHYDROGENASE (EC 1.5.1.6) (10-FTHFDH) (FBP-CI).//2.30E-302//731aa//72%//P28037 HCHON20003440//*Homo sapiens* cyclin-D binding Myb-like protein mRNA, complete cds.//1.30E-64//155aa//87%//AF084530 HCHON20007380//*Homo sapiens* mRNA for HELG protein.//3.90E-129//331aa//76%//AJ277291 HCHON20007510//rab6 GTPase activating protein (GAP and centrosome-associated)//0//765aa//62%//NP_036329 HCHON20008150 HCHON20008180 HCHON20008320//ZINC FINGER PROTEIN 135.//2.20E-130//345aa//62%//P52742 HCHON20008980 HCHON20009350 HCHON20009560//ZINC FINGER PROTEIN 74.//1.50E-22//113aa//46%//Q16587 HCHON20010990 HCHON20011160 HCHON20014970 HCHON20015230//*Homo sapiens* nuclear pore-associated protein (NPAP60L) mRNA, complete cds.//1.40E-78//158aa//97%//AF107840

HCHON20015350//PUTATIVE RRNA METHYLTRANSFERASE SPB1 (EC 2.1.1.-).//1.90E-117//771aa//36%//P25582 HCHON20015980//*Homo sapiens* integrin alpha 11 subunit precursor (ITGA11) mRNA, complete cds.//1.00E-227//419aa//99%//AF137378 HCHON20016040//INSULIN-LIKE GROWTH FACTOR BINDING PROTEIN 3 PRECURSOR (IGFBP-3) (IBP-3) (IGF-BINDING PROTEIN 3).//2.00E-21//45aa//97%//P17936 HCHON20016650//*Mus musculus* seven-pass transmembrane receptor precursor (Celsr1) mRNA, complete cds.//6.20E-27//343aa//27%//AF031572 HCHON20022470 HCHON20035130//ZINC FINGER PROTEIN 22 (ZINC FINGER PROTEIN KOX15) (FRAGMENT).//1.10E-18//64aa//56%//P17026 HCHON20036420//*Homo sapiens* mRNA for PED phosphoprotein.//1.30E-64//130aa//100%//Y13736 HCHON20036760 HCHON20040020//TNF-α INDUCIBLE PROTEIN CG12_1.//8.80E-40//302aa//36%//095236 HCHON20043590 HCHON20059870//Hypothetical protein.//4.20E-204//667aa//56%//AL163279 HCHON20064590//ALPHA-2-MACROGLOBULIN PRECURSOR (ALPHA-2-M).//5.00E-38//654aa//27%//PO1023 HCHON20067220 HCHON20067700//*Homo sapiens* gremlin mRNA, complete cds.//5.70E-76//106aa//99%//AF045800 HCHON20068410//*Drosophila melanogaster* microtubule associated protein (asp) mRNA,complete cds.//8.10E-47//803aa//27%//U95171 HCHON20068710 HCHON20074820 HCHON20076500 HCHON20086720//INSULIN-LIKE GROWTH FACTOR BINDING PROTEIN 3 PRECURSOR (IGFBP-3) (IBP-3) (IGF-BINDING PROTEIN 3).//4.10E-113//205aa//100%//P17936 HCHON20097490//dedicator of cyto-kinesis 1//1.00E-154//860aa//37%//NP_001371 HCHON20100740//LACTADHERIN PRECURSOR (MILK FAT GLOBULE-EGF FACTOR 8) (MFG-E8) (HMFG) (BREAST EPITHELIAL ANTIGEN BA46) (MFGM) [CONTAINS: MEDIN].//1.60E-205//363aa//99%//Q08431 HEART20003060//BASIGIN PRECURSOR (LEUKOCYTE ACTIVATION ANTIGEN M6) (COLLAGENASE STIMULATORY FACTOR) (EXTRACELLULAR MATRIX METALLOPROTEINASE INDUCER) (EMMPRIN) (5F7) (CD147 ANTIGEN).//1.30E-132//248aa//100%//P35613 HEART20005410 HEART20017730//ANKYRIN 2 (BRAIN ANKYRIN) (ANKYRIN B) (ANKYRIN, NONERYTHROID).//2.40E-25//368aa//30%//Q01484 HEART20021840 HEART20025980//*Homo sapiens* smoothelin large isoform L2 (SMTN) mRNA, complete cds.//9.00E-152//223aa//97%//AF064238 HEART20034320//ENDOGLUCANASE Z PRECURSOR (EC 3.2.1.4) (ENDO-1,4-BETA-GLUCANASE) (THERMOACTIVE CELLULASE) (AVICELASE I).//1.20E-64//480aa//32%//P23659 HEART20037810 HEART20049400 HEART20049410//*Homo sapiens* cerberus-related protein (CER1) gene, complete cds.//1.10E-12//144aa//29%//AF090189 HEART20049800 HEART20061950//*Homo sapiens* mRNA for myopodin.//1.30E-28//327aa//35%//AJ010482 HEART20063340 HEART20067870 HEART20067890 HEART20072310 HEART20074430 HEART20077670//*Mus musculus* mRNA for E-MAP-115 protein.//1.70E-50//363aa//41%//Y15197 HEART20083640//*Mus musculus* Xin mRNA, complete cds.//3.10E-63//272aa//58%//AF051945 HEART20089940 HEART20090000//*Rattus norvegicus* PIPP mRNA for proline-rich inositol polyphosphate 5-phosphatase, complete cds.//0//639aa//91%//ABO32551 HEART20095990 HHDPC10000650 HHDPC10000830//HYPOTHETICAL 24.9 KDA PROTEIN C16C10.7 IN CHROMOSOME III.//1.50E-23//56aa//60%//Q09463 HHDPC20001040 HHDPC20006920 HHDPC20014320//ADAM 12 PRECURSOR (EC 3.4.24.-) (A DISINTEGRIN AND METALLOPROTEINASE DOMAIN 12) (MELTRIN ALPHA).//1.20E-14//139aa//38%//043184 HHDPC20030490//LIPOPOLYSACCHARIDE-INDUCED TUMOR NECROSIS FACTOR-ALPHA FACTOR (LPS-INDUCED TNF-α ALPHA FACTOR) (P53-INDUCED PROTEIN 7).//1.90E-69//134aa//95%//Q99732 HHDPC20031130//Kruppel-type zinc finger (C2H2) [*Homo sapiens*]//3.30E-196//607aa//57%//NP_005806 HHDPC20034390 HHDPC20034720//CHLORIDE INTRACELLULAR CHANNEL PROTEIN 4 (INTRACELLULAR CHLORIDE ION CHANNEL PROTEIN P64H1).//1.50E-121//213aa//99%//Q9Y696 HHDPC20057420//*Mus musculus* proline-rich protein (Bprp) mRNA, complete cds.//5.40E-45//143aa//69%//AF085348 HHDPC20057940 HHDPC20064600//SUPPRESSOR PROTEIN SRP40.//8.00E-05//175aa//24%//P32583 HHDPC20068620//Ig kappa chain precursor V region (0-81VL)-human (fragment)//8.10E-06//132aa//31%//S22658 HHDPC20084140//*Homo sapiens* polyadenylate binding protein-interacting protein-1 (PAIP1) mRNA, complete cds.//8.10E-12//230aa//23%//AF013758 HHDPC20091140//*Homo sapiens* gremlin mRNA, complete cds.//2.20E-60//105aa//100%//AF045800 HHDPC20091780//coagulation factor V (proaccelerin, labile factor)//2.00E-26//170aa//40%//NP_000121 HHDPC20092080//INSULIN-LIKE GROWTH FACTOR BINDING PROTEIN 3 PRECURSOR (IGFBP-3) (IBP-3) (IGF-BINDING PROTEIN 3).//3.30E-100//185aa//94%//P17936 HHDPC20095280 HLUNG10000550 HLUNG20016330//*Homo sapiens* actin filament associated protein (AFAP) mRNA, complete cds.//6.70E-130//531aa//49%//AF188700 HLUNG20016770 HLUNG20017120//PEPTIDE CHAIN RELEASE FACTOR 2 (RF-2).//8.40E-11//82aa//40%//Q53915 HLUNG20023340//*Mus musculus* SLM-1 (Slm1) mRNA, complete cds.//8.80E-141//270aa//95%//AF098796 HLUNG20033780//Rho guanine nucleotide exchange factor 5//6.00E-60//440aa//38%//NP_005426 HLUNG20084390 IMR3220002430//CHROMATIN ASSEMBLY FACTOR 1 P48 SUBUNIT (CAF-1 P48 SUBUNIT) (RETINOBLASTOMA BINDING PROTEIN P48) (RETINOBLASTOMA-BINDING PROTEIN 4) (MSII PROTEIN HOMOLOG).//7.10E-09//303aa//24%//Q09028 KIDNE20002520//glutamyl tRNA synthetase homolog//9.90E-156//290aa//100%//T00743 KIDNE20003940//RENAL SODIUM-DEPENDENT PHOSPHATE TRANSPORT PROTEIN 2 (SODIUM/PHOSPHATE COTRANSPORTER 2) (NA(+)/PI COTRANSPORTER 2) (RENAL SODIUM-PHOSPHATE TRANSPORT PROTEIN 2) (RENAL NA+-DEPENDENT PHOSPHATE COTRANSPORTER 2).//1.80E-151//582aa//51%//Q06496 KIDNE20006780 KIDNE20007210//*Xenopus laevis* mRNA for RPA interacting protein alpha (ripalpha gene).//8.30E-17//104aa//47%//AJ243177 KIDNE20007770//CARCINOEMBRYONIC ANTIGEN CGM6 PRECURSOR (NONSPECIFIC CROSS-REACTING ANTIGEN NCA-95) (ANTIGEN CD67) (CD66B ANTIGEN).//1.20E-17//326aa//27%//P31997 KIDNE20008010//*Homo sapiens* mRNA for putative protein kinase (WNK1 gene).//2.50E-25//460aa//29%//AJ296290 KIDNE20009470 KIDNE20011170 KIDNE20011400 KIDNE20013730 KIDNE20017130//*Oreochromis niloticus* sex-determining protein DM0 mRNA, complete cds.//5.10E-43//252aa//43%//AF203490 KIDNE20018730 KIDNE20018970 KIDNE20020150//HEAT SHOCK 70 KDA PROTEIN 1 (HSP70.1) (HSP70-1/HSP70-2).//9.90E-251//458aa//98%//P08107 KIDNE20021680//SHORT CHAIN 3-HYDROXYACYL- COA DEHYDROGENASE PRECURSOR (EC 1.1.1.35) (HCDH).//7.10E-141//273aa//98%//Q16836 KIDNE20021910//Homo sapiens MRS1 mRNA, complete cds.//2.30E-30//339aa//27%//AF093239 KIDNE20021980 KIDNE20022620//like-glycosyltransferase//8.50E-253// 633aa//70%//NP_004728 KIDNE20024830//Homo sapiens copine I mRNA, complete cds.//1.30E-46//134aa//47%// U83246 KIDNE20027250//ZINC FINGER PROTEIN 41 (ZFP-41) (CTFIN92) (FRAGMENT).//3.80E-55//105aa// 91%//Q02526 KIDNE20027950//ZINC FINGER PROTEIN 7 (ZINC FINGER PROTEIN KOX4) (ZINC FINGER PROTEIN HF.16).//2.40E-40//82aa//100%//P17097 KIDNE20028390//GALACTOSE-1-PHOSPHATE URIDYLYLTRANSFERASE (EC 2.7.7.10).//6.00E-70// 85aa//90%//P43424 KIDNE20028720//Mus musculus Ac39/physophilin mRNA, complete cds.//2.70E-130// 345aa//68%//U21549 KIDNE20028830 KIDNE20029800 KIDNE20067330 KIDNE20079440 KIDNE20096280 KIDNE20096470 KIDNE20100070//Rattus norvegicus kidney-specific protein (KS) mRNA, complete cds.//1.20E-253//572aa//77%//AF062389 KIDNE20100840 KIDNE20101370//GOLGIN-95.//3.40E-20//76aa//68%// Q08379 KIDNE20101510//UROMODULIN PRECURSOR (TAMM-HORSFALL URINARY GLYCOPROTEIN) (THP).//0//519aa//95%//P07911 KIDNE20102650 KIDNE20102710//Mus musculus mRNA for Shank3b protein (shank3 gene).//1.20E-81//203aa//71%//AJ245904 KIDNE20104300 KIDNE20106740 KIDNE20107390// Homo sapiens CHRAC17 (CHRAC17) mRNA, complete cds.//1.50E-40//105aa//86%//AF226077 KIDNE20107500 KIDNE20107620//Rattus norvegicus protein kinase WNK1 (WNK1) mRNA, complete cds.//8.70E-140//266aa//74%// AF227741 KIDNE20109730//Mus musculus orphan transporter isoform B9 (Xtrp2) mRNA, alternatively spliced, complete cds.//8.70E-34//103aa//65%//AF075266 KIDNE20109890//Rattus norvegicus TGF-beta resistance-associated protein (TRAG) mRNA, complete cds.//2.60E-141//774aa//37%//AF305813 KIDNE20112000 KIDNE20115080//Homo sapiens mRNA for hNBL4, complete cds.//6.20E-115//226aa//96%//AB030240 KIDNE20118580//actin interacting protein [Arabidopsis thaliana].//5.00E-34//140aa//56%//CAB16815 KIDNE20120090 KIDNE20121880//Mus musculus claudin-19 mRNA, partial cds.//6.10E-97//193aa//95%// AF249889 KIDNE20122910 KIDNE20124400//Homo sapiens mRNA for ALEX1, complete cds.//1.00E-18// 167aa//28%//AB039670 KIDNE20125630 KIDNE20126010 KIDNE20126130 KIDNE20127100// Drosophila melanogaster Diablo (dbo) mRNA, complete cds.//1.10E-10//254aa//26%//AF237711 KIDNE20127450 KIDNE20127750//Homo sapiens partial mRNA for transport-secretion protein 2.1 (TTS-2.1 gene).//6.50E-45// 178aa//46%//AJ278475 KIDNE20130450 KIDNE20131580//Homo sapiens mRNA for LAK-4p, complete cds.//1.80E-111//211aa//100%//AB002405 KIDNE20132180 KIDNE20137340//HYPOTHETICAL 49.1 KDA PROTEIN C11D3.06 IN CHROMOSOME I.// 5.80E-13//149aa//30%//Q10085 KIDNE20138010 KIDNE20141190 KIDNE20144890 KIDNE20148900 KIDNE20163880 KIDNE20180710 KIDNE20181660 KIDNE20182690//Homo sapiens mRNA for RERE, complete cds.//3.50E-222//401aa//99%//AB036737 KIDNE20186780 KIDNE20190740//Rattus norvegicus SNIP-b mRNA, complete cds.//6.70E-20//51aa//92%// AF156982 LIVER10001260 LIVER10004790 LIVER20002160//HEAT SHOCK COGNATE 71 KDA PROTEIN.//0//585aa//95%//P11142 LIVER20011130// Homo sapiens F-box protein FBL9 mRNA, partial cds.// 5.50E-107//210aa//99%//AF176701 LIVER20011910 LIVER20028420 LIVER20035110 LIVER20035680 LIVER20038540 LIVER20045650 LIVER20055200// Homo sapiens leucocyte immunoglobulin-like receptor-8 (LIR-8) mRNA, complete cds.//2.,50E-43//132aa//71%// AF025534 LIVER20055440//Homo sapiens Rho GAP pl90-A mRNA, complete cds.//2.90E-101//195aa//98%// AF159851 LIVER20059810//UDP-GLUCOSE 4-EPIMERASE (EC 5.1.3.2) (GALACTOWALDENASE) (UDP-GALACTOSE 4-EPIMERASE).//1.60E-15//39aa//100%// Q14376 LIVER20062510 LIVER20064100//Ciona intestinalis mRNA for myoplasmin-C1, complete cds.// 2.90E-14//167aa//26%//D42167 LIVER20064690// PLASMA SERINE PROTEASE INHIBITOR PRECURSOR (PCI) (PROTEIN C INHIBITOR) (PLASMINOGEN ACTIVATOR INHIBITOR-3) (PAI3).//1.70E-146//319aa// 89%//P05154 LIVER20075680 LIVER20080530//Drosophila melanogaster forked mRNA for large Forked protein, complete cds.//1.10E-11//198aa//32%//D21203 LIVER20084730 LIVER20085800 LIVER20087060//Mus musculus putative purine nucleotide binding protein mRNA, complete cds.//2.70E-233//619aa//70%//U44731 LIVER20087510 LIVER20091180 MAMGL10000830// Drosophila melanogaster L82B (L82) mRNA, complete cds. //3.00E-27//231aa//38%//AF125385 MESAN10001260//Drosophila melanogaster Crossveinless 2 (CV-2) mRNA, complete cds.//6.50E-104//628aa//35%// AF288223 MESAN20004570//MEDIAN BODY PROTEIN.//3.00E-07//343aa//23%//Q08014 MESAN20014500//Drosophila melanogaster Dispatched (dispatched) mRNA, complete cds.//1.60E-46//225aa// 37%//AF200691 MESAN20025190//Mus musculus cell cycle checkpoint control protein Mrad9 gene, complete cds.//7.30E-19//43aa//97%//AF045662 MESAN20027090 MESAN20029400 MESAN20031900//Homo sapiens mRNA for zinc-binding protein (Rbcc728 gene-).//2.90E-161//724aa//43%//AJ272269 MESAN20035290 MESAN20036460 MESAN20038510 MESAN20089360 MESAN20101140//PINCH PROTEIN (PARTICULARY INTERESTING NEW CYS-HIS PROTEIN).//2.30E-25// 52aa//98%//P48059 MESAN20103120//Homo sapiens sodium/calcium exchanger NCKX3 (SLC24A3) mRNA, complete cds.//4.10E-66//289aa//37%//AF169257 MESAN20106640 MESAN20115970 MESAN20121130 MESAN20125860//MELANOTRANSFERRIN PRECURSOR (MELANOMA-ASSOCIATED ANTIGEN P97).// 1.30E-40//81aa//100%//P08582 MESAN20127350//myelin expression factor-3//2.80E-15//227aa//29%//JE0163 MESAN20130220//Homo sapiens testis-specific chromodomain Y-like protein (CDYL) mRNA, alternatively processed, complete cds.//2.10E-126//319aa//63%//AF081258 MESAN20132110 MESAN20136110//Ciona savignyi mRNA for PEM-3, complete cds.//1.90E-85//236aa//65%// AB001769 MESAN20138450 MESAN20139360 MESAN20141920//Human ovarian cancer downregulated myosin heavy chain homolog (Doc1) mRNA, complete cds.//0//691aa//97%//U53445 MESAN20152770 MESAN20153910 MESAN20154010//Homo sapiens mRNA for putative ribulose-5-phosphate-epimerase, partial cds.//9.10E-60//69aa//100%//AJ224326 MESAN20157080 MESAN20161590 MESAN20164090 MESAN20171520// Homo sapiens TNF intracellular domain-interacting protein mRNA, complete cds.//9.30E-30//198aa//40%//AF168676 MESAN20174170//REGULATOR OF G-PROTEIN SIGNALING 4 (RGS4) (RGP4).//1.80E-39//80aa//98%// P49798 MESAN20182090 MESAN20186700

NESOP10001080 NOVAR10000150 NOVAR10000910//COLORECTAL MUTANT CANCER PROTEIN (MCC PROTEIN).//6.00E-199//392aa//98%//P23508 NOVAR10001020 NOVAR20000380 NOVAR20003520 NT2NE20003740 NT2NE20010050 NT2NE20010210 NT2NE20010400//*Homo sapiens* GL013 mRNA, complete cds.//2.90E-51//223aa//60%//AF267859 NT2NE20010490//ZINC FINGER PROTEIN 85 (ZINC FINGER PROTEIN HPF4) (HTF1).//1.30E-194//464aa//72%//Q03923 NT2NE20015240 NT2NE20021620//Saccharomyces cerevisiae Vps9p (VPS9) gene, complete cds.//1.00E-13//250aa//24%//U20373 NT2NE20043780 NT2NE20053580 NT2NE20068130//CELL SURFACE GLYCOPROTEIN 1 PRECURSOR (OUTER LAYER PROTEIN B) (S-LAYER PROTEIN 1).//2.50E-34//377aa//40%//Q06852 NT2NE20072200 NT2NE20074250 NT2NE20080170//HUNTINGTIN-ASSOCIATED PROTEIN-INTERACTING PROTEIN (DUO PROTEIN) (KALIRIN) (PAM COOH-TERMINAL INTERACTOR PROTEIN 10) (P-CIP10).//6.60E-57//661aa//27%//P97924 NT2NE20089610 NT2NE20089970//ZINC FINGER PROTEIN 91 (ZINC FINGER PROTEIN HTF10) (HPF7).//1.60E-29//77aa//81%//Q05481 NT2NE20108540 NT2NE20110360 NT2NE20118960//DOLICHYL-DIPHOSPHOOLIGOSACCHARIDE-PROTEIN GLYCOSYLTRANSFERASE 63 KDA SUBUNIT PRECURSOR (EC 2.4.1.119) (RIBOPHORIN II).//9.30E-274//562aa//94%//P04844 NT2NE20122430//GLYOXYLATE-INDUCED PROTEIN.//7.70E-25//144aa//38%//P30147 NT2NE20124480 NT2NE20125050//Gallus gallus mRNA for avena, complete cds.//5.80E-199//468aa//84%//AB017437 NT2NE20130190 NT2NE20131890 NT2NE20132170//*Rattus norvegicus* lysosomal amino acid transporter 1 mRNA, complete cds.//3.70E-97//357aa//52%//AF361239 NT2NE20142210//SINGLE-MINDED HOMOLOG 2 (SIM TRANSCRIPTION FACTOR) (MSIM).//3.00E-24//660aa//26%//Q61079 NT2NE20146810 NT2NE20152750 NT2NE20155110 NT2NE20156260 NT2NE20157470//COMPLEMENT C2 PRECURSOR (EC 3.4.21.43) (C3/C5 CONVERTASE).//6.60E-138//256aa//100%//P06681 NT2NE20158600//erythroid ankyrin-Synechocystis sp. (strain PCC 6803).//7.00E-13//160aa//31%//S74626 NT2NE20159740 NT2NE20172590 NT2NE20174800 NT2NE20174920 NT2NE20177520//Guinea pig mRNA for decay-accelerating factor (isoform GDab-SEC), complete cds.//1.70E-15//273aa//28%//D49421 NT2NE20181650//Shb=Src homology 2 protein//2.90E-36//115aa//43%//AAB29780 NT2NE20183760 NT2NE20184900//*Mus musculus* mRNA for transcription factor CA150b, complete cds.//8.60E-29//98aa//55%//AB023485 NT2NE20187390 NT2RI20001330//*Homo sapiens* KE03 protein mRNA, partial cds.//3.40E-103//339aa//57%//AF064604 NT2RI20003480//GLYPICAN-2 PRECURSOR (CEREBROGLYCAN) (HSPG M13).//1.80E-261//581aa//82%//P51653 NT2RI20005750//*Rattus norvegicus* GTP-binding protein REM2 (Rem2) mRNA, complete cds.//8.90E-139//272aa//95%//AF084464 NT2RI20009870//lunatic fringe precursor [Mus musculus]//5.50E-123//237aa//91%//U94351 NT2RI20022600 NT2RI20023160 NT2RI20023590 NT2RI20023910//*Homo sapiens* TMTSP mRNA for transmembrane molecule with thrombospondin module, complete cds.//0//480aa//96%//AB044385 NT2RI20025400//Mouse mRNA for P24 protein, complete cds.//9.70E-94//196aa//91%//D83206 NT2RI20025640 NT2RI20028470 NT2RI20036670 NT2RI20040930//MITOCHONDRIAL CARRIER PROTEIN YMC2 PRECURSOR.//1.10E-27//194aa//38%//P38087 NT2RI20040990//ANKYRIN 2 (BRAIN ANKYRIN) (ANKYRIN B) (ANKYRIN, NONERYTHROID).//2.40E-25//368aa//30%//Q01484 NT2RI20041880//MYOSIN HEAVY CHAIN, NONMUSCLE TYPE A (CELLULAR MYOSIN HEAVY CHAIN, TYPE A) (NMMHC-A).//8.10E-10//322aa//21%//P35579 NT2RI20046080 NT2RI20048840//GUANINE NUCLEOTIDE-BINDING PROTEIN G(I), ALPHA-2 SUBUNIT (ADENYLATE CYCLASE-INHIBITING G ALPHA PROTEIN).//2.10E-171//316aa//100%//P04899 NT2RI20050960//*Homo sapiens* p53 regulated PA26-T2 nuclear protein (PA26) mRNA, complete cds.//5.40E-164//496aa//61%//AF033120 , NT2RI20054050//*Drosophila melanogaster* Abnormal X segregation (Axs) gene, complete cds.//2.40E-83//487aa//37%//AF101361 NT2RI20055790 NT2RI20056700//NEURONAL OLFACTOMEDIN-RELATED ER LOCALIZED PROTEIN PRECURSOR (NOEL) (1B426B).//3.40E-237//439aa//97%//Q62609 NT2RI20069730 NT2RI20076290 NT2RI20086220 NT2RI20091730 NT2RI20091940//CORNICHON-LIKE PROTEIN.//9.70E-73//159aa//81%//035089 NT2RI20198260 NT2RI20203900 NT2RI20207030 NT2RI20216250 NT2RI20240080//SMALL GLUTAMINE-RICH TETRATRICOPEPTIDE REPEAT-CONTAINING PROTEIN.//1.30E-86//311aa//58%//043765 NT2RI20244600//*Homo sapiens* mRNA for sphingosine-1-phosphatase (ORFI).//2.60E-50//273aa//36%//AJ293294 NT2RI20244960 NT2RI20250750 NT2RI20252550 NT2RI20273230//PUTATIVE HELICASE YGR271W.//1.10E-14//152aa//38%//P53327 NT2RP60000770//*Homo sapiens* mRNA for ZAC zinc finger protein.//5.80E-179//325aa//98%//AJ006354 NT2RP60000850//Bos taurus RPGR-interacting protein-1 (RPGRIPl) mRNA, complete cds.//2.10E-139//751aa//38%//AF227258 NT2RP70010740 NT2RP70027380//N-CHIMAERIN (NC) (N-CHIMERIN) (ALPHA CHIMERIN) (A-CHIMAERIN).//7.40E-31//203aa//36%//P15882 NT2RP70032610//ALPHA ENOLASE (EC 4.2.1.11) (2-PHOSPHO-D-GLYCERATE HYDROLYASE) (NON- NEURAL ENOLASE) (NNE) (PHOSPHOPYRUVATE HYDRATASE).//4.40E-180//387aa//88%//P06733 NT2RP70036880//Gtpase activating protein for Yptlp; Gyplp [Saccharomyce scerevisiae].//2.00E-66//250aa//50%//NP_014713 NT2RP70037240//*H.sapiens* E-MAP-115 mRNA.//1.10E-79//475aa//41%//X73882 NT2RP70043480//ZINC FINGER PROTEIN 93 (ZINC FINGER PROTEIN HTF34) (FRAGMENT).//0//588aa//91%//P35789 NT2RP70044280//CTD-BINDING SR-LIKE PROTEIN RA4 (FRAGMENT).//1.20E-11//190aa//31%//095104 NT2RP70045590//PUTATIVE ENDONUCLEASE ClF12.06C (EC 3.1.-.-).//3.60E-34//246aa//36%//Q10348 NT2RP70056750 NT2RP70062230//NEUROFILAMENT TRIPLET H PROTEIN (200 KDA NEUROFILAMENT PROTEIN) (NF-H).//2.50E-29//622aa//29%//P19246 NT2RP70063950//PUTATIVE RHO/RAC GUANINE NUCLEOTIDE EXCHANGE FACTOR (RHO/RAC GEF) (FACIOGENITAL DYSPLASIA PROTEIN HOMOLOG).//4.90E-13//417aa//26%//P52734 NT2RP70072690 NT2RP70075240 NT2RP70077660 NT2RP70078420//*Drosophila melanogaster* Centaurin Gamma 1A (ceng1A) mRNA, complete cds.//1.00E-120//700aa//40%//AF254741 NT2RP70080850 NT2RP70081610//*Mus musculus* 10F6 protein mRNA, complete cds.//5.20E-52//214aa//50%//AF131206 NT2RP70085440 NT2RP70102350//*Mus musculus* mRNA for 0lig3 bHLH protein, complete cds.//1.90E-134//257aa//98%//AB038698 NT2RP70105210 NT2RP70110860 NT2RP70111320 NT2RP70122910

NT2RP70125160 NT2RP70130020 NT2RP70133740//SECRETORY CARRIER-ASSOCIATED MEMBRANE PROTEIN 2.//2.60E-136//267aa//94%//015127 NT2RP70134990 NT2RP70137290 NT2RP70137640 NT2RP70143480 NT2RP70147210 NT2RP70150800 NT2RP70157890//zinc finger protein 267; zinc finger (C2H2) [Homo sapiens]//1.60E-125//228aa//99%//NP_003405 NT2RP70159960//Rattus norvegicus p135 SynGAP mRNA, partial cds.//4.80E-60//177aa//69%//AF053938 NT2RP70169110 NT2RP70175670 NT2RP70179710 NT2RP70181970 NT2RP70188020 NT2RP70188710 NT2RP70190640 NT2RP70192730//LYSOSOMAL ACID LIPASE/CHOLESTERYL ESTER HYDROLASE PRECURSOR (EC 3.1.1.13) (LAL) (ACID CHOLESTERYL ESTER HYDROLASE) (STEROL ESTERASE) (LIPASE A) (CHOLESTERYL ESTERASE).//3.00E-181//323aa//99%//P38571 NT2RP70194450 NT2RP70195430//PUTATIVE NADP-DEPENDENT OXIDOREDUCTASE IN TEHB-rHSE INTERGENIC REGION (EC 1.-.-.-).//1.10E-57//349aa//38%//P76113 NT2RP70198350//HEPATOMA-DERIVED GROWTH FACTOR (HDGF).//2.60E-111//213aa//98%//P51858 NT2RP70203790 NTONG20009770//NEUROLYSIN PRECURSOR (EC 3.4.24.16) (NEUROTENSIN ENDOPEPTIDASE) (MITOCHONDRIAL OLIGOPEPTIDASE M) (MICROSOMAL ENDOPEPTIDASE) (MEP).//1.30E-304//599aa//92%//P42675 NTONG20013620//Homo sapiens hydroxysteroid sulfotransferase SULT2Blb (HSST2) mRNA, complete cds.//9.10E-82//151aa//100%//U92315 NTONG20015870//KERATIN, TYPE II CYTOSKELETAL 4 (CYTOKERATIN 4) (K4) (CK4).//3.30E-132//489aa//54%//P19013 NTONG20028070//CYR61 PROTEIN PRECURSOR (GIG1 PROTEIN) (INSULIN-LIKE GROWTH FACTOR-BINDING PROTEIN 10).//1.60E-65//133aa//92%//000622 NTONG20029480//Mus musculus Xin.mRNA, complete cds.//7.20E-93//409aa//54%//AF051945
NTONG20029700//Homo sapiens laminin alpha 3b chain mRNA, partial cds.//6.60E-230//425aa//92%//AF005258 NTONG20046140//Homo sapiens mRNA for MNK1, complete cds.//5.70E-89//177aa//98%//AB000409 NTONG20048060 NTONG20049910 NTONG20050620 NTONG20050860 NTONG20051530//KUPFFER CELL RECEPTOR.//6.30E-85//391aa//45%//P70194
NTONG20052650//Gallus gallus Xin mRNA, complete cds.//5.40E-146//768aa//40%//AF051944
NTONG20056570//CORONIN-LIKE PROTEIN P57.//2.20E-121//356aa//62%//Q92176 NTONG20061870 NTONG20063010//Mus musculus EF-9 mRNA, partial cds.//1.70E-78//154aa//92%//U72678 NTONG20064400//REPETIN.//2.20E-107//446aa//50%//P97347
NTONG20064840//Mus musculus slpl mRNA for synaptotagmin-like protein 1, complete cds.//2.60E-1-28//258aa//90%//AB050741 NTONG20065010 NTONG20066460//Mus musculus Gd mRNA for gasdermin, complete cds.//8.30E-207//446aa//88%//AB033595 NTONG20067090//Mus musculus mRNA for Sh3yl1, complete cds.//2.00E-63//136aa//91%//D85926 NTONG20067830//ANKYRIN 1 (ERYTHROCYTE ANKYRIN) (ANKYRIN R) (ANKYRINS 2.1 AND 2.2).//1.10E-24//227aa//34%//P16157 NTONG20070200//ZINC FINGER PROTEIN 83 (ZINC FINGER PROTEIN HPFl).//1.30E-134//352aa//65%//P51522 NTONG20070340//collagen alpha 1(IX) chain//1.50E-43//220aa//45%//S42617 NTONG20075220//Rattus norvegicus SNIP-a-mRNA, complete cds.//1.80E-121//436aa//41%//AF156981 NTONG20076930//ALPHA-1-INHIBITOR III PRECURSOR.//1.20E-124//513aa//47%//P14046 NTONG20077560 NTONG20083650 NTONG20088620//Homo sapiens genethonin 3 mRNA, partial cds.//4.90E-202//390aa//99%//AF177292 NTONG20090600//SYNAPSIN I (BRAIN PROTEIN 4.1).//2.10E-07//198aa//29%//P17600 NTONG20090680 NTONG20092290 NTONG20092330//BESTROPHIN (VITELLIFORM MACULAR DYSTROPHY PROTEIN) (TU15B).//1.40E-135//414aa//59%//076090
OCBBF10000540//Mus musculus rjs (rjs) mRNA, complete cds.//4.00E-14//105aa//36%//AF061529
OCBBF10001750//Mus musculus mRNA for sprouty-4, complete cds.//1.50E-159//300aa//92%//AB019280 OCBBF10001850//ZINC FINGER PROTEIN 84 (ZINC FINGER PROTEIN HPF2).//8.90E-166//605aa//51%//P51523 OCBBF20005230 OCBBF20006770//TREACLE PROTEIN (TREACHER COLLINS SYNDROME PROTEIN).//2.50E-287//693aa//84%//Q13428
OCBBF20013890 OCBBF20019380//seizure related gene 6//6.00E-170//336aa//90%//NP_067261 OCBBF20019830 OCBBF20020150 OCBBF20020830//Homo sapiens Pumilio 1 (PUMH1) mRNA, complete cds.//0//814aa//99%//AF315592 OCBBF20022900//Homo sapiens SCHIP-1 mRNA, complete cds.//2.80E-250//469aa//99%//AF145713 OCBBF20023570 OCBBF20026630 OCBBF20028050//Homo sapiens B2 gene partial cDNA, clone B2E.//7.70E-38//246aa//33%//AJ002220 OCBBF20028650//DOSAGE COMPENSATION REGULATOR (MALE-LESS PROTEIN) (NO ACTION POTENTIAL PROTEIN).//1.40E-50//160aa//47%//P24785 OCBBF20029800 OCBBF20030280//Rattus norvegicus hfb2 mRNA, complete cds.//5.20E-63//175aa//68%//AF031483 OCBBF20030910//PUROMYCIN-SENSITIVE AMINOPEPTIDASE (EC 3.4.11.-) (PSA).//2.90E-146//279aa//98%//P55786 OCBBF20032460 OCBBF20035930//BETA-SOLUBLE NSF ATTACHMENT PROTEIN (SNAP-BETA).//7.80E-135//264aa//96%//P81126
OCBBF20037440//ZINC-FINGER PROTEIN HT2A (72 KDA TAT-INTERACTING PROTEIN).//2.10E-08//80aa//40%//Q13049 OCBBF20039250//Homo sapiens breast cancer metastasis-suppressor 1 (BRMS1) mRNA, complete cds.//2.20E-55//188aa//56%//AF159141 OCBBF20041680 OCBBF20045330 OCBBF20046120//zinc finger protein 16 (KOX 9)//1.00E-131//350aa//59%//NP_008889 OCBBF20046470//ARFAPTIN 1.//5.80E-114//229aa//97%//P53367 OCBBF20046690//PROBABLE CATION-TRANSPORTING ATPASE W08D2.5 IN CHROMOSOME IV (EC 3.6.1.-).//4.20E-105//249aa//39%//Q27533 OCBBF20047570 OCBBF20048660 OCBBF20049300//ZINC FINGER PROTEIN 184 (FRAGMENT).//7.10E-141//566aa//45%//Q99676 OCBBF20049840//Homo sapiens mRNA for neurabin II protein.//4.90E-166//808aa//47%//AJ401189 OCBBF20050770//CARNITINE O-PALMITOYLTRANSFERASE I, MITOCHONDRIAL LIVER ISOFORM (EC 2.3.1.21) (CPT I) (CPTI-L).//3.10E-211//653aa//56%//P32198 OCBBF20051610 OCBBF20053430//Mus musculus MAST205 protein kinase mRNA, complete cds.//0//498aa//94%//U02313 OCBBF20053490//MANNOSE-6-PHOSPHATE ISOMERASE (EC 5.3.1.8) (PHOSPHOMANNOSE ISOMERASE) (PMI) (PHOSPHOHEXOMUTASE).//1.10E-24//52aa//100%//P34949 OCBBF20053730//85 KDA CALCIUM-INDEPENDENT PHOSPHOLIPASE A2 (EC 3.1.1.4) (IPLA2) (CAI- PLA2).//0//636aa//91%//060733 OCBBF20054200//DEVELOPMENTAL PROTEIN SEVEN IN ABSENTIA.//1.10E-27//97aa//54%//P21461 OCBBF20054760//SERINE/THREONINE PROTEIN KINASE RIP (EC 2.7.1.-) (CELL DEATH PROTEIN RIP) (RECEPTOR INTERACTING PROTEIN).//4.00E-122//

230aa//97%//Q13546 OCBBF20059560//*Homo sapiens* (clone D320) C219-reactive peptide mRNA, partial cds.//6.70E-39//140aa//62%//L34688 OCBBF20060300 OCBBF20061720 OCBBF20062140 OCBBF20062410 OCBBF20063320 OCBBF20066390//ZINC FINGER PROTEIN 84 (ZINC FINGER PROTEIN HPF2).//8.90E-63//173aa//65%//P51523 OCBBF20068490//*Mus musculus* RW1 protein mRNA, complete cds.//4.60E-40//310aa//37%//AF060565 OCBBF20071210//M-PHASE PHOSPHOPROTEIN 9 (FRAGMENT).//1.80E-96//184aa//100%//Q99550 OCBBF20071840//ZINC FINGER PROTEIN 135.//1.OOE-139//416aa//57%//P52742 OCBBF20071960//Coturnix coturnix japonica qMEF2D gene.//6.50E-06//124aa//31%///AJ002238 OCBBF20072240//*Homo sapiens* candidate tumor suppressor protein DICE1 mRNA, complete cds.//7.60E-165//354aa//83%//AF097645 OCBBF20072320 OCBBF20073540//*Homo sapiens* p30 DBC mRNA, complete cds.//4.00E-65//146aa//91%//AF293335 OCBBF20074140 OCBBF20076220 OCBBF20078920// *Homo sapiens* zinc-,finger helicase (hZFH) mRNA, complete cds.//3.10E-67//152aa//92%//U91543 OCBBF20079310 OCBBF20079460 OCBBF20080050// RTOA PROTEIN (RATIO-A).//3.50E-07//191aa//32%// P54681 OCBBF20080410//ZINC FINGER PROTEIN 43 (ZINC PROTEIN HTF6).//6.90E-145//445aa//51%//P28160 OCBBF20081380 OCBBF20082830//NDRG1 PROTEIN (DIFFERENTIATION-RELATED GENE 1 PROTEIN) (DRG1) (REDUCING AGENTS AND TUNICAMYCIN-RESPONSIVE PROTEIN) (RTP) (NICKEL-SPECIFIC INDUCTION PROTEIN CAP43). //3.10E-190//282aa//99%//Q92597 OCBBF20084660 OCBBF20085200 OCBBF20086400//*Mus musculus* ADP-ribosylation factor-like membrane-associated protein (Arml) mRNA, complete cds.//2.10E-114//244aa//87%//AF205936
OCBBF20086910//*Mus musculus* mSox5L mRNA, complete cds.//9.30E-253//528aa//91%//AB006330 OCBBF20087010 OCBBF20088140 OCBBF20088220 OCBBF20091150 OCBBF20094240 OCBBF20097720 OCBBF20100400 OCBBF20103130 OCBBF20104040 OCBBF20105570 OCBBF20107090//*Homo sapiens* protocadherin 68 (PCH68) mRNA, complete cds.//2.60E-77//359aa//49%//AF029343 OCBBF20107920 OCBBF20108190//ZINC FINGER PROTEIN ZFP-36 (FRAGMENT).//2.90E-151//429aa//61%//P16415
OCBBF20108430//GUANINE NUCLEOTIDE-BINDING PROTEIN G(I), ALPHA-2 SUBUNIT (ADENYLATE CYCLASE-INHIBITING G ALPHA PROTEIN).//2.10E-171//316aa//100%//P04899 OCBBF20108580//APICAL-LIKE PROTEIN (APXL PROTEIN).//1.00E-196//376aa//100%//Q13796 OCBBF20108630//ATP-BINDING CASSETTE, SUB-FAMILY A, MEMBER 1 (ATP-BINDING CASSETTE TRANSPORTER 1) (ATP-BINDING CASSETTE 1).//1.00E-63//268aa//46%//P41233 OCBBF20109310 OCBBF20111770 OCBBF20116850// *Mus musculus* Islr(immunoglobulin superfamily containing leucine-rich repeat) mRNA, complete cds.//2.10E-88//285aa//57%//ABO24538 OCBBF200118970 OCBBF20120390//SODIUM-DEPENDENT PROLINE TRANSPORTER (FRAGMENT).//0//636aa//100%// Q99884 OCBBF20121390//RING CANAL PROTEIN (KELCH PROTEIN).//7.80E-28//220aa//31%//Q04652 OCBBF20122620 OCBBF20124360//*Homo sapiens* mRNA for Misshapen/NIK-related kinase MINK-1, complete cds.// 2.70E-98//185aa//100%//AB035698 OCBBF20125530// *Mus musculus* PRAJAL (Prajal) mRNA, complete cds.// 3.60E-110//281aa//77%//U06944 OCBBF20126780 OCBBF20127040//*Drosophila melanogaster* woc gene, exons 1-11.//1.10E-09//284aa//24%//AJ276394 OCBBF20127140//GUANINE NUCLEOTIDE-BINDING PROTEIN G(I)/G(S)/G(T) BETA SUBUNIT 1 (TRANSDUCIN BETA CHAIN 1).//5.50E-63//119aa//100%// P04901 OCBBF20127550 OCBBF20128120//*Mus musculus* mmDNAJA4 mRNA for mmDj4, complete cds.//1.20E-205//397aa//93%//AB032401 OCBBF20129360//1-PHOSPHATIDYLINOSITOL-4,5-BISPHOSPHATE PHOSPHODIESTERASE DELTA 1 (EC 3.1.4.11) (PLC-DELTA-1) (PHOSPHOLIPASE C-DELTA-1) (PLC-III).// 1.00E-130//461aa//36%//P51178 OCBBF20130110 OCBBF20130910 OCBBF20132850//*Homo sapiens* brain tumor associated protein NAG14 (NAG14) mRNA, complete cds.//3.80E-24//399aa//27%//AF196976 OCBBF20139260 OCBBF20140640 OCBBF20140890 OCBBF20145760//GLYPICAN-1 PRECURSOR.//3.40E-118//222aa//100%//P35052 OCBBF20148280//*Mus musculus* mlt 1 gene, complete cds.//1.70E-151//502aa//63%// AB032418 OCBBF20148730//RING CANAL PROTEIN (KELCH PROTEIN).//2.90E-43//509aa//26%//Q04652 OCBBF20149280//*Mus musculus* WAVE-1 mRNA, complete cds.//4.30E-07//210aa//29%//AF290877 OCBBF20151150 OCBBF20153340//*Rattus norvegicus* cytosolic sorting protein PACS-1a (PACS-1) mRNA, complete cds.//0//701aa//93%//AF076183 OCBBF20153350//G PROTEIN PATHWAY SUPPRESSOR 2 (GPS2 PROTEIN) .//1.20E-49//103aa//99%//Q13227 OCBBF20155060// CADHERIN-RELATED TUMOR SUPPRESSOR PRECURSOR (FAT PROTEIN).//1.90E-67//307aa//37%// P33450 OCBBF20164050 OCBBF20164670 OCBBF20170690 OCBBF20173060 OCBBF20173250 OCBBF20173980//*Homo sapiens* RCCl-like G exchanging factor RLG mRNA, complete cds.//3.70E-211//531aa// 70%//AF060219 OCBBF20178150//Plasmodium falciparum ADA2-like protein gene, partial cds.//2.20E-19// 322aa//27%//AF184590 OCBBF20178880//11-CIS RETINOL DEHYDROGENASE (EC 1.1.1.105) (11-CIS RDH).//3.90E-37//101aa//78%//Q92781 OCBBF20178990 OCBBF20180120//*Homo sapiens* sodium-dependent high-affinity dicarboxylate transporter (NADC3) mRNA, complete cds.//1.50E-272//320aa//89%//AF154121 OCBBF20180840 OCBBF20186870 OCBBF20188730 OCBBF20189560 PANCR10000910//ATP-binding cassette, sub-family A member 8//2.00E-17//230aa//30%//NP_009099 PEBLM10000240 PEBLM10000710//leptin receptor//2.10E-29//69aa//91%//U66496 PEBLM20013120// *Homo sapiens* rhotekin mRNA, partial cds.//4.10E-25// 164aa//36%//AF290512 PEBLM20024320//zinc resistance protein homolog //3.80E-28//139aa//45%//T27544 PEBLM20024550 PEBLM20040150 PEBLM20042900 PEBLM20044520//PAB-DEPENDENT POLY(A)-SPECIFIC RIBONUCLEASE SUBUNIT PAN2 (EC 3.1.13.4) (PABlP-DEPENDENT POLY(A)-NUCLEASE).//2.40E-54//331aa//39%//P53010 PEBLM20052820//PROTEIN PHOSPHATASE 2C HOMOLOG 3 (EC 3.1.3.16) (PP2C-3).//7.60E-09//96aa//36%//Q09173 PEBLM20060310 PEBLM20060360//ZINC FINGER PROTEIN 33A (ZINC FINGER PROTEIN KOX31) (KIAA0065) (HA0946) (FRAGMENT).//5.10E-12//57aa//56%//Q06730
PEBLM20060490//polymerase (RNA) III (DNA directed) (39kD) [*Homo sapiens*]//1.50E-72//143aa//100%//NP_006457 PEBLM20071880 PEBLM20072960 PEBLM20074370 PEBLM20075980//*Mus musculus* immunoglobulin scavenger receptor IgSR mRNA, complete cds.// 2.30E-69//285aa//52%//AF302046 PEBLM20078320// ZINC FINGER PROTEIN 84 (ZINC FINGER PROTEIN HPF2).//2.00E-184//543aa//59%//P51523
PEBLM20085760//*Homo sapiens* mRNA for TOLLIP protein.//1.10E-106//153aa//98%//AJ242972
PERIC10000250//DNA TOPOISOMERASE III BETA-1 (EC 5.99.1.2).//1.20E-138//271aa//94%//O95985 PERIC20002140 PERIC20003860 PERIC20003870//*Mus musculus* transcriptional activator alpha-NAC (Naca) gene, complete cds.//1.20E-152//956aa//43%//U48363 PERIC20004220 PERIC20004780//*Rattus norvegicus* Jun dimerization protein 1 (jdp-1) gene, complete cds.//2.00E-15//73aa//49%//U53450 PLACE50000660//PROTEIN ARGININE N-METHYLTRANSFERASE 1 (EC 2.1.1.-).//1.60E-12//200aa//27%//Q63009 PLACE60003480//*Rattus norvegicus* protein associating with small stress protein PASS1 (Pass1) mRNA, complete cds.//4.60E-119//255aa//82%//AF168362 PLACE60004630 PLACE60060420//60S RIBOSOMAL PROTEIN L44 (L36A).//1.70E-29//58aa//100%//P09896 PLACE60079250//*Homo sapiens* mRNA for actin binding protein ABP620, complete cds.//0//979aa//61%//AB029290 PLACE60086400 PLACE60119750 PLACE60121080 PLACE60136500 PLACE60136720 PLACE60138830 PLACE60153220 PLACE60155130 PLACE60161600 PLACE60169420 PLACE60177140//PROSTACYCLIN RECEPTOR (PROSTANOID IP RECEPTOR) (PGI RECEPTOR).//9.90E-135//257aa//99%//P43119 PLACE60181070 PLACE60187690 PLACE60188340 PROST10003220//HOMEOBOX PROTEIN HOX-A2.//5.00E-69//139aa//95%//O43364 PROST10004800 PROST20005050 PROST20005670 PROST20021010 PROST20024890 PROST20029270 PROST20047270 PROST20047390//ZINC FINGER PROTEIN 84 (ZINC FINGER PROTEIN HPF2).//5.70E- 52//427aa//31%//P51523 PROST20050670 PROST20052280 PROST20057930 PROST20059040 PROST20066880//*Mus musculus* zinc finger protein 276 C2H2 type (Zfp276) mRNA, complete cds.//9.80E-101//192aa//94%//AF178935 PROST20079500 PROST20083600//Bos taurus pyruvate dehydrogenase phosphatase regulatory subunit precursor, mRNA, complete cds.//1.40E-101//243aa//83%//AF026954 PROST20087700 PROST20097950 PROST20100460//*Homo sapiens* secretory mucin MUC6 (MUC6) mRNA, partial cds.//3.10E-216//421aa//98%//U97698 PROST20104000//SPLICEOSOME ASSOCIATED PROTEIN 62 (SAP 62) (SF3A66).//1.40E-20//128aa//39%//Q62203 PROST20107820//Human C3f mRNA, complete cds.//9.90E-140//252aa//100%//U72515 PROST20111050 PROST20112970 PROST20114390 PROST20116600 PROST20120050 PROST20120160 PROST20121900 PROST20123530 PROST20127400 PROST20127800 PROST20130530 PROST20132600 PROST20133270 PROST20144220 PROST20146010 PROST20149160 PROST20149250 PROST20151240 PROST20152460 PROST20153320 PROST20159240//*Homo sapiens* 0pa-interacting protein OIP2 MRNA, partial cds.//1.10E-19//46aa//100%//AF025438 PROST20161950//*Mus musculus* RalGDS-like protein 3 mRNA, complete cds.//8.30E-88//205aa//85%//AF237669 PROST20164440 PROST20166680 PROST20168290 PROST20169800//CYTOCHROME P450 4F2 (EC 1.14.13.30) (CYPIVF2) (LEUKOTRIENE-B4 OMEGA-HYDROXYLASE), (LEUKOTRIENE-B4 20-MONOOXYGENASE) (CYTOCHROME P450-LTB-OMEGA).//6.30E-188//507aa//66%//P78329 PROST20170980 PROST20171280//hematopoietic zinc finger//2.00E-70//380aa//50%//NP_038894 PROST20175290 PROST20176170//*Homo sapiens*-ENIGMA protein mRNA, complete cds.//2.60E-156//270aa//98%//AF265209 PROST20178360 PROST20185830//NITROGEN REGULATORY PROTEIN AREA.//5.50E-07//141aa//28%//O13412 PROST20189770//ZINC FINGER PROTEIN 84 (ZINC FINGER PROTEIN HPF2).//5.00E-155//459aa//53%//P51523
PROST20191640//*Mus musculus* UbcM4-interacting protein 4 mRNA, complete cds.//1.50E-91//279aa//57%//AF360998 PUAEN10000850 PUAEN20003740 PUAEN20011880//*Mus musculus* mRNA for MIWI (piwi), complete cds.//2.70E-190//670aa//51%//AB032604 PUAEN20015260//*Rattus norvegicus* inositol polyphosphate multikinase (Ipmk) mRNA, complete cds.//2.40E-111//246aa//85%//AY014898 PUAEN20015860//*Mus musculus* PDZ-rGS3 protein mRNA, complete cds.//1.50E-205//469aa//82%//AF350047 PUAEN20018820//C-ETS-2 PROTEIN.//7.90E-261//469aa//99%//P15036 PUAEN20025680 PUAEN20027580 PUAEN20030180//CARBONIC ANHYDRASE XII PRECURSOR (EC 4.2.1.1) (CARBONATE DEHYDRATASE XII) (CA-XII) (TUMOR ANTIGEN HOM-rCC-3.1.3).//7.60E-148//259aa//95%//O43570 PUAEN20040670//*Mus musculus* neuronal protein 4.1 mRNA, complete cds.//0//733aa//93%//AF061283 PUAEN20044000 PUAEN20045110 PUAEN20045250 PUAEN20051100//*Mus musculus* otogelin mRNA, complete cds.//2.60E-89//368aa//43%//U96411 PUAEN20052470 PUAEN20055020//*Homo sapiens* goodpasture antigen-binding protein (COL4A3BP) mRNA, complete cds.//0//624aa//100%//AF136450 PUAEN20078980//faciogenital dysplasia homolog//1.00E-19//200aa//39%//NP_032027 PUAEN20081230 PUAEN20083140//*Homo sapiens* SWAP-70 mRNA, complete cds.//2.70E-280//451aa//99%//AF210818 PUAEN20085150 PUAEN20108240//*Drosophila melanogaster* ankyrin 2 (Ank2) mRNA, complete cds.//5.00E-22//200aa//35%//AF190635 RECTM10001410 RECTM20003490 RECTM20005100 SALGL10001710//*Homo sapiens* mRNA for C11ORF25 gene.//1.80E-88//455aa//41%//AJ300461 SKMUS2Q001980//*Mus musculus* N-rAP mRNA, complete cds.//1.40E-63//141aa//88%//U76618 SKMUS20003610//PUTATIVE MITOCHONDRIAL CARRIER PROTEIN PET8.//7.40E-59//274aa//47%//P38921 SKMUS20007010//VESTIGIAL PROTEIN.//2.70E-14//209aa//32%//Q26366 SKMUS20007800//PROSTAGLANDIN TRANSPORTER (PGT) (MATRIN F/G).//4.20E-47//274aa//36%//Q00910 SKMUS20011640 SKMUS20012010 SKMUS20016220//*Mus musculus* N-rAP mRNA, complete cds.//1.80E-85//352aa//47%//U76618 SKMUS20018230//*Homo sapiens* MYPT2 mRNA, complete cds.//8.10E-13//107aa//40%//AB003062 SKMUS20018500//*Homo sapiens* t(3;5)(q25.1;p34) fusion gene NPM-MLF1 mRNA, complete cds.//2.30E-131//268aa//94%//L49054 SKMUS20020840 SKMUS20021530//*Homo sapiens* SPG protein (SPG) mRNA, complete cds.//1.50E-278//506aa//99%//AF302154 SKMUS20024750//RAS SUPPRESSOR PROTEIN 1 (RSU-1) (RSP-1 PROTEIN) (RSP-1).//3.90E-21//203aa//33%//Q15404 SKMUS20028210 SKMUS20028400//*Mus musculus* YIP1B (Yiplb) mRNA, complete cds.//2.90E-53//142aa//74%//AF217188 SKMUS20029200//*Homo sapiens* ASB-1 protein mRNA, complete cds.//1.20E-45//302aa//39%//AF156777 SKMUS20031680 SKMUS20046670 SKMUS20048970//ACTIN, ALPHA SKELETAL MUSCLE (ALPHA-ACTIN 1).//8.00E-181//263aa//99%//P02568 SKMUS20049030//*H.sapiens* mRNA for nebulin.//3.50E-148//286aa//99%//X83957 SKMUS20077400 SKMUS20084740 SKNMC20006220 SKNSH20008190//ZINC FINGER PROTEIN 133.//2.80E-165//503aa//56%//P52736 SKNSH20020540 SKNSH20028660 SKNSH20031740

SKNSH20034660 SKNSH20051940 SKNSH20062340 SKNSH20063040//*Homo sapiens* tetraspan NET-4 mRNA, complete cds.//1.00E-20//177aa//41%//AF065389 SKNSH20080430 SKNSH20087770 SKNSH20089400// *Homo sapiens* Rad5l-interacting protein mRNA, complete cds.//2.20E-172//292aa//93%//AF006259 SKNSH20091970 SMINT20001760//ZINC FINGER PROTEIN 83 (ZINC FINGER PROTEIN HPFl).//1.40E-37//138aa//37%// P51522 SMINT20005410 SMINT20008240 SMINT20009840//IG KAPPA CHAIN V-II REGION GM607 PRECURSOR (FRAGMENT).//9.00E-54//117aa// 90%//P06309 SMINT20011140 SMINT20011580 SMINT20011990 SMINT20013480 SMINT20014580 SMINT20015590 SMINT20022020 SMINT20023280 SMINT20024570//tektin Ai//6.90E-26//124aa//45%// M97188 SMINT20026890//SMOOTHELIN.//3.10E-278// 611aa//88%//P53814 SMINT20028820//*Homo sapiens* mRNA for F5-2, complete cds.//2.40E-83//162aa//98%// AB020739 SMINT20029760 SMINT20033170 SMINT20033400 SMINT20035690 SMINT20040860 SMINT20042990 SMINT20047810 SMINT20049090// *Homo sapiens* mRNA for partial putative mitogen-activated protein kinase kinase.//2.20E-32//69aa//98%// AJ242724 SMINT20050750//SPARC PRECURSOR (SECRETED PROTEIN ACIDIC AND RICH IN CYSTEINE) (OSTEONECTIN) (ON) (BASEMENT MEMBRANE PROTEIN BM-40).//4.20E-111//259aa//82%//P09486 SMINT20051610//*Mus musculus* ES18 mRNA, complete cds.//6.90E-235//485aa//88%//AF083929
SMINT20053300//*Homo sapiens* hepatocellular carcinoma-associated antigen 59 mRNA, complete cds.//7.00E-20// 44aa//100%//AF218421 SMINT20053870 SMINT20056210 SMINT20058000 SMINT20060780 SMINT20065960 SMINT20068010 SMINT20071400 SMINT20073650//IG ALPHA-1 CHAIN C REGION.// 7.90E-197//353aa//100%//P01876 SMINT20076470 SMINT20080540 SMINT20089170 SMINT20092330 SMINT20092720 SMINT20095050 SMINT20098320 SMINT20100680 SMINT20101440//Human cisplatin resistance associated alpha protein (hCRA alpha) mRNA, complete cds.//1.70E-96//182aa//100%//U78556 SMINT20102780//NICOTINATE PHOSPHORIBOSYL-TRANSFERASE (EC 2.4.2.11) (NAPRTASE).//5.30E-05// 123aa//33%//P18133 SMINT20103690 SMINT20105000 SMINT20105330//BETA-GALACTOSIDASE PRECURSOR (EC 3.2.1.23) (LACTASE) (ACID BETA- GALACTOSIDASE).//1.00E-54//138aa//78%//P16278 SMINT20106290//FORMAMIDOPYRIMIDINE-DNA GLYCOSYLASE (EC 3.2.2.23) (FAPY-DNA GLYCOSYLASE).//7.00E-07//214aa//32%//050606
SMINT20106720//*Homo sapiens* mRNA for immunoglobulin lambda heavy chain.//3.30E-235//477aa//89%//Y14737 SMINT20108530 SMINT20109970 SMINT20110330 SMINT20110660//*Homo sapiens* mammalian inositol hexakisphosphate kinase 2 (IP6K2) mRNA, complete cds.// 1.20E-33//68aa//100%//AF177145 SMINT20112730//IG ALPHA-1 CHAIN C REGION.//1.70E-196//353aa//99%// P01876 SMINT20115880//Kruppel associated box (KRAB) zinc finger 1 *[Rattus norvegicus]*//1.50E-42//211aa//45%// NP_062566 SMINT20121220//MYOSIN HEAVY CHAIN, NONMUSCLE TYPE B (CELLULAR MYOSIN HEAVY CHAIN, TYPE B) (NMMHC-B).//1.00E-18// 493aa//24%//P35580 SMINT20121950//HYPOTHETICAL 70.2 KDA PROTEIN C22E12.10C IN CHROMOSOME I.//5.70E-16//90aa//45%//Q10361 SMINT20122850 SMINT20122910//*Mus musculus* StAR-related protein 1-4E mRNA, partial cds.//1.50E-77//170aa//82%//AY007808

SMINT20127350//U1 SMALL NUCLEAR RIBONUCLEOPROTEIN 70 KDA (Ul SNRNP 70 KDA) (SNRP70).// 3.50E-14//186aa//32%//P08621 SMINT20127930//IG ALPHA-1 CHAIN C REGION.//7.90E-197//353aa//100%// P01876 SMINT20130320//*Rattus norvegicus* MHC class II transactivator type IV (CIITA) mRNA, complete cds.// 2.50E-33//645aa//26%//AF251307 SMINT20131810 SMINT20132280 SMINT20136130//IG LAMBDA CHAIN C REGIONS.//4.00E-51//10Saa//95%//P01842 SMINT20138900//DESMIN.//7.20E-203//425aa//94%// P17661 SMINT20144430//IG LAMBDA CHAIN V-I REGION BL2 PRECURSOR.//3.80E-55//130aa//83%// P06316 SMINT20144800//Human zinc finger protein zfp6 (ZF6) mRNA, partial cds.//1.60E-139//354aa//70%// U71363 SMINT20144890 SMINT20152940//*Mus musculus* ATP-dependent zinc metalloprotease (Afg3ll) mRNA, complete cds; nuclear gene for mitochondrial product.// 1.10E-52//75aa//84%//AF329695 SMINT20153260//EXTRACELLULAR MATRIX PROTEIN 1 PRECURSOR (SECRETORY COMPONENT P85).//3.50E-274//476aa// 98%//Q16610 SMINT20153530 SMINT20154540//CHLORINE CHANNEL PROTEIN P64.//1.10E-135//419aa// 68%//P35526 SMINT20155180//*Homo sapiens* GBAS (GBAS) mRNA, complete cds.//6.70E-115//142aa//70%// AF029786 SMINT20157450 SMINT20158100 SMINT20161220 SMINT20162860 SMINT20163960 SMINT20164400 SMINT20164770 SMINT20168570// *Homo sapiens* mRNA for stabilin-1 (stab1 gene).//5.50E-61//128aa//98%//AJ275213 SMINT20173190 SMINT20173240 SMINT20174360//RHYTHMICALLY EXPRESSED GENE 2 PROTEIN (DREG-2).//6.90E-24// 242aa//28%//Q94915 SMINT20177360//SPLICING FACTOR, ARGININE/SERINE-RICH 2 (SPLICING FACTOR SC35) (SC-35) (SPLICING COMPONENT, 35 KDA) (PR264 PROTEIN).//6.40E- 37//82aa//92%//P30352 SMINT20178550 SMINT20179740//IG MU CHAIN C REGION.//8.50E-248//454aa//99%//P01871
SMINT20183530//GCN20 PROTEIN.//5.50E-118//410aa// 52%//P43535 SMINT20190170//IG ALPHA-1 CHAIN C REGION.//8.50E-199//353aa//100%//P01876
SMINT20191420//AMP DEAMINASE 1 (EC 3.5.4.6) (MYOADENYLATE DEAMINASE) (AMP DEAMINASE ISOFORM M).//5.40E-214//401aa//97%//P23109 SMINT20191530//PUTATIVE ATP-DEPENDENT RNA HELICASE DBP73D.//5.00E- 85//547aa//42%//P26802 SMINT20192000 SPLEN10000830 SPLEN20000640 SPLEN20002220 SPLEN20003070 SPLEN20006070// ANKYRIN 1 (ERYTHROCYTE ANKYRIN) (ANKYRIN R) (ANKYRINS 2.1 AND 2.2).//1.50E-81//788aa//30%// P16157 SPLEN20008390//Human placenta (Diff48) mRNA, complete cds.//4.60E-108//337aa//60%//U49187 SPLEN20008740//IMPORTIN ALPHA SUBUNIT (KARYOPHERIN ALPHA SUBUNIT) (SERINE- RICH RNA POLYMERASE I SUPPRESSOR PROTEIN).//5.50E-12//490aa//22%//Q02821 SPLEN20008820 SPLEN20011410//RHO-GTPASE-ACTIVATING PROTEIN 1 (GTPASE-ACTIVATING PROTEIN RHOGAP) (RHO-RELATED SMALL GTPASE PROTEIN ACTIVATOR) (CDC42 GTPASE-ACTIVATING PROTEIN) (P50-rHOGAP).//1.50E-21//183aa//34%//Q07960
SPLEN20013540 SPLEN20016260 SPLEN20019450 SPLEN20020070 SPLEN20021660//GAMMA-GLUTAMYLTRANSPEPTIDASE PRECURSOR (EC 2.3.2.2) (GAMMA-GLUTAMYLTRANSFERASE) (GGT) .//9.00E-23//167aa//33%//P07314 SPLEN20022230 SPLEN20023140 SPLEN20026950//POSSIBLE GLOBAL TRANSCRIPTION ACTIVATOR SNF2L2 (SNF2-AL- PHA).//0//766aa//81%//P51531 SPLEN20027440//ANKYRIN 2 (BRAIN ANKYRIN) (ANKYRIN B) (ANKYRIN, NONERYTHROID).//6.10E-25//368aa//30%//Q01484 SPLEN20029310 SPLEN20031600 SPLEN20032040 SPLEN20032190 SPLEN20033960 SPLEN20039240//HEAT SHOCK 70 KDA PROTEIN 1 (HSP70.1) (HSP70-1/HSP70-2).//9.80E-112//213aa//100%//P08107 SPLEN20040600 SPLEN20054290//Fugu rubripes zinc finger protein, isotocin, fatty acid binding protein, sepiapterin reductase and vasotocin genes, complete cds.//4.20E-180//448aa//71%//U90880 SPLEN20076530 SPLEN20077500//Mus musculus Niban mRNA, complete cds.//1.30E-39//351aa//31%//AB049355 SPLEN20079260//ZINC FINGER PROTEIN 132.//6.30E-117//320aa//61%//P52740 SPLEN20079510 SPLEN20084600//RING CANAL PROTEIN (KELCH PROTEIN).//5.20E-58//558aa//29%//Q04652 SPLEN20095410//ZINC FINGER PROTEIN 184 (FRAGMENT).//6.50E-83//236aa//58%//Q99676 SPLEN20095550 SPLEN20095810 SPLEN20097330 SPLEN20099700//TAT-BINDING HOMOLOG 7.//1.50E-142//553aa//48%//P54816 SPLEN20101190 SPLEN20103950//40S RIBOSOMAL PROTEIN S17.//7.10E-22//49aa//100%//P06584 SPLEN20106250 SPLEN20117660//Homo sapiens BCL-6 corepressor (BCOR) mRNA, complete cds; alternatively spliced.//1.30E-38//139aa//61%//AF317391 SPLEN20118300//Rattus norvegicus amino acid transport system A3 (Ata3) mRNA, complete cds.//1.70E-20//210aa//28%//AF295535 SPLEN20119810 SPLEN20121750//Danio rerio uridine kinase mRNA, complete cds.//1.60E-29//130aa//50%//AF195851 SPLEN20126190 SPLEN20128000//Xenopus laevis XMAB21 (Xmab-21) mRNA, complete cds.//6.80E-12//287aa//24%//AF040992 SPLEN20129610 SPLEN20140800//ZINC FINGER PROTEIN 84 (ZINC FINGER PROTEIN HPF2).//1.20E-145//586aa//47%//P51523 SPLEN20141360 SPLEN20141990 SPLEN20142100//Rattus norvegicus alpha D integrin mRNA, complete cds.//7.10E-37//105aa//76%//AF021334 SPLEN20143180//Mus musculus EWS/FLI1 activated transcript 2 (EAT-2) mRNA, complete cds.//2.50E-45//132aa//65%//AF020263 SPLEN20144520 SPLEN20145720//Rattus norvegicus nuclear GTPase PIKE mRNA, complete cds.//2.00E-24//120aa//45%//AF280816 SPLEN20146450//H.sapiens mRNA for plakophilin 2a and b.//1.20E-08//87aa//42%//X97675 SPLEN20146690 SPLEN20147110//cyclin-E binding protein 1//0//580aa//58%//NP_057407 SPLEN20147390//ZINC FINGER PROTEIN 136.//1.40E-105//417aa//49%//P52737 SPLEN20149110 SPLEN20149190 SPLEN20149240//Cricetulus longicaudatus arginine N-methyltransferase p82 isoform mRNA, complete cds, alternatively spliced.//3.50E-259//525aa//86%//AF336043 SPLEN20150940//Mus musculus histone deacetylase mHDA1 mRNA, complete cds.//4.20E-187//550aa//51%//AF006602 SPLEN20151210//protein tyrosine phosphatase, non-receptor type 13(APO-1/CD95 (Fas)-associated phosphatase)//3.00E-25//250aa//29%//NP_006255 SPLEN20152610 SPLEN20152760 SPLEN20157300 SPLEN20157880//Homo sapiens Ig superfamily receptor LNIR precursor, mRNA, complete cds.//1.70E-05//137aa//29%//AF160477 SPLEN20158900 SPLEN20158990 SPLEN20160450//Homo sapiens mRNA for Hrs, complete cds.//5.60E-28//59aa//100%//D84064 SPLEN20160690 SPLEN20160980 SPLEN20162680//NUCLEAR PROTEIN SNF7.//4.20E-11//189aa//25%//P39929 SPLEN20163560 SPLEN20165310//Homo sapiens mRNA for immunoglobulin lambda heavy chain.//4.90E-230//477aa//88%//Y14737 SPLEN20166270 SPLEN20167200//Mus musculus MPS1 gene and mRNA, 3' end.//1.50E-15//46aa//84%//L20315 SPLEN20169220 SPLEN20169720 SPLEN20170310//Homo sapiens Asef mRNA for APC-stimulated guanine nucleotide exchange factor, complete cds.//8.40E-95//305aa//62%//AB042199 SPLEN20171210 SPLEN20171470 SPLEN20171890 SPLEN20172120 SPLEN20173510//Xenopus laevis putative N-terminal acetyltransferase mRNA, complete cds.//3.90E-210//413aa//66%//AF247679 SPLEN20174260 SPLEN20176200 SPLEN20179180//Homo sapiens EH domain containing 2 (EHD2) mRNA, complete cds.//1.10E-181//340aa//94%//AF181263 SPLEN20179810//Mus musculus pecanex 1 mRNA, complete cds.//3.80E-131//534aa//51%//AF096286 SPLEN20181810//Mus musculus faciogenital dysplasia protein 2 (Fgd2) mRNA, complete cds.//6.60E-68//144aa//86%//AF017368 SPLEN20186430//PROBABLE G PROTEIN-COUPLED RECEPTOR APJ.//2.20E-163//226aa//96%//P35414 SPLEN20193110 SPLEN20194050//Homo sapiens HOTTL protein mRNA, complete cds.//9.50E-135//264aa//93%//AF078842 SPLEN20198110 SPLEN20204170 SPLEN20211220 SPLEN20211570 SPLEN20211940 SPLEN20212730//CALPAIN 2, LARGE [CATALYTIC] SUBUNIT (EC 3.4.22.17) (CALCIUM-ACTIVATED NEUTRAL PROTEINASE) (CANP) (M-TYPE).//1.70E-137//265aa//98%//P17655 SPLEN20212950 SPLEN20213830 SPLEN20214400 SPLEN20214580//Mus musculus mdgl-1 mRNA, complete cds.//1.40E-16//39aa//94%//AF190624 SPLEN20222270//Mus musculus adaptor protein (Dok1) mRNA, complete cds.//1.10E-42//123aa//61%//AF179242 SPLEN20225220 SPLEN20242320 SPLEN20242730 SPLEN20243830//TRANSCRIPTION INITIATION FACTOR TFIID 135 KDA SUBUNIT (TAFII-135) (TAFII135) (TAFII-130) (TAFII130).//4.70E-38//98aa//87%//000268 SPLEN20245300// ADP-ribosylation factor binding protein GGA1//3.00E-39//120aa//76%//NP_037497 SPLEN20249560 SPLEN20250170//PUTATIVE RHO/RAC GUANINE NUCLEOTIDE EXCHANGE FACTOR (RHO/RAC GEF) (FACIOGENITAL DYSPLASIA PROTEIN HOMOLOG).//1.40E-51//488aa//27%//P52734 SPLEN20250390//CALPAIN 1, LARGE [CATALYTIC] SUBUNIT (EC 3.4.22.17) (CALCIUM-ACTIVATED NEUTRAL PROTEINASE) (CANP) (MU-TYPE). //3.00E-55//115aa//94%//P07384 SPLEN20252190//ZINC FINGER PROTEIN 135.//6.00E-89//303aa//52%//P52742 SPLEN20261440 SPLEN20264110 SPLEN20267650//ZINC FINGER PROTEIN 184 (FRAGMENT).//5.20E-90//410aa//45%//Q99676 SPLEN20273950 SPLEN20279950 SPLEN20280660 SPLEN20283650//Mus musculus ras activator RasGRP (Rasgrp) mRNA, complete cds.//9.80E-54//182aa//57%//AF106070 SPLEN20284240//Homo sapiens hOBDPF mRNA for osteoblast differentiation promoting factor, complete cds.//9.80E-93//177aa//98%//AB048363 SPLEN20292950//ATP-binding cassette, sub-family A member 8 //3.30E-211//469aa//64%//NP_009099 SPLEN20293800 SPLEN20303970 SPLEN20304950//Homo sapiens CAGH32 mRNA, partial cds.//9.60E-44//86aa//98%//U80743 SPLEN20305620//DIHYDROOROTATE DEHYDROGENASE PRECURSOR (EC 1.3.3.1) (DIHYDROOROTATE OXIDASE) (FRAGMENT).//3.60E-59//124aa//96%//Q02127 SPLEN20329240 STOMA20001830//IG ALPHA-1 CHAIN C REGION.//2.10E-196//353aa//99%//P01876 STOMA20005390//IG ALPHA-1 CHAIN C REGION.//7.90E-197//353aa//100%//P01876 STOMA20005670//Homo sapiens mRNA for immunoglobulin lambda heavy chain.//1.90E-216//478aa//83%//Y14737 STOMA20006400//Homo sapiens IGHG3 gene for immunoglobulin heavy chain gamma 3 constant region, 4-exon hinge, isolate Lib-A2.//8.40E-214//377aa//100o%//AJ390247 STOMA20006780 STOMA20006860//*Homo sapiens* TOB3 mRNA, complete cds.//1.80E-74//159aa//97%//AF343078 STOMA20008880//MYOCILIN PRECURSOR (TRABECULAR MESHIWORK-INDUCED GLUCOCORTICOID RESPONSE PROTEIN).//1.00E-196//405aa//91%//Q99972 STOMA20010250//*Homo sapiens* RNA-binding protein (RBMS3) mRNA, complete cds.//7.70E-46//116aa//86%//AF023259 STOMA20013890 STOMA20026880 STOMA20032890//ZINC FINGER PROTEIN CKR1.//5.80E-30//162aa//38%//P30373 STOMA20034770//IG ALPHA-1 CHAIN C REGION.//4.40E-196//353aa//99%//P01876 STOMA20036460 STOMA20046680//FOSB PROTEIN (GO/GI SWITCH REGULATORY PROTEIN 3).//4.10E-14//36aa//100%//P53539 STOMA20048520 STOMA20048840 STOMA20051200 STOMA20056640//Ig lambda chain V region //6.80E-54//150aa//73%//S23626 STOMA20056670//IG ALPHA-1 CHAIN C REGION.//7.90E-197//353aa//100%//P01876 STOMA20057820 STOMA20062130//IG KAPPA CHAIN V-III REGION HAH PRECURSOR.//3.10E-53//129aa//80%//P18135 STOMA20062290 STOMA20063250//TRANSCRIPTION FACTOR COE3 (EARLY B-CELL FACTOR 3) (EBF-3) (OLF-1/EBF- LIKE 2) (OE-2) (O/E-2).//7.50E-50//105aa//93%//008791 STOMA20063980 STOMA20064470//PLACENTAL RIBONUCLEASE INHIBITOR (RIBONUCLEASE/ANGIOGENIN INHIBITOR) (RAI) (RI).//3.60E-14//262aa//30%//P13489 STOMA20067800 STOMA20069040 STOMA20072690 STOMA20076800 STOMA20077450//UBIQUITIN-ACTIVATING ENZYME E1 (AlS9 PROTEIN).//2.70E-228//430aa//97%//P22314 STOMA20080500//ATP-binding cassette, sub-family A, member 7, isoform a//1.00E-297//538aa//94%//NP_061985 STOMA20083610//IG ALPHA-1 CHAIN C REGION.//7.90E-197//353aa//100%//P01876 STOMA20086140 STOMA20088380//IG ALPHA-1 CHAIN C REGION.//2.10E-196//352aa//100%//P01876 STOMA20092530//*Homo sapiens* mRNA for immunoglobulin lambda heavy chain.//3.10E-239//477aa//91%//Y14737 STOMA20092560 STOMA20092890 SYNOV20001520//*Homo sapiens* kappa 1 immunoglobulin light chain mRNA, complete cds.//5.50E-107//236aa//86%//AF113887 SYNOV20001730//Human (hybridoma H210) anti-hepatitis A IgG variable region, constant region, complementarity-determining regions mRNA, complete cds.//2.60E-226//479aa//86%//M87789 SYNOV20002510//*Homo sapiens* IGHG3 gene for immunoglobulin heavy chain gamma 3 constant region, 4-exon hinge, isolate Kp-25.//6.60E-214//377aa//100%//AJ390254 SYNOV20002790//Human (hybridoma H210) anti-hepatitis A IgG variable region, constant region, complementarity-determining regions mRNA, complete cds.//1.30E-238//476aa//91%//M87789 SYNOV20002970//Human (hybridoma H210) anti-hepatitis A IgG variable region, constant region, complementarity-determining regions mRNA, complete cds.//7.00E-226//476aa//86%//M87789 SYNOV20003970 SYNOV20004260//*Homo sapiens* mRNA for immunoglobulin lambda heavy chain.//1.10E-225//477aa//86%//Y14737 SYNOV20007000//Human (hybridoma H210) anti-hepatitis A IgG variable region, constant region, complementarity-determining regions mRNA, complete cds.//4.00E-239//478aa//91%//M87789 SYNOV20008240//Human (hybridoma H210) anti-hepatitis A IgG variable region, constant region, complementarity-determining regions mRNA, complete cds.//4.10E-237//479aa//90%//M87789 SYNOV20009230//IG ALPHA-1 CHAIN C REGION.//7.90E-197//353aa//100%//P01876 SYNOV20010880//Human (hybridoma H210) anti-hepatitis A IgG variable region, constant region, complementarity-determining regions mRNA, complete cds.//1.60E-233//476aa//89%//M87789 SYNOV20011110//Human (hybridoma H210) anti-hepatitis A IgG variable region, constant region, complementarity-determining regions mRNA, complete cds.//6.90E-235//476aa//89%//M87789 SYNOV20013000//Ig gamma =immunoglobulin heavy chain [rats, humanized lympholytic MoAb CAMPATH-lH, mRNA, 1465 nt].//7.70E-220//472aa//86%//S79307 SYNOV20013560//*Homo sapiens* mRNA for immunoglobulin lambda heavy chain.//1.40E-234//477aa//89%//Y14737 SYNOV20013900//*Homo sapiens* mRNA for immunoglobulin kappa heavy chain.//3.50E-231//476aa//89%//Y14735 SYNOV20017080 SYNOV30001840 TBAES20000590 TBAES20002550//AMINOPEPTIDASE B (EC 3.4.11.6) (ARGINYL AMINOPEPTIDASE) (ARGININE AMINOPEPTIDASE) (CYTOSOL AMINOPEPTIDASE IV) (AP-B).//2.10E-310//586aa//89%//O09175 TBAES20003150//CYTOCHROME P450 4A1 (EC 1.14.15.3) (CYPIVAL) (LAURIC ACID OMEGA-HYDROXYLASE) (P450-LA-OMEGA -) (P452).//1.40E-82//323aa//44%//P08516 TBAES20003770//SPERM-SPECIFIC ANTIGEN 2 (CLEAVAGE SIGNAL-1 PROTEIN) (CS-1).//1.90E-122//249aa//97%//P28290 TCOLN20001390 TESOP20000900 TESOP20003120 TESOP20004000//CATHEPSIN B PRECURSOR (EC 3.4.22.1) (CATHEPSIN B1) (APP SECRETASE).//3.30E-111//194aa//98%//P07858 TESOP20005270//MONOAMINE-SULFATING PHENOL SULFOTRANSFERASE (EC 2.8.2.1) (SULFOTRANSFERASE, MONOAMINE-PREFERRING) (M-PST) (THERMOLABILE PHENOL SULFOTRANSFERASE) (TL-PST) (PLACENTAL ESTROGEN SULFOTRANSFERASE) (CATECHOLAMINE-SULFATING PHENOL SULFOTRANSFERASE) (HAST3).//3.40E-47//92aa//100%//P50224 TESOP20005690//*Mus musculus* p53 apoptosis-associated target (Perp) mRNA, complete cds.//2.30E-53//113aa//91%//AF249870 TESTI10000940 TESTI20001000//FORMAMIDOPYRIMIDINE-DNA GLYCOSYLASE (EC 3.2.2.23) (FAPY-DNA GLYCOSYLASE).//7.80E-06//238aa//28%//P74290 TESTI20001170 TESTI20001720 TESTI20002720//TUBULIN-TYROSINE LIGASE (EC 6.3.2.25) (TTL).//1.70E-18//237aa//29%//P38584 TESTI20002780//ADENYLATE CYCLASE (EC 4.6.1.1) (ATP PYROPHOSPHATE-LYASE) (ADENYLYL CYCLASE).//1.90E-11//140aa//36%//P08678 TESTI20004890 TESTI20011200 TESTI20017950 TESTI20018230 ,TESTI20023510 TESTI20029930 TESTI20030310 TESTI20030890 TESTI20031270//TUMOR NECROSIS FACTOR, ALPHA-INDUCED PROTEIN 1, ENDOTHELIAL (B12 PROTEIN).//7.30E-52//146aa//71%//Q13829 TESTI20031810 TESTI20035960//VEGETATIBLE INCOMPATIBILITY PROTEIN HET-E-1.//1.70E-67//329aa//40%//Q00808 TESTI20036380//DRA PROTEIN (DOWN-REGULATED IN ADENOMA).//6.40E-46//243aa//35%//P40879 TESTI20037560 TESTI20038270 TESTI20039400//EBNA-1 NUCLEAR PROTEIN.//3.60E-43//298aa//43%//P03211 TESTI20041690//TRANSCRIPTION INTERMEDIARY FACTOR 1-BETA (KRAB-A INTERACTING PROTEIN) (KRIP-1).//1.00E-12//341aa//21%//Q62318 TESTI20044230//*Mus musculus* testis-specific Y-encoded-like protein (Tspyl1) mRNA, complete cds.//1.70E-94//291aa//64%//AF042180 TESTI20044310//RAS SUPPRESSOR PROTEIN 1 (RSU-1) (RSP-1 PROTEIN) (RSP-1).//6.70E-06//118aa//32%//Q15404 TESTI20046750

TESTI20057750 TESTI20060400//Columba livia mRNA for 5'-nucleotidase.//3.80E-115//328aa//66%//AJ131243 TESTI20061110//*Xenopus laevis* katanin p60 MRNA, partial cds.//11.80E-170//489aa//66%//AF177942 TESTI20063830//*Drosophila melanogaster* nuclear fallout (nuf) mRNA, nuf-1 allele, complete cds.//2.10E-34//371aa//29%//AF045015 TESTI20066670//probable acyl-CoA dehydrogenase //1.90E-72//222aa//60%//D75616 TESTI20066770 TESTI20067200//PRE-B-CELL LEUKEMIA TRANSCRIPTION FACTOR-3 (HOMEOBOX PROTEIN PBX3).//4.20E-132//352aa//71%//P40426 TESTI20076850 TESTI20082330//helicase II homolog//4.10E-44//775aa//25%//T13889 TESTI20083200//*Homo sapiens* mitogen-activated protein kinase phosphatase x (MKPX) mRNA, complete cds.//1.00E-41//131aa//58%//AF165519 TESTI20083940 TESTI20086210 TESTI20087620 TESTI20088220//ZINC FINGER PROTEIN 91 (ZINC FINGER PROTEIN HTF10) (HPF7).//8.50E-175//633aa//48%//Q05481 TESTI20094020 TESTI20094120 TESTI20094230//Strongylocentrotus purpuratus tektin Al mRNA, complete cds//4.50E-64//252aa//50%//M97188 TESTI20094470//ETS-RELATED PROTEIN 71 (ETS TRANSLOCATION VARIANT 2).//1.40E-183//318aa//99%//000321 TESTI20098350 TESTI20098530 TESTI20102800 TESTI20105720 TESTI20108720//PROTEIN PHOSPHATASE 2C BETA ISOFORM (EC 3.1.3.16) (PP2C-BETA) (IA) (PROTEIN PHOSPHATASE 1B).//3.30E-49//249aa//46%//P36993 TESTI20110280 TESTI20112940 TESTI20114070 TESTI20116650 TESTI20116830//*Homo sapiens* liprin-beta2 mRNA, partial cds.//8.20E-17//50aa//92%//AF034803 TESTI20121550//NUCLEOPORIN-LIKE PROTEIN RIP (REV INTERACTING PROTEIN) (REV/REX ACTIVATION DOMAIN-BINDING PROTEIN).//1.60E-152//363aa//85%//P52594 TESTI20122310 TESTI20123080 TESTI20123560 TESTI20127760 TESTI20128350 TESTI20129150 TESTI20129220 TESTI20130010//ZINC FINGER PROTEIN 84 (ZINC FINGER PROTEIN HPF2).//2.10E-63//173aa//65%//P51523 TESTI20130120 TESTI2Q135660 TESTI20136100//ZINC/CADMIUM RESISTANCE PROTEIN. //3. 70E-12//10Iaa//35%//P20107 TESTI20136710 TESTI20136990 TESTI20137370 TESTI20137670 TESTI20143240 TESTI20143390//*Mus musculus* testicular condensing enzyme (AMAC1) mRNA, complete cds.//1.60E-51//123aa//79%//AF016712 TESTI20143620 TESTI20148000//PROTEIN DISULFIDE ISOMERASE (PDI) (EC 5.3.4.1) (PROLYL 4-HYDROXYLASE BETA SUBUNIT) (CELLULAR THYROID HORMONE BINDING PROTEIN) (RETINA COGNIN) (R-COGNIN).//2.80E-75//493aa//34%//P09102 TESTI20152460//MLO2 PROTEIN.//9.60E-42//170aa//40%//Q09329 TESTI20155900 TESTI20156100//KRUPPEL-LIKE FACTOR 4 (EPITHELIAL ZINC-FINGER PROTEIN EZF).//2.30E-32//254aa//32%//043474 TESTI20157100 TESTI20157520 TESTI20159140 TESTI20161970 TESTI20164100 TESTI20168480//*H.sapiens* mRNA for titin protein (clone hhl-hh54).//6.30E-48//393aa//31%//X90568 TESTI20168630 TESTI20168960 TESTI20169960 TESTI20170350 TESTI20171020 TESTI20178160 TESTI20179320 TESTI20183370 TESTI20184620//OXYSTEROL-BINDING PROTEIN.//6.20E-27//181aa//28%//P16258 TESTI20185650//*Xenopus laevis* ubiquitin-like fusion protein mRNA, complete cds.//2.90E-129//543aa//46%//LO8474 TESTI20185810 TESTI20189410//*Mus musculus* axotrophin mRNA, complete cds.//7.50E-43//142aa//57%//AF155739 TESTI20192280 TESTI20192800//*Homo sapiens* nasopharyngeal carcinoma susceptibility protein LZ16 mRNA, complete cds.//2.40E-23//164aa//41%//AF121775 TESTI20193360 TESTI20194300 TESTI20194810 TESTI20197940 TESTI20199170 TESTI20199760//TRICHOHYALIN.//8.80E-59//547aa//30%//P37709 TESTI20200260 TESTI20200710//*Mus musculus* epithelial protein lost in neoplasm-a (Eplin) mRNA, complete cds.//4.40E-40//212aa//42%//AF307844 TESTI20202650 TESTI20203440 TESTI20204450//M.musculus of DNA encoding DNA-binding protein.//1.90E-58//477aa//32%//Z54200 TESTI20208400//PROLIFERATING-CELL NUCLEOLAR ANTIGEN P120 (PROLIFERATION-ASSOCIATED NUCLEOLAR PROTEIN P120).//1.70E-16//181aa//33%//P46087 TESTI20208710 TESTI20209460 TESTI20209810 TESTI20209990 TESTI20211160 TESTI20211220 TESTI20211240 TESTI20213150 TESTI20213580 TESTI20214250//MITOCHONDRIAL CARRIER PROTEIN PMT.//1.00E-34//242aa//36%//P32332 TESTI20215990//*Homo sapiens* leucine-rich repeats containing F-box protein FBL3 mRNA, complete cds.//1.10E-39//375aa//28%//AF186273 TESTI20216370//LIVER CARBOXYLESTERASE PRECURSOR (EC 3.1.1.1) (ES-MALE) (ESTERASE-31).//1.50E-60//164aa//68%//Q63880 TESTI20220100 TESTI20220650 TESTI20224620 TESTI20226230//*Rattus norvegicus* KPL2 (Kpl2) mRNA, complete cds.//8.90E-111//371aa//59%//AF102129 TESTI20226490 TESTI20229600//*Drosophila melanogaster* SP2353 mRNA, complete cds.//8.30E-117//607aa//33%//AF239610 TESTI20230250 TESTI20230850//CIRCADIAN LOCOMOTER OUTPUT CYCLES KAPUT PROTEIN (MCLOCK).//1.00E-23//186aa//30%//008785 TESTI20231920 TESTI20231940//Human OB binding protein-2 (OB-BP2) mRNA, complete cds.//4.60E-14//140aa//36%//U71383 TESTI20232140//i-PHOSPHATIDYLINOSITOL-4,5-BISPHOSPHATE PHOSPHODIESTERASE DELTA 1 (EC 3.1.4.11) (PLC-DELTA-1) (PHOSPHOLIPASE C-DELTA-1) (PLC-III) (FRAGMENT).//2.50E-90//388aa//47%//P10895 TESTI20234140 TESTI20234270 TESTI20234360//PEPTIDYL-PROLYL CIS-TRANS ISOMERASE NIMA-INTERACTING 1 (EC 5.2.1.8).//5.90E-66//128aa//98%//Q13526 TESTI20237520//poly(A)-specific ribonuclease (deadenylation nuclease)//i. 10E-34//311aa//26%//NP_002573 TESTI20238000 TESTI20238610//MELANOMA-ASSOCIATED ANTIGEN B1 (MAGE-B1 ANTIGEN) (MAGE-XP ANTIGEN) (DAM10).//6.80E-69//268aa//51%//P43366 TESTI20239470 TESTI20239510//ubiquitin specific protease 6//5. 60E-43//182aa//50%//NP_004496 TESTI20240090 TESTI20241530 TESTI20241920 TESTI20242830 TESTI20242990 TESTI20244190//*Homo sapiens* IGHG3 gene for immunoglobulin heavy chain gamma 3 constant region, 4-exon hinge, isolate Lib-A2.//8.40E-214//377aa//100%//AJ390247 TESTI20244760 TESTI20249990//ATAXIN 7 (SPINOCEREBELLAR ATAXIA TYPE 7 PROTEIN).//7.30E-49//388aa//37%//015265 TESTI20254220 TESTI20254540//*Homo sapiens* hepatocellular carcinoma-associated antigen 59 mRNA, complete cds.//1.60E-100//197aa//98%//AF218421 TESTI20254860//TUMOR SUPPRESSOR PROTEIN DCC PRECURSOR.//1.20E-35//564aa//28%//P70211 TESTI20255820 TESTI20258460//*Homo sapiens* 0SBP-related protein 4 mRNA, complete cds.//8.20E-196//369aa//99%//AF323731 TESTI20262330 TESTI20262910 TESTI20265250 TESTI20265370 TESTI20265970 TESTI20266740//*Homo sapiens* topoisomerase-related function protein (TRF4-1) mRNA, partial cds.//2.70E-105//278aa//71%//AF089896 TESTI20269570 TESTI20271850

TESTI20272060 TESTI20272390 TESTI20272960//*Mus musculus* gene for odorant receptor MOR83, complete cds.//3.30E-84//306aa//50%//AB030894 TESTI20275030 TESTI20275620 TESTI20277360 TESTI20278200 TESTI20278400//INTRACELLULAR PROTEIN TRANSPORT PROTEIN USO1.//2.50E-11//604aa//21%//P25386 TESTI20280980 TESTI20282540 TESTI20284880 TESTI20285830 TESTI20288110 TESTI20288910//*Mus musculus* ' endophilin II mRNA, complete cds.//2.10E-110//225aa//92%//U58885 TESTI20289850 TESTI20291310 TESTI20291620 TESTI20291960//RHOMBOID PROTEIN (VEINLET PROTEIN).//2.00E-40//230aa//38%//P20350 TESTI20294700 TESTI20297850 TESTI20301360 TESTI20303220//*Rattus norvegicus* neural cell adhesion protein BIG-2 precursor (BIG-2) mRNA, complete cds.//0//807aa//94%//U35371 TESTI20303360 TESTI20303420 TESTI20305540//M.musculus mRNA for IB3/5-polypeptide.//1.30E-183//684aa//56%//X79131 TESTI20305560 TESTI20307540 TESTI20307700 TESTI20308600 TESTI20309170//Mucor circinelloides crgA gene for carotenoid regulatory protein.//3.10E-41//198aa//40%//AJ250998 TESTI20310070 TESTI20311290 TESTI20314180//TRYPSIN I-P1 PRECURSOR (EC 3.4.21.4).//2.10E-25//86aa//40%//Q90627 TESTI20316870//*Homo sapiens* mRNA for cartilage-associated protein (CASP).//4.90E-106//199aa//99%//AJ006470 TESTI20317600 TESTI20318090//ZINC FINGER PROTEIN 135.//2.00E-56//208aa//50%//P52742 TESTI20319190 TESTI20320440//THIOREDOXIN.//4.30E-32//103aa//63%//P50413 TESTI20320670//*Rattus norvegicus* mRNA for type A/B hnRNP protein p40.//2.20E-170//337aa//91%//AJ238854 TESTI20326810//RAN-SPECIFIC GTPASE-ACTIVATING PROTEIN (RAN BINDING PROTEIN 1) (RANBP1).//2.00E-33//66aa//100%//P34022 TESTI20327680 TESTI20327740 TESTI20328280 TESTI20330310 TESTI20332420//*Mus musculus* cell cycle checkpoint control protein Mrad9 gene, complete cds.//5.80E-20//246aa//28%//AF045662 TESTI20333000 TESTI20333950 TESTI20334410//Sus scrofa RNA helicase (RHIV-1) mRNA, complete cds.//4.40E-58//281aa//33%//AF181119 TESTI20335050//*Homo sapiens* cell cycle checkpoint protein CHFR mRNA, complete cds.//6.00E-188//333aa//99%//AF170724 TESTI20335200//BILIARY GLYCOPROTEIN 1 PRECURSOR (BGP-1) (ANTIGEN CD66) (CD66A ANTIGEN).//8.10E-20//87aa//50%//P13688 TESTI20336410 TESTI20337100 TESTI20342430 TESTI20343070 TESTI20343570//TRIPEPTIDYL-PEPTIDASE II (EC 3.4.14.10) (TPP II) (TRIPEPTIDYL AMINOPEPTIDASE).//2.00E-75//201aa//75%//P29144 TESTI20345060 TESTI20347180//*Mus musculus* membrane protein TMS-2 mRNA, complete cds.//6.00E-35//186aa//41%//AF181685 TESTI20347300 TESTI20347740 TESTI20347770 TESTI20351830 TESTI20352620//PROACTIVATOR POLYPEPTIDE PRECURSOR [CONTAINS: SAPOSIN A (PROTEIN A); SAPOSIN B (SPHINGOLIPID ACTIVATOR PROTEIN 1) (SAP-1) (DISPERSIN) (SULFATIDE/GM1 ACTIVATOR); SAPOSIN C (CO-BETA-GLUCOSIDASE) (Al ACTIVATOR) (GLUCOSYLCERAMIDASE ACTIVATOR) (SPHINGOLIPID ACTIVATOR PROTEIN 2) (SAP-2); SAPOSIN D (PROTEIN C) (COMPONENT C)].//1.30E-52//240aa//44%//P07602 TESTI20355020//Drosophila sp. Hls (hls) mRNA, complete cds.//9.80E-30//416aa//28%//S79915 TESTI20357750 TESTI20357930 TESTI20357960 TESTI20358980//Volvox carteri mRNA for hydroxyproline-rich glycoprotein (HRGP gene).//2.90E-37//155aa//50%//AJ242540 TESTI20361140 TESTI20366910//*Homo sapiens* mRNA for thioredoxin reductase II beta, complete cds.//2.00E-233//442aa//93%//ABO19695 TESTI20367360 TESTI20368330//M-PHASE INDUCER PHOSPHATASE3 (EC 3.1.3.48).//2.10E-258//473aa//99%//P30307 TESTI20369130 TESTI20369220 TESTI20369650//*Homo sapiens* mRNA for HsGAK, complete cds.//2.40E-269//493aa//99%//D88435 TESTI20369690 TESTI20370020 TESTI20370550 TESTI20370810//*Homo sapiens* mRNA for LAK-4p, complete cds.//1.10E-74//385aa//38%//AB002405 TESTI20371030//TIP ELONGATION ABERRANT PROTEIN 1 (CELL POLARITY PROTEIN TEA1).//7.80E-23//243aa//29%//P87061 TESTI20371060 TESTI20373820 TESTI20375340//1-PHOSPHATIDYLINOSITOL-4,5-BISPHOSPHATE PHOSPHODIESTERASE DELTA 1 (EC 3.1.4.11) (PLC-DELTA-1) (PHOSPHOLIPASE C-DELTA-1) (PLC-III) (FRAGMENT).//4.80E-68//273aa//45%//P10895 TESTI20377230 TESTI20378190//ZINC FINGER PROTEIN 91 (ZINC FINGER PROTEIN HTF10) (HPF7).//2.30E-114//323aa//52%//Q05481 TESTI20378450 TESTI20380650 TESTI20381040 TESTI20382750//*Homo sapiens* hookl protein (HOOKI) mRNA, complete cds.//2.60E-96//195aa//99%//AF044923 TESTI20383880//*Homo sapiens* gamma cysteine string protein mRNA, partial cds.//6.50E-61//109aa//100%//AF368277 TESTI20385960//*Homo sapiens* mRNA for RET finger protein-like 3.//4.80E-156//288aa//100%//AJ010232 TESTI20386230 TESTI20386440 TESTI20388580 TESTI20390260 TESTI20390410 TESTI20391130 TESTI20391210 TESTI20391770 TESTI20392090 TESTI20392250//*Homo sapiens* VAV-3 protein mRNA, complete cds.//9.80E-145//268aa//98%//AF067817 TESTI20392270 TESTI20392760//PROTEIN PHOSPHATASES PP1 REGULATORY SUBUNIT SDS22.//5.70E-22//226aa//31%//P36047 TESTI20393530//MITOCHONDRIAL PHOSPHATE CARRIER PROTEIN PRECURSOR (PTP).//9.00E-34//105aa//68%//P12234 TESTI20396130 TESTI20397760//POTENTIAL PHOSPHOLIPID-TRANSPORTING ATPASE IIB (EC 3.6.1.-).//1.60E-109//221aa//90%//P98195 TESTI20400940//CENTROMERIC PROTEIN E (CENP-E PROTEIN).//4.70E-16//669aa//23%//Q02224 TESTI20401020//Oryctolagus cuniculus peroxisomal Ca-dependent solute carrier mRNA, complete cds.//5.80E-64//234aa//56%//AF004161 TESTI20401280 TESTI20401430 TESTI20404240//INTERFERON-RELATED DEVELOPMENTAL REGULATOR 2 (SKMC15 PROTEIN).//4.60E-36//46aa//93%//QI2894 TESTI20406420 TESTI20408150 TESTI20408970//NUCLEAR ENVELOPE PORE MEMBRANE PROTEIN POM 121 (PORE MEMBRANE PROTEIN OF 121 KDA) (P145).//4.30E-16//264aa//30%//P52591 TESTI20409440 TESTI20409890//GCD14 PROTEIN.//2.30E-46//263aa//40%//P46959 TESTI20413300 TESTI20415170 TESTI20415640 TESTI20416640//CHOLINE/ETHANOLAMINE KINASE [INCLUDES: CHOLINE KINASE (EC 2.7.1.32) (CK); ETHANOLAMINE KINASE (EC 2.7.1.82) (EK)].//2.10E-77//139aa//100%//Q9Y259 TESTI20417300//DYNEIN BETA CHAIN, CILIARY.//6.80E-129//552aa//45%//P39057 TESTI20419560 TESTI20420620//TRANSCRIPTION INITIATION FACTOR TFIID 70 KDA SUBUNIT (TAFII-70) (TAFII-80) (TAFII80).//0//526aa//99%//P49848 TESTI20421490 TESTI20422640 TESTI20423020 TESTI20424000 TESTI20424730 TESTI20425070 TESTI20427830 TESTI20428060 TESTI20429280 TESTI20429580 TESTI20432750//*Mus musculus* pantothenate kinase 1 beta (panKIbeta) mRNA, complete cds.//9.70E-165//363aa//82%//AF200357 TESTI20432820//

ZINC FINGER PROTEIN 43 (ZINC PROTEIN HTF6).//1.00E-173//403aa//75%//P28160 TESTI20433130 TESTI20436560//LAMIN C.//9.20E-235//453aa//99%//P02546 TESTI20438570//*Homo sapiens* nolp mRNA, complete cds.//2.70E-43//146aa//60%//AB017800 TESTI20438660 TESTI20441940//Human K-Cl cotransporter (hKCCl) mRNA, complete cds.//5.50E-139//264aa//99%//U55054 TESTI20442760//*Homo sapiens* Ig-like membrane protein (IGSF3) mRNA, complete cds.//0//545aa//93%//AF031174 TESTI20443090//DNA REPAIR PROTEIN RAD51 HOMOLOG 4 (R51H3) (TRAD).//2.70E-68//141aa//100%//075771 TESTI20444130 TESTI20444180 TESTI20447540 TESTI20449200//METABOTROPIC GLUTAMATE RECEPTOR 7 PRECURSOR.//9.00E-173//313aa//99%//Q14831 TESTI20451710 TESTI20451990 TESTI20455090//KERATIN, TYPE I CYTOSKELETAL 18 (CYTOKERATIN 18) (K18) (CK 18).//1.20E-76//199aa//80%//P05783 TESTI20455620//HEAT SHOCK-RELATED 70 KDA PROTEIN 2 (HEAT SHOCK 70 KDA PROTEIN 2).//4.80E-218//336aa//99%//P54652 TESTI20456110//52 KDA RO PROTEIN (SJOGREN SYNDROME TYPE A ANTIGEN (SS-A)) (RO (SS-A)).//9.40E-75//382aa//43%//P19474 TESTI20458190 TESTI20463520 TESTI20463580//UBIQUITIN CARBOXYL-TERMINAL HYDROLASE 4 (EC 3.1.2.15) (UBIQUITIN THIOLESTERASE 4) (UBIQUITIN-SPECIFIC PROCESSING PROTEASE 4) (DEUBIQUITINATING ENZYME 4) (UBIQUITOUS NUCLEAR PROTEIN HOMOLOG).//1.50E-17//190aa//28%//Q13107 TESTI20465350//2', 3'-CYCLIC NUCLEOTIDE 3'-PHOSPHODIESTERASE (EC 3.1.4.37) (CNP) (CNPASE).//2.20E-123//231aa//100%//P09543 TESTI20465520 TESTI20465690//*Homo sapiens* Borg4 mRNA, complete cds.//2.00E-152//235aa//99%//AB042237 TESTI20467210//*Homo sapiens* mRNA for HELG protein.//2.00E-166//368aa//83%//AJ27729 1 TESTI20467320//*Mus musculus* WAVE-1 mRNA, complete cds.//1.20E-111//233aa//88%//AF290877 TESTI20467970 TESTI20468630 TESTI20471410//PROTEIN PHOSPHATASE 2C ALPHA ISOFORM (EC 3.1.3.16) (PP2C-ALPHA) (IA) (PROTEIN PHOSPHATASE 1A).//1.30E-210//382aa//99%//P35813 TESTI20471470 TESTI20471530 TESTI20472120 TESTI20473420 TESTI20473830//Columba livia mRNA for 5'-nucleotidase.//2.00E-14//75aa//49%//AJ131243 TESTI20477920 TESTI20478010 TESTI20478180 TESTI20478850 TESTI20479300 THYMU10005360//Human T cell receptor beta chain (TCRB) mRNA, VNDNJC region, 5' end.//1.20E-130//270aa//91%//L07294 THYMU10005540//*Homo sapiens* mRNA for immunoglobulin lambda heavy chain.//1.20E-237//479aa//90%//Y14737 THYMU20000570 THYMU20011950 THYMU20015210 THYMU20018190 THYMU20023380//*Homo sapiens* m6A methyltransferase (MT-A70) gene, complete cds.//1.20E-38//86aa//100%//AF014837 THYMU20027560 THYMU20029100 THYMU20032870 THYMU20039810//MPS1 protein//2.60E-283//646aa//77%//I52603 THYMU20045120 THYMU20058070 THYMU20061700 THYMU20066100 THYMU20070360 THYMU20075320 THYMU20081490//*Homo sapiens* ICB-1 mRNA, complete cds.//1.50E-23//267aa//33%//AF044896 THYMU20095960 THYMU20100410 THYMU20101610 THYMU20101920 THYMU20105190//MYOSIN I ALPHA (MMI-ALPHA).//7.50E-54//282aa//45%//P46735 THYMU20106710//*Homo sapiens* T-cell receptor alpha delta locus from bases 501613 to 752736 (section 3 of 5) of the Complete Nucleotide Sequence.//1.20E-54//113aa//98%//AE000660 THYMU20108310//Mouse NCBP-29 mRNA for PW29, complete cds.//7.70E-93//102aa//99%//D49429 THYMU20111180 THYMU20111420 THYMU20111830//protease, serine, 16 (thymus)//1.40E-129//175aa//98%//NP_005856 THYMU20114470 THYMU20115850 THYMU20118060 THYMU20118520//*Xenopus laevis* ubiquitin-like fusion protein mRNA, complete cds//3.00E-42//109aa//77%//L08475 THYMU20119390 THYMU20122730//target of myb1 (chicken) homolog//1.00E-122//233aa//100%//NP_005479 THYMU20126900//UDP-GLUCOSE 6-DEHYDROGENASE (EC 1.1.1.22) (UDP-GLC DEHYDROGENASE) (UDP-GLCDH) (UDPGDH).//1.40E-229//341aa//99%//060701 THYMU20128070 THYMU20128260 THYMU20130890//40S RIBOSOMAL PROTEIN S16.//1.90E-28//125aa//57%//P17008 THYMU20141670 THYMU20142040//WISKOTT-ALDRICH SYNDROME PROTEIN HOMOLOG (WASP).//2.60E-12//155aa//32%//P70315 THYMU20142970 THYMU20143270//*Homo sapiens* HSNFRK (HSNFRK) mRNA, complete cds.//5.40E-171//321aa//100%//AF226044 THYMU20147770//*Homo sapiens* mRNA for immunoglobulin lambda heavy chain.//5.40E-235//477aa//89%//Y14737 THYMU20153160 THYMU20158250 THYMU20159430//IG ALPHA-1 CHAIN C REGION.//7.90E-197//353aa//100%//P01876 THYMU20161640//*Mus musculus* p53 apoptosis-associated target (Perp) mRNA, complete cds.//1.40E-92//188aa//89%//AF249870 THYMU20162190 THYMU20169680//DIACYLGLYCEROL KINASE, ZETA (EC 2.7.1.107) (DIGLYCERIDE KINASE) (DGK- ZETA) (DAG KINASE ZETA).//1.40E-64//124aa//99%//Q13574 THYMU20172150//CORONIN-LIKE PROTEIN P57 (CORONIN 1A).//1.60E-49//96aa//100%//P31146 THYMU20173980 THYMU20180280//RED PROTEIN (RER PROTEIN) (IK FACTOR) (CYTOKINE IK).//2.60E-40//83aa//96%//Q13123 THYMU20186390 THYMU20186730 THYMU20187720 THYMU20193640//HETEROGENEOUS NUCLEAR RIBONUCLEOPROTEIN L (HNRNP L).//1.70E-82//157aa//99%//P14866 THYMU20194360 THYMU20194420 THYMU20195990 THYMU20201980//*Mus musculus* faciogenital dysplasia protein 2 (Fgd2) mRNA, complete cds.//2.90E-122//259aa//86%//AF017368 THYMU20202890//PROTEIN KINASE CLK3 (EC 2.7.1.-).//1.10E-204//367aa//99%//035492 THYMU20204160 THYMU20204990 THYMU20208300 THYMU20209590//DYNAMIN 2.//2.10E-189//363aa//97%//P50570 THYMU20215090 THYMU20215970 THYMU20216840 THYMU20222890 THYMU20226600 THYMU20228540 THYMU20229220 THYMU20232090//SYNTAXIN BINDINGPROTEIN 2 (UNC-18 HOMOLOG 2) (UNC-18B).//2.10E-54//112aa//99%//Q15833 THYMU20235760 THYMU20239000//collagen alpha 1(XI) chain //1.70E-37//579aa//33%//S18251 THYMU20239430 THYMU20240710//Halocynthia roretzi mRNA for HrPET-3, complete cds.//5.60E-54//1 55aa//44%//AB029335 THYMU20241210//*Homo sapiens* mRNA for nuclear protein, NP220, complete cds.//2.00E-58//117aa//100%//D83032 THYMU20241850//HLA CLASS II HISTOCOMPATIBILITY ANTIGEN, DX BETA CHAIN PRECURSOR.//4.40E-141//261aa//100%//P05538 THYMU20246840 THYMU20247480//ZINC FINGER PROTEIN 135.//1.20E-97//191aa//90%//P52742 THYMU20250420 THYMU20251890 THYMU20253250 THYMU20255570 THYMU20255720 THYMU20259090 THYMU20265300 THYMU20271250 THYMU20272490 THYMU20277390 THYMU20279750 THYMU20283790 THYMU20284120 THYMU20286290 THYMU20286320

TKIDN10000010//translocase of inner mitochondrial membrane 23 (yeast) homolog//6.30E-67//133aa//98%//NP_006318 TKIDN20004640//GALACTOKINASE 2 (EC 2.7.1.6).//5.10E-99//200aa//97%//Q01415 TKIDN20005210 TKIDN20030590 TKIDN20030620 TKIDN20047480//MITOGEN-ACTIVATED PROTEIN KINASE 12 (EC 2.7.1.-) (EXTRACELLULAR SIGNAL-REGULATED KINASE 6) (EC 2.7.1.-) (ERK6) (ERK5) (STRESS-ACTIVATED PROTEIN KINASE-3) (MITOGEN-ACTIVATED PROTEIN KINASE P38 GAMMA) (MAP KINASE P38 GAMMA).//2.20E-52//104aa//100%//P53778 TOVAR20004760 TOVAR20005750 TRACH20002870//CLAUDIN-6.//1.30E-27//175aa//42%//Q9Z262 TRACH20003590//CYTOCHROME P450 4A4 (EC 1.14.14.1) (CYPIVA4) (PROSTAGLANDIN OMEGA-HYDROXYLASE) (P450-P-2).//1.50E-138//493aa//49%//P10611 TRACH20005020 TRACH20005400//*Mus musculus* GTPase Rab37 (Rab37) mRNA, complete cds.//3.30E-109//223aa//93%//AF233582 TRACH20007020//TRICHOHYALIN.//5.60E-24//532aa//23%//P37709 TRACH20016210//ALPHA- (1, 3) -FUCOSYLTRANSFERASE (EC 2.4.1.65) (GALACTOSIDE 3-L-FUCOSYLTRANSFERASE) (FUCOSYLTRANSFERASE 6) (FUCT-VI).//5.00E-192//254aa//99%//P51993 TRACH20019960//SODIUM/POTASSIUM-TRANSPORTING ATPASE ALPHA-1 CHAIN PRECURSOR (EC 3.6.1.37) (SODIUM PUMP) (NA+/K+ ATPASE).//9.50E-185//410aa//84%//P05023 TRACH20027840 TRACH20028030//*Mus musculus* mmDNAJA4 mRNA for mmDj4, complete cds.//8.50E-205//397aa//92%//AB032401 TRACH20029540 TRACH20032720 TRACH20033230//MALTOSE PERMEASE.//1.20E-10//197aa//23%//Q45632 TRACH20034840//SKIN SECRETORY PROTEIN XP2 PRECURSOR (APEG PROTEIN).//5.90E-14//342aa//28%//P17437 TRACH20037360 TRACH20041830//Aedes triseriatus putative disulfide-isomerase mRNA, partial cds.//3.10E-29//134aa//47%//AF306866 TRACH20042920//Human C3f mRNA, complete cds.//7.80E-195//381aa//89%//U72515 TRACH20048450//PROTEIN K4 (PROTEIN K3).//4.70E-57//431aa//32%//P18377 TRACH20050040//PUTATIVE SURFACE GLYCOPROTEIN C210RF1 PRECURSOR (C210RF3).//8.50E-74//177aa//74%//P53801 TRACH20056980 TRACH20057690//RAC-BETA SERINE/THREONINE KINASE (EC 2.7.1.-) (RAC-PK-BETA) (AKT2 KINASE).//8.80E-22//48aa//100%//P31751 TRACH20060150 TRACH20067620//N-ACETYLLACTOSAMINIDE BETA-1, 6-N-ACETYLGLUCOSAMINYLTRANSFERASE (EC 2.4.1.150) (N-ACETYLGLUCOSAMINYLTRANSFERASE) (I-BRANCHING ENZYME) (IGNT).//8.20E-76//145aa//92%//Q06430 TRACH20068660//Mouse 19.5 mRNA, complete cds.//1.00E-55//263aa//41%//M32486 TRACH20068700//*Homo sapiens* adaptor protein CIKS mRNA, complete cds.//1.50E-232//572aa//79%//AF272151 TRACH20069180//*Homo sapiens* IGHG3 gene for immunoglobulin heavy chain gamma 3 constant region, 4-exon hinge, isolate Lib-A2.//1.00E-213//377aa//100%//AJ390247 TRACH20076740//FOLATE-LIKE TRANSPORTER DJ206D15.1 0N CHROMOSOME 1 (FRAGMENT).//1.00E-61//276aa//46%//060779 TRACH20076760 TRACH20077540//DXS8237E PROTEIN (FRAGMENT).//6.00E-96//189aa//95%//P98175 TRACH20079690//ZINC FINGER PROTEIN 136.//1.50E-113//368aa//58%//P52737 TRACH20082780 TRACH20084720//METHIONYL-TRNA SYNTHETASE, MITOCHONDRIAL (EC 6.1.1.10) (METHIONINE-TRNA LIGASE) (METRS).//8.50E-90//525aa//38%//074634 TRACH20085400//*Mus musculus* immunoglobulin scavenger receptor IgSR mRNA, complete cds.//1.30E-89//384aa//47%//AF302046 TRACH20085830//CYTOCHROME P450 4A8 (EC 1.14.14.1) (CYPIVA8) (P450-KP1) (P450-PP1).//3.70E-247//508aa//87%//P24464 TRACH20091230 TRACH20092680 TRACH20096610//LAMIN A (70 KDA LAMIN).//1.70E-77//164aa//93%//P02545 TRACH20099340 TRACH20105870//EUKARYOTIC TRANSLATION INITIATION FACTOR 4 GAMMA (EIF-4-GAMMA) (EIF- 4G) (EIF4G) (P220).//9.20E-95//204aa//92%//Q04637 TRACH20107710 TRACH20109650 TRACH20111130 TRACH20115740 TRACH20118940 TRACH20121380//REGULATOR OF G-PROTEIN SIGNALING 14 (RGS14) (FRAGMENT).//7.60E-144//308aa//92%//043566 TRACH20128110//*Rattus norvegicus* TM6P1 (TM6P1) mRNA, complete cds.//2.10E-87//187aa//88%//AF186469 TRACH20128230//*Homo sapiens* IGHG3 gene for immunoglobulin heavy chain gamma 3 constant region, 4-exon hinge, isolate Lib-A2.//9.60E-213//377aa//99%//AJ390247 TRACH20134950 TRACH20135520 TRACH20136710//IG LAMBDA CHAIN V-II REGION NIG-84.//2.20E-43//112aa//75%//P04209 TRACH20139820//SIGNAL RECOGNITION PARTICLE 68 KDA PROTEIN (SRP68).//3.70E-48//107aa//92%//Q00004 TRACH20140820 TRACH20141240//*Mus musculus* G21 protein mRNA, complete cds.//6.10E-26//60aa//93%//AF131207 TRACH20145440 TRACH20147250 TRACH20149970//*Rattus norvegicus* Ca2+-dependent activator protein (CAPS) mRNA, complete cds.//2.30E-205//512aa//74%//U16802 TRACH20153810 TRACH20154860//RETINOIC ACID RECEPTOR ALPHA (RAR-ALPHA).//8.90E-221//443aa//92%//P10276 TRACH20162860//NADH-UBIQUINONE OXIDOREDUCTASE SUBUNIT B14. 5B (EC 1.6.5.3) (EC 1.6.99.3) (COMPLEX I-B14.5B) (CI-B14.5B).//1.80E-39//80aa//98%//095298 TRACH20163170//HOMEOBOX PROTEIN MEIS1.//1.50E-131//238aa//100%//000470 TRACH20164980//ZINC FINGER PROTEIN 184 (FRAGMENT).//1.50E-163//488aa//56%//Q99676 TRACH20167220 TRACH20168350 TRACH20169800 TRACH20180840 TRACH20183170//*Rattus norvegicus* Sprague-Dawley SM-20 mRNA, complete cds.//1.60E-75//215aa//61%//U06713 TRACH20184490//*Homo sapiens* mRNA for zinc finger protein (ZNF304 gene).//3.20E-111//477aa//46%//AJ276316 TRACH20187180 TRACH20190240//*Homo sapiens* mRNA for fibulin-4.//1.00E-98//179aa//97%//AJ132819 TSTOM10001860 TSTOM20001390 TSTOM20003150 TSTOM20005690//kelch (Drosophila)-like 3 [*Homo sapiens*]//5.60E-211//399aa//98%//NP_059111 TUTER20002830//*Homo sapiens* transformer-2-beta (SFRS10) gene, alternatively spliced products, complete cds.//4.70E-122//253aa//90%//AF057159 UMVENI0001560//Anthocidaris crassispina mRNA for outer arm dynein light chain 1, complete cds.//1.90E-24//119aa//47%//AB010055 UMVEN10001860//N-CHIMAERIN (NC) (N-CHIMERIN) (ALPHA CHIMERIN) (A-CHIMAERIN).//5.90E-25//180aa//33%//P30337 UMVEN20000690 UMVEN20003540 UTERU20000740//Human fusion protein mRNA, complete cds.//4.90E-47//97aa//100%//M82829 UTERU20004240//CGI-96 protein//2.10E-39//108aa//81%//NP_056518 UTERU20006290 UTERU20006960//endoplasmic reticulum resident protein 58//5.90E-51//150aa//63%//NP_076994 UTERU20020010 UTERU20022940//Human (p23) mRNA, complete cds.//2.80E-80//147aa//99%//L24804 UTERU20030570//CHLORIDE CHANNEL PROTEIN CLC-KB (CLC-K2).//3.00E-252//469aa//99%//P51801 UTERU20040610 UTERU20046640//*Mus musculus* ld1Bp (LDLB) mRNA, complete cds.//0//839aa//83%//AF109377 UTERU20046980//*Mus musculus* mRNA for thrombospondin type 1 domain, complete cds.//7.30E-117//232aa//87%//AB016768 UTERU20050690 UTERU20054460 UTERU20055330 UTERU20055480 UTERU20055930 UTERU20056010 UTERU20059050 UTERU20061030 UTERU20064000 UTERU20064860//GLUCOAMYLASE S1/S2 PRECURSOR (EC 3.2.1.3) (GLUCAN 1,4-ALPHA-GLUCOSIDASE) (1,4-ALPHA-D-GLUCAN GLUCOHYDROLASE).//1.50E-29//595aa//28%//P08640 UTERU20065930//GTP-rHO BINDING PROTEIN 1 (RHOPHILIN).//6.10E-131//489aa//48%//Q61085 UTERU20067050 UTERU20068990 UTERU20070040 UTERU20070810 UTERU20076390 UTERU20081300 UTERU20084260 UTERU20094350 UTERU20095380 UTERU20095400 UTERU20097760//OVCA2=candidate tumor suppressor [human, fetal brain, Peptide, 120 aa]//6.00E-30//66aa//95%//AAB36422 UTERU20099720//*Homo sapiens* mRNA for SPIN protein.//6.50E-72//186aa//79%//Y14946 UTERU20101240 UTERU20114100 UTERU20115740//Human PMS2 related (hPMSR3) gene, complete cds.//1.00E-43//84aa//98%//U38979 UTERU20116570//*Homo sapiens* actin-binding double-zinc-finger protein (abLIM) mRNA, complete cds.//4.80E-163//468aa//71%//AF005654 UTERU20118110 UTERU20118970 UTERU20119060 UTERU20119680 UTERU20120310//*Rattus norvegicus* rexo70mRNA, complete cds.//1.50E-65//178aa//78%//AF032667 UTERU20124070 UTERU20126880 UTERU20134910 UTERU20135860 UTERU20143980 UTERU20144640//ACID CERAMIDASE PRECURSOR (EC 3.5.1.23) (ACYLSPHINGOSINE DEACYLASE) (N-ACYLSPHINGOSINE AMIDOHYDROLASE) (AC) (PUTATIVE 32 KDA HEART PROTEIN) (PHP32).//1.90E-166//243aa//100%//Q13510 UTERU20145480//*Homo sapiens* ZK1 mRNA for Kruppel-type zinc finger protein, complete cds.//4.40E-213//673aa//57%//AB011414 UTERU20146310//DIACYLGLYCEROL KINASE ETA (EC 2.7.1.107) (DIGLYCERIDE KINASE) (DGK- ETA) (DAG KINASE ETA).//4.50E-242//485aa//92%//Q64398 UTERU20146680 UTERU20150870 UTERU20151980//DUAL SPECIFICITY PROTEIN PHOSPHATASE 8 (EC 3.1.3.48) (EC 3.1.3.16) (DUAL SPECIFICITY PROTEIN PHOSPHATASE HVH-5).//5.20E-15//248aa//31%//Q13202 UTERU20158300 UTERU20158800//P-SELECTIN GLYCOPROTEIN LIGAND 1 PRECURSOR (PSGL-1) (SELECTIN P LIGAND) (CD162 ANTIGEN).//2.20E-185//384aa//95%//Q14242 UTERU20161570//PROBABLE G PROTEIN-COUPLED RECEPTOR RTA.//2.70E-141//303aa//85%//P23749 UTERU20164260 UTERU20168220//AIG1 PROTEIN.//7.70E-16//145aa//35%//P54120 UTERU20176130//*Mus musculus* zinc finger protein 289 (Zfp289) mRNA, complete cds.//4.00E-143//297aa//94%//AF229439 UTERU20176320//DNA REPAIR PROTEIN RAD18.//I1.10E-40//333aa//32%//P53692 UTERU20178100 UTERU20179880 UTERU20183640//SEMAPHORIN 3B PRECURSOR (SEMAPHORIN V) (SEMA V).//1.20E-69//135aa//100%//Q13214 UTERU20185230//Human androgen-induced prostate proliferative shutoff associated protein (AS3) mRNA, complete cds.//1.90E-255//571aa//80%//U95825 UTERU20186740 UTERU20188110//*Rattus norvegicus* cytosolic sorting protein PACS-la (PACS-1) mRNA, complete cds.//4.10E-157//315aa//97%//AF076183 UTERU20188810

What is claimed is:

1. An isolated polynucleotide comprising the nucleotide sequence of SEQ ID No: 1578.

2. A vector comprising the polynucleotide of claim 1.

3. An isolated host cell carrying the polynucleotide of claim 1 or a vector comprising said polynucleotide.

4. An isolated host cell carrying the polynucleotide of claim 1 or a vector comprising said polynucleotide in an expressible manner.

5. A method for producing a polypeptide or a peptide, said method comprising the steps of culturing the isolated host cell of claim 4 and recovering an expression product of SEQ ID No: 1578.

* * * * *